US010093630B2

(12) United States Patent
Boger et al.

(10) Patent No.: US 10,093,630 B2
(45) Date of Patent: Oct. 9, 2018

(54) PYRAZOLE COMPOUNDS AND METHODS OF MAKING AND USING SAME

(71) Applicants: ABIDE THERAPEUTICS, INC., San Diego, CA (US); THE SCRIPPS RESEARCH INSTITUTE, La Jolla, CA (US)

(72) Inventors: Dale L. Boger, La Jolla, CA (US); Katerina Otrubova, San Diego, CA (US); Justin S. Cisar, San Diego, CA (US); Cheryl A. Grice, Encinitas, CA (US); Todd K. Jones, Solana Beach, CA (US)

(73) Assignees: ABIDE THERAPEUTICS, INC., San Diego, CA (US); THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/312,998

(22) PCT Filed: May 20, 2015

(86) PCT No.: PCT/US2015/031834
§ 371 (c)(1),
(2) Date: Nov. 21, 2016

(87) PCT Pub. No.: WO2015/179559
PCT Pub. Date: Nov. 26, 2015

(65) Prior Publication Data
US 2017/0190669 A1 Jul. 6, 2017

Related U.S. Application Data

(60) Provisional application No. 62/001,491, filed on May 21, 2014.

(51) Int. Cl.
| | | |
|---|---|---|
| *C07D 231/14* | (2006.01) | |
| *C07D 491/107* | (2006.01) | |
| *C07D 403/12* | (2006.01) | |
| *C07D 417/12* | (2006.01) | |
| *C07D 405/12* | (2006.01) | |
| *C07D 401/12* | (2006.01) | |

(52) U.S. Cl.
CPC ......... *C07D 231/14* (2013.01); *C07D 401/12* (2013.01); *C07D 403/12* (2013.01); *C07D 405/12* (2013.01); *C07D 417/12* (2013.01); *C07D 491/107* (2013.01)

(58) Field of Classification Search
None
See application file for complete search history.

(56) References Cited

U.S. PATENT DOCUMENTS 3,308,130 A    3/1967  Bousquet

FOREIGN PATENT DOCUMENTS

| WO | WO-2010074588 A2 | 7/2010 |
| WO | WO-2013078771 A1 | 6/2013 |
| WO | WO-2015179559 A2 | 11/2015 |

OTHER PUBLICATIONS

Kohnz et al., Chemical Approaches to Therapeutically Target the Metabolism and Signaling of the Endocannabinoid 2-AG and Eicosanoids. Chemical Society Review, 2014, 43, 6859-6869.*
Lysenko et al., Monoacylglycerol Lipase Inhibitors JZL184 Improves Behavior and Neural Properties in Ts65Dn Mice, a Model of Down Syndrome. PloS ONE, 2014, 9:e114521, p. 1-25.*
Mulvihill et al., Therapeutic Potential of Monoacylglycerol Lipase Inhibitors. Life Science, 2013, 92, 492-497.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Fleisher et al. Improved oral drug delivery: solubility limitations overcome by the use of prodrugs. Advanced Drug Delivery Reviews 19:115-130 (1996).
Long et al. Selective blockade of 2-arachidonoylglycerol hydrolysis produces cannabinoid behavioral effects. Nat Chem Biol. 5(1):37-44 (2009).
Morren et al. The filaricidal derivatives of 1-methylpiperazine. Bulletin des Societes Chimiques Belges 59(3-4):228-237 (1950).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Otrubova et al. Discovery libraries targeting the major enzyme classes: the serine hydrolases. Bioorg Med Chem Lett 24(16):3807-3813 (2014).

(Continued)

*Primary Examiner* — Po-Chih Chen
(74) *Attorney, Agent, or Firm* — Wilson, Sonsini, Goodrich & Rosati

(57) ABSTRACT

Provided herein are pyrazole compounds and pharmaceutical compositions comprising said compounds. The subject compounds and compositions are useful as modulators of one or more of MAGL, ABHD6, and FAAH. Furthermore, the subject compounds and compositions are useful for the treatment of, for example, pain, solid tumors and/or obesity.

16 Claims, No Drawings

(56) References Cited

OTHER PUBLICATIONS

PCT/US2015/031834 International Search Report and Written Opinion dated Apr. 20, 2016.
PCT/US2015/031834 International Preliminary Report on Patentability dated Dec. 1, 2016.

* cited by examiner

PYRAZOLE COMPOUNDS AND METHODS OF MAKING AND USING SAME

CROSS-REFERENCE

This application is a U.S. National Stage Entry of PCT/US2015/031834, filed May 20, 2015; which claims the benefit of priority from U.S. Provisional Application No. 62/001,491, filed May 21, 2014, which are all incorporated herein by reference in their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system. The serine hydrolase α-β-hydrolase domain 6 (ABHD6) is another lipid mediator. Fatty acid amide hydrolase (FAAH) is another enzyme responsible for hydrolyzing endocannabinoids such as anandamide.

BRIEF SUMMARY OF THE INVENTION

This disclosure provides, for example, compounds and compositions which are modulators of one or more of MAGL, ABHD6, and FAAH, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of one or more of MAGL, ABHD6, and FAAH activity in warm-blooded animals such as humans.

One embodiment provides a compound of Formula (I):

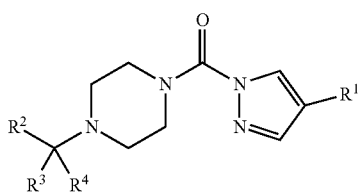

Formula (I)

wherein:
  $R^1$ is H, —$CF_3$, $C_{1-4}$ alkyl, cyano, halo, optionally substituted phenyl, —$CO_2R^5$, or —$C(O)NR^6R^7$;
  $R^2$ is optionally substituted aryl, optionally substituted heteroaryl, or optionally substituted $C_{3-8}$ cycloalkyl;
  $R^3$ is H;
  $R^4$ is H or optionally substituted phenyl;
  $R^5$ is H or $C_{1-4}$ alkyl; and
  $R^6$ and $R^7$ are each independently H, $C_{1-4}$ alkyl, or $C_{3-8}$ cycloalkyl; or $R^6$ and $R^7$ together with the nitrogen to which they are attached form a 4-, 5-, 6-, 7-, or 8-member heterocyclyl ring, optionally containing another heteroatom selected from S or O;
  or a solvate, hydrate, tautomer, N-oxide, or pharmaceutically acceptable salt thereof.

Another embodiment provides a compound of Formula (Ia):

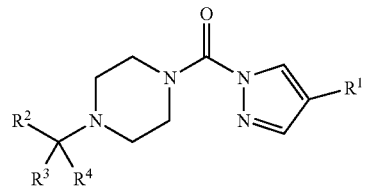

Formula (Ia)

wherein:
  $R^1$ is H, —$CF_3$, $C_{1-4}$ alkyl, cyano, halo, optionally substituted phenyl, —$CO_2R^5$, —$C(O)NR^6R^7$;
  $R^2$ is optionally substituted aryl or optionally substituted heteroaryl;
  $R^3$ is H;
  $R^4$ is H or optionally substituted phenyl;
  $R^5$ is H or $C_{1-4}$ alkyl; and
  $R^6$ and $R^7$ are each independently H, $C_{1-4}$ alkyl, or $C_{3-8}$ cycloalkyl; or $R^6$ and $R^7$ together with the nitrogen to which they are attached form a 4-, 5-, 6-, 7-, or 8-member heterocyclyl ring, optionally containing another heteroatom selected from S or O;
  or a solvate, hydrate, tautomer, N-oxide, or pharmaceutically acceptable salt thereof.

Another embodiment provides a compound of Formula (II):

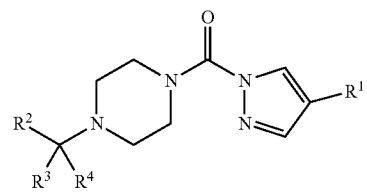

Formula (II)

wherein:
  $R^1$ is H, —$CF_3$, $C_{1-4}$ alkyl, halo, optionally substituted phenyl,

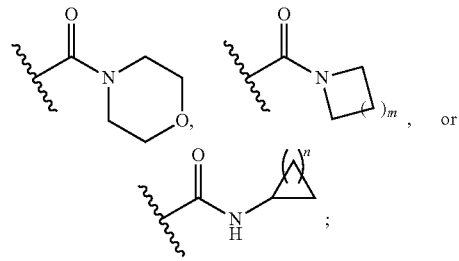

$R^2$ is optionally substituted aryl or optionally substituted heteroaryl;
  $R^3$ is H;
  $R^4$ is H or optionally substituted phenyl;
  m is 1, 2 or 3; and
  n is 1, 2, 3, 4, or 5;
  or a solvate, hydrate, tautomer, N-oxide, or pharmaceutically acceptable salt thereof.

Another embodiment provides a compound of Formula (III):

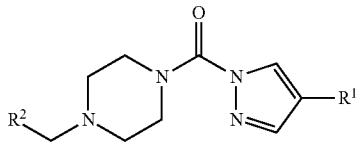

Formula (III)

wherein:
R$^1$ is H, C$_{1-4}$ alkyl, CF$_3$, cyano, halo, or —CO$_2$R$^3$;
R$^2$ is optionally substituted aryl; and
R$^3$ is H or C$_{1-4}$ alkyl;
or a solvate, hydrate, tautomer, N-oxide, or pharmaceutically acceptable salt thereof.

Another embodiment provides a compound of Formula (IIIa):

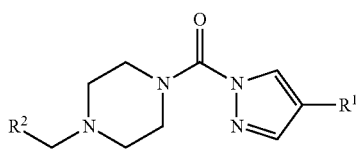

Formula (IIIa)

wherein:
R$^1$ is H, C$_{1-4}$ alkyl, cyano, halo, or —CO$_2$R$^3$;
R$^2$ is optionally substituted aryl; and
R$^3$ is H or C$_{1-4}$ alkyl;
or a solvate, hydrate, tautomer, N-oxide, or pharmaceutically acceptable salt thereof.

Another embodiment provides a compound of Formula (IV):

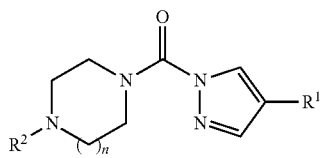

Formula (IV)

wherein:
R$^1$ is H, C$_{1-4}$ alkyl, halo, CF$_3$, optionally substituted aryl, or cyano;
R$^2$ is CO$_2$(t-Bu), C$_{1-4}$ alkyl, —C(O)R$^3$, —SO$_2$R$^3$, optionally substituted aryl, or optionally substituted heteroaryl;
R$^3$ is C$_{1-4}$ alkyl or optionally substituted aryl; and
n is 1 or 2;
or a solvate, hydrate, tautomer, N-oxide, or pharmaceutically acceptable salt thereof.

Another embodiment provides a compound of Formula (IVa):

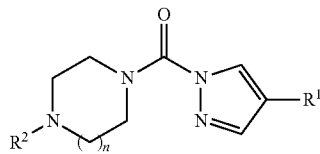

Formula (IVa)

wherein:
R$^1$ is H, C$_{1-4}$ alkyl, or cyano;
R$^2$ is CO$_2$(t-Bu); and
n is 1 or 2;
or a solvate, hydrate, tautomer, N-oxide, or pharmaceutically acceptable salt thereof.

Another embodiment provides a compound of Formula (V):

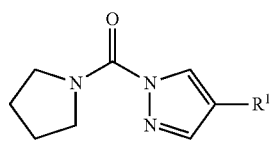

Formula (V)

wherein:
R$^1$ is halo, cyano, CF$_3$, or optionally substituted phenyl;
or a solvate, hydrate, tautomer, N-oxide, or pharmaceutically acceptable salt thereof.

Another embodiment provides a compound of Formula (Va):

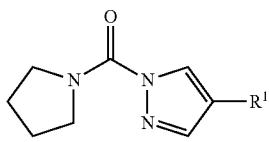

Formula (Va)

wherein:
R$^1$ is halo or optionally substituted phenyl;
or a solvate, hydrate, tautomer, N-oxide, or pharmaceutically acceptable salt thereof.

Another embodiment provides a compound of Formula (VI):

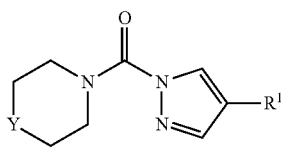

Formula (VI)

wherein:
Y is O or CH$_2$;
R$^1$ is H, C$_{1-4}$ alkyl, CF$_3$, halo, cyano, or optionally substituted phenyl;
or a solvate, hydrate, tautomer, N-oxide, or pharmaceutically acceptable salt thereof.

Another embodiment provides a compound of Formula (VIa):

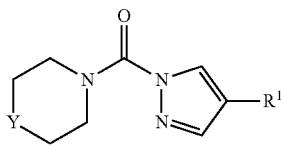

Formula (VIa)

wherein:
Y is O or CH$_2$;
R$^1$ is H, C$_{1-4}$ alkyl, halo, or cyano;
or a solvate, hydrate, tautomer, N-oxide, or pharmaceutically acceptable salt thereof.

Another embodiment provides a compound of Formula (VII):

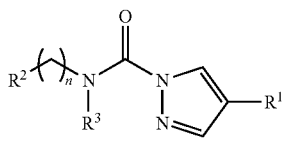

Formula (VII)

wherein:
R$^1$ is H, C$_{1-4}$ alkyl, cyano, CF$_3$, halo, —CO$_2$R$^4$, or optionally substituted phenyl;
R$^2$ is —N(Boc)CH$_3$, —NR$^5$C(O)R$^6$, —NR$^5$SO$_2$R$^6$, —NR$^5$R$^6$, optionally substituted phenyl or optionally substituted naphthyl;
R$^3$ is H or C$_{1-4}$ alkyl;
R$^4$ is H or C$_{1-4}$ alkyl;
R$^5$ is C$_{1-4}$ alkyl;
R$^6$ is C$_{1-4}$ alkyl, optionally substituted aryl, or optionally substituted aralkyl; and
n is 0-6;
or a solvate, hydrate, tautomer, N-oxide, or pharmaceutically acceptable salt thereof.

Another embodiment provides a compound of Formula (VIIa):

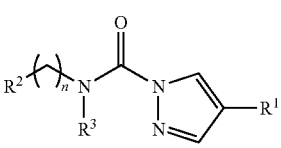

Formula (VIIa)

wherein:
R$^1$ is H, C$_{1-4}$ alkyl, cyano, halo, or —CO$_2$R$^4$;
R$^2$ is —N(Boc)CH$_3$, optionally substituted phenyl or optionally substituted naphthyl;
R$^3$ is H or C$_{1-4}$ alkyl;
R$^4$ is H or C$_{1-4}$ alkyl; and
n is 0-6;
or a solvate, hydrate, tautomer, N-oxide, or pharmaceutically acceptable salt thereof.

Another embodiment provides a compound of Formula (VIII):

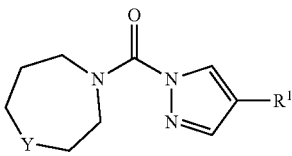

Formula (VIII)

wherein:
Y is CH$_2$ or NR$^2$;
R$^1$ is H, C$_{1-4}$ alkyl, cyano, CF$_3$, or halo;
R$^2$ is —C(O)R$^3$, —SO$_2$R$^3$, optionally substituted aralkyl, or C$_{1-4}$ alkyl; and
R$^3$ is C$_{1-4}$ alkyl or optionally substituted aryl;
or a solvate, hydrate, tautomer, N-oxide, or pharmaceutically acceptable salt thereof.

Another embodiment provides a pharmaceutical composition comprising a pyrazole compound described herein, or a solvate, hydrate, tautomer, N-oxide, or a pharmaceutically acceptable salt thereof, and at least one pharmaceutically acceptable excipient.

Another embodiment provides a method of treating a disorder selected from the group consisting of a solid tumor cancer, obesity, Down's syndrome, Alzheimer's disease, and an infection, comprising administering a therapeutically effective amount of a pyrazole compound described herein to a patient in need thereof. In some embodiments, the disorder is a solid tumor cancer. In some embodiments, the disorder is obesity. In some embodiments, the disorder is Down's syndrome or Alzheimer's disease. In some embodiments, the disorder is an infection by a bacterium, fungus, parasite, or virus.

Another embodiment provides a method of treating a disorder selected from the group consisting of a solid tumor cancer, obesity, Down's syndrome, Alzheimer's disease, and inflammation, comprising administering a therapeutically effective amount of a pyrazole compound described herein to a patient in need thereof. In some embodiments, the disorder is a solid tumor cancer. In some embodiments, the disorder is obesity. In some embodiments, the disorder is Down's syndrome or Alzheimer's disease. In some embodiments, the disorder is inflammation.

Another embodiment provides a method of treating pain in a patient, comprising administering a therapeutically effective amount of a pyrazole compound described herein to a patient in need thereof to treat said pain. Another embodiment provides a method of reducing the amount of adipose tissue in a patient, comprising administering an effective amount of a pyrazole compound described herein to a patient in need thereof to reduce the amount of adipose tissue in the patient.

Another embodiment provides a method of treating inflammation in a patient, comprising administering a therapeutically effective amount of a pyrazole compound described herein to a patient in need thereof to treat said inflammation.

DETAILED DESCRIPTION OF THE INVENTION

This disclosure is directed, at least in part, to modulators or inhibitors of one or more of MAGL, ABHD6, and FAAH. For example, provided herein are compounds capable of inhibiting one or more of MAGL, ABHD6, and FAAH.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—N$R^a R^f$, —N($R^a$)C(O)$R^f$, —N($R^a$)S(O)$_t R^f$ (where t is 1 or 2), —S(O)$_t OR^a$ (where t is 1 or 2), —S(O)$_t R^f$ (where t is 1 or 2) and —S(O)$_t N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—N$R^a R^f$, —N($R^a$)C(O)$R^f$, —N($R^a$)S(O)$_t R^f$ (where t is 1 or 2), —S(O)$_t OR^a$ (where t is 1 or 2), —S(O)$_t R^f$ (where t is 1 or 2) and —S(O)$_t N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—N$R^a R^f$, —N($R^a$)C(O)$R^f$, —N($R^a$)S(O)$_t R^f$ (where t is 1 or 2), —S(O)$_t OR^a$ (where t is 1 or 2), —S(O)$_t R^f$ (where t is 1 or 2) and —S(O)$_t N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—N$R^aR^f$, —N($R^a$)C(O)$R^f$, —N($R^a$)S(O)$_tR^f$ (where t is 1 or 2), —S(O)$_tOR^a$ (where t is 1 or 2), —S(O)$_tR^f$ (where t is 1 or 2) and —S(O)$_tN(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N(R^a)S(O)$_tR^a$ (where t is 1 or 2), —$R^b$—S(O)$_tOR^a$ (where t is 1 or 2), —$R^b$—S(O)$_tR^a$ (where t is 1 or 2) and —$R^b$—S(O)$_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^c$-aryl, where $R^c$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl are saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N (R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Halo" or "halogen" refers to bromo, chloro, fluoro or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which include fused or bridged ring systems. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)OR$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Heterocyclylalkyl" refers to a radical of the formula —R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno

[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

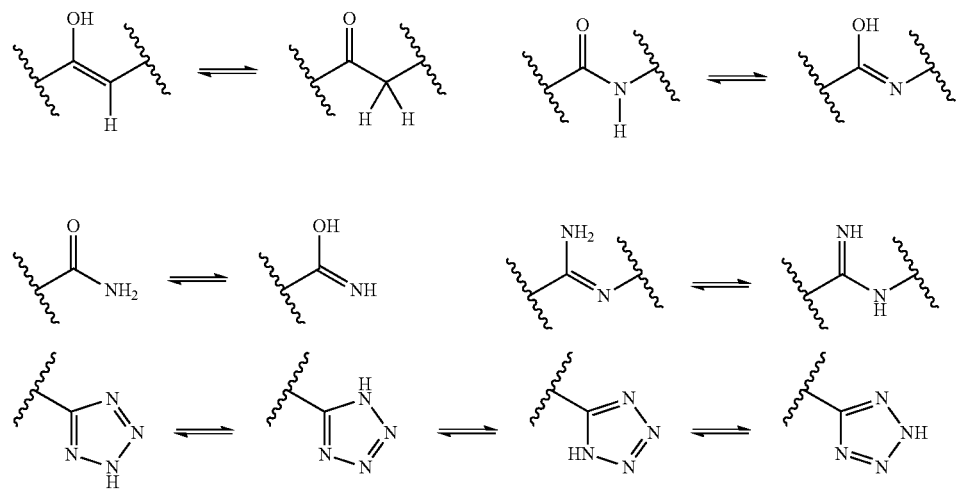

-continued

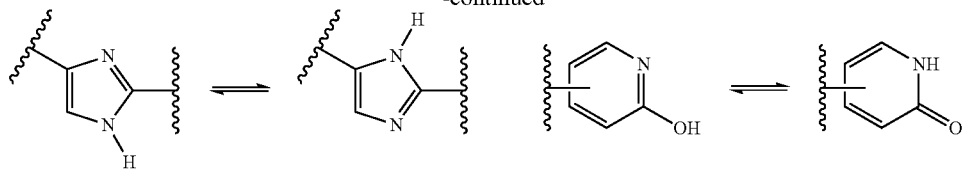

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, the prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound.

Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Compounds

Pyrazole compounds are described herein which are modulators of one or more of MAGL, ABHD6, and FAAH. In some embodiments, the compounds are modulators of MAGL. In some embodiments, the compounds are modulators of ABHD6. In some embodiments, the compounds are modulators of FAAH. In some embodiments, the compounds are modulators of MAGL and ABHD6. In some embodiments, the compounds are modulators of MAGL and FAAH. In some embodiments, the compounds are modulators of ABHD6 and FAAH. In some embodiments, the compounds are modulators of MAGL, ABHD6, and FAAH. These compounds, and compositions comprising these compounds, are useful for the treatment of pain, solid tumor cancer, and/or obesity.

One embodiment provides a compound of Formula (I):

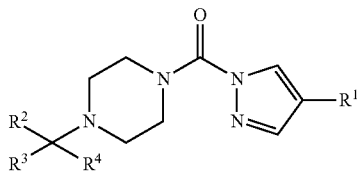

Formula (I)

wherein:
  $R^1$ is H, —$CF_3$, $C_{1-4}$ alkyl, cyano, halo, optionally substituted phenyl, —$CO_2R^5$, or —$C(O)NR^6R^7$;
  $R^2$ is optionally substituted aryl, optionally substituted heteroaryl, or optionally substituted $C_{3-8}$ cycloalkyl;
  $R^3$ is H;
  $R^4$ is H or optionally substituted phenyl;
  $R^5$ is H or $C_{1-4}$ alkyl; and
  $R^6$ and $R^7$ are each independently H, $C_{1-4}$ alkyl, or $C_{3-8}$ cycloalkyl; or $R^6$ and $R^7$ together with the nitrogen to which they are attached form a 4-, 5-, 6-, 7-, or 8-member heterocyclyl ring, optionally containing another heteroatom selected from S or O;
  or a solvate, hydrate, tautomer, N-oxide, or pharmaceutically acceptable salt thereof.

In another embodiment is a compound of Formula (I), wherein $R^1$ is optionally substituted phenyl. In another embodiment is a compound of Formula (I), wherein $R^1$ is

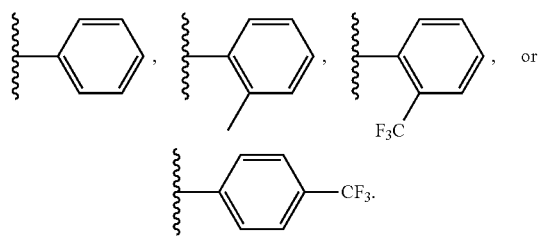

In another embodiment is a compound of Formula (I), wherein $R^1$ is —$C(O)NR^6R^7$; and $R^6$ and $R^7$ are each independently H, $C_{1-4}$ alkyl, or $C_{3-8}$ cycloalkyl. In another embodiment is a compound of Formula (I), wherein $R^1$ is —$C(O)NR^6R^7$; and $R^6$ and $R^7$ are each independently H or $C_{1-4}$ alkyl. In another embodiment is a compound of Formula (I), wherein $R^1$ is —$C(O)NR^6R^7$; and $R^6$ and $R^7$ are each independently H or $C_{3-8}$ cycloalkyl.

In another embodiment is a compound of Formula (I), wherein $R^1$ is —$C(O)NR^6R^7$; and $R^6$ and $R^7$ together with the nitrogen to which they are attached form a 4-, 5-, 6-, 7-, or 8-member heterocyclyl ring, optionally containing another heteroatom selected from S or O. In another embodiment is a compound of Formula (I), wherein $R^1$ s

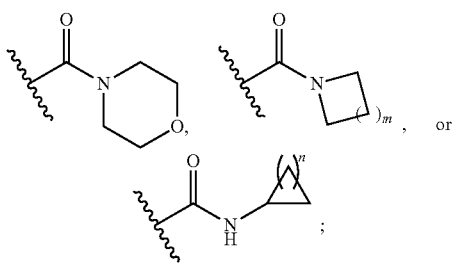

m is 1, 2 or 3; and n is 1, 2, 3, 4, or 5. In another embodiment is a compound of Formula (I), wherein $R^1$ is

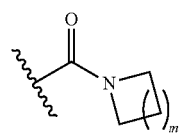

and m is 1, 2 or 3. In another embodiment is a compound of Formula (I), wherein $R^1$ is

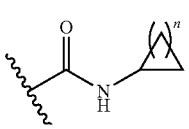

and n is 1, 2, 3, 4, or 5. In another embodiment is a compound of Formula (I), wherein $R^1$ is

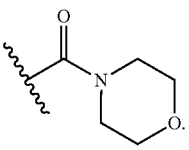 [SMILES: *C(=O)N1CCOCC1]

In another embodiment is a compound of Formula (I), wherein $R^1$ is halo. In another embodiment is a compound of Formula (I), wherein $R^1$ is fluoro or chloro. In another embodiment is a compound of Formula (I), wherein $R^1$ is iodo or bromo.

In another embodiment is a compound of Formula (I), wherein $R^1$ is $C_{1-4}$ alkyl. In another embodiment is a compound of Formula (I), wherein $R^1$ is isopropyl.

In another embodiment is a compound of Formula (I), wherein $R^1$ is —$CF_3$.

In another embodiment is a compound of Formula (I), wherein $R^1$ is —$CO_2R^5$. In another embodiment is a compound of Formula (I), wherein $R^5$ is H. In another embodiment is a compound of Formula (I), wherein $R^5$ is $C_{1-4}$ alkyl. In another embodiment is a compound of Formula (I), wherein $R^1$ is —$CO_2Me$.

In another embodiment is a compound of Formula (I), wherein $R^2$ is optionally substituted aryl. In another embodiment is a compound of Formula (I), wherein $R^2$ is optionally substituted phenyl. In another embodiment is a compound of Formula (I), wherein $R^2$ is

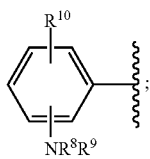

$R^8$ and $R^9$ together with the nitrogen to which they are attached form a 4-, 5-, 6-, 7-, or 8-member optionally substituted heterocyclyl ring, optionally containing another heteroatom selected from S or O; and $R^{10}$ is H, —$CF_3$, or halo. In another embodiment is a compound of Formula (I), wherein $R^{10}$ is —$CF_3$. In another embodiment is a compound of Formula (I), wherein $R^{10}$ is halo. In another embodiment is a compound of Formula (I), wherein $R^{10}$ is chloro. In another embodiment is a compound of Formula (I), wherein $R^8$ and $R^9$ together with the nitrogen to which they are attached form an optionally substituted pyrrolidine. In another embodiment is a compound of Formula (I), wherein $R^8$ and $R^9$ together with the nitrogen to which they are attached form an optionally substituted piperidine. In another embodiment is a compound of Formula (I), wherein $R^8$ and $R^9$ together with the nitrogen to which they are attached form an optionally substituted morpholine.

In another embodiment is a compound of Formula (I), wherein $R^2$ is a bisubstituted phenyl. In another embodiment is a compound of Formula (I), wherein $R^2$ is a monosubstituted phenyl. In another embodiment is a compound of Formula (I), wherein $R^2$ is

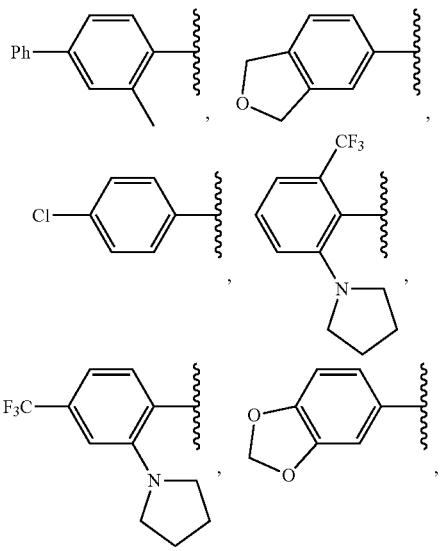

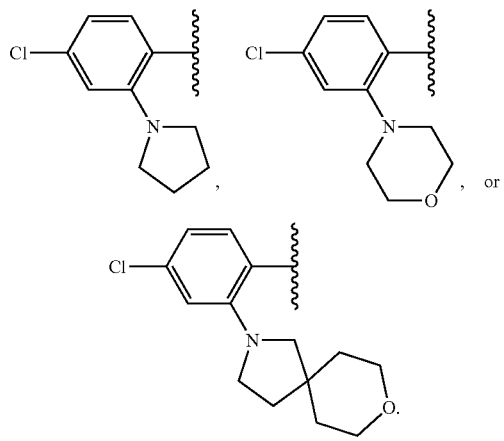

In another embodiment is a compound of Formula (I), wherein $R^2$ is

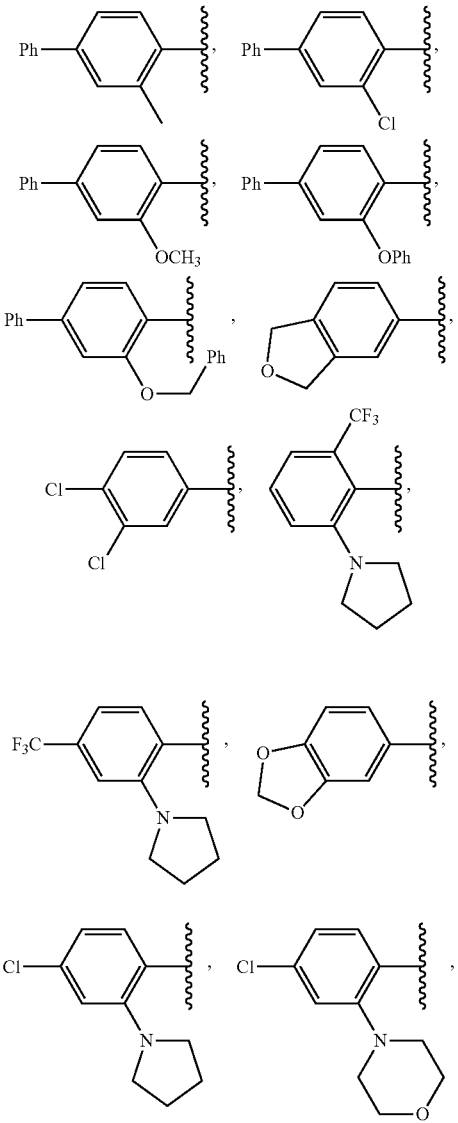

-continued

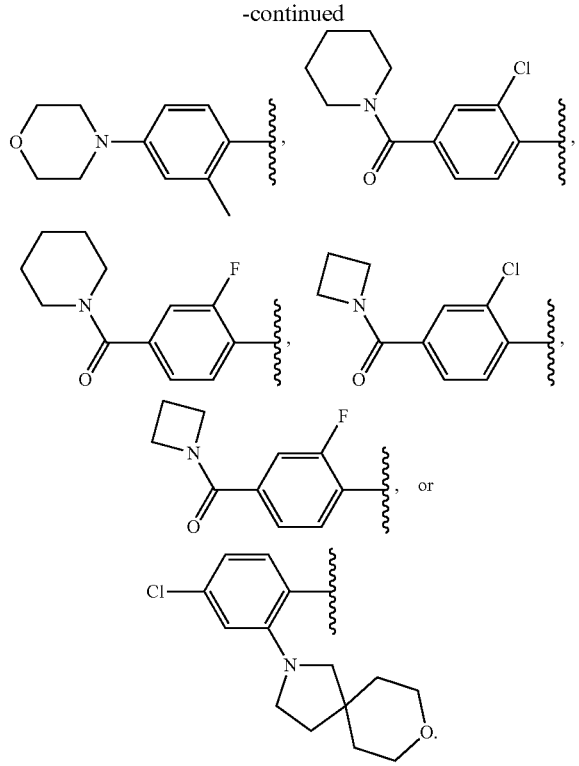

In another embodiment is a compound of Formula (I), wherein R² is:

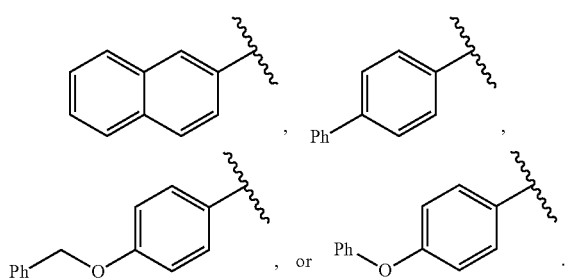

In another embodiment is a compound of Formula (I), wherein R² is:

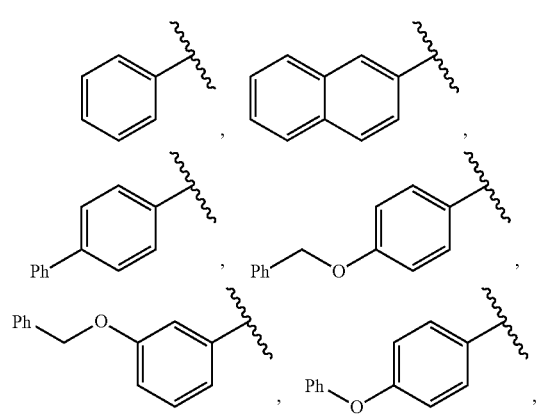

-continued

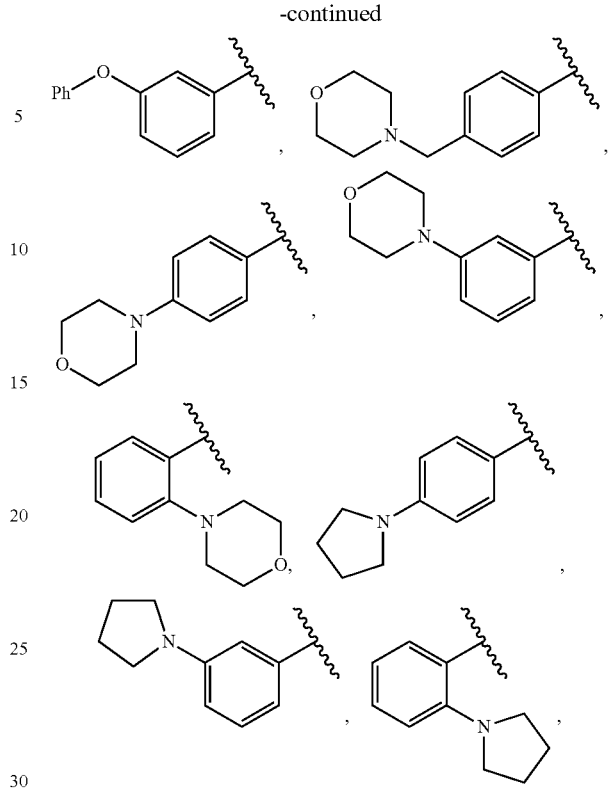

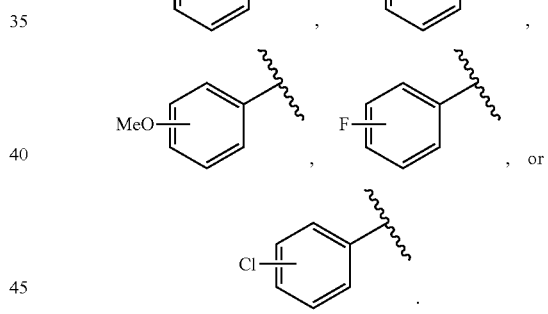

In another embodiment is a compound of Formula (I), wherein R² is optionally substituted naphthyl.

In another embodiment is a compound of Formula (I), wherein R² is optionally substituted heteroaryl. In another embodiment is a compound of Formula (I), wherein R² is optionally substituted pyrazolyl, optionally substituted pyrimidinyl, optionally substituted thiazolyl, or optionally substituted pyridinyl. In another embodiment is a compound of Formula (I), wherein R² is

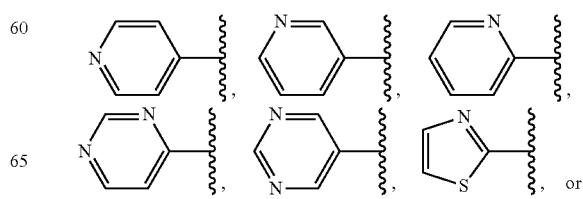

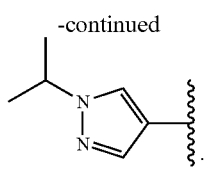

In another embodiment is a compound of Formula (I), wherein $R^2$ is optionally substituted $C_{3-8}$ cycloalkyl. In another embodiment is a compound of Formula (I), wherein $R^2$ is optionally substituted $C_{3-8}$ cycloalkyl and $R^1$ is —C(O)NR$^6$R$^7$. In another embodiment is a compound of Formula (I), wherein $R^2$ is optionally substituted $C_{3-8}$ cycloalkyl and $R^1$ is H, —CF$_3$, $C_{1-4}$ alkyl, cyano, or halo. In another embodiment is a compound of Formula (I), wherein $R^2$ is optionally substituted $C_{3-8}$ cycloalkyl and $R^1$ is H. In another embodiment is a compound of Formula (I), wherein $R^2$ is optionally substituted $C_{3-8}$ cycloalkyl and $R^1$ is —CF$_3$ or halo. In another embodiment is a compound of Formula (I), wherein $R^2$ is optionally substituted $C_{3-8}$ cycloalkyl and $R^1$ is $C_{1-4}$ alkyl. In another embodiment is a compound of Formula (I), wherein $R^2$ is optionally substituted $C_{3-8}$ cycloalkyl and $R^1$ is cyano.

In another embodiment is a compound of Formula (I), wherein $R^4$ is H. In another embodiment is a compound of Formula (I), wherein $R^4$ is optionally substituted phenyl. In another embodiment is a compound of Formula (I), wherein $R^4$ is

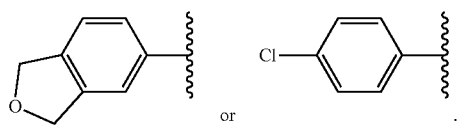 [SMILES: *c1ccc2c(c1)COC2 ; *c1ccc(Cl)cc1]

or

Another embodiment provides a compound of Formula (II):

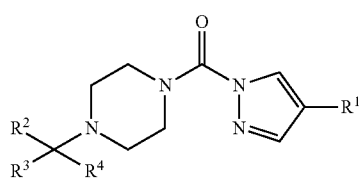

Formula (II)

wherein:
$R^1$ is H, —CF$_3$, $C_{1-4}$ alkyl, halo, optionally substituted phenyl,

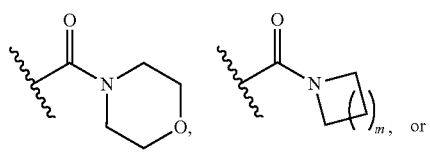

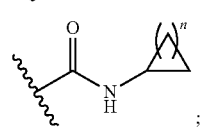

;

$R^2$ is optionally substituted aryl or optionally substituted heteroaryl;
$R^3$ is H;
$R^4$ is H or optionally substituted phenyl;
m is 1, 2, or 3; and
n is 1, 2, 3, 4, or 5;
or a solvate, hydrate, tautomer, N-oxide, or pharmaceutically acceptable salt thereof.

In another embodiment is a compound of Formula (II), wherein $R^1$ is optionally substituted phenyl. In another embodiment is a compound of Formula (II), wherein $R^1$ is

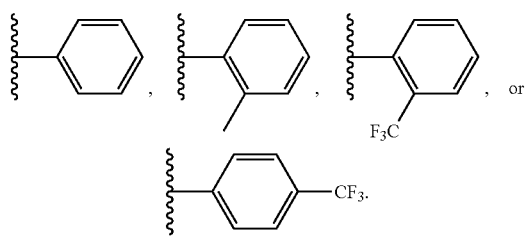

In another embodiment is a compound of Formula (II), wherein $R^1$ is

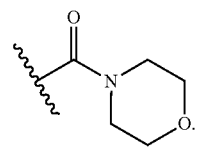 [SMILES: *C(=O)N1CCOCC1]

In another embodiment is a compound of Formula (II), wherein $R^1$ is

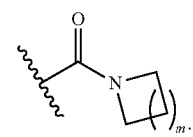

In another embodiment is a compound of Formula (II), wherein $R^1$ is

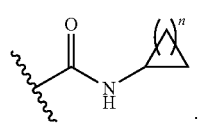

In another embodiment is a compound of Formula (II), wherein $R^1$ is,

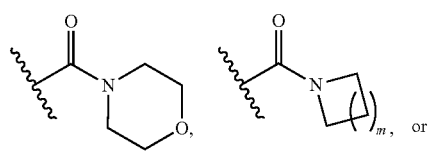

-continued

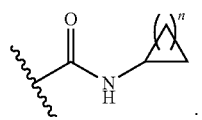

In another embodiment is a compound of Formula (II), wherein $R^1$ is,

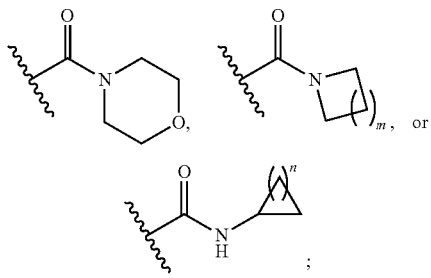

and $R^2$ is optionally substituted aryl. In another embodiment is a compound of Formula (II), wherein $R^1$ is,

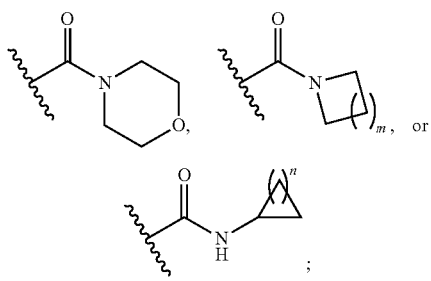

and $R^2$ is bisubstituted or monosubstituted phenyl. In another embodiment is a compound of Formula (II), wherein $R^1$ is,

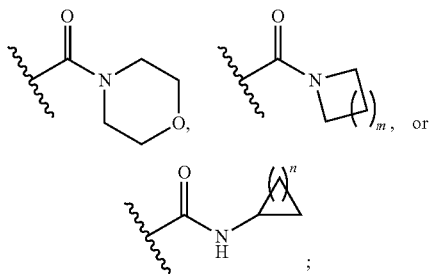

$R^2$ is bisubstituted or monosubstituted phenyl; and $R^4$ is H. In another embodiment is a compound of Formula (II), wherein $R^1$ is,

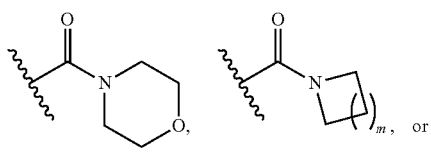

-continued

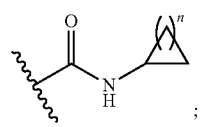

$R^2$ is bisubstituted or monosubstituted phenyl; and $R^4$ is optionally substituted phenyl. In another embodiment is a compound of Formula (II), wherein $R^1$ is,

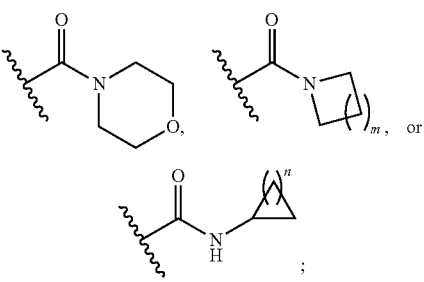

and $R^2$ is optionally substituted heteroaryl.

In another embodiment is a compound of Formula (II), wherein $R^1$ is halo. In another embodiment is a compound of Formula (II), wherein $R^1$ is fluoro or chloro. In another embodiment is a compound of Formula (II), wherein $R^1$ is halo and $R^2$ is optionally substituted aryl. In another embodiment is a compound of Formula (II), wherein $R^1$ is halo and $R^2$ is bisubstituted or monosubstituted phenyl. In another embodiment is a compound of Formula (II), wherein $R^1$ is halo and $R^2$ is optionally substituted heteroaryl.

In another embodiment is a compound of Formula (II), wherein $R^1$ is $C_{1-4}$ alkyl. In another embodiment is a compound of Formula (II), wherein $R^1$ is isopropyl. In another embodiment is a compound of Formula (II), wherein $R^1$ is $C_{1-4}$ alkyl and $R^2$ is optionally substituted aryl. In another embodiment is a compound of Formula (II), wherein $R^1$ is $C_{1-4}$ alkyl and $R^2$ is bisubstituted or monosubstituted phenyl. In another embodiment is a compound of Formula (II), wherein $R^1$ is $C_{1-4}$ alkyl and $R^2$ is optionally substituted heteroaryl.

In another embodiment is a compound of Formula (II), wherein $R^1$ is —$CF_3$. In another embodiment is a compound of Formula (II), wherein $R^1$ is —$CF_3$ and $R^2$ is optionally substituted aryl. In another embodiment is a compound of Formula (II), wherein $R^1$ is —$CF_3$ and $R^2$ is bisubstituted or monosubstituted phenyl. In another embodiment is a compound of Formula (II), wherein $R^1$ is —$CF_3$ and $R^2$ is optionally substituted heteroaryl.

In another embodiment is a compound of Formula (II), wherein $R^1$ is H. In another embodiment is a compound of Formula (II), wherein $R^2$ is optionally substituted aryl. In another embodiment is a compound of Formula (II), wherein $R^2$ is optionally substituted phenyl. In another embodiment is a compound of Formula (II), wherein $R^2$ is

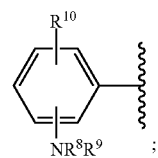

$R^8$ and $R^9$ together with the nitrogen to which they are attached form a 4-, 5-, 6-, 7-, or 8-member optionally substituted heterocyclyl ring, optionally containing another heteroatom selected from S or O; and $R^{10}$ is H, —CF$_3$, or halo. In another embodiment is a compound of Formula (II), wherein $R^{10}$ is —CF$_3$. In another embodiment is a compound of Formula (II), wherein $R^{10}$ is halo. In another embodiment is a compound of Formula (II), wherein $R^{10}$ is chloro. In another embodiment is a compound of Formula (II), wherein $R^8$ and $R^9$ together with the nitrogen to which they are attached form an optionally substituted pyrrolidine. In another embodiment is a compound of Formula (II), wherein $R^8$ and $R^9$ together with the nitrogen to which they are attached form an optionally substituted piperidine. In another embodiment is a compound of Formula (II), wherein $R^8$ and $R^9$ together with the nitrogen to which they are attached form an optionally substituted morpholine.

In another embodiment is a compound of Formula (II), wherein $R^2$ is a bisubstituted phenyl. In another embodiment is a compound of Formula (II), wherein $R^2$ is a monosubstituted phenyl. In another embodiment is a compound of Formula (II), wherein $R^2$ is

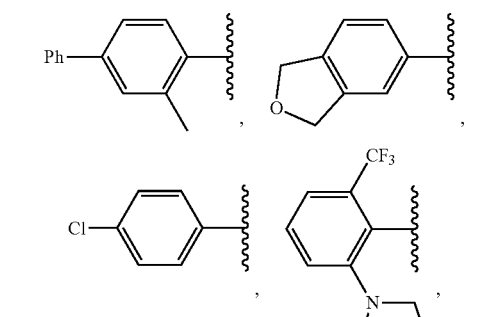

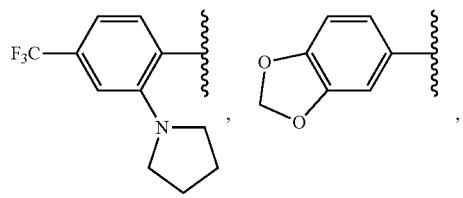

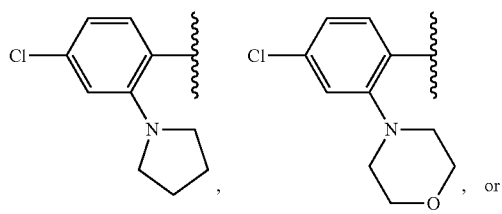

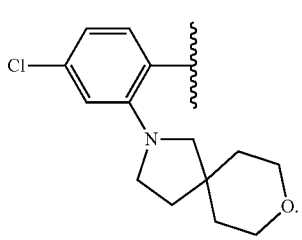

In another embodiment is a compound of Formula (II), wherein $R^2$ is

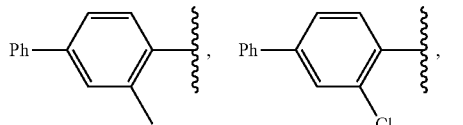

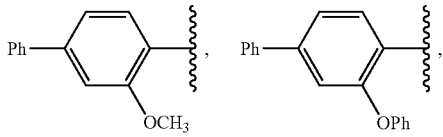

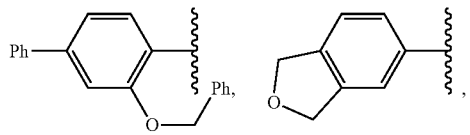

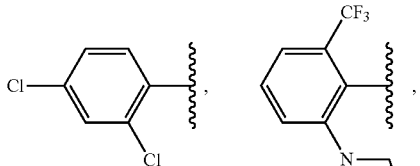

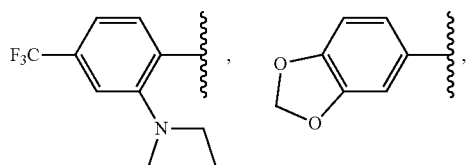

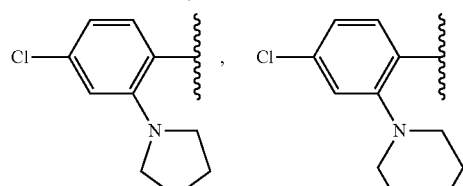

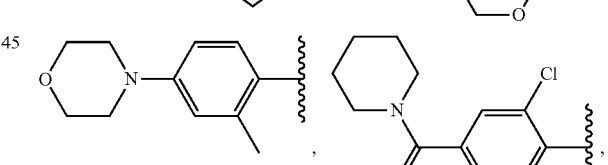

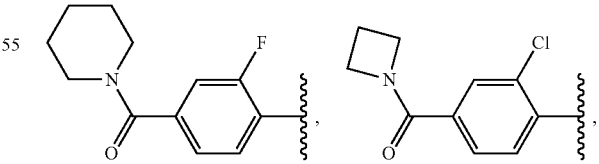

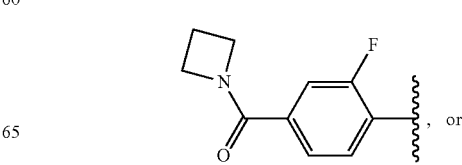

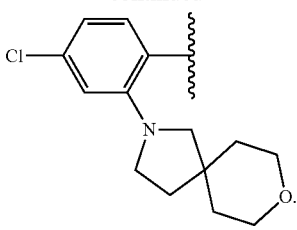

In another embodiment is a compound of Formula (II), wherein R² is:

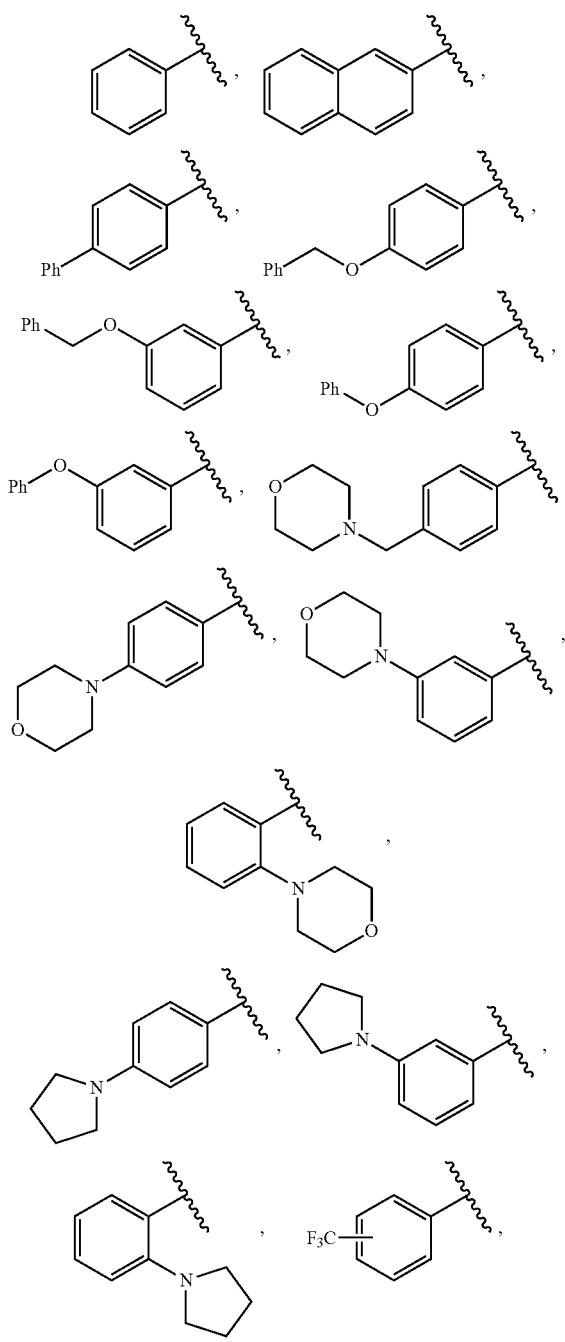

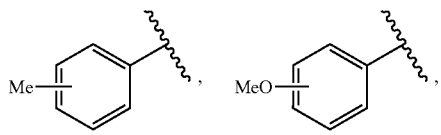

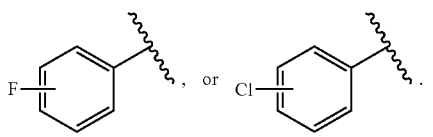

In another embodiment is a compound of Formula (II), wherein R² is optionally substituted heteroaryl. In another embodiment is a compound of Formula (II), wherein R² is optionally substituted pyrazolyl, optionally substituted pyrimidinyl, optionally substituted thiazolyl, or optionally substituted pyridinyl.

In another embodiment is a compound of Formula (II), wherein R² is

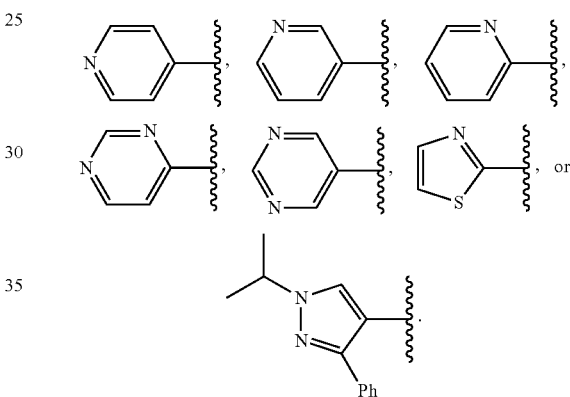

In another embodiment is a compound of Formula (II), wherein R⁴ is H. In another embodiment is a compound of Formula (II), wherein R⁴ is optionally substituted phenyl. In another embodiment is a compound of Formula (II), wherein R⁴ is

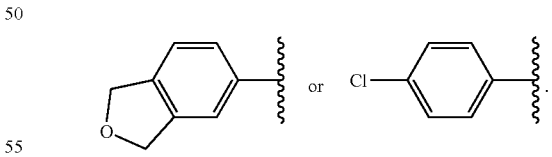

In another embodiment is a compound of Formula (II), wherein R⁴ is H. In another embodiment is a compound of Formula (II), wherein R⁴ is optionally substituted phenyl. In another embodiment is a compound of Formula (II), wherein R⁴ is monosubstituted phenyl. In another embodiment is a compound of Formula (II), wherein R⁴ is bisubstituted phenyl.

Another embodiment provides a compound of Formula (III):

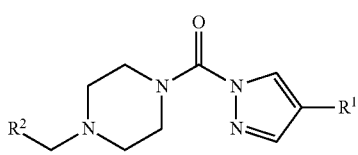

Formula (III)

wherein:
R¹ is H, $C_{1-4}$ alkyl, $CF_3$, cyano, halo, or —$CO_2R^3$;
R² is optionally substituted aryl; and
R³ is H or $C_{1-4}$ alkyl;
or a solvate, hydrate, tautomer, N-oxide, or pharmaceutically acceptable salt thereof.

In another embodiment is a compound of Formula (III), wherein R¹ is H.

In another embodiment is a compound of Formula (III), wherein R¹ is —$CO_2R^3$. In another embodiment is a compound of Formula (III), wherein R³ is H. In another embodiment is a compound of Formula (III), wherein R³ is $C_{1-4}$ alkyl. In another embodiment is a compound of Formula (III), wherein R¹ is —$CO_2Me$.

In another embodiment is a compound of Formula (III), wherein R¹ is halo. In another embodiment is a compound of Formula (III), wherein R¹ is iodo or bromo. In another embodiment is a compound of Formula (III), wherein R¹ is iodo. In another embodiment is a compound of Formula (III), wherein R¹ is bromo. In another embodiment is a compound of Formula (III), wherein R¹ is fluoro or chloro. In another embodiment is a compound of Formula (III), wherein R¹ is fluoro. In another embodiment is a compound of Formula (III), wherein R¹ is chloro.

In another embodiment is a compound of Formula (III), wherein R¹ is cyano. In another embodiment is a compound of Formula (III), wherein R² is optionally substituted phenyl or optionally substituted naphthyl. In another embodiment is a compound of Formula (III), wherein R² is optionally substituted phenyl. In another embodiment is a compound of Formula (III), wherein R² is monosubstituted phenyl. In another embodiment is a compound of Formula (III), wherein R² is bisubstituted phenyl. In another embodiment is a compound of Formula (III), wherein R² is phenyl substituted with one or more substituents selected from the group consisting of $C_{1-4}$ alkyl, haloalkyl, (heterocyclyl)alkyl, alkoxy, aryloxy, aralkyloxy, halo, —C(O)NR$^a$R$^b$, and NR$^a$R$^b$; and R$^a$ and R$^b$ are independently selected from $C_{1-4}$ alkyl or R$^a$ and R$^b$ together with the nitrogen to which they are attached form an optionally substituted 4-, 5-, 6-, 7-, or 8-member heterocyclyl ring, optionally containing another heteroatom selected from N, S, or O. In another embodiment is a compound of Formula (III), wherein R² is phenyl substituted with one or more substituents selected from the group consisting of $C_{1-4}$ alkyl, haloalkyl, (heterocyclyl)alkyl, alkoxy, phenyloxy, benzyloxy, halo, —C(O)NR$^a$R$^b$, and NR$^a$R$^b$; and R$^a$ and R$^b$ are independently selected from $C_{1-4}$ alkyl or R$^a$ and R$^b$ together with the nitrogen to which they are attached form a 4-, 5-, 6-, 7-, or 8-member heterocyclyl ring, optionally containing another heteroatom selected from S or O. In another embodiment is a compound of Formula (III), wherein R² is optionally substituted naphthyl. In another embodiment is a compound of Formula (III), wherein R² is

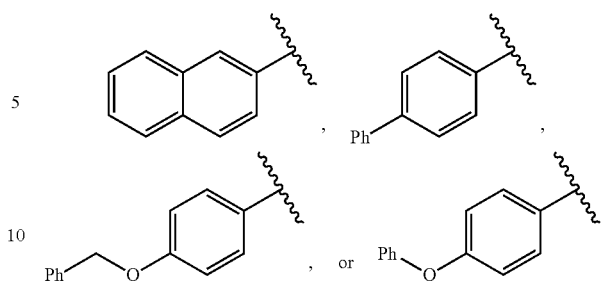

In another embodiment is a compound of Formula (III), wherein R² is

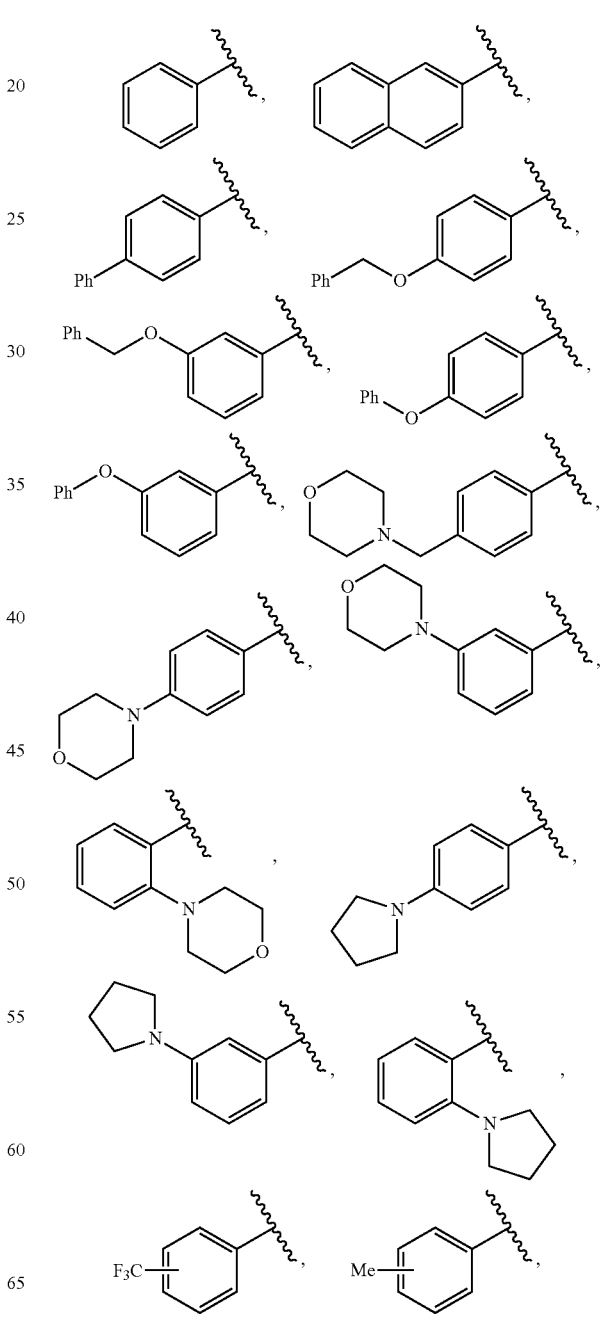

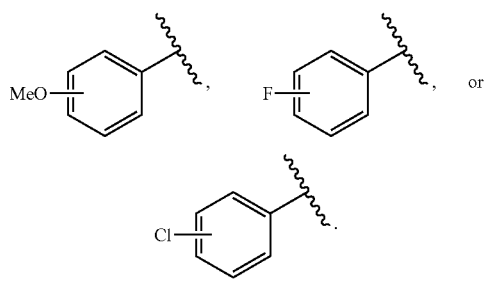

In another embodiment is a compound of Formula (III), wherein $R^2$ is

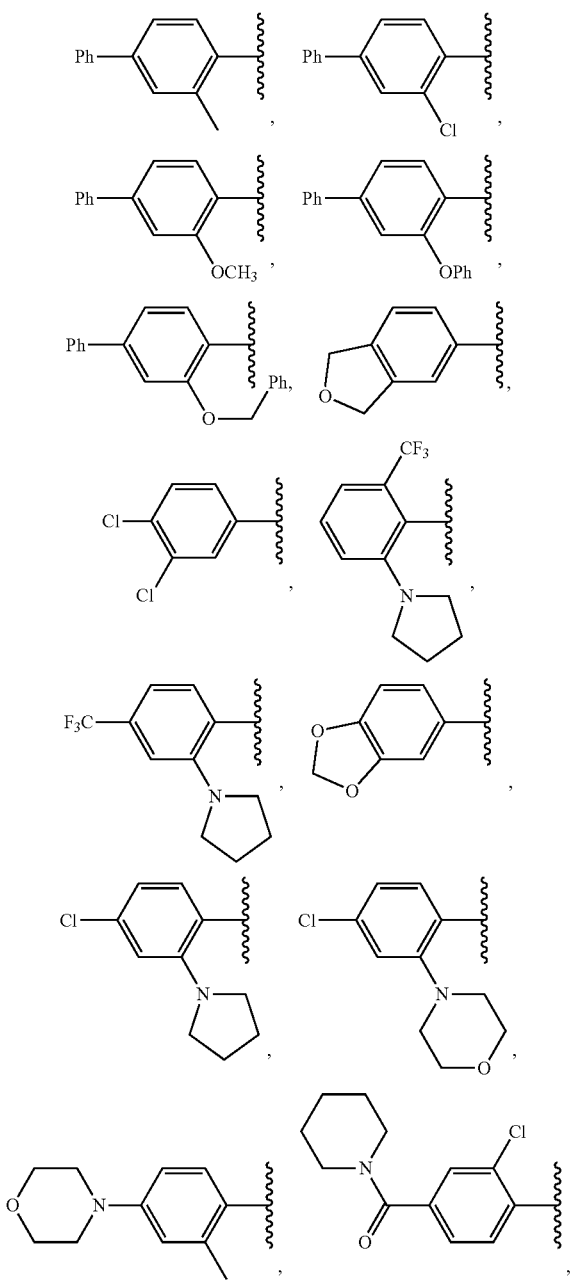

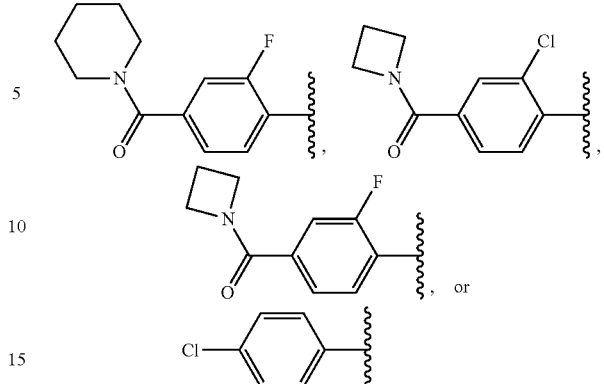

Another embodiment provides a compound of Formula (IV):

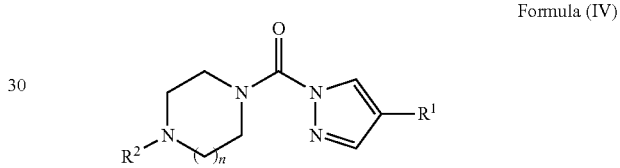

Formula (IV)

wherein:
  $R^1$ is H, $C_{1-4}$ alkyl, halo, $CF_3$, optionally substituted aryl, or cyano;
  $R^2$ is $CO_2$(t-Bu), $C_{1-4}$ alkyl, —C(O)$R^3$, —SO$_2R^3$, optionally substituted aryl, or optionally substituted heteroaryl;
  $R^3$ is $C_{1-4}$ alkyl or optionally substituted aryl; and
  n is 1 or 2;
  or a solvate, hydrate, tautomer, N-oxide, or pharmaceutically acceptable salt thereof.

In another embodiment is a compound of Formula (IV), wherein n is 1. In another embodiment is a compound of Formula (IV), wherein n is 2.

In another embodiment is a compound of Formula (IV), wherein $R^3$ is $C_{1-4}$ alkyl or optionally substituted phenyl. In another embodiment is a compound of Formula (IV), wherein $R^3$ is $C_{1-4}$ alkyl. In another embodiment is a compound of Formula (IV), wherein $R^3$ is optionally substituted phenyl.

In another embodiment is a compound of Formula (IV), wherein $R^1$ is H, $C_{1-4}$ alkyl, halo, $CF_3$, optionally substituted phenyl, or cyano. In another embodiment is a compound of Formula (IV), wherein $R^1$ is H, $C_{1-4}$ alkyl, halo, $CF_3$, or cyano. In another embodiment is a compound of Formula (IV), wherein $R^1$ is optionally substituted aryl. In another embodiment is a compound of Formula (IV), wherein $R^1$ is optionally substituted phenyl. In another embodiment is a compound of Formula (IV), wherein $R^1$ is monosubstituted phenyl. In another embodiment is a compound of Formula (IV), wherein $R^1$ is bisubstituted phenyl.

In another embodiment is a compound of Formula (IV), wherein $R^2$ is $CO_2$(t-Bu), $C_{1-4}$ alkyl, —C(O)$R^3$, —SO$_2R^3$, optionally substituted phenyl, or optionally substituted heteroaryl. In another embodiment is a compound of Formula (IV), wherein $R^2$ is $-C(O)R^3$ or $-SO_2R^3$. In another embodiment is a compound of Formula (IV), wherein $R^2$ is $C_{1-4}$ alkyl.

In another embodiment is a compound of Formula (IV), wherein $R^2$ is phenyl substituted with one or more substituents selected from the group consisting of $C_{1-4}$ alkyl, alkoxy, halo, and $NR^aR^b$; and $R^a$ and $R^b$ are independently selected from $C_{1-4}$ alkyl or $R^a$ and $R^b$ together with the nitrogen to which they are attached form an optionally substituted 4-, 5-, 6-, 7-, or 8-member heterocyclyl ring, optionally containing another heteroatom selected from N, S, or O. In another embodiment is a compound of Formula (IV), wherein $R^2$ is phenyl substituted with one or more substituents selected from the group consisting of $C_{1-4}$ alkyl, alkoxy, halo, and $NR^aR^b$; and $R^a$ and $R^b$ are independently selected from $C_{1-4}$ alkyl or $R^a$ and $R^b$ together with the nitrogen to which they are attached form a 4-, 5-, 6-, 7-, or 8-member heterocyclyl ring, optionally containing another heteroatom selected from S or O.

In another embodiment is a compound of Formula (IV), wherein $R^1$ is H, $C_{1-4}$ alkyl, halo, $CF_3$, or cyano; and $R^2$ is $-C(O)R^3$ or $-SO_2R^3$. In another embodiment is a compound of Formula (IV), wherein $R^1$ is H, $C_{1-4}$ alkyl, halo, $CF_3$, or cyano; and $R^2$ is $C_{1-4}$ alkyl. In another embodiment is a compound of Formula (IV), wherein $R^1$ is H, $C_{1-4}$ alkyl, halo, $CF_3$, or cyano; and $R^2$ is phenyl substituted with one or more substituents selected from the group consisting of $C_{1-4}$ alkyl, alkoxy, halo, and $NR^aR^b$; and $R^a$ and $R^b$ are independently selected from $C_{1-4}$ alkyl or $R^a$ and $R^b$ together with the nitrogen to which they are attached form an optionally substituted 4-, 5-, 6-, 7-, or 8-member heterocyclyl ring, optionally containing another heteroatom selected from N, S, or O.

In another embodiment is a compound of Formula (IV), wherein $R^1$ is optionally substituted phenyl; and $R^2$ is $-C(O)R^3$ or $-SO_2R^3$. In another embodiment is a compound of Formula (IV), wherein $R^1$ is optionally substituted phenyl; and $R^2$ is $C_{1-4}$ alkyl. In another embodiment is a compound of Formula (IV), wherein $R^1$ is optionally substituted phenyl; and $R^2$ is phenyl substituted with one or more substituents selected from the group consisting of $C_{1-4}$ alkyl, alkoxy, halo, and $NR^aR^b$; and $R^a$ and $R^b$ are independently selected from $C_{1-4}$ alkyl or $R^a$ and $R^b$ together with the nitrogen to which they are attached form an optionally substituted 4-, 5-, 6-, 7-, or 8-member heterocyclyl ring, optionally containing another heteroatom selected from N, S, or O.

Another embodiment provides a compound of Formula (V):

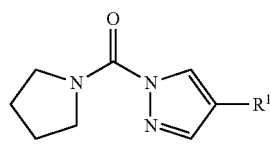

Formula (V)

wherein:
$R^1$ is halo, cyano, $CF_3$, or optionally substituted phenyl;
or a solvate, hydrate, tautomer, N-oxide, or pharmaceutically acceptable salt thereof.

In another embodiment is a compound of Formula (V), wherein $R^1$ is halo. In another embodiment is a compound of Formula (V), wherein $R^1$ is cyano. In another embodiment is a compound of Formula (V), wherein $R^1$ is $CF_3$. In another embodiment is a compound of Formula (V), wherein $R^1$ is optionally substituted phenyl. In another embodiment is a compound of Formula (V), wherein $R^1$ is monosubstituted or bisubstituted phenyl. In another embodiment is a compound of Formula (V), wherein $R^1$ is monosubstituted phenyl. In another embodiment is a compound of Formula (V), wherein $R^1$ is bisubstituted phenyl. In another embodiment is a compound of Formula (V), wherein $R^1$ is chloro,

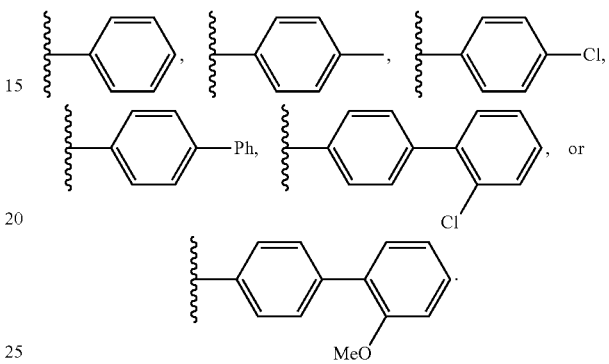

In another embodiment is a compound of Formula (V), wherein $R^1$ is chloro. In another embodiment is a compound of Formula (V), wherein $R^1$ is

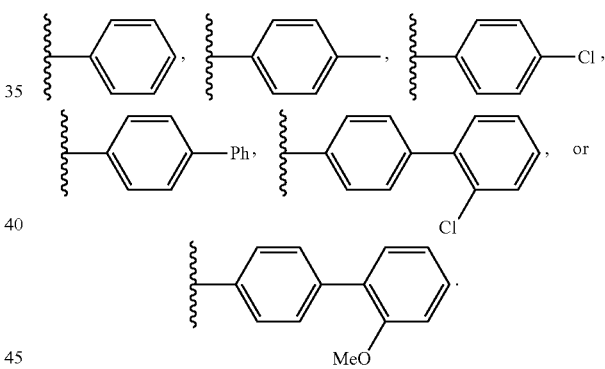

Another embodiment provides a compound of Formula (VI):

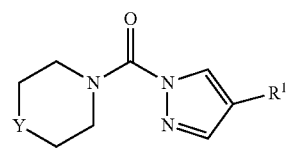

Formula (VI)

wherein:
Y is O or $CH_2$;
$R^1$ is H, $C_{1-4}$ alkyl, $CF_3$, halo, cyano, or optionally substituted phenyl;
or a solvate, hydrate, tautomer, N-oxide, or pharmaceutically acceptable salt thereof.

In another embodiment is a compound of Formula (VI), wherein Y is O. In another embodiment is a compound of Formula (VI), wherein Y is $CH_2$.

In another embodiment is a compound of Formula (VI), wherein $R^1$ is H, $C_{1-4}$ alkyl, or cyano. In another embodiment is a compound of Formula (VI), wherein $R^1$ is methyl. In another embodiment is a compound of Formula (VI), wherein $R^1$ is $CF_3$. In another embodiment is a compound of Formula (VI), wherein $R^1$ is chloro. In another embodiment is a compound of Formula (VI), wherein $R^1$ is chloro or fluoro. In another embodiment is a compound of Formula (VI), wherein $R^1$ is optionally substituted phenyl. In another embodiment is a compound of Formula (VI), wherein $R^1$ is monosubstituted phenyl. In another embodiment is a compound of Formula (VI), wherein $R^1$ is bisubstituted phenyl.

In another embodiment is a compound of Formula (VI), wherein Y is O; and $R^1$ is H, $C_{1-4}$ alkyl, or cyano. In another embodiment is a compound of Formula (VI), wherein Y is O; and $R^1$ is methyl. In another embodiment is a compound of Formula (VI), wherein Y is O; and $R^1$ is $CF_3$. In another embodiment is a compound of Formula (VI), wherein Y is O; and $R^1$ is chloro. In another embodiment is a compound of Formula (VI), wherein Y is O; and $R^1$ is chloro or fluoro. In another embodiment is a compound of Formula (VI), wherein Y is O; and $R^1$ is optionally substituted phenyl. In another embodiment is a compound of Formula (VI), wherein Y is O; and $R^1$ is monosubstituted phenyl. In another embodiment is a compound of Formula (VI), wherein Y is O; and $R^1$ is bisubstituted phenyl.

In another embodiment is a compound of Formula (VI), wherein Y is $CH_2$; and $R^1$ is H, $C_{1-4}$ alkyl, or cyano. In another embodiment is a compound of Formula (VI), wherein Y is $CH_2$; and $R^1$ is methyl. In another embodiment is a compound of Formula (VI), wherein Y is $CH_2$; and $R^1$ is $CF_3$. In another embodiment is a compound of Formula (VI), wherein Y is $CH_2$; and $R^1$ is chloro. In another embodiment is a compound of Formula (VI), wherein Y is $CH_2$; and $R^1$ is chloro or fluoro. In another embodiment is a compound of Formula (VI), wherein Y is $CH_2$; and $R^1$ is optionally substituted phenyl. In another embodiment is a compound of Formula (VI), wherein Y is $CH_2$; and $R^1$ is monosubstituted phenyl. In another embodiment is a compound of Formula (VI), wherein Y is $CH_2$; and $R^1$ is bisubstituted phenyl.

Another embodiment provides a compound of Formula (VII):

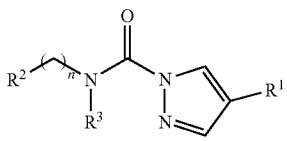

Formula (VII)

wherein:
$R^1$ is H, $C_{1-4}$ alkyl, cyano, $CF_3$, halo, $-CO_2R^4$, or optionally substituted phenyl;
$R^2$ is $-N(Boc)CH_3$, $-NR^5C(O)R^6$, $-NR^5SO_2R^6$, $-NR^5R^6$, optionally substituted phenyl or optionally substituted naphthyl;
$R^3$ is H or $C_{1-4}$ alkyl;
$R^4$ is H or $C_{1-4}$ alkyl;
$R^5$ is $C_{1-4}$ alkyl;
$R^6$ is $C_{1-4}$ alkyl, optionally substituted aryl, or optionally substituted aralkyl; and
n is 0-6;
or a solvate, hydrate, tautomer, N-oxide, or pharmaceutically acceptable salt thereof.

In another embodiment is a compound of Formula (VII), wherein $R^1$ is H, $C_{1-4}$ alkyl, cyano, $CF_3$, halo, or $-CO_2R^4$. In another embodiment is a compound of Formula (VII), wherein $R^1$ is H, $C_{1-4}$ alkyl, cyano, $CF_3$, or halo. In another embodiment is a compound of Formula (VII), wherein $R^1$ is chloro, iodo, bromo, $CF_3$, methyl, $-CO_2Me$, or phenyl.

In another embodiment is a compound of Formula (VII), wherein $R^1$ is H. In another embodiment is a compound of Formula (VII), wherein $R^1$ is cyano.

In another embodiment is a compound of Formula (VII), wherein $R^1$ is halo. In another embodiment is a compound of Formula (VII), wherein $R^1$ is iodo or bromo. In another embodiment is a compound of Formula (VII), wherein $R^1$ is iodo. In another embodiment is a compound of Formula (VII), wherein $R^1$ is bromo. In another embodiment is a compound of Formula (VII), wherein $R^1$ is fluoro or chloro. In another embodiment is a compound of Formula (VII), wherein $R^1$ is fluoro. In another embodiment is a compound of Formula (VII), wherein $R^1$ is chloro.

In another embodiment is a compound of Formula (VII), wherein $R^1$ is $-CO_2R^4$. In another embodiment is a compound of Formula (VII), wherein $R^4$ is H. In another embodiment is a compound of Formula (VII), wherein $R^4$ is $C_{1-4}$ alkyl. In another embodiment is a compound of Formula (VII), wherein $R^1$ is $-CO_2Me$.

In another embodiment is a compound of Formula (VII), wherein $R^1$ is $C_{1-4}$ alkyl. In another embodiment is a compound of Formula (VII), wherein $R^1$ is methyl.

In another embodiment is a compound of Formula (VII), wherein $R^1$ is optionally substituted phenyl. In another embodiment is a compound of Formula (VII), wherein $R^1$ is phenyl. In another embodiment is a compound of Formula (VII), wherein $R^1$ is monosubstituted phenyl. In another embodiment is a compound of Formula (VII), wherein $R^1$ is bisubstituted phenyl.

In another embodiment is a compound of Formula (VII), wherein $R^2$ is optionally substituted phenyl. In another embodiment is a compound of Formula (VII), wherein $R^2$ is phenyl. In another embodiment is a compound of Formula (VII), wherein $R^2$ is phenyl substituted with one or more substituents selected from the group consisting of $C_{1-4}$ alkyl, $CF_3$, halo, (cycloalkyl)alkyl, (heterocyclyl)alkyl, alkoxy, optionally substituted aryloxy, optionally substituted aralkyloxy, optionally substituted aryl, optionally substituted heteroaryl, and $NR^aR^b$; and $R^a$ and $R^b$ are independently selected from $C_{1-4}$ alkyl or $R^a$ and $R^b$ together with the nitrogen to which they are attached form an optionally substituted 4-, 5-, 6-, 7-, or 8-member heterocyclyl ring, optionally containing another heteroatom selected from N, S or O. In another embodiment is a compound of Formula (VII), wherein $R^2$ is phenyl substituted with one or more substituents selected from the group consisting of $C_{1-4}$ alkyl, halo, alkoxy, optionally substituted aryloxy, optionally substituted aralkyloxy, optionally substituted heteroaryl, and $NR^aR^b$; and $R^a$ and $R^b$ are independently selected from $C_{1-4}$ alkyl or $R^a$ and $R^b$ together with the nitrogen to which they are attached form an optionally substituted 4-, 5-, 6-, 7-, or 8-member heterocyclyl ring, optionally containing another heteroatom selected from N, S or O.

In another embodiment is a compound of Formula (VII), wherein $R^2$ is optionally substituted naphthyl. In another embodiment is a compound of Formula (VII), wherein $R^2$ is naphthyl.

In another embodiment is a compound of Formula (VII), wherein $R^2$ is $-N(Boc)CH_3$.

In another embodiment is a compound of Formula (VII), wherein $R^2$ is $-NR^5C(O)R^6$, $-NR^5SO_2R^6$, or $-NR^5R^6$. In another embodiment is a compound of Formula (VII), wherein $R^2$ is —$NR^5C(O)R^6$. In another embodiment is a compound of Formula (VII), wherein $R^2$ is —$NR^5SO_2R^6$. In another embodiment is a compound of Formula (VII), wherein $R^2$ is —$NR^5R^6$.

In another embodiment is a compound of Formula (VII), wherein $R^3$ is H. In another embodiment is a compound of Formula (VII), wherein $R^3$ is $C_{1-4}$ alkyl. In another embodiment is a compound of Formula (VII), wherein $R^3$ is ethyl or methyl. In another embodiment is a compound of Formula (VII), wherein $R^3$ is methyl. In another embodiment is a compound of Formula (VII), wherein $R^3$ is ethyl.

In another embodiment is a compound of Formula (VII), wherein $R^2$ is —N(Boc)CH$_3$ and $R^3$ is methyl.

In another embodiment is a compound of Formula (VII), wherein $R^6$ is $C_{1-4}$ alkyl, optionally substituted phenyl, or optionally substituted benzyl. In another embodiment is a compound of Formula (VII), wherein $R^6$ is $C_{1-4}$ alkyl. In another embodiment is a compound of Formula (VII), wherein $R^6$ is optionally substituted phenyl or optionally substituted benzyl. In another embodiment is a compound of Formula (VII), wherein $R^6$ is optionally substituted phenyl. In another embodiment is a compound of Formula (VII), wherein $R^6$ is optionally substituted benzyl.

In another embodiment is a compound of Formula (VII), wherein n is 2. In another embodiment is a compound of Formula (VII), wherein n is 2; and $R^2$ is —$NR^5C(O)R^6$, —$NR^5SO_2R^6$, or —$NR^5R^6$. In another embodiment is a compound of Formula (VII), wherein n is 2; $R^1$ is H, $C_{1-4}$ alkyl, cyano, $CF_3$, or halo; and $R^2$ is —$NR^5C(O)R^6$, —$NR^5SO_2R^6$, or —$NR^5R^6$. In another embodiment is a compound of Formula (VII), wherein n is 2; $R^1$ is optionally substituted phenyl; and $R^2$ is —$NR^5C(O)R^6$, —$NR^5SO_2R^6$, or —$NR^5R^6$.

In another embodiment is a compound of Formula (VII), wherein n is 1. In another embodiment is a compound of Formula (VII), wherein n is 1; and $R^2$ is monosubstituted phenyl. In another embodiment is a compound of Formula (VII), wherein n is 1; and $R^2$ is bisubstituted phenyl. In another embodiment is a compound of Formula (VII), wherein n is 1; and $R^2$ is phenyl substituted with one or more substituents selected from the group consisting of $C_{1-4}$ alkyl, $CF_3$, halo, (cycloalkyl)alkyl, (heterocyclyl)alkyl, alkoxy, optionally substituted aryloxy, optionally substituted aralkyloxy, optionally substituted aryl, optionally substituted heteroaryl, and $NR^aR^b$; and $R^a$ and $R^b$ are independently selected from $C_{1-4}$ alkyl or $R^a$ and $R^b$ together with the nitrogen to which they are attached form an optionally substituted 4-, 5-, 6-, 7-, or 8-member heterocyclyl ring, optionally containing another heteroatom selected from N, S or O. In another embodiment is a compound of Formula (VII), wherein n is 1; and $R^2$ is phenyl substituted with one or more substituents selected from the group consisting of $C_{1-4}$ alkyl, halo, alkoxy, optionally substituted aryloxy, optionally substituted aralkyloxy, optionally substituted heteroaryl, and $NR^aR^b$; and $R^a$ and $R^b$ are independently selected from $C_{1-4}$ alkyl or $R^a$ and $R^b$ together with the nitrogen to which they are attached form an optionally substituted 4-, 5-, 6-, 7-, or 8-member heterocyclyl ring, optionally containing another heteroatom selected from N, S or O. In another embodiment is a compound of Formula (VII), wherein n is 1; $R^1$ is H, $C_{1-4}$ alkyl, cyano, $CF_3$, or halo; and $R^2$ is phenyl substituted with one or more substituents selected from the group consisting of $C_{1-4}$ alkyl, halo, alkoxy, optionally substituted aryloxy, optionally substituted aralkyloxy, optionally substituted heteroaryl, and $NR^aR^b$; and $R^a$ and $R^b$ are independently selected from $C_{1-4}$ alkyl or $R^a$ and $R^b$ together with the nitrogen to which they are attached form an optionally substituted 4-, 5-, 6-, 7-, or 8-member heterocyclyl ring, optionally containing another heteroatom selected from N, S or O. In another embodiment is a compound of Formula (VII), wherein n is 1; $R^1$ is optionally substituted phenyl; and $R^2$ is phenyl substituted with one or more substituents selected from the group consisting of $C_{1-4}$ alkyl, halo, alkoxy, optionally substituted aryloxy, optionally substituted aralkyloxy, optionally substituted heteroaryl, and $NR^aR^b$; and $R^a$ and $R^b$ are independently selected from $C_{1-4}$ alkyl or $R^a$ and $R^b$ together with the nitrogen to which they are attached form an optionally substituted 4-, 5-, 6-, 7-, or 8-member heterocyclyl ring, optionally containing another heteroatom selected from N, S or O.

In another embodiment is a compound of Formula (VII), wherein n is 1; $R^1$ is H, $C_{1-4}$ alkyl, cyano, $CF_3$, or halo; and $R^2$ is monosubstituted phenyl. In another embodiment is a compound of Formula (VII), wherein n is 1; $R^1$ is optionally substituted phenyl; and $R^2$ is monosubstituted phenyl. In another embodiment is a compound of Formula (VII), wherein n is 1; $R^1$ is H, $C_{1-4}$ alkyl, cyano, $CF_3$, or halo; and $R^2$ is bisubstituted phenyl. In another embodiment is a compound of Formula (VII), wherein n is 1; $R^1$ is optionally substituted phenyl; and $R^2$ is bisubstituted phenyl.

Another embodiment provides a compound of Formula (VIII):

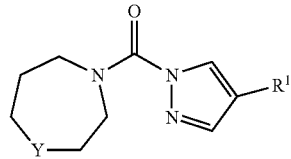

Formula (VIII)

wherein:
Y is $CH_2$ or $NR^2$;
$R^1$ is H, $C_{1-4}$ alkyl, cyano, $CF_3$, or halo;
$R^2$ is —$C(O)R^3$, —$SO_2R^3$, optionally substituted aralkyl, or $C_{1-4}$ alkyl; and
$R^3$ is $C_{1-4}$ alkyl or optionally substituted aryl;
or a solvate, hydrate, tautomer, N-oxide, or pharmaceutically acceptable salt thereof.

In another embodiment is a compound of Formula (VIII), wherein Y is $CH_2$. In another embodiment is a compound of Formula (VIII), wherein Y is $NR^2$.

In another embodiment is a compound of Formula (VIII), wherein $R^2$ is —$C(O)R^3$, —$SO_2R^3$, optionally substituted benzyl, or $C_{1-4}$ alkyl. In another embodiment is a compound of Formula (VIII), wherein $R^2$ is —$C(O)R^3$ or —$SO_2R^3$. In another embodiment is a compound of Formula (VIII), wherein $R^2$ is —$C(O)R^3$. In another embodiment is a compound of Formula (VIII), wherein $R^2$ is —$SO_2R^3$. In another embodiment is a compound of Formula (VIII), wherein $R^2$ is optionally substituted aralkyl. In another embodiment is a compound of Formula (VIII), wherein $R^2$ is optionally substituted benzyl. In another embodiment is a compound of Formula (VIII), wherein $R^2$ is $C_{1-4}$ alkyl. In another embodiment is a compound of Formula (VIII), wherein $R^2$ is

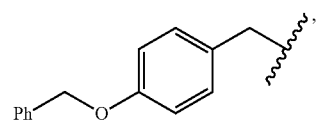

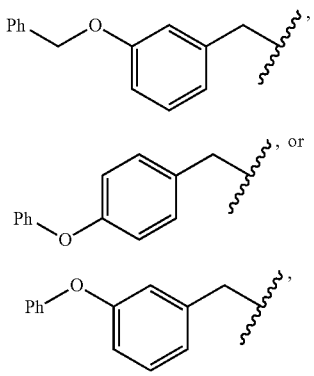

In another embodiment is a compound of Formula (VIII), wherein $R^3$ is $C_{1-4}$ alkyl or optionally substituted phenyl. In another embodiment is a compound of Formula (VIII), wherein $R^3$ is $C_{1-4}$ alkyl. In another embodiment is a compound of Formula (VIII), wherein $R^3$ is optionally substituted phenyl.

In another embodiment is a compound of Formula (VIII), wherein Y is $NR^2$; and $R^2$ is —C(O)$R^3$, —SO$_2$$R^3$, optionally substituted benzyl, or $C_{1-4}$ alkyl. In another embodiment is a compound of Formula (VIII), wherein Y is $NR^2$; and $R^2$ is —C(O)$R^3$ or —SO$_2$$R^3$. In another embodiment is a compound of Formula (VIII), wherein Y is $NR^2$; and $R^2$ is —C(O)$R^3$. In another embodiment is a compound of Formula (VIII), wherein Y is $NR^2$; and $R^2$ is —SO$_2$$R^3$. In another embodiment is a compound of Formula (VIII), wherein Y is $NR^2$; and $R^2$ is optionally substituted aralkyl. In another embodiment is a compound of Formula (VIII), wherein Y is $NR^2$; and $R^2$ is optionally substituted benzyl. In another embodiment is a compound of Formula (VIII), wherein Y is $NR^2$; and $R^2$ is $C_{1-4}$ alkyl. In another embodiment is a compound of Formula (VIII), wherein Y is $NR^2$; and $R^2$ is

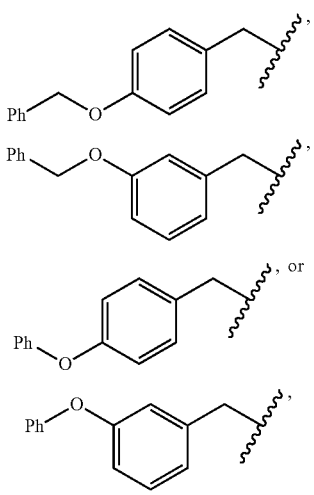

Another embodiment provides a compound of Formula (Ia):

Formula (Ia)

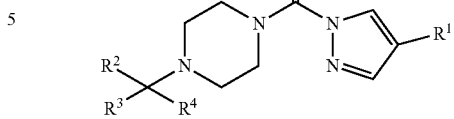

wherein:
$R^1$ is H, —CF$_3$, $C_{1-4}$ alkyl, cyano, halo, optionally substituted phenyl, —CO$_2$$R^5$, —C(O)NR$^6$R$^7$;
$R^2$ is optionally substituted aryl or optionally substituted heteroaryl;
$R^3$ is H;
$R^4$ is H or optionally substituted phenyl;
$R^5$ is H or $C_{1-4}$ alkyl; and
$R^6$ and $R^7$ are each independently H, $C_{1-4}$ alkyl, or $C_{3-8}$ cycloalkyl; or $R^6$ and $R^7$ together with the nitrogen to which they are attached form a 4-, 5-, 6-, 7-, or 8-member heterocyclyl ring, optionally containing another heteroatom selected from S or O;
or a solvate, hydrate, tautomer, N-oxide, or pharmaceutically acceptable salt thereof.

In another embodiment is a compound of Formula (Ia), wherein $R^1$ is optionally substituted phenyl. In another embodiment is a compound of Formula (Ia), wherein $R^1$ is

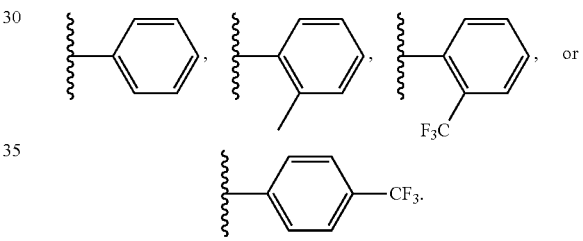

In another embodiment is a compound of Formula (Ia), wherein $R^1$ is —C(O)NR$^6$R$^7$; and $R^6$ and $R^7$ are each independently H, $C_{1-4}$ alkyl, or $C_{3-8}$ cycloalkyl. In another embodiment is a compound of Formula (Ia), wherein $R^1$ is —C(O)NR$^6$R$^7$; and $R^6$ and $R^7$ are each independently H or $C_{1-4}$ alkyl. In another embodiment is a compound of Formula (Ia), wherein $R^1$ is —C(O)NR$^6$R$^7$; and $R^6$ and $R^7$ are each independently H or $C_{3-8}$ cycloalkyl.

In another embodiment is a compound of Formula (Ia), wherein $R^1$ is —C(O)NR$^6$R$^7$; and $R^6$ and $R^7$ together with the nitrogen to which they are attached form a 4-, 5-, 6-, 7-, or 8-member heterocyclyl ring, optionally containing another heteroatom selected from S or O. In another embodiment is a compound of Formula (Ia), wherein $R^1$ s

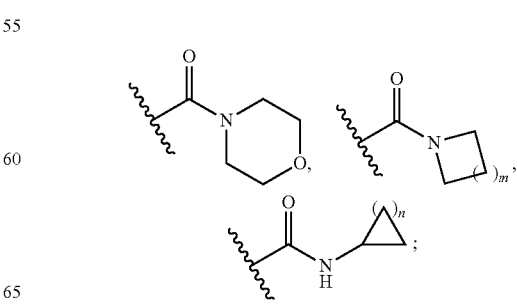

m is 1, 2 or 3; and n is 1, 2, 3, 4, or 5. In another embodiment is a compound of Formula (Ia), wherein $R^1$ is

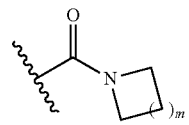

and m is 1, 2 or 3. In another embodiment is a compound of Formula (Ia), wherein $R^1$ is

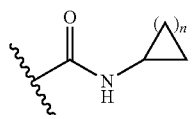

and n is 1, 2, 3, 4, or 5. In another embodiment is a compound of Formula (Ia), wherein $R^1$ is

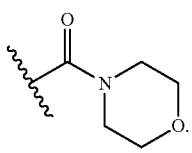

In another embodiment is a compound of Formula (Ia), wherein $R^1$ is halo. In another embodiment is a compound of Formula (Ia), wherein $R^1$ is fluoro or chloro. In another embodiment is a compound of Formula (Ia), wherein $R^1$ is iodo or bromo.

In another embodiment is a compound of Formula (Ia), wherein $R^1$ is $C_{1-4}$ alkyl. In another embodiment is a compound of Formula (Ia), wherein $R^1$ is isopropyl.

In another embodiment is a compound of Formula (Ia), wherein $R^1$ is —$CF_3$.

In another embodiment is a compound of Formula (Ia), wherein $R^1$ is —$CO_2R^5$. In another embodiment is a compound of Formula (Ia), wherein $R^5$ is H. In another embodiment is a compound of Formula (Ia), wherein $R^5$ is $C_{1-4}$ alkyl. In another embodiment is a compound of Formula (Ia), wherein $R^1$ is —$CO_2Me$.

In another embodiment is a compound of Formula (Ia), wherein $R^2$ is optionally substituted aryl. In another embodiment is a compound of Formula (Ia), wherein $R^2$ is optionally substituted phenyl. In another embodiment is a compound of Formula (Ia), wherein $R^2$ is

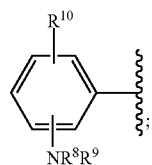

$R^8$ and $R^9$ together with the nitrogen to which they are attached form a 4-, 5-, 6-, 7-, or 8-member optionally substituted heterocyclyl ring, optionally containing another heteroatom selected from S or O; and $R^{10}$ is H, —$CF_3$, or halo. In another embodiment is a compound of Formula (Ia), wherein $R^{10}$ is —$CF_3$. In another embodiment is a compound of Formula (Ia), wherein $R^{10}$ is halo. In another embodiment is a compound of Formula (Ia), wherein $R^{10}$ is chloro. In another embodiment is a compound of Formula (Ia), wherein $R^8$ and $R^9$ together with the nitrogen to which they are attached form an optionally substituted pyrrolidine. In another embodiment is a compound of Formula (Ia), wherein $R^8$ and $R^9$ together with the nitrogen to which they are attached form an optionally substituted piperidine. In another embodiment is a compound of Formula (Ia), wherein $R^8$ and $R^9$ together with the nitrogen to which they are attached form an optionally substituted morpholine.

In another embodiment is a compound of Formula (Ia), wherein $R^2$ is a bisubstituted phenyl. In another embodiment is a compound of Formula (Ia), wherein $R^2$ is a monosubstituted phenyl. In another embodiment is a compound of Formula (Ia), wherein $R^2$ is

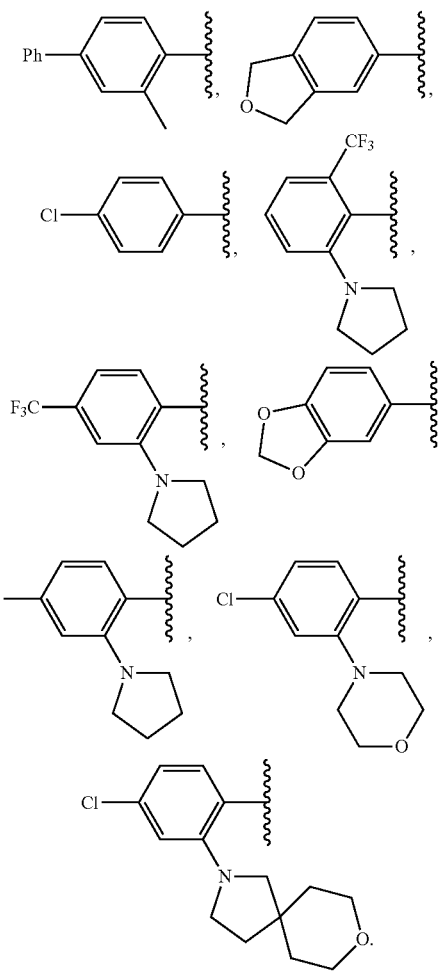

In another embodiment is a compound of Formula (Ia), wherein $R^2$ is:

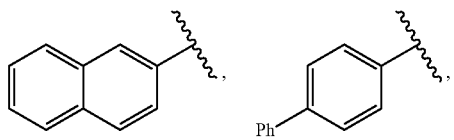

-continued

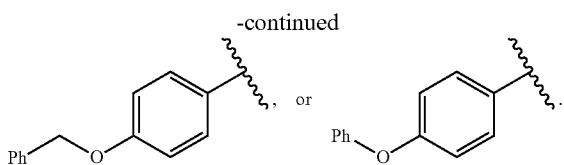

In another embodiment is a compound of Formula (Ia), wherein R² is optionally substituted naphthyl.

In another embodiment is a compound of Formula (Ia), wherein R² is optionally substituted heteroaryl. In another embodiment is a compound of Formula (Ia), wherein R² is optionally substituted pyrazolyl, optionally substituted pyrimidinyl, optionally substituted thiazolyl, or optionally substituted pyridinyl. In another embodiment is a compound of Formula (Ia), wherein R² is

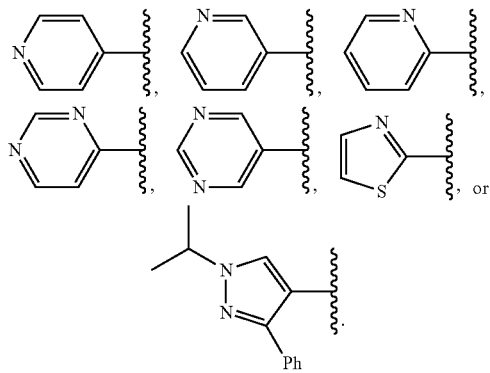

In another embodiment is a compound of Formula (Ia), wherein R⁴ is H. In another embodiment is a compound of Formula (Ia), wherein R⁴ is optionally substituted phenyl. In another embodiment is a compound of Formula (Ia), wherein R⁴ is

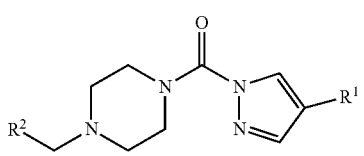

Another embodiment provides a compound of Formula (IIIa):

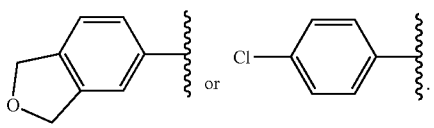 [SMILES: *c1ccc2c(c1)COC2 ; *c1ccc(Cl)cc1]

Formula (IIIa)

wherein:
R¹ is H, $C_{1-4}$ alkyl, cyano, halo, or —CO₂R³;
R² is optionally substituted aryl; and
R³ is H or $C_{1-4}$ alkyl;
or a solvate, hydrate, tautomer, N-oxide, or pharmaceutically acceptable salt thereof.

In another embodiment is a compound of Formula (IIIa), wherein R¹ is H.

In another embodiment is a compound of Formula (IIIa), wherein R¹ is —CO₂R³. In another embodiment is a compound of Formula (IIIa), wherein R³ is H. In another embodiment is a compound of Formula (IIIa), wherein R³ is $C_{1-4}$ alkyl. In another embodiment is a compound of Formula (IIIa), wherein R¹ is —CO₂Me.

In another embodiment is a compound of Formula (IIIa), wherein R¹ is halo. In another embodiment is a compound of Formula (IIIa), wherein R¹ is iodo or bromo. In another embodiment is a compound of Formula (IIIa), wherein R¹ is iodo. In another embodiment is a compound of Formula (IIIa), wherein R¹ is bromo.

In another embodiment is a compound of Formula (IIIa), wherein R¹ is cyano. In another embodiment is a compound of Formula (IIIa), wherein R² is optionally substituted phenyl or optionally substituted naphthyl. In another embodiment is a compound of Formula (IIIa), wherein R² is

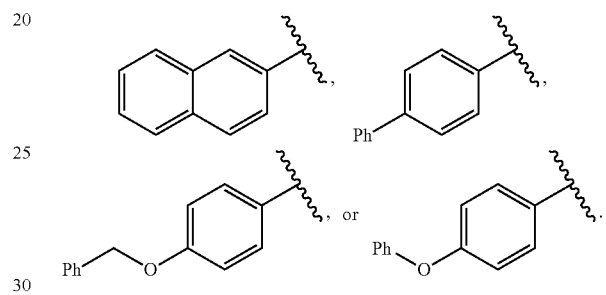

Another embodiment provides a compound of Formula (IVa):

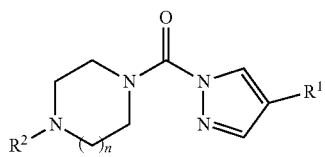

Formula (IVa)

wherein:
R¹ is H, $C_{1-4}$ alkyl, or cyano;
R² is CO₂(t-Bu); and
n is 1 or 2;
or a solvate, hydrate, tautomer, N-oxide, or pharmaceutically acceptable salt thereof.

In another embodiment is a compound of Formula (IVa), wherein n is 1. In another embodiment is a compound of Formula (IVa), wherein n is 2.

Another embodiment provides a compound of Formula (Va):

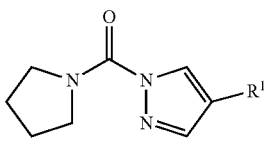

Formula (Va)

wherein:
R¹ is halo or optionally substituted phenyl;
or a solvate, hydrate, tautomer, N-oxide, or pharmaceutically acceptable salt thereof.

In another embodiment is a compound of Formula (Va), wherein $R^1$ is halo. In another embodiment is a compound of Formula (Va), wherein $R^1$ is optionally substituted phenyl. In another embodiment is a compound of Formula (Va), wherein $R^1$ is chloro,

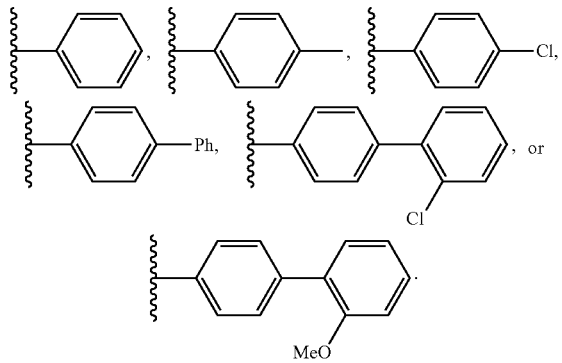

In another embodiment is a compound of Formula (Va), wherein $R^1$ is chloro. In another embodiment is a compound of Formula (Va), wherein $R^1$ is

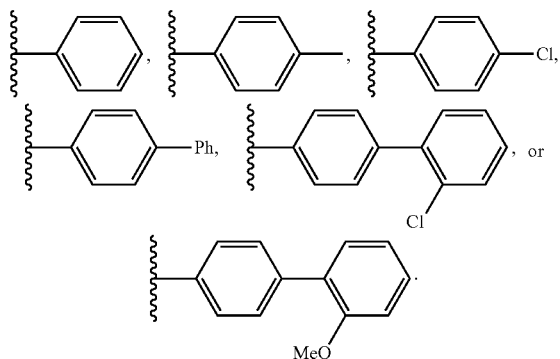

Another embodiment provides a compound of Formula (VIa):

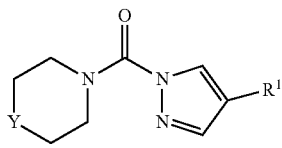

Formula (VIa)

wherein:
Y is O or $CH_2$;
$R^1$ is H, $C_{1-4}$ alkyl, halo, or cyano;
or a solvate, hydrate, tautomer, N-oxide, or pharmaceutically acceptable salt thereof.

In another embodiment is a compound of Formula (VIa), wherein Y is O. In another embodiment is a compound of Formula (VIa), wherein Y is $CH_2$.

In another embodiment is a compound of Formula (VIa), wherein $R^1$ is H, $C_{1-4}$ alkyl, or cyano. In another embodiment is a compound of Formula (VIa), wherein $R^1$ is methyl. In another embodiment is a compound of Formula (VIa), wherein $R^1$ is chloro.

Another embodiment provides a compound of Formula (VIIa):

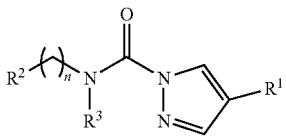

Formula (VIIa)

wherein:
$R^1$ is H, $C_{1-4}$ alkyl, cyano, halo, or $-CO_2R^4$;
$R^2$ is $-N(Boc)CH_3$, optionally substituted phenyl or optionally substituted naphthyl;
$R^3$ is H or $C_{1-4}$ alkyl;
$R^4$ is H or $C_{1-4}$ alkyl; and
n is 0-6;
or a solvate, hydrate, tautomer, N-oxide, or pharmaceutically acceptable salt thereof.

In another embodiment is a compound of Formula (VIIa), wherein $R^1$ is H. In another embodiment is a compound of Formula (VIIa), wherein $R^1$ is cyano.

In another embodiment is a compound of Formula (VIIa), wherein $R^1$ is halo. In another embodiment is a compound of Formula (VIIa), wherein $R^1$ is iodo or bromo. In another embodiment is a compound of Formula (VIIa), wherein $R^1$ is iodo. In another embodiment is a compound of Formula (VIIa), wherein $R^1$ is bromo.

In another embodiment is a compound of Formula (VIIa), wherein $R^1$ is $-CO_2R^4$. In another embodiment is a compound of Formula (VIIa), wherein $R^4$ is H. In another embodiment is a compound of Formula (VIIa), wherein $R^4$ is $C_{1-4}$ alkyl. In another embodiment is a compound of Formula (VIIa), wherein $R^1$ is $-CO_2Me$.

In another embodiment is a compound of Formula (VIIa), wherein $R^1$ is $C_{1-4}$ alkyl. In another embodiment is a compound of Formula (VIIa), wherein $R^1$ is methyl.

In another embodiment is a compound of Formula (VIIa), wherein $R^2$ is optionally substituted phenyl. In another embodiment is a compound of Formula (VIIa), wherein $R^2$ is phenyl. In another embodiment is a compound of Formula (VIIa), wherein $R^2$ is optionally substituted naphthyl. In another embodiment is a compound of Formula (VIIa), wherein $R^2$ is naphthyl.

In another embodiment is a compound of Formula (VIIa), wherein $R^2$ is $-N(Boc)CH_3$.

In another embodiment is a compound of Formula (VIIa), wherein $R^3$ is H. In another embodiment is a compound of Formula (VIIa), wherein $R^3$ is $C_{1-4}$ alkyl. In another embodiment is a compound of Formula (VIIa), wherein $R^3$ is methyl.

In another embodiment is a compound of Formula (VIIa), wherein $R^2$ is $-N(Boc)CH_3$ and $R^3$ is methyl.

Further embodiments provided herein include combinations of one or more of the particular embodiments set forth above.

In some embodiments, the compound disclosed herein has the structure provided in Table 1.

TABLE 1

| Chemical Synthesis Example | Structure | Name |
|---|---|---|
| 1 | 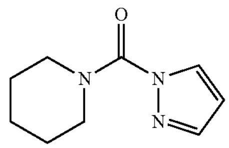 [SMILES: O=C(N1CCCCC1)n1cccn1] | Piperidin-1-yl(1H-pyrazol-1-yl)methanone |
| 2 | 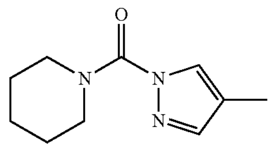 | (4-Methyl-1H-pyrazol-1-yl)(piperidin-1-yl)methanone |
| 3 | 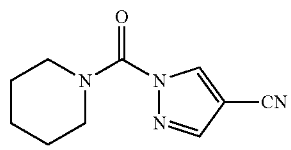 [SMILES: N#Cc1cnn(C(=O)N2CCCCC2)c1] | 1-(Piperidine-1-carbonyl)-1H-pyrazole-4-carbonitrile |
| 4 | 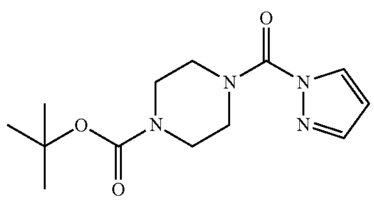 [SMILES: CC(C)(C)OC(=O)N1CCN(C(=O)n2cccn2)CC1] | tert-Butyl 4-(1H-pyrazole-1-carbonyl)piperazine-1-carboxylate |
| 5 | 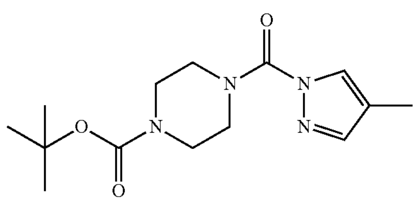 [SMILES: Cc1cnn(C(=O)N2CCN(C(=O)OC(C)(C)C)CC2)c1] | tert-Butyl 4-(4-methyl-1H-pyrazole-1-carbonyl)piperazine-1-carboxylate |
| 6 | 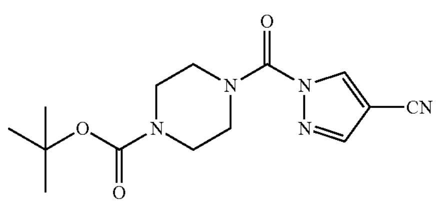 [SMILES: CC(C)(C)OC(=O)N1CCN(C(=O)n2cc(C#N)cn2)CC1] | tert-Butyl 4-(4-cyano-1H-pyrazole-1-carbonyl)piperazine-1-carboxylate |
| 7 | 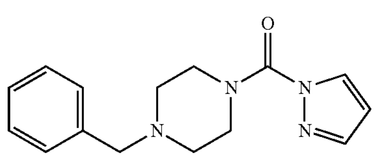 [SMILES: O=C(N1CCN(Cc2ccccc2)CC1)n1cccn1] | (4-Benzylpiperazin-1-yl)(1H-pyrazol-1-yl)methanone |
| 8 | 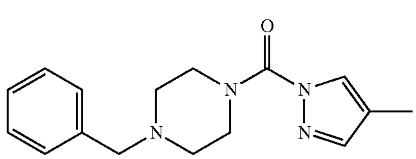 [SMILES: Cc1cnn(C(=O)N2CCN(Cc3ccccc3)CC2)c1] | (4-Benzylpiperazin-1-yl)(4-methyl-1H-pyrazol-1-yl)methanone |
| 9 | 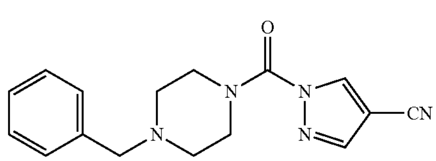 [SMILES: N#Cc1cnn(C(=O)N2CCN(Cc3ccccc3)CC2)c1] | 1-(4-Benzylpiperazine-1-carbonyl)-1H-pyrazol-4-carbonitrile |

TABLE 1-continued

| Chemical Synthesis Example | Structure | Name |
|---|---|---|
| 10 | 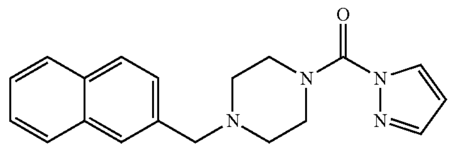 [SMILES: O=C(N1CCN(Cc2ccc3ccccc3c2)CC1)n1cccn1] | (4-(Naphthalen-2-ylmethyl)piperazin-1-yl)(1H-pyrazol-1-yl)methanone |
| 11 | 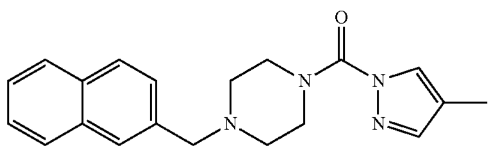 [SMILES: Cc1cnn(C(=O)N2CCN(Cc3ccc4ccccc4c3)CC2)c1] | (4-Methyl-1H-pyrazol-1-yl)(4-(naphthalen-2-ylmethyl)piperazin-1-yl)methanone |
| 12 | 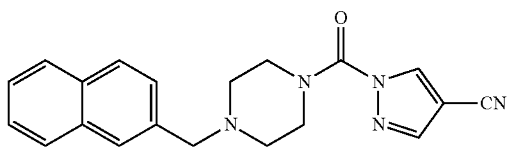 [SMILES: N#Cc1cnn(C(=O)N2CCN(Cc3ccc4ccccc4c3)CC2)c1] | 1-(4-(Naphthalen-2-ylmethyl)piperazine-1-carbonyl)-1H-pyrazole-4-carbonitrile |
| 13 | 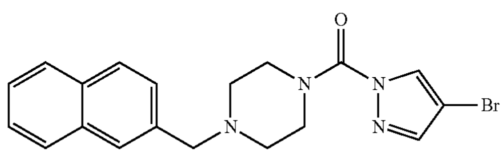 [SMILES: O=C(N1CCN(Cc2ccc3ccccc3c2)CC1)n1cc(Br)cn1] | (4-Bromo-1H-pyrazol-1-yl)(4-(naphthalen-2-ylmethyl)piperazin-1-yl)methanone |
| 14 | 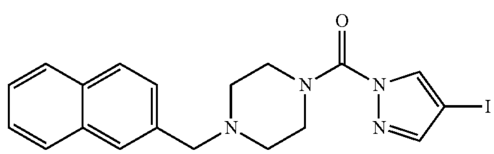 [SMILES: O=C(N1CCN(Cc2ccc3ccccc3c2)CC1)n1cc(I)cn1] | (4-Iodo-1H-pyrazol-1-yl)(4-(naphthalen-2-ylmethyl)piperazin-1-yl)methanone |
| 15 | 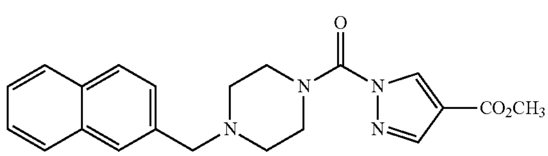 [SMILES: COC(=O)c1cnn(C(=O)N2CCN(Cc3ccc4ccccc4c3)CC2)c1] | Methyl 1-(4-(naphthalen-2-ylmethyl)piperazine-1-carbonyl)-1H-pyrazole-4-carboxylate |
| 16 | 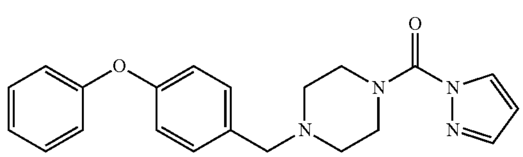 [SMILES: O=C(N1CCN(Cc2ccc(Oc3ccccc3)cc2)CC1)n1cccn1] | (4-(4-Phenoxybenzyl)piperazin-1-yl)(1H-pyrazol-1-yl)methanone |
| 17 | 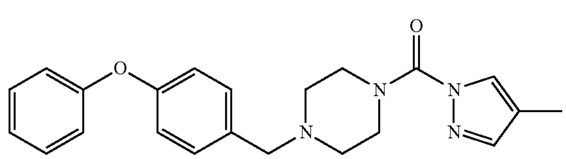 [SMILES: Cc1cnn(C(=O)N2CCN(Cc3ccc(Oc4ccccc4)cc3)CC2)c1] | (4-Methyl-1H-pyrazol-1-yl)(4-(4-phenoxybenzyl)piperazin-1-yl)methanone |
| 18 | 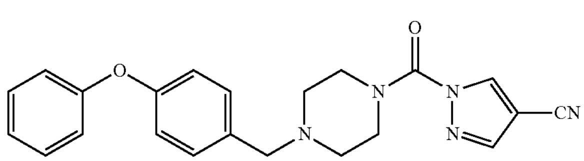 [SMILES: N#Cc1cnn(C(=O)N2CCN(Cc3ccc(Oc4ccccc4)cc3)CC2)c1] | 1-(4-(4-Phenoxybenzyl)piperazine-1-carbonyl)-1H-pyrazole-4-carbonitrile |

TABLE 1-continued

| Chemical Synthesis Example | Structure | Name |
|---|---|---|
| 19 | 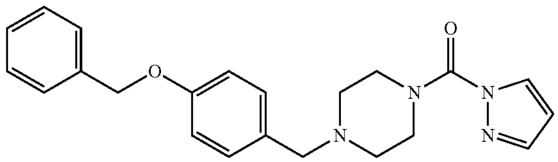 [SMILES: O=C(N1CCN(Cc2ccc(OCc3ccccc3)cc2)CC1)n1cccn1] | (4-(4-(Benzyloxy)benzyl)piperazin-1-yl)(1H-pyrazol-1-yl)methanone |
| 20 | 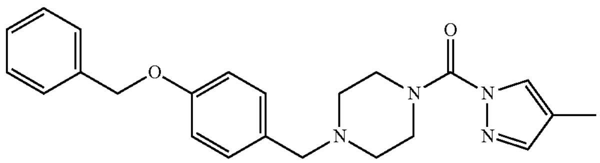 [SMILES: Cc1cnn(C(=O)N2CCN(Cc3ccc(OCc4ccccc4)cc3)CC2)c1] | (4-(4-(Benzyloxy)benzyl)piperazin-1-yl)(4-methyl-1H-pyrazol-1-yl)methanone |
| 21 | 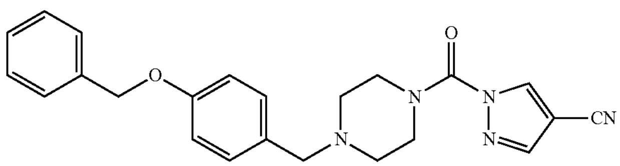 [SMILES: N#Cc1cnn(C(=O)N2CCN(Cc3ccc(OCc4ccccc4)cc3)CC2)c1] | 1-(4-(4-(Benzyloxy)benzyl)piperazine-1-carbonyl)-1H-pyrazole-4-carbonitrile |
| 22 | 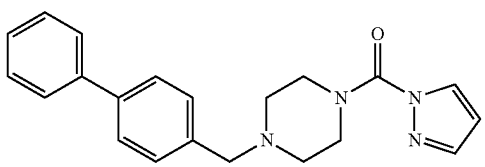 [SMILES: O=C(N1CCN(Cc2ccc(-c3ccccc3)cc2)CC1)n1cccn1] | (4-([1,1'-Biphenyl]-4-ylmethyl)piperazin-1-yl)(1H-pyrazol-1-yl)methanone |
| 23 | 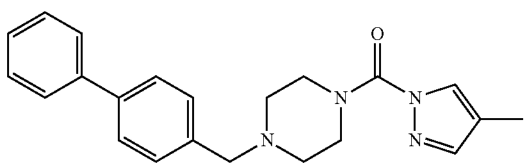 [SMILES: Cc1cnn(C(=O)N2CCN(Cc3ccc(-c4ccccc4)cc3)CC2)c1] | (4-([1,1'-Biphenyl]-4-ylmethyl)piperazin-1-yl)(4-methyl-1H-pyrazol-1-yl)methanone |
| 24 | 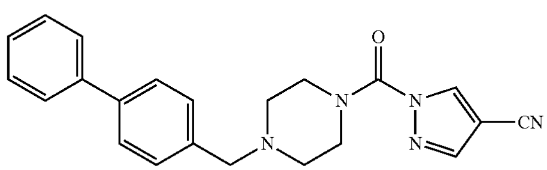 [SMILES: N#Cc1cnn(C(=O)N2CCN(Cc3ccc(-c4ccccc4)cc3)CC2)c1] | 1-(4-([1,1'-Biphenyl]-4-ylmethyl)piperazine-1-carbonyl)-1H-pyrazole-4-carbonitrile |
| 25 | 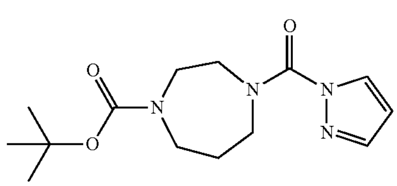 [SMILES: CC(C)(C)OC(=O)N1CCCN(C(=O)n2cccn2)CC1] | tert-Butyl 4-(1H-pyrazole-1-carbonyl)-1,4-diazepane-1-carboxylate |
| 26 | 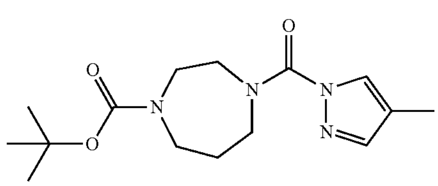 [SMILES: Cc1cnn(C(=O)N2CCCN(C(=O)OC(C)(C)C)CC2)c1] | tert-Butyl 4-(4-methyl-1H-pyrazole-1-carbonyl)-1,4-diazepane-1-carboxylate |

TABLE 1-continued

| Chemical Synthesis Example | Structure | Name |
|---|---|---|
| 27 | 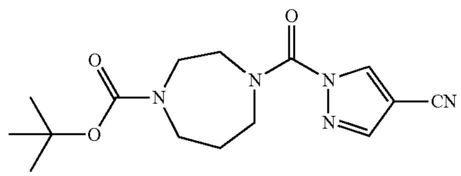 [SMILES: CC(C)(C)OC(=O)N1CCCN(C(=O)n2cc(C#N)cn2)CC1] | tert-Butyl 4-(4-cyano-1H-pyrazole-1-carbonyl)-1,4-diazepane-1-carboxylate |
| 28 | 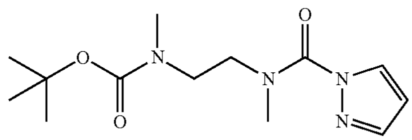 [SMILES: CN(CCN(C)C(=O)n1cccn1)C(=O)OC(C)(C)C] | tert-Butyl methyl(2-(N-methyl-1H-pyrazole-1-carboxamido)ethyl)carbamate |
| 29 | 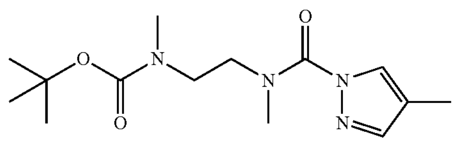 [SMILES: Cc1cnn(C(=O)N(C)CCN(C)C(=O)OC(C)(C)C)c1] | tert-Butyl (2-(N,4-dimethyl-1H-pyrazole-1-carboxamido)ethyl)(methyl)carbamate |
| 30 | 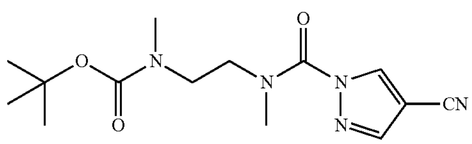 [SMILES: CN(CCN(C)C(=O)n1cc(C#N)cn1)C(=O)OC(C)(C)C] | tert-Butyl (2-(4-cyano-N-methyl-1H-pyrazole-1-carboxamido)ethyl)(methyl)carbamate |
| 31 | 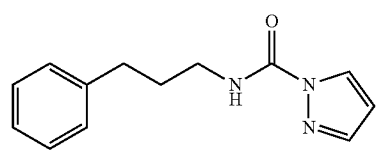 [SMILES: O=C(NCCCc1ccccc1)n1cccn1] | N-(3-Phenylpropyl)-1H-pyrazole-1-carboxamide |
| 32 | 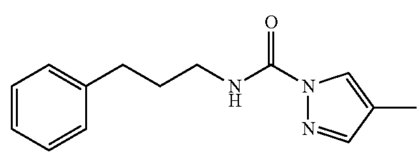 [SMILES: Cc1cnn(C(=O)NCCCc2ccccc2)c1] | 4-Methyl-N-(3-phenylpropyl)-1H-pyrazole-1-carboxamide |
| 33 | 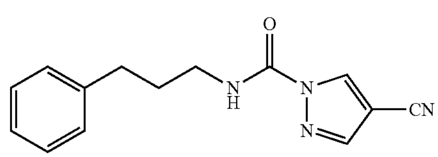 [SMILES: N#Cc1cnn(C(=O)NCCCc2ccccc2)c1] | 4-Cyano-N-(3-phenylpropyl)-1H-pyrazole-1-carboxamide |
| 34 | 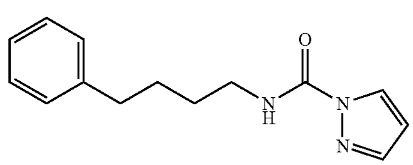 [SMILES: O=C(NCCCCc1ccccc1)n1cccn1] | N-(4-Phenylbutyl)-1H-pyrazole-1-carboxamide |
| 35 | 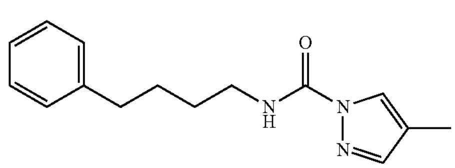 [SMILES: Cc1cnn(C(=O)NCCCCc2ccccc2)c1] | 4-Methyl-N-(4-phenylbutyl)-1H-pyrazole-1-carboxamide |

TABLE 1-continued

| Chemical Synthesis Example | Structure | Name |
|---|---|---|
| 36 | 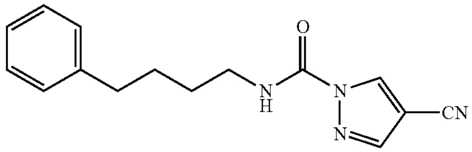 [SMILES: N#Cc1cnn(C(=O)NCCCCc2ccccc2)c1] | 4-Cyano-N-(4-phenylbutyl)-1H-pyrazole-1-carboxamide |
| 37 | 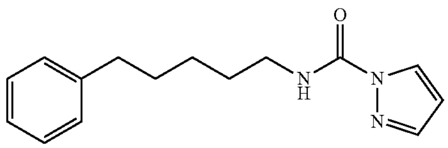 [SMILES: O=C(NCCCCCc1ccccc1)n1cccn1] | N-(5-phenylpentyl)-1H-pyrazole-1-carboxamide |
| 38 | 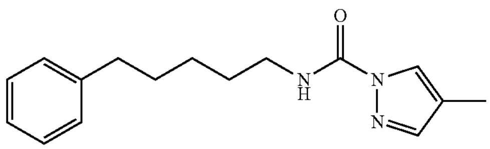 [SMILES: Cc1cnn(C(=O)NCCCCCc2ccccc2)c1] | 4-Methyl-N-(5-(5-phenylpentyl)-1H-pyrazole-1-carboxamide |
| 39 | 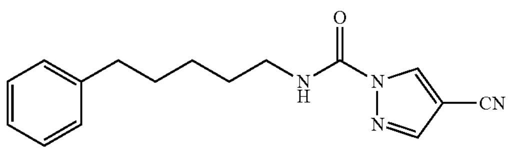 [SMILES: N#Cc1cnn(C(=O)NCCCCCc2ccccc2)c1] | 4-Cyano-N-(5-phenylpentyl)-1H-pyrazole-1-carboxamide |
| 40 | 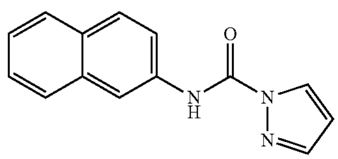 [SMILES: O=C(Nc1ccc2ccccc2c1)n1cccn1] | N-(Naphthalen-2-yl)-1H-pyrazole-1-carboxamide |
| 41 | 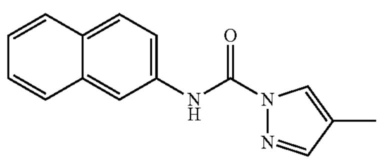 [SMILES: Cc1cnn(C(=O)Nc2ccc3ccccc3c2)c1] | 4-Methyl-N-(naphthalen-2-yl)-1H-pyrazole-1-carboxamide |
| 42 | 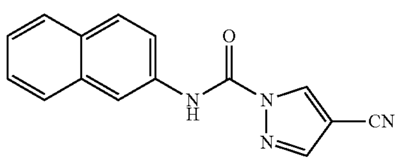 [SMILES: N#Cc1cnn(C(=O)Nc2ccc3ccccc3c2)c1] | 4-Cyano-N-(naphthalen-2-yl)-1H-pyrazole-1-carboxamide |
| 43 | 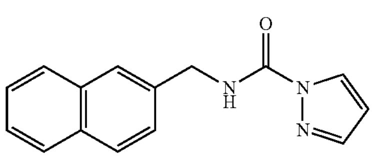 [SMILES: O=C(NCc1ccc2ccccc2c1)n1cccn1] | N-(Naphthalen-2-ylmethyl)-1H-pyrazole-1-carboxamide |
| 44 | 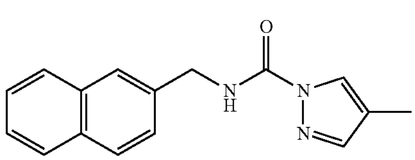 [SMILES: Cc1cnn(C(=O)NCc2ccc3ccccc3c2)c1] | 4-Methyl-N-(naphthalen-2-ylmethyl)-1H-pyrazole-1-carboxamide |

TABLE 1-continued

| Chemical Synthesis Example | Structure | Name |
|---|---|---|
| 45 | 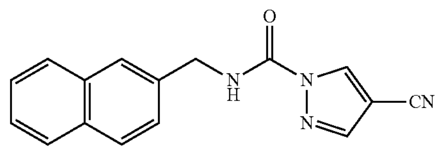 [SMILES: N#Cc1cnn(C(=O)NCc2ccc3ccccc3c2)c1] | 4-Cyano-N-(naphthalen-2-ylmethyl)-1H-pyrazole-1-carboxamide |
| 46 | 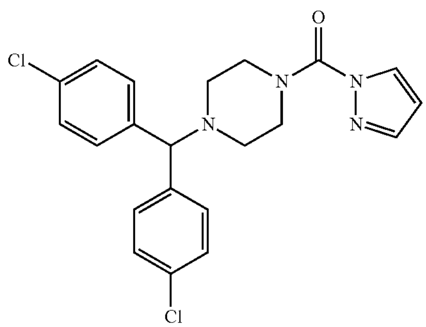 [SMILES: O=C(N1CCN(C(c2ccc(Cl)cc2)c2ccc(Cl)cc2)CC1)n1cccn1] | (4-(Bis(4-chlorophenyl)methyl)piperazin-1-yl)(1H-pyrazol-1-yl)methanone |
| 47 | 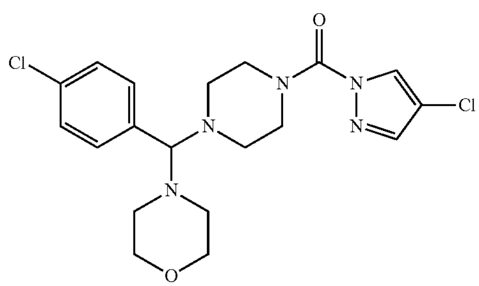 [SMILES: O=C(N1CCN(C(c2ccc(Cl)cc2)N2CCOCC2)CC1)n1cc(Cl)cn1] | (4-Chloro-1H-pyrazol-1-yl)(4-(4-chloro-2-morpholinobenzyl)piperazin-1-yl)methanone |
| 48 | 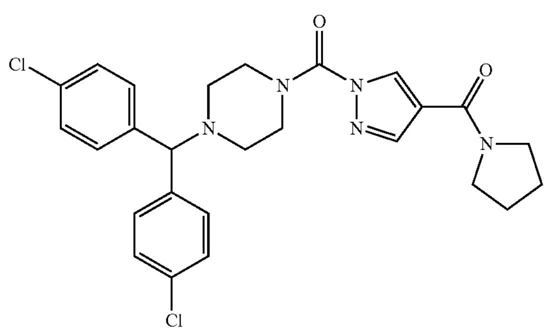 [SMILES: O=C(c1cnn(C(=O)N2CCN(C(c3ccc(Cl)cc3)c3ccc(Cl)cc3)CC2)c1)N1CCCC1] | (4-(Bis(4-chlorophenyl)methyl)piperazin-1-yl)(4-(pyrrolidine-1-carbonyl)-1H-pyrazol-1-yl)methanone |
| 49 | 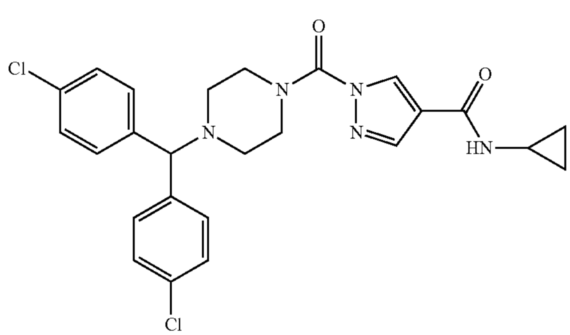 [SMILES: O=C(NC1CC1)c1cnn(C(=O)N2CCN(C(c3ccc(Cl)cc3)c3ccc(Cl)cc3)CC2)c1] | 1-(4-(Bis(4-chlorophenyl)methyl)piperazine-1-carbonyl)-N-cyclopropyl-1H-pyrazole-4-carboxamide |

TABLE 1-continued

| Chemical Synthesis Example | Structure | Name |
|---|---|---|
| 50 | 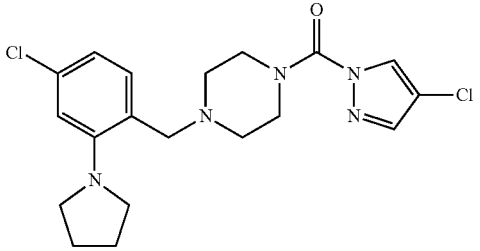 [SMILES: O=C(N1CCN(Cc2ccc(Cl)cc2N2CCCC2)CC1)n1cc(Cl)cn1] | (4-Chloro-1H-pyrazol-1-yl)(4-(4-chloro-2-(pyrrolidin-1-yl)benzyl)piperazin-1-yl)methanone |
| 51 | 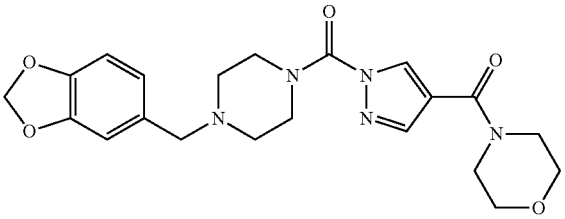 [SMILES: O=C(c1cnn(C(=O)N2CCN(Cc3ccc4c(c3)OCO4)CC2)c1)N1CCOCC1] | (4-(Benzo[d][1,3]dioxol-5-ylmethyl)piperazin-1-yl)(4-(morpholine-4-carbonyl)-1H-pyrazol-1-yl)methanone |
| 52 | 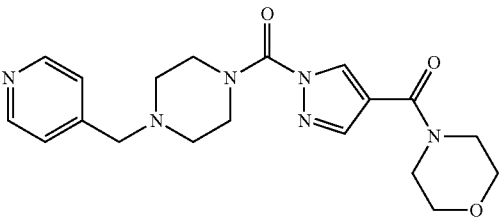 [SMILES: O=C(c1cnn(C(=O)N2CCN(Cc3ccncc3)CC2)c1)N1CCOCC1] | (4-(Morpholine-4-carbonyl)-1H-pyrazol-1-yl)(4-(pyridin-4-ylmethyl)piperazin-1-yl)methanone |
| 53 | 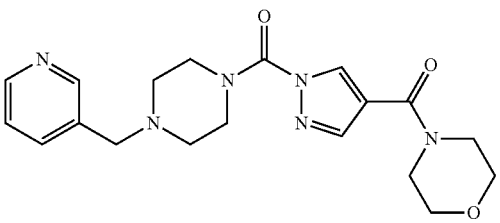 [SMILES: O=C(c1cnn(C(=O)N2CCN(Cc3cccnc3)CC2)c1)N1CCOCC1] | (4-(Morpholine-4-carbonyl)-1H-pyrazol-1-yl)(4-(pyridin-3-ylmethyl)piperazin-1-yl)methanone |
| 54 | 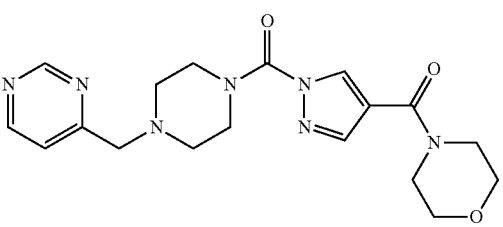 [SMILES: O=C(c1cnn(C(=O)N2CCN(Cc3ccncn3)CC2)c1)N1CCOCC1] | (4-(Morpholine-4-carbonyl)-1H-pyrazol-1-yl)(4-(pyrimidin-4-ylmethyl)piperazin-1-yl)methanone |
| 55 | 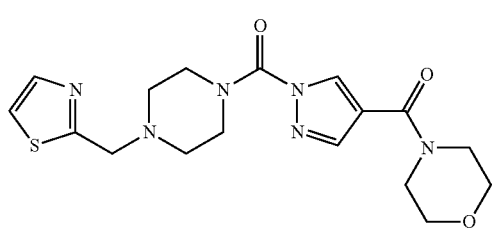 [SMILES: O=C(c1cnn(C(=O)N2CCN(Cc3nccs3)CC2)c1)N1CCOCC1] | (4-(Morpholine-4-carbonyl)-1H-pyrazol-1-yl)(4-(thiazol-2-ylmethyl)piperazin-1-yl)methanone |

TABLE 1-continued

| Chemical Synthesis Example | Structure | Name |
|---|---|---|
| 56 | 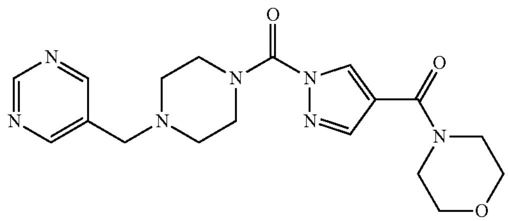 [SMILES: O=C(c1cnn(C(=O)N2CCN(Cc3cncnc3)CC2)c1)N1CCOCC1] | (4-(Morpholine-4-carbonyl)-1H-pyrazol-1-yl)(4-(pyrimidin-5-ylmethyl)piperazin-1-yl)methanone |
| 57 | 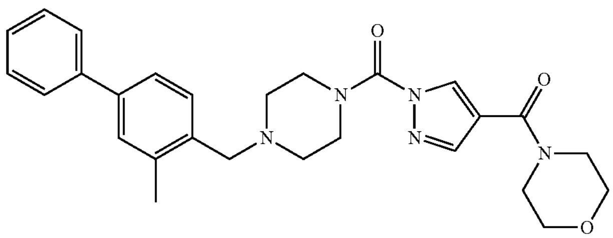 [SMILES: Cc1cc(-c2ccccc2)ccc1CN1CCN(C(=O)n2cc(C(=O)N3CCOCC3)cn2)CC1] | (4-((3-Methyl-[1,1'-biphenyl]-4-yl)methyl)piperazin-1-yl)(4-(morpholine-4-carbonyl)-1H-pyrazol-1-yl)methanone |
| 58 | 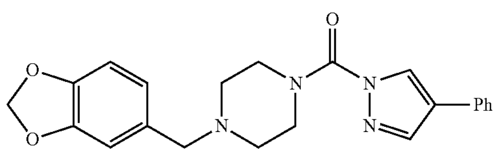 [SMILES: O=C(N1CCN(Cc2ccc3c(c2)OCO3)CC1)n1cc(-c2ccccc2)cn1] | (4-(Benzo[d][1,3]dioxol-5-ylmethyl)piperazin-1-yl)(4-phenyl-1H-pyrazol-1-yl)methanone |
| 59 | 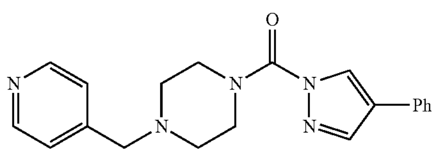 [SMILES: O=C(N1CCN(Cc2ccncc2)CC1)n1cc(-c2ccccc2)cn1] | (4-Phenyl-1H-pyrazol-1-yl)(4-(pyridin-4-ylmethyl)piperazin-1-yl)methanone |
| 60 | 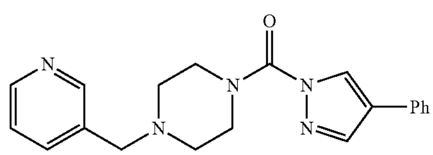 [SMILES: O=C(N1CCN(Cc2cccnc2)CC1)n1cc(-c2ccccc2)cn1] | (4-Phenyl-1H-pyrazol-1-yl)(4-(pyridin-3-ylmethyl)piperazin-1-yl)methanone |
| 61 | 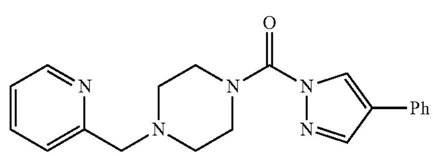 [SMILES: O=C(N1CCN(Cc2ccccn2)CC1)n1cc(-c2ccccc2)cn1] | (4-Phenyl-1H-pyrazol-1-yl)(4-(pyridin-3-ylmethyl)piperazin-1-yl)methanone |
| 62 | 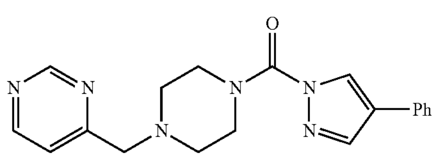 [SMILES: O=C(N1CCN(Cc2ccncn2)CC1)n1cc(-c2ccccc2)cn1] | (4-Phenyl-1H-pyrazol-1-yl)(4-(pyrimidin-4-ylmethyl)piperazin-1-yl)methanone |
| 63 | 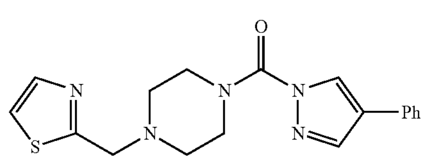 [SMILES: O=C(N1CCN(Cc2nccs2)CC1)n1cc(-c2ccccc2)cn1] | (4-Phenyl-1H-pyrazol-1-yl)(4-(thiazol-2-ylmethyl)piperazin-1-yl)methanone |
| 64 | 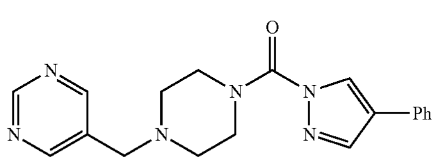 [SMILES: O=C(N1CCN(Cc2cncnc2)CC1)n1cc(-c2ccccc2)cn1] | (4-Phenyl-1H-pyrazol-1-yl)(4-(pyrimidin-5-ylmethyl)piperazin-1-yl)methanone |

TABLE 1-continued

| Chemical Synthesis Example | Structure | Name |
|---|---|---|
| 65 | 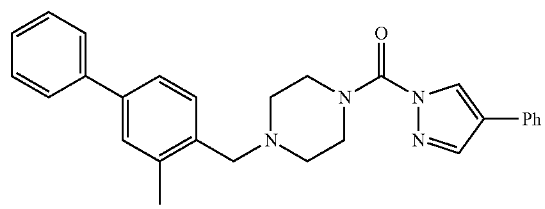 [SMILES: Cc1cc(-c2ccccc2)ccc1CN1CCN(C(=O)n2cc(-c3ccccc3)cn2)CC1] | (4-((3-Methyl-[1,1'-biphenyl]-4-yl)methyl)piperazin-1-yl)(4-phenyl-1H-pyrazol-1-yl)methanone |
| 66 | 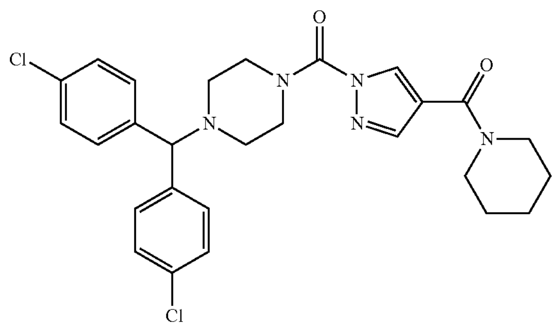 [SMILES: O=C(c1cnn(C(=O)N2CCN(C(c3ccc(Cl)cc3)c3ccc(Cl)cc3)CC2)c1)N1CCCCC1] | (4-(Bis(4-chlorophenyl)methyl)piperazin-1-yl)(4-(piperidine-1-carbonyl)-1H-pyrazol-1-yl)methanone |
| 67 | 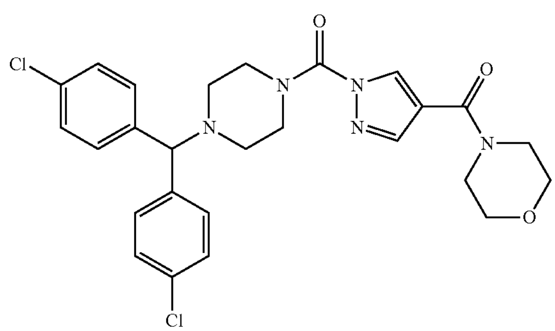 [SMILES: O=C(c1cnn(C(=O)N2CCN(C(c3ccc(Cl)cc3)c3ccc(Cl)cc3)CC2)c1)N1CCOCC1] | (4-(Bis(4-chlorophenyl)methyl)piperazin-1-yl)(4-(morpholine-4-carbonyl)-1H-pyrazol-1-yl)methanone |
| 68 | 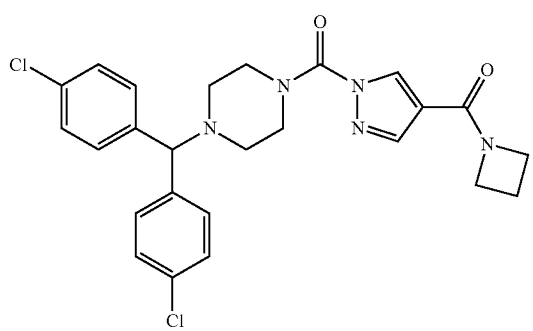 [SMILES: O=C(c1cnn(C(=O)N2CCN(C(c3ccc(Cl)cc3)c3ccc(Cl)cc3)CC2)c1)N1CCC1] | Azetidin-1-yl(1-(4-(bis(4-chlorophenyl)methyl)piperazine-1-carbonyl)-1H-pyrazol-4-yl)methanone |
| 69 | 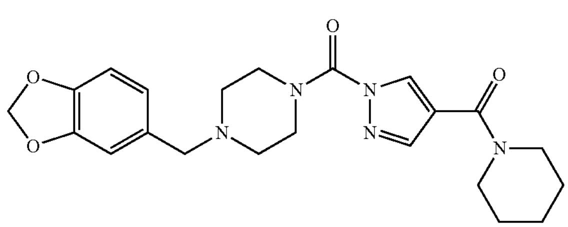 [SMILES: O=C(c1cnn(C(=O)N2CCN(Cc3ccc4c(c3)OCO4)CC2)c1)N1CCCCC1] | (4-(Benzo[d][1,3]dioxol-5-ylmethyl)piperazin-1-yl)(4-(piperidine-1-carbonyl)-1H-pyrazol-1-yl)methanone |

TABLE 1-continued

| Chemical Synthesis Example | Structure | Name |
|---|---|---|
| 70 | 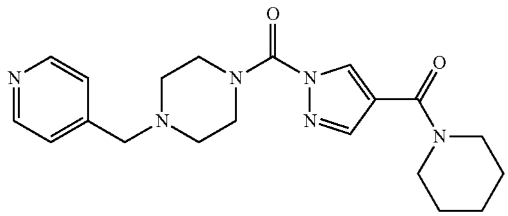 [SMILES: O=C(c1cnn(C(=O)N2CCN(Cc3ccncc3)CC2)c1)N1CCCCC1] | Piperidin-1-yl(1-(4-(pyridin-4-ylmethyl)piperazine-1-carbonyl)-1H-pyrazol-4-yl)methanone |
| 71 | 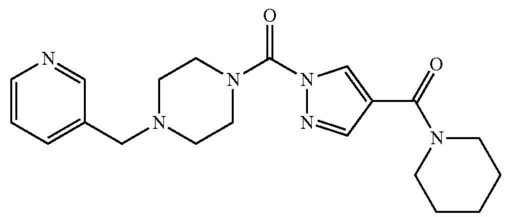 [SMILES: O=C(c1cnn(C(=O)N2CCN(Cc3cccnc3)CC2)c1)N1CCCCC1] | Piperidin-1-yl(1-(4-(pyridin-3-ylmethyl)piperazine-1-carbonyl)-1H-pyrazol-4-yl)methanone |
| 72 | 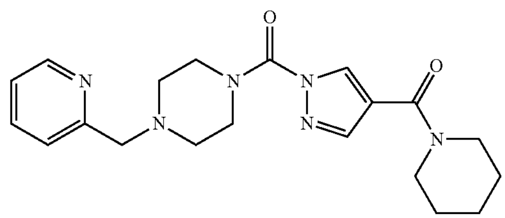 [SMILES: O=C(c1cnn(C(=O)N2CCN(Cc3ccccn3)CC2)c1)N1CCCCC1] | Piperidin-1-yl(1-(4-(pyridin-2-ylmethyl)piperazine-1-carbonyl)-1H-pyrazol-4-yl)methanone |
| 73 | 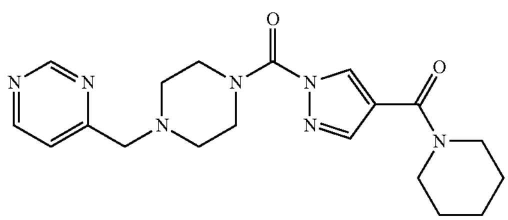 [SMILES: O=C(c1cnn(C(=O)N2CCN(Cc3ccncn3)CC2)c1)N1CCCCC1] | Piperidin-1-yl(1-(4-(pyrimidin-4-ylmethyl)piperazine-1-carbonyl)-1H-pyrazol-4-yl)methanone |
| 74 | 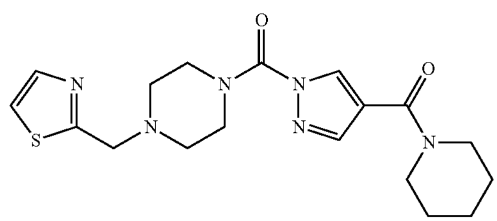 [SMILES: O=C(c1cnn(C(=O)N2CCN(Cc3nccs3)CC2)c1)N1CCCCC1] | Piperidin-1-yl(1-(4-(thiazol-2-ylmethyl)piperazine-1-carbonyl)-1H-pyrazol-4-yl)methanone |
| 75 | 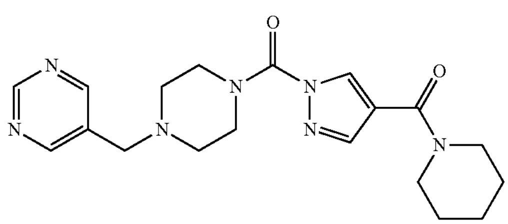 [SMILES: O=C(c1cnn(C(=O)N2CCN(Cc3cncnc3)CC2)c1)N1CCCCC1] | Piperidin-1-yl(1-(4-(pyrimidin-5-ylmethyl)piperazine-1-carbonyl)-1H-pyrazol-4-yl)methanone |
| 76 | 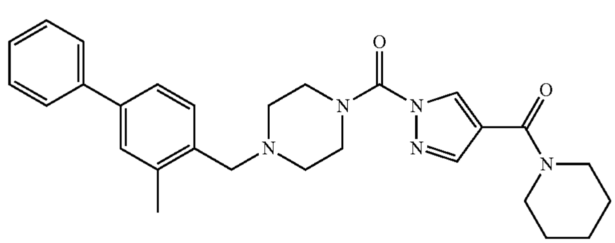 [SMILES: Cc1cc(-c2ccccc2)ccc1CN1CCN(C(=O)n2cc(C(=O)N3CCCCC3)cn2)CC1] | (4-((3-Methyl-[1,1'-biphenyl]-4-yl)methyl)piperazin-1-yl)(4-(piperidine-1-carbonyl)-1H-pyrazol-1-yl)methanone |

TABLE 1-continued

| Chemical Synthesis Example | Structure | Name |
|---|---|---|
| 77 | 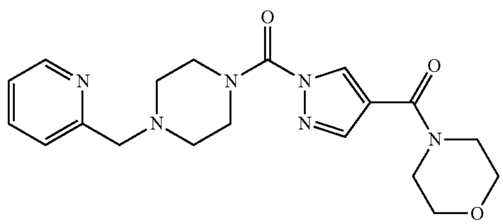 [SMILES: O=C(c1cnn(C(=O)N2CCN(Cc3ccccn3)CC2)c1)N1CCOCC1] | (4-(Morpholine-4-carbonyl)-1H-pyrazol-1-yl)(4-(pyridin-2-ylmethyl)piperazin-1-yl)methanone |
| 78 | 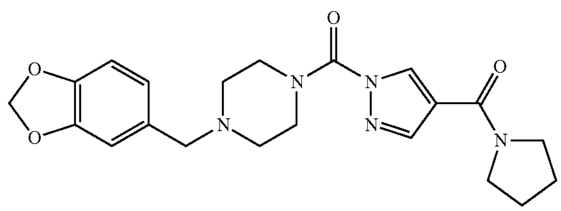 [SMILES: O=C(c1cnn(C(=O)N2CCN(Cc3ccc4c(c3)OCO4)CC2)c1)N1CCCC1] | (4-(Benzo[d][1,3]dioxol-5-ylmethyl)piperazin-1-yl)(4-(pyrrolidine-1-carbonyl)-1H-pyrazol-1-yl)methanone |
| 79 | 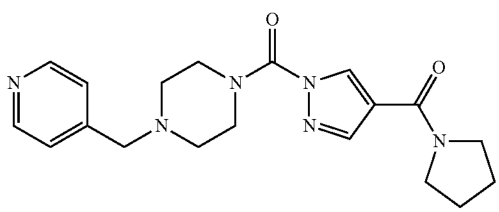 [SMILES: O=C(c1cnn(C(=O)N2CCN(Cc3ccncc3)CC2)c1)N1CCCC1] | (4-(Pyridin-4-ylmethyl)piperazin-1-yl)(4-(pyrrolidine-1-carbonyl)-1H-pyrazol-1-yl)methanone |
| 80 | 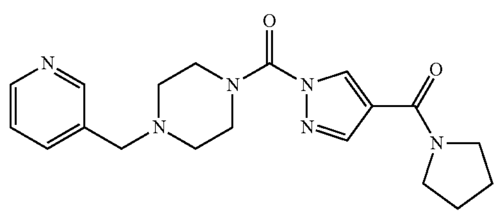 [SMILES: O=C(c1cnn(C(=O)N2CCN(Cc3cccnc3)CC2)c1)N1CCCC1] | (4-(Pyridin-3-ylmethyl)piperazin-1-yl)(4-(pyrrolidine-1-carbonyl)-1H-pyrazol-1-yl)methanone |
| 81 | 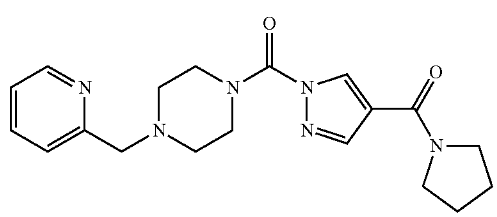 [SMILES: O=C(c1cnn(C(=O)N2CCN(Cc3ccccn3)CC2)c1)N1CCCC1] | (4-(Pyridin-2-ylmethyl)piperazin-1-yl)(4-(pyrrolidine-1-carbonyl)-1H-pyrazol-1-yl)methanone |
| 82 | 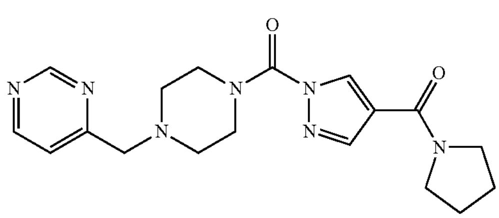 [SMILES: O=C(c1cnn(C(=O)N2CCN(Cc3ccncn3)CC2)c1)N1CCCC1] | (4-(Pyrimidin-4-ylmethyl)piperazin-1-yl)(4-(pyrrolidine-1-carbonyl)-1H-pyrazol-1-yl)methanone |
| 83 | 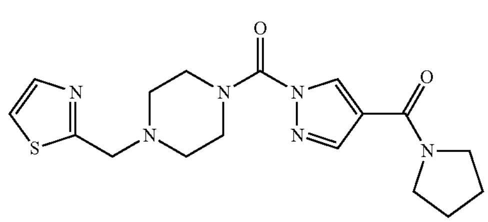 [SMILES: O=C(c1cnn(C(=O)N2CCN(Cc3nccs3)CC2)c1)N1CCCC1] | Pyrrolidin-1-yl(1-(4-(thiazol-2-ylmethyl)piperazine-1-carbonyl)-1H-pyrazol-4-yl)methanone |

TABLE 1-continued

| Chemical Synthesis Example | Structure | Name |
|---|---|---|
| 84 | 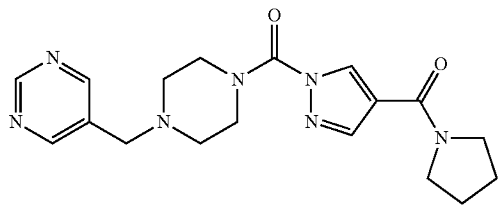 [SMILES: O=C(c1cnn(C(=O)N2CCN(Cc3cncnc3)CC2)c1)N1CCCC1] | (4-(Pyrimidin-5-ylmethyl)piperazin-1-yl)(4-(pyrrolidine-1-carbonyl)-1H-pyrazol-1-yl)methanone |
| 85 | 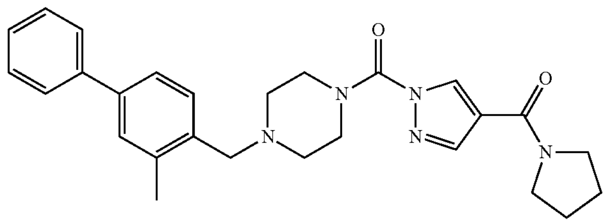 [SMILES: Cc1cc(-c2ccccc2)ccc1CN1CCN(C(=O)n2cc(C(=O)N3CCCC3)cn2)CC1] | (4-((3-Methyl-[1,1'-biphenyl]-4-yl)methyl)piperazin-1-yl)(4-(pyrrolidine-1-carbonyl)-1H-pyrazol-1-yl)methanone |
| 86 | 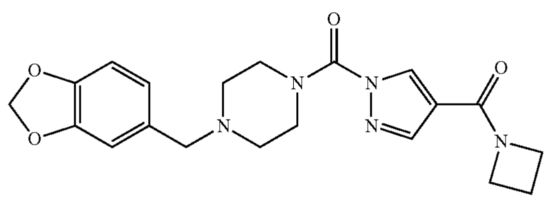 [SMILES: O=C(c1cnn(C(=O)N2CCN(Cc3ccc4c(c3)OCO4)CC2)c1)N1CCC1] | Azetidin-1-yl(1-(4-(benzo[d][1,3]dioxol-5-ylmethyl)piperazine-1-carbonyl)-1H-pyrazol-4-yl)methanone |
| 87 | 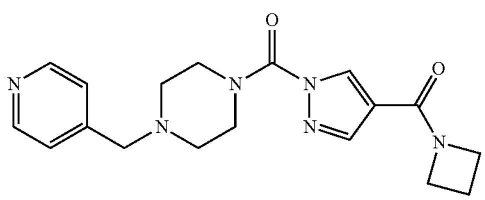 | Azetidin-1-yl(1-(4-(pyridin-4-ylmethyl)piperazine-1-carbonyl)-1H-pyrazol-4-yl)methanone |
| 88 | 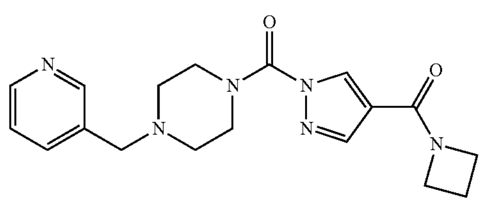 [SMILES: O=C(c1cnn(C(=O)N2CCN(Cc3cccnc3)CC2)c1)N1CCC1] | Azetidin-1-yl(1-(4-(pyridin-3-ylmethyl)piperazine-1-carbonyl)-1H-pyrazol-4-yl)methanone |
| 89 | 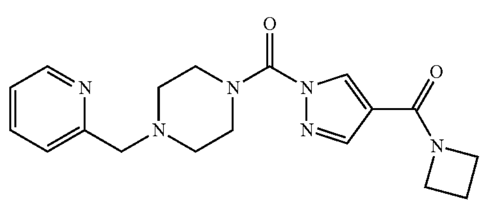 [SMILES: O=C(c1cnn(C(=O)N2CCN(Cc3ccccn3)CC2)c1)N1CCC1] | Azetidin-1-yl(1-(4-(pyridin-2-ylmethyl)piperazine-1-carbonyl)-1H-pyrazol-4-yl)methanone |
| 90 | 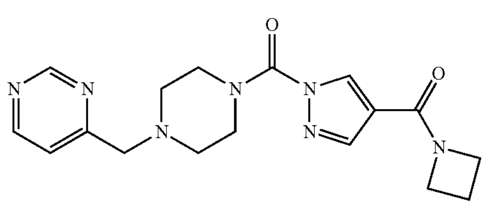 | Azetidin-1-yl(1-(4-(pyrimidin-4-ylmethyl)piperazine-1-carbonyl)-1H-pyrazol-4-yl)methanone |

TABLE 1-continued

| Chemical Synthesis Example | Structure | Name |
|---|---|---|
| 91 | 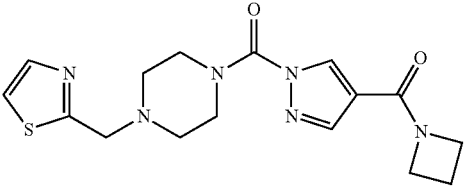 [SMILES: O=C(c1cnn(C(=O)N2CCN(Cc3nccs3)CC2)c1)N1CCC1] | Azetidin-1-yl(1-(4-((thiazol-2-ylmethyl)piperazine-1-carbonyl)-1H-pyrazol-4-yl)methanone |
| 92 | 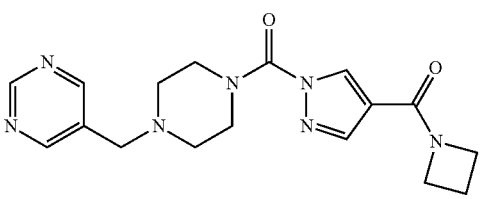 | Azetidin-1-yl(1-(4-(pyrimidin-5-ylmethyl)piperazine-1-carbonyl)-1H-pyrazol-4-yl)methanone |
| 93 | 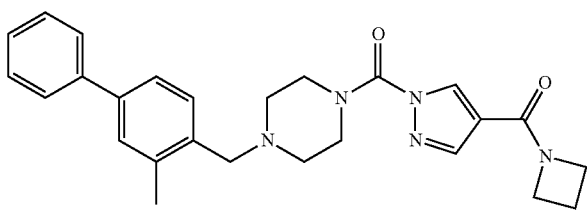 [SMILES: Cc1cc(-c2ccccc2)ccc1CN1CCN(C(=O)n2cc(C(=O)N3CCC3)cn2)CC1] | Azetidin-1-yl(1-(4-((3-methyl-[1,1'-biphenyl]-4-yl)methyl)piperazine-1-carbonyl)-1H-pyrazol-4-yl)methanone |
| 94 | 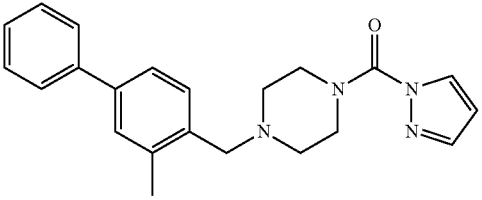 [SMILES: Cc1cc(-c2ccccc2)ccc1CN1CCN(C(=O)n2cccn2)CC1] | (4-((3-Methyl-[1,1'-biphenyl]-4-yl)methyl)piperazin-1-yl)(1H-pyrazol-1-yl)methanone |
| 95 | 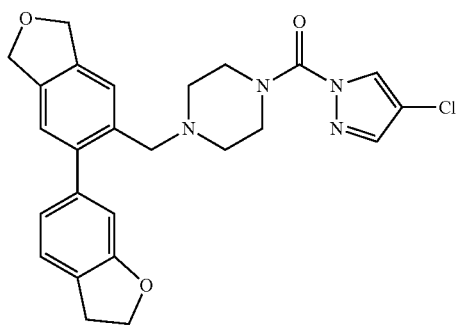 [SMILES: O=C(N1CCN(Cc2cc3c(cc2-c2ccc4c(c2)OCC4)COC3)CC1)n1cc(Cl)cn1] | (4-(Bis(1,3-dihydroisobenzofuran-5-yl)methyl)piperazin-1-yl)(4-chloro-1H-pyrazol-1-yl)methanone |
| 96 | 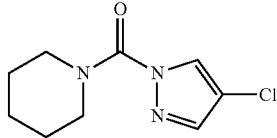 [SMILES: O=C(N1CCCCC1)n1cc(Cl)cn1] | (4-Chloro-1H-pyrazol-1-yl)(piperidin-1-yl)methanone |
| 97 | 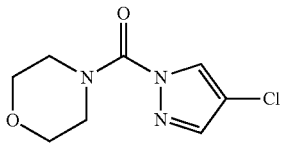 [SMILES: O=C(N1CCOCC1)n1cc(Cl)cn1] | (4-Chloro-1H-pyrazol-1-yl)(morpholino)methanone |

TABLE 1-continued

| Chemical Synthesis Example | Structure | Name |
|---|---|---|
| 98 | 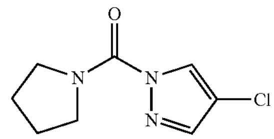 [SMILES: O=C(N1CCCC1)n1cc(Cl)cn1] | (4-Chloro-1H-pyrazol-1-yl)(pyrrolidin-1-yl)methanone |
| 99 | 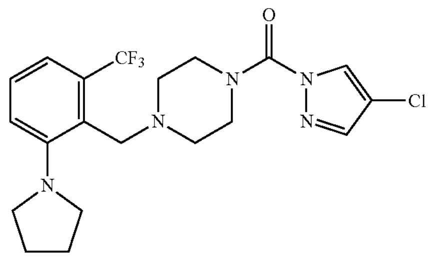 [SMILES: O=C(N1CCN(Cc2c(N3CCCC3)cccc2C(F)(F)F)CC1)n1cc(Cl)cn1] | (4-Chloro-1H-pyrazol-1-yl)(4-(2-(pyrrolidin-1-yl)-6-(trifluoromethyl)benzyl)piperazin-1-yl)methanone |
| 100 | 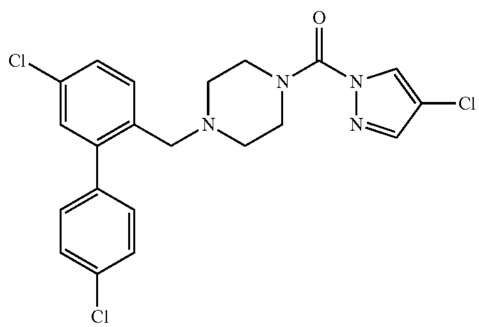 [SMILES: O=C(N1CCN(Cc2ccc(Cl)cc2-c2ccc(Cl)cc2)CC1)n1cc(Cl)cn1] | (4-(Bis(4-chlorophenyl)methyl)piperazin-1-yl)(4-chloro-1H-pyrazol-1-yl)methanone |
| 101 | 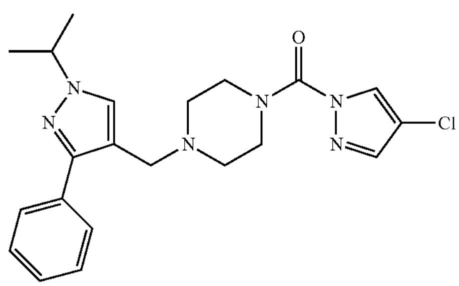 [SMILES: CC(C)n1cc(CN2CCN(C(=O)n3cc(Cl)cn3)CC2)c(-c2ccccc2)n1] | (4-Chloro-1H-pyrazol-1-yl)(4-((1-isopropyl-3-phenyl-1H-pyrazol-4-yl)methyl)piperazin-1-yl)methanone |
| 102 | 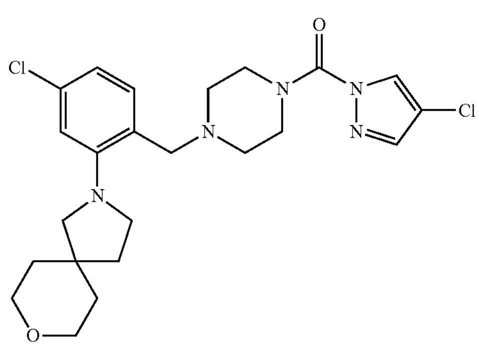 [SMILES: O=C(N1CCN(Cc2ccc(Cl)cc2N2CCC3(CCOCC3)C2)CC1)n1cc(Cl)cn1] | (4-Chloro-1H-pyrazol-1-yl)(4-(4-chloro-2-(8-oxa-2-azaspiro[4.5]decan-2-yl)benzyl)piperazin-1-yl)methanone |
| 103 | 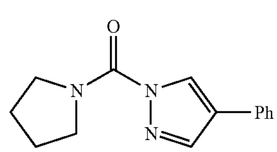 [SMILES: O=C(N1CCCC1)n1cc(-c2ccccc2)cn1] | (4-Phenyl-1H-pyrazol-1-yl)(pyrrolidin-1-yl)methanone |

TABLE 1-continued

| Chemical Synthesis Example | Structure | Name |
|---|---|---|
| 104 | 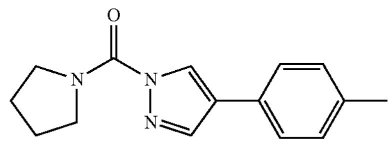 [SMILES: Cc1ccc(-c2cnn(C(=O)N3CCCC3)c2)cc1] | Pyrrolidin-1-yl(4-(p-tolyl)-1H-pyrazol-1-yl)methanone |
| 105 | 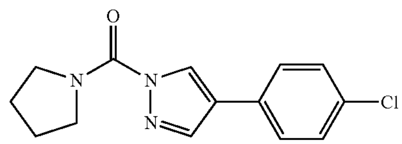 [SMILES: O=C(N1CCCC1)n1cc(-c2ccc(Cl)cc2)cn1] | (4-(4-Chlorophenyl)-1H-pyrazol-1-yl)(pyrrolidin-1-yl)methanone |
| 106 | 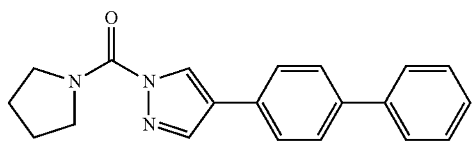 [SMILES: O=C(N1CCCC1)n1cc(-c2ccc(-c3ccccc3)cc2)cn1] | (4-([1,1'-Biphenyl]-4-yl)-1H-pyrazol-1-yl)(pyrrolidin-1-yl)methanone |
| 107 | 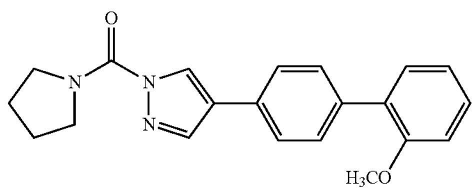 [SMILES: COc1ccccc1-c1ccc(-c2cnn(C(=O)N3CCCC3)c2)cc1] | (4-(2'-Methoxy-[1,1'-biphenyl]-4-yl)-1H-pyrazol-1-yl)(pyrrolidin-1-yl)methanone |
| 108 | 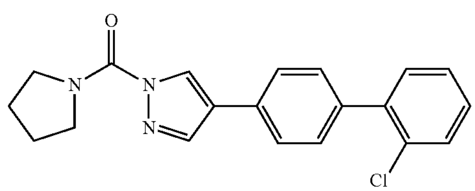 [SMILES: O=C(N1CCCC1)n1cc(-c2ccc(-c3ccccc3Cl)cc2)cn1] | (4-(2'-Chloro[1,1'-biphenyl]-4-yl)-1H-pyrazol-1-yl)(pyrrolidin-1-yl)methanone |
| 109 | 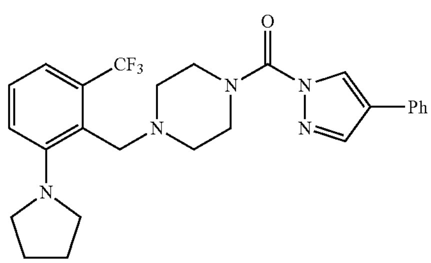 [SMILES: O=C(N1CCN(Cc2c(N3CCCC3)cccc2C(F)(F)F)CC1)n1cc(-c2ccccc2)cn1] | (4-Phenyl-1H-pyrazol-1-yl)(4-(2-(pyrrolidin-1-yl)-6-(trifluoromethyl)benzyl)piperazin-1-yl)methanone |
| 110 | 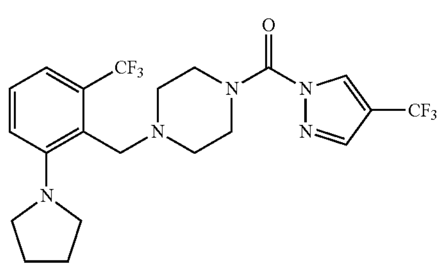 [SMILES: O=C(N1CCN(Cc2c(N3CCCC3)cccc2C(F)(F)F)CC1)n1cc(C(F)(F)F)cn1] | (4-(2-(Pyrrolidin-1-yl)-6-(trifluoromethyl)benzyl)piperazin-1-yl)(4-(trifluoromethyl)-1H-pyrazol-1-yl)methanone |

TABLE 1-continued

| Chemical Synthesis Example | Structure | Name |
|---|---|---|
| 111 | 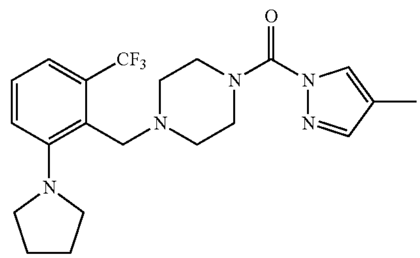 [SMILES: Cc1cnn(C(=O)N2CCN(Cc3c(N4CCCC4)cccc3C(F)(F)F)CC2)c1] | (4-Methyl-1H-pyrazol-1-yl)(4-(2-(pyrrolidin-1-yl)-6-(trifluoromethyl)benzyl)piperazin-1-yl)methanone |
| 112 | 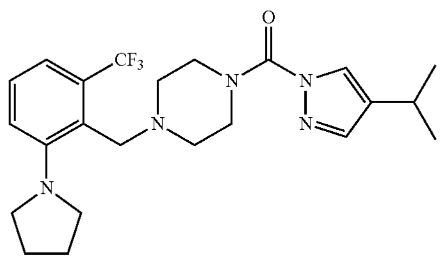 [SMILES: CC(C)c1cnn(C(=O)N2CCN(Cc3c(N4CCCC4)cccc3C(F)(F)F)CC2)c1] | (4-Isopropyl-1H-pyrazol-1-yl)(4-(2-(pyrrolidin-1-yl)-6-(trifluoromethyl)benzyl)piperazin-1-yl)methanone |
| 113 | 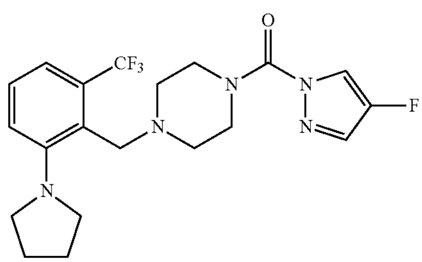 [SMILES: O=C(N1CCN(Cc2c(N3CCCC3)cccc2C(F)(F)F)CC1)n1cc(F)cn1] | (4-Fluoro-1H-pyrazol-1-yl)(4-(2-(pyrrolidin-1-yl)-6-(trifluoromethyl)benzyl)piperazin-1-yl)methanone |
| 114 | 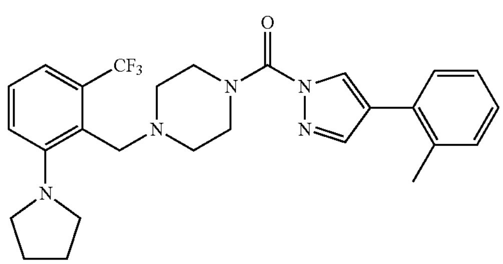 [SMILES: Cc1ccccc1-c1cnn(C(=O)N2CCN(Cc3c(N4CCCC4)cccc3C(F)(F)F)CC2)c1] | (4-(2-(Pyrrolidin-1-yl)-6-(trifluoromethyl)benzyl)piperazin-1-yl)(4-(o-tolyl)-1H-pyrazol-1-yl)methanone |
| 115 | 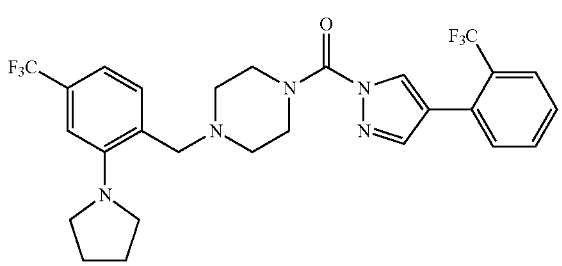 [SMILES: O=C(N1CCN(Cc2ccc(C(F)(F)F)cc2N2CCCC2)CC1)n1cc(-c2ccccc2C(F)(F)F)cn1] | (4-(2-(Pyrrolidin-1-yl)-4-(trifluoromethyl)benzyl)piperazin-1-yl)(4-(2-(trifluoromethyl)phenyl)-1H-pyrazol-1-yl)methanone |
| 116 | 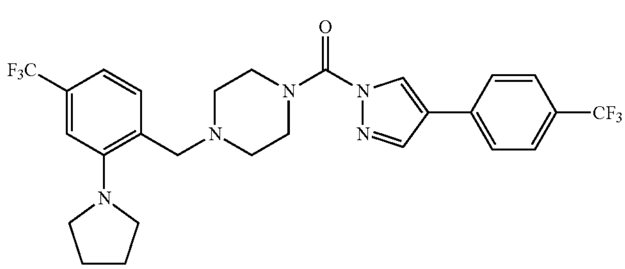 [SMILES: O=C(N1CCN(Cc2ccc(C(F)(F)F)cc2N2CCCC2)CC1)n1cc(-c2ccc(C(F)(F)F)cc2)cn1] | (4-(2-(Pyrrolidin-1-yl)-4-(trifluoromethyl)benzyl)piperazin-1-yl)(4-(4-(trifluoromethyl)phenyl)-1H-pyrazol-1-yl)methanone |

TABLE 1-continued

| Chemical Synthesis Example | Structure | Name |
|---|---|---|
| 117 | 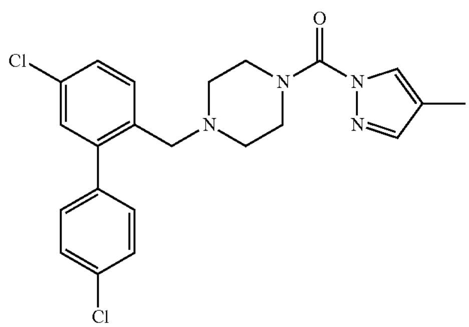 [SMILES: Cc1cnn(C(=O)N2CCN(Cc3ccc(Cl)cc3-c3ccc(Cl)cc3)CC2)c1] | (4-(Bis(4-chlorophenyl)methyl)piperazin-1-yl)(4-methyl-1H-pyrazol-1-yl)methanone |
| 118 | 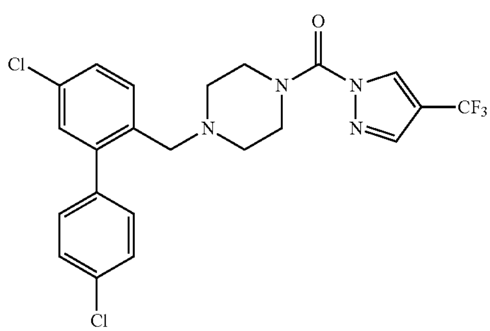 [SMILES: O=C(N1CCN(Cc2ccc(Cl)cc2-c2ccc(Cl)cc2)CC1)n1cc(C(F)(F)F)cn1] | (4-(Bis(4-chlorophenyl)methyl)piperazin-1-yl)(4-(trifluoromethyl)-1H-pyrazol-1-yl)methanone |
| 119 | 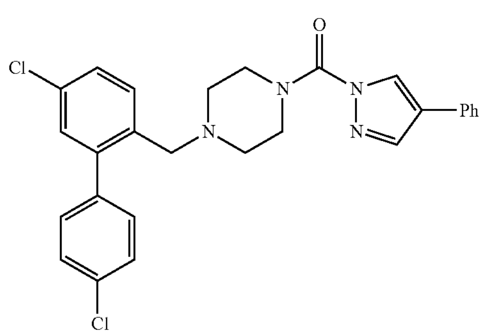 [SMILES: O=C(N1CCN(Cc2ccc(Cl)cc2-c2ccc(Cl)cc2)CC1)n1cc(-c2ccccc2)cn1] | (4-(Bis(4-chlorophenyl)methyl)piperazin-1-yl)(4-phenyl-1H-pyrazol-1-yl)methanone |
| 120 | 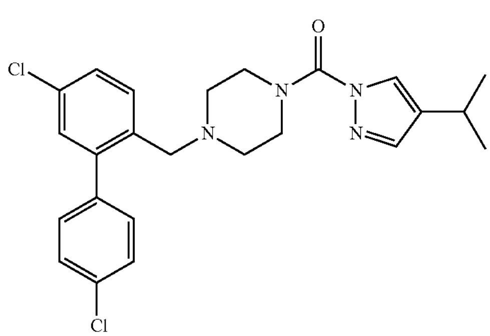 [SMILES: CC(C)c1cnn(C(=O)N2CCN(Cc3ccc(Cl)cc3-c3ccc(Cl)cc3)CC2)c1] | (4-(Bis(4-chlorophenyl)methyl)piperazin-1-yl)(4-isopropyl-1H-pyrazol-1-yl)methanone |

TABLE 1-continued

| Chemical Synthesis Example | Structure | Name |
|---|---|---|
| 121 | 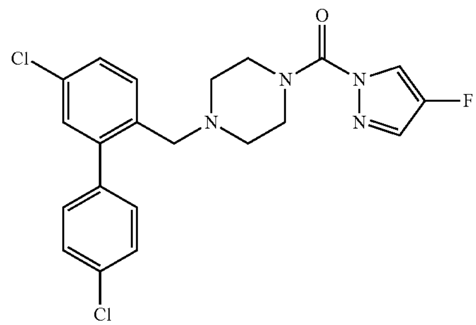 [SMILES: O=C(N1CCN(Cc2ccc(Cl)cc2-c2ccc(Cl)cc2)CC1)n1cc(F)cn1] | (4-(Bis(4-chlorophenyl)methyl)piperazin-1-yl)(4-fluoro-1H-pyrazol-1-yl)methanone |
| 122 | 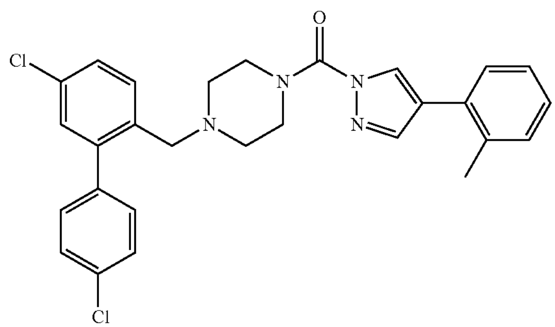 [SMILES: Cc1ccccc1-c1cnn(C(=O)N2CCN(Cc3ccc(Cl)cc3-c3ccc(Cl)cc3)CC2)c1] | (4-(Bis(4-chlorophenyl)methyl)piperazin-1-yl)(4-(o-tolyl)-1H-pyrazol-1-yl)methanone |
| 123 | 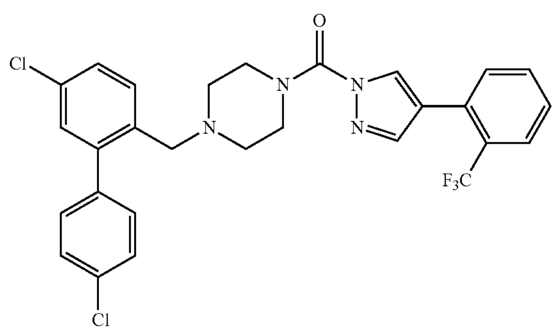 [SMILES: O=C(N1CCN(Cc2ccc(Cl)cc2-c2ccc(Cl)cc2)CC1)n1cc(-c2ccccc2C(F)(F)F)cn1] | (4-(Bis(4-chlorophenyl)methyl)piperazin-1-yl)(4-(2-(trifluoromethyl)phenyl)-1H-pyrazol-1-yl)methanone |
| 124 | 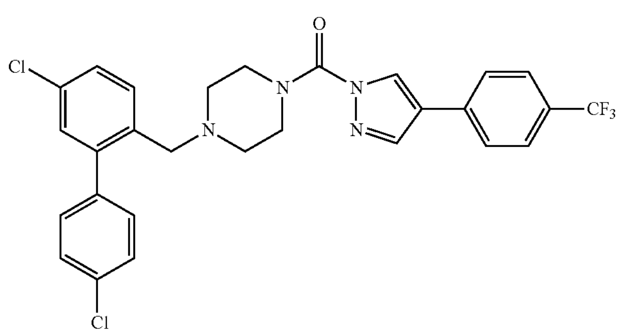 [SMILES: O=C(N1CCN(Cc2ccc(Cl)cc2-c2ccc(Cl)cc2)CC1)n1cc(-c2ccc(C(F)(F)F)cc2)cn1] | (4-(Bis(4-chlorophenyl)methyl)piperazin-1-yl)(4-(4-(trifluoromethyl)phenyl)-1H-pyrazol-1-yl)methanone |
| 125 | 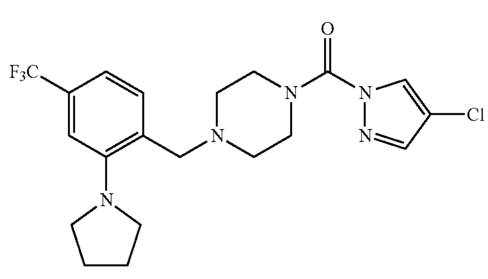 [SMILES: O=C(N1CCN(Cc2ccc(C(F)(F)F)cc2N2CCCC2)CC1)n1cc(Cl)cn1] | (4-Chloro-1H-pyrazol-1-yl)(4-(2-(pyrrolidin-1-yl)-4-(trifluoromethyl)benzyl)piperazin-1-yl)methanone |

TABLE 1-continued

| Chemical Synthesis Example | Structure | Name |
|---|---|---|
| 126 | 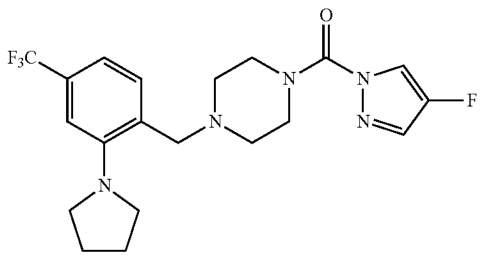 [SMILES: O=C(N1CCN(Cc2ccc(C(F)(F)F)cc2N2CCCC2)CC1)n1cc(F)cn1] | (4-Fluoro-1H-pyrazol-1-yl)(4-(2-(pyrrolidin-1-yl)-4-(trifluoromethyl)benzyl)piperazin-1-yl)methanone |
| 127 | 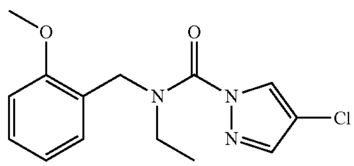 [SMILES: CCN(Cc1ccccc1OC)C(=O)n1cc(Cl)cn1] | 4-Chloro-N-ethyl-N-(2-methoxybenzyl)-1H-pyrazole-1-carboxamide |
| 128 | 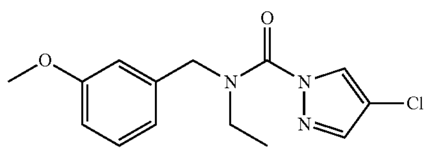 [SMILES: CCN(Cc1cccc(OC)c1)C(=O)n1cc(Cl)cn1] | 4-Chloro-N-ethyl-N-(3-methoxybenzyl)-1H-pyrazole-1-carboxamide |
| 129 | 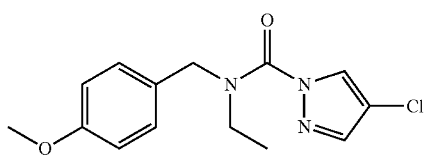 [SMILES: CCN(Cc1ccc(OC)cc1)C(=O)n1cc(Cl)cn1] | 4-Chloro-N-ethyl-N-(4-methoxybenzyl)-1H-pyrazole-1-carboxamide |
| 130 | 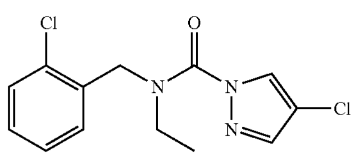 [SMILES: CCN(Cc1ccccc1Cl)C(=O)n1cc(Cl)cn1] | 4-Chloro-N-(2-chlorobenzyl)-N-ethyl-1H-pyrazole-1-carboxamide |
| 131 | 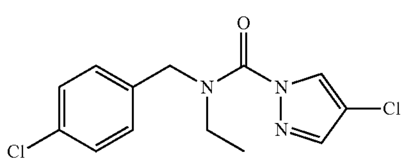 [SMILES: CCN(Cc1ccc(Cl)cc1)C(=O)n1cc(Cl)cn1] | 4-Chloro-N-(4-chlorobenzyl)-N-ethyl-1H-pyrazole-1-carboxamide |
| 132 | 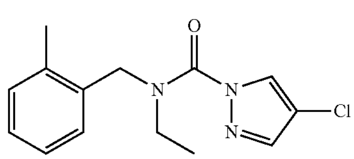 [SMILES: CCN(Cc1ccccc1C)C(=O)n1cc(Cl)cn1] | 4-Chloro-N-ethyl-N-(2-methylbenzyl)-1H-pyrazole-1-carboxamide |
| 133 | 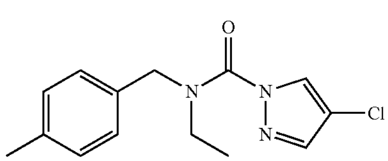 [SMILES: CCN(Cc1ccc(C)cc1)C(=O)n1cc(Cl)cn1] | 4-Chloro-N-ethyl-N-(4-methylbenzyl)-1H-pyrazole-1-carboxamide |
| 134 | 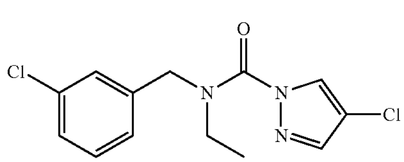 [SMILES: CCN(Cc1cccc(Cl)c1)C(=O)n1cc(Cl)cn1] | 4-Chloro-N-(3-chlorobenzyl)-N-ethyl-1H-pyrazole-1-carboxamide |

TABLE 1-continued

| Chemical Synthesis Example | Structure | Name |
|---|---|---|
| 135 | 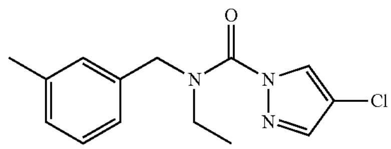 [SMILES: CCN(Cc1cccc(C)c1)C(=O)n1cc(Cl)cn1] | 4-Chloro-N-ethyl-N-(3-methylbenzyl)-1H-pyrazole-1-carboxamide |
| 136 | 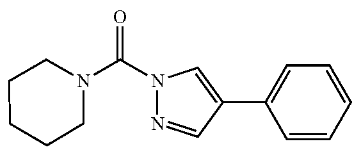 [SMILES: O=C(N1CCCCC1)n1cc(-c2ccccc2)cn1] | (4-Phenyl-1H-pyrazol-1-yl)(piperidin-1-yl)methanone |
| 137 | 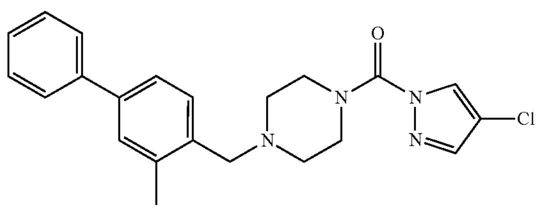 [SMILES: Cc1cc(-c2ccccc2)ccc1CN1CCN(C(=O)n2cc(Cl)cn2)CC1] | (4-chloro-1H-pyrazol-1-yl)(4-((3-methylbiphenyl-4-yl)methyl)piperazin-1-yl)methanone |
| 138 | 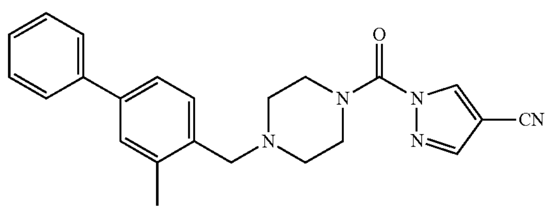 [SMILES: Cc1cc(-c2ccccc2)ccc1CN1CCN(C(=O)n2cc(C#N)cn2)CC1] | 1-(4-((3-methylbiphenyl-4-yl)methyl)piperazine-1-carbonyl)-1H-pyrazole-4-carbonitrile |
| 139 | 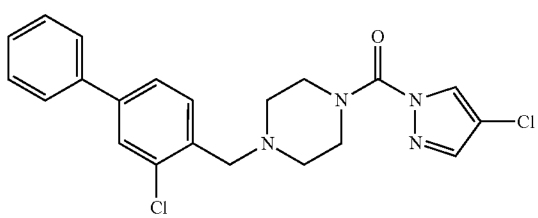 [SMILES: O=C(N1CCN(Cc2ccc(-c3ccccc3)cc2Cl)CC1)n1cc(Cl)cn1] | (4-chloro-1H-pyrazol-1-yl)(4-((3-chlorobiphenyl-4-yl)methyl)piperazin-1-yl)methanone |
| 140 | 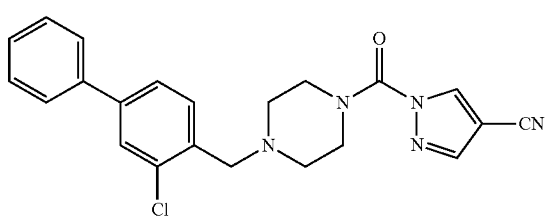 [SMILES: N#Cc1cnn(C(=O)N2CCN(Cc3ccc(-c4ccccc4)cc3Cl)CC2)c1] | 1-(4-((3-Chlorobiphenyl-4-yl)methyl)piperazine-1-carbonyl)-1H-pyrazole-4-carbonitrile |
| 141 | 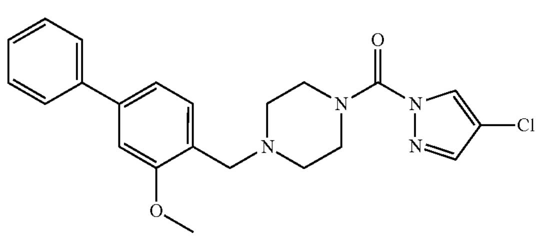 [SMILES: COc1cc(-c2ccccc2)ccc1CN1CCN(C(=O)n2cc(Cl)cn2)CC1] | (4-Chloro-1H-pyrazol-1-yl)(4-((3-methoxybiphenyl-4-yl)methyl)piperazin-1-yl)methanone |

TABLE 1-continued

| Chemical Synthesis Example | Structure | Name |
|---|---|---|
| 142 | 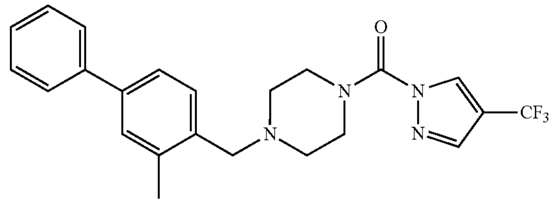 [SMILES: Cc1cc(-c2ccccc2)ccc1CN1CCN(C(=O)n2cc(C(F)(F)F)cn2)CC1] | (4-((3-Methylbiphenyl-4-yl)methyl)piperazin-1-yl)(4-(trifluoromethyl)-1H-pyrazol-1-yl)methanone |
| 143 | 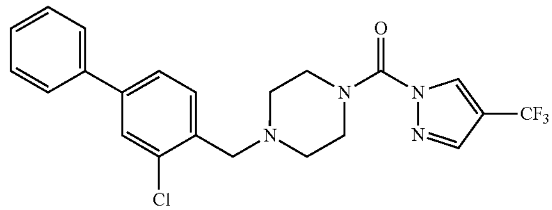 [SMILES: O=C(N1CCN(Cc2ccc(-c3ccccc3)cc2Cl)CC1)n1cc(C(F)(F)F)cn1] | (4-((3-Chlorobiphenyl-4-yl)methyl)piperazin-1-yl)(4-(trifluoromethyl)-1H-pyrazol-1-yl)methanone |
| 144 | 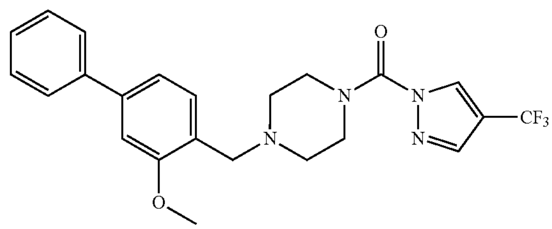 [SMILES: COc1cc(-c2ccccc2)ccc1CN1CCN(C(=O)n2cc(C(F)(F)F)cn2)CC1] | (4-((3-Methoxybiphenyl-4-yl)methyl)piperazin-1-yl)(4-(trifluoromethyl)-1H-pyrazol-1-yl)methanone |
| 145 | 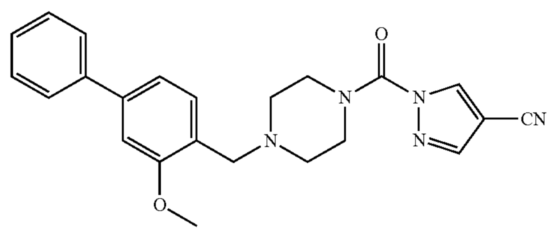 [SMILES: COc1cc(-c2ccccc2)ccc1CN1CCN(C(=O)n2cc(C#N)cn2)CC1] | 1-(4-((3-Methoxybiphenyl-4-yl)methyl)piperazine-1-carbonyl)-1H-pyrazole-4-carbonitrile |
| 146 | 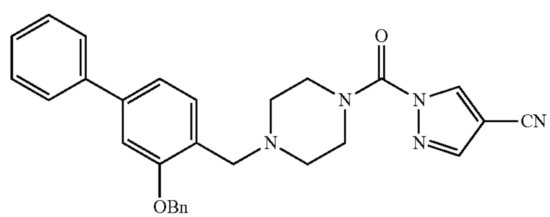 [SMILES: N#Cc1cnn(C(=O)N2CCN(Cc3ccc(-c4ccccc4)cc3OCc3ccccc3)CC2)c1] | 1-(4-((3-(Benzyloxy)biphenyl-4-yl)methyl)piperazine-1-carbonyl)-1H-pyrazole-4-carbonitrile |
| 147 | 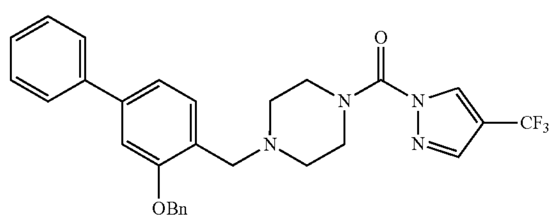 [SMILES: O=C(N1CCN(Cc2ccc(-c3ccccc3)cc2OCc2ccccc2)CC1)n1cc(C(F)(F)F)cn1] | (4-((3-(Benzyloxy)biphenyl-4-yl)methyl)piperazin-1-yl)(4-(trifluoromethyl)-1H-pyrazol-1-yl)methanone |
| 148 | 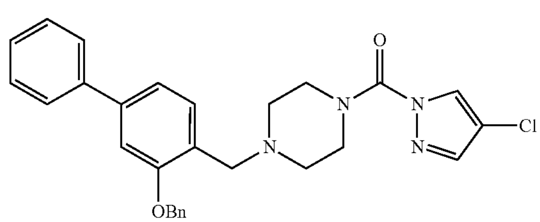 [SMILES: O=C(N1CCN(Cc2ccc(-c3ccccc3)cc2OCc2ccccc2)CC1)n1cc(Cl)cn1] | (4-((3-(Benzyloxy)biphenyl-4-yl)methyl)piperazin-1-yl)(4-chloro-1H-pyrazol-1-yl)methanone |

TABLE 1-continued

| Chemical Synthesis Example | Structure | Name |
|---|---|---|
| 149 | 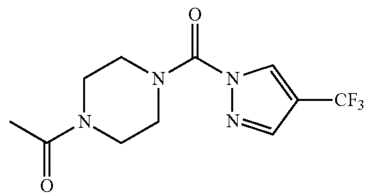 [SMILES: CC(=O)N1CCN(C(=O)n2cc(C(F)(F)F)cn2)CC1] | 1-(4-(4-(Trifluoromethyl)-1H-pyrazole-1-carbonyl)piperazin-1-yl)ethanone |
| 150 | 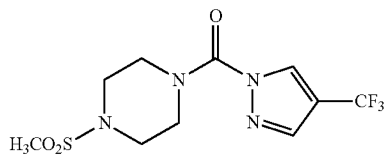 | (4-(Methylsulfonyl)piperazin-1-yl)(4-(trifluoromethyl)-1H-pyrazol-1-yl)methanone |
| 151 | 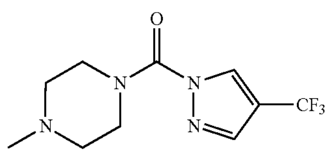 [SMILES: CN1CCN(C(=O)n2cc(C(F)(F)F)cn2)CC1] | (4-Methylpiperazin-1-yl)(4-(trifluoromethyl)-1H-pyrazol-1-yl)methanone |
| 152 | 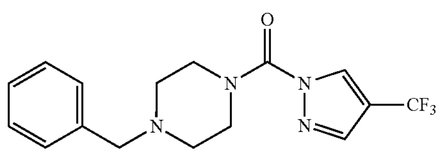 [SMILES: O=C(N1CCN(Cc2ccccc2)CC1)n1cc(C(F)(F)F)cn1] | (4-Benzylpiperazin-1-yl)(4-(trifluoromethyl)-1H-pyrazol-1-yl)methanone |
| 153 | 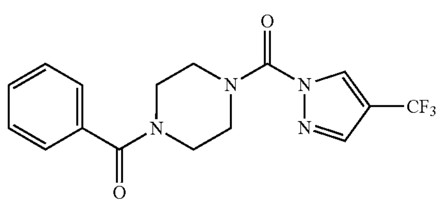 [SMILES: O=C(c1ccccc1)N1CCN(C(=O)n2cc(C(F)(F)F)cn2)CC1] | (4-Benzoylpiperazin-1-yl)(4-(trifluoromethyl)-1H-pyrazol-1-yl)methanone |
| 154 | 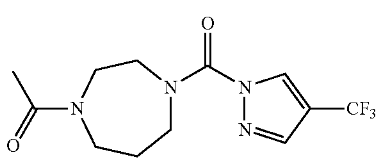 [SMILES: CC(=O)N1CCCN(C(=O)n2cc(C(F)(F)F)cn2)CC1] | 1-(4-(4-(trifluoromethyl)-1H-pyrazole-1-carbonyl)-1,4-diazepan-1-yl)ethanone |
| 155 | 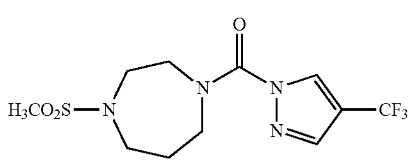 | (4-(Methylsulfonyl)-1,4-diazepan-1-yl)(4-(trifluoromethyl)-1H-pyrazol-1-yl)methanone |
| 156 | 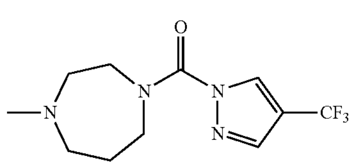 [SMILES: CN1CCCN(C(=O)n2cc(C(F)(F)F)cn2)CC1] | (4-Methyl-1,4-diazepan-1-yl)(4-(trifluoromethyl)-1H-pyrazol-1-yl)methanone |
| 157 | 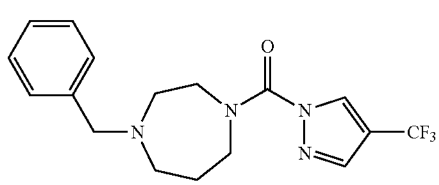 [SMILES: O=C(N1CCCN(Cc2ccccc2)CC1)n1cc(C(F)(F)F)cn1] | (4-Benzyl-1,4-diazepan-1-yl)(4-(trifluoromethyl)-1H-pyrazol-1-yl)methanone |

TABLE 1-continued

| Chemical Synthesis Example | Structure | Name |
|---|---|---|
| 158 | 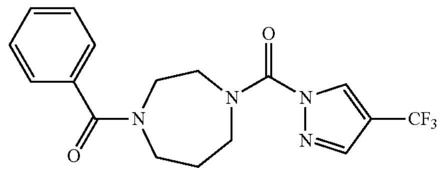 [SMILES: O=C(c1ccccc1)N1CCCN(C(=O)n2cc(C(F)(F)F)cn2)CC1] | (4-Benzoyl-1,4-diazepan-1-yl)(4-(trifluoromethyl)-1H-pyrazol-1-yl)methanone |
| 159 | 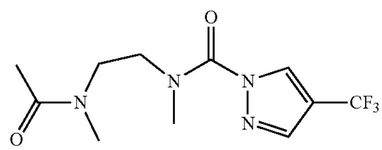 [SMILES: CC(=O)N(C)CCN(C)C(=O)n1cc(C(F)(F)F)cn1] | N-Methyl-N-(2-(N-methylacetamido)ethyl)-4-(trifluoromethyl)-1H-pyrazole-1-carboxamide |
| 160 | 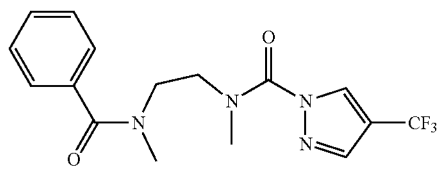 [SMILES: CN(CCN(C)C(=O)n1cc(C(F)(F)F)cn1)C(=O)c1ccccc1] | N-methyl-N-(2-(N-methylbenzamido)ethyl)-4-(trifluoromethyl)-1H-pyrazole-1-carboxamide |
| 161 | 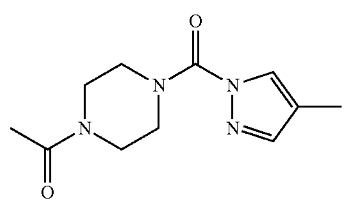 [SMILES: CC(=O)N1CCN(C(=O)n2cc(C)cn2)CC1] | 1-(4-(4-Methyl-1H-pyrazole-1-carbonyl)piperazin-1-yl)ethanone |
| 162 | 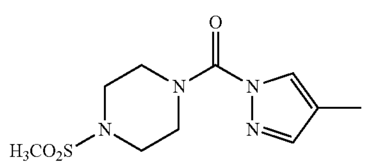 | (4-Methyl-1H-pyrazol-1-yl)(4-(methylsulfonyl)piperazin-1-yl)methanone |
| 163 | 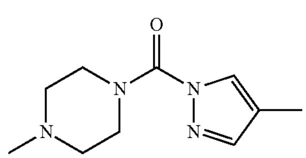 | (4-Methyl-1H-pyrazol-1-yl)(4-methylpiperazin-1-yl)methanone |
| 164 | 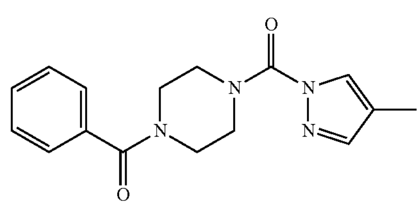 [SMILES: Cc1cnn(C(=O)N2CCN(C(=O)c3ccccc3)CC2)c1] | (4-Benzoylpiperazin-1-yl)(4-methyl-1H-pyrazol-1-yl)methanone |
| 165 | 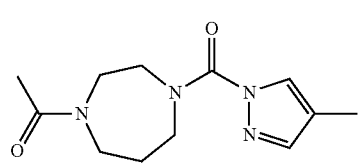 [SMILES: CC(=O)N1CCCN(C(=O)n2cc(C)cn2)CC1] | 1-(4-(4-Methyl-1H-pyrazole-1-carbonyl)-1,4-diazepan-1-yl)ethanone |

TABLE 1-continued

| Chemical Synthesis Example | Structure | Name |
|---|---|---|
| 166 | 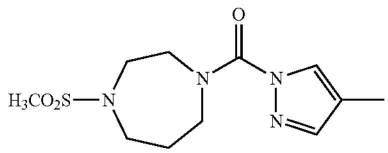 | (4-Methyl-1H-pyrazol-1-yl)(4-(methylsulfonyl)-1,4-diazepan-1-yl)methanone |
| 167 | 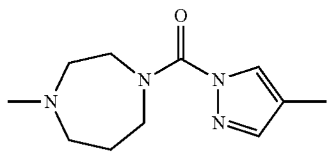 | (4-Methyl-1,4-diazepan-1-yl)(4-methyl-1H-pyrazol-1-yl)methanone |
| 168 | 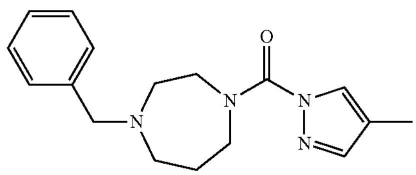 [SMILES: Cc1cnn(C(=O)N2CCCN(Cc3ccccc3)CC2)c1] | (4-Benzyl-1,4-diazepan-1-yl)(4-methyl-1H-pyrazol-1-yl)methanone |
| 169 | 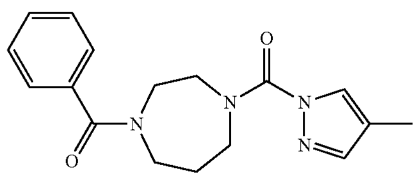 [SMILES: Cc1cnn(C(=O)N2CCCN(C(=O)c3ccccc3)CC2)c1] | (4-Benzoyl-1,4-diazepan-1-yl)(4-methyl-1H-pyrazol-1-yl)methanone |
| 170 | 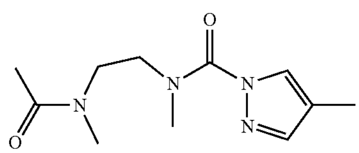 [SMILES: CC(=O)N(C)CCN(C)C(=O)n1cc(C)cn1] | N,4-Dimethyl-N-(2-(N-methylacetamido)ethyl)-1H-pyrazole-1-carboxamide |
| 171 | 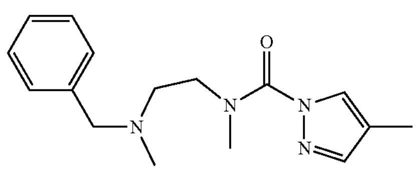 [SMILES: Cc1cnn(C(=O)N(C)CCN(C)Cc2ccccc2)c1] | N-(2-(benzyl(methyl)amino)ethyl)-N,4-dimethyl-1H-pyrazole-1-carboxamide |
| 172 | 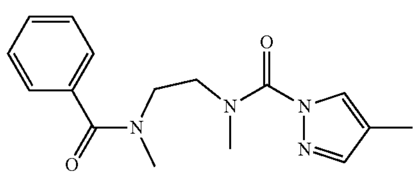 [SMILES: Cc1cnn(C(=O)N(C)CCN(C)C(=O)c2ccccc2)c1] | N,4-Dimethyl-N-(2-(N-methylbenzamido)ethyl)-1H-pyrazole-1-carboxamide |
| 173 | 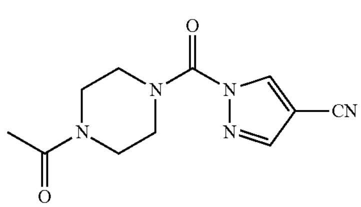 [SMILES: CC(=O)N1CCN(C(=O)n2cc(C#N)cn2)CC1] | 1-(4-Acetylpiperazine-1-carbonyl)-1H-pyrazole-4-carbonitrile |
| 174 | 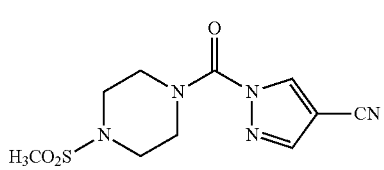 | 1-(4-(Methylsulfonyl)piperazine-1-carbonyl)-1H-pyrazole-4-carbonitrile |

TABLE 1-continued

| Chemical Synthesis Example | Structure | Name |
|---|---|---|
| 175 | 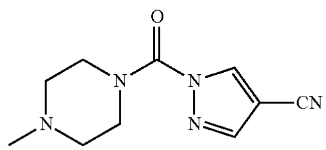 [SMILES: CN1CCN(C(=O)n2cc(C#N)cn2)CC1] | 1-(4-Methylpiperazine-1-carbonyl)-1H-pyrazole-4-carbonitrile |
| 176 | 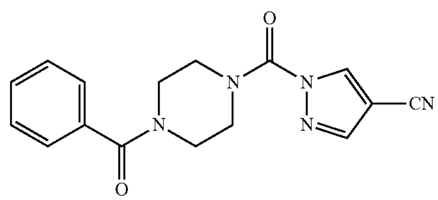 [SMILES: N#Cc1cnn(C(=O)N2CCN(C(=O)c3ccccc3)CC2)c1] | 1-(4-Benzoylpiperazine-1-carbonyl)-1H-pyrazole-4-carbonitrile |
| 177 | 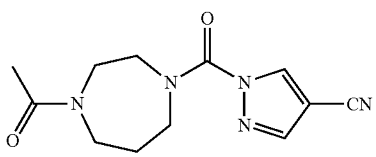 [SMILES: CC(=O)N1CCCN(C(=O)n2cc(C#N)cn2)CC1] | 1-(4-Acetyl-1,4-diazepane-1-carbonyl)-1H-pyrazole-4-carbonitrile |
| 178 | 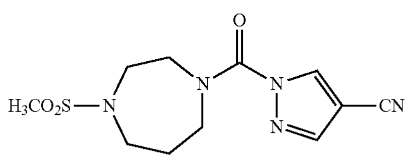 | 1-(4-(Methylsulfonyl)-1,4-diazepane-1-carbonyl)-1H-pyrazole-4-carbonitrile |
| 179 | 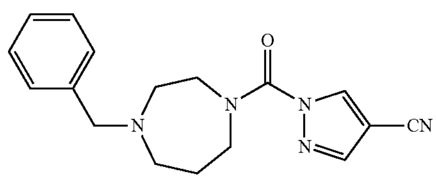 [SMILES: N#Cc1cnn(C(=O)N2CCCN(Cc3ccccc3)CC2)c1] | 1-(4-Benzyl-1,4-diazepane-1-carbnonyl)-1H-pyrazole-4-carbonitrile |
| 180 | 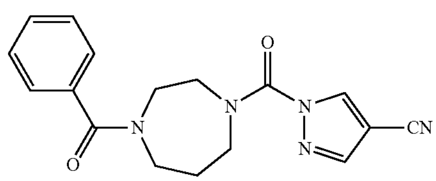 [SMILES: N#Cc1cnn(C(=O)N2CCCN(C(=O)c3ccccc3)CC2)c1] | 1-(4-Benzoyl-1,4-diazepane-1-carbonyl)-1H-pyrazole-4-carbonitrile |
| 181 | 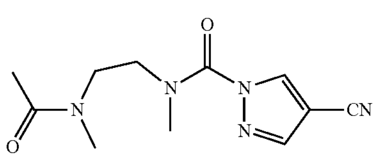 [SMILES: CC(=O)N(C)CCN(C)C(=O)n1cc(C#N)cn1] | 4-Cyano-N-methyl-N-(2-(N-methylacetamido)ethyl)-1H-pyrazole-1-carboxamide |
| 182 | 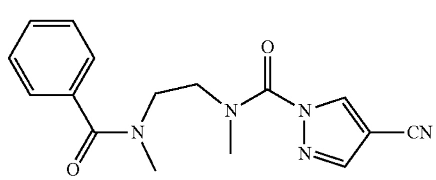 [SMILES: CN(CCN(C)C(=O)n1cc(C#N)cn1)C(=O)c1ccccc1] | 4-Cyano-N-methyl-N-(2-(N-methylbenzamido)ethyl)-1H-pyrazole-1-carboxamide |

TABLE 1-continued

| Chemical Synthesis Example | Structure | Name |
|---|---|---|
| 183 | 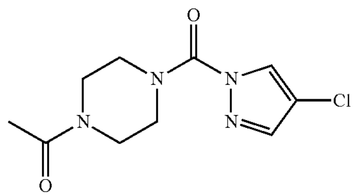 [SMILES: CC(=O)N1CCN(C(=O)n2cc(Cl)cn2)CC1] | 1-(4-(4-Chloro-1H-pyrazole-1-carbonyl)piperazin-1-yl)ethanone |
| 184 | 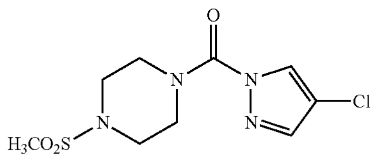 | (4-Chloro-1H-pyrazol-1-yl)(4-(methylsulfonyl)piperazin-1-yl)methanone |
| 185 | 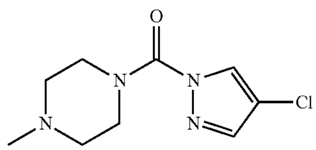 | (4-Chloro-1H-pyrazol-1-yl)(4-methylpiperazin-1-yl)methanone |
| 186 | 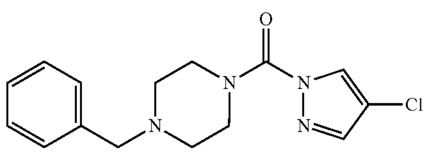 [SMILES: O=C(N1CCN(Cc2ccccc2)CC1)n1cc(Cl)cn1] | (4-Benzylpiperazin-1-yl)(4-chloro-1H-pyrazol-1-yl)methanone |
| 187 | 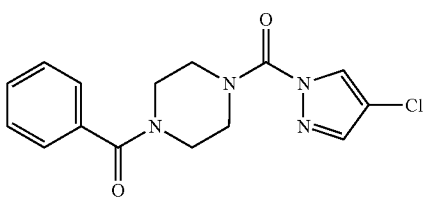 [SMILES: O=C(c1ccccc1)N1CCN(C(=O)n2cc(Cl)cn2)CC1] | (4-Benzoylpiperazin-1-yl)(4-chloro-1H-pyrazol-1-yl)methanone |
| 188 | 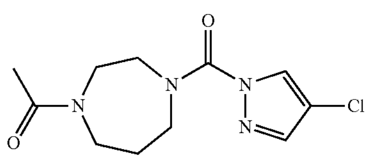 [SMILES: CC(=O)N1CCCN(C(=O)n2cc(Cl)cn2)CC1] | 1-(4-(4-Chloro-1H-pyrazole-1-carbonyl)-1,4-diazepan-1-yl)ethanone |
| 189 | 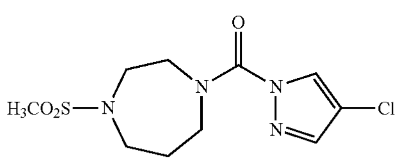 | (4-Chloro-1H-pyrazol-1-yl)(4-(methylsulfonyl)-1,4-diazepan-1-yl)methanone |
| 190 | 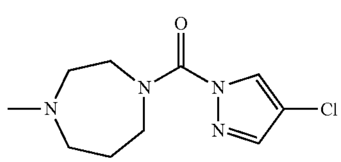 [SMILES: CN1CCCN(C(=O)n2cc(Cl)cn2)CC1] | (4-Chloro-1H-pyrazol-1-yl)(4-methyl-1,4-diazepan-1-yl)methanone |
| 191 | 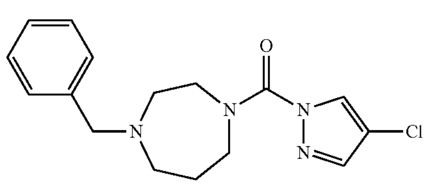 [SMILES: O=C(N1CCCN(Cc2ccccc2)CC1)n1cc(Cl)cn1] | (4-Benzyl-1,4-diazepan-1-yl)(4-chloro-1H-pyrazol-1-yl)methanone |

TABLE 1-continued

| Chemical Synthesis Example | Structure | Name |
|---|---|---|
| 192 | 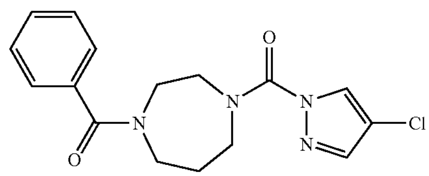 [SMILES: O=C(c1ccccc1)N1CCCN(C(=O)n2cc(Cl)cn2)CC1] | (4-Benzoyl-1,4-diazepan-1-yl)(4-chloro-1H-pyrazol-1-yl)methanone |
| 193 | 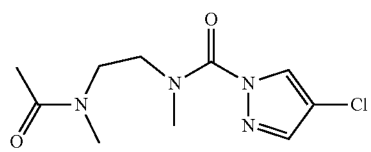 [SMILES: CC(=O)N(C)CCN(C)C(=O)n1cc(Cl)cn1] | 4-Chloro-N-methyl-N-(2-(N-methylacetamido)ethyl)-1H-pyrazole-1-carboxamide |
| 194 | 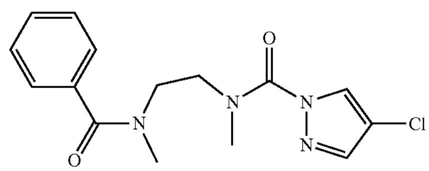 [SMILES: CN(CCN(C)C(=O)n1cc(Cl)cn1)C(=O)c1ccccc1] | 4-Chloro-N-methyl-N-(2-(N-methylbenzamido)ethyl)-1H-pyrazole-1-carboxamide |
| 195 | 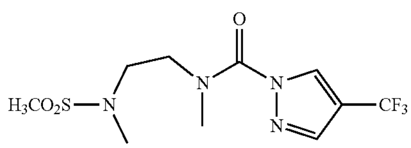 | N-methyl-N-(2-(N-methylmethylsulfonamido)ethyl)-4-(trifluoromethyl)-1H-pyrazole-1-carboxamide |
| 196 | 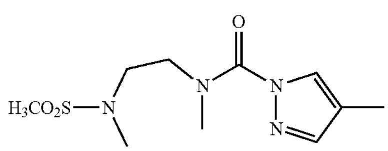 | N,4-dimethyl-N-(2-(N-methylmethylsulfonamido)ethyl)-1H-pyrazole-1-carboxamide |
| 197 | 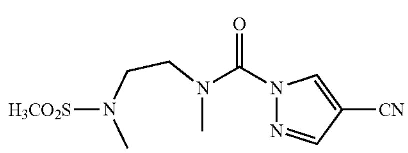 | 4-Cyano-N-methyl-N-(2-(N-methylmethylsulfonamido)ethyl)-1H-pyrazole-1-carboxamide |
| 198 | 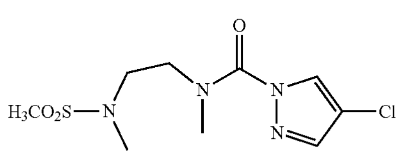 | 4-Chloro-N-methyl-N-(2-(N-methylmethylsulfonamido)ethyl)-1H-pyrazole-1-carboxamide |
| 199 | 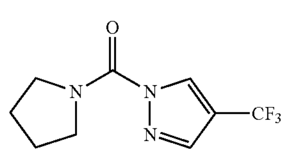 [SMILES: O=C(N1CCCC1)n1cc(C(F)(F)F)cn1] | Pyrrolidin-1-yl(4-(trifluoromethyl)-1H-pyrazol-1-yl)methanone |
| 200 | 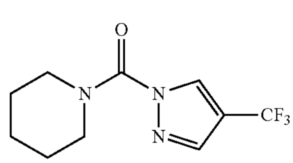 [SMILES: O=C(N1CCCCC1)n1cc(C(F)(F)F)cn1] | Piperidin-1-yl(4-(trifluoromethyl)-1H-pyrazol-1-yl)methanone |

TABLE 1-continued

| Chemical Synthesis Example | Structure | Name |
|---|---|---|
| 201 | 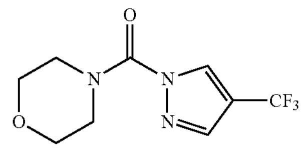 [SMILES: O=C(N1CCOCC1)n1cc(C(F)(F)F)cn1] | Morpholino(4-(trifluoromethyl)-1H-pyrazol-1-yl)methanone |
| 202 | 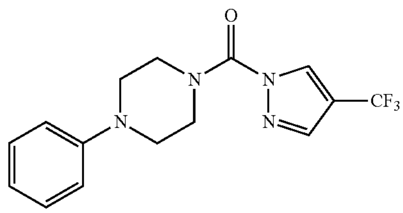 [SMILES: O=C(N1CCN(c2ccccc2)CC1)n1cc(C(F)(F)F)cn1] | (4-Phenylpiperazin-1-yl)(4-(trifluoromethyl)-1H-pyrazol-1-yl)methanone |
| 203 | 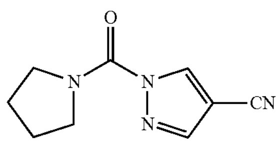 [SMILES: N#Cc1cnn(C(=O)N2CCCC2)c1] | 1-(Pyrrolidine-1-carbonyl)-1H-pyrazole-4-carbonitrile |
| 204 | 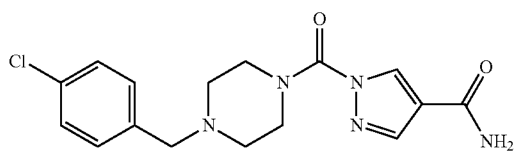 [SMILES: NC(=O)c1cnn(C(=O)N2CCN(Cc3ccc(Cl)cc3)CC2)c1] | 1-(4-(4-Chlorobenzyl)piperazine-1-carbonyl)-1H-pyrazole-4-carboxamide |
| 205 | 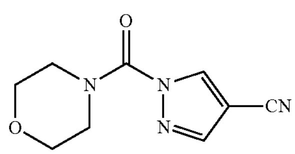 [SMILES: N#Cc1cnn(C(=O)N2CCOCC2)c1] | 1-(Morpholine-4-carbonyl)-1H-pyrazole-4-carbonitrile |
| 206 | 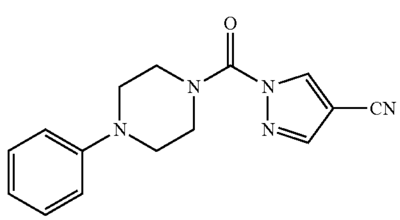 [SMILES: N#Cc1cnn(C(=O)N2CCN(c3ccccc3)CC2)c1] | 1-(4-Phenylpiperazine-1-carbonyl)-1H-pyrazole-4-carbonitrile |
| 207 | 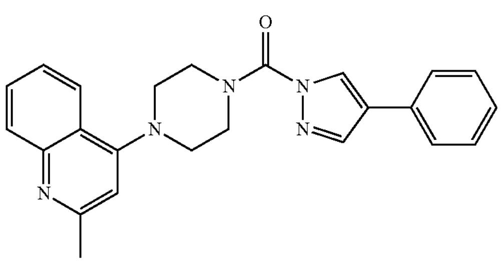 [SMILES: Cc1cc(N2CCN(C(=O)n3cc(-c4ccccc4)cn3)CC2)c2ccccc2n1] | (4-(2-Methylquinolin-4-yl)piperazin-1-yl)(4-phenyl-1H-pyrazol-1-yl)methanone |

TABLE 1-continued

| Chemical Synthesis Example | Structure | Name |
|---|---|---|
| 208 | 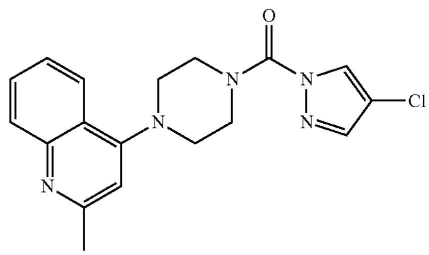 [SMILES: Cc1cc(N2CCN(C(=O)n3cc(Cl)cn3)CC2)c2ccccc2n1] | (4-Chloro-1H-pyrazol-1-yl)(4-(2-methylquinolin-4-yl)piperazin-1-yl)methanone |
| 209 | 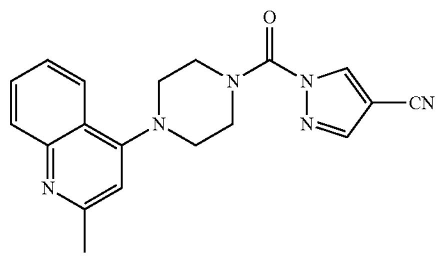 [SMILES: Cc1cc(N2CCN(C(=O)n3cc(C#N)cn3)CC2)c2ccccc2n1] | 1-(4-(2-Methylquinolin-4-yl)piperazine-1-carbonyl)-1H-pyrazole-4-carbonitrile |
| 210 | 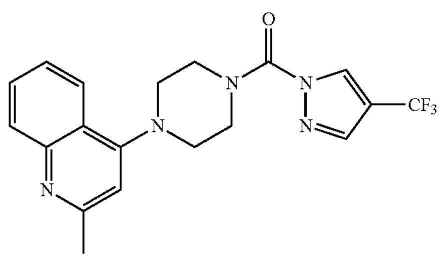 [SMILES: Cc1cc(N2CCN(C(=O)n3cc(C(F)(F)F)cn3)CC2)c2ccccc2n1] | (4-(2-Methylquinolin-4-yl)piperazin-1-yl)(4-(trifluoromethyl)-1H-pyrazol-1-yl)methanone |
| 211 | 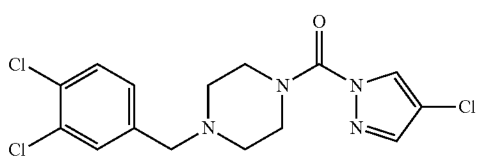 [SMILES: O=C(N1CCN(Cc2ccc(Cl)c(Cl)c2)CC1)n1cc(Cl)cn1] | (4-Chloro-1H-pyrazol-1-yl)(4-(3,4-dichlorobenzyl)piperazin-1-yl)methanone |
| 212 | 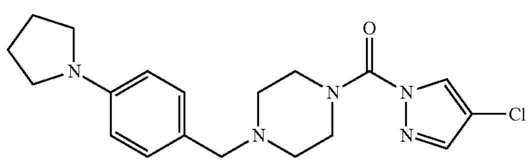 [SMILES: O=C(N1CCN(Cc2ccc(N3CCCC3)cc2)CC1)n1cc(Cl)cn1] | (4-Chloro-1H-pyrazol-1-yl)(4-(4-(pyrrolidin-1-yl)benzyl)piperazin-1-yl)methanone |
| 213 | 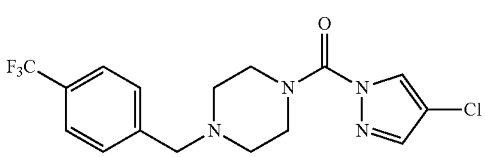 [SMILES: O=C(N1CCN(Cc2ccc(C(F)(F)F)cc2)CC1)n1cc(Cl)cn1] | (4-Chloro-1H-pyrazol-1-yl)(4-(4-(trifluoromethyl)benzyl)piperazin-1-yl)methanone |
| 214 | 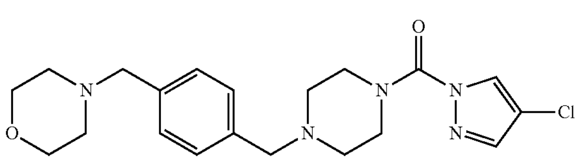 [SMILES: O=C(N1CCN(Cc2ccc(CN3CCOCC3)cc2)CC1)n1cc(Cl)cn1] | (4-Chloro-1H-pyrazol-1-yl)(4-(4-(morpholinomethyl)benzyl)piperazin-1-yl)methanone |

TABLE 1-continued

| Chemical Synthesis Example | Structure | Name |
|---|---|---|
| 215 | 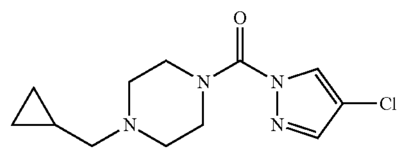 [SMILES: O=C(N1CCN(CC2CC2)CC1)n1cc(Cl)cn1] | (4-Chloro-1H-pyrazol-1-yl)(4-(cyclopropylmethyl)piperazin-1-yl)methanone |
| 216 | 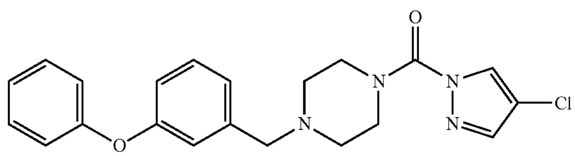 [SMILES: O=C(N1CCN(Cc2cccc(Oc3ccccc3)c2)CC1)n1cc(Cl)cn1] | (4-Chloro-1H-pyrazol-1-yl)(4-(3-phenoxybenzyl)piperazin-1-yl)methanone |
| 217 | 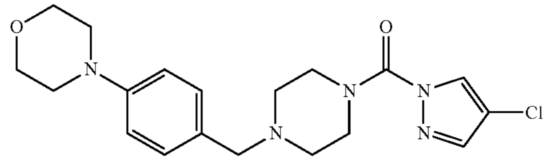 [SMILES: O=C(N1CCN(Cc2ccc(N3CCOCC3)cc2)CC1)n1cc(Cl)cn1] | (4-Chloro-1H-pyrazol-1-yl)(4-(4-morpholinobenzyl)piperazin-1-yl)methanone |
| 218 | 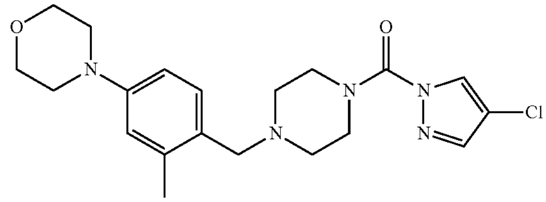 [SMILES: Cc1cc(N2CCOCC2)ccc1CN1CCN(C(=O)n2cc(Cl)cn2)CC1] | (4-Chloro-1H-pyrazol-1-yl)(4-(2-methyl-4-morpholinobenzyl)piperazin-1-yl)methanone |
| 219 | 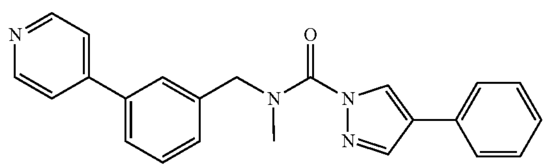 [SMILES: CN(Cc1cccc(-c2ccncc2)c1)C(=O)n1cc(-c2ccccc2)cn1] | N-Methyl-4-phenyl-N-(3-(pyridin-4-yl)benzyl)-1H-pyrazole-1-carboxamide |
| 220 | 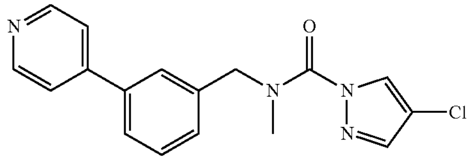 [SMILES: CN(Cc1cccc(-c2ccncc2)c1)C(=O)n1cc(Cl)cn1] | 4-Chloro-N-methyl-N-(3-(pyridin-4-yl)benzyl)-1H-pyrazole-1-carboxamide |
| 221 | 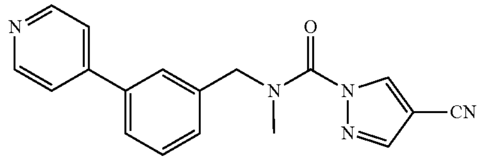 [SMILES: CN(Cc1cccc(-c2ccncc2)c1)C(=O)n1cc(C#N)cn1] | 4-Cyano-N-methyl-N-(3-(pyridin-4-yl)benzyl)-1H-pyrazole-1-carboxamide |
| 222 | 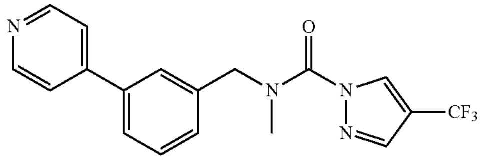 [SMILES: CN(Cc1cccc(-c2ccncc2)c1)C(=O)n1cc(C(F)(F)F)cn1] | N-methyl-N-(3-(pyridin-4-yl)benzyl)-4-(trifluoromethyl)-1H-pyrazole-1-carboxamide |

TABLE 1-continued

| Chemical Synthesis Example | Structure | Name |
|---|---|---|
| 223 | 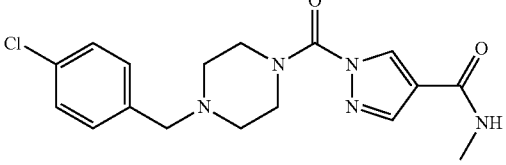 | 1-(4-(4-Chlorobenzyl)piperazine-1-carbonyl)-N-methyl-1H-pyrazole-4-carboxamide |
| 224 | 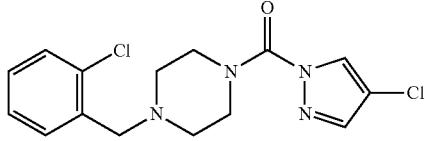 [SMILES: O=C(N1CCN(Cc2ccccc2Cl)CC1)n1cc(Cl)cn1] | (4-Chloro-1H-pyrazol-1-yl)(4-(2-chlorobenzyl)piperazin-1-yl)methanone |
| 225 | 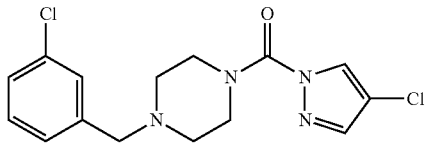 [SMILES: O=C(N1CCN(Cc2cccc(Cl)c2)CC1)n1cc(Cl)cn1] | (4-Chloro-1H-pyrazol-1-yl)(4-(3-chlorobenzyl)piperazin-1-yl)methanone |
| 226 | 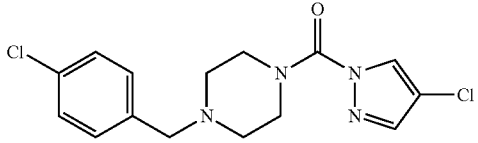 [SMILES: O=C(N1CCN(Cc2ccc(Cl)cc2)CC1)n1cc(Cl)cn1] | (4-chloro-1H-pyrazol-1-yl)(4-(4-chlorobenzyl)piperazin-1-yl)methanone |
| 227 | 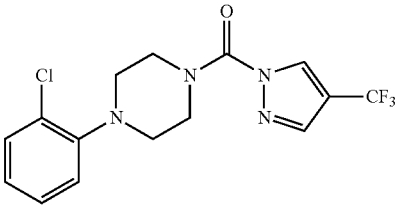 [SMILES: O=C(N1CCN(c2ccccc2Cl)CC1)n1cc(C(F)(F)F)cn1] | (4-(2-Chlorophenyl)piperazin-1-yl)(4-(trifluoromethyl)-1H-pyrazol-1-yl)methanone |
| 228 | 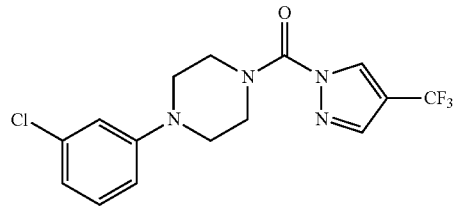 [SMILES: O=C(N1CCN(c2cccc(Cl)c2)CC1)n1cc(C(F)(F)F)cn1] | (4-(3-Chlorophenyl)piperazin-1-yl)(4-(trifluoromethyl)-1H-pyrazol-1-yl)methanone |
| 229 | 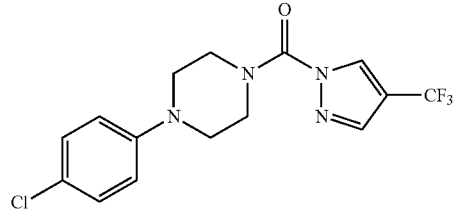 [SMILES: O=C(N1CCN(c2ccc(Cl)cc2)CC1)n1cc(C(F)(F)F)cn1] | (4-(4-Chlorophenyl)piperazin-1-yl)(4-(trifluoromethyl)-1H-pyrazol-1-yl)methanone |
| 230 | 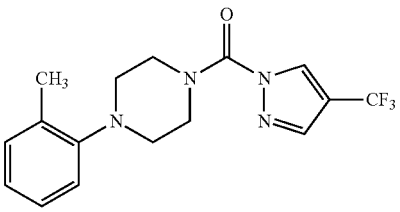 | (4-o-Tolylpiperazin-1-yl)(4-(trifluoromethyl)-1H-pyrazol-1-yl)methanone |

TABLE 1-continued

| Chemical Synthesis Example | Structure | Name |
|---|---|---|
| 231 | 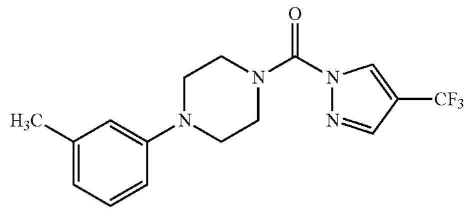 [SMILES: Cc1cccc(N2CCN(C(=O)n3cc(C(F)(F)F)cn3)CC2)c1] | (4-m-Tolylpiperazin-1-yl)(4-(trifluoromethyl)-1H-pyrazol-1-yl)methanone |
| 232 | 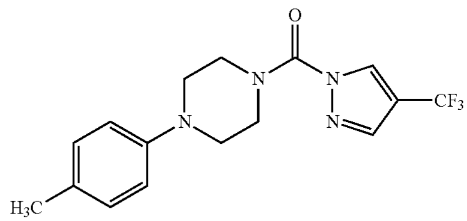 [SMILES: Cc1ccc(N2CCN(C(=O)n3cc(C(F)(F)F)cn3)CC2)cc1] | (4-p-Tolylpiperazin-1-yl)(4-(trifluoromethyl)-1H-pyrazol-1-yl)methanone |
| 233 | 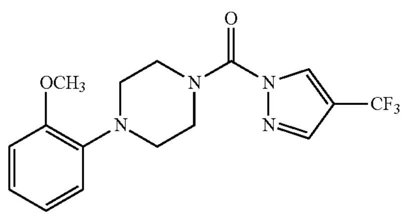 [SMILES: COc1ccccc1N1CCN(C(=O)n2cc(C(F)(F)F)cn2)CC1] | (4-(2-Methoxyphenyl)piperazin-1-yl)(4-(trifluoromethyl)-1H-pyrazol-1-yl)methanone |
| 234 | 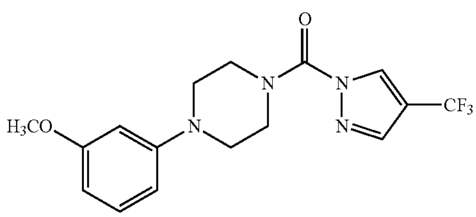 [SMILES: COc1cccc(N2CCN(C(=O)n3cc(C(F)(F)F)cn3)CC2)c1] | (4-(3-Methoxyphenyl)piperazin-1-yl)(4-(trifluoromethyl)-1H-pyrazol-1-yl)methanone |
| 235 | 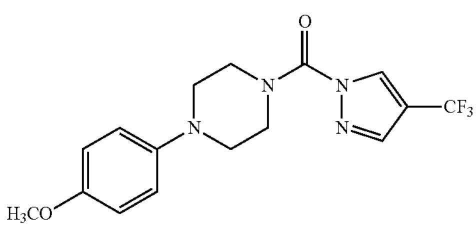 [SMILES: COc1ccc(N2CCN(C(=O)n3cc(C(F)(F)F)cn3)CC2)cc1] | (4-(4-Methoxyphenyl)piperazin-1-yl)(4-(trifluoromethyl)-1H-pyrazol-1-yl)methanone |
| 236 | 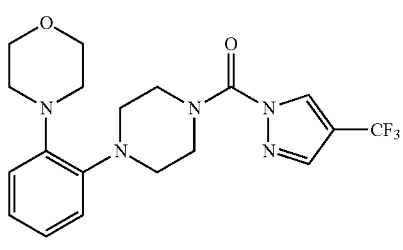 [SMILES: O=C(N1CCN(c2ccccc2N2CCOCC2)CC1)n1cc(C(F)(F)F)cn1] | (4-(2-Morpholinophenyl)piperazin-1-yl)(4-(trifluoromethyl)-1H-pyrazol-1-yl)methanone |
| 237 | 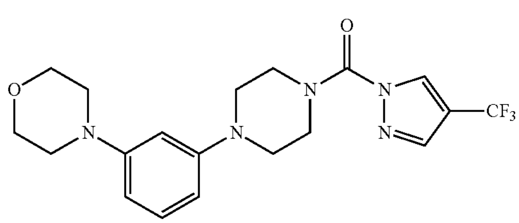 [SMILES: O=C(N1CCN(c2cccc(N3CCOCC3)c2)CC1)n1cc(C(F)(F)F)cn1] | (4-(3-Morpholinophenyl)piperazin-1-yl)(4-(trifluoromethyl)-1H-pyrazol-1-yl)methanone |

TABLE 1-continued

| Chemical Synthesis Example | Structure | Name |
|---|---|---|
| 238 | 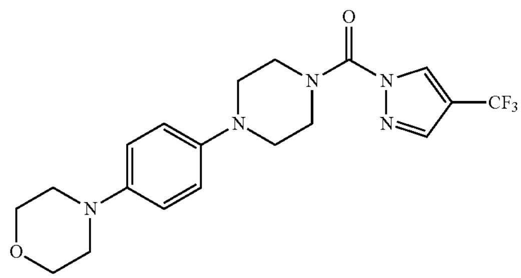 [SMILES: O=C(N1CCN(c2ccc(N3CCOCC3)cc2)CC1)n1cc(C(F)(F)F)cn1] | (4-(4-Morpholinophenyl)piperazin-1-yl)(4-(trifluoromethyl)-1H-pyrazol-1-yl)methanone |
| 239 | 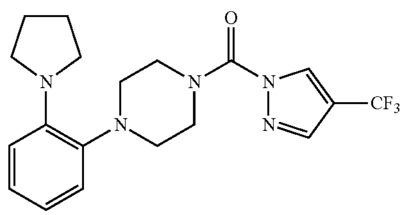 [SMILES: O=C(N1CCN(c2ccccc2N2CCCC2)CC1)n1cc(C(F)(F)F)cn1] | (4-(2-(Pyrrolidin-1-yl)phenyl)piperazin-1-yl)(4-(trifluoromethyl)-1H-pyrazol-1-yl)methanone |
| 240 | 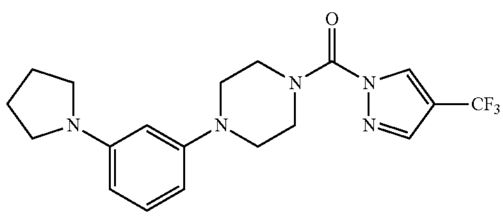 [SMILES: O=C(N1CCN(c2cccc(N3CCCC3)c2)CC1)n1cc(C(F)(F)F)cn1] | (4-(3-(Pyrrolidin-1-yl)phenyl)piperazin-1-yl)(4-(trifluoromethyl)-1H-pyrazol-1-yl)methanone |
| 241 | 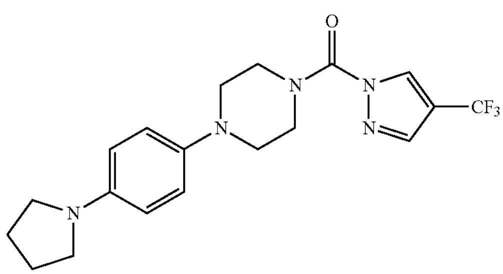 [SMILES: O=C(N1CCN(c2ccc(N3CCCC3)cc2)CC1)n1cc(C(F)(F)F)cn1] | (4-(4-(Pyrrolidin-1-yl)phenyl)piperazin-1-yl)(4-(trifluoromethyl)-1H-pyrazol-1-yl)methanone |
| 242 | 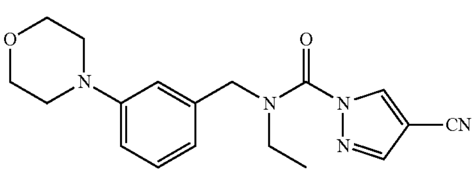 [SMILES: CCN(Cc1cccc(N2CCOCC2)c1)C(=O)n1cc(C#N)cn1] | 4-Cyano-N-ethyl-N-(3-morpholinobenzyl)-1H-pyrazole-1-carboxamide |
| 243 | 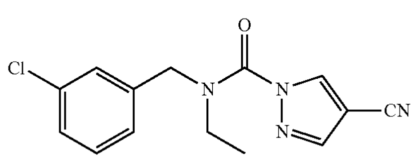 [SMILES: CCN(Cc1cccc(Cl)c1)C(=O)n1cc(C#N)cn1] | N-(3-Chlorobenzyl)-4-cyano-N-ethyl-1H-pyrazole-1-carboxamide |
| 244 | 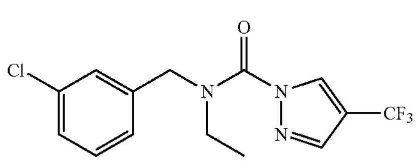 [SMILES: CCN(Cc1cccc(Cl)c1)C(=O)n1cc(C(F)(F)F)cn1] | N-(3-Chlorobenzyl)-N-ethyl-4-(trifluoromethyl)-1H-pyrazole-1-carboxamide |

TABLE 1-continued

| Chemical Synthesis Example | Structure | Name |
|---|---|---|
| 245 | 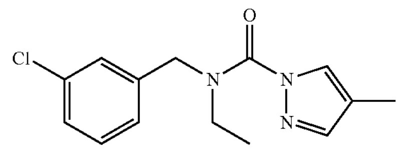 [SMILES: CCN(Cc1cccc(Cl)c1)C(=O)n1cc(C)cn1] | N-(3-chlorobenzyl)-N-ethyl-4-methyl-1H-pyrazole-1-carboxamide |
| 246 | 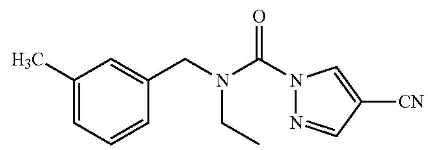 [SMILES: CCN(Cc1cccc(C)c1)C(=O)n1cc(C#N)cn1] | 4-Cyano-N-ethyl-N-(3-methylbenzyl)-1H-pyrazole-1-carboxamide |
| 247 | 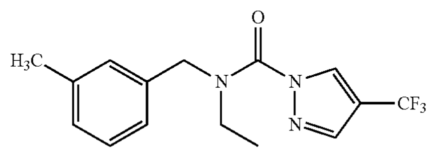 [SMILES: CCN(Cc1cccc(C)c1)C(=O)n1cc(C(F)(F)F)cn1] | N-Ethyl-N-(3-methylbenzyl)-4-(trifluoromethyl)-1H-pyrazole-1-carboxamide |
| 248 | 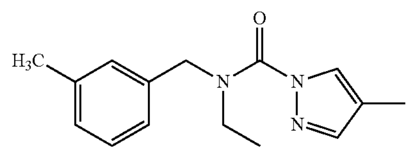 | N-ethyl-4-methyl-N-(3-methylbenzyl)-1H-pyrazole-1-carboxamide |
| 249 | 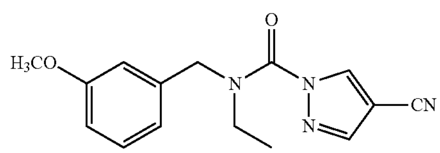 [SMILES: CCN(Cc1cccc(OC)c1)C(=O)n1cc(C#N)cn1] | 4-Cyano-N-ethyl-N-(3-methoxybenzyl)-1H-pyrazole-1-carboxamide |
| 250 | 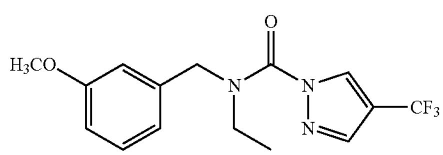 [SMILES: CCN(Cc1cccc(OC)c1)C(=O)n1cc(C(F)(F)F)cn1] | N-Ethyl-N-(3-methoxybenzyl)-4-(trifluoromethyl)-1H-pyrazole-1-carboxamide |
| 251 | 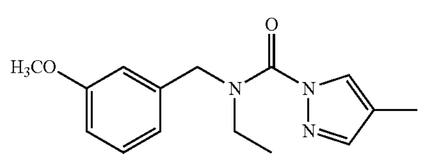 [SMILES: CCN(Cc1cccc(OC)c1)C(=O)n1cc(C)cn1] | N-Ethyl-N-(3-methoxybenzyl)-4-methyl-1H-pyrazole-1-carboxamide |
| 252 | 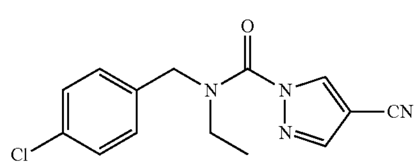 [SMILES: CCN(Cc1ccc(Cl)cc1)C(=O)n1cc(C#N)cn1] | N-(4-Chlorobenzyl)-4-cyano-N-ethyl-1H-pyrazole-1-carboxamide |
| 253 | 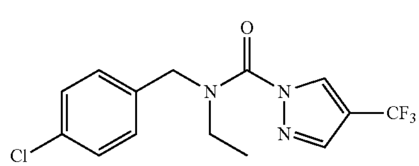 [SMILES: CCN(Cc1ccc(Cl)cc1)C(=O)n1cc(C(F)(F)F)cn1] | N-(4-Chlorobenzyl)-N-ethyl-4-(trifluoromethyl)-1H-pyrazole-1-carboxamide |

TABLE 1-continued

| Chemical Synthesis Example | Structure | Name |
|---|---|---|
| 254 | 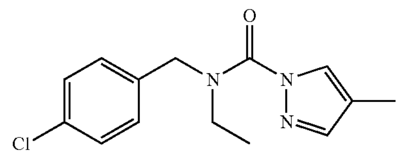 [SMILES: CCN(Cc1ccc(Cl)cc1)C(=O)n1cc(C)cn1] | N-(4-Chlorobenzyl)-N-ethyl-4-methyl-1H-pyrazole-1-carboxamide |
| 255 | 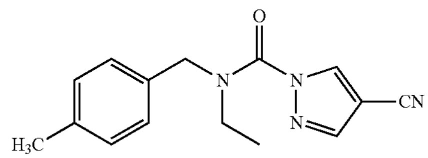 | 4-Cyano-N-ethyl-N-(4-methylbenzyl)-1H-pyrazole-1-carboxamide |
| 256 | 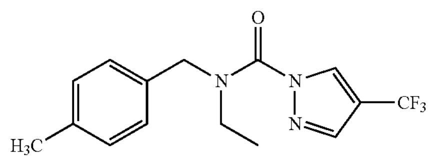 [SMILES: CCN(Cc1ccc(C)cc1)C(=O)n1cc(C(F)(F)F)cn1] | N-Ethyl-N-(4-methylbenzyl)-4-(trifluoromethyl)-1H-pyrazole-1-carboxamide |
| 257 | 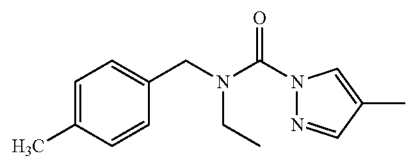 | N-Ethyl-4-methyl-N-(4-methylbenzyl)-1H-pyrazole-1-carboxamide |
| 258 | 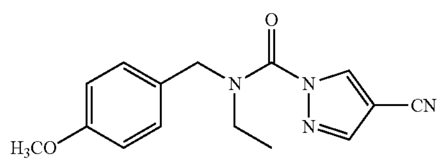 [SMILES: CCN(Cc1ccc(OC)cc1)C(=O)n1cc(C#N)cn1] | 4-Cyano-N-ethyl-N-(4-methoxybenzyl)-1H-pyrazole-1-carboxamide |
| 259 | 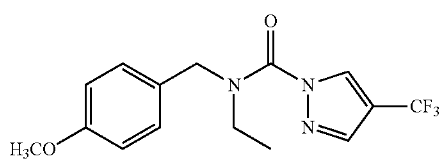 [SMILES: CCN(Cc1ccc(OC)cc1)C(=O)n1cc(C(F)(F)F)cn1] | N-Ethyl-N-(4-methoxybenzyl)-4-(trifluoromethyl)-1H-pyrazole-1-carboxamide |
| 260 | 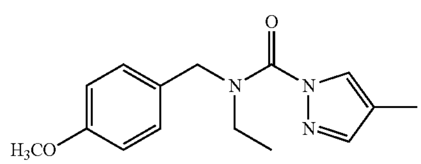 [SMILES: CCN(Cc1ccc(OC)cc1)C(=O)n1cc(C)cn1] | N-Ethyl-N-(4-methoxybenzyl)-4-(trifluoromethyl)-1H-pyrazole-1-carboxamide |
| 261 | 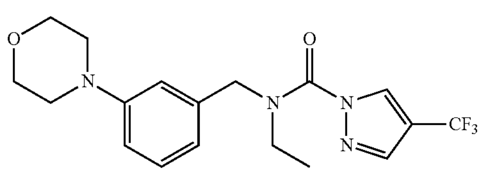 [SMILES: CCN(Cc1cccc(N2CCOCC2)c1)C(=O)n1cc(C(F)(F)F)cn1] | N-Ethyl-N-(3-morpholinobenzyl)-4-(trifluoromethyl)-1H-pyrazole-1-carboxamide |
| 262 | 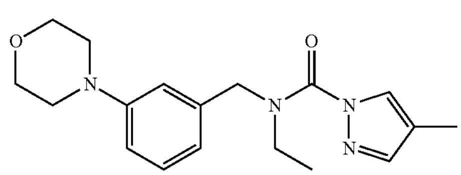 [SMILES: CCN(Cc1cccc(N2CCOCC2)c1)C(=O)n1cc(C)cn1] | N-Ethyl-4-methyl-N-(3-morpholinobenzyl)-1H-pyrazole-1-carboxamide |

TABLE 1-continued

| Chemical Synthesis Example | Structure | Name |
|---|---|---|
| 263 | 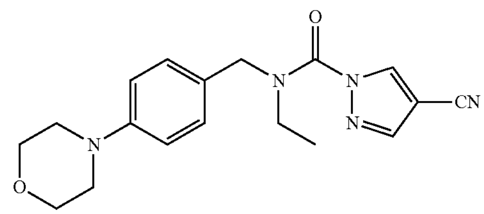 [SMILES: CCN(Cc1ccc(N2CCOCC2)cc1)C(=O)n1cc(C#N)cn1] | 4-Cyano-N-ethyl-N-(4-morpholinobenzyl)-1H-pyrazole-1-carboxamide |
| 264 | 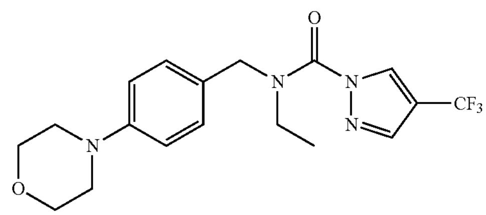 [SMILES: CCN(Cc1ccc(N2CCOCC2)cc1)C(=O)n1cc(C(F)(F)F)cn1] | N-Ethyl-N-(4-morpholinobenzyl)-4-(trifluoromethyl)-1H-pyrazole-1-carboxamide |
| 265 | 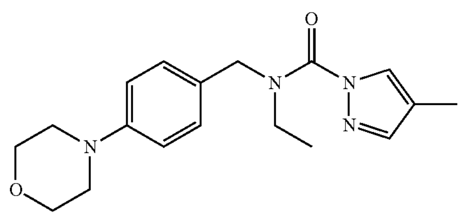 [SMILES: CCN(Cc1ccc(N2CCOCC2)cc1)C(=O)n1cc(C)cn1] | N-Ethyl-4-methyl-N-(4-morpholinobenzyl)-1H-pyrazole-1-carboxamide |
| 266 | 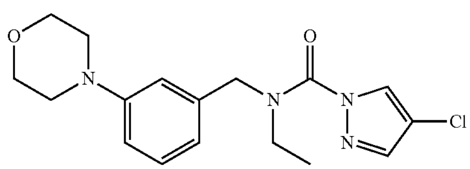 [SMILES: CCN(Cc1cccc(N2CCOCC2)c1)C(=O)n1cc(Cl)cn1] | 4-Chloro-N-ethyl-N-(3-morpholinobenzyl)-1H-pyrazole-1-carboxamide |
| 267 | 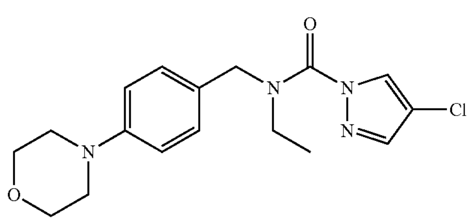 [SMILES: CCN(Cc1ccc(N2CCOCC2)cc1)C(=O)n1cc(Cl)cn1] | 4-Chloro-N-ethyl-N-(4-morpholinobenzyl)-1H-pyrazole-1-carboxamide |
| 268 | 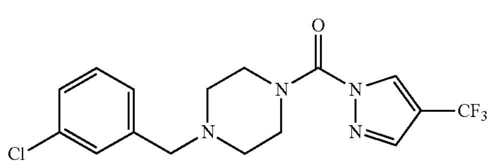 [SMILES: O=C(N1CCN(Cc2cccc(Cl)c2)CC1)n1cc(C(F)(F)F)cn1] | (4-(3-Chlorobenzyl)piperazin-1-yl)(4-(trifluoromethyl)-1H-pyrazol-1-yl)methanone |
| 269 | 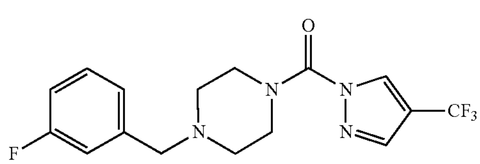 [SMILES: O=C(N1CCN(Cc2cccc(F)c2)CC1)n1cc(C(F)(F)F)cn1] | (4-(3-Fluorobenzyl)piperazin-1-yl)(4-(trifluoromethyl)-1H-pyrazol-1-yl)methanone |
| 270 | 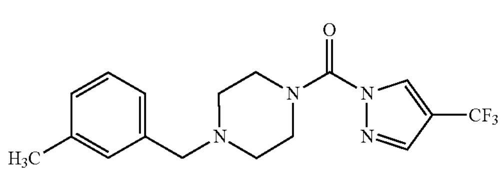 [SMILES: Cc1cccc(CN2CCN(C(=O)n3cc(C(F)(F)F)cn3)CC2)c1] | (4-(3-Methylbenzyl)piperazin-1-yl)(4-(trifluoromethyl)-1H-pyrazol-1-yl)methanone |

TABLE 1-continued

| Chemical Synthesis Example | Structure | Name |
|---|---|---|
| 271 | 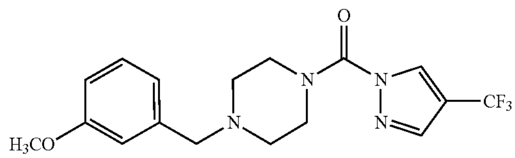 [SMILES: COc1cccc(CN2CCN(C(=O)n3cc(C(F)(F)F)cn3)CC2)c1] | (4-(3-Methoxybenzyl)piperazin-1-yl)(4-(trifluoromethyl)-1H-pyrazol-1-yl)methanone |
| 272 | 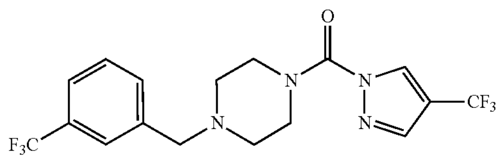 [SMILES: O=C(N1CCN(Cc2cccc(C(F)(F)F)c2)CC1)n1cc(C(F)(F)F)cn1] | (4-(Trifluoromethyl)-1H-pyrazol-1-yl)(4-(3-(trifluoromethyl)benzyl)piperazin-1-yl)methanone |
| 273 | 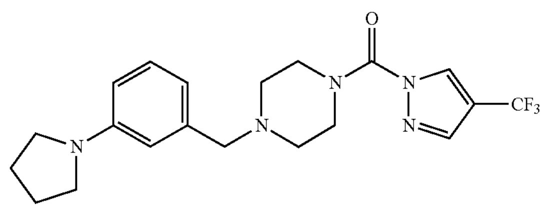 [SMILES: O=C(N1CCN(Cc2cccc(N3CCCC3)c2)CC1)n1cc(C(F)(F)F)cn1] | (4-(3-(Pyrrolidin-1-yl)benzyl)piperazin-1-yl)(4-(trifluoromethyl)-1H-pyrazol-1-yl)methanone |
| 274 | 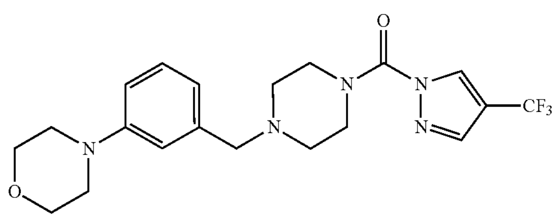 [SMILES: O=C(N1CCN(Cc2cccc(N3CCOCC3)c2)CC1)n1cc(C(F)(F)F)cn1] | (4-(3-Morpholinobenzyl)piperazin-1-yl)(4-(trifluoromethyl)-1H-pyrazol-1-yl)methanone |
| 275 | 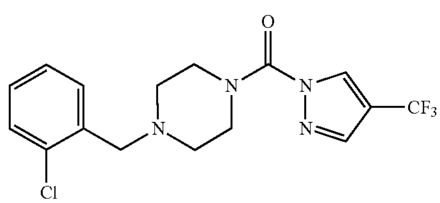 [SMILES: O=C(N1CCN(Cc2ccccc2Cl)CC1)n1cc(C(F)(F)F)cn1] | (4-(2-Chlorobenzyl)piperazin-1-yl)(4-(trifluoromethyl)-1H-pyrazol-1-yl)methanone |
| 276 | 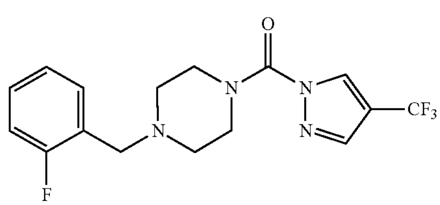 [SMILES: O=C(N1CCN(Cc2ccccc2F)CC1)n1cc(C(F)(F)F)cn1] | (4-(2-Fluorobenzyl)piperazin-1-yl)(4-(trifluoromethyl)-1H-pyrazol-1-yl)methanone |
| 277 | 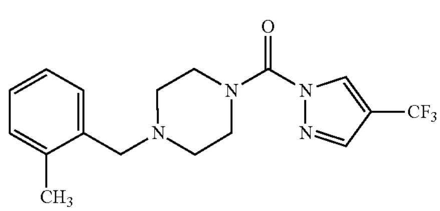 [SMILES: Cc1ccccc1CN1CCN(C(=O)n2cc(C(F)(F)F)cn2)CC1] | (4-(2-Methylbenzyl)piperazin-1-yl)(4-(trifluoromethyl)-1H-pyrazol-1-yl)methanone |

TABLE 1-continued

| Chemical Synthesis Example | Structure | Name |
|---|---|---|
| 278 | 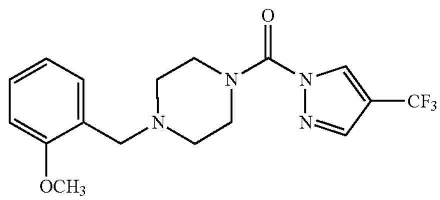 [SMILES: COc1ccccc1CN1CCN(C(=O)n2cc(C(F)(F)F)cn2)CC1] | (4-(2-Methoxybenzyl)piperazin-1-yl)(4-(trifluoromethyl)-1H-pyrazol-1-yl)methanone |
| 279 | 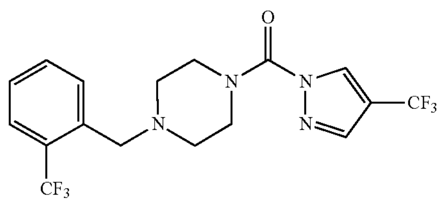 [SMILES: O=C(N1CCN(Cc2ccccc2C(F)(F)F)CC1)n1cc(C(F)(F)F)cn1] | (4-(Trifluoromethyl)-1H-pyrazol-1-yl)(4-(2-(trifluoromethyl)benzyl)piperazin-1-yl)methanone |
| 280 | 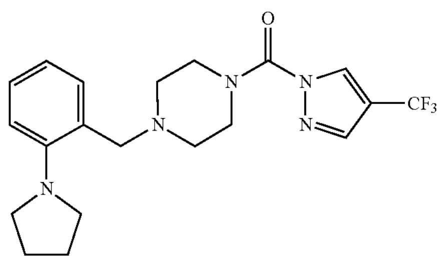 [SMILES: O=C(N1CCN(Cc2ccccc2N2CCCC2)CC1)n1cc(C(F)(F)F)cn1] | (4-(2-(Pyrrolidin-1-yl)benzyl)piperazin-1-yl)(4-(trifluoromethyl)-1H-pyrazol-1-yl)methanone |
| 281 | 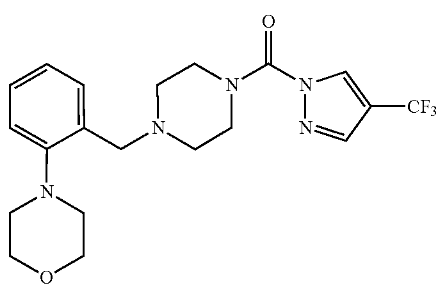 [SMILES: O=C(N1CCN(Cc2ccccc2N2CCOCC2)CC1)n1cc(C(F)(F)F)cn1] | (4-(2-Morpholinobenzyl)piperazin-1-yl)(4-(trifluoromethyl)-1H-pyrazol-1-yl)methanone |
| 282 | 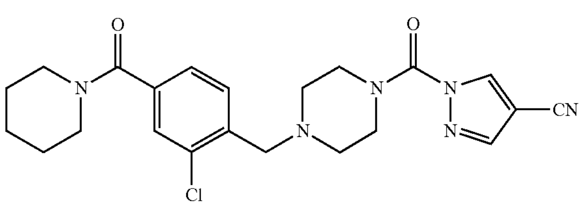 | 1-(4-(2-Chloro-4-(piperidine-1-carbonyl)benzyl)piperazine-1-carbonyl)-1H-pyrazole-4-carbonitrile |
| 283 | 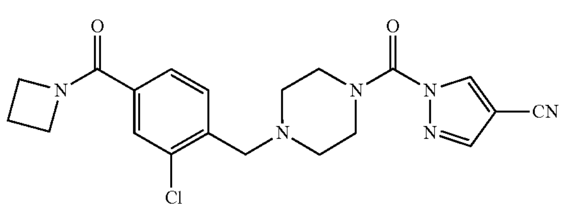 [SMILES: N#Cc1cnn(C(=O)N2CCN(Cc3ccc(C(=O)N4CCC4)cc3Cl)CC2)c1] | 1-(4-(4-(Azetidine-1-carbonyl)-2-chlorobenzyl)piperazine-1-carbonyl)-1H-pyrazole-4-carbonitrile |
| 284 | 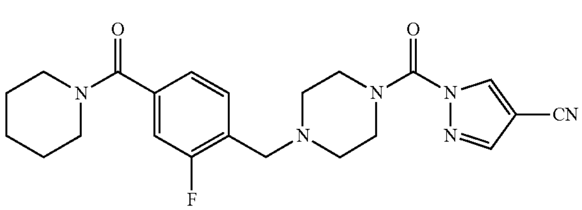 [SMILES: N#Cc1cnn(C(=O)N2CCN(Cc3ccc(C(=O)N4CCCCC4)cc3F)CC2)c1] | 1-(4-(2-Fluoro-4-(piperidine-1-carbonyl)benzyl)piperazine-1-carbonyl)-1H-pyrazole-4-carbonitrile |

TABLE 1-continued

| Chemical Synthesis Example | Structure | Name |
|---|---|---|
| 285 | 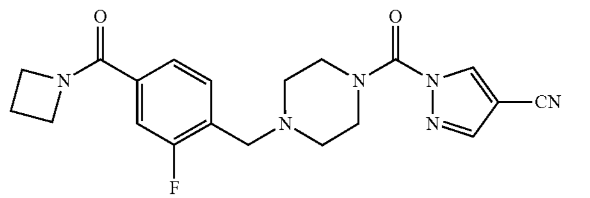 [SMILES: N#Cc1cnn(C(=O)N2CCN(Cc3ccc(C(=O)N4CCC4)cc3F)CC2)c1] | 1-(4-(4-(Azetidine-1-carbonyl)-2-fluorobenzyl)piperazine-1-carbonyl)-1H-pyrazole-4-carbonitrile |
| 286 | 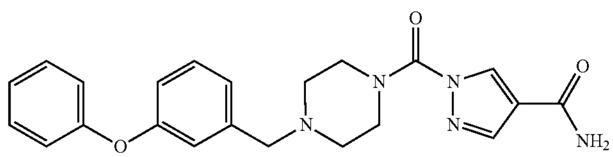 [SMILES: NC(=O)c1cnn(C(=O)N2CCN(Cc3cccc(Oc4ccccc4)c3)CC2)c1] | 1-(4-(3-Phenoxybenzyl)piperazine-1-carbonyl)-1H-pyrazole-4-carboxamide |
| 287 | 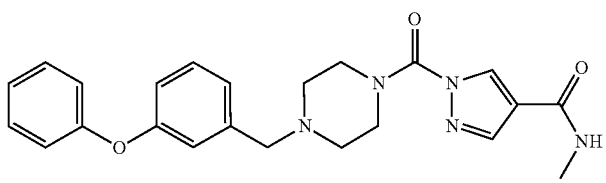 [SMILES: CNC(=O)c1cnn(C(=O)N2CCN(Cc3cccc(Oc4ccccc4)c3)CC2)c1] | N-Methyl-1-(4-(3-phenoxybenzyl)piperazine-1-carbonyl)-1H-pyrazole-4-carboxamide |
| 288 | 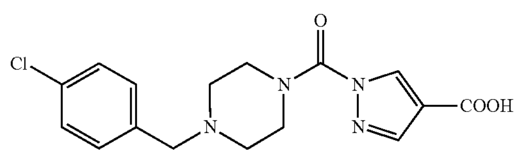 [SMILES: O=C(O)c1cnn(C(=O)N2CCN(Cc3ccc(Cl)cc3)CC2)c1] | 1-(4-(4-Chlorobenzyl)piperazine-1-carbonyl)-1H-pyrazole-4-carboxylic acid |
| 289 | 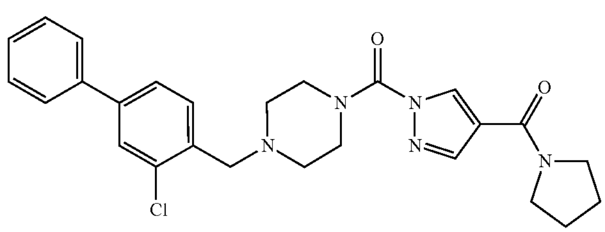 [SMILES: O=C(c1cnn(C(=O)N2CCN(Cc3ccc(-c4ccccc4)cc3Cl)CC2)c1)N1CCCC1] | (4-((3-Chlorobiphenyl-4-yl)methyl)piperazin-1-yl)(4-(pyrrolidine-1-carbonyl)-1H-pyrazol-1-yl)methanone |
| 290 | 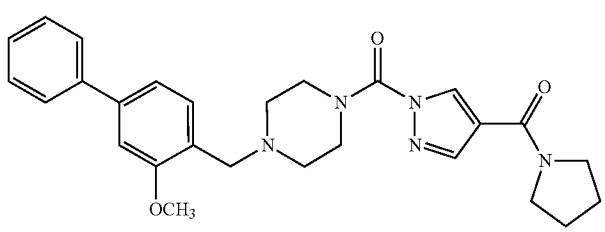 [SMILES: COc1cc(-c2ccccc2)ccc1CN1CCN(C(=O)n2cc(C(=O)N3CCCC3)cn2)CC1] | (4-((3-Methoxybiphenyl-4-yl)methyl)piperazin-1-yl)(4-(pyrrolidine-1-carbonyl)-1H-pyrazol-1-yl)methanone |
| 291 | 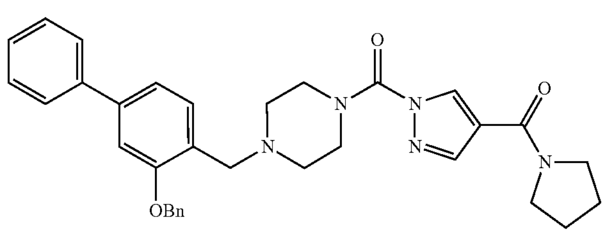 [SMILES: O=C(c1cnn(C(=O)N2CCN(Cc3ccc(-c4ccccc4)cc3OCc3ccccc3)CC2)c1)N1CCCC1] | (4-((3-(Benzyloxy)biphenyl-4-yl)methyl)piperazin-1-yl)(4-(pyrrolidine-1-carbonyl)-1H-pyrazol-1-yl)methanone |

TABLE 1-continued

| Chemical Synthesis Example | Structure | Name |
|---|---|---|
| 292 | 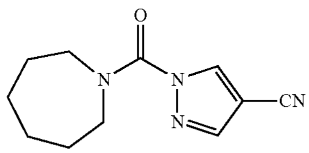 [SMILES: N#Cc1cnn(C(=O)N2CCCCCC2)c1] | 1-(Azepane-1-carbonyl)-1H-pyrazole-4-carbonitrile |
| 293 | 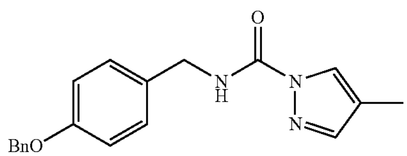 [SMILES: Cc1cnn(C(=O)NCc2ccc(OCc3ccccc3)cc2)c1] | N-(4-(Benzyloxy)benzyl)-4-methyl-1H-pyrazole-1-carboxamide |
| 294 | 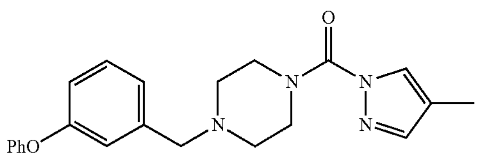 [SMILES: Cc1cnn(C(=O)N2CCN(Cc3cccc(Oc4ccccc4)c3)CC2)c1] | (4-Methyl-1H-pyrazol-1-yl)(4-(3-phenoxybenzyl)piperazin-1-yl)methanone |
| 295 | 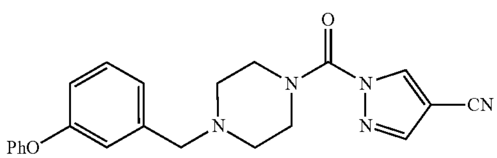 [SMILES: N#Cc1cnn(C(=O)N2CCN(Cc3cccc(Oc4ccccc4)c3)CC2)c1] | 1-(4-(3-Phenoxybenzyl)piperazine-1-carbonyl)-1H-pyrazole-4-carbonitrile |
| 296 | 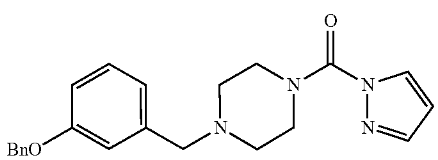 [SMILES: O=C(N1CCN(Cc2cccc(OCc3ccccc3)c2)CC1)n1cccn1] | (4-(3-(Benzyloxy)benzyl)piperazin-1-yl)(1H-pyrazol-1-yl)methanone |
| 297 | 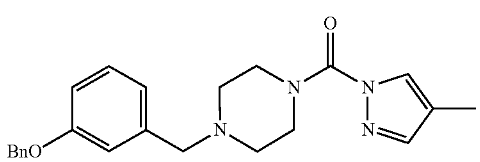 [SMILES: Cc1cnn(C(=O)N2CCN(Cc3cccc(OCc4ccccc4)c3)CC2)c1] | (4-(3-(Benzyloxy)benzyl)piperazin-1-yl)(4-methyl-1H-pyrazol-1-yl)methanone |
| 298 | 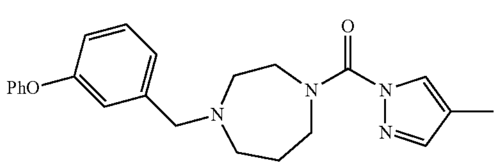 [SMILES: Cc1cnn(C(=O)N2CCCN(Cc3cccc(Oc4ccccc4)c3)CC2)c1] | (4-Methyl-1H-pyrazol-1-yl)(4-(3-phenoxybenzyl)-1,4-diazepan-1-yl)methanone |
| 299 | 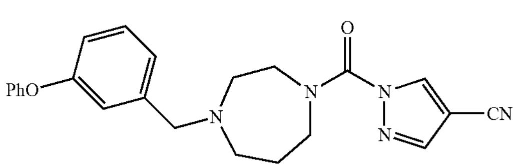 [SMILES: N#Cc1cnn(C(=O)N2CCCN(Cc3cccc(Oc4ccccc4)c3)CC2)c1] | 1-(4-(3-Phenoxybenzyl)-1,4-diazepane-1-carbonyl)-1H-pyrazole-4-carbonitrile |
| 300 | 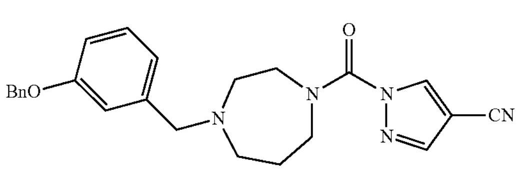 [SMILES: N#Cc1cnn(C(=O)N2CCCN(Cc3cccc(OCc4ccccc4)c3)CC2)c1] | 1-(4-(3-(Benzyloxy)benzyl)-1,4-diazepane-1-carbonyl)-1H-pyrazole-4-carbonitrile |

TABLE 1-continued

| Chemical Synthesis Example | Structure | Name |
|---|---|---|
| 301 | PhO-C6H4-CH2-N(diazepane)-C(O)-N(pyrazole)-CN | 1-(4-(4-Phenoxybenzyl)-1,4-diazepane-1-carbonyl)-1H-pyrazole-4-carbonitrile |
| 302 | BnO-C6H4-CH2-N(diazepane)-C(O)-N(pyrazole)-CH3 | (4-(4-(Benzyloxy)benzyl)-1,4-diazepan-1-yl)(4-methyl-1H-pyrazol-1-yl)methanone |
| 303 | BnO-C6H4-CH2-N(diazepane)-C(O)-N(pyrazole)-CN | 1-(4-(4-(Benzyloxy)benzyl)-1,4-diazepane-1-carbonyl)-1H-pyrazole-4-carbonitrile |

Preparation of the Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J.C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the pyrazole compounds described herein is P. H. Stahl & C. G. Wermuth "Handbook of Pharmaceutical Salts", Verlag Helvetica Chimica Acta, Zurich, 2002.

The pyrazole compounds are prepared by the general synthetic routes described below in Schemes 1-7, wherein $R^1$ is as defined herein, and $Q^1$, $Q^2$, and $Q^3$ are defined such that compounds of formula (D), formula (H), and formula (T) are compounds of Formulas (I), (Ia), (II), (III), (IIIa), (IV), (IVa), (V), (Va), (VI), (VIa), (VII), (VIIa), or (VIII).

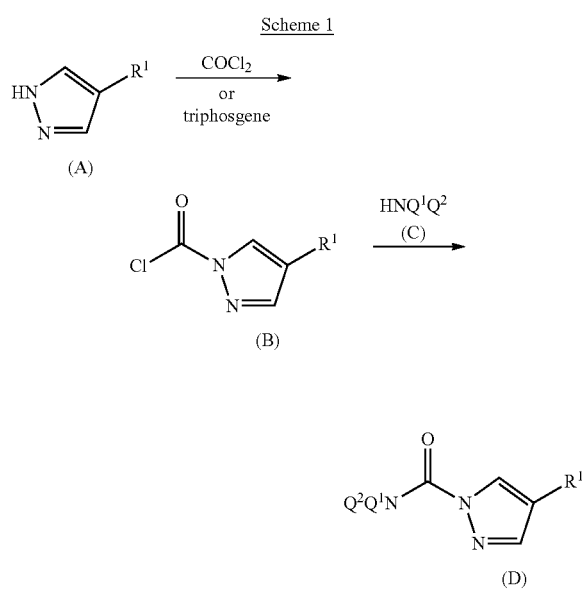

A method for preparing compounds of formula D is provided in Scheme 1. Reaction of a pyrazole of formula A with phosgene or triphosgene affords intermediate B. Coupling with an amine of formula C leads to a pyrazole compound of formula D.

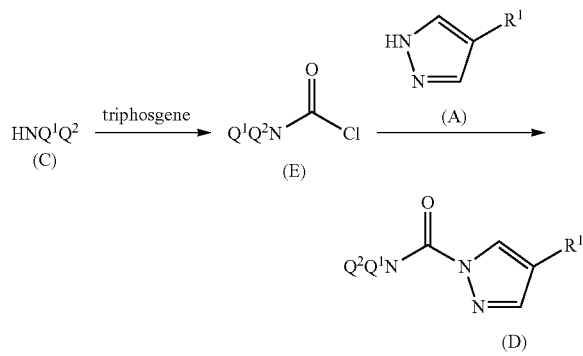

Another method for preparing compounds of formula D is provided in Scheme 2. Reaction of an amine of formula C with triphosgene affords intermediate E. Coupling of intermediate E with a pyrazole of formula A leads to a pyrazole compound of formula D.

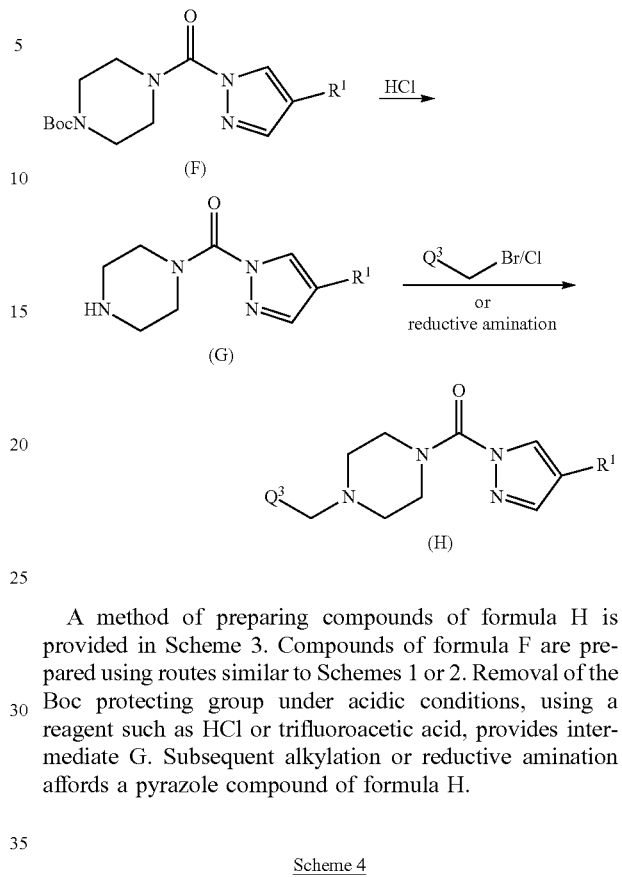

A method of preparing compounds of formula H is provided in Scheme 3. Compounds of formula F are prepared using routes similar to Schemes 1 or 2. Removal of the Boc protecting group under acidic conditions, using a reagent such as HCl or trifluoroacetic acid, provides intermediate G. Subsequent alkylation or reductive amination affords a pyrazole compound of formula H.

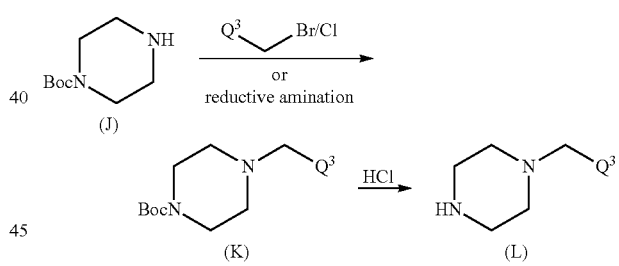

A method of preparing intermediates L is provided in Scheme 4. Compound J is reacted with the appropriate alkylating reagent or undergoes reductive amination to provide intermediate K. Removal of the Boc protecting group under acidic conditions, using a reagent such as HCl or trifluoroacetic acid, provides an intermediate L. Intermediate compound L is used subsequently as a compound of formula C in Schemes 1 or 2.

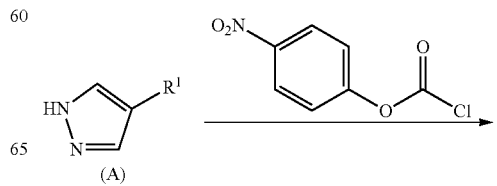

-continued

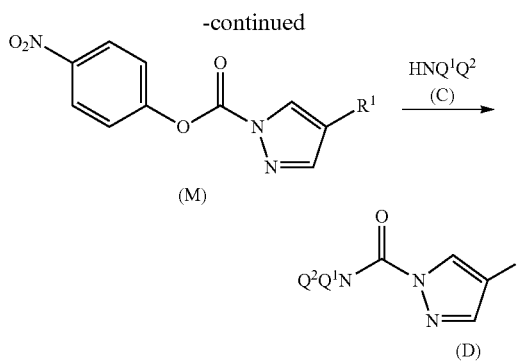

An alternative method for preparing compounds of formula D is provided in Scheme 1. Reaction of a pyrazole of formula A with 4-nitrophenyl chloroformate affords intermediate M. Coupling with an amine of formula C leads to a pyrazole compound of formula D.

Scheme 6

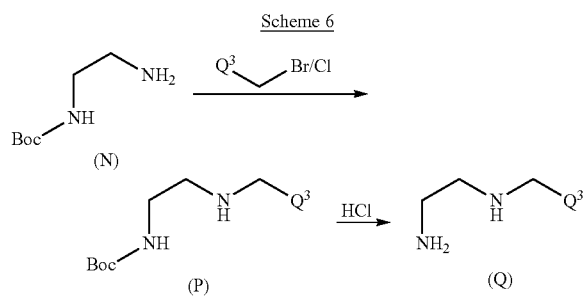

A method of preparing intermediates Q is provided in scheme 6. Compound N is reacted with the appropriate alkylating reagent to provide intermediate P. Removal of the Boc protecting group under acidic conditions, using a reagent such as HCl or trifluoroacetic acid, provides an intermediate Q. Intermediate compound Q is used subsequently as a compound of formula C in Scheme 5.

Scheme 7

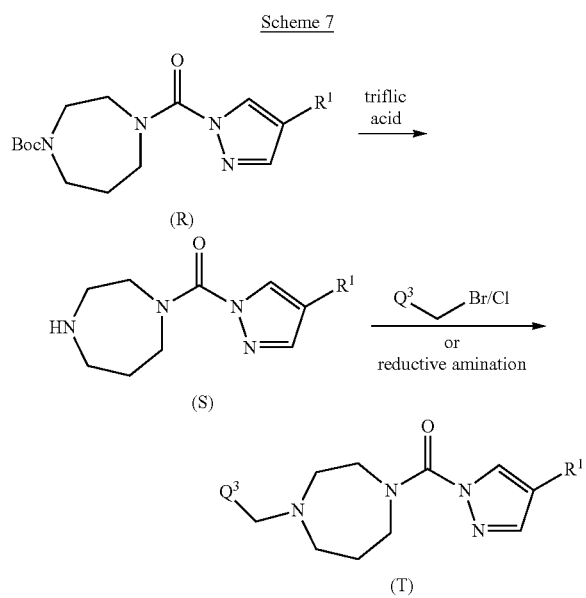

A method of preparing compounds of formula T is provided in Scheme 7. Compounds of formula R are prepared using routes similar to Schemes 1 and 2. Removal of the Boc protecting group under acidic conditions, using a reagent such as HCl or trifluoroacetic acid, provides intermediate S. Subsequent alkylation or reductive amination affords a pyrazole compound of formula T.

Further Forms of Pyrazole Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, citrulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

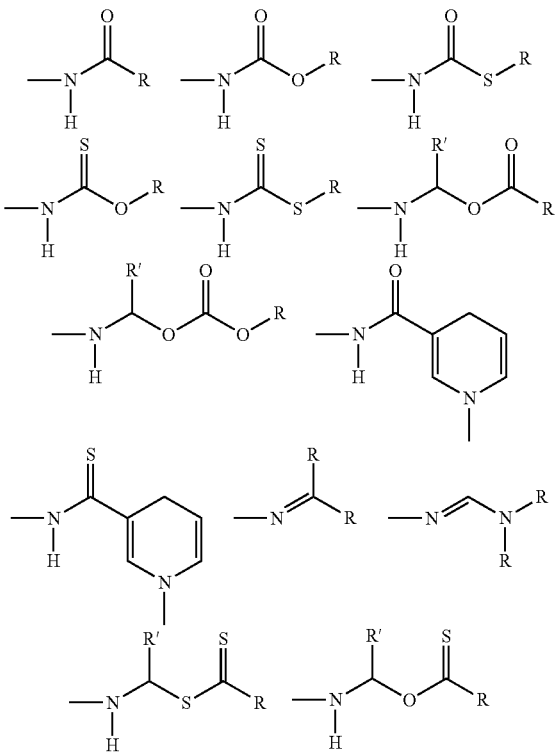

-continued

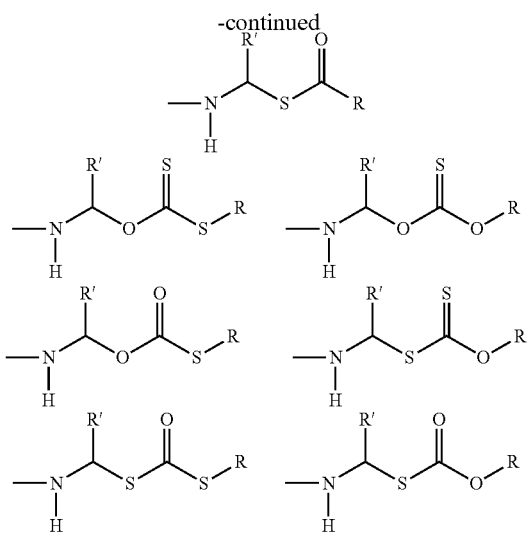

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Metabolites

In some embodiments, pyrazole compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, pyrazole compounds described herein are metabolized upon administration to an organism in need to produce a metabolite that is then used to produce a desired effect, including a desired therapeutic effect.

Pharmaceutical Compositions

In certain embodiments, the pyrazole compound as described herein is administered as a pure chemical. In other embodiments, the pyrazole compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one pyrazole compound described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof. One embodiment provides a pharmaceutical composition comprising a pharmaceutically acceptable carrier and a compound of Formula (Ia), or a pharmaceutically acceptable salt thereof.

One embodiment provides a pharmaceutical composition comprising a pharmaceutically acceptable carrier and a compound of Formula (II), or a pharmaceutically acceptable salt thereof.

One embodiment provides a pharmaceutical composition comprising a pharmaceutically acceptable carrier and a compound of Formula (III), or a pharmaceutically acceptable salt thereof. One embodiment provides a pharmaceutical composition comprising a pharmaceutically acceptable carrier and a compound of Formula (IIIa), or a pharmaceutically acceptable salt thereof.

One embodiment provides a pharmaceutical composition comprising a pharmaceutically acceptable carrier and a compound of Formula (IV), or a pharmaceutically acceptable salt thereof. One embodiment provides a pharmaceutical composition comprising a pharmaceutically acceptable carrier and a compound of Formula (IVa), or a pharmaceutically acceptable salt thereof.

One embodiment provides a pharmaceutical composition comprising a pharmaceutically acceptable carrier and a compound of Formula (V), or a pharmaceutically acceptable salt thereof. One embodiment provides a pharmaceutical composition comprising a pharmaceutically acceptable carrier and a compound of Formula (Va), or a pharmaceutically acceptable salt thereof.

One embodiment provides a pharmaceutical composition comprising a pharmaceutically acceptable carrier and a compound of Formula (VI), or a pharmaceutically acceptable salt thereof. One embodiment provides a pharmaceutical composition comprising a pharmaceutically acceptable carrier and a compound of Formula (VIa), or a pharmaceutically acceptable salt thereof.

One embodiment provides a pharmaceutical composition comprising a pharmaceutically acceptable carrier and a compound of Formula (VII), or a pharmaceutically acceptable salt thereof. One embodiment provides a pharmaceutical composition comprising a pharmaceutically acceptable carrier and a compound of Formula (VIIa), or a pharmaceutically acceptable salt thereof.

One embodiment provides a pharmaceutical composition comprising a pharmaceutically acceptable carrier and a compound of Formula (VIII), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof. Another embodiment provides a pharmaceutical composition consisting essentially of a pharmaceutically acceptable carrier and a compound of Formula (II), or a pharmaceutically acceptable salt thereof. Another embodiment provides a pharmaceutical composition consisting essentially of a pharmaceutically acceptable carrier and a compound of Formula (III), or a pharmaceutically acceptable salt thereof. Another embodiment provides a pharmaceutical composition consisting essentially of a pharmaceutically acceptable carrier and a compound of Formula (IV), or a pharmaceutically acceptable salt thereof. Another embodiment provides a pharmaceutical composition consisting essentially of a pharmaceutically acceptable carrier and a compound of Formula (V), or a pharmaceutically acceptable salt thereof. Another embodiment provides a pharmaceutical composition consisting essentially of a pharmaceutically acceptable carrier and a compound of Formula (VI), or a pharmaceutically acceptable salt thereof. Another embodiment provides a pharmaceutical composition consisting essentially of a pharmaceutically acceptable carrier and a compound of Formula (VII), or a pharmaceutically acceptable salt thereof. Another embodiment provides a pharmaceutical composition consisting essentially of a pharmaceutically acceptable carrier and a compound of Formula (VIII), or a pharmaceutically acceptable salt thereof. Another embodiment provides a pharmaceutical composition consisting essentially of a pharmaceutically acceptable carrier and a compound of Formula (Ia), or a pharmaceutically acceptable salt thereof. Another embodiment provides a pharmaceutical composition consisting essentially of a pharmaceutically acceptable carrier and a compound of Formula (IIIa), or a pharmaceutically acceptable salt thereof. Another embodiment provides a pharmaceutical composition consisting essentially of a pharmaceutically acceptable carrier and a compound of Formula (IVa), or a pharmaceutically acceptable salt thereof. Another embodiment provides a pharmaceutical composition consisting essentially of a pharmaceutically acceptable carrier and a compound of Formula (Va), or a pharmaceutically acceptable salt thereof. Another embodiment provides a pharmaceutical composition consisting essentially of a pharmaceutically acceptable carrier and a compound of Formula (VIa), or a pharmaceutically acceptable salt thereof. Another embodiment provides a pharmaceutical composition consisting essentially of a pharmaceutically acceptable carrier and a compound of Formula (VIIa), or a pharmaceutically acceptable salt thereof.

In certain embodiments, the pyrazole compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid or liquid form, which includes one or more of a disclosed compound, as an active ingredient, in admixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one pyrazole compound as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of one or more of MAGL, ABHD6, and FAAH. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (Ia), (II), (III), (IIIa), (IV), (IVa), (V), (Va), (VI), (VIa), (VII), (VIIa), or (VIII). The ability of compounds described herein to modulate or inhibit one or more of MAGL, ABHD6, and FAAH is evaluated by procedures known in the art and/or described herein. Another aspect of this disclosure provides methods of treating a disease associated with expression or activity of one or more of MAGL, ABHD6, and FAAH in a patient. For example, provided herein are compounds that are selective in inhibiting MAGL or ABHD6, or both, as compared to inhibition of other serine hydrolases e.g., FAAH, e.g., 10, 100, 1000 or more fold inhibition of MAGL over FAAH. In other embodiments, disclosed compounds are more selective in inhibition of MAGL as compared to ABHD6. In some embodiments, disclosed compounds are selective in inhibiting MAGL, ABHD6, and FAAH over the inhibitor of other serine hydrolases e.g., PLA2G7.

Also contemplated herein are methods of treating and/or preventing in a patient in need thereof a disorder such as one or more of acute or chronic pain, obesity, metabolic disorders (such as syndrome X), vomiting or nausea, eating disorders such as anorexia and/or bulimia; dyslipidaemia, neuropathy such as diabetic neuropathy, pellagric neuropathy, alcoholic neuropathy, Beriberi neuropathy, burning feet syndrome, neurodegenerative disorders such as multiple sclerosis, Parkinson's disease, Huntington's chorea, Alzheimer's disease, amyotrophic lateral sclerosis, epilepsy, sleep disorders, cardiovascular diseases, hypertension, dyslipidemia, atherosclerosis, osteoporosis, osteoarthritis, emesis, epilepsy, mental disorders such as schizophrenia and depression, glaucoma, cachexia, insomnia, traumatic brain injury, spinal cord injury, seizures, excitotoxin exposure, ischemia, AIDS wasting syndrome, renal ischaemia, cancers (e.g., solid tumor cancers such as breast, lung, head and neck, ovarian, sarcoma, melanoma, and/or prostate cancer); cancers such as melanoma, metastatic tumors, kidney or bladder cancers, brain, gastrointestinal cancers (e.g., colon cancer), leukemia or blood cancers (e.g., myeloid, lymphoid or monocytic cancers), inflammatory disorders (e.g., bladder inflammation), including inflammatory pain, and/or psychological disorders including anxiety disorders (e.g., panic disorder, acute stress disorder, post-traumatic stress disorder, substance-induced anxiety disorders, obsessive-compulsive disorder, agoraphobia, specific phobia, social phobia. Contemplated methods include administering a pharmaceutically effective amount of a disclosed compound.

In an embodiment, provided herein is a method for treating, ameliorating and/or preventing damage from ischemia, for example, hepatic ischemia or reperfusion in a patient in need thereof, comprising administering a disclosed compound. Methods of treating patients with liver conditions resulting from oxidative stress and/or inflammatory damage are contemplated herein, e.g., contemplated herein are methods of treating liver fibrosis, iron overload, and/or corticosteroid therapy that result in liver damage, in a patient in need thereof.

For example, provide herein is a method for treating chronic pain such as inflammatory pain, visceral pain, post operative pain, pain related to migraine, osteoarthritis, or rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

For example, contemplated herein are methods for treating neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents) in a patient in need thereof, comprising administering a pharmaceutically effective amount of a disclosed compound.

Also contemplated herein are methods for ameliorating cognitive function in a patient suffering from Down's syndrome or Alzheimer's disease, comprising administering an effective amount of a disclosed compound. Exemplary patients suffering from Down's syndrome are a pediatric patient (e.g., a patient of age 0-11 years, 0-18 years, 0-6 years, or e.g., 12 to 18 years), an adult patient (e.g., 18 years or older), or e.g., an older patient e.g., 18-40 years, 20-50 years). In some embodiments, such patients also suffer from further cognitive impairment and/or dementia, and/or seizures which, in some embodiments are due to production of prostaglandins and/or amyloid beta. For example, such patients also are suffering from, or have one or more of the following symptoms associated with early-mid or late stage cognitive impairment: loss of language, impairment of social skills, progressive loss of activities of daily living, and include psychotic behavior. Provided herein, for example, is a method for treating a patient having Down's syndrome or Alzheimer's disease with cognitive impairment, comprising administering an effective amount of a disclosed compound. Such disclosed methods result in cognitive improvement, for example, measured by IQ or the Arizona Cognitive Test Battery (e.g., measured with a cognitive test battery designed for use in individuals with Down's syndrome). For example, a treated patient using a disclosed method has at least one of: increased memory, improved memory or improved speech. In some embodiments, such disclosed methods result in a patient having an increased quality of life as measured by an adaptive behavior scale after said administration.

In other embodiments, a method for at least partially providing a Down's syndrome patient a neuroprotective (such as a disclosed compounds), that results in delayed onset of neurodegeneration or substantially prevents neurodegeneration, is provided. Administration to a patient is initiated before onset of neurodegeneration and/or onset of neurodegeneration symptoms. Contemplated herein are methods for treating and/or ameliorating cognitive decline, improving sleep duration and/or quality, and/or treating PANDAS (pediatric autoimmune neuropsychiatric disorders associated with streptococcal infections) in a patient in need thereof, comprising administering a disclosed compound.

In certain embodiments, a disclosed compound utilized by one or more of the foregoing methods is one of the generic, subgeneric, or specific compounds described herein, such as a compound of Formula (I), (Ia), (II), (III), (IIIa), (IV), (IVa), (V), (Va), (VI), (VIa), (VII), (VIIa), or (VIII).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

For example, e.g., for contemplated treatment of pain or other contemplated indications (e.g., Alzheimer' or Down's syndrome), a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxic.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:
ACN or MeCN acetonitrile
Bn benzyl
BOC or Boc tert-butyl carbamate
t-Bu tert-butyl
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
Dppf or dppf 1,1'-bis(diphenylphosphino)ferrocene
equiv or eq equivalent(s)
Et ethyl
$Et_2O$ diethyl ether
EtOH ethanol
EtOAc ethyl acetate
HPLC high performance liquid chromatography
LAH lithium aluminum anhydride
Me methyl
MeOH methanol
MS mass spectroscopy
NMM N-methyl-morpholine
NMP N-methyl-pyrrolidin-2-one
NMR nuclear magnetic resonance
RP-HPLC reverse phase-high pressure liquid chromatography
TFA trifluoroacetic acid
THF tetrahydrofuran
TLC thin layer chromatography
I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

In some instances the examples were purified using preparative HPLC according to the following conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm, 5 um. Mobile phase: Phase A: aqueous NH$_4$HCO$_3$ (0.05%); Phase B: CH$_3$CN. Detector: UV 220 & 254 nm.

Example 1: Piperidin-1-yl(1H-pyrazol-1-yl)methanone

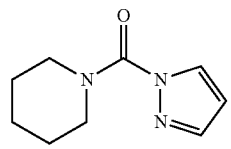

Preparation of piperidin-1-yl(1H-pyrazol-1-yl)methanone

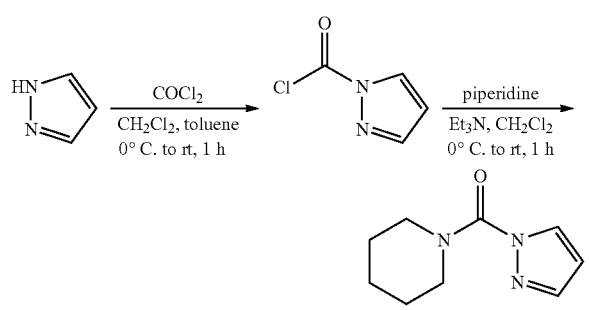

A round-bottom flask, equipped with a magnetic stir bar, was charged with 1H-pyrazole (110 mg, 1.62 mmol) in CH$_2$Cl$_2$ (1 mL). The resulting solution was cooled to 0° C. and treated with phosgene (3 mL, 20% in toluene). The resulting mixture was stirred at room temperature for 1 h. The reaction mixture was concentrated under reduced pressure and dissolved in CH$_2$Cl$_2$ (3 mL). A separate round-bottom flask, equipped with a magnetic stir bar, was charged with triethylamine (226 μL), CH$_2$Cl$_2$ (3 mL) and piperidine (200 μL, 1.94 mmol). The resulting solution was cooled to 0° C. The crude carbamoyl chloride prepared above was then added dropwise. The resulting mixture was allowed to warm to room temperature and was stirred for 16 h. The reaction mixture was then diluted with EtOAc (10 mL), and the organic layer washed with saturate aqueous NaCl (2×10 mL). The organic layer was dried over sodium sulfate, filtered and concentrated under reduced pressure. The resulting colorless oil was purified by flash chromatography (60 g SiO$_2$, 20% EtOAc-hexanes) to provide piperidin-1-yl(1H-pyrazol-1-yl)methanone (210 mg, 73%) as a white solid. $^1$H NMR (400 MHz, Chloroform-d) δ 7.92 (d, 1H, J=7.3 Hz), 7.47 (d, 1H, J=6.9 Hz), 6.19 (t, 1H, J=7.4 Hz), 3.58 (m, 4H), 1.36 (m, 6H); $^{13}$C NMR (125 MHz, Chloroform-d) δ 156.8, 146.6, 128.8, 134.5, 109.2, 49.4, 25.9, 23.8. LCMS (ESI, m/z): 180 [M+H]$^+$.

Example 2: (4-Methyl-1H-pyrazol-1-yl)(piperidin-1-yl)methanone

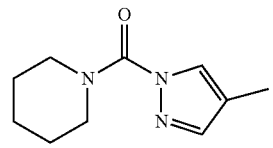

The title compound was prepared from 4-methyl-1H-pyrazole (80 mg, 0.98 mmol) and piperidine (0.12 mL, 1.17 mmol) according to the representative procedure of Example 1 to provide (4-methyl-1H-pyrazol-1-yl)(piperidin-1-yl)methanone (105 mg, 55%) as a colorless oil. $^1$H NMR (400 MHz, Chloroform-d) δ 8.09 (s, 1H) 7.50 (s, 1H), 3.77 (t, 4H, J=6.3 Hz), 2.03 (s, 3H), 1.36 (m, 6H); $^{13}$C NMR (125 MHz, Chloroform-d) δ 154.8, 136.6, 128.0, 117.2, 49.4, 25.9, 23.8, 12.2. LCMS (ESI, m/z): 194 [M+H]$^+$.

Example 3: 1-(Piperidine-1-carbonyl)-1H-pyrazole-4-carbonitrile

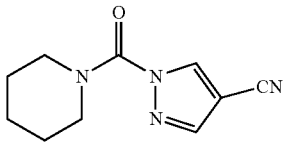 [SMILES: N#Cc1cnn(C(=O)N2CCCCC2)c1]

The title compound was prepared from 1H-pyrazole-4-carbonitrile (42 mg, 0.45 mmol) and piperidine (90 μL, 0.90 mmol) according to the representative procedure of Example 1 to provide 1-(piperidine-1-carbonyl)-1H-pyrazole-4-carbonitrile (56 mg, 61%) as a colorless oil. $^1$H NMR (400 MHz, Chloroform-d) δ 8.59 (s, 1H), 7.96 (s, 1H), 3.79 (m, 4H), 1.79 (m, 6H); $^{13}$C NMR (125 MHz, Chloroform-d) δ 154.8, 146.6, 132.5, 113.2, 91.0, 49.4, 25.9, 23.8. LCMS (ESI, m/z): 205 [M+H]$^+$.

Example 4: tert-Butyl 4-(1H-pyrazole-1-carbonyl)piperazine-1-carboxylate

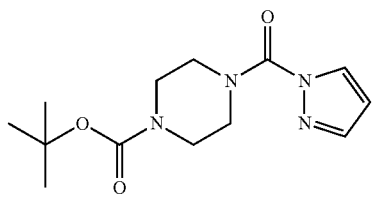 [SMILES: CC(C)(C)OC(=O)N1CCN(C(=O)n2cccn2)CC1]

The title compound was prepared from 1H-pyrazole (40 mg, 0.57 mmol) and 4-Boc-piperazine (160 mg, 0.86 mmol) according to the representative procedure of Example 1 to provide tert-butyl 4-(1H-pyrazole-1-carbonyl)piperazine-1-carboxylate (102 mg, 65%) as a white solid. $^1$H NMR (400 MHz, Chloroform-d) δ 8.26 (d, 1H, J=7.3 Hz), 7.45 (d, 1H, J=6.9 Hz), 6.89 (t, 1H, J=7.4 Hz), 3.37 (s, 8H), 1.36 (s, 9H); $^{13}$C NMR (125 MHz, Chloroform-d) δ 156.8, 151.1, 146.6, 128.8, 134.5, 109.2, 79.8, 51.4, 50.1, 24.8. LCMS (ESI, m/z): 281 [M+H]$^+$.

Example 5: tert-Butyl 4-(4-methyl-1H-pyrazole-1-carbonyl)piperazine-1-carboxylate

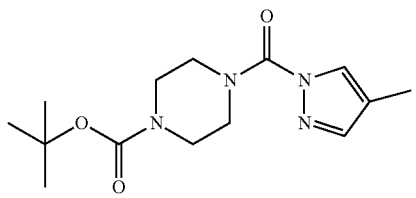 [SMILES: Cc1cnn(C(=O)N2CCN(C(=O)OC(C)(C)C)CC2)c1]

The title compound was prepared from 4-methyl-1H-pyrazole (45 mg, 0.31 mmol) and 4-Boc-piperazine (70 mg, 0.38 mmol) according to the representative procedure of Example 1 to provide tert-butyl 4-(4-methyl-1H-pyrazole-1-carbonyl)piperazine-1-carboxylate (60 mg, 65%) as a white solid. $^1$H NMR (400 MHz, Chloroform-d) δ 8.09 (s, 1H) 7.50 (s, 1H), 3.46 (s, 8H), 2.04 (s, 3H), 1.36 (s, 9H); $^{13}$C NMR (125 MHz, Chloroform-d) δ 157.2, 154.8, 136.6, 128.0, 117.2, 79.8, 51.4, 49.9, 24.8, 12.2. LCMS (ESI, m/z): 295 [M+H]$^+$.

Example 6: tert-Butyl 4-(4-cyano-1H-pyrazole-1-carbonyl)piperazine-1-carboxylate

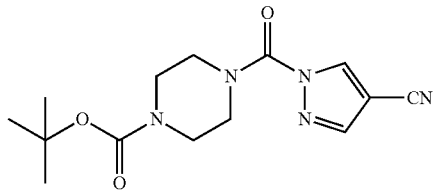 [SMILES: CC(C)(C)OC(=O)N1CCN(C(=O)n2cc(C#N)cn2)CC1]

The title compound was prepared from 1H-pyrazole-4-carbonitrile (35 mg, 0.37 mmol) and 4-Boc-piperazine (80 mg, 0.45 mmol) according to the representative procedure of Example 1 to provide tert-butyl 4-(4-cyano-1H-pyrazole-1-carbonyl)piperazine-1-carboxylate (66 mg, 45%) as a white solid. $^1$H NMR (400 MHz, Chloroform-d) δ 8.89 (s, 1H), 8.22 (s, 1H), 3.35 (s, 8H), 1.36 (s, 9H); $^{13}$C NMR (125 MHz, Chloroform-d) δ 154.8, 151.2, 146.6, 132.5, 113.2, 91.0, 80.1, 51.4, 49.9, 28.4. LCMS (ESI, m/z): 306 [M+H]$^+$.

Example 7: (4-Benzylpiperazin-1-yl)(1H-pyrazol-1-yl)methanone

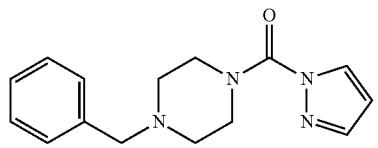 [SMILES: O=C(N1CCN(Cc2ccccc2)CC1)n1cccn1]

Step 1: Preparation of piperazin-1-yl(1H-pyrazol-1-yl)methanone

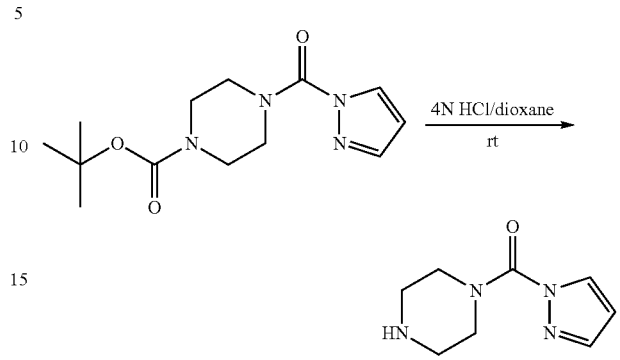

A round-bottom flask, equipped with a magnetic stir bar, was charged with tert-butyl 4-(1H-pyrazole-1-carbonyl)piperazine-1-carboxylate (Example 4, 30 mg, 0.11 mmol) in CH$_2$Cl$_2$ (1 mL) and cooled to 0° C. A solution of 4 N HCl in 1,4-dioxane (0.5 mL) was added dropwise. The mixture was stirred at room temperature for 2 h and then concentrated under reduced pressure to afford the crude amine, which was dissolved with EtOAc (5 mL), washed with saturated aqueous NaCl (2×10 mL) and dried over Na$_2$SO$_4$. The solvent was removed under reduced pressure, and the mixture was subsequently purified by flash chromatography (SiO$_2$, 90% EtOAc-hexanes) to yield piperazin-1-yl(1H-pyrazol-1-yl)methanone (18 mg, 90%) as a tan oil. $^1$H NMR (400 MHz, Chloroform-d) δ 8.26 (d, 1H, J=7.3 Hz), 7.45 (d, 1H, J=6.9 Hz), 6.89 (t, 1H, J=7.4 Hz), 3.37 (s, 8H).

Step 2: Preparation of (4-benzylpiperazin-1-yl)(1H-pyrazol-1-yl)methanone

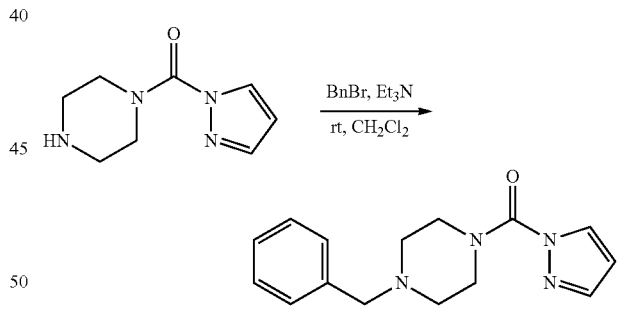

A round-bottom flask, equipped with a magnetic stir bar, was charged with piperazin-1-yl(1H-pyrazol-1-yl)methanone (18 mg, 0.11 mmol) and CH$_2$Cl$_2$ (1 mL). The resulting solution was treated with Et$_3$N (20 μL, 0.14 mmol) and benzyl bromide (26 μL, 0.22 mmol). The reaction mixture was stirred at room temperature for 24 h. The mixture was then diluted with EtOAc (2 mL), washed with saturated aqueous NaCl (2×5 mL) and dried over Na$_2$SO$_4$. The solvent was removed under reduced pressure, and the mixture was subsequently purified by flash chromatography (SiO$_2$, 50% EtOAc-hexanes) to yield (4-benzylpiperazin-1-yl)(1H-pyrazol-1-yl)methanone (11 mg, 38%) as a colorless oil. $^1$H NMR (400 MHz, Chloroform-d) δ 8.26 (s, 1H), 7.45 (s, 1H), 7.33-7.28 (m, 5H), 6.44 (t, 1H, J=6.4 Hz), 3.60 (s, 2H), 3.20 (s, 4H), 2.51 (s, 4H). LCMS (ESI, m/z): 271 [M+H]$^+$.

Example 8: (4-Benzylpiperazin-1-yl)(4-methyl-1H-pyrazol-1-yl)methanone

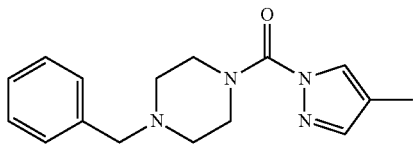 [SMILES: Cc1cnn(C(=O)N2CCN(Cc3ccccc3)CC2)c1]

The title compound was prepared from tert-butyl 4-(4-methyl-1H-pyrazole-1-carbonyl)piperazine-1-carboxylate (Example 5, 0.15 mmol) according to the representative procedure of Example 7 to provide (4-benzylpiperazin-1-yl)(4-methyl-1H-pyrazol-1-yl)methanone (11 mg, 34%) as a colorless oil. $^1$H NMR (400 MHz, Chloroform-d) δ 8.06 (s, 1H), 7.45 (s, 1H), 7.33-7.28 (m, 5H), 3.60 (s, 2H), 3.20 (s, 4H), 2.51 (s, 4H), 2.04 (s, 3H). LCMS (ESI, m/z): 285 [M+H]$^+$.

Example 9: 1-(4-Benzylpiperazine-1-carbonyl)-1H-pyrazole-4-carbonitrile

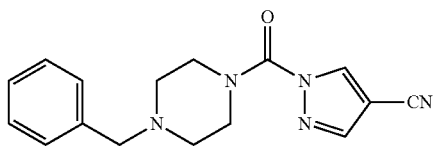 [SMILES: N#Cc1cnn(C(=O)N2CCN(Cc3ccccc3)CC2)c1]

The title compound was prepared from tert-butyl 4-(4-cyano-1H-pyrazole-1-carbonyl)piperazine-1-carboxylate (Example 6, 0.066 mmol) according to the representative procedure of Example 7 to provide 1-(4-benzylpiperazine-1-carbonyl)-1H-pyrazole-4-carbonitrile (6 mg, 45%) as a colorless oil. $^1$H NMR (400 MHz, Chloroform-d) δ 8.06 (s, 1H), 8.02 (s, 1H), 7.33-7.28 (m, 5H), 3.60 (s, 2H), 3.20 (s, 4H), 2.51 (s, 4H). LCMS (ESI, m/z): 296 [M+H]$^+$.

Example 10: (4-(Naphthalen-2-ylmethyl)piperazin-1-yl)(1H-pyrazol-1-yl)methanone

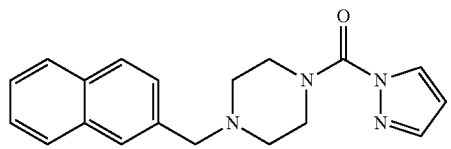 [SMILES: O=C(N1CCN(Cc2ccc3ccccc3c2)CC1)n1cccn1]

Step 1: Preparation of tert-butyl 4-(naphthalen-2-ylmethyl)piperazine-1-carboxylate

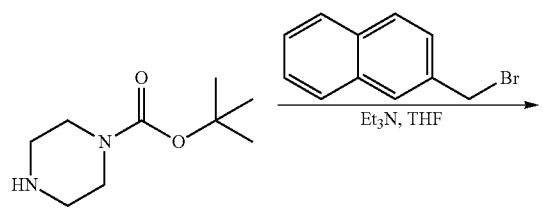

-continued

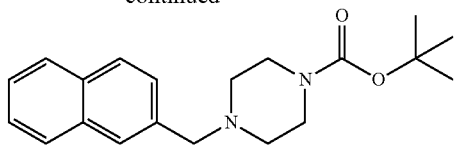

A round-bottom flask, equipped with a magnetic stir bar, was charged with tert-butyl piperazine-1-carboxylate (330 mg, 1.78 mmol) in THF (3 mL). The resulting solution was treated with Et$_3$N (0.25 mL, 1.78 mmol) followed by 2-(bromomethyl)naphthalene (250 mg, 1.48 mmol) and allowed to stir at room temperature for 24 h. The reaction mixture was then diluted with EtOAc (10 mL), washed with saturated aqueous NaCl (2×10 mL), dried over Na$_2$SO$_4$, filtered and concentrated under reduced pressure. The crude residue was purified by flash chromatography (SiO$_2$, 40% EtOAc-hexanes) to provide tert-butyl 4-(naphthalen-2-ylmethyl)piperazine-1-carboxylate (360 mg, 62%) as a tan solid. $^1$H NMR (400 MHz, Chloroform-d) δ 7.99 (m, 3H), 7.55 (m, 2H), 7.53 (s, 1H), 7.32 (d, 1H, J=6.2 Hz), 7.18 (s, 2H), 3.70 (s, 2H), 3.32 (t, 4H, J=7.2 Hz), 2.50 (t, 4H, J=7.2 Hz), 1.26 (s, 9H).

Step 2: Preparation of 1-(naphthalen-2-ylmethyl)piperazine

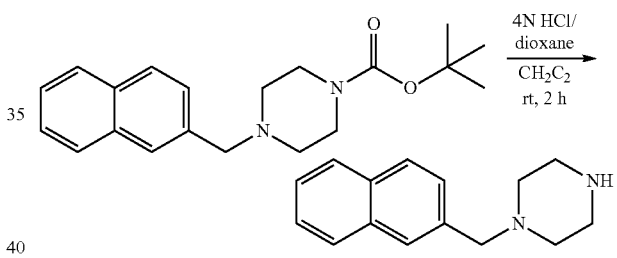

A round-bottom flask, equipped with a magnetic stir bar, was charged with tert-butyl 4-(naphthalen-2-ylmethyl)piperazine-1-carboxylate (40 mg, 0.098 mmol) in CH$_2$Cl$_2$ (1 mL) and cooled to 0° C. A solution of 4 N HCl in 1,4-dioxane (0.2 mL, 0.12 mmol) was added dropwise. The mixture was stirred at room temperature for 2 h, and then the solvent was removed under nitrogen to afford the crude amine, which was dissolved with EtOAc, washed with saturated aqueous NaCl and dried over Na$_2$SO$_4$. The solvent was removed under reduced pressure, and the mixture was subsequently purified by flash chromatography (SiO$_2$, 80% EtOAc-hexanes) to yield 1-(naphthalen-2-ylmethyl)piperazine (20 mg, 56%) as a tan oil. $^1$H NMR (400 MHz, Chloroform-d) δ 7.99 (m, 3H), 7.55 (m, 2H), 7.53 (s, 1H), 7.32 (d, 1H, J=6.2 Hz), 7.18 (s, 2H), 3.70 (s, 2H), 3.32 (t, 4H, J=7.2 Hz), 2.50 (t, 4H, J=7.2 Hz).

Step 3: Preparation of (4-(naphthalen-2-ylmethyl)piperazin-1-yl)(1H-pyrazol-1-yl)methanone The title compound was prepared from 1H-pyrazole (30 mg, 0.44 mmol) and 1-(naphthalen-2-ylmethyl)piperazine (100 mg, 0.44 mmol) according to the representative procedure of Example 1 to yield (4-(naphthalen-2-ylmethyl)piperazin-1-yl)(1H-pyrazol-1-yl)methanone (71 mg, 51%) as a white solid. $^1$H NMR (400 MHz, Chloroform-d) δ 8.25

(d, 1H, J=6.5 Hz), 7.99 (m, 3H), 7.55 (m, 2H), 7.53 (s, 1H), 7.50 (d, 1H, J=6.4 Hz), 7.32 (d, 1H, J=6.2 Hz), 7.18 (s, 2H), 6.44 (t, 1H, J=6.4 Hz), 3.70 (s, 2H), 3.32 (t, 4H, J=7.2 Hz), 2.55 (t, 4H, J=7.2 Hz). LCMS (ESI, m/z): 321 [M+H]⁺.

Example 11: (4-Methyl-1H-pyrazol-1-yl)(4-(naphthalen-2-ylmethyl)piperazin-1-yl)methanone

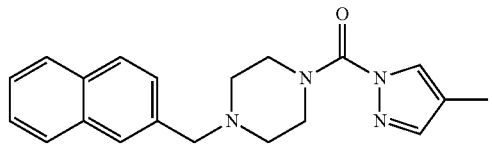 [SMILES: Cc1cnn(C(=O)N2CCN(Cc3ccc4ccccc4c3)CC2)c1]

The title compound was prepared from 4-methyl-1H-pyrazole (20 mg, 0.24 mmol) and 1-(naphthalen-2-ylmethyl)piperazine (Example 10, Step 2; 55 mg, 0.24 mmol) according to the representative procedure of Example 1 to provide (4-methyl-1H-pyrazol-1-yl)(4-(naphthalen-2-ylmethyl)piperazin-1-yl)methanone (38 mg, 48%) as a white solid. ¹H NMR (400 MHz, Chloroform-d) δ 8.07 (s, 1H), 7.99 (m, 3H), 7.55 (m, 2H), 7.53 (s, 1H), 7.50 (d, 1H, J=6.4 Hz), 7.32 (d, 1H, J=6.2 Hz), 7.18 (s, 2H), 3.70 (s, 2H), 3.32 (t, 4H, J=7.2 Hz), 2.57 (t, 4H, J=7.2 Hz), 2.05 (s, 3H). LCMS (ESI, m/z): 335 [M+H]⁺.

Example 12: 1-(4-(Naphthalen-2-ylmethyl)piperazine-1-carbonyl)-1H-pyrazole-4-carbonitrile

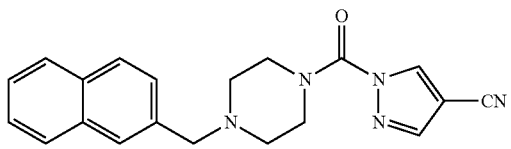 [SMILES: N#Cc1cnn(C(=O)N2CCN(Cc3ccc4ccccc4c3)CC2)c1]

The title compound was prepared from 1H-pyrazole-4-carbonitrile (20 mg, 0.21 mmol) and 1-(naphthalen-2-ylmethyl)piperazine (Example 10, Step 2; 48 mg, 0.21 mmol) according to the representative procedure of Example 1 to provide 1-(4-(naphthalen-2-ylmethyl)piperazine-1-carbonyl)-1H-pyrazole-4-carbonitrile (35 mg, 49%) as a white solid. ¹H NMR (400 MHz, Chloroform-d) δ 8.80 (s, 1H), 8.24 (s, 1H), 7.99 (m, 3H), 7.55 (m, 2H), 7.53 (s, 1H), 7.32 (d, 1H, J=6.2 Hz), 7.18 (s, 2H), 3.70 (s, 2H), 3.32 (t, 4H, J=7.2 Hz), 2.50 (t, 4H, J=7.2 Hz). LCMS (ESI, m/z): 346 [M+H]⁺.

Example 13: (4-Bromo-1H-pyrazol-1-yl)(4-(naphthalen-2-ylmethyl)piperazin-1-yl)methanone

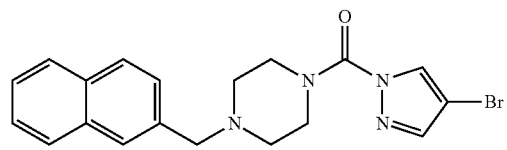 [SMILES: O=C(N1CCN(Cc2ccc3ccccc3c2)CC1)n1cc(Br)cn1]

The title compound was prepared from 4-bromo-1H-pyrazole (66 mg, 0.45 mmol) and 1-(naphthalen-2-ylmethyl)piperazine (Example 10, Step 2; 122 mg, 0.54 mmol) according to the representative procedure of Example 1 to provide (4-bromo-1H-pyrazol-1-yl)(4-(naphthalen-2-ylmethyl)piperazin-1-yl)methanone (101 mg, 56%) as a white solid. ¹H NMR (400 MHz, Chloroform-d) δ 8.42 (s, 1H), 8.30 (s, 1H), 7.99 (m, 3H), 7.55 (m, 2H), 7.53 (s, 1H), 7.30 (d, 1H, J=7.4 Hz), 3.70 (s, 2H), 3.32 (t, 4H, J=7.2 Hz), 2.50 (t, 4H, J=7.2 Hz). LCMS (ESI, m/z): 399.1 [M+H]⁺.

Example 14: (4-Iodo-1H-pyrazol-1-yl)(4-(naphthalen-2-ylmethyl)piperazin-1-yl)methanone

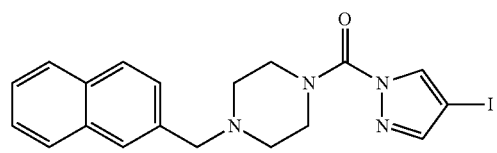 [SMILES: O=C(N1CCN(Cc2ccc3ccccc3c2)CC1)n1cc(I)cn1]

The title compound was prepared from 4-iodo-1H-pyrazole (75 mg, 0.40 mmol) and 1-(naphthalen-2-ylmethyl)piperazine (Example 10, Step 2; 105 mg, 0.47 mmol) according to the representative procedure of Example 1 to provide (4-iodo-1H-pyrazol-1-yl)(4-(naphthalen-2-ylmethyl)piperazin-1-yl)methanone (96 mg, 57%) as a white solid. ¹H NMR (400 MHz, Chloroform-d) δ 8.35 (s, 1H), 7.99 (m, 3H), 7.66 (s, 1H), 7.55 (m, 2H), 7.53 (s, 1H), 7.30 (d, 1H, J=7.4 Hz), 3.70 (s, 2H), 3.32 (t, 4H, J=7.2 Hz), 2.55 (t, 4H, J=7.2 Hz). LCMS (ESI, m/z): 447 [M+H]⁺.

Example 15: Methyl 1-(4-(naphthalen-2-ylmethyl)piperazine-1-carbonyl)-1H-pyrazole-4-carboxylate

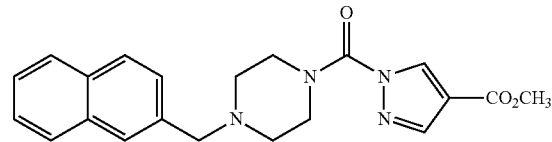 [SMILES: COC(=O)c1cnn(C(=O)N2CCN(Cc3ccc4ccccc4c3)CC2)c1]

The title compound was prepared from methyl 1H-pyrazole-4-carboxylate (52 mg, 0.33 mmol) and 1-(naphthalen-2-ylmethyl)piperazine (Example 10, Step 2; 74 mg, 0.33 mmol) according to the representative procedure of Example 1 to provide methyl 1-(4-(naphthalen-2-ylmethyl)piperazine-1-carbonyl)-1H-pyrazole-4-carboxylate (54 mg, 43%) as a white solid. ¹H NMR (400 MHz, Chloroform-d) δ 8.85 (s, 1H), 8.10 (s, 1H), 7.99 (m, 3H), 7.55 (m, 2H), 7.53 (s, 1H), 7.30 (d, 1H, J=7.4 Hz), 3.89 (s, 3H), 3.70 (s, 2H), 3.32 (t, 4H, J=7.2 Hz), 2.55 (t, 4H, J=7.2 Hz). LCMS (ESI, m/z): 379 [M+H]⁺.

Example 16: (4-(4-Phenoxybenzyl)piperazin-1-yl)(1H-pyrazol-1-yl)methanone

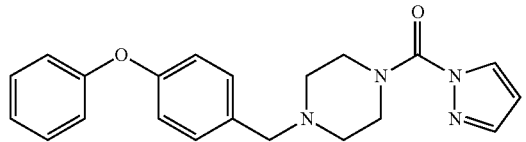 [SMILES: O=C(N1CCN(Cc2ccc(Oc3ccccc3)cc2)CC1)n1cccn1]

The title compound was prepared from 1-(bromomethyl)-4-phenoxybenzene, tert-butyl piperazine-1-carboxylate and 1H-pyrazole (10 mg, 0.15 mmol) according to the representative procedure of Example 10 to provide (4-(4-phenoxybenzyl)piperazin-1-yl)(1H-pyrazol-1-yl)methanone (22 mg, 40%) as a white solid. ¹H NMR (400 MHz, Chloroform-d) δ 8.25 (s, 1H), 7.44 (m, 3H), 7.28 (m, 4H), 7.24 (m, 3H), 6.67 (t, 1H, J=6.2 Hz), 3.66 (s, 2H), 3.22 (t, 4H, J=6.2 Hz), 2.68 (t, 4H, J=6.0 Hz). LCMS (ESI, m/z): 363 [M+H]⁺.

Example 17: (4-Methyl-1H-pyrazol-1-yl)(4-(4-phenoxybenzyl)piperazin-1-yl)methanone

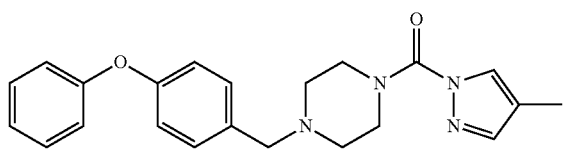 [SMILES: Cc1cnn(C(=O)N2CCN(Cc3ccc(Oc4ccccc4)cc3)CC2)c1]

The title compound was prepared from 1-(bromomethyl)-4-phenoxybenzene, tert-butyl piperazine-1-carboxylate and 4-methyl-1H-pyrazole (11 mg, 0.13 mmol) according to the representative procedure of Example 10 to provide (4-methyl-1H-pyrazol-1-yl)(4-(4-phenoxybenzyl)piperazin-1-yl)methanone (21 mg, 44%) as a white solid. ¹H NMR (400 MHz, Chloroform-d) δ 8.07 (s, 1H), 7.55 (s, 1H), 7.44 (m, 2H), 7.28 (m, 4H), 7.24 (m, 3H), 3.66 (s, 2H), 3.22 (t, 4H, J=6.2 Hz), 2.68 (t, 4H, J=6.0 Hz), 2.04 (s, 3H). LCMS (ESI, m/z): 377 [M+H]⁺.

Example 18: 1-(4-(4-Phenoxybenzyl)piperazine-1-carbonyl)-1H-pyrazole-4-carbonitrile

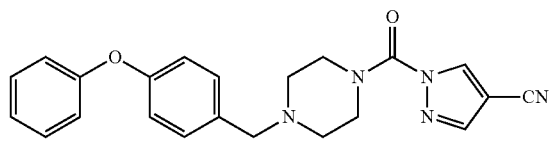 [SMILES: N#Cc1cnn(C(=O)N2CCN(Cc3ccc(Oc4ccccc4)cc3)CC2)c1]

The title compound was prepared from 1-(bromomethyl)-4-phenoxybenzene, tert-butyl piperazine-1-carboxylate and 1H-pyrazole-4-carbonitrile (10 mg, 0.11 mmol) according to the representative procedure of Example 10 to provide 1-(4-(4-phenoxybenzyl)piperazine-1-carbonyl)-1H-pyrazole-4-carbonitrile (16 mg, 39%) as a white solid. ¹H NMR (400 MHz, Chloroform-d) δ 8.80 (s, 1H), 8.24 (s, 1H), 7.44 (m, 2H), 7.28 (m, 4H), 7.24 (m, 3H), 3.66 (s, 2H), 3.22 (t, 4H, J=6.2 Hz), 2.68 (t, 4H, J=6.0 Hz). LCMS (ESI, m/z): 388 [M+H]⁺.

Example 19: (4-(4-(Benzyloxy)benzyl)piperazin-1-yl)(1H-pyrazol-1-yl)methanone

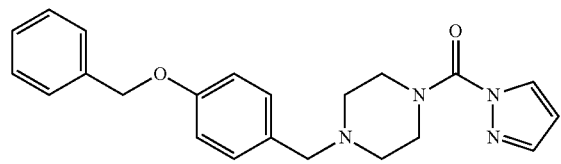 [SMILES: O=C(N1CCN(Cc2ccc(OCc3ccccc3)cc2)CC1)n1cccn1]

The title compound was prepared from 1-(benzyloxy)-4-(bromomethyl)benzene, tert-butyl piperazine-1-carboxylate and 1H-pyrazole (20 mg, 0.32 mmol) according to the representative procedure of Example 10 to provide (4-(4-(benzyloxy)benzyl)piperazin-1-yl)(1H-pyrazol-1-yl)methanone (45 mg, 38%) as a white solid. ¹H NMR (400 MHz, Chloroform-d) δ 8.25 (s, 1H), 7.47 (m, 2H), 7.42 (m, 4H), 7.25 (m, 2H), 7.18 (m, 2H), 6.44 (s, 1H), 5.11 (s, 2H), 3.65 (s, 2H), 3.22 (t, 4H, J=6.7 Hz), 2.54 (t, 4H, J=6.4 Hz). LCMS (ESI, m/z): 377 [M+H]⁺.

Example 20: (4-(4-(Benzyloxy)benzyl)piperazin-1-yl)(4-methyl-1H-pyrazol-1-yl)methanone

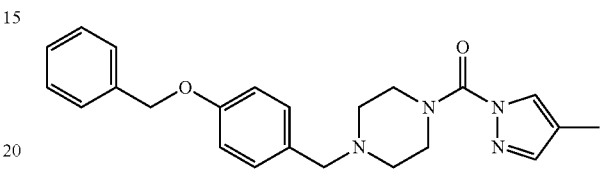

The title compound was prepared from 1-(benzyloxy)-4-(bromomethyl)benzene, tert-butyl piperazine-1-carboxylate and 4-methyl-1H-pyrazole (10 mg, 0.12 mmol) according to the representative procedure of Example 10 to provide (4-(4-(benzyloxy)benzyl)piperazin-1-yl)(4-methyl-1H-pyrazol-1-yl)methanone (16 mg, 34%) as a white solid. ¹H NMR (400 MHz, Chloroform-d) δ 8.20 (s, 1H), 7.47 (m, 3H), 7.42 (m, 3H), 7.25 (m, 2H), 7.18 (m, 2H), 5.11 (s, 2H), 3.65 (s, 2H), 3.22 (t, 4H, J=6.7 Hz), 2.54 (t, 4H, J=6.4 Hz), 2.04 (s, 3H). LCMS (ESI, m/z): 391 [M+H]⁺.

Example 21: 1-(4-(4-(Benzyloxy)benzyl)piperazine-1-carbonyl)-1H-pyrazole-4-carbonitrile

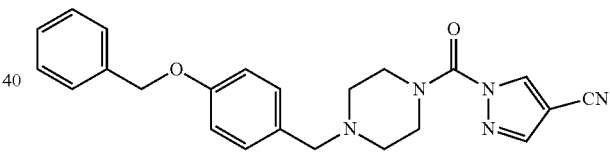

The title compound was prepared from 1-(benzyloxy)-4-(bromomethyl)benzene, tert-butyl piperazine-1-carboxylate and 1H-pyrazole-4-carbonitrile (8 mg, 0.086 mmol) according to the representative procedure of Example 10 to provide 1-(4-(4-(benzyloxy)benzyl)piperazine-1-carbonyl)-1H-pyrazole-4-carbonitrile (13 mg, 40%) as a white solid. ¹H NMR (400 MHz, Chloroform-d) δ 8.80 (s, 1H), 8.24 (s, 1H), 7.47 (m, 2H), 7.42 (m, 3H), 7.25 (m, 2H), 7.18 (m, 2H), 5.11 (s, 2H), 3.65 (s, 2H), 3.22 (t, 4H, J=6.7 Hz), 2.54 (t, 4H, J=6.4 Hz). LCMS (ESI, m/z): 402 [M+H]⁺.

Example 22: (4-([1,1'-Biphenyl]-4-ylmethyl)piperazin-1-yl)(1H-pyrazol-1-yl)methanone

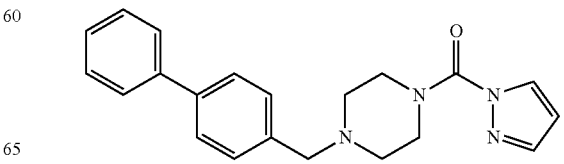

The title compound was prepared from 4-(bromomethyl)-1,1'-biphenyl, tert-butyl piperazine-1-carboxylate and 1H-pyrazole (10 mg, 0.15 mmol) according to the representative procedure of Example 10 to provide (4-([1,1'-biphenyl]-4-ylmethyl)piperazin-1-yl)(1H-pyrazol-1-yl)methanone (18 mg, 36%) as a white solid. $^1$H NMR (400 MHz, Chloroform-d) δ 8.25 (s, 1H), 7.67 (s, 1H), 7.53 (m, 4H), 7.40-7.38 (m, 6H), 3.67 (s, 2H), 3.22 (t, 4H, J=6.7 Hz), 2.68 (t, 4H, J=6.2 Hz). LCMS (ESI, m/z): 347 [M+H]$^+$.

Example 23: (4-([1,1'-Biphenyl]-4-ylmethyl)piperazin-1-yl)(4-methyl-1H-pyrazol-1-yl)methanone

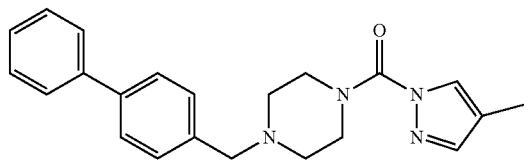 [SMILES: Cc1cnn(C(=O)N2CCN(Cc3ccc(-c4ccccc4)cc3)CC2)c1]

The title compound was prepared from 4-(bromomethyl)-1,1'-biphenyl, tert-butyl piperazine-1-carboxylate and 4-methyl-1H-pyrazole (8 mg, 0.097 mmol) according to the representative procedure of Example 10 to provide (4-([1,1'-biphenyl]-4-ylmethyl)piperazin-1-yl)(4-methyl-1H-pyrazol-1-yl)methanone (11 mg, 34%) as a white solid. $^1$H NMR (400 MHz, Chloroform-d) δ 8.08 (s, 1H), 7.53 (m, 5H), 7.40-7.38 (m, 5H), 3.67 (s, 2H), 3.22 (t, 4H, J=6.7 Hz), 2.68 (t, 4H, J=6.2 Hz), 2.04 (s, 3H). LCMS (ESI, m/z): 361 [M+H]$^+$.

Example 24: 1-(4-([1,1'-Biphenyl]-4-ylmethyl)piperazine-1-carbonyl)-1H-pyrazole-4-carbonitrile

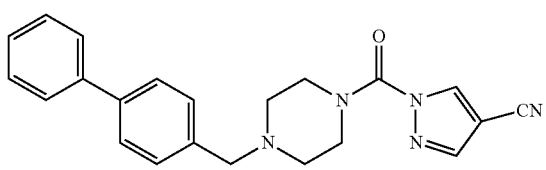 [SMILES: N#Cc1cnn(C(=O)N2CCN(Cc3ccc(-c4ccccc4)cc3)CC2)c1]

The title compound was prepared from 4-(bromomethyl)-1,1'-biphenyl, tert-butyl piperazine-1-carboxylate and 1H-pyrazole-4-carbonitrile (10 mg, 0.11 mmol) according to the representative procedure of Example 10 to provide 1-(4-([1,1'-biphenyl]-4-ylmethyl)piperazine-1-carbonyl)-1H-pyrazole-4-carbonitrile (15 mg, 38%) as a white solid. $^1$H NMR (400 MHz, Chloroform-d) δ 8.80 (s, 1H), 8.24 (s, 1H), 7.53 (m, 4H), 7.40-7.38 (m, 5H), 3.67 (s, 2H), 3.22 (t, 4H, J=6.7 Hz), 2.68 (t, 4H, J=6.2 Hz). LCMS (ESI, m/z): 372 [M+H]$^+$.

Example 25: tert-Butyl 4-(1H-pyrazole-1-carbonyl)-1,4-diazepane-1-carboxylate

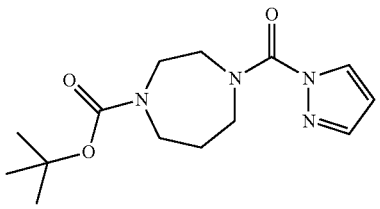 [SMILES: CC(C)(C)OC(=O)N1CCCN(C(=O)n2cccn2)CC1]

The title compound was prepared from 1H-pyrazole (15 mg, 0.22 mmol) and tert-butyl 1,4-diazepane-1-carboxylate (44 mg, 0.22 mmol) according to the representative procedure of Example 1 to provide tert-butyl 4-(1H-pyrazole-1-carbonyl)-1,4-diazepane-1-carboxylate (34 mg, 50%) as a white solid. $^1$H NMR (400 MHz, Chloroform-d) δ 8.14 (s, 1H), 7.65 (s, 1H), 6.36 (s, 1H), 3.64-3.44 (m, 8H), 1.80 (m, 2H), 1.46 (s, 9H). LCMS (ESI, m/z): 295 [M+H]$^+$.

Example 26: tert-Butyl 4-(4-methyl-1H-pyrazole-1-carbonyl)-1,4-diazepane-1-carboxylate

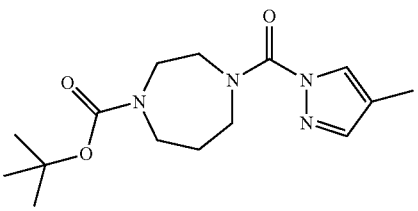 [SMILES: Cc1cnn(C(=O)N2CCCN(C(=O)OC(C)(C)C)CC2)c1]

The title compound was prepared from 4-methyl-1H-pyrazole (13 mg, 0.16 mmol) and tert-butyl 1,4-diazepane-1-carboxylate (32 mg, 0.16 mmol) according to the representative procedure of Example 1 to provide tert-butyl 4-(4-methyl-1H-pyrazole-1-carbonyl)-1,4-diazepane-1-carboxylate (23 mg, 48%) as a white solid. $^1$H NMR (400 MHz, Chloroform-d) δ 7.86 (s, 1H) 7.41 (s, 1H), 3.59-3.41 (m, 8H), 2.07 (s, 3H), 1.96 (m, 2H), 1.44 (s, 9H). LCMS (ESI, m/z): 309 [M+H]$^+$.

Example 27: tert-Butyl 4-(4-cyano-1H-pyrazole-1-carbonyl)-1,4-diazepane-1-carboxylate

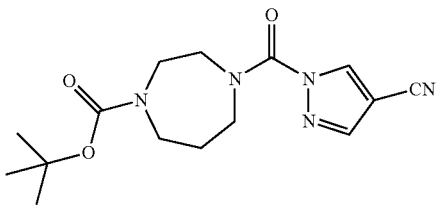 [SMILES: CC(C)(C)OC(=O)N1CCCN(C(=O)n2cc(C#N)cn2)CC1]

The title compound was prepared from 1H-pyrazole-4-carbonitrile (10 mg, 0.11 mmol) and tert-butyl 1,4-diazepane-1-carboxylate (22 mg, 0.11 mmol) according to the representative procedure of Example 1 to provide tert-butyl 4-(4-cyano-1H-pyrazole-1-carbonyl)-1,4-diazepane-1-carboxylate (19 mg, 55%) as a white solid. $^1$H NMR (400 MHz, Chloroform-d) δ 7.86 (s, 1H) 7.41 (s, 1H), 3.59-3.41 (m, 8H), 1.96 (m, 2H), 1.44 (s, 9H). LCMS (ESI, m/z): 320 [M+H]+.

Example 28: tert-Butyl methyl(2-(N-methyl-1H-pyrazole-1-carboxamido)ethyl)carbamate

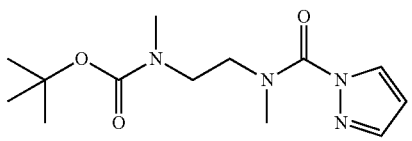 [SMILES: CN(CCN(C)C(=O)n1cccn1)C(=O)OC(C)(C)C]

The title compound was prepared from 1H-pyrazole (12 mg, 0.18 mmol) and tert-butyl methyl(2-(methylamino)ethyl)carbamate (33 mg, 0.18 mmol) according to the representative procedure of Example 1 to provide tert-butyl methyl(2-(N-methyl-1H-pyrazole-1-carboxamido)ethyl)carbamate (26 mg, 52%) as a white solid. $^1$H NMR (400 MHz, Chloroform-d) δ 8.12 (d, 1H, J=7.3 Hz), 7.62 (s, 1H), 6.34 (t, 1H, J=7.4 Hz), 3.82 (m, 2H), 3.75 (m, 2H), 3.20 (s, 3H), 2.82 (s, 3H), 1.43 (s, 9H). LCMS (ESI, m/z): 283 [M+H]+.

Example 29: tert-Butyl (2-(N,4-dimethyl-1H-pyrazole-1-carboxamido)ethyl)(methyl)carbamate

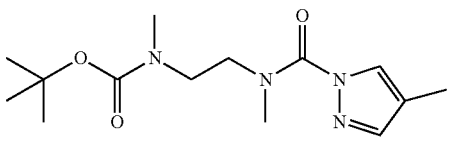 [SMILES: Cc1cnn(C(=O)N(C)CCN(C)C(=O)OC(C)(C)C)c1]

The title compound was prepared from 4-methyl-1H-pyrazole (12 mg, 0.15 mmol) and tert-butyl methyl(2-(methylamino)ethyl)carbamate (26 mg, 0.15 mmol) according to the representative procedure of Example 1 to provide tert-butyl (2-(N,4-dimethyl-1H-pyrazole-1-carboxamido)ethyl)(methyl)carbamate (20 mg, 48%) as a white solid. $^1$H NMR (400 MHz, Chloroform-d) δ 7.85 (s, 1H) 7.42 (s, 1H), 3.50 (m, 2H), 2.89 (m, 2H), 2.07 (s, 3H), 2.03 (s, 6H), 1.42 (s, 9H). LCMS (ESI, m/z): 297 [M+H]+.

Example 30: tert-Butyl (2-(4-cyano-N-methyl-1H-pyrazole-1-carboxamido)ethyl)(methyl)carbamate

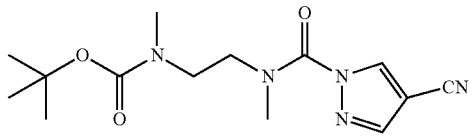 [SMILES: CN(CCN(C)C(=O)n1cc(C#N)cn1)C(=O)OC(C)(C)C]

The title compound was prepared from 1H-pyrazole-4-carbonitrile (12 mg, 0.13 mmol) and tert-butyl methyl(2-(methylamino)ethyl)carbamate (24 mg, 0.13 mmol) according to the representative procedure of Example 1 to provide tert-butyl (2-(4-cyano-N-methyl-1H-pyrazole-1-carboxamido)ethyl)(methyl)carbamate (20 mg, 50%) as a white solid. $^1$H NMR (400 MHz, Chloroform-d) δ 7.85 (s, 1H) 7.42 (s, 1H), 3.50 (m, 2H), 2.89 (m, 2H), 2.07 (s, 6H), 1.42 (s, 9H). LCMS (ESI, m/z): 308 [M+H]+.

Example 31: N-(3-Phenylpropyl)-1H-pyrazole-1-carboxamide

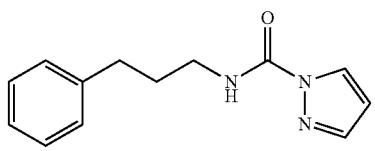 [SMILES: O=C(NCCCc1ccccc1)n1cccn1]

The title compound was prepared from 1H-pyrazole (10 mg, 0.15 mmol) and 3-phenylpropan-1-amine (20 mg, 0.15 mmol) according to the representative procedure of Example 1 to provide N-(3-phenylpropyl)-1H-pyrazole-1-carboxamide (18 mg, 52%) as a colorless oil. $^1$H NMR (400 MHz, Chloroform-d) δ 8.26 (d, 1H, J=7.3 Hz), 7.45-7.43 (m, 3H), 7.26 (m, 3H), 6.44 (t, 1H, J=6.4 Hz), 3.22 (t, 2H, J=7.4 Hz), 2.64 (t, 2H, J=7.2 Hz), 2.03 (m, 2H). LCMS (ESI, m/z): 230 [M+H]+.

Example 32: 4-Methyl-N-(3-phenylpropyl)-1H-pyrazole-1-carboxamide

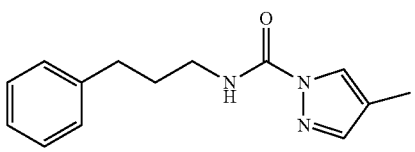 [SMILES: Cc1cnn(C(=O)NCCCc2ccccc2)c1]

The title compound was prepared from 4-methyl-1H-pyrazole (10 mg, 0.12 mmol) and 3-phenylpropan-1-amine (16 mg, 0.12 mmol) according to the representative procedure of Example 1 to provide 4-methyl-N-(3-phenylpropyl)-1H-pyrazole-1-carboxamide (14 mg, 49%) as a colorless oil. $^1$H NMR (400 MHz, Chloroform-d) δ 8.21 (s, 1H), 7.51 (s, 1H), 7.43 (m, 3H), 7.26 (m, 2H), 3.22 (t, 2H, J=7.4 Hz), 2.64 (t, 2H, J=7.2 Hz), 2.04 (s, 3H), 1.62 (m, 2H). LCMS (ESI, m/z): 244 [M+H]+.

Example 33: 4-Cyano-N-(3-phenylpropyl)-1H-pyrazole-1-carboxamide

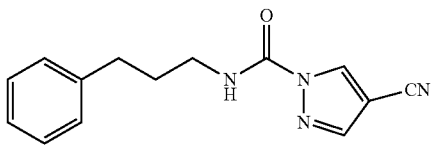 [SMILES: N#Cc1cnn(C(=O)NCCCc2ccccc2)c1]

The title compound was prepared from 1H-pyrazole-4-carbonitrile (9 mg, 0.098 mmol) and 3-phenylpropan-1-amine (13 mg, 0.098 mmol) according to the representative procedure of Example 1 to provide 4-cyano-N-(3-phenylpropyl)-1H-pyrazole-1-carboxamide (12 mg, 47%) as a colorless oil. $^1$H NMR (400 MHz, Chloroform-d) δ 8.82 (s, 1H), 8.23 (s, 1H), 7.43 (m, 3H), 7.26 (m, 2H), 3.22 (t, 2H, J=7.4 Hz), 2.64 (t, 2H, J=7.2 Hz), 1.62 (m, 2H). LCMS (ESI, m/z): 255 [M+H]+.

Example 34: N-(4-Phenylbutyl)-1H-pyrazole-1-carboxamide

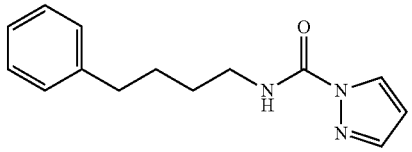 [SMILES: O=C(NCCCCc1ccccc1)n1cccn1]

The title compound was prepared from 1H-pyrazole (20 mg, 0.29 mmol) and 4-phenylbutan-1-amine (44 mg, 0.29 mmol) according to the representative procedure of Example 1 to provide N-(4-phenylbutyl)-1H-pyrazole-1-carboxamide (44 mg, 62%) as a colorless oil. $^1$H NMR (400 MHz, Chloroform-d) δ 8.26 (d, 1H, J=7.3 Hz), 7.45-7.43 (m, 3H), 7.26 (m, 4H), 6.44 (d, 1H, J=6.4 Hz), 3.22 (t, 2H, J=7.4 Hz), 2.64 (t, 2H, J=7.2 Hz), 1.62 (m, 2H), 1.57 (m, 2H). LCMS (ESI, m/z): 244 [M+H]$^+$.

Example 35: 4-Methyl-N-(4-phenylbutyl)-1H-pyrazole-1-carboxamide

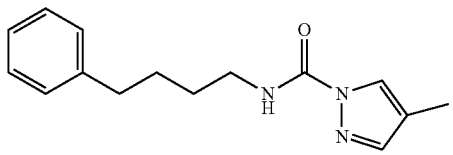 [SMILES: Cc1cnn(C(=O)NCCCCc2ccccc2)c1]

The title compound was prepared from 4-methyl-1H-pyrazole (20 mg, 0.24 mmol) and 4-phenylbutan-1-amine (36 mg, 0.24 mmol) according to the representative procedure of Example 1 to provide 4-methyl-N-(4-phenylbutyl)-1H-pyrazole-1-carboxamide (30 mg, 49%) as a colorless oil. $^1$H NMR (400 MHz, Chloroform-d) δ 8.21 (s, 1H), 7.51 (s, 1H), 7.43 (m, 3H), 7.26 (m, 2H), 3.22 (t, 2H, J=7.4 Hz), 2.64 (t, 2H, J=7.2 Hz), 2.04 (s, 3H), 1.62 (m, 2H), 1.57 (m, 2H). LCMS (ESI, m/z): 258 [M+H]$^+$.

Example 36: 4-Cyano-N-(4-phenylbutyl)-1H-pyrazole-1-carboxamide

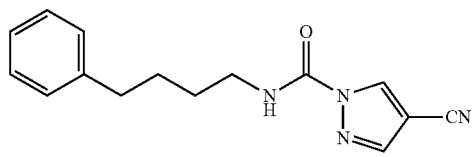 [SMILES: N#Cc1cnn(C(=O)NCCCCc2ccccc2)c1]

The title compound was prepared from 1H-pyrazole-4-carbonitrile (10 mg, 0.11 mmol) and 4-phenylbutan-1-amine (17 mg, 0.11 mmol) according to the representative procedure of Example 1 to provide 4-cyano-N-(4-phenylbutyl)-1H-pyrazole-1-carboxamide (14 mg, 47%) as a colorless oil. $^1$H NMR (400 MHz, Chloroform-d) δ 8.82 (s, 1H), 8.23 (s, 1H), 7.43 (m, 3H), 7.26 (m, 2H), 3.22 (t, 2H, J=7.4 Hz), 2.64 (t, 2H, J=7.2 Hz), 2.04 (s, 3H), 1.62 (m, 2H), 1.57 (m, 2H). LCMS (ESI, m/z): 269 [M+H]$^+$.

Example 37: N-(5-phenylpentyl)-1H-pyrazole-1-carboxamide

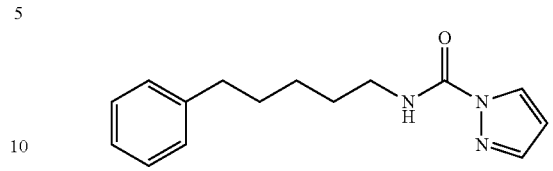

The title compound was prepared from 1H-pyrazole (10 mg, 0.15 mmol) and 5-phenylpentan-1-amine (24 mg, 0.15 mmol) according to the representative procedure of Example 1 to provide N-(5-phenylpentyl)-1H-pyrazole-1-carboxamide (20 mg, 52%) as a colorless oil. $^1$H NMR (400 MHz, Chloroform-d) δ 8.26 (d, 1H, J=6.4 Hz), 8.00 (br s, 1H), 7.43 (m, 3H), 7.26 (m, 3H), 6.44 (t, 1H, J=6.4 Hz), 3.22 (t, 2H, J=7.4 Hz), 2.64 (t, 2H, J=7.2 Hz), 1.62 (m, 4H), 1.57 (m, 2H). LCMS (ESI, m/z): 258 [M+H]$^+$.

Example 38: 4-Methyl-N-(5-phenylpentyl)-1H-pyrazole-1-carboxamide

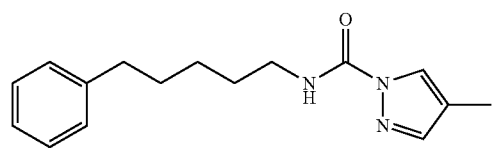 [SMILES: Cc1cnn(C(=O)NCCCCCc2ccccc2)c1]

The title compound was prepared from 4-methyl-1H-pyrazole (9 mg, 0.11 mmol) and 5-phenylpentan-1-amine (18 mg, 0.11 mmol) according to the representative procedure of Example 1 to provide 4-methyl-N-(5-phenylpentyl)-1H-pyrazole-1-carboxamide (14 mg, 49%) as a colorless oil. $^1$H NMR (400 MHz, Chloroform-d) δ 8.21 (s, 1H), 8.08 (br s, 1H), 7.51 (s, 1H), 7.43 (m, 3H), 7.26 (m, 2H), 3.22 (t, 2H, J=7.4 Hz), 2.64 (t, 2H, J=7.2 Hz), 2.04 (s, 3H), 1.62 (m, 4H), 1.57 (m, 2H). LCMS (ESI, m/z): 272 [M+H]$^+$.

Example 39: 4-Cyano-N-(5-phenylpentyl)-1H-pyrazole-1-carboxamide

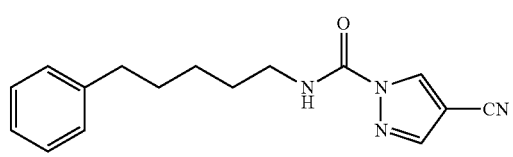 [SMILES: N#Cc1cnn(C(=O)NCCCCCc2ccccc2)c1]

The title compound was prepared from 1H-pyrazole-4-carbonitrile (9 mg, 0.098 mmol) and 5-phenylpentan-1-amine (16 mg, 0.98 mmol) according to the representative procedure of Example 1 to provide 4-cyano-N-(5-phenylpentyl)-1H-pyrazole-1-carboxamide (12 mg, 45%) as a colorless oil. $^1$H NMR (400 MHz, Chloroform-d) δ 8.81 (s, 1H), 8.21 (s, 1H), 8.02 (br s, 1H), 7.43 (m, 3H), 7.26 (m, 2H), 3.22 (t, 2H, J=7.4 Hz), 2.64 (t, 2H, J=7.2 Hz), 1.62 (m, 4H), 1.57 (m, 2H). LCMS (ESI, m/z): 283 [M+H]$^+$.

Example 40: N-(Naphthalen-2-yl)-1H-pyrazole-1-carboxamide

The title compound was prepared from 1H-pyrazole (18 mg, 0.26 mmol) and naphthalen-2-amine (38 mg, 0.26 mmol) according to the representative procedure of Example 1 to provide N-(naphthalen-2-yl)-1H-pyrazole-1-carboxamide (27 mg, 44%) as a red solid. $^1$H NMR (400 MHz, Chloroform-d) δ 9.15 (br s, 1H), 8.10 (m, 2H), 7.98-7.96 (m, 3H), 7.66-7.48 (m, 3H), 7.40 (s, 1H, 6.46 (t, 1H, J=6.4 Hz). LCMS (ESI, m/z): 238 [M+H]$^+$.

Example 41: 4-Methyl-N-(naphthalen-2-yl)-1H-pyrazole-1-carboxamide

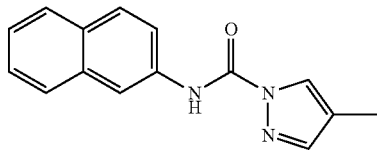 [SMILES: Cc1cnn(C(=O)Nc2ccc3ccccc3c2)c1]

The title compound was prepared from 4-methyl-1H-pyrazole (10 mg, 0.12 mmol) and naphthalen-2-amine (17 mg, 0.12 mmol) according to the representative procedure of Example 1 to provide 4-methyl-N-(naphthalen-2-yl)-1H-pyrazole-1-carboxamide (12 mg, 39%) as a red solid. $^1$H NMR (400 MHz, Chloroform-d) δ 9.15 (br s, 1H), 8.07 (s, 1H), 7.98-7.96 (m, 2H), 7.66-7.48 (m, 3H), 7.40 (m, 2H), 7.16 (d, 1H, J=6.7 Hz), 2.04 (s, 3H). LCMS (ESI, m/z): 252 [M+H]$^+$.

Example 42: 4-Cyano-N-(naphthalen-2-yl)-1H-pyrazole-1-carboxamide

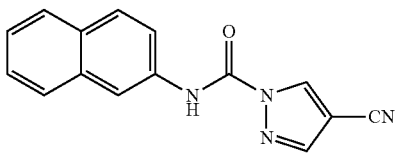 [SMILES: N#Cc1cnn(C(=O)Nc2ccc3ccccc3c2)c1]

The title compound was prepared from 1H-pyrazole-4-carbonitrile (12 mg, 0.13 mmol) and naphthalen-2-amine (18 mg, 0.13 mmol) according to the representative procedure of Example 1 to provide 4-cyano-N-(naphthalen-2-yl)-1H-pyrazole-1-carboxamide (14 mg, 43%) as a red solid. $^1$H NMR (400 MHz, Chloroform-d) δ 9.05 (br s, 1H), 8.10 (s, 2H), 7.98-7.96 (m, 2H), 7.66-7.48 (m, 3H), 7.40-7.35 (m, 3H). LCMS (ESI, m/z): 263 [M+H]$^+$.

Example 43: N-(Naphthalen-2-ylmethyl)-1H-pyrazole-1-carboxamide

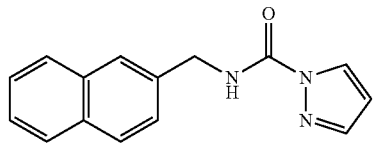 [SMILES: O=C(NCc1ccc2ccccc2c1)n1cccn1]

The title compound was prepared from 1H-pyrazole (10 mg, 0.15 mmol) and naphthalen-2-ylmethanamine (23 mg, 0.15 mmol) according to the representative procedure of Example 1 to provide N-(naphthalen-2-ylmethyl)-1H-pyrazole-1-carboxamide (19 mg, 51%) as a white solid. $^1$H NMR (400 MHz, Chloroform-d) δ 8.22 (d, 1H, J=6.4 Hz), 8.01-7.96 (m, 4H), 7.58-7.55 (m, 2H), 7.44 (m, 2H), 7.11 (s, 1H), 6.44 (t, 1H, J=6.2 Hz), 4.33 (s, 2H). LCMS (ESI, m/z): 252 [M+H]$^+$.

Example 44: 4-Methyl-N-(naphthalen-2-ylmethyl)-1H-pyrazole-1-carboxamide

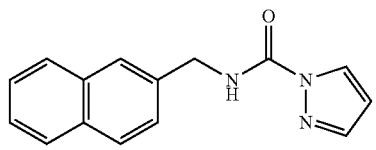 [SMILES: O=C(NCc1ccc2ccccc2c1)n1cccn1]

The title compound was prepared from 4-methyl-1H-pyrazole (10 mg, 0.12 mmol) and naphthalen-2-ylmethanamine (18 mg, 0.12 mmol) according to the representative procedure of Example 1 to provide 4-methyl-N-(naphthalen-2-ylmethyl)-1H-pyrazole-1-carboxamide (14 mg, 45%) as a tan solid. $^1$H NMR (400 MHz, Chloroform-d) δ 8.06 (s, 1H), 8.03-7.98 (m, 4H), 7.58-7.55 (m, 3H), 7.46 (s, 1H), 7.18 (s, 1H), 4.34 (s, 2H), 2.02 (s, 3H). LCMS (ESI, m/z): 266 [M+H]$^+$.

Example 45: 4-Cyano-N-(naphthalen-2-ylmethyl)-1H-pyrazole-1-carboxamide

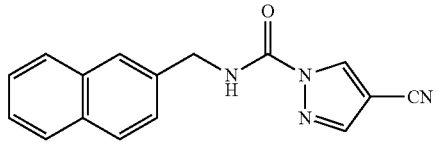 [SMILES: N#Cc1cnn(C(=O)NCc2ccc3ccccc3c2)c1]

The title compound was prepared from 1H-pyrazole-4-carbonitrile (11 mg, 0.12 mmol) and naphthalen-2-ylmethanamine (18 mg, 0.12 mmol) according to the representative procedure of Example 1 to provide 4-cyano-N-(naphthalen-2-ylmethyl)-1H-pyrazole-1-carboxamide (13 mg, 40%) as a white solid. $^1$H NMR (400 MHz, Chloroform-d) δ 8.80 (s, 1H), 8.20 (s, 1H), 8.01-7.96 (m, 4H), 7.58-7.56 (m, 2H), 7.44 (s, 1H), 7.15 (s, 1H), 4.34 (s, 2H). LCMS (ESI, m/z): 277 [M+H]$^+$.

Example 46: (4-(Bis(4-chlorophenyl)methyl)piperazin-1-yl)(1H-pyrazol-1-yl)methanone

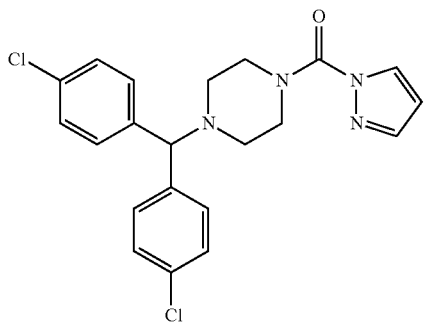 [SMILES: O=C(N1CCN(C(c2ccc(Cl)cc2)c2ccc(Cl)cc2)CC1)n1cccn1]

Preparation of (4-(Bis(4-chlorophenyl)methyl)piperazin-1-yl)(1H-pyrazol-1-yl)methanone

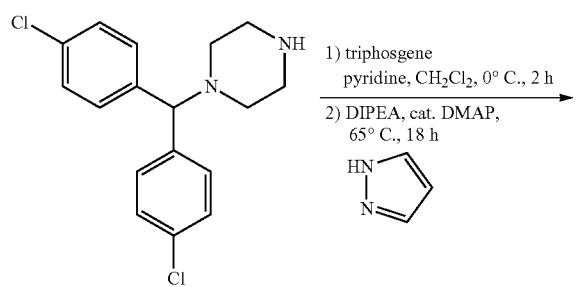

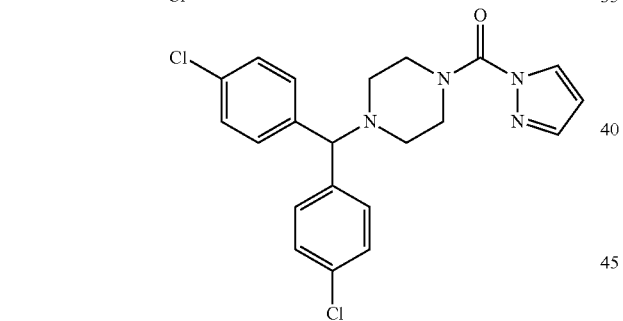

A flask was equipped with a magnetic stirbar and charged with triphosgene (46 mg, 0.160 mmol, 0.5 equiv) and CH$_2$Cl$_2$ (3.0 mL). The solution was cooled to 0° C., and pyridine (0.030 mL, 0.310 mmol, 1.0 equiv) was added. After stirring at 0° C. for 5 min, 1-(bis(4-chlorophenyl)methyl)piperazine (100 mg, 0.310 mmol, 1.0 equiv) was added, and the reaction mixture was stirred at 0° C. for 30 min, then at rt for 1 h. The resulting mixture was poured into brine (20 mL) and extracted with CH$_2$Cl$_2$ (3×40 mL). The combined organic layers were washed with saturated NaHCO$_3$ (2×20 mL), dried over anhydrous Na$_2$SO$_4$ and concentrated under reduced pressure to provide 4-[bis(4-chlorophenyl)methyl]-piperazine-1-carbonyl chloride (100 mg, 0.260 mmol, 84% yield), which was used without further purification. Crude 4-[bis(4-chlorophenyl)methyl]piperazine-1-carbonyl chloride (40 mg, 0.100 mmol, 1.0 equiv) was taken up in CH$_2$Cl$_2$ (1.0 mL), and DIPEA (0.05 mL, 0.310 mmol, 3.1 equiv), 1H-pyrazole (18 mg, 0.260 mmol, 2.6 equiv) and DMAP (2 mg, 0.010 mmol, 0.1 equiv) were added. The reaction mixture was heated to 65° C. for 18 h. The resulting mixture was concentrated and purified by silica chromatography (0 to 30% EtOAc in hexane) to provide (4-(bis(4-chlorophenyl)methyl)piperazin-1-yl)(1H-pyrazol-1-yl)methanone (25 mg, 0.060 mmol, 58% yield) as a colorless oil. $^1$H NMR (400 MHz, Chloroform-d) δ 8.02 (d, J=2.7 Hz, 1H), 7.55-7.49 (m, 1H), 7.25 (d, J=2.3 Hz, 4H), 7.22-7.16 (m, 4H), 6.30-6.24 (m, 1H), 4.17 (s, 1H), 3.80 (s, 5H), 2.44-2.36 (m, 4H). LCMS (ESI, m/z): 437.1 [M+Na]$^+$.

Example 47: (4-Chloro-1H-pyrazol-1-yl)(4-(4-chloro-2-morpholinobenzyl)piperazin-1-yl)methanone

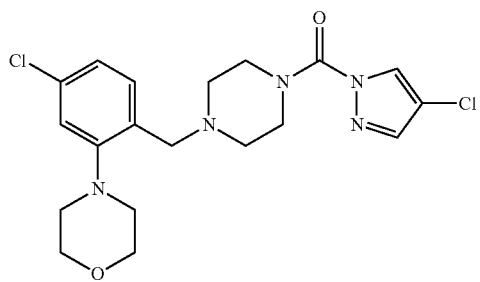 [SMILES: O=C(N1CCN(Cc2ccc(Cl)cc2N2CCOCC2)CC1)n1cc(Cl)cn1]

Step 1: Preparation of 4-chloro-2-morpholinobenzaldehyde

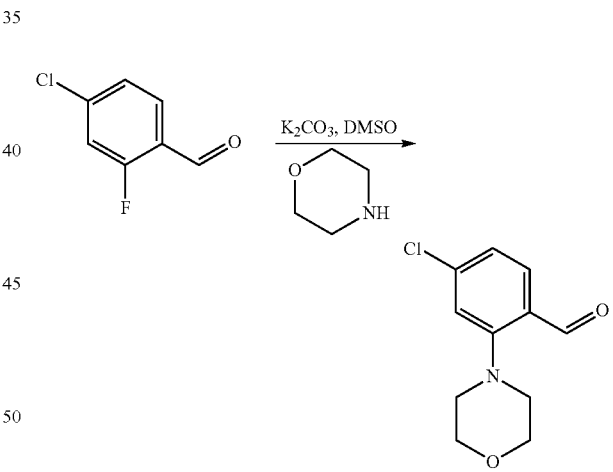

A 20-mL vial with a screwtop was charged with 4-chloro-2-fluorobenzaldehyde (2.0 g, 12.7 mmol), morpholine (1.67 g, 19.05 mmol) and DMSO (15 mL). Potassium carbonate (2.76 g, 20 mmol) was added, and the reaction mixture was heated to 120° C. for 3.5 h. The resulting mixture was diluted in EtOAc (150 mL) and extracted with brine (3×50 mL). The combined organic layers were dried (Na$_2$SO$_4$), filtered and concentrated by rotary evaporation. Purification by silica chromatography (0 to 20% EtOAc in hexanes) yielded 4-chloro-2-morpholinobenzaldehyde (2.21 g, 77%). $^1$H NMR (400 MHz, Chloroform-d) δ 10.21 (s, 1H), 7.73 (d, J=8.3 Hz, 1H), 7.20-6.96 (m, 2H), 4.11-3.77 (m, 4H), 3.17-2.96 (m, 4H). LCMS (ESI, m/z): 226.0 [M+H]$^+$.

Step 2: Preparation of tert-butyl 4-(4-chloro-2-morpholinobenzyl)piperazine-1-carboxylate

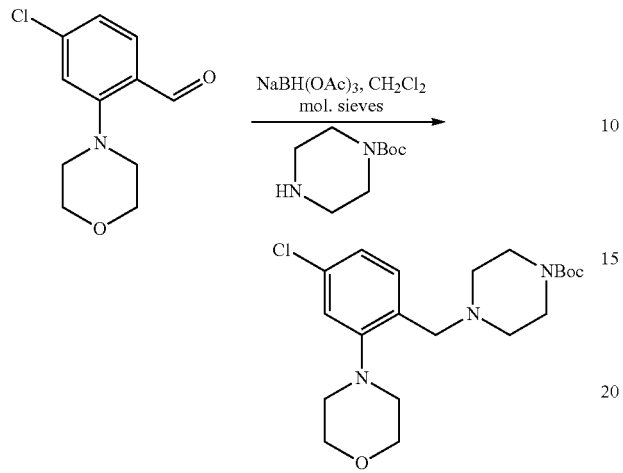

A 100-mL flask was charged with 4-chloro-2-morpholinobenzaldehyde (2.21 g, 9.79 mmol), CH$_2$Cl$_2$ (10 mL), tert-butyl piperazine-1-carboxylate (2.0 g, 10.77 mmol) and molecular sieves (1 g). The contents were stirred at rt for 10 min. NaBH(OAc)$_3$ (2.4 g, 12.7 mmol) was added, and the reaction mixture was stirred for 18 h at rt. The resulting mixture was filtered, diluted in CH$_2$Cl$_2$ (150 mL) and extracted with brine (2×50 ml). The combined organic layers were dried (Na$_2$SO$_4$), filtered and concentrated by rotary evaporation. Purification by silica chromatography (100% hexanes to 75% hexanes in EtOAc) yielded tert-butyl 4-(4-chloro-2-morpholinobenzyl)piperazine-1-carboxylate (2.73 g, 70%) as a white foam. $^1$H NMR (400 MHz, Chloroform-d) δ 7.38 (d, J=7.6 Hz, 1H), 7.11-7.04 (m, 3H), 3.88-3.82 (m, 8H), 3.53 (s, 3H), 3.43-3.37 (m, 6H), 3.02-2.95 (m, 8H), 2.42 (s, 4H), 1.48 (s, 9H). LCMS (ESI, m/z): 396.1 [M+H]$^+$.

Step 3: Preparation of 4-(5-chloro-2-(piperazin-1-ylmethyl)phenyl)-morpholine

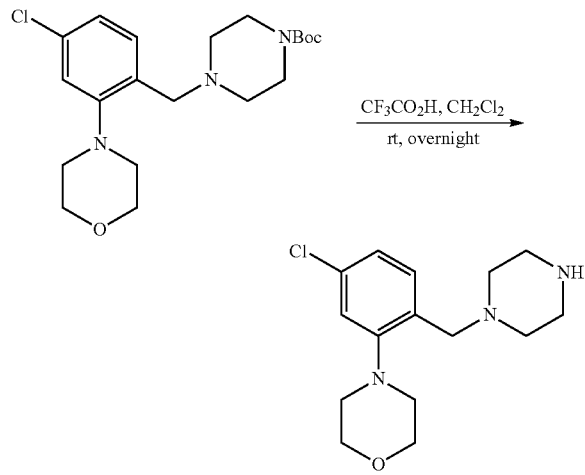

A flask was charged with tert-butyl 4-(4-chloro-2-morpholinobenzyl)piperazine-1-carboxylate (994 mg, 2.5 mmol) dissolved in CH$_2$Cl$_2$ (8 mL). Trifluoroacetic acid (2 mL) was added, and the reaction mixture was stirred at rt for 3 h. The resulting mixture was concentrated, and cold 1N NaOH (100 mL) was added until the solution was basic. This basic mixture was extracted with CH$_2$Cl$_2$ (3×100 mL). The combined organic layers were dried over Na$_2$SO$_4$, filtered and concentrated to yield crude 4-(5-chloro-2-(piperazin-1-ylmethyl)phenyl)-morpholine (594 mg, 80%) as an orange oil, which was used without further purification. LCMS (ESI, m/z): 296 [M+H]$^+$.

Step 4: Preparation of (4-chloro-1H-pyrazol-1-yl)(4-(4-chloro-2-morpholinobenzyl)piperazin-1-yl)methanone The title compound was synthesized directly from 4-chloro-1H-pyrazole and 4-(5-chloro-2-(piperazin-1-ylmethyl)phenyl)morpholine according to the representative procedure of Example 46 to provide (4-chloro-1H-pyrazol-1-yl)(4-(4-chloro-2-morpholinobenzyl)piperazin-1-yl) methanone as an oil. $^1$H NMR (400 MHz, Chloroform-d) δ 8.07 (s, 1H), 7.54 (s, 1H), 7.37 (d, J=8.0 Hz, 1H), 7.10-7.02 (m, 2H), 3.90-3.68 (m, 8H), 3.55 (s, 2H), 2.98-2.91 (m, 4H), 2.55 (t, J=5.4 Hz, 4H). LCMS (ESI, m/z): 424.1 [M+H]$^+$.

Example 48: (4-(Bis(4-chlorophenyl)methyl)piperazin-1-yl)(4-(pyrrolidine-1-carbonyl)-1H-pyrazol-1-yl)methanone

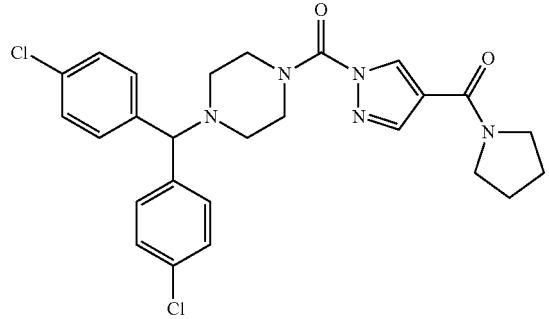 [SMILES: O=C(c1cnn(C(=O)N2CCN(C(c3ccc(Cl)cc3)c3ccc(Cl)cc3)CC2)c1)N1CCCC1]

Step 1: Preparation of (1H-pyrazol-4-yl)(pyrrolidin-1-yl)methanone

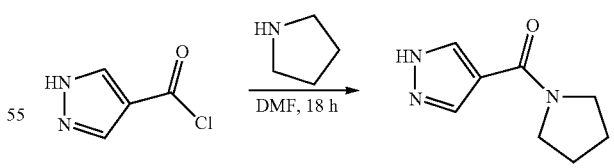

A flask was charged with 1H-pyrazole-4-carbonyl chloride (880 mg, 6.12 mmol, 1.0 equiv) and N,N-dimethylformamide (30 mL). Pyrrolidine (780 μL, 9.80 mmol, 1.6 equiv) was added, followed by N,N-diisopropylamine (5.3 mL, 30.6 mmol, 5.0 equiv), and the reaction mixture was stirred at rt. After 18 h, the resulting mixture was concentrated. Purification by silica chromatography (0 to 10% CH$_3$OH in CH$_2$Cl$_2$) yielded (1H-pyrazol-4-yl)(pyrrolidin-1-yl)methanone (500 mg, 50%) as a white solid. $^1$H NMR (400

MHz, Chloroform-d) δ 7.94 (s, 2H), 3.66 (dt, J=29.6, 6.6 Hz, 4H), 2.07-1.87 (m, 4H). LCMS (ESI, m/z): 166.1 [M+H]⁺.

Step 2: Preparation of (4-(bis(4-chlorophenyl)methyl)piperazin-1-yl)(4-(pyrrolidine-1-carbonyl)-1H-pyrazol-1-yl)methanone The title compound was synthesized directly from (1H-pyrazol-4-yl)(pyrrolidin-1-yl)methanone and 1-(bis(4-chlorophenyl)methyl)piperazine according to the representative procedure of Example 46 to provide (4-(bis(4-chlorophenyl)methyl)piperazin-1-yl)(4-(pyrrolidine-1-carbonyl)-1H-pyrazol-1-yl)methanone as a white solid. ¹H NMR (400 MHz, Chloroform-d) δ 8.31 (s, 1H), 7.89 (s, 1H), 7.29-7.22 (m, 4H), 7.22-7.16 (m, 4H), 4.18 (s, 1H), 3.79 (br s, 4H), 3.56 (dt, J=10.3, 6.6 Hz, 4H), 2.44-2.37 (m, 4H), 1.99-1.79 (m, 4H). LCMS (ESI, m/z): 512.1 [M+H]⁺.

Example 49: 1-(4-(Bis(4-chlorophenyl)methyl)piperazine-1-carbonyl)-N-cyclopropyl-1H-pyrazole-4-carboxamide

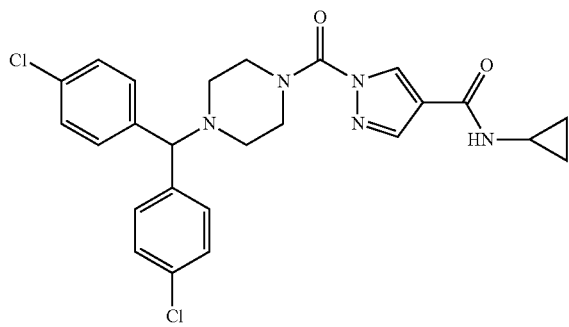 [SMILES: O=C(NC1CC1)c1cnn(C(=O)N2CCN(C(c3ccc(Cl)cc3)c3ccc(Cl)cc3)CC2)c1]

The title compound was synthesized directly from commercially available 1H-pyrazole-4-carbonyl chloride, cyclopropylamine and 1-(bis(4-chlorophenyl)methyl)piperazine according to the representative procedure of Example 48, Steps 1-2 to provide 1-(4-(bis(4-chlorophenyl)methyl)piperazine-1-carbonyl)-N-cyclopropyl-1H-pyrazole-4-carboxamide as an oil. ¹H NMR (400 MHz, Chloroform-d) δ 8.44 (s, 1H), 7.88 (s, 1H), 7.36-7.30 (m, 4H), 7.29-7.23 (m, 4H), 6.23 (d, J=3.1 Hz, 1H), 4.25 (s, 1H), 3.85 (s, 4H), 2.88-2.77 (m, 1H), 2.51-2.43 (m, 4H), 0.92-0.76 (m, 2H), 0.58 (dd, J=3.4, 1.7 Hz, 2H). LCMS (ESI, m/z): 498.1 [M+H]⁺.

Example 50: (4-Chloro-1H-pyrazol-1-yl)(4-(4-chloro-2-(pyrrolidin-1-yl)benzyl)piperazin-1-yl)methanone

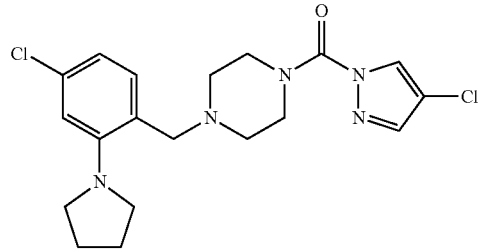 [SMILES: O=C(N1CCN(Cc2ccc(Cl)cc2N2CCCC2)CC1)n1cc(Cl)cn1]

The title compound was synthesized from 4-chloro-2-fluorobenzaldehyde, pyrrolidine, tert-butyl piperazine-1-carboxylate and 4-chloro-1H-pyrazole according to the representative procedure of Example 47, steps 1-4 to provide (4-chloro-1H-pyrazol-1-yl)(4-(4-chloro-2-(pyrrolidin-1-yl)benzyl)piperazin-1-yl)methanone as a white solid. ¹H NMR (400 MHz, Chloroform-d) δ 7.99 (s, 1H), 7.46 (s, 1H), 7.19 (d, J=5.6 Hz, 1H), 6.79-6.69 (m, 2H), 3.74 (s, 4H), 3.44 (s, 2H), 3.21-3.05 (m, 4H), 2.56-2.36 (m, 4H), 1.88-1.80 (m, 4H). LCMS (ESI, m/z): 408.1 [M+H]⁺.

Example 51: (4-(Benzo[d][1,3]dioxol-5-ylmethyl)piperazin-1-yl)(4-(morpholine-4-carbonyl)-1H-pyrazol-1-yl)methanone

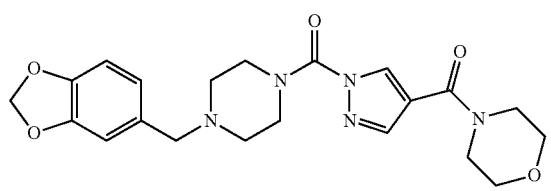 [SMILES: O=C(c1cnn(C(=O)N2CCN(Cc3ccc4c(c3)OCO4)CC2)c1)N1CCOCC1]

Step 1: Preparation of morpholino(1H-pyrazol-4-yl)methanone

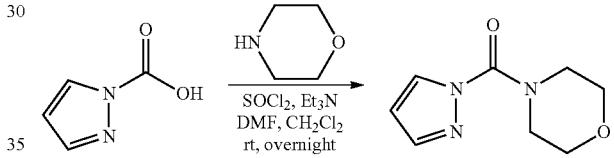

A 250-mL round-bottom flask was charged with 1H-pyrazole-4-carboxylic acid (2.00 g, 17.8 mmol, 1.00 equiv), CH₂Cl₂ (20 mL), thionyl dichloride (4.22 g, 35.5 mmol, 2.00 equiv) and N,N-dimethylformamide (0.2 mL). The mixture was stirred overnight at 45° C. and concentrated under reduced pressure. To this was added CH₂Cl₂ (20 mL), morpholine (4.67 g, 53.6 mmol, 3.00 equiv) and triethylamine (1.81 g, 17.9 mmol, 1.00 equiv). The resulting solution was stirred overnight at rt and concentrated under reduced pressure. The residue was purified by flash chromatography on a silica gel column with CH₂Cl₂/CH₃OH (93/7) to provide 3.00 g (93% yield) of morpholino(1H-pyrazol-4-yl)methanone as a colorless oil. LCMS (ESI, m/z): 182 [M+H]⁺.

Step 2: Preparation of tert-butyl 4-(chlorocarbonyl)piperazine-1-carboxylate

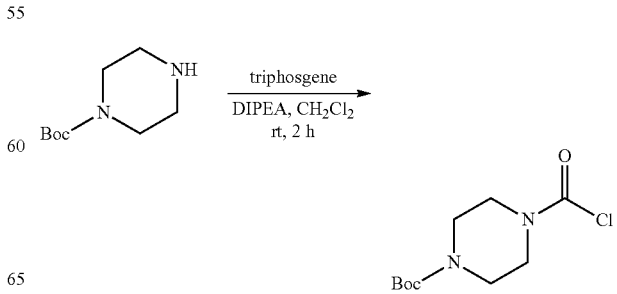

A 100-mL round-bottom flask was charged with triphosgene (3.20 g, 10.8 mmol, 0.50 equiv), CH$_2$Cl$_2$ (30 mL) and tert-butyl piperazine-1-carboxylate (4.00 g, 21.5 mmol, 1.00 equiv). DIPEA (8.32 g, 64.4 mmol, 3.00 equiv) was added dropwise. The reaction mixture was stirred for 2 h at room temperature and diluted with water (50 mL). The resulting solution was extracted with CH$_2$Cl$_2$ (2×100 mL), and the organic layers were combined, dried over anhydrous sodium sulfate, filtered and concentrated under reduced pressure to provide 3.00 g (crude) of tert-butyl 4-(chlorocarbonyl)piperazine-1-carboxylate as a yellow solid.

Step 3: Preparation of tert-butyl 4-(4-(morpholine-4-carbonyl)-1H-pyrazole-1-carbonyl)piperazine-1-carboxylate

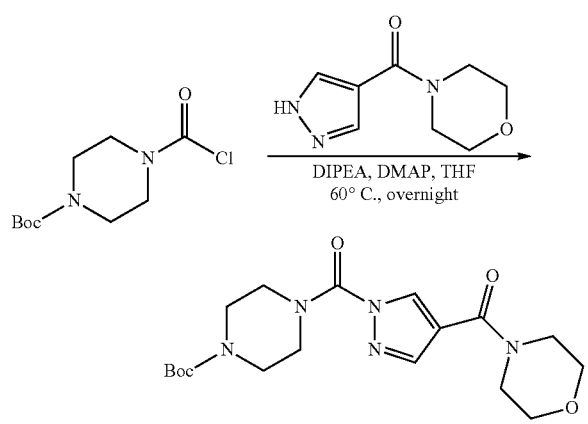

A 250-mL round-bottom flask was charged with tert-butyl 4-(chlorocarbonyl)piperazine-1-carboxylate (4.93 g, 19.8 mmol, 1.20 equiv), THF (35 mL), morpholino(1H-pyrazol-4-yl)methanone (3.00 g, 16.6 mmol, 1.00 equiv), DIPEA (6.41 g, 49.6 mmol, 3.00 equiv) and 4-dimethylaminopyridine (404 mg, 3.31 mmol, 0.20 equiv). The reaction mixture was stirred overnight at 60° C. and diluted with water (50 mL). The resulting solution was extracted with CH$_2$Cl$_2$ (2×250 mL), and the organic layers were combined, dried over anhydrous sodium sulfate, filtered and concentrated under reduced pressure. The residue was purified by flash chromatography on a silica gel column with EtOAc/petroleum ether (100/1). The crude product was recrystallized from EtOAc to provide 2.00 g (31% yield) of tert-butyl 4-(4-(morpholine-4-carbonyl)-1H-pyrazole-1-carbonyl)piperazine-1-carboxylate as a white solid. LCMS (ESI, m/z): 394 [M+H]$^+$.

Step 4: Preparation of (4-(morpholine-4-carbonyl)-1H-pyrazol-1-yl)(piperazin-1-yl)methanone

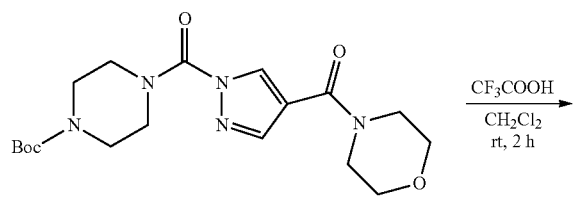

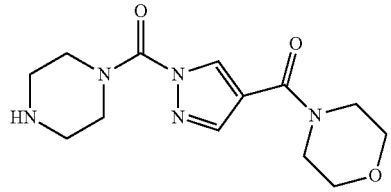

A 50-mL round-bottom flask was charged with tert-butyl 4-(4-(morpholine-4-carbonyl)-1H-pyrazole-1-carbonyl)piperazine-1-carboxylate (200 mg, 0.510 mmol, 1.00 equiv), CH$_2$Cl$_2$ (10 mL) and trifluoroacetic acid (2.0 mL). The resulting solution was stirred for 2.0 h at rt and concentrated under reduced pressure to provide 149 mg (crude) of (4-(morpholine-4-carbonyl)-1H-pyrazol-1-yl)(piperazin-1-yl)methanone as a colorless oil. LCMS (ESI, m/z): 294 [M+H]$^+$.

Step 5: Preparation of (4-(benzo[d][1,3]dioxol-5-ylmethyl)piperazin-1-yl)(4-(morpholine-4-carbonyl)-1H-pyrazol-1-yl)methanone

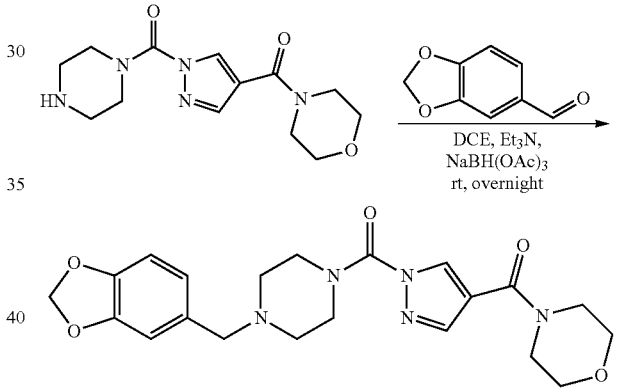

A 50-mL round-bottom flask was charged with (4-(morpholine-4-carbonyl)-1H-pyrazol-1-yl)(piperazin-1-yl)methanone (149 mg, 0.510 mmol, 1.00 equiv), 1,2-dichloroethane (15 mL), triethylamine (154 mg, 1.52 mmol, 3.00 equiv) and benzo[d][1,3]dioxole-5-carbaldehyde (99.0 mg, 0.660 mmol, 1.30 equiv). The mixture was stirred for 1 h at rt. Sodium triacetoxyborohydride (324 mg, 1.53 mmol, 3.00 equiv) was added. The resulting solution was stirred overnight at room temperature and diluted with water (50 mL). The resulting solution was extracted with CH$_2$Cl$_2$ (2×50 mL), and the organic layers were combined, dried over anhydrous sodium sulfate, filtered and concentrated under reduced pressure. The crude product (300 mg) was purified by preparative HPLC to provide (4-(benzo[d][1,3]dioxol-5-ylmethyl)piperazin-1-yl)(4-(morpholine-4-carbonyl)-1H-pyrazol-1-yl)methanone (108.2 mg, 50% yield) as a white solid. $^1$H NMR (300 MHz, Chloroform-d) δ 8.42 (s, 1H), 7.90 (s, 1H), 6.88 (s, 1H), 6.75-6.81 (m, 2H), 5.93 (s, 2H), 3.81 (br, 4H), 3.71 (br, 8H), 3.49 (s, 2H), 2.53-2.56 (m, 4H). LCMS (ESI, m/z): 428 [M+H]$^+$.

Example 52: (4-(Morpholine-4-carbonyl)-1H-pyrazol-1-yl)(4-(pyridin-4-ylmethyl)piperazin-1-yl)methanone

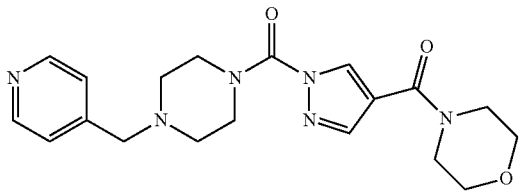 [SMILES: O=C(c1cnn(C(=O)N2CCN(Cc3ccncc3)CC2)c1)N1CCOCC1]

The title compound was synthesized directly from 1H-pyrazole-4-carboxylic acid, morpholine, tert-butyl piperazine-1-carboxylate and isonicotinaldehyde according to the representative procedure of Example 51, Steps 1-5 to provide (4-(morpholine-4-carbonyl)-1H-pyrazol-1-yl)(4-(pyridin-4-ylmethyl)piperazin-1-yl)methanone as a yellow semi-solid. $^1$H NMR (300 MHz, Chloroform-d) δ 8.50 (d, J=5.7 Hz, 2H), 8.44 (s, 1H), 7.90 (s, 1H), 7.47 (d, J=5.1 Hz, 2H), 3.84 (br, 4H), 3.70 (br, 8H), 3.65 (s, 2H), 2.58-2.60 (m, 4H). LCMS (ESI, m/z): 385 [M+H]$^+$.

Example 53: (4-(Morpholine-4-carbonyl)-1H-pyrazol-1-yl)(4-(pyridin-3-ylmethyl)piperazin-1-yl)methanone

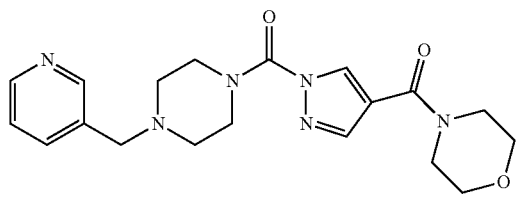

The title compound was synthesized directly from 1H-pyrazole-4-carboxylic acid, morpholine, tert-butyl piperazine-1-carboxylate and nicotinaldehyde according to the representative procedure of Example 51, Steps 1-5 to provide (4-(morpholine-4-carbonyl)-1H-pyrazol-1-yl)(4-(pyridin-3-ylmethyl)piperazin-1-yl)methanone as a yellow oil. $^1$H NMR (300 MHz, Chloroform-d) δ 8.53 (s, 1H), 8.45-8.47 (m, 1H), 8.43 (s, 1H), 7.91 (s, 1H), 7.86-7.90 (m, 1H), 7.42-7.46 (m, 1H), 3.83 (br, 4H), 3.71 (br, 8H), 3.64 (s, 2H), 2.57-2.60 (m, 4H). LCMS (ESI, m/z): 385 [M+H]$^+$.

Example 54: (4-(Morpholine-4-carbonyl)-1H-pyrazol-1-yl)(4-(pyrimidin-4-ylmethyl)piperazin-1-yl)methanone

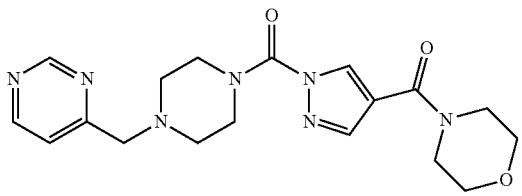 [SMILES: O=C(c1cnn(C(=O)N2CCN(Cc3ccncn3)CC2)c1)N1CCOCC1]

The title compound was synthesized directly from 1H-pyrazole-4-carboxylic acid, morpholine, tert-butyl piperazine-1-carboxylate and pyrimidine-4-carbaldehyde according to the representative procedure of Example 51, Steps 1-5 to provide (4-(morpholine-4-carbonyl)-1H-pyrazol-1-yl)(4-(pyrimidin-4-ylmethyl)piperazin-1-yl)methanone as a white solid. $^1$H NMR (300 MHz, Chloroform-d) δ 9.10 (s, 1H), 8.76 (d, J=5.4 Hz, 1H), 8.44 (s, 1H), 7.91 (s, 1H), 7.70-7.72 (m, 1H), 3.88 (br, 4H), 3.75 (s, 2H), 3.72 (br, 8H), 2.64-2.67 (m, 4H). LCMS (ESI, m/z): 386 [M+H]$^+$.

Example 55: (4-(Morpholine-4-carbonyl)-1H-pyrazol-1-yl)(4-(thiazol-2-ylmethyl)piperazin-1-yl)methanone

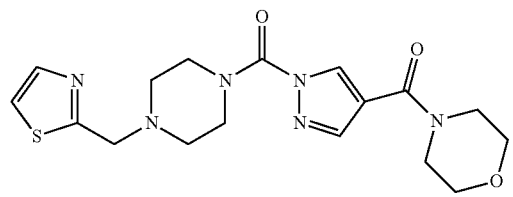

The title compound was synthesized directly from 1H-pyrazole-4-carboxylic acid, morpholine, tert-butyl piperazine-1-carboxylate and thiazole-2-carbaldehyde according to the representative procedure of Example 51, Steps 1-5 to provide (4-(morpholine-4-carbonyl)-1H-pyrazol-1-yl)(4-(thiazol-2-ylmethyl)piperazin-1-yl)methanone as a white solid. $^1$H NMR (300 MHz, Chloroform-d) δ 8.43 (s, 1H), 7.91 (s, 1H), 7.74 (d, J=3.3 Hz, 1H), 7.57 (d, J=3.3 Hz, 1H), 3.96 (s, 2H), 3.86 (br, 4H), 3.72 (br, 8H), 2.68-2.72 (m, 4H). LCMS (ESI, m/z): 391 [M+H]$^+$.

Example 56: (4-(Morpholine-4-carbonyl)-1H-pyrazol-1-yl)(4-(pyrimidin-5-ylmethyl)piperazin-1-yl)methanone

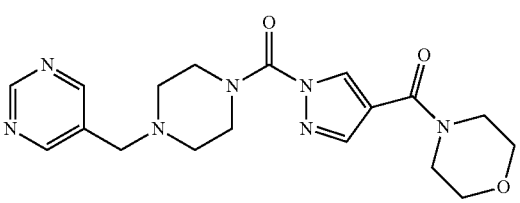 [SMILES: O=C(c1cnn(C(=O)N2CCN(Cc3cncnc3)CC2)c1)N1CCOCC1]

The title compound was synthesized directly from 1H-pyrazole-4-carboxylic acid, morpholine, tert-butyl piperazine-1-carboxylate and pyrimidine-5-carbaldehyde according to the representative procedure of Example 51, Steps 1-5 to provide (4-(morpholine-4-carbonyl)-1H-pyrazol-1-yl)(4-(pyrimidin-5-ylmethyl)piperazin-1-yl)methanone as an off-white semi-solid. $^1$H NMR (300 MHz, Chloroform-d) δ 9.08 (s, 1H), 8.80 (s, 2H), 8.43 (s, 1H), 7.91 (s, 1H), 3.84 (br, 4H), 3.72 (br, 8H), 3.67 (s, 2H), 2.59-2.63 (m, 4H). LCMS (ESI, m/z): 386 [M+H]$^+$.

Example 57: (4-((3-Methyl-[1,1'-biphenyl]-4-yl)methyl)piperazin-1-yl)(4-(morpholine-4-carbonyl)-1H-pyrazol-1-yl)methanone

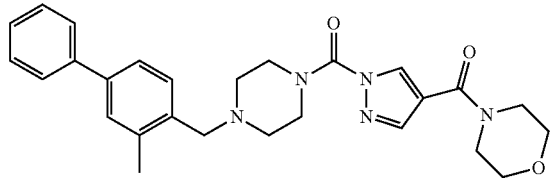 [SMILES: Cc1cc(-c2ccccc2)ccc1CN1CCN(C(=O)n2cc(C(=O)N3CCOCC3)cn2)CC1]

The title compound was synthesized directly from 1H-pyrazole-4-carboxylic acid, morpholine, tert-butyl piperazine-1-carboxylate and 3-methyl-[1,1'-biphenyl]-4-carbaldehyde (Example 94, Step 1) according to the representative procedure of Example 51, Steps 1-5 to provide (4-((3-methyl-[1,1'-biphenyl]-4-yl)methyl)piperazin-1-yl)(4-(morpholine-4-carbonyl)-1H-pyrazol-1-yl)methanone as a colorless oil. $^1$H NMR (300 MHz, Chloroform-d) δ 8.29 (s, 1H), 7.81 (s, 1H), 7.57-7.60 (m, 2H), 7.31-7.46 (m, 6H), 3.86 (br, 4H), 3.72 (br, 8H), 3.55 (s, 2H), 2.59 (br, 4H), 2.45 (s, 3H). LCMS (ESI, m/z): 474 [M+H]$^+$.

Example 58: (4-(Benzo[d][1,3]dioxol-5-ylmethyl)piperazin-1-yl)(4-phenyl-1H-pyrazol-1-yl)methanone

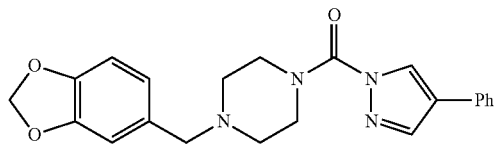 [SMILES: O=C(N1CCN(Cc2ccc3c(c2)OCO3)CC1)n1cc(-c2ccccc2)cn1]

The title compound was synthesized directly from commercially available 4-phenyl-1H-pyrazole, tert-butyl piperazine-1-carboxylate and benzo[d][1,3]dioxole-5-carbaldehyde according to the representative procedure of Example 51, Steps 2-5 to provide (4-(benzo[d][1,3]dioxol-5-ylmethyl)piperazin-1-yl)(4-phenyl-1H-pyrazol-1-yl)methanone as a white solid. $^1$H NMR (300 MHz, Chloroform-d) δ 8.34 (s, 1H), 7.90 (s, 1H), 7.51-7.54 (m, 2H), 7.39 (t, J=7.5 Hz, 2H), 7.28-7.31 (m, 1H), 6.88 (br, 1H), 6.76 (s, 2H), 5.97 (s, 2H), 3.91 (br, 4H), 3.49 (s, 2H), 2.57 (br, 4H). LCMS (ESI, m/z): 391 [M+H]$^+$.

Example 59: (4-Phenyl-1H-pyrazol-1-yl)(4-(pyridin-4-ylmethyl)piperazin-1-yl)methanone

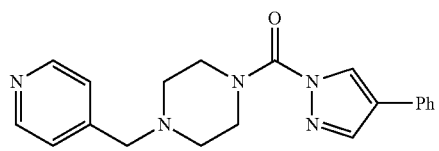

The title compound was synthesized directly from commercially available 4-phenyl-1H-pyrazole, tert-butyl piperazine-1-carboxylate and isonicotinaldehyde according to the representative procedure of Example 51, Steps 2-5 to provide (4-phenyl-1H-pyrazol-1-yl)(4-(pyridin-4-ylmethyl)piperazin-1-yl)methanone as a white solid. $^1$H NMR (300 MHz, Chloroform-d) δ 8.58 (d, J=6.0 Hz, 2H), 8.35 (s, 1H), 7.90 (s, 1H), 7.51-7.54 (m, 2H), 7.28-7.42 (m, 5H), 3.96 (br, 4H), 3.60 (s, 2H), 2.60-2.63 (m, 4H). LCMS (ESI, m/z): 348 [M+H]$^+$.

Example 60: (4-Phenyl-1H-pyrazol-1-yl)(4-(pyridin-3-ylmethyl)piperazin-1-yl)methanone

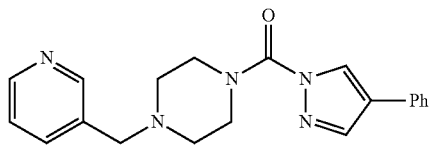 [SMILES: O=C(N1CCN(Cc2cccnc2)CC1)n1cc(-c2ccccc2)cn1]

The title compound was synthesized directly from commercially available 4-phenyl-1H-pyrazole, tert-butyl piperazine-1-carboxylate and nicotinaldehyde according to the representative procedure of Example 51, Steps 2-5 to provide (4-phenyl-1H-pyrazol-1-yl)(4-(pyridin-3-ylmethyl)piperazin-1-yl)methanone as a white solid. $^1$H NMR (300 MHz, Chloroform-d) δ 8.55-8.58 (m, 2H), 8.35 (s, 1H), 7.90 (s, 1H), 7.77-7.78 (m, 1H), 7.51-7.54 (m, 2H), 7.39-7.42 (m, 2H), 7.29-7.37 (m, 2H), 3.96 (br, 4H), 3.64 (s, 2H), 2.64 (br, 4H). LCMS (ESI, m/z): 348 [M+H]$^+$.

Example 61: (4-Phenyl-1H-pyrazol-1-yl)(4-(pyridin-2-ylmethyl)piperazin-1-yl)methanone

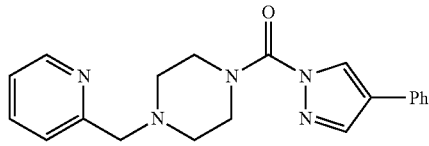 [SMILES: O=C(N1CCN(Cc2ccccn2)CC1)n1cc(-c2ccccc2)cn1]

The title compound was synthesized directly from commercially available 4-phenyl-1H-pyrazole, tert-butyl piperazine-1-carboxylate and picolinaldehyde according to the representative procedure of Example 51, Steps 2-5 to provide (4-phenyl-1H-pyrazol-1-yl)(4-(pyridin-2-ylmethyl)piperazin-1-yl)methanone as a white solid. $^1$H NMR (300 MHz, Chloroform-d) δ 8.59-8.61 (m, 1H), 8.35 (s, 1H), 7.90 (s, 1H), 7.65-7.71 (m, 1H), 7.51-7.54 (m, 2H), 7.37-7.42 (m, 3H), 7.26-7.31 (m, 1H), 7.12-7.22 (m, 1H), 3.95 (br, 4H), 3.82 (s, 2H), 2.63-2.66 (m, 4H). LCMS (ESI, m/z): 348 [M+H]$^+$.

Example 62: (4-Phenyl-1H-pyrazol-1-yl)(4-(pyrimidin-4-ylmethyl)piperazin-1-yl)methanone

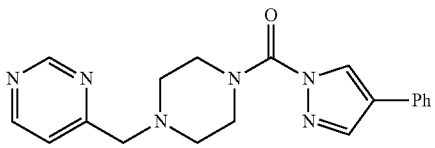 [SMILES: O=C(N1CCN(Cc2ccncn2)CC1)n1cc(-c2ccccc2)cn1]

The title compound was synthesized directly from commercially available 4-phenyl-1H-pyrazole, tert-butyl piperazine-1-carboxylate and pyrimidine-4-carbaldehyde according to the representative procedure of Example 51, Steps 2-5 to provide (4-phenyl-1H-pyrazol-1-yl)(4-(pyrimidin-4-ylmethyl)piperazin-1-yl)methanone as a white solid. $^1$H NMR (300 MHz, Chloroform-d) δ 9.18 (s, 1H), 8.72 (d, J=5.4 Hz, 1H), 8.35 (s, 1H), 7.91 (s, 1H), 7.51-7.54 (m, 3H), 7.37-7.42 (m, 2H), 7.28-7.31 (m, 1H), 3.97 (br, 4H), 3.72 (s, 2H), 2.65-2.68 (m, 4H). LCMS (ESI, m/z): 349 [M+H]$^+$.

Example 63: (4-Phenyl-1H-pyrazol-1-yl)(4-(thiazol-2-ylmethyl)piperazin-1-yl)methanone

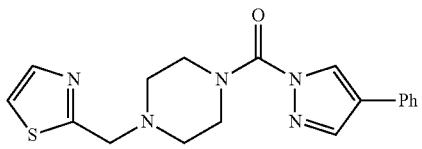 [SMILES: O=C(N1CCN(Cc2nccs2)CC1)n1cc(-c2ccccc2)cn1]

The title compound was synthesized directly from commercially available 4-phenyl-1H-pyrazole, tert-butyl piperazine-1-carboxylate and thiazole-2-carboxylate according to the representative procedure of Example 51, Steps 2-5 to provide (4-phenyl-1H-pyrazol-1-yl)(4-(thiazol-2-ylmethyl) piperazin-1-yl)methanone as a white solid. $^1$H NMR (300 MHz, Chloroform-d) δ 8.35 (s, 1H), 7.91 (s, 1H), 7.75-7.76 (m, 1H), 7.51-7.54 (m, 2H), 7.28-7.42 (m, 4H), 3.98 (br, 6H), 2.76 (br, 4H). LCMS (ESI, m/z): 354 [M+H]$^+$.

Example 64: (4-Phenyl-1H-pyrazol-1-yl)(4-(pyrimidin-5-ylmethyl)piperazin-1-yl)methanone

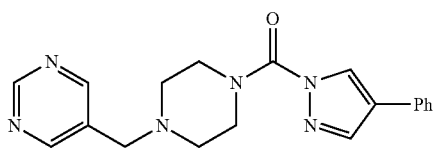 [SMILES: O=C(N1CCN(Cc2cncnc2)CC1)n1cc(-c2ccccc2)cn1]

The title compound was synthesized directly from commercially available 4-phenyl-1H-pyrazole, tert-butyl piperazine-1-carboxylate and pyrimidine-5-carbaldehyde according to the representative procedure of Example 51, Steps 2-5 to provide (4-phenyl-1H-pyrazol-1-yl)(4-(pyrimidin-5-ylmethyl)piperazin-1-yl)methanone as a white solid. $^1$H NMR (300 MHz, Chloroform-d) δ 9.16 (s, 1H), 8.73 (s, 2H), 8.35 (s, 1H), 7.91 (s, 1H), 7.52 (d, J=7.2 Hz, 2H), 7.40 (t, J=7.5 Hz, 2H), 7.29-7.31 (m, 1H), 3.94 (br, 4H), 3.57 (s, 2H), 2.58-2.62 (m, 4H). LCMS (ESI, m/z): 349 [M+H]$^+$.

Example 65: (4-((3-Methyl-[1,1'-biphenyl]-4-yl) methyl)piperazin-1-yl)(4-phenyl-1H-pyrazol-1-yl) methanone

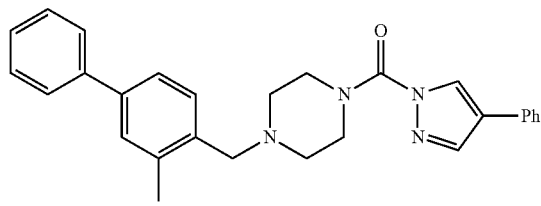 [SMILES: Cc1cc(-c2ccccc2)ccc1CN1CCN(C(=O)n2cc(-c3ccccc3)cn2)CC1]

The title compound was synthesized directly from commercially available 4-phenyl-1H-pyrazole, tert-butyl piperazine-1-carboxylate and 3-methyl-[1,1'-biphenyl]-4-carbaldehyde (Example 94, Step 1) according to the representative procedure of Example 51, Steps 2-5 to provide (4-((3-methyl-[1,1'-biphenyl]-4-yl)methyl)piperazin-1-yl)(4-phenyl-1H-pyrazol-1-yl)methanone as a white solid. $^1$H NMR (300 MHz, Chloroform-d) δ 8.35 (s, 1H), 7.91 (s, 1H), 7.58-7.62 (m, 2H), 7.52-7.58 (m, 2H), 7.29-7.46 (m, 9H), 3.91 (br, 4H), 3.57 (s, 2H), 2.61 (br, 4H), 2.46 (s, 3H). LCMS (ESI, m/z): 437 [M+H]$^+$.

Example 66: (4-(Bis(4-chlorophenyl)methyl)piperazin-1-yl)(4-(piperidine-1-carbonyl)-1H-pyrazol-1-yl)methanone

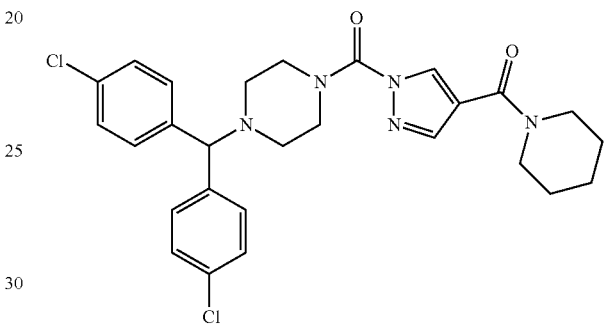

Step 1: Preparation of Piperidin-1-yl(1H-pyrazol-4-yl)methanone

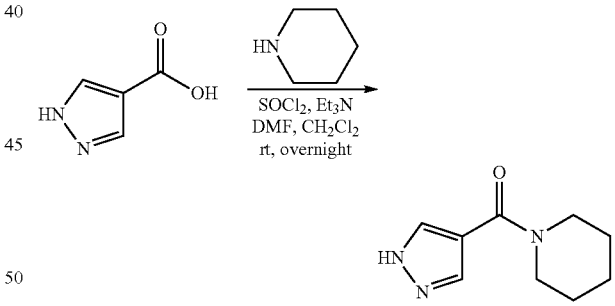

A 250-mL round-bottom flask was charged with 1H-pyrazole-4-carboxylic acid (2.00 g, 17.8 mmol, 1.00 equiv), CH$_2$Cl$_2$ (25 mL), thionyl chloride (4.22 g, 35.5 mmol, 2.00 equiv), and N,N-dimethylformamide (0.2 mL). The mixture was stirred overnight at 45° C. and concentrated under reduced pressure. To this was added CH$_2$Cl$_2$ (25 mL), piperidine (4.56 g, 53.6 mmol, 3.00 equiv), and triethylamine (1.81 g, 17.9 mmol, 1.00 equiv). The resulting solution was stirred overnight at room temperature and concentrated under reduced pressure. The residue was purified by flash chromatography on a silica gel column with CH$_2$Cl$_2$/CH$_3$OH (92/8) to provide 2.90 g (91% yield) of piperidin-1-yl(1H-pyrazol-4-yl)methanone as a colorless oil. LCMS (ESI, m/z): 180 [M+H]$^+$.

Step 2: Preparation of 4,4'-(chloromethylene)bis(chlorobenzene)

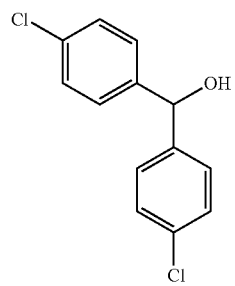

A 50-mL round-bottom flask was charged with bis(4-chlorophenyl)methanol (3.00 g, 11.8 mmol, 1.00 equiv), N,N-dimethylformamide (1 mL), and CH$_2$Cl$_2$ (10 mL). Thionyl chloride (4.23 g, 35.5 mmol, 4.00 equiv) was added dropwise. The resulting solution was stirred overnight at 40° C. The resulting mixture was concentrated under reduced pressure and diluted with CH$_2$Cl$_2$ (20 mL). The mixture was washed with H$_2$O (3×5 mL), dried over anhydrous sodium sulfate, filtered and concentrated under reduced pressure. The residue was purified by flash chromatography on a silica gel column with EtOAc/petroleum ether (1/99) to provide 2.80 g (87% yield) of 4,4'-(chloromethylene)bis(chlorobenzene) as a light yellow solid. $^1$H NMR (300 MHz, Chloroform-d) δ 7.29-7.39 (m, 8H), 6.05 (s, 1H).

Step 3: Preparation of tert-butyl 4-(bis(4-chlorophenyl)methyl)piperazine-1-carboxylate

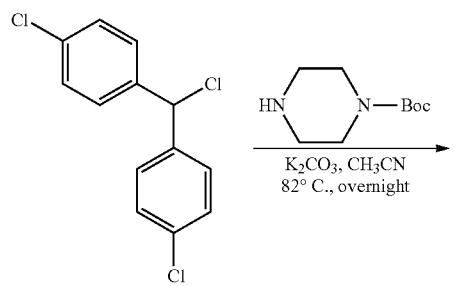

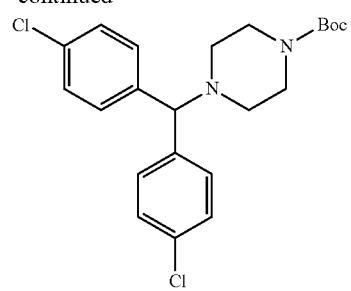

A 25-mL round-bottom flask was charged with 4,4'-(chloromethylene)bis(chlorobenzene) (550 mg, 2.03 mmol, 1.00 equiv), potassium carbonate (417 mg, 3.02 mmol, 1.49 equiv), tert-butyl piperazine-1-carboxylate (375 mg, 2.01 mmol, 0.99 equiv), and acetonitrile (10 mL). The resulting solution was stirred overnight at 82° C. and diluted with H$_2$O (20 mL). The mixture was extracted with CH$_2$Cl$_2$ (3×30 mL), and the organic layers were combined, washed with water (3×10 mL), dried over anhydrous sodium sulfate, filtered and concentrated under reduced pressure. The residue was purified by flash chromatography on a silica gel column with EtOAc/petroleum ether (1/9) to provide 530 mg (62% yield) of tert-butyl 4-(bis(4-chlorophenyl)methyl)piperazine-1-carboxylate as a white solid. LCMS (ESI, m/z): 421 [M+H]$^+$.

Step 4: Preparation of 1-(bis(4-chlorophenyl)methyl)piperazine

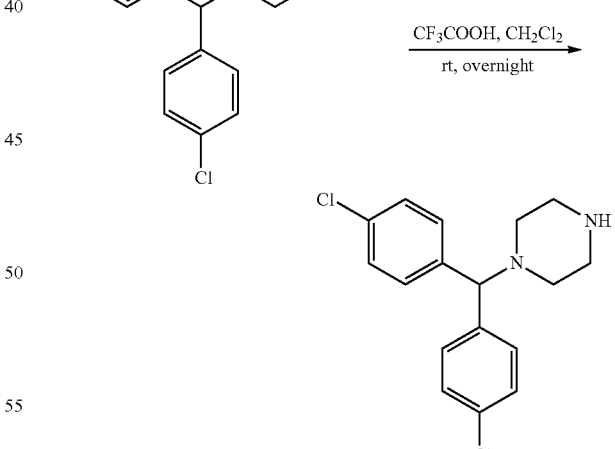

A 25-mL round-bottom flask was charged with tert-butyl 4-(bis(4-chlorophenyl)methyl)piperazine-1-carboxylate (530 mg, 1.26 mmol, 1.00 equiv), and CH$_2$Cl$_2$ (5 mL). Trifluoroacetic acid (1 mL) was added dropwise. The resulting solution was stirred overnight at room temperature. The resulting mixture was concentrated under reduced pressure to provide 390 mg (crude) of 1-(bis(4-chlorophenyl)methyl)piperazine as a brown oil. LCMS (ESI, m/z): 321 [M+H]$^+$.

Step 5: Preparation of 4-(bis(4-chlorophenyl)methyl)piperazine-1-carbonyl chloride

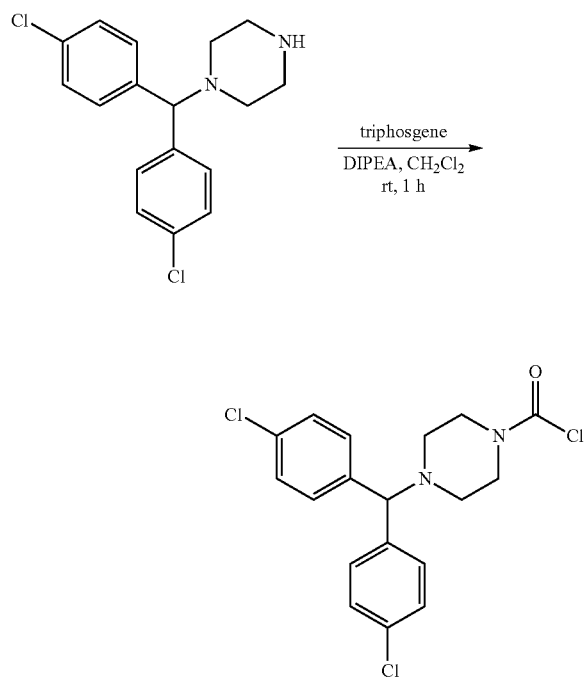

A 100-mL round-bottom flask was charged with triphosgene (372 mg, 1.25 mmol, 0.40 equiv), CH$_2$Cl$_2$ (15 mL), and 1-(bis(4-chlorophenyl)methyl)piperazine (1.00 g, 3.11 mmol, 1.00 equiv). DIPEA (1.21 g, 9.36 mmol, 3.00 equiv) was added dropwise. The resulting solution was stirred for 1 h at room temperature and diluted with water (50 mL). The resulting solution was extracted with CH$_2$Cl$_2$ (100 mL), and the organic layers were combined, dried over anhydrous sodium sulfate, filtered and concentrated under reduced pressure to provide 1.20 g (crude) of 4-(bis(4-chlorophenyl)methyl)piperazine-1-carbonyl chloride as a yellow oil.

Step 6: Preparation of (4-(bis(4-chlorophenyl)methyl)piperazin-1-yl)(4-(piperidine-1-carbonyl)-1H-pyrazol-1-yl)methanone

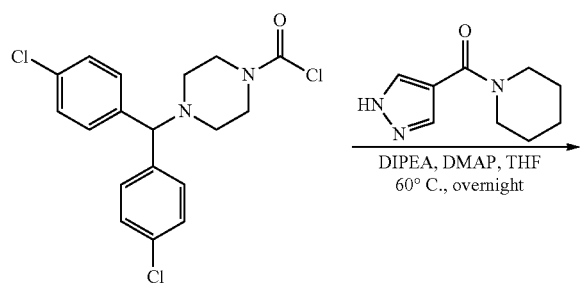

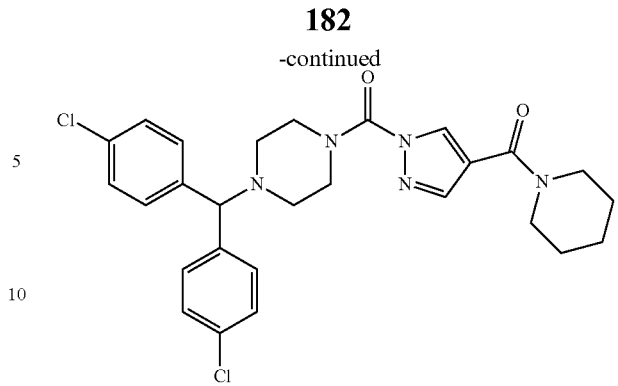

A 50-mL round-bottom flask was charged with 4-(bis(4-chlorophenyl)methyl)piperazine-1-carbonyl chloride (298 mg, 0.780 mmol, 1.00 equiv), THF (10 mL), piperidin-1-yl (1H-pyrazol-4-yl)methanone (168 mg, 0.940 mmol, 1.20 equiv), DIPEA (302 mg, 2.34 mmol, 3.00 equiv), and 4-dimethylaminopyridine (19.0 mg, 0.160 mmol, 0.20 equiv). The resulting solution was stirred overnight at 60° C. and concentrated under reduced pressure. The crude product (400 mg) was purified by preparative HPLC to provide (4-(bis(4-chlorophenyl)methyl)piperazin-1-yl)(4-(piperidine-1-carbonyl)-1H-pyrazol-1-yl)methanone (131.6 mg, 32% yield) as a white solid. $^1$H NMR (300 MHz, Chloroform-d) δ 8.24 (s, 1H), 7.75 (m, 1H), 7.19-7.34 (m, 8H), 4.25 (s, 1H), 3.86 (br, 4H), 3.61 (br, 4H), 2.47 (br, 4H), 1.60-1.69 (m, 6H). LCMS (ESI, m/z): 526 [M+H]$^+$.

Example 67: (4-(Bis(4-chlorophenyl)methyl)piperazin-1-yl)(4-(morpholine-4-carbonyl)-1H-pyrazol-1-yl)methanone

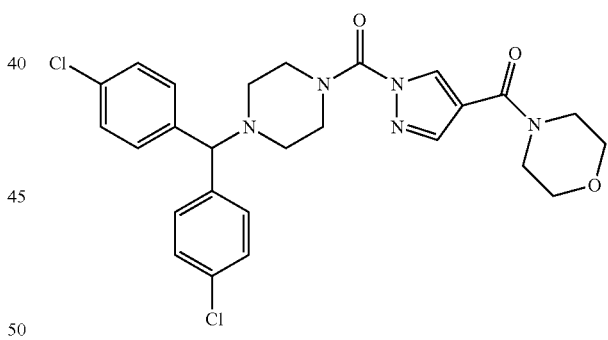

Preparation of (4-(bis(4-chlorophenyl)methyl)piperazin-1-yl)(4-(morpholine-4-carbonyl)-1H-pyrazol-1-yl)methanone

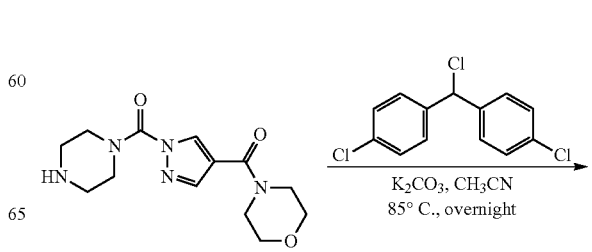

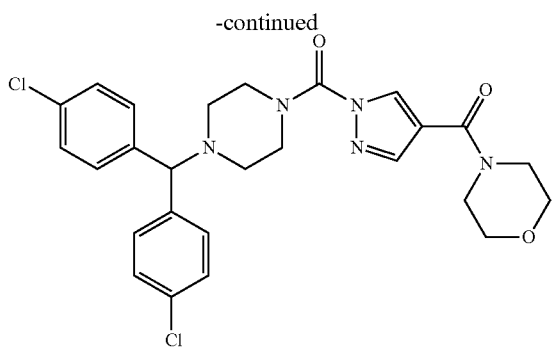

A 50-mL round-bottom flask was charged with 4,4'-(chloromethylene)bis(chlorobenzene) (184 mg, 0.68 mmol, 2.00 equiv; Example 66, Step 2), (4-(morpholine-4-carbonyl)-1H-pyrazol-1-yl)(piperazin-1-yl)methanone (100 mg, 0.341 mmol, 1.00 equiv; Example 51, Steps 1-4), acetonitrile (15 mL), and potassium carbonate (141 mg, 1.02 mmol, 3.00 equiv). The reaction mixture was stirred overnight at 85° C. and diluted with water (30 mL). The resulting solution was extracted with CH$_2$Cl$_2$ (2×50 mL), and the organic layers were combined, dried over anhydrous sodium sulfate, filtered and concentrated under reduced pressure. The residue was purified by flash chromatography on a silica gel column with EtOAc/petroleum ether (2/1). The crude product (300 mg) was purified by preparative HPLC to provide 45.6 mg (25% yield) of (4-(bis(4-chlorophenyl)methyl)piperazin-1-yl)(4-(morpholine-4-carbonyl)-1H-pyrazol-1-yl)methanone as a white semi-solid. $^1$H NMR (300 MHz, Chloroform-d) δ 8.27 (s, 1H), 7.77 (s, 1H), 7.26-7.31 (m, 8H), 4.26 (s, 1H), 3.86 (br, 4H), 3.70 (br, 8H), 2.48 (br, 4H). LCMS (ESI, m/z): 528 [M+H]$^+$.

Example 68: Azetidin-1-yl(1-(4-(bis(4-chlorophenyl)methyl)piperazine-1-carbonyl)-1H-pyrazol-4-yl)methanone

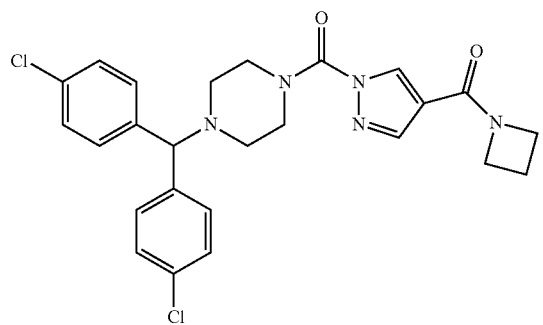 [SMILES: O=C(c1cnn(C(=O)N2CCN(C(c3ccc(Cl)cc3)c3ccc(Cl)cc3)CC2)c1)N1CCC1]

The title compound was synthesized directly from commercially available 1H-pyrazole-4-carboxylic acid, azetidine, bis(4-chlorophenyl)methanol and tert-butyl piperazine-1-carboxylate according to the representative procedure of Example 66, Steps 1-6 to provide azetidin-1-yl(1-(4-(bis(4-chlorophenyl)methyl)piperazine-1-carbonyl)-1H-pyrazol-4-yl)methanone as a white solid. $^1$H NMR (300 MHz, Chloroform-d) δ 8.32 (s, 1H), 7.91 (s, 1H), 7.26-7.34 (m, 8H), 4.35-4.40 (m, 2H), 4.16-4.25 (m, 3H), 3.86 (br, 4H), 2.26-2.48 (m, 6H). LCMS (ESI, m/z): 498 [M+H]$^+$.

Example 69: (4-(Benzo[d][1,3]dioxol-5-ylmethyl)piperazin-1-yl)(4-(piperidine-1-carbonyl)-1H-pyrazol-1-yl)methanone

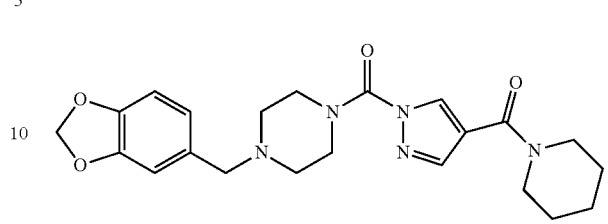

The title compound was synthesized directly from 1H-pyrazole-4-carboxylic acid, piperidine, tert-butyl piperazine-1-carboxylate and benzo[d][1,3]dioxole-5-carbaldehyde according to the representative procedure of Example 51, Steps 1-5 to provide (4-(benzo[d][1,3]dioxol-5-ylmethyl)piperazin-1-yl)(4-(piperidine-1-carbonyl)-1H-pyrazol-1-yl)methanone as a light yellow oil. $^1$H NMR (300 MHz, Chloroform-d) δ 8.25 (s, 1H), 7.79 (s, 1H), 6.86 (s, 1H), 6.72-6.77 (m, 2H), 5.95 (s, 2H), 3.85 (br, 4H), 3.62 (br, 4H), 3.46 (s, 2H), 2.52 (t, J=5.0 Hz, 4H), 1.61-1.73 (m, 6H). LCMS (ESI, m/z): 426 [M+H]$^+$.

Example 70: Piperidin-1-yl(1-(4-(pyridin-4-ylmethyl)piperazine-1-carbonyl)-1H-pyrazol-4-yl)methanone

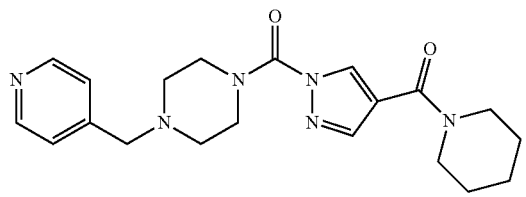 [SMILES: O=C(c1cnn(C(=O)N2CCN(Cc3ccncc3)CC2)c1)N1CCCCC1]

The title compound was synthesized directly from 1H-pyrazole-4-carboxylic acid, piperidine, tert-butyl piperazine-1-carboxylate and isonicotinaldehyde according to the representative procedure of Example 51, Steps 1-5 to provide piperidin-1-yl(1-(4-(pyridin-4-ylmethyl)piperazine-1-carbonyl)-1H-pyrazol-4-yl)methanone as a brown oil $^1$H NMR (300 MHz, Chloroform-d) δ 8.58-8.59 (m, 2H), 8.27 (s, 1H), 7.79 (s, 1H), 7.34-7.36 (m, 2H), 3.91 (br, 4H), 3.61 (br, 6H), 2.60 (t, J=4.7 Hz, 4H), 1.61-1.70 (m, 6H). LCMS (ESI, m/z): 383 [M+H]$^+$.

Example 71: Piperidin-1-yl(1-(4-(pyridin-3-ylmethyl)piperazine-1-carbonyl)-1H-pyrazol-4-yl)methanone

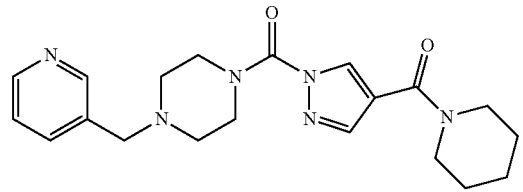 [SMILES: O=C(c1cnn(C(=O)N2CCN(Cc3cccnc3)CC2)c1)N1CCCCC1]

The title compound was synthesized directly from 1H-pyrazole-4-carboxylic acid, piperidine, tert-butyl piperazine-1-carboxylate and nicotinaldehyde according to the representative procedure of Example 51, Steps 1-5 to provide piperidin-1-yl(1-(4-(pyridin-3-ylmethyl)piperazine-1-carbonyl)-1H-pyrazol-4-yl)methanone as a yellow oil. $^1$H NMR (300 MHz, Chloroform-d) δ 8.52-8.57 (m, 2H), 8.27 (s, 1H), 7.79 (s, 1H), 7.26-7.30 (m, 2H), 3.87 (br, 4H), 3.57-3.62 (m, 6H), 2.56 (t, J=4.8 Hz, 4H), 1.61-1.70 (m, 6H). LCMS (ESI, m/z): 383 [M+H]$^+$.

Example 72: Piperidin-1-yl(1-(4-(pyridin-2-ylmethyl)piperazine-1-carbonyl)-1H-pyrazol-4-yl)methanone

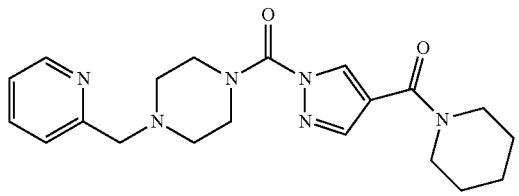 [SMILES: O=C(c1cnn(C(=O)N2CCN(Cc3ccccn3)CC2)c1)N1CCCCC1]

The title compound was synthesized directly from 1H-pyrazole-4-carboxylic acid, piperidine, tert-butyl piperazine-1-carboxylate and picolinaldehyde according to the representative procedure of Example 51, Steps 1-5 to provide piperidin-1-yl(1-(4-(pyridin-2-ylmethyl)piperazine-1-carbonyl)-1H-pyrazol-4-yl)methanone as a yellow oil. $^1$H NMR (300 MHz, Chloroform-d) δ 8.58-8.60 (m, 1H), 8.26 (s, 1H), 7.79 (s, 1H), 7.65-7.71 (m, 1H), 7.40 (d, J=7.8 Hz, 1H), 7.18-7.22 (m, 1H), 3.90 (br, 4H), 3.49-3.72 (m, 6H), 2.62 (t, J=5.0 Hz, 4H), 1.61-1.70 (m, 6H). LCMS (ESI, m/z): 383 [M+H]$^+$.

Example 73: Piperidin-1-yl(1-(4-(pyrimidin-4-ylmethyl)piperazine-1-carbonyl)-1H-pyrazol-4-yl)methanone

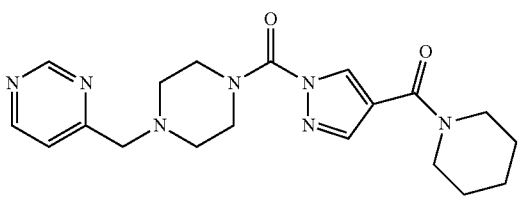 [SMILES: O=C(c1cnn(C(=O)N2CCN(Cc3ccncn3)CC2)c1)N1CCCCC1]

The title compound was synthesized directly from 1H-pyrazole-4-carboxylic acid, piperidine, tert-butyl piperazine-1-carboxylate and pyrimidine-4-carbaldehyde according to the representative procedure of Example 51, Steps 1-5 to provide piperidin-1-yl(1-(4-(pyrimidin-4-ylmethyl)piperazine-1-carbonyl)-1H-pyrazol-4-yl)methanone as a yellow oil. $^1$H NMR (300 MHz, Chloroform-d) δ 9.18 (s, 1H), 8.72 (d, J=5.4 Hz, 1H), 8.27 (s, 1H), 7.80 (s, 1H), 7.50 (d, J=5.4 Hz, 1H), 3.93 (br, 4H), 3.62-3.70 (m, 6H), 2.64 (t, J=5.0 Hz, 4H), 1.62-1.73 (m, 6H). LCMS (ESI, m/z): 384 [M+H]$^+$.

Example 74: Piperidin-1-yl(1-(4-(thiazol-2-ylmethyl)piperazine-1-carbonyl)-1H-pyrazol-4-yl)methanone

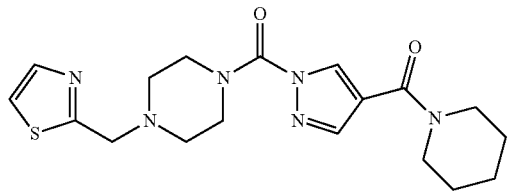 [SMILES: O=C(c1cnn(C(=O)N2CCN(Cc3nccs3)CC2)c1)N1CCCCC1]

The title compound was synthesized directly from 1H-pyrazole-4-carboxylic acid, piperidine, tert-butyl piperazine-1-carboxylate and thiazole-2-carbaldehyde according to the representative procedure of Example 51, Steps 1-5 to provide piperidin-1-yl(1-(4-(thiazol-2-ylmethyl)piperazine-1-carbonyl)-1H-pyrazol-4-yl)methanone as an off-white solid. $^1$H NMR (300 MHz, Chloroform-d) δ 8.26 (s, 1H), 7.79 (s, 1H), 7.73 (d, J=3.3 Hz, 1H), 7.32 (d, J=3.3 Hz, 1H), 3.91-3.94 (m, 6H), 3.62 (br, 4H), 2.70 (t, J=5.0 Hz, 4H), 1.62-1.70 (m, 6H). LCMS (ESI, m/z): 389 [M+H]$^+$.

Example 75: Piperidin-1-yl(1-(4-(pyrimidin-5-ylmethyl)piperazine-1-carbonyl)-1H-pyrazol-4-yl)methanone

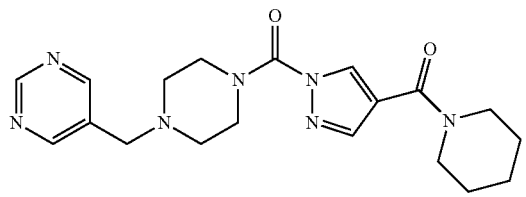 [SMILES: O=C(c1cnn(C(=O)N2CCN(Cc3cncnc3)CC2)c1)N1CCCCC1]

The title compound was synthesized directly from 1H-pyrazole-4-carboxylic acid, piperidine, tert-butyl piperazine-1-carboxylate and pyrimidine-5-carbaldehyde according to the representative procedure of Example 51, Steps 1-5 to provide piperidin-1-yl(1-(4-(pyrimidin-5-ylmethyl)piperazine-1-carbonyl)-1H-pyrazol-4-yl)methanone as a light yellow semi-solid. $^1$H NMR (300 MHz, Chloroform-d) δ 9.16 (s, 1H), 8.72 (s, 2H), 8.26 (s, 1H), 7.79 (s, 1H), 3.88 (br, 4H), 3.58-3.62 (m, 6H), 2.58 (t, J=5.0 Hz, 4H), 1.63-1.70 (m, 6H). LCMS (ESI, m/z): 384 [M+H]$^+$.

Example 76: (4-((3-Methyl-[1,1'-biphenyl]-4-yl)methyl)piperazin-1-yl)(4-(piperidine-1-carbonyl)-1H-pyrazol-1-yl)methanone

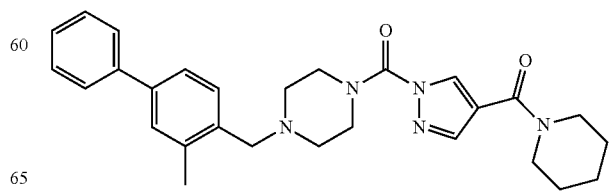

The title compound was synthesized directly from 1H-pyrazole-4-carboxylic acid, piperidine, tert-butyl piperazine-1-carboxylate and 3-methyl-[1,1'-biphenyl]-4-carbaldehyde (Example 94, Step 1) according to the representative procedure of Example 51, Steps 1-5 to provide (4-((3-methyl-[1,1'-biphenyl]-4-yl)methyl)piperazin-1-yl)(4-(piperidine-1-carbonyl)-1H-pyrazol-1-yl)methanone as a light yellow oil $^1$H NMR (300 MHz, Chloroform-d) δ 8.26 (s, 1H), 7.79 (s, 1H), 7.58-7.60 (m, 2H), 7.31-7.46 (m, 6H), 3.85 (br, 4H), 3.55-3.62 (m, 6H), 2.58 (br, 4H), 2.45 (s, 3H), 1.57-1.70 (m, 6H). LCMS (ESI, m/z): 472 [M+H]$^+$.

Example 77: (4-(Morpholine-4-carbonyl)-1H-pyrazol-1-yl)(4-(pyridin-2-ylmethyl)piperazin-1-yl)methanone

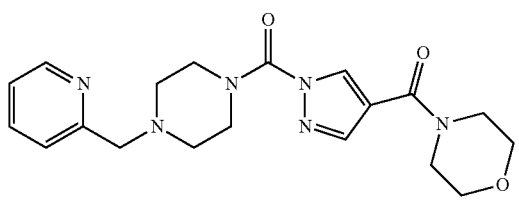 [SMILES: O=C(c1cnn(C(=O)N2CCN(Cc3ccccn3)CC2)c1)N1CCOCC1]

The title compound was synthesized directly from 1H-pyrazole-4-carboxylic acid, morpholine, tert-butyl piperazine-1-carboxylate and picolinaldehyde according to the representative procedure of Example 51, Steps 1-5 to provide (4-(morpholine-4-carbonyl)-1H-pyrazol-1-yl)(4-(pyridin-2-ylmethyl)piperazin-1-yl)methanone as a yellow oil. $^1$H NMR (300 MHz, CD$_3$OD) δ 8.49-8.51 (m, 1H), 8.43 (s, 1H), 7.95 (s, 1H), 7.57-7.60 (m, 1H), 7.58 (t, J=7.8 Hz, 1H), 7.32-7.36 (m, 1H), 3.84 (br, 4H), 3.72 (br, 10H), 2.62 (t, J=5.1 Hz, 4H). LCMS (ESI, m/z): 385 [M+H]$^+$.

Example 78: (4-(Benzo[d][1,3]dioxol-5-ylmethyl)piperazin-1-yl)(4-(pyrrolidine-1-carbonyl)-1H-pyrazol-1-yl)methanone

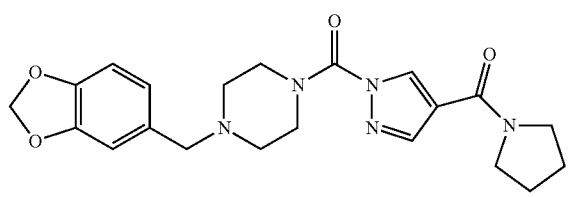 [SMILES: O=C(c1cnn(C(=O)N2CCN(Cc3ccc4c(c3)OCO4)CC2)c1)N1CCCC1]

The title compound was synthesized directly from 1H-pyrazole-4-carboxylic acid, pyrrolidine, tert-butyl piperazine-1-carboxylate and benzo[d][1,3]dioxole-5-carbaldehyde according to the representative procedure of Example 51, Steps 1-5 to provide (4-(benzo[d][1,3]dioxol-5-ylmethyl)piperazin-1-yl)(4-(pyrrolidine-1-carbonyl)-1H-pyrazol-1-yl)methanone as a colorless oil $^1$H NMR (300 MHz, Chloroform-d) δ 8.39 (s, 1H), 8.00 (s, 1H), 6.86 (s, 1H), 6.72-6.77 (m, 2H), 5.95 (s, 2H), 3.86 (br, 4H), 3.61-3.72 (m, 4H), 3.46 (s, 2H), 2.53 (t, J=4.8 Hz, 4H), 1.89-2.05 (m, 4H). LCMS (ESI, m/z): 412 [M+H]$^+$.

Example 79: (4-(Pyridin-4-ylmethyl)piperazin-1-yl)(4-(pyrrolidine-1-carbonyl)-1H-pyrazol-1-yl)methanone

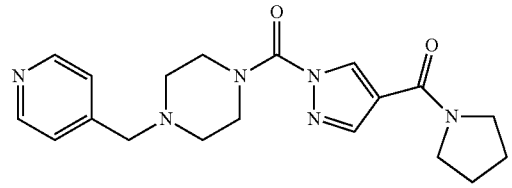 [SMILES: O=C(c1cnn(C(=O)N2CCN(Cc3ccncc3)CC2)c1)N1CCCC1]

The title compound was synthesized directly from 1H-pyrazole-4-carboxylic acid, pyrrolidine, tert-butyl piperazine-1-carboxylate and isonicotinaldehyde according to the representative procedure of Example 51, Steps 1-5 to provide (4-(pyridin-4-ylmethyl)piperazin-1-yl)(4-(pyrrolidine-1-carbonyl)-1H-pyrazol-1-yl)methanone as a yellow solid. $^1$H NMR (300 MHz, Chloroform-d) δ 8.56-8.58 (m, 2H), 8.40 (s, 1H), 8.00 (s, 1H), 7.27-7.31 (m, 2H), 4.03 (br, 4H), 3.62-3.90 (m, 4H), 3.57 (s, 2H), 2.57 (t, J=5.0 Hz, 4H), 1.89-2.06 (m, 4H). LCMS (ESI, m/z): 369 [M+H]$^+$.

Example 80: (4-(Pyridin-3-ylmethyl)piperazin-1-yl)(4-(pyrrolidine-1-carbonyl)-1H-pyrazol-1-yl)methanone

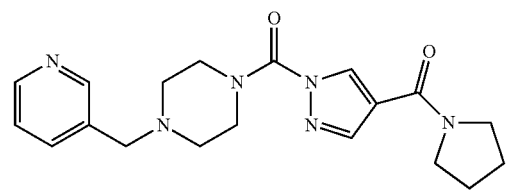 [SMILES: O=C(c1cnn(C(=O)N2CCN(Cc3cccnc3)CC2)c1)N1CCCC1]

The title compound was synthesized directly from 1H-pyrazole-4-carboxylic acid, pyrrolidine, tert-butyl piperazine-1-carboxylate and nicotinaldehyde according to the representative procedure of Example 51, Steps 1-5 to provide (4-(pyridin-3-ylmethyl)piperazin-1-yl)(4-(pyrrolidine-1-carbonyl)-1H-pyrazol-1-yl)methanone as an off-white semi-solid. $^1$H NMR (300 MHz, Chloroform-d) δ 8.52-8.57 (m, 2H), 8.39 (s, 1H), 8.00 (s, 1H), 7.66-7.70 (m, 1H), 7.26-7.30 (m, 1H), 3.87 (br, 4H), 3.61-3.69 (m, 4H), 3.57 (s, 2H), 2.57 (t, J=5.0 Hz, 4H), 1.89-2.06 (m, 4H). LCMS (ESI, m/z): 369 [M+H]$^+$.

Example 81: (4-(Pyridin-2-ylmethyl)piperazin-1-yl)(4-(pyrrolidine-1-carbonyl)-1H-pyrazol-1-yl)methanone

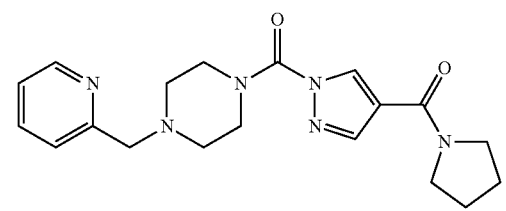 [SMILES: O=C(c1cnn(C(=O)N2CCN(Cc3ccccn3)CC2)c1)N1CCCC1]

The title compound was synthesized directly from 1H-pyrazole-4-carboxylic acid, pyrrolidine, tert-butyl piperazine-1-carboxylate and picolinaldehyde according to the representative procedure of Example 51, Steps 1-5 to provide (4-(pyridin-2-ylmethyl)piperazin-1-yl)(4-(pyrrolidine-1-carbonyl)-1H-pyrazol-1-yl)methanone as a white solid. ¹H NMR (300 MHz, Chloroform-d) δ 8.58-8.60 (m, 1H), 8.39 (s, 1H), 8.00 (s, 1H), 7.65-7.70 (m, 1H), 7.40 (d, J=7.8 Hz, 1H), 7.17-7.22 (m, 1H), 3.90 (br, 4H), 3.77 (s, 2H), 3.61-3.72 (m, 4H), 2.63 (t, J=5.0 Hz, 4H), 1.89-2.05 (m, 4H). LCMS (ESI, m/z): 369 [M+H]⁺.

Example 82: (4-(Pyrimidin-4-ylmethyl)piperazin-1-yl)(4-(pyrrolidine-1-carbonyl)-1H-pyrazol-1-yl)methanone

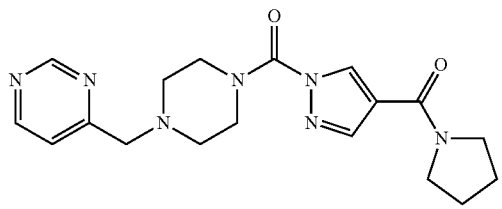 [SMILES: O=C(c1cnn(C(=O)N2CCN(Cc3ccncn3)CC2)c1)N1CCCC1]

The title compound was synthesized directly from 1H-pyrazole-4-carboxylic acid, pyrrolidine, tert-butyl piperazine-1-carboxylate and pyrimidine-4-carbaldehyde according to the representative procedure of Example 51, Steps 1-5 to provide (4-(pyrimidin-4-ylmethyl)piperazin-1-yl)(4-(pyrrolidine-1-carbonyl)-1H-pyrazol-1-yl)methanone as a yellow solid. ¹H NMR (300 MHz, Chloroform-d) δ 9.18 (s, 1H), 8.72 (d, J=5.1 Hz, 1H), 8.41 (s, 1H), 8.01 (s, 1H), 7.50-7.52 (m, 1H), 3.93 (br, 4H), 3.71 (s, 2H), 3.62-3.69 (m, 4H), 2.65 (t, J=5.1 Hz, 4H), 1.87-2.06 (m, 4H). LCMS (ESI, m/z): 370 [M+H]⁺.

Example 83: Pyrrolidin-1-yl(1-(4-(thiazol-2-ylmethyl)piperazine-1-carbonyl)-1H-pyrazol-4-yl)methanone

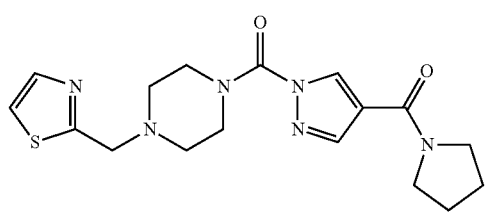 [SMILES: O=C(c1cnn(C(=O)N2CCN(Cc3nccs3)CC2)c1)N1CCCC1]

The title compound was synthesized directly from 1H-pyrazole-4-carboxylic acid, pyrrolidine, tert-butyl piperazine-1-carboxylate and thiazole-2-carbaldehyde according to the representative procedure of Example 51, Steps 1-5 to provide pyrrolidin-1-yl(1-(4-(thiazol-2-ylmethyl)piperazine-1-carbonyl)-1H-pyrazol-4-yl)methanone as a light yellow solid. ¹H NMR (300 MHz, Chloroform-d) δ 8.52 (s, 1H), 8.00 (s 1H), 7.73 (d, J=3.3 Hz, 1H), 7.32 (d, J=3.3 Hz, 1H), 3.94 (br, 6H), 3.62-3.69 (m, 4H), 2.71 (t, J=4.8 Hz, 4H), 1.89-2.06 (m, 4H). LCMS (ESI, m/z): 375 [M+H]⁺.

Example 84: (4-(Pyrimidin-5-ylmethyl)piperazin-1-yl)(4-(pyrrolidine-1-carbonyl)-1H-pyrazol-1-yl)methanone

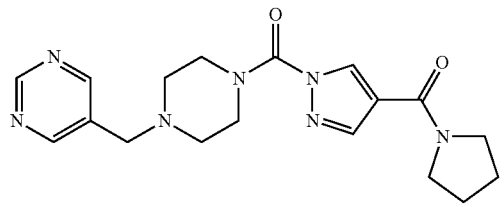 [SMILES: O=C(c1cnn(C(=O)N2CCN(Cc3cncnc3)CC2)c1)N1CCCC1]

The title compound was synthesized directly from 1H-pyrazole-4-carboxylic acid, pyrrolidine, tert-butyl piperazine-1-carboxylate and pyrimidine-5-carbaldehyde according to the representative procedure of Example 51, Steps 1-5 to provide (4-(pyrimidin-5-ylmethyl)piperazin-1-yl)(4-(pyrrolidine-1-carbonyl)-1H-pyrazol-1-yl)methanone as a white solid. ¹H NMR (300 MHz, Chloroform-d) δ 9.16 (s, 1H), 8.73 (s, 2H), 8.40 (s, 1H), 8.00 (s, 1H), 3.89 (br, 4H), 3.58 (s, 2H), 3.62-3.69 (m, 4H), 2.58 (t, J=5.0 Hz, 4H), 1.90-2.06 (m, 4H). LCMS (ESI, m/z): 370 [M+H]⁺.

Example 85: (4-((3-Methyl-[1,1'-biphenyl]-4-yl)methyl)piperazin-1-yl)(4-(pyrrolidine-1-carbonyl)-1H-pyrazol-1-yl)methanone

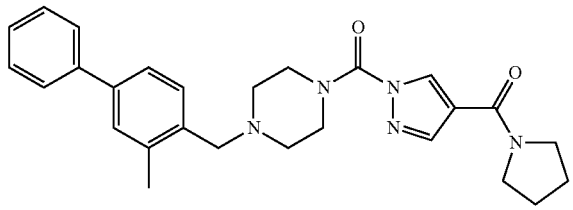 [SMILES: Cc1cc(-c2ccccc2)ccc1CN1CCN(C(=O)n2cc(C(=O)N3CCCC3)cn2)CC1]

The title compound was synthesized directly from 1H-pyrazole-4-carboxylic acid, pyrrolidine, tert-butyl piperazine-1-carboxylate and 3-methyl-[1,1'-biphenyl]-4-carbaldehyde (Example 94, Step 1) according to the representative procedure of Example 51, Steps 1-5 to provide (4-((3-methyl-[1,1'-biphenyl]-4-yl)methyl)piperazin-1-yl)(4-(pyrrolidine-1-carbonyl)-1H-pyrazol-1-yl)methanone as a white solid. ¹H NMR (300 MHz, CD₃OD) δ 8.53 (s, 1H), 8.04 (s, 1H), 7.59-7.62 (m, 2H), 7.34-7.45 (m, 6H), 3.73-3.84 (m, 6H), 3.59-3.65 (m, 4H), 2.66 (br, 4H), 2.48 (s, 3H), 1.97-2.04 (m, 4H). LCMS (ESI, m/z): 458 [M+H]⁺.

Example 86: Azetidin-1-yl(1-(4-(benzo[d][1,3]dioxol-5-ylmethyl)piperazine-1-carbonyl)-1H-pyrazol-4-yl)methanone

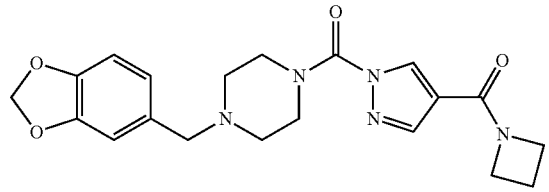 [SMILES: O=C(c1cnn(C(=O)N2CCN(Cc3ccc4c(c3)OCO4)CC2)c1)N1CCC1]

The title compound was synthesized directly from 1H-pyrazole-4-carboxylic acid, azetidine, tert-butyl piperazine-1-carboxylate and benzo[d][1,3]dioxole-5-carbaldehyde according to the representative procedure of Example 51, Steps 1-5 to provide azetidin-1-yl(1-(4-(benzo[d][1,3]dioxol-5-ylmethyl)piperazine-1-carbonyl)-1H-pyrazol-4-yl)methanone as an off-white solid. ¹H NMR (300 MHz, Chloroform-d) δ 8.33 (s, 1H), 7.94 (s, 1H), 6.86 (s, 1H), 6.72-6.77 (m, 2H), 5.95 (s, 2H), 4.37-4.42 (m, 2H), 4.17-4.22 (m, 2H), 3.85 (br, 4H), 3.46 (s, 2H), 2.53 (t, J=5.0 Hz, 4H), 2.34-2.46 (m, 2H). LCMS (ESI, m/z): 398 [M+H]⁺.

Example 87: Azetidin-1-yl(1-(4-(pyridin-4-ylmethyl)piperazine-1-carbonyl)-1H-pyrazol-4-yl)methanone

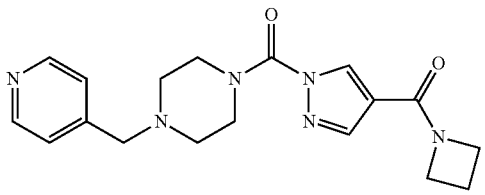 [SMILES: O=C(c1cnn(C(=O)N2CCN(Cc3ccncc3)CC2)c1)N1CCC1]

The title compound was synthesized directly from 1H-pyrazole-4-carboxylic acid, azetidine, tert-butyl piperazine-1-carboxylate and isonicotinaldehyde according to the representative procedure of Example 51, Steps 1-5 to provide azetidin-1-yl(1-(4-(pyridin-4-ylmethyl)piperazine-1-carbonyl)-1H-pyrazol-4-yl)methanone as a white solid. ¹H NMR (300 MHz, Chloroform-d) δ 8.56-8.58 (m, 2H), 8.34 (s, 1H), 7.95 (s, 1H), 7.26-7.30 (m, 2H), 4.37-4.42 (m, 2H), 4.17-4.22 (m, 2H), 3.88 (br, 4H), 3.56 (s, 2H), 2.57 (t, J=5.0 Hz, 4H), 2.34-2.45 (m, 2H). LCMS (ESI, m/z): 355 [M+H]⁺.

Example 88: Azetidin-1-yl(1-(4-(pyridin-3-ylmethyl)piperazine-1-carbonyl)-1H-pyrazol-4-yl)methanone

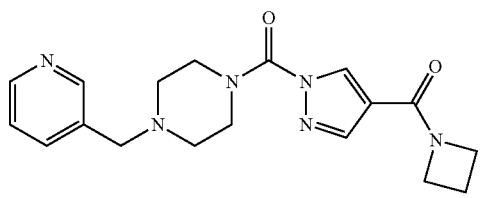 [SMILES: O=C(c1cnn(C(=O)N2CCN(Cc3cccnc3)CC2)c1)N1CCC1]

The title compound was synthesized directly from 1H-pyrazole-4-carboxylic acid, azetidine, tert-butyl piperazine-1-carboxylate and nicotinaldehyde according to the representative procedure of Example 51, Steps 1-5 to provide azetidin-1-yl(1-(4-(pyridin-3-ylmethyl)piperazine-1-carbonyl)-1H-pyrazol-4-yl)methanone as a light yellow solid. ¹H NMR (300 MHz, Chloroform-d) δ 8.52-8.56 (m, 2H), 8.34 (s, 1H), 7.95 (s, 1H), 7.61-7.69 (m, 1H), 7.26-7.30 (m, 1H), 4.37-4.42 (m, 2H), 4.17-4.22 (m, 2H), 3.86 (br, 4H), 3.57 (s, 2H), 2.56 (t, J=5.0 Hz, 4H), 2.34-2.45 (m, 2H). LCMS (ESI, m/z): 355 [M+H]⁺.

Example 89: Azetidin-1-yl(1-(4-(pyridin-2-ylmethyl)piperazine-1-carbonyl)-1H-pyrazol-4-yl)methanone

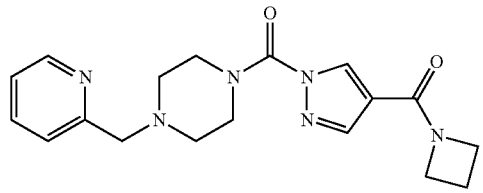 [SMILES: O=C(c1cnn(C(=O)N2CCN(Cc3ccccn3)CC2)c1)N1CCC1]

The title compound was synthesized directly from 1H-pyrazole-4-carboxylic acid, azetidine, tert-butyl piperazine-1-carboxylate and picolinaldehyde according to the representative procedure of Example 51, Steps 1-5 to provide azetidin-1-yl(1-(4-(pyridin-2-ylmethyl)piperazine-1-carbonyl)-1H-pyrazol-4-yl)methanone as a yellow solid. ¹H NMR (300 MHz, Chloroform-d) δ 8.58-8.60 (m, 1H), 8.33 (s, 1H), 7.95 (s, 1H), 7.65-7.70 (m, 1H), 7.39 (d, J=7.8 Hz, 1H), 7.18-7.22 (m, 1H), 4.37-4.42 (m, 2H), 4.17-4.22 (m, 2H), 3.90 (br, 4H), 3.72 (s, 2H), 2.62 (t, J=5.0 Hz, 4H), 2.34-2.44 (m, 2H). LCMS (ESI, m/z): 355 [M+H]⁺.

Example 90: Azetidin-1-yl(1-(4-(pyrimidin-4-ylmethyl)piperazine-1-carbonyl)-1H-pyrazol-4-yl)methanone

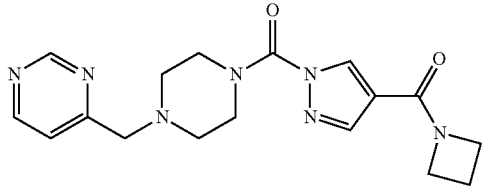 [SMILES: O=C(c1cnn(C(=O)N2CCN(Cc3ccncn3)CC2)c1)N1CCC1]

The title compound was synthesized directly from 1H-pyrazole-4-carboxylic acid, azetidine, tert-butyl piperazine-1-carboxylate and pyrimidine-4-carbaldehyde according to the representative procedure of Example 51, Steps 1-5 to provide azetidin-1-yl(1-(4-(pyrimidin-4-ylmethyl)piperazine-1-carbonyl)-1H-pyrazol-4-yl)methanone as a yellow solid. ¹H NMR (300 MHz, Chloroform-d) δ 9.18 (s, 1H), 8.72 (d, J=5.1 Hz, 1H), 8.35 (s, 1H), 7.95 (s, 1H), 7.50 (d, J=5.1 Hz, 1H), 4.37-4.42 (m, 2H), 4.17-4.22 (m, 2H), 3.93 (br, 4H), 3.71 (s, 2H), 2.65 (t, J=5.0 Hz, 4H), 2.35-2.42 (m, 2H). LCMS (ESI, m/z): 356 [M+H]⁺.

Example 91: Azetidin-1-yl(1-(4-(thiazol-2-ylmethyl)piperazine-1-carbonyl)-1H-pyrazol-4-yl)methanone

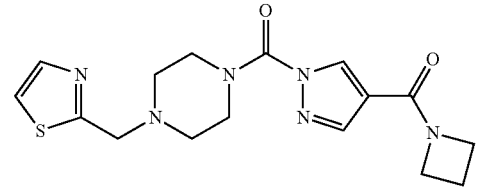 [SMILES: O=C(c1cnn(C(=O)N2CCN(Cc3nccs3)CC2)c1)N1CCC1]

The title compound was synthesized directly from 1H-pyrazole-4-carboxylic acid, azetidine, tert-butyl piperazine-1-carboxylate and thiazole-2-carbaldehyde according to the representative procedure of Example 51, Steps 1-5 to provide azetidin-1-yl(1-(4-(thiazol-2-ylmethyl)piperazine-1-carbonyl)-1H-pyrazol-4-yl)methanone as a light yellow solid. $^1$H NMR (300 MHz, Chloroform-d) δ 8.34 (s, 1H), 7.95 (s, 1H), 7.73 (d, J=3.3 Hz, 1H), 7.32 (d, J=3.3 Hz, 1H), 4.37-4.42 (m, 2H), 4.17-4.22 (m, 2H), 3.90-3.94 (m, 6H), 2.71 (t, J=5.0 Hz, 4H), 2.35-2.42 (m, 2H). LCMS (ESI, m/z): 361 [M+H]$^+$.

Example 92: Azetidin-1-yl(1-(4-(pyrimidin-5-ylmethyl)piperazine-1-carbonyl)-1H-pyrazol-4-yl)methanone

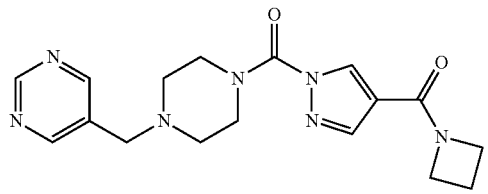 [SMILES: O=C(c1cnn(C(=O)N2CCN(Cc3cncnc3)CC2)c1)N1CCC1]

The title compound was synthesized directly from 1H-pyrazole-4-carboxylic acid, azetidine, tert-butyl piperazine-1-carboxylate and pyrimidine-5-carbaldehyde according to the representative procedure of Example 51, Steps 1-5 to provide azetidin-1-yl(1-(4-(pyrimidin-5-ylmethyl)piperazine-1-carbonyl)-1H-pyrazol-4-yl)methanone as a white solid. $^1$H NMR (300 MHz, Chloroform-d) δ 9.16 (s, 1H), 8.72 (s, 2H), 8.34 (s, 1H), 7.95 (s, 1H), 4.37-4.42 (m, 2H), 4.17-4.22 (m, 2H), 3.88 (br, 4H), 3.58 (s, 2H), 2.58 (t, J=5.0 Hz, 4H), 2.34-2.45 (m, 2H). LCMS (ESI, m/z): 356 [M+H]$^+$.

Example 93: Azetidin-1-yl(1-(4-((3-methyl-[1,1'-biphenyl]-4-yl)methyl)piperazine-1-carbonyl)-1H-pyrazol-4-yl)methanone

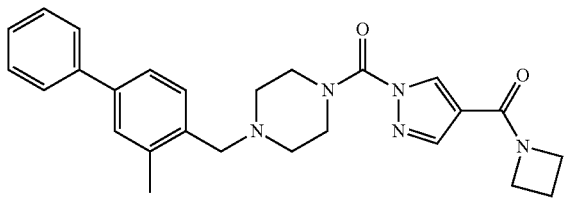 [SMILES: Cc1cc(-c2ccccc2)ccc1CN1CCN(C(=O)n2cc(C(=O)N3CCC3)cn2)CC1]

The title compound was synthesized directly from 1H-pyrazole-4-carboxylic acid, azetidine, tert-butyl piperazine-1-carboxylate and 3-methyl-[1,1'-biphenyl]-4-carbaldehyde (Example 94, Step 1) according to the representative procedure of Example 51, Steps 1-5 to provide azetidin-1-yl(1-(4-((3-methyl-[1,1'-biphenyl]-4-yl)methyl)piperazine-1-carbonyl)-1H-pyrazol-4-yl)methanone as a white solid. $^1$H NMR (300 MHz, Chloroform-d) δ 8.34 (s, 1H), 7.95 (s, 1H), 7.58 (d, J=7.2 Hz, 2H), 7.31-7.46 (m, 6H), 4.37-4.42 (m, 2H), 4.17-4.22 (m, 2H), 3.85 (br, 4H), 3.55 (s, 2H), 2.59 (br, 4H), 2.34-2.45 (m, 5H). LCMS (ESI, m/z): 444 [M+H]$^+$.

Example 94: (4-((3-Methyl-[1,1'-biphenyl]-4-yl)methyl)piperazin-1-yl)(1H-pyrazol-1-yl)methanone

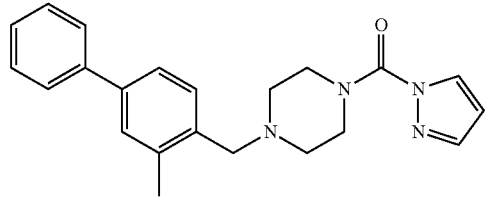 [SMILES: Cc1cc(-c2ccccc2)ccc1CN1CCN(C(=O)n2cccn2)CC1]

Step 1: Preparation of 3-methyl-[1,1'-biphenyl]-4-carbaldehyde

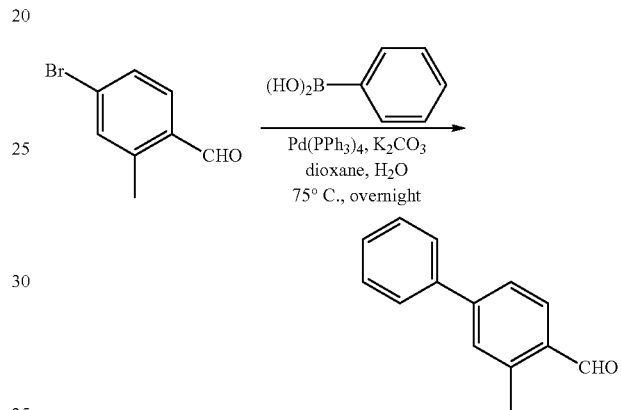

A 250-mL round-bottom flask was charged with 4-bromo-2-methylbenzaldehyde (8.00 g, 40.2 mmol, 1.00 equiv), phenylboronic acid (9.76 g, 80.0 mmol, 1.99 equiv), tetrakis(triphenylphosphine)palladium(0) (4.26 g, 3.69 mmol, 0.09 equiv), potassium carbonate (16.6 g, 120 mmol, 2.98 equiv), dioxane (80 mL) and water (8 mL) under nitrogen. The resulting solution was stirred overnight at 75° C. and diluted with H$_2$O (30 mL). The mixture was extracted with CH$_2$Cl$_2$ (3×30 mL), and the organic layers were combined, washed with water (3×10 mL), dried over anhydrous sodium sulfate, filtered and concentrated under reduced pressure. The residue was purified by flash chromatography on a silica gel column with EtOAc/petroleum ether (1/50) to provide 3-methyl-[1,1'-biphenyl]-4-carbaldehyde (7.00 g, 89% yield) as a colorless oil. LCMS (ESI, m/z): 197 [M+H]$^+$.

Step 2: Preparation of tert-butyl 4-((3-methyl-[1,1'-biphenyl]-4-yl)methyl)piperazine-1-carboxylate

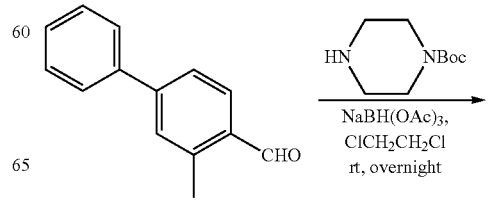

-continued

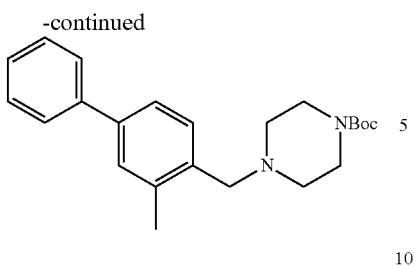

A 500-mL round-bottom flask was charged with 3-methyl-[1,1'-biphenyl]-4-carbaldehyde (7.00 g, 35.7 mmol, 1.00 equiv), tert-butyl piperazine-1-carboxylate (6.04 g, 32.4 mmol, 0.91 equiv) and 1,2-dichloroethane (50 mL). The mixture was stirred at room temperature for 0.5 hour. Sodium triacetoxyborohydride (20.6 g, 97.4 mmol, 2.73 equiv) was added. The resulting solution was stirred overnight at room temperature. The resulting mixture was diluted with H$_2$O (50 mL) and extracted with CH$_2$Cl$_2$ (3×50 mL). The organic layers were combined, washed with water (3×10 mL), dried over anhydrous sodium sulfate, filtered and concentrated under reduced pressure. The residue was purified by flash chromatography on a silica gel column with EtOAc/hexane (1/9) to provide tert-butyl 4-((3-methyl-[1,1'-biphenyl]-4-yl)methyl)piperazine-1-carboxylate (8.80 g, 67.3% yield) as a white solid. LCMS (ESI, m/z): 367 [M+H]$^+$.

Step 3: Preparation of 1-((3-methyl-[1,1'-biphenyl]-4-yl)methyl)piperazine

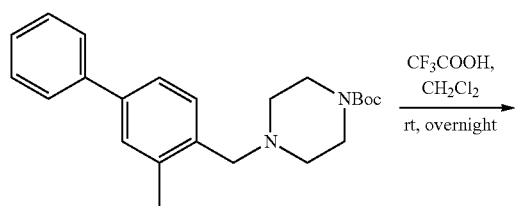

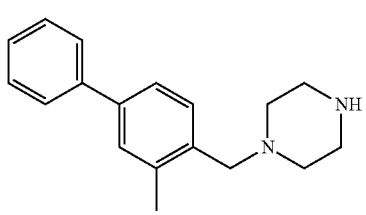

A 500-mL round-bottom flask was charged with tert-butyl 4-((3-methyl-[1,1'-biphenyl]-4-yl)methyl)piperazine-1-carboxylate (4.40 g, 12.0 mmol, 1.00 equiv) and CH$_2$Cl$_2$ (70 mL). The mixture was cooled to 0° C. Trifluoroacetic acid (7 mL) was added dropwise. The resulting solution was stirred overnight at room temperature. The resulting mixture was concentrated under reduced pressure to provide 1-((3-methyl-[1,1'-biphenyl]-4-yl)methyl)piperazine (11.0 g, crude) as a colorless oil. LCMS (ESI, m/z): 267 [M+H]$^+$.

Step 4: Preparation of (3,5-dimethyl-1H-pyrazol-1-yl)(4-((3-methyl-[1,1'-biphenyl]-4-yl)methyl)piperazin-1-yl)methanone

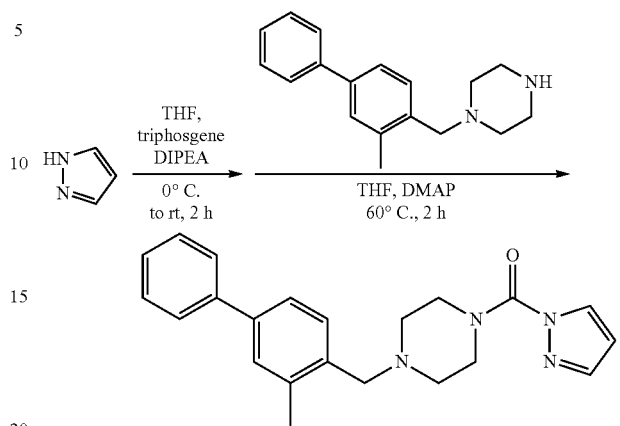

A 50-mL round-bottom flask was charged with 1H-pyrazole (68.0 mg, 1.00 mmol, 1.00 equiv), THF (10 mL), and triphosgene (150 mg, 0.505 mmol, 0.50 equiv). The mixture was cooled to 0° C. DIPEA (706 mg, 5.47 mmol, 5.47 equiv) was added dropwise at 0° C. The mixture was stirred at room temperature for 2 hours. The resulting mixture was diluted with H$_2$O (20 mL). The mixture was extracted with CH$_2$Cl$_2$ (3×30 mL) and the organic layers were combined, washed with water (3×10 mL), dried over anhydrous sodium sulfate, filtered and concentrated under reduced pressure. THF (10 mL), 4-dimethylaminopyridine (36.0 mg, 0.295 mmol, 0.30 equiv), 1-((3-methyl-[1,1'-biphenyl]-4-yl)methyl)piperazine (266 mg, 1.00 mmol, 1.00 equiv) were added. The resulting solution was stirred for 2 h at 60° C. The resulting mixture was diluted with H$_2$O (20 mL). The mixture was extracted with CH$_2$Cl$_2$ (3×30 mL) and the organic layers were combined, washed with water (3×10 mL), dried over anhydrous sodium sulfate, filtered and concentrated under reduced pressure. The residue was purified by flash chromatography on a silica gel column with EtOAc/petroleum ether (1/3). The crude product (300 mg) was purified by preparative HPLC to provide 1-[(2-methyl-4-phenylphenyl)methyl]-4-[(1H-pyrazol-1-yl)carbonyl]piperazine (67.5 mg 19% yield) as light yellow oil. $^1$H NMR (300 MHz, Chloroform-d) δ: 8.12 (s, 1H), 7.50-7.63 (m, 3H), 7.30-7.44 (m, 6H), 6.34 (s, 1H), 3.87 (br, 4H), 3.54 (br, 2H), 2.58 (br, 4H), 2.44 (s, 3H). LCMS (ESI, m/z): 361 [M+H]$^+$.

Example 95: (4-(Bis(1,3-dihydroisobenzofuran-5-yl)methyl)piperazin-1-yl)(4-chloro-1H-pyrazol-1-yl)methanone

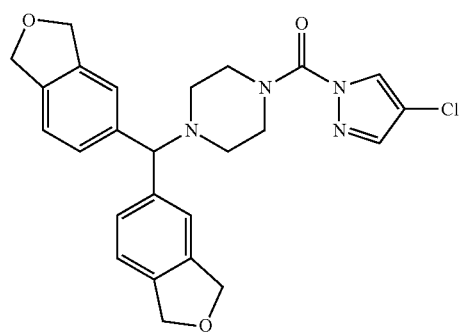 [SMILES: O=C(N1CCN(C(c2ccc3c(c2)COC3)c2ccc3c(c2)COC3)CC1)n1cc(Cl)cn1]

Step 1: Preparation of bis(1,3-dihydroisobenzofuran-5-yl)methanol

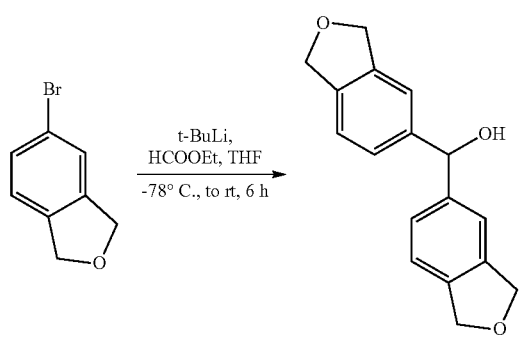 [SMILES: Brc1ccc2c(c1)COC2 ; OC(c1ccc2c(c1)COC2)c1ccc2c(c1)COC2]

A 100-mL 3-necked round-bottom flask was charged with tert-butyllithium (3.20 mL, 5.02 mmol, 2.00 equiv) and THF (10 mL) under nitrogen. The mixture was cooled to −78° C., and 5-bromo-1,3-dihydroisobenzofuran (500 mg, 2.51 mmol, 1.00 equiv) in THF (3 mL) was added. The mixture was stirred for 0.5 h at −78° C. Ethyl formate (66.0 mg, 0.890 mmol, 0.360 equiv) was added dropwise. The mixture was stirred for 1 h at −78° C. and then for 4 h at room temperature. The mixture was quenched by saturated $NH_4Cl$ solution (10 mL). The resulting solution was extracted with $CH_2Cl_2$ (3×10 mL), and the organic layers were combined, dried over anhydrous sodium sulfate, filtered and concentrated under reduced pressure. The residue was purified by flash chromatography on a silica gel column with EtOAc/petroleum ether (1/4) to provide bis(1,3-dihydroisobenzofuran-5-yl)methanol (190 mg, 28.2% yield) as a light yellow oil. LCMS (ESI, m/z): 251 [M-OH]$^+$.

Step 2: Preparation of 5,5'-(chloromethylene)bis(1,3-dihydroisobenzofuran)

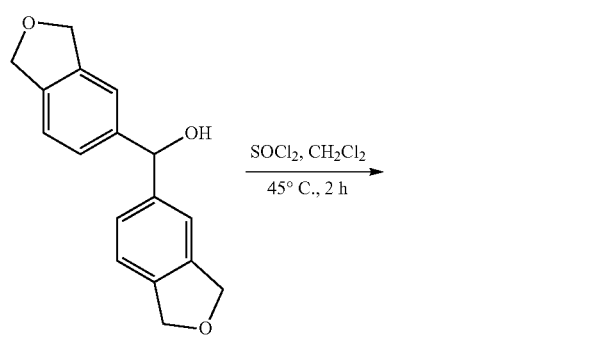

A 50-mL round-bottom flask was charged with bis(1,3-dihydroisobenzofuran-5-yl)methanol (360 mg, 1.34 mmol, 1.00 equiv), $CH_2Cl_2$ (10 mL) and thionyl chloride (951 mg, 8.06 mmol, 6.01 equiv). The reaction mixture was stirred for 2 h at 45° C. The resulting mixture was concentrated under reduced pressure to provide 5,5'-(chloromethylene)bis(1,3-dihydroisobenzofuran) (390 mg, crude) as a light yellow oil.

Step 3: Preparation of tert-butyl 4-(bis(1,3-dihydroisobenzofuran-5-yl)methyl)piperazine-1-carboxylate

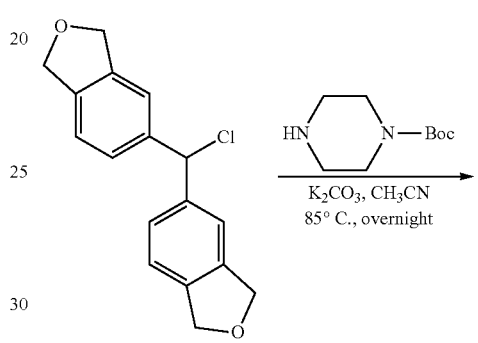

A 100-mL round-bottom flask was charged with 5,5'-(chloromethylene)bis(1,3-dihydroisobenzofuran) (390 mg, 1.36 mmol, 1.00 equiv), tert-butyl piperazine-1-carboxylate (322 mg, 1.73 mmol, 1.27 equiv), potassium carbonate (788 mg, 5.70 mmol, 4.19 equiv) and acetonitrile (10 mL). The mixture was stirred overnight at 85° C. and diluted with water (15 mL). The resulting solution was extracted with EtOAc (3×15 mL), and the organic layers were combined, dried over anhydrous sodium sulfate, filtered and concentrated under reduced pressure. The residue was purified by flash chromatography on a silica gel column with EtOAc/petroleum ether (1/5) to provide tert-butyl 4-(bis(1,3-dihydroisobenzofuran-5-yl)methyl)piperazine-1-carboxylate (360 mg, 55% yield) as a light yellow solid. LCMS (ESI, m/z): 437 [M+H]$^+$.

Step 4: Preparation of 1-(bis(1,3-dihydroisobenzofuran-5-yl)methyl)piperazine

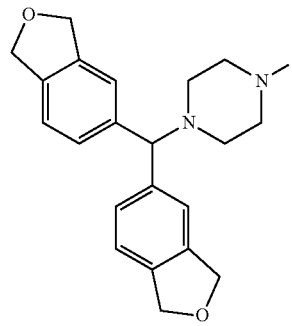

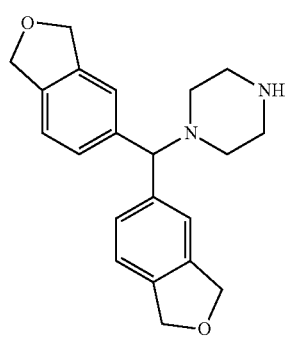

A 100-mL 3-necked round-bottom flask was charged with tert-butyl 4-(bis(1,3-dihydroisobenzofuran-5-yl)methyl)piperazine-1-carboxylate (360 mg, 0.82 mmol, 1.00 equiv), CH$_2$Cl$_2$ (10 mL) and N-methylmorpholine (254 mg, 2.51 mmol, 3.05 equiv) under nitrogen. Trimethyiodosilane (329 mg, 1.66 mmol, 2.01 equiv) was added dropwise. The resulting mixture was stirred for 2 h at 0° C. and concentrated under reduced pressure to provide 1-(bis(1,3-dihydroisobenzofuran-5-yl)methyl)piperazine (278 mg, crude) as a light yellow solid. LCMS (ESI, m/z): 337 [M+H]$^+$.

Step 5: Preparation of 4-(bis(1,3-dihydroisobenzofuran-5-yl)methyl)piperazine-1-carbonyl chloride

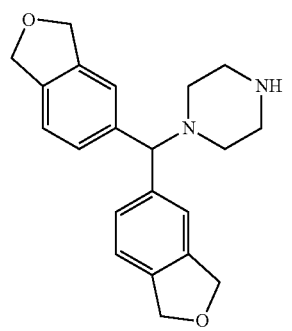

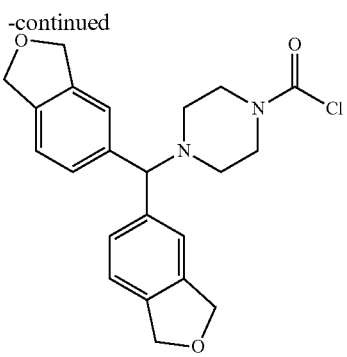

A 100-mL 3-necked round-bottom flask was charged with 1-(bis(1,3-dihydroisobenzofuran-5-yl)methyl)piperazine (150 mg, 0.450 mmol, 1.00 equiv), THF (10 mL) and triphosgene (66.3 mg, 0.221 mmol, 0.500 equiv). DIPEA (232 mg, 1.80 mmol, 4.03 equiv) was added dropwise. The reaction mixture was stirred overnight at room temperature and diluted with water (15 mL). The resulting solution was extracted with EtOAc (3×15 mL), and the organic layers were combined, dried over anhydrous sodium sulfate, filtered and concentrated under reduced pressure to provide 4-(bis(1,3-dihydroisobenzofuran-5-yl)methyl)piperazine-1-carbonyl chloride (170 mg, crude) as a light yellow oil.

Step 6: Preparation of (4-(bis(1,3-dihydroisobenzofuran-5-yl)methyl)piperazin-1-yl)(4-chloro-1H-pyrazol-1-yl)methanone

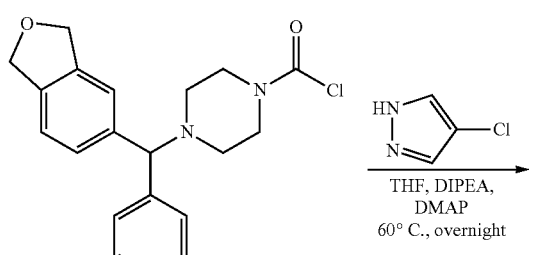

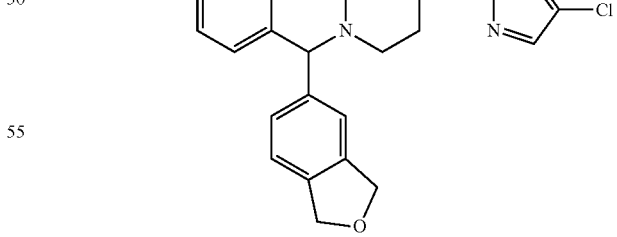

A 50-mL round-bottom flask was charged with 4-(bis(1,3-dihydroisobenzofuran-5-yl)methyl)piperazine-1-carbonyl chloride (170 mg, 0.430 mmol, 1.00 equiv), 4-chloro-1H-pyrazole (50.0 mg, 0.49 mmol, 1.14 equiv), THF (10 mL), DIPEA (168 mg, 1.30 mmol, 3.05 equiv) and 4-dimethylaminopyridine (28.3 mg, 0.231 mmol, 0.542 equiv). The reaction mixture was stirred overnight at 60° C. The resulting mixture was concentrated under reduced pressure. The crude product (190 mg) was purified by preparative HPLC to provide (4-(bis(1,3-dihydroisobenzofuran-5-yl)methyl)piperazin-1-yl)(4-chloro-1H-pyrazol-1-yl)methanone (46.6 mg, 23% yield) as a light yellow oil. $^1$H NMR (300 MHz, Chloroform-d) δ 8.06 (s, 1H), 7.50 (s, 1H), 7.29-7.35 (m, 4H), 7.16 (d, J=7.5 Hz, 2H), 5.05-5.06 (m, 8H), 4.31 (s, 1H), 3.85 (br, 4H), 2.50 (br, 4H). LCMS (ESI, m/z): 465 [M+H]$^+$.

Example 96: (4-Chloro-1H-pyrazol-1-yl)(piperidin-1-yl)methanone

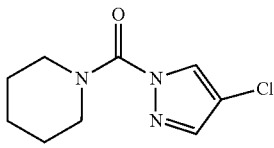 [SMILES: O=C(N1CCCCC1)n1cc(Cl)cn1]

The title compound was prepared from piperidine and 4-chloro-1H-pyrazole according to the representative procedure of Example 94, Step 4 to provide (4-chloro-1H-pyrazol-1-yl)(piperidin-1-yl)methanone as a white solid. $^1$H NMR (300 MHz, Chloroform-d) δ 8.04 (s, 1H), 7.54 (s, 1H), 3.72 (br, 4H), 1.69 (br, 6H). LCMS (ESI, m/z): 214 [M+H]$^+$.

Example 97: (4-Chloro-1H-pyrazol-1-yl)(morpholino)methanone

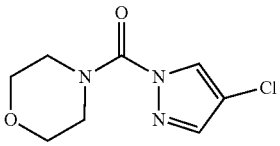 [SMILES: O=C(N1CCOCC1)n1cc(Cl)cn1]

The title compound was prepared from morpholine and 4-chloro-1H-pyrazole according to the representative procedure of Example 94, Step 4 to provide (4-chloro-1H-pyrazol-1-yl)(morpholino)methanone as a white solid. $^1$H NMR (300 MHz, Chloroform-d) δ 8.09 (s, 1H), 7.55 (s, 1H), 3.69-4.04 (m, 8H).

Example 98: (4-Chloro-1H-pyrazol-1-yl)(pyrrolidin-1-yl)methanone

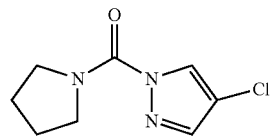 [SMILES: O=C(N1CCCC1)n1cc(Cl)cn1]

The title compound was prepared from pyrrolidine and 4-chloro-1H-pyrazole according to the representative procedure of Example 94, Step 4 to provide (4-chloro-1H-pyrazol-1-yl)(pyrrolidin-1-yl)methanone as a white solid. $^1$H NMR (300 MHz, Chloroform-d) δ 8.21 (s, 1H), 7.54 (s, 1H), 3.94 (br, 2H), 3.66 (br, 2H), 1.84 (br, 4H). LCMS (ESI, m/z): 200 [M+H]$^+$.

Example 99: (4-Chloro-1H-pyrazol-1-yl)(4-(2-(pyrrolidin-1-yl)-6-(trifluoromethyl)benzyl)piperazin-1-yl)methanone

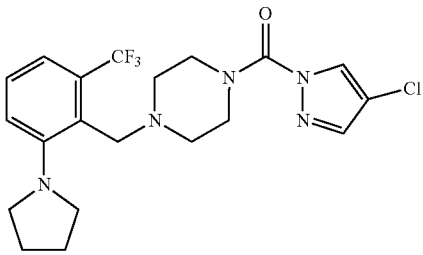 [SMILES: O=C(N1CCN(Cc2c(N3CCCC3)cccc2C(F)(F)F)CC1)n1cc(Cl)cn1]

Step 1: Preparation of 2-(pyrrolidin-1-yl)-6-(trifluoromethyl)benzaldehyde

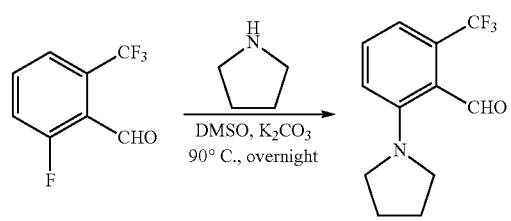 [SMILES: O=Cc1c(F)cccc1C(F)(F)F ; C1CCNC1 ; O=Cc1c(N2CCCC2)cccc1C(F)(F)F]

A 100-mL round-bottom flask was charged with 2-fluoro-6-(trifluoromethyl)benzaldehyde (950 mg, 4.95 mmol, 1.00 equiv), dimethyl sulfoxide (15 mL), pyrrolidine (528 mg, 7.42 mmol, 1.50 equiv) and potassium carbonate (2.06 g, 14.9 mmol, 3.00 equiv) under nitrogen. The reaction mixture was stirred overnight at 90° C. and diluted with water (100 mL). The resulting solution was extracted with EtOAc (2×200 mL), and the organic layers were combined, dried over anhydrous sodium sulfate, filtered and concentrated under reduced pressure. The residue was purified by flash chromatography on a silica gel column with EtOAc/petroleum ether (1/10) to provide 1.12 g (93% yield) of 2-(pyrrolidin-1-yl)-6-(trifluoromethyl)benzaldehyde as a yellow solid. LCMS (ESI, m/z): 244 [M+H]$^+$.

Step 2: Preparation of tert-butyl 4-(2-(pyrrolidin-1-yl)-6-(trifluoromethyl)benzyl)piperazine-1-carboxylate

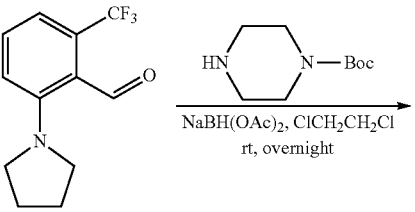

-continued

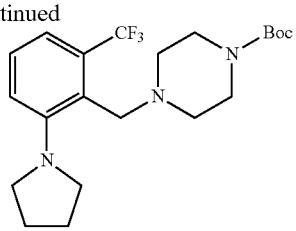

A 250-mL round-bottom flask was charged with 2-(pyrrolidin-1-yl)-6-(trifluoromethyl)benzaldehyde (2.00 g, 8.22 mmol, 1.00 equiv), 1,2-dichloroethane (40 mL) and tert-butyl piperazine-1-carboxylate (1.68 g, 9.02 mmol, 1.10 equiv). The mixture was stirred for 1 h at room temperature. Sodium triacetoxyborohydride (5.24 g, 24.7 mmol, 3.00 equiv) was added. The reaction mixture was stirred overnight at room temperature and diluted with water (100 mL). The resulting solution was extracted with $CH_2Cl_2$ (2×150 mL), and the organic layers were combined, dried over anhydrous sodium sulfate, filtered and concentrated under reduced pressure. The residue was purified by flash chromatography on a silica gel column with EtOAc/petroleum ether (1/10) to provide 2.20 g (65% yield) of tert-butyl 4-(2-(pyrrolidin-1-yl)-6-(trifluoromethyl)benzyl)piperazine-1-carboxylate as a yellow oil. LCMS (ESI, m/z): 414 $[M+H]^+$.

Step 3: Preparation of 1-(2-(pyrrolidin-1-yl)-6-(trifluoromethyl)benzyl)piperazine

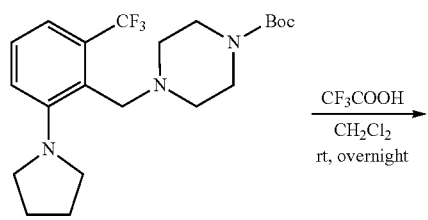

A 100-mL round-bottom flask was charged with tert-butyl 4-(2-(pyrrolidin-1-yl)-6-(trifluoromethyl)benzyl)piperazine-1-carboxylate (2.20 g, 5.32 mmol, 1.00 equiv), $CH_2Cl_2$ (25 mL) and trifluoroacetic acid (4.0 mL). The reaction mixture was stirred overnight at room temperature, and diluted $NaHCO_3$ saturated solution (200 mL) was added. The resulting solution was extracted with $CH_2Cl_2$ (2×250 mL), and the organic layers were combined, dried over anhydrous sodium sulfate, filtered and concentrated under reduced pressure. The residue was purified by flash chromatography on a silica gel column with EtOAc/petroleum ether (100/1) to provide 1.60 g (96% yield) of 1-(2-(pyrrolidin-1-yl)-6-(trifluoromethyl)benzyl)piperazine as a brown solid. LCMS (ESI, m/z): 314 $[M+H]^+$.

Step 4: 4-(2-(pyrrolidin-1-yl)-6-(trifluoromethyl)benzyl)piperazine-1-carbonyl chloride

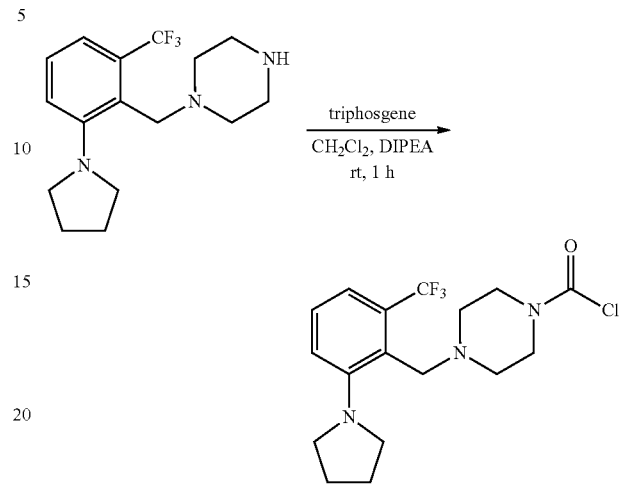

A 50-mL round-bottom flask was charged with triphosgene (228 mg, 0.768 mmol, 0.40 equiv) and $CH_2Cl_2$ (10 mL). 1-(2-(Pyrrolidin-1-yl)-6-(trifluoromethyl)benzyl)piperazine (600 mg, 1.91 mmol, 1.00 equiv) was added at 0° C. DIPEA (743 mg, 5.75 mmol, 3.00 equiv) was added dropwise at 0° C. The reaction mixture was stirred for 1 h at room temperature and diluted with water (50 mL). The resulting solution was extracted with $CH_2Cl_2$ (2×100 mL), and the organic layers were combined, dried over anhydrous sodium sulfate, filtered and concentrated under reduced pressure to provide 718 mg (crude) of 4-(2-(pyrrolidin-1-yl)-6-(trifluoromethyl)benzyl)piperazine-1-carbonyl chloride as a yellow oil.

Step 5: Preparation of (4-chloro-1H-pyrazol-1-yl)(4-(2-(pyrrolidin-1-yl)-6-(trifluoromethyl)benzyl)piperazin-1-yl)methanone

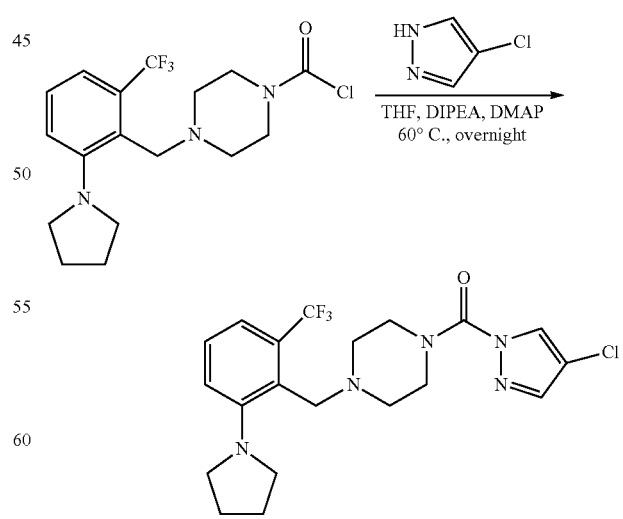

The title compound was prepared from 4-(2-(pyrrolidin-1-yl)-6-(trifluoromethyl)benzyl)piperazine-1-carbonyl chloride and 4-chloro-1H-pyrazole according to the representative procedure of Example 95, Step 6 to provide (4-chloro-1H-pyrazol-1-yl)(4-(2-(pyrrolidin-1-yl)-6-(trifluoromethyl)benzyl)piperazin-1-yl)methanone as a white solid. ¹H NMR (300 MHz, Chloroform-d) δ: 8.04 (s, 1H), 7.52 (s, 1H), 7.19-7.32 (m, 3H), 3.73-3.75 (m, 6H), 3.07-3.10 (m, 4H), 2.42-2.45 (m, 4H), 1.91-1.97 (m, 4H). LCMS (ESI, m/z): 442 [M+H]⁺.

Example 100: (4-(Bis(4-chlorophenyl)methyl)piperazin-1-yl)(4-chloro-1H-pyrazol-1-yl)methanone

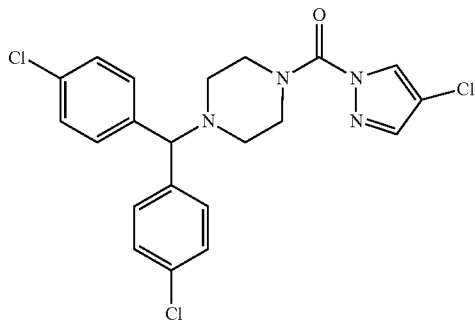 [SMILES: O=C(N1CCN(C(c2ccc(Cl)cc2)c2ccc(Cl)cc2)CC1)n1cc(Cl)cn1]

The title compound was prepared from bis(4-chlorophenyl)methanol, tert-butyl piperazine-1-carboxylate and 4-chloro-1H-pyrazole according to the representative procedure of Example 66, Steps 2-6 to provide (4-(bis(4-chlorophenyl)methyl)piperazin-1-yl)(4-chloro-1H-pyrazol-1-yl)methanone as a white solid. ¹H NMR (300 MHz, Chloroform-d) δ 8.05 (s, 1H), 7.50 (s, 1H), 7.17-7.33 (m, 8H), 4.24 (s, 1H), 3.84 (br, 4H), 2.45-2.48 (m, 4H). LCMS (ESI, m/z): 449 [M+H]⁺.

Example 101: (4-Chloro-1H-pyrazol-1-yl)(4-((1-isopropyl-3-phenyl-1H-pyrazol-4-yl)methyl)piperazin-1-yl)methanone

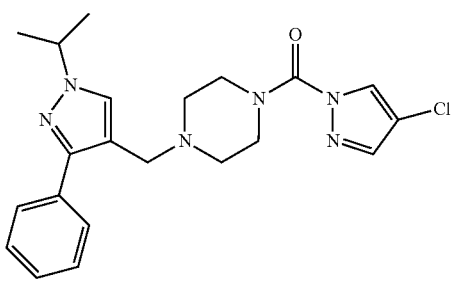 [SMILES: CC(C)n1cc(CN2CCN(C(=O)n3cc(Cl)cn3)CC2)c(-c2ccccc2)n1]

Step 1: Preparation of (E)-1-isopropyl-2-(1-phenylethylidene)hydrazine

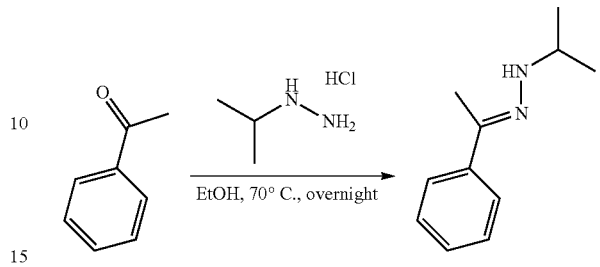

A 100-mL round-bottom flask was charged with acetophenone (1.50 g, 12.5 mmol, 1.00 equiv), isopropylhydrazine hydrochloride (2.75 g, 24.9 mmol, 1.99 equiv) and ethanol (25 mL). The resulting solution was stirred overnight at 70° C. The resulting mixture was concentrated under reduced pressure to provide 3.5 g (crude) of (E)-1-isopropyl-2-(1-phenylethylidene)hydrazine as a yellow oil. LCMS (ESI, m/z): 177 [M+H]⁺.

Step 2: Preparation of 1-isopropyl-3-phenyl-1H-pyrazole-4-carbaldehyde

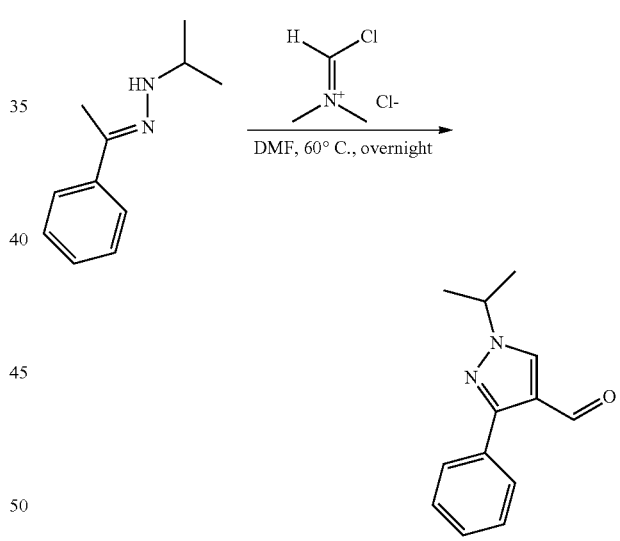

A 100-mL round-bottom flask was charged with (E)-1-isopropyl-2-(1-phenylethylidene)hydrazine (500 mg, 2.84 mmol, 1.00 equiv), N-(chloromethylene)-N-methylmethanaminium chloride (2.50 g, 19.5 mmol, 6.89 equiv) and N,N-dimethylformamide (15 mL). The solution was stirred overnight at 60° C. and diluted with saturated sodium carbonate solution (50 mL). The resulting solution was extracted with EtOAc (2×100 mL), and the organic layers were combined, dried over anhydrous sodium sulfate, filtered and concentrated under reduced pressure. The residue was purified by flash chromatography on a silica gel column with EtOAc/petroleum ether (1/2) to provide 360 mg (59% yield) of 1-isopropyl-3-phenyl-1H-pyrazole-4-carbaldehyde as a yellow oil. LCMS (ESI, m/z): 215 [M+H]⁺.

Step 3: Preparation of tert-butyl 4-((1-isopropyl-3-phenyl-1H-pyrazol-4-yl)methyl)piperazine-1-carboxylate

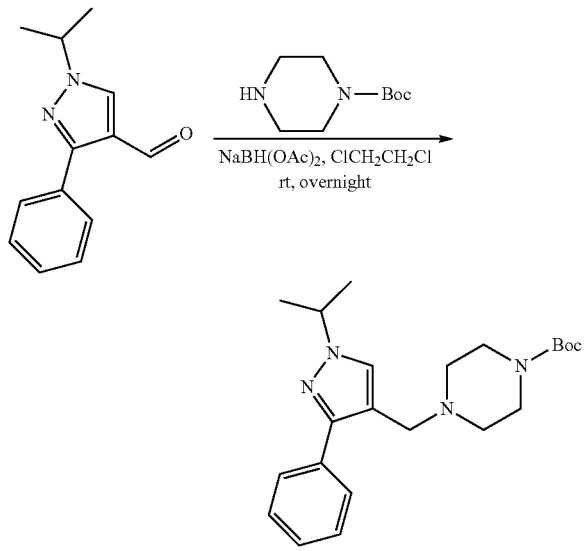

A 50-mL round-bottom flask was charged with 1-isopropyl-3-phenyl-1H-pyrazole-4-carbaldehyde (350 mg, 1.63 mmol, 1.00 equiv), tert-butyl piperazine-1-carboxylate (276 mg, 1.48 mmol, 0.91 equiv) and 1,2-dichloroethane (10 mL). The mixture was stirred at room temperature for 30 min. Sodium triacetoxyborohydride (630 mg, 2.97 mmol, 1.82 equiv) was added. The resulting mixture was diluted with H$_2$O (20 mL) and then extracted with CH$_2$Cl$_2$ (3×30 mL). The combined organic layers were washed with water (3×10 mL), dried over anhydrous sodium sulfate, filtered and concentrated under reduced pressure. The residue was purified by flash chromatography on a silica gel column with EtOAc/petroleum ether (1/4) to provide 600 mg (96% yield) of tert-butyl 4-((1-isopropyl-3-phenyl-1H-pyrazol-4-yl)methyl)piperazine-1-carboxylate as a colorless oil. LCMS (ESI, m/z): 385 [M+H]$^+$.

Step 4: Preparation of (4-chloro-1H-pyrazol-1-yl)(4-((1-isopropyl-3-phenyl-1H-pyrazol-4-yl)methyl)piperazin-1-yl)methanone The title compound was prepared from tert-butyl 4-((1-isopropyl-3-phenyl-1H-pyrazol-4-yl)methyl)piperazine-1-carboxylate and 4-chloro-1H-pyrazole according to the representative procedure of Example 99, Steps 3-5 to provide (4-chloro-1H-pyrazol-1-yl)(4-((1-isopropyl-3-phenyl-1H-pyrazol-4-yl)methyl)piperazin-1-yl)methanone as a white solid. $^1$H NMR (300 MHz, Chloroform-d) δ 8.06 (s, 1H), 7.81 (d, J=7.2 Hz, 2H), 7.54 (s, 1H), 7.28-7.42 (m, 4H), 4.48-4.57 (m, 1H), 3.84 (br, 4H), 3.49 (br, 2H), 2.54-2.57 (m, 4H), 1.54 (d, J=6.6 Hz, 6H). LCMS (ESI, m/z): 413 [M+H]$^+$.

Example 102: (4-Chloro-1H-pyrazol-1-yl)(4-(4-chloro-2-(8-oxa-2-azaspiro[4.5]decan-2-yl)benzyl)piperazin-1-yl)methanone

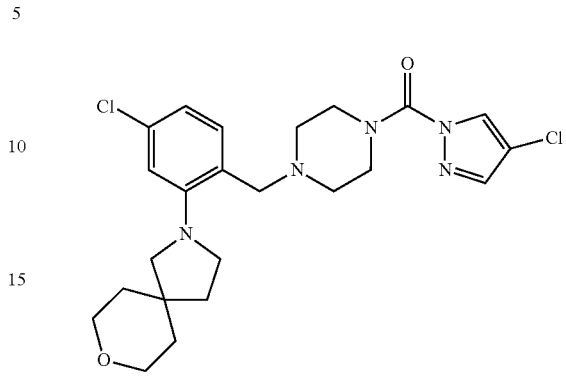

The title compound was prepared from 4-chloro-2-fluorobenzaldehyde, 8-oxa-2-azaspiro[4.5]decane, tert-butyl piperazine-1-carboxylate and 4-chloro-1H-pyrazole according to the representative procedure of Example 99, Steps 1-5 to provide (4-chloro-1H-pyrazol-1-yl)(4-(4-chloro-2-(8-oxa-2-azaspiro[4.5]decan-2-yl)benzyl)piperazin-1-yl)methanone as a light yellow oil. $^1$H NMR (300 MHz, Chloroform-d) δ 8.07 (s, 1H), 7.53 (s, 1H), 7.22 (s, 1H), 6.82 (s, 2H), 3.62-3.95 (m, 8H), 3.50 (br, 2H), 3.29-3.34 (m, 2H), 3.18 (br, 2H), 2.52 (br, 4H), 1.81-1.89 (m, 2H), 1.64-1.67 (m, 4H). LCMS (ESI, m/z): 478 [M+H]$^+$.

Example 103: (4-Phenyl-1H-pyrazol-1-yl)(pyrrolidin-1-yl)methanone

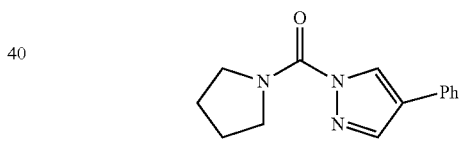

The title compound was synthesized directly from pyrrolidine and 4-phenyl-1H-pyrazole according to the representative procedure of Example 99, Steps 4 and 5 to provide (4-phenyl-1H-pyrazol-1-yl)(pyrrolidin-1-yl)methanone (29.5 mg, 6% yield) as a white solid. $^1$H NMR (300 MHz, Chloroform-d) δ 8.49 (s, 1H), 7.91 (s, 1H), 7.22-7.55 (m, 2H), 7.37-7.42 (m, 2H), 7.25-7.31 (m, 1H), 4.02 (br, 2H), 3.70 (br, 2H), 1.96-2.01 (m, 4H). LCMS (ESI, m/z): 242 [M+H]$^+$.

Example 104: Pyrrolidin-1-yl(4-(p-tolyl)-1H-pyrazol-1-yl)methanone

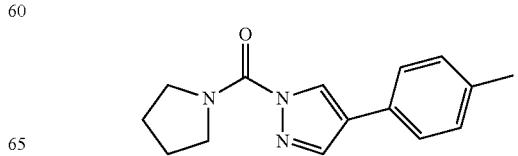

Step 1: Preparation of 4-(p-tolyl)-1H-pyrazole

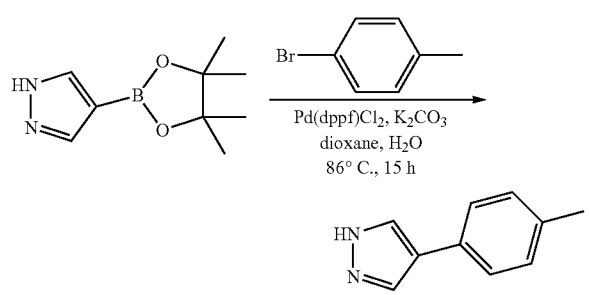

A 100-mL round-bottom flask was charged with 4-(tetramethyl-1,3,2-dioxaborolan-2-yl)-1H-pyrazole (2.00 g, 10.3 mmol, 1.31 equiv), 1-bromo-4-methylbenzene (1.35 g, 7.89 mmol, 1.00 equiv), potassium carbonate (1.75 g, 12.7 mmol, 1.60 equiv), dioxane (9 mL), water (3 mL) and [1,1'-bis(diphenylphosphino)ferrocene]dichloropalladium (II) (579 mg, 0.790 mmol, 0.10 equiv) under nitrogen. The resulting solution was stirred for 15 h at 86° C. and concentrated under reduced pressure. The residue was purified by flash chromatography on a silica gel column with EtOAc/petroleum ether (87/13) to provide 900 mg (72% yield) of 4-(p-tolyl)-1H-pyrazole as a brown solid. LCMS (ESI, m/z): 159 [M+H]+.

Step 2: Pyrrolidin-1-yl(4-(p-tolyl)-1H-pyrazol-1-yl)methanone

The title compound was synthesized directly from pyrrolidine and 4-(p-tolyl)-1H-pyrazole according to the representative procedure of Example 99, Steps 4 and 5 to provide pyrrolidin-1-yl(4-(p-tolyl)-1H-pyrazol-1-yl)methanone as a white solid. ¹H NMR (300 MHz, Chloroform-d) δ 8.45 (s, 1H), 7.88 (s, 1H), 7.41-7.44 (m, 2H), 7.19-7.26 (m, 2H), 4.01 (br, 2H), 3.70 (br, 2H), 2.36 (s, 3H), 1.96 (br, 4H). LCMS (ESI, m/z): 256 [M+H]+.

Example 105: (4-(4-Chlorophenyl)-1H-pyrazol-1-yl)(pyrrolidin-1-yl)methanone

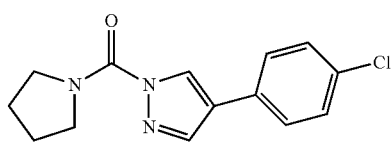 [SMILES: O=C(N1CCCC1)n1cc(-c2ccc(Cl)cc2)cn1]

The title compound was synthesized directly from pyrrolidine and 4-(4-chlorophenyl)-1H-pyrazole (prepared from 4-(tetramethyl-1,3,2-dioxaborolan-2-yl)-1H-pyrazole and 1-bromo-4-chlorobenzene according to the representative procedure of Example 104, Step 1) according to the representative procedure of Example 99, Steps 4 and 5 to provide (4-(4-chlorophenyl)-1H-pyrazol-1-yl)(pyrrolidin-1-yl)methanone as a white solid. ¹H NMR (300 MHz, Chloroform-d) δ 8.47 (s, 1H), 7.87 (s, 1H), 7.44-7.47 (m, 2H), 7.34-7.37 (m, 2H), 4.00 (br, 2H), 3.70 (br, 2H), 1.96 (br, 4H). LCMS (ESI, m/z): 276 [M+H]+.

Example 106: (4-([1,1'-Biphenyl]-4-yl)-1H-pyrazol-1-yl)(pyrrolidin-1-yl)methanone

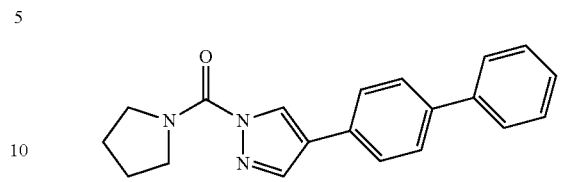

The title compound was synthesized directly from 4-([1,1'-biphenyl]-4-yl)-1H-pyrazole (prepared from 4-(tetramethyl-1,3,2-dioxaborolan-2-yl)-1H-pyrazole and 4-bromo-1,1'-biphenyl according to the representative procedure of Example 104, Step 1) and pyrrolidine according to the representative procedure of Example 99, Steps 4 and 5 to provide (4-([1,1'-biphenyl]-4-yl)-1H-pyrazol-1-yl)(pyrrolidin-1-yl)methanone as a white solid. ¹H NMR (300 MHz, Chloroform-d) δ 8.53 (s, 1H), 8.53 (s, 1H), 7.59-7.95 (m, 6H), 7.45-7.48 (m, 2H), 7.33-7.42 (m, 1H), 4.02 (br, 2H), 3.71 (br, 2H), 2.00 (br, 4H). LCMS (ESI, m/z): 318 [M+H]+.

Example 107: (4-(2'-Methoxy-[1,1'-biphenyl]-4-yl)-1H-pyrazol-1-yl)(pyrrolidin-1-yl)methanone

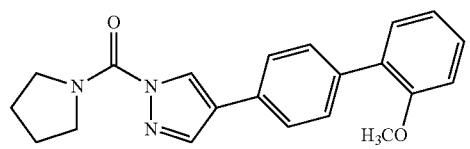 [SMILES: COc1ccccc1-c1ccc(-c2cnn(C(=O)N3CCCC3)c2)cc1]

Step 1: Preparation of 4'-bromo-2-methoxy-1,1'-biphenyl

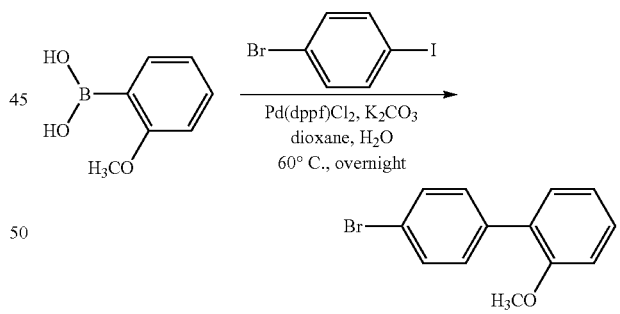

A 100-mL round-bottom flask was charged with 1-bromo-4-iodobenzene (2.00 g, 7.07 mmol, 1.00 equiv), (2-methoxyphenyl)boronic acid (1.07 g, 7.04 mmol, 1.00 equiv), potassium carbonate (2.92 g, 21.1 mmol, 2.99 equiv), dioxane (27 mL), water (3 mL) and [1,1'-bis(diphenylphosphino)ferrocene]dichloropalladium(II) (517 mg, 0.710 mmol, 0.10 equiv) under nitrogen. The resulting solution was stirred overnight at 60° C. and concentrated under reduced pressure. The residue was purified by flash chromatography on a silica gel column with EtOAc/petroleum ether (0/100) to provide 1.46 g (78% yield) of 4'-bromo-2-methoxy-1,1'-biphenyl as a white solid. GCMS (EI, m/z): 262 [M]+.

Steps 2-3: Preparation of (4-(2'-methoxy-[1,1'-biphenyl]-4-yl)-1H-pyrazol-1-yl)(pyrrolidin-1-yl)methanone 4'-Bromo-2-methoxy-1,1'-biphenyl and 4-(tetramethyl-1,3,2-dioxaborolan-2-yl)-1H-pyrazole were used according to the representative procedure of Example 104, Step 1 to prepare 4-(2'-methoxy-[1,1'-biphenyl]-4-yl)-1H-pyrazole. The title compound was synthesized directly from this latter pyrazole and pyrrolidine according to the representative procedure of Example 99, Steps 4 and 5 to provide (4-(2'-methoxy-[1,1'-biphenyl]-4-yl)-1H-pyrazol-1-yl)(pyrrolidin-1-yl)methanone as a white solid. $^1$H NMR (300 MHz, Chloroform-d) δ 8.52 (s, 1H), 7.94 (s, 1H), 7.57 (s, 4H), 7.30-7.36 (m, 2H), 6.98-7.07 (m, 2H), 4.03-4.07 (m, 2H), 3.83 (s, 3H), 3.71 (br, 2H), 1.96-2.00 (m, 4H). LCMS (ESI, m/z): 348 [M+H]$^+$.

Example 108: (4-(2'-Chloro-[1,1'-biphenyl]-4-yl)-1H-pyrazol-1-yl)(pyrrolidin-1-yl)methanone

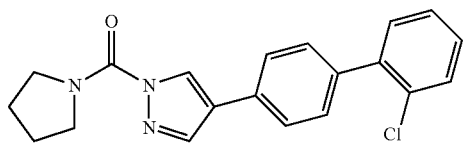 [SMILES: O=C(N1CCCC1)n1cc(-c2ccc(-c3ccccc3Cl)cc2)cn1]

4'-Bromo-2-chloro-1,1'-biphenyl (prepared from (2-chlorophenyl)boronic acid and 1-bromo-4-iodobenzene and according to the representative procedure of Example 104, Step 1 and 4-(tetramethyl-1,3,2-dioxaborolan-2-yl)-1H-pyrazole were used according to the representative procedure of Example 99, Steps 4 and 5 to prepare 4-(2'-chloro-[1,1'-biphenyl]-4-yl)-1H-pyrazole. The title compound was synthesized directly from this latter pyrazole and pyrrolidine according to the representative procedure of Example 134 to provide (4-(2'-chloro-[1,1'-biphenyl]-4-yl)-1H-pyrazol-1-yl)(pyrrolidin-1-yl)methanone as a white solid. $^1$H NMR (300 MHz, Chloroform-d) δ 8.54 (s, 1H), 7.96 (s, 1H), 7.60-7.62 (m, 2H), 7.45-7.54 (m, 3H), 7.26-7.38 (m, 3H), 4.03 (br, 2H), 3.72 (br, 2H), 1.97 (br, 4H). LCMS (ESI, m/z): 352 [M+H]$^+$.

Example 109: (4-Phenyl-1H-pyrazol-1-yl)(4-(2-(pyrrolidin-1-yl)-6-(trifluoromethyl)benzyl)piperazin-1-yl)methanone

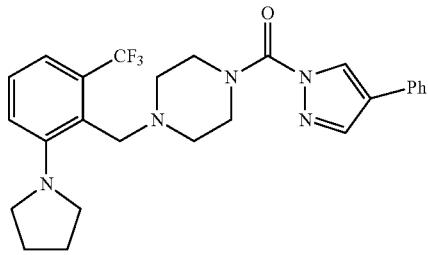 [SMILES: O=C(N1CCN(Cc2c(N3CCCC3)cccc2C(F)(F)F)CC1)n1cc(-c2ccccc2)cn1]

A 50-mL round-bottom flask was charged with 4-(2-(pyrrolidin-1-yl)-6-(trifluoromethyl)benzyl)piperazine-1-carbonyl chloride, prepared in Example 99, Steps 1-4 (298 mg, 0.792 mmol, 1.00 equiv), THF (10 mL), 4-phenyl-1H-pyrazole (137 mg, 0.950 mmol, 1.20 equiv), DIPEA (309 mg, 2.39 mmol, 3.00 equiv) and 4-dimethylaminopyridine (20.0 mg, 0.160 mmol, 0.20 equiv). The reaction mixture was stirred overnight at 60° C. and diluted with water (50 mL). The resulting solution was extracted with CH$_2$Cl$_2$ (2×100 mL), and the organic layers were combined, dried over anhydrous sodium sulfate, filtered and concentrated under reduced pressure. The residue was purified by flash chromatography on a silica gel column with EtOAc/petroleum ether (1/10). The crude product (300 mg) was purified by preparative HPLC to provide (4-phenyl-1H-pyrazol-1-yl)(4-(2-(pyrrolidin-1-yl)-6-(trifluoromethyl)benzyl)piperazin-1-yl)methanone (130.5 mg, 34% yield) as a light yellow oil. $^1$H NMR (300 MHz, Chloroform-d) δ 8.32 (s, 1H), 7.88 (s, 1H), 7.50-7.60 (m, 2H), 7.36-7.41 (m, 2H), 7.20-7.32 (m, 4H), 3.77 (br, 6H), 3.08-3.30 (m, 4H), 2.38-2.48 (m, 4H), 1.82-1.95 (m, 4H). LCMS (ESI, m/z): 484 [M+H]$^+$.

Example 110: (4-(2-(Pyrrolidin-1-yl)-6-(trifluoromethyl)benzyl)piperazin-1-yl)(4-(trifluoromethyl)-1H-pyrazol-1-yl)methanone

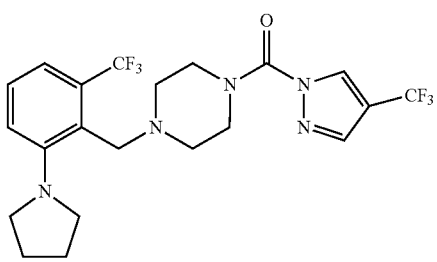 [SMILES: O=C(N1CCN(Cc2c(N3CCCC3)cccc2C(F)(F)F)CC1)n1cc(C(F)(F)F)cn1]

The title compound was synthesized directly from 4-(2-(pyrrolidin-1-yl)-6-(trifluoromethyl)benzyl)piperazine-1-carbonyl chloride (Example 99, Steps 1-4) and 4-(trifluoromethyl)-1H-pyrazole according to the representative procedure of Example 109 to provide (4-(2-(pyrrolidin-1-yl)-6-(trifluoromethyl)benzyl)piperazin-1-yl)(4-(trifluoromethyl)-1H-pyrazol-1-yl)methanone as a light yellow oil. $^1$H NMR (300 MHz, Chloroform-d) δ 8.37 (s, 1H), 7.77 (s, 1H), 7.20-7.33 (m, 3H), 3.77 (br, 6H), 3.07-3.11 (m, 4H), 2.45 (br, 4H), 1.89-2.00 (m, 4H). LCMS (ESI, m/z): 476 [M+H]$^+$.

Example 111: (4-Methyl-1H-pyrazol-1-yl)(4-(2-(pyrrolidin-1-yl)-6-(trifluoromethyl)benzyl)piperazin-1-yl)methanone

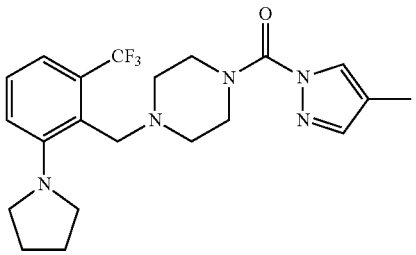 [SMILES: Cc1cnn(C(=O)N2CCN(Cc3c(N4CCCC4)cccc3C(F)(F)F)CC2)c1]

The title compound was synthesized directly from 4-(2-(pyrrolidin-1-yl)-6-(trifluoromethyl)benzyl)piperazine-1-carbonyl chloride (Example 99, Steps 1-4) and 4-methyl-1H-pyrazole according to the representative procedure of Example 109 to provide (4-methyl-1H-pyrazol-1-yl)(4-(2-(pyrrolidin-1-yl)-6-(trifluoromethyl)benzyl)piperazin-1-yl) methanone as a yellow oil. $^1$H NMR (300 MHz, Chloroform-d) δ 7.82 (s, 1H), 7.42 (s, 1H), 7.19-7.31 (m, 3H), 3.75 (br, 6H), 3.07-3.11 (m, 4H), 2.41-2.44 (m, 4H), 2.08 (s, 3H), 1.86-1.97 (m, 4H). LCMS (ESI, m/z): 422 [M+H]+.

Example 112: (4-Isopropyl-1H-pyrazol-1-yl)(4-(2-(pyrrolidin-1-yl)-6-(trifluoromethyl)benzyl)piperazin-1-yl)methanone

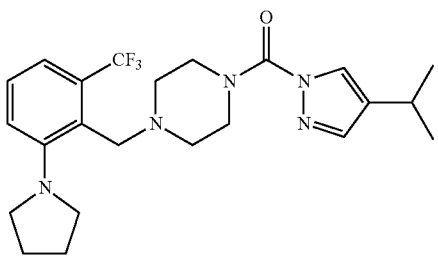 [SMILES: CC(C)c1cnn(C(=O)N2CCN(Cc3c(N4CCCC4)cccc3C(F)(F)F)CC2)c1]

The title compound was synthesized directly from 4-(2-(pyrrolidin-1-yl)-6-(trifluoromethyl)benzyl)piperazine-1-carbonyl chloride (Example 99, Steps 1-4) and 4-isopropyl-1H-pyrazole according to the representative procedure of Example 109 to provide (4-isopropyl-1H-pyrazol-1-yl)(4-(2-(pyrrolidin-1-yl)-6-(trifluoromethyl)benzyl)piperazin-1-yl)methanone as a light yellow solid. $^1$H NMR (300 MHz, Chloroform-d) δ 7.83 (s, 1H), 7.47 (s, 1H), 7.19-7.32 (m, 3H), 3.75 (br, 6H), 3.07-3.11 (m, 4H), 2.78-2.88 (m, 1H), 2.41-2.44 (m, 4H), 1.88-1.96 (m, 4H), 1.22 (d, J=6.9 Hz, 6H). LCMS (ESI, m/z): 450 [M+H]$^+$.

Example 113: (4-Fluoro-1H-pyrazol-1-yl)(4-(2-(pyrrolidin-1-yl)-6-(trifluoromethyl)benzyl)piperazin-1-yl)methanone

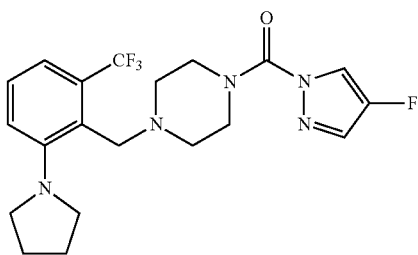 [SMILES: O=C(N1CCN(Cc2c(N3CCCC3)cccc2C(F)(F)F)CC1)n1cc(F)cn1]

The title compound was synthesized directly from 4-(2-(pyrrolidin-1-yl)-6-(trifluoromethyl)benzyl)piperazine-1-carbonyl chloride (Example 99, Steps 1-4) and 4-fluoro-1H-pyrazole according to the representative procedure of Example 109 to provide (4-fluoro-1H-pyrazol-1-yl)(4-(2-(pyrrolidin-1-yl)-6-(trifluoromethyl)benzyl)piperazin-1-yl) methanone as a yellow solid. $^1$H NMR (300 MHz, Chloroform-d) δ 7.90-7.92 (m, 1H), 7.47-7.48 (m, 1H), 7.19-7.32 (m, 3H), 3.75 (br, 6H), 3.07-3.11 (m, 4H), 2.37-2.45 (m, 4H), 1.87-1.98 (m, 4H). LCMS (ESI, m/z): 426 [M+H]$^+$.

Example 114: (4-(2-(Pyrrolidin-1-yl)-6-(trifluoromethyl)benzyl)piperazin-1-yl)(4-(o-tolyl)-1H-pyrazol-1-yl)methanone Step 1: Preparation of 4-(o-tolyl)-1H-pyrazole

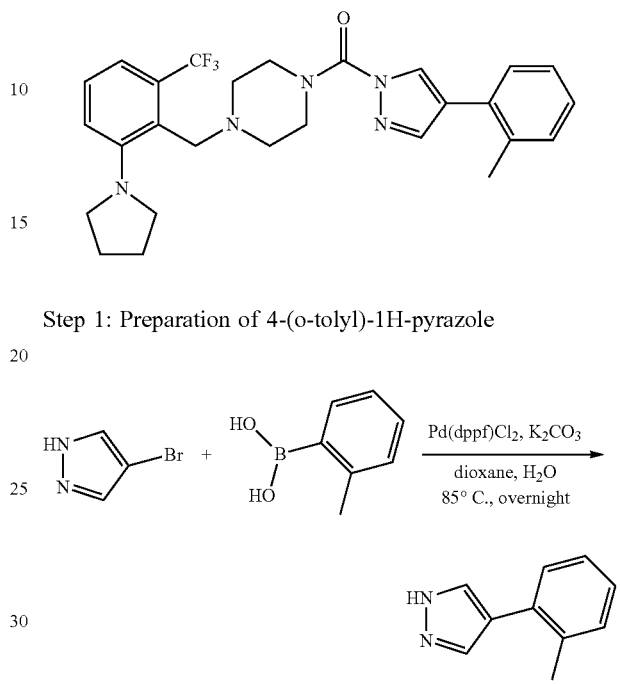

A 50-mL round-bottom flask was charged with 4-bromo-1H-pyrazole (1.00 g, 6.80 mmol, 1.00 equiv), o-tolylboronic acid (1.40 g, 10.3 mmol, 1.50 equiv), [1,1'-bis(diphenylphosphino)ferrocene]dichloropalladium(II) (501 mg, 0.685 mmol, 0.10 equiv), potassium carbonate (2.84 g, 20.6 mmol, 3.00 equiv), 1,4-dioxane (18 mL) and water (2 mL) under nitrogen. The reaction mixture was stirred overnight at 85° C. and diluted with water (100 mL). The resulting solution was extracted with EtOAc (2×150 mL), and the organic layers were combined, dried over anhydrous sodium sulfate, filtered and concentrated under reduced pressure. The residue was purified by flash chromatography on a silica gel column with EtOAc/petroleum ether (1/3) to provide 200 mg (19% yield) of 4-(o-tolyl)-1H-pyrazole as a brown solid. LCMS (ESI, m/z): 159 [M+H]$^+$.

Step 2: Preparation of (4-(2-(pyrrolidin-1-yl)-6-(trifluoromethyl)benzyl)piperazin-1-yl)(4-(o-tolyl)-1H-pyrazol-1-yl)methanone The title compound was synthesized directly from 4-(2-(pyrrolidin-1-yl)-6-(trifluoromethyl)benzyl)piperazine-1-carbonyl chloride (Example 99, Steps 1-4) and 4-(o-tolyl)-1H-pyrazole according to the representative procedure of Example 109 to provide (4-(2-(pyrrolidin-1-yl)-6-(trifluoromethyl)benzyl)piperazin-1-yl)(4-(o-tolyl)-1H-pyrazol-1-yl)methanone as a light yellow oil. $^1$H NMR (300 MHz, Chloroform-d) δ 8.17 (s, 1H), 7.74 (s, 1H), 7.20-7.36 (m, 7H), 3.78-3.81 (m, 6H), 3.08-3.12 (m, 4H), 2.46-2.49 (m, 4H), 2.40 (s, 3H), 1.89-1.98 (m, 4H). LCMS (ESI, m/z): 498 [M+H]$^+$.

Example 115: (4-(2-(Pyrrolidin-1-yl)-4-(trifluoromethyl)benzyl)piperazin-1-yl)(4-(2-(trifluoromethyl)phenyl)-1H-pyrazol-1-yl)methanone

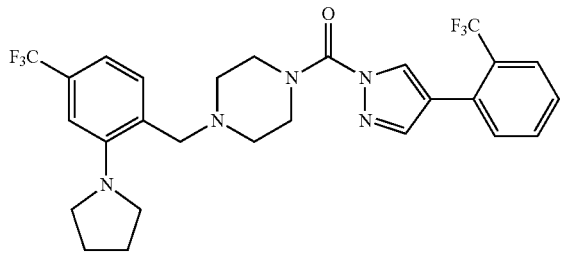 [SMILES: O=C(N1CCN(Cc2ccc(C(F)(F)F)cc2N2CCCC2)CC1)n1cc(-c2ccccc2C(F)(F)F)cn1]

Step 1: Preparation of 4-bromo-1-trityl-1H-pyrazole

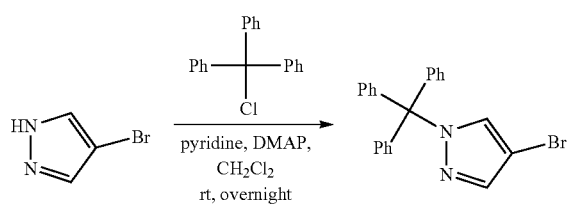 [SMILES: Brc1cn[nH]c1 ; ClC(c1ccccc1)(c1ccccc1)c1ccccc1 ; Brc1cnn(C(c2ccccc2)(c2ccccc2)c2ccccc2)c1]

A 250-mL round-bottom flask was charged with 4-bromo-1H-pyrazole (5.00 g, 34.2 mmol, 1.00 equiv), CH$_2$Cl$_2$ (50 mL), 4-dimethylaminopyridine (834 mg, 6.83 mmol, 0.20 equiv), pyridine (5.40 g, 68.4 mmol, 2.00 equiv) and (chloromethanetriyl)tribenzene (11.4 g, 40.9 mmol, 1.20 equiv). The reaction mixture was stirred overnight at room temperature and diluted with water (200 mL). The resulting solution was extracted with EtOAc (2×250 mL), and the organic layers were combined, dried over anhydrous sodium sulfate, filtered and concentrated under reduced pressure to provide 13.0 g (crude) of 4-bromo-1-trityl-1H-pyrazole as a white solid. LCMS (ESI, m/z): 389 [M+H]$^+$.

Step 2: Preparation of 4-(2-(trifluoromethyl)phenyl)-1-trityl-1H-pyrazole

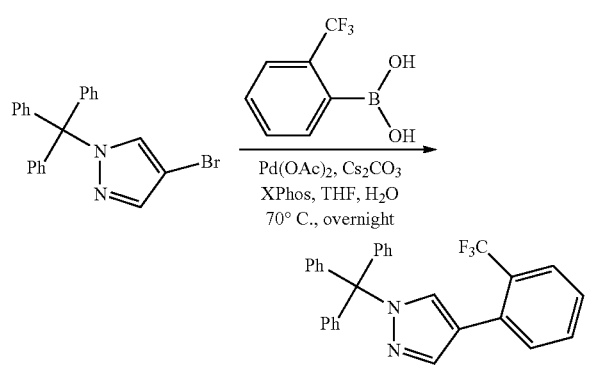

A 50-mL round-bottom flask was charged with 4-bromo-1-trityl-1H-pyrazole (2.00 g, 5.14 mmol, 1.00 equiv), (2-(trifluoromethyl)phenyl)boronic acid (1.17 g, 6.16 mmol, 1.20 equiv), dicyclohexyl(2',4',6'-triisopropyl-[1,1'-biphenyl]-2-yl)phosphine (147 mg, 0.310 mmol, 0.06 equiv), palladium acetate (35.0 mg, 0.155 mmol, 0.03 equiv), cesium carbonate (5.05 g, 15.5 mmol, 3.00 equiv), THF (20 mL) and water (4.0 mL) under nitrogen. The resulting solution was stirred overnight at 70° C. and diluted with water (150 mL). The mixture was extracted with EtOAc (2×200 mL), and the organic layers were combined, dried over anhydrous sodium sulfate, filtered and concentrated under reduced pressure. The residue was purified by flash chromatography on a silica gel column with EtOAc/petroleum ether (1/3) to provide 1.00 g (43% yield) of 4-(2-(trifluoromethyl)phenyl)-1-trityl-1H-pyrazole as a brown oil. LCMS (ESI, m/z): 455 [M+H]$^+$.

Step 3: Preparation of 4-(2-(trifluoromethyl)phenyl)-1H-pyrazole

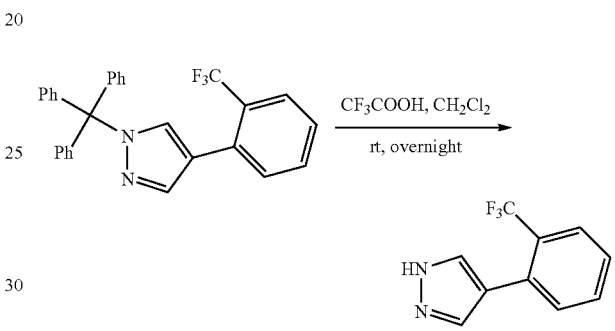

A 100-mL round-bottom flask was charged with 4-(2-(trifluoromethyl)phenyl)-1-trityl-1H-pyrazole (1.00 g, 2.20 mmol, 1.00 equiv), CH$_2$Cl$_2$ (15 mL) and trifluoroacetic acid (3.0 mL). The reaction mixture was stirred at room temperature and diluted with NaHCO$_3$ saturation solution (100 mL). The resulting solution was extracted with CH$_2$Cl$_2$ (2×150 mL), and the organic layers were combined, dried over anhydrous sodium sulfate, filtered and concentrated under reduced pressure. The residue was purified by flash chromatography on a silica gel column with EtOAc/petroleum ether (100/1) to provide 400 mg (86% yield) of 4-(2-(trifluoromethyl)phenyl)-1H-pyrazole as a brown oil. LCMS (ESI, m/z): 213 [M+H]$^+$.

Preparation of (4-(2-(pyrrolidin-1-yl)-4-(trifluoromethyl)benzyl)piperazin-1-yl)(4-(2-(trifluoromethyl)phenyl)-1H-pyrazol-1-yl)methanone The title compound was synthesized directly from 4-(2-(pyrrolidin-1-yl)-4-(trifluoromethyl)benzyl)piperazine-1-carbonyl chloride [prepared from 2-fluoro-4-(trifluoromethyl)benzaldehyde, pyrrolidine and tert-butyl piperazine-1-carboxylate according to the representative procedure of Example 99, Steps 1-4] and 4-(2-(trifluoromethyl)phenyl)-1H-pyrazole according to the representative procedure of Example 109 to provide (4-(2-(pyrrolidin-1-yl)-4-(trifluoromethyl)benzyl)piperazin-1-yl)(4-(2-(trifluoromethyl)phenyl)-1H-pyrazol-1-yl)methanone as a yellow oil. $^1$H NMR (300 MHz, Chloroform-d) δ 8.21 (s, 1H), 7.72-7.77 (m, 2H), 7.54-7.61 (m, 2H), 7.36-7.48 (m, 2H), 7.10-7.12 (m, 2H), 3.92 (br, 4H), 3.61 (s, 2H), 3.25 (br, 4H), 2.59 (br, 4H), 1.96 (br, 4H). LCMS (ESI, m/z): 552 [M+H]$^+$.

Example 116: (4-(2-(Pyrrolidin-1-yl)-4-(trifluoromethyl)benzyl)piperazin-1-yl)(4-(4-(trifluoromethyl)phenyl)-1H-pyrazol-1-yl)methanone

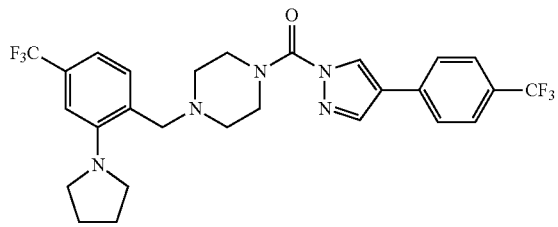 [SMILES: O=C(N1CCN(Cc2ccc(C(F)(F)F)cc2N2CCCC2)CC1)n1cc(-c2ccc(C(F)(F)F)cc2)cn1]

Preparation of 4-(4-(trifluoromethyl)phenyl)-1H-pyrazole 4-(4-(Trifluoromethyl)phenyl)-1H-pyrazole was synthesized from 4-bromo-1H-pyrazole and (4-(trifluoromethyl)phenyl)boronic acid according to the representative procedure of Example 115, Steps 1-3, providing a light yellow solid. LCMS (ESI, m/z): 213 [M+H]$^+$.

Preparation of (4-(2-(pyrrolidin-1-yl)-4-(trifluoromethyl)benzyl)piperazin-1-yl)(4-(4-(trifluoromethyl)phenyl)-1H-pyrazol-1-yl)methanone The title compound was synthesized directly from 4-(2-(pyrrolidin-1-yl)-4-(trifluoromethyl)benzyl)piperazine-1-carbonyl chloride [prepared from 2-fluoro-4-(trifluoromethyl)benzaldehyde, pyrrolidine and tert-butyl piperazine-1-carboxylate according to the representative procedure of Example 99, Steps 1-4] and 4-(4-(trifluoromethyl)phenyl)-1H-pyrazole according to the representative procedure of Example 109 to provide (4-(2-(pyrrolidin-1-yl)-4-(trifluoromethyl)benzyl)piperazin-1-yl)(4-(4-(trifluoromethyl)phenyl)-1H-pyrazol-1-yl)methanone as a light yellow solid. $^1$H NMR (300 MHz, Chloroform-d) δ 8.43 (s, 1H), 7.94 (s, 1H), 7.61-7.68 (m, 4H), 7.54-7.57 (m, 1H), 7.06-7.13 (m, 2H), 3.92 (br, 4H), 3.62 (s, 2H), 3.26 (br, 4H), 2.59 (br, 4H), 1.97 (br, 4H). LCMS (ESI, m/z): 552 [M+H]$^+$.

Example 117: (4-(Bis(4-chlorophenyl)methyl)piperazin-1-yl)(4-methyl-1H-pyrazol-1-yl)methanone

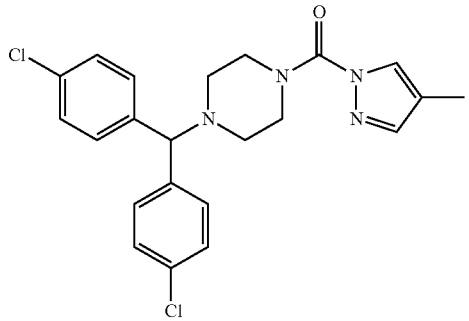 [SMILES: Cc1cnn(C(=O)N2CCN(C(c3ccc(Cl)cc3)c3ccc(Cl)cc3)CC2)c1]

The title compound was synthesized directly from 4-(bis(4-chlorophenyl)methyl)piperazine-1-carbonyl chloride (Example 66, Steps 2-5) and 4-methyl-1H-pyrazole according to the representative procedure of Example 66, Step 6 to provide (4-(bis(4-chlorophenyl)methyl)piperazin-1-yl)(4-methyl-1H-pyrazol-1-yl)methanone as a white solid. $^1$H NMR (300 MHz, Chloroform-d) δ 7.83 (s, 1H), 7.40 (s, 1H), 7.25-7.34 (m, 8H), 4.24 (s, 1H), 3.86 (br, 4H), 2.44-2.47 (m, 4H), 2.07 (s, 3H). LCMS (ESI, m/z): 492 [M+Na+CH$_3$CN]$^+$.

Example 118: (4-(Bis(4-chlorophenyl)methyl)piperazin-1-yl)(4-(trifluoromethyl)-1H-pyrazol-1-yl)methanone

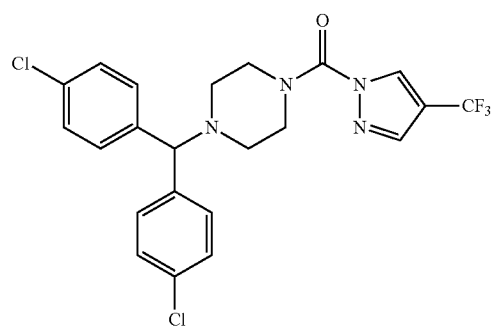 [SMILES: O=C(N1CCN(C(c2ccc(Cl)cc2)c2ccc(Cl)cc2)CC1)n1cc(C(F)(F)F)cn1]

The title compound was synthesized directly from 4-(bis(4-chlorophenyl)methyl)piperazine-1-carbonyl chloride (Example 66, Steps 2-5) and 4-(trifluoromethyl)-1H-pyrazole according to the representative procedure of Example 66, Step 6 to provide (4-(bis(4-chlorophenyl)methyl)piperazin-1-yl)(4-(trifluoromethyl)-1H-pyrazol-1-yl)methanone as a white solid. $^1$H NMR (300 MHz, Chloroform-d) δ 8.40 (s, 1H), 7.77 (s, 1H), 6.92-7.35 (m, 8H), 4.27 (s, 1H), 3.88 (br, 4H), 2.50 (br, 4H). LCMS (ESI, m/z): 483 [M+H]$^+$.

Example 119: (4-(Bis(4-chlorophenyl)methyl)piperazin-1-yl)(4-phenyl-1H-pyrazol-1-yl)methanone

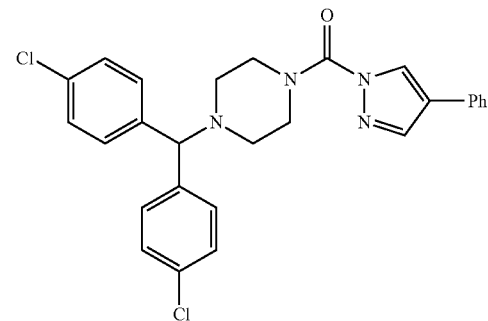 [SMILES: O=C(N1CCN(C(c2ccc(Cl)cc2)c2ccc(Cl)cc2)CC1)n1cc(-c2ccccc2)cn1]

The title compound was synthesized directly from 4-(bis(4-chlorophenyl)methyl)piperazine-1-carbonyl chloride (Example 66, Steps 2-5) and 4-phenyl-1H-pyrazole according to the representative procedure of Example 66, Step 6 to provide (4-(bis(4-chlorophenyl)methyl)piperazin-1-yl)(4-phenyl-1H-pyrazol-1-yl)methanone as a white solid. $^1$H NMR (300 MHz, Chloroform-d) δ 8.32 (s, 1H), 7.86 (s, 1H), 7.49-7.52 (m, 2H), 7.28-7.41 (m, 11H), 4.26 (s, 1H), 3.91 (br, 4H), 2.47-2.51 (m, 4H). LCMS (ESI, m/z): 554 [M+Na+CH$_3$CN]$^+$.

Example 120: (4-(Bis(4-chlorophenyl)methyl)piperazin-1-yl)(4-isopropyl-1H-pyrazol-1-yl)methanone

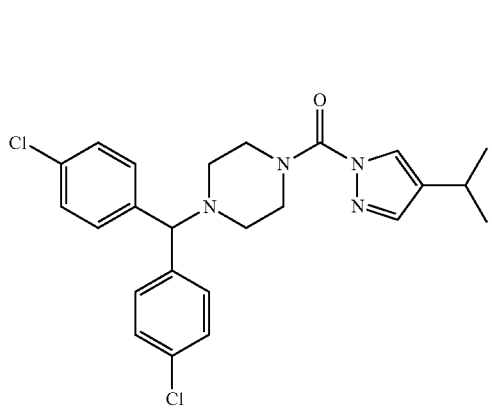 [SMILES: CC(C)c1cnn(C(=O)N2CCN(C(c3ccc(Cl)cc3)c3ccc(Cl)cc3)CC2)c1]

The title compound was synthesized directly from 4-(bis (4-chlorophenyl)methyl)piperazine-1-carbonyl chloride (Example 66, Steps 2-5) and 4-isopropyl-1H-pyrazole according to the representative procedure of Example 66, Step 6 to provide (4-(bis(4-chlorophenyl)methyl)piperazin-1-yl)(4-isopropyl-1H-pyrazol-1-yl)methanone as a white solid. $^1$H NMR (300 MHz, Chloroform-d) δ 7.85 (s, 1H), 7.46 (s, 1H), 7.27-7.35 (m, 8H), 4.25 (s, 1H), 3.88 (br, 4H), 2.79-2.88 (m, 1H), 2.45-2.48 (m, 4H), 1.22 (d, J=6.9 Hz, 6H). LCMS (ESI, m/z): 457 [M+H]$^+$.

Example 121: (4-(Bis(4-chlorophenyl)methyl)piperazin-1-yl)(4-fluoro-1H-pyrazol-1-yl)methanone

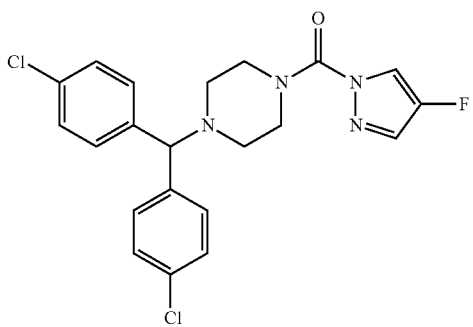 [SMILES: O=C(N1CCN(C(c2ccc(Cl)cc2)c2ccc(Cl)cc2)CC1)n1cc(F)cn1]

The title compound was synthesized directly from 4-(bis (4-chlorophenyl)methyl)piperazine-1-carbonyl chloride (Example 66, Steps 2-5) and 4-fluoro-1H-pyrazole according to the representative procedure of Example 66, Step 6 to provide (4-(bis(4-chlorophenyl)methyl)piperazin-1-yl)(4-fluoro-1H-pyrazol-1-yl)methanone as a white solid. $^1$H NMR (300 MHz, Chloroform-d) δ 7.92 (d, J=4.2 Hz, 1H), 7.46 (d, J=4.2 Hz, 1H), 7.26-7.34 (m, 8H), 4.24 (s, 1H), 3.85 (br, 4H), 2.46 (br, 4H). LCMS (ESI, m/z): 433 [M+H]$^+$.

Example 122: (4-(Bis(4-chlorophenyl)methyl)piperazin-1-yl)(4-(o-tolyl)-1H-pyrazol-1-yl)methanone

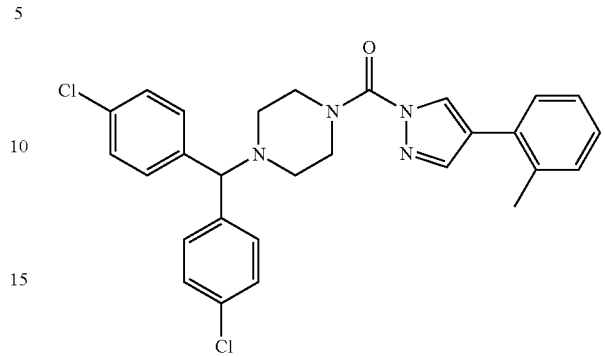

The title compound was synthesized directly from 4-(bis (4-chlorophenyl)methyl)piperazine-1-carbonyl chloride (Example 66, Steps 2-5) and 4-(o-tolyl)-1H-pyrazole (Example 114, Step 1) according to the representative procedure of Example 66, Step 6 to provide (4-(bis(4-chlorophenyl)methyl)piperazin-1-yl)(4-(o-tolyl)-1H-pyrazol-1-yl)methanone as a white solid. $^1$H NMR (300 MHz, Chloroform-d) δ 8.19 (s, 1H), 7.74 (s, 1H), 7.21-7.37 (m, 12H), 4.28 (s, 1H), 3.94 (br, 4H), 2.50-2.53 (m, 4H), 2.40 (s, 3H). LCMS (ESI, m/z): 505 [M+H]$^+$.

Example 123: (4-(Bis(4-chlorophenyl)methyl)piperazin-1-yl)(4-(2-(trifluoromethyl)phenyl)-1H-pyrazol-1-yl)methanone

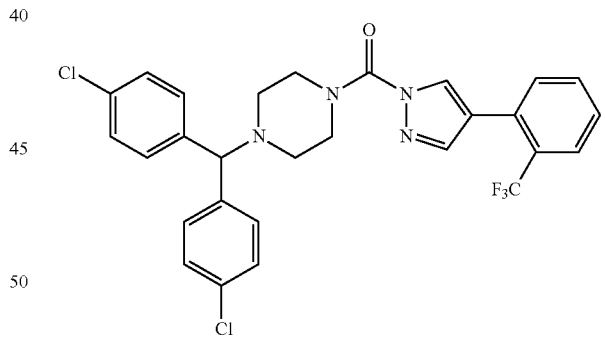

The title compound was synthesized directly from 4-(bis (4-chlorophenyl)methyl)piperazine-1-carbonyl chloride (Example 66, Steps 2-5) and 4-(2-(trifluoromethyl)phenyl)-1H-pyrazole (Example 115, Steps 1-3) according to the representative procedure of Example 66, Step 6 to provide (4-(bis(4-chlorophenyl)methyl)piperazin-1-yl)(4-(2-(trifluoromethyl)phenyl)-1H-pyrazol-1-yl)methanone as a white solid. $^1$H NMR (300 MHz, Chloroform-d) δ 8.19 (s, 1H), 7.75 (d, J=7.8 Hz, 1H), 7.69 (s, 1H), 7.53-7.61 (m, 1H), 7.29-7.47 (m, 10H), 4.27 (s, 1H), 3.92 (br, 4H), 2.49-2.52 (m, 4H). LCMS (ESI, m/z): 559 [M+H]$^+$.

Example 124: (4-(Bis(4-chlorophenyl)methyl)piperazin-1-yl)(4-(4-(trifluoromethyl)phenyl)-1H-pyrazol-1-yl)methanone

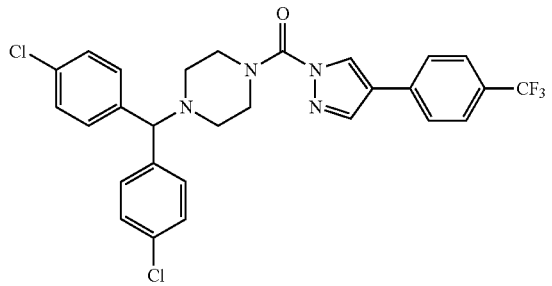 [SMILES: O=C(N1CCN(C(c2ccc(Cl)cc2)c2ccc(Cl)cc2)CC1)n1cc(-c2ccc(C(F)(F)F)cc2)cn1]

The title compound was synthesized directly from 4-(bis(4-chlorophenyl)methyl)piperazine-1-carbonyl chloride (Example 66, Steps 2-5) and 4-(4-(trifluoromethyl)phenyl)-1H-pyrazole [synthesized from 4-bromo-1H-pyrazole and (4-(trifluoromethyl)phenyl)boronic acid according to the representative procedure of Example 115, Steps 1-3] according to the representative procedure of Example 66, Step 6 to provide (4-(bis(4-chlorophenyl)methyl)piperazin-1-yl)(4-(4-(trifluoromethyl)phenyl)-1H-pyrazol-1-yl)methanone 1-[bis(4-chlorophenyl)methyl]-4-([4-[4-(trifluoromethyl)phenyl]-1H-pyrazol-1-yl]carbonyl)piperazine as a white solid. $^1$H NMR (300 MHz, Chloroform-d) δ 8.40 (s, 1H), 7.89 (s, 1H), 7.59-7.66 (m, 4H), 7.29-7.35 (m, 8H), 4.26 (s, 1H), 3.91 (br, 4H), 2.50 (br, 4H). LCMS (ESI, m/z): 559 [M+H]$^+$.

Example 125: (4-Chloro-1H-pyrazol-1-yl)(4-(2-(pyrrolidin-1-yl)-4-(trifluoromethyl)benzyl)piperazin-1-yl)methanone

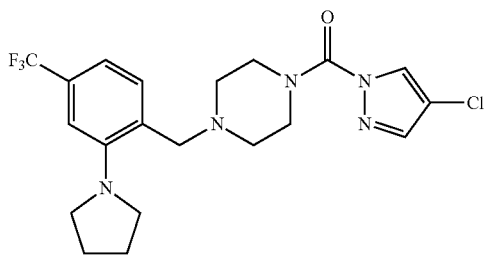

1-(2-(Pyrrolidin-1-yl)-4-(trifluoromethyl)benzyl)piperazine was synthesized from 2-fluoro-4-(trifluoromethyl)benzaldehyde, pyrrolidine and tert-butyl piperazine-1-carboxylate according to the representative procedure of Example 47, Steps 1-4, to provide (4-chloro-1H-pyrazol-1-yl)(4-(2-(pyrrolidin-1-yl)-4-(trifluoromethyl)benzyl)piperazin-1-yl)methanone (62.0 mg, 18% yield) as a white solid. $^1$H NMR (300 MHz, Chloroform-d) δ 8.07 (s, 1H), 7.51-7.54 (m, 2H), 7.09-7.11 (m, 2H), 3.84 (br, 4H), 3.59 (br, 2H), 3.24 (t, J=6.4 Hz, 4H), 2.54 (t, J=4.8 Hz, 4H), 1.90-1.99 (m, 4H). LCMS (ESI, m/z): 442 [M+H]$^+$.

Example 126: (4-Fluoro-1H-pyrazol-1-yl)(4-(2-(pyrrolidin-1-yl)-4-(trifluoromethyl)benzyl)piperazin-1-yl)methanone

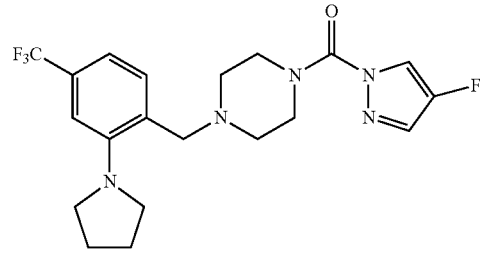 [SMILES: O=C(N1CCN(Cc2ccc(C(F)(F)F)cc2N2CCCC2)CC1)n1cc(F)cn1]

1-(2-(Pyrrolidin-1-yl)-4-(trifluoromethyl)benzyl)piperazine was synthesized from 2-fluoro-4-(trifluoromethyl)benzaldehyde, pyrrolidine and tert-butyl piperazine-1-carboxylate according to the representative procedure of Example 47, Steps 1-4, to provide (4-fluoro-1H-pyrazol-1-yl)(4-(2-(pyrrolidin-1-yl)-4-(trifluoromethyl)benzyl)piperazin-1-yl)methanone (109.3 mg, 48% yield) as a yellow solid. $^1$H NMR (300 MHz, Chloroform-d) δ 7.93-7.95 (m, 1H), 7.49-7.61 (m, 2H), 7.09 (br, 2H), 4.07 (br, 4H), 3.86 (s, 2H), 3.22-3.26 (m, 4H), 2.55 (br, 4H), 1.91-2.01 (m, 4H). LCMS (ESI, m/z): 426 [M+H]$^+$.

Example 127: 4-Chloro-N-ethyl-N-(2-methoxybenzyl)-1H-pyrazole-1-carboxamide

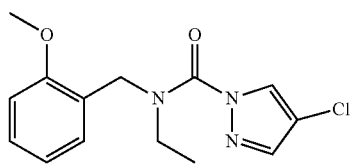 [SMILES: CCN(Cc1ccccc1OC)C(=O)n1cc(Cl)cn1]

Step 1: Preparation of ethyl(2-methoxybenzyl)carbamic chloride

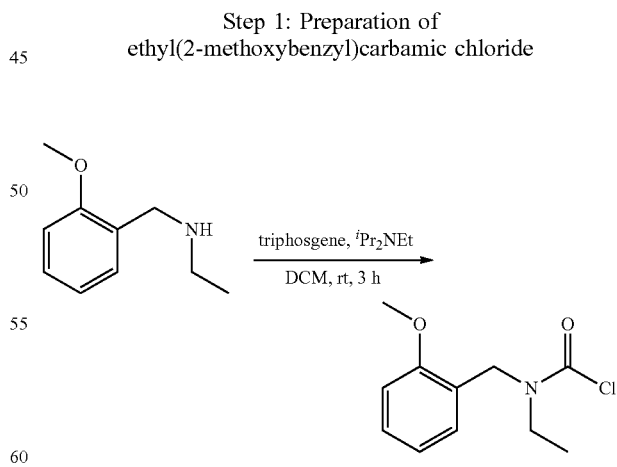

A 40-mL round-bottom flask was charged with triphosgene (252 mg, 0.850 mmol, 0.70 equiv), dichloromethane (10 mL). N,N-Diisopropylethylamine (469 mg, 3.63 mmol, 3.00 equiv) was added at 0° C. Ethyl[(2-methoxyphenyl)methyl]amine (200 mg, 1.21 mmol, 1.00 equiv) was added at 0° C. The resulting solution was stirred for 3 h at room temperature and concentrated under reduced pressure to provide ethyl(2-methoxybenzyl)carbamic chloride (270 mg, 98% yield) as yellow oil. LCMS (ESI, m/z): 228 [M+H]$^+$.

Step 2: Preparation of 4-chloro-N-ethyl-N-(2-methoxybenzyl)-1H-pyrazole-1-carboxamide

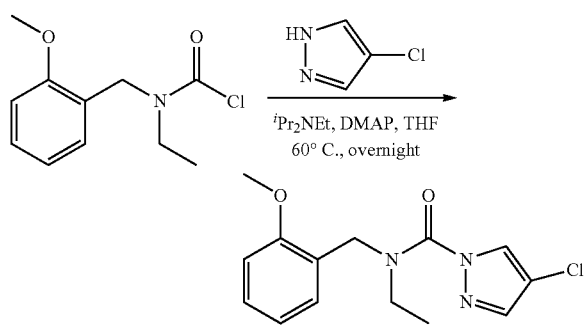

A 100-mL round-bottom flask was charged with ethyl(2-methoxybenzyl)carbamic chloride (270 mg, 1.19 mmol, 1.00 equiv), 4-chloro-1H-pyrazole (146 mg, 1.42 mmol, 1.20 equiv), 4-dimethylaminopyridine (14.4 mg, 0.120 mmol, 0.10 equiv), N,N-diisopropylethylamine (458 mg, 3.54 mmol, 3.00 equiv) and tetrahydrofuran (10 mL). The resulting solution was stirred overnight at 60° C. and concentrated under reduced pressure. The crude product (400 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm 5 μm; Mobile phase: Phase A: aqueous NH$_4$HCO$_3$ (0.05%); Phase B: CH$_3$CN; Detector, UV 220 & 254 nm. Purification yielded 4-chloro-N-ethyl-N-(2-methoxybenzyl)-1H-pyrazole-1-carboxamide (206.5 mg, 59% yield) as yellow oil. $^1$H NMR (400 MHz, Chloroform-d) δ 8.13 (s, 1H), 7.52 (s, 1H), 7.24-7.29 (m, 2H), 6.91-6.95 (m, 1H), 6.86-6.88 (m, 1H), 4.87 (br, 2H), 3.80 (s, 3H), 3.55 (br, 2H), 1.22 (t, J=7.0 Hz, 3H). LCMS (ESI, m/z): 294 [M+H]$^+$.

Example 128: 4-Chloro-N-ethyl-N-(3-methoxybenzyl)-1H-pyrazole-1-carboxamide

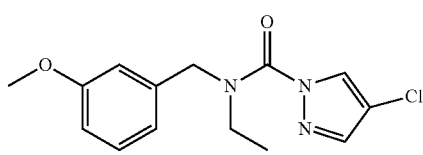 [SMILES: CCN(Cc1cccc(OC)c1)C(=O)n1cc(Cl)cn1]

The title compound was prepared from ethyl[(3-methoxyphenyl)methyl]amine (200 mg, 1.21 mmol) and 4-chloro-1H-pyrazole (146 mg, 1.42 mmol) according to the representative procedure of Example 127 to provide of 4-chloro-N-ethyl-N-(3-methoxybenzyl)-1H-pyrazole-1-carboxamide (177.9 mg, 51% yield) as yellow oil. $^1$H NMR (400 MHz, Chloroform-d) δ 8.15 (s, 1H), 7.53 (s, 1H), 7.24-7.28 (m, 1H), 6.89-6.91 (m, 2H), 6.82-6.84 (m, 1H), 4.82 (br, 2H), 3.80 (s, 3H), 3.57 (br, 2H), 1.24 (t, J=7.0 Hz, 3H). LCMS (ESI, m/z): 294 [M+H]$^+$.

Example 129: 4-Chloro-N-ethyl-N-(4-methoxybenzyl)-1H-pyrazole-1-carboxamide

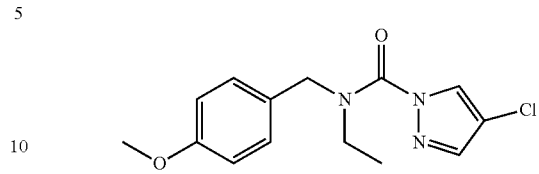

The title compound was prepared from ethyl[(4-methoxyphenyl)methyl]amine (200 mg, 1.21 mmol) and 4-chloro-1H-pyrazole (146 mg, 1.42 mmol) according to the representative procedure of Example 127 to provide 4-chloro-N-ethyl-N-(4-methoxybenzyl)-1H-pyrazole-1-carboxamide (60.7 mg, 17% yield) as yellow solid. $^1$H NMR (400 MHz, Chloroform-d) δ 8.14 (s, 1H), 7.54 (s, 1H), 7.28 (br, 2H), 6.86-6.89 (m, 2H), 4.76 (br, 2H), 3.80 (s, 3H), 3.54 (br, 2H), 1.22 (t, J=7.2 Hz, 3H). LCMS (ESI, m/z): 294 [M+H]$^+$.

Example 130: 4-Chloro-N-(2-chlorobenzyl)-N-ethyl-1H-pyrazole-1-carboxamide

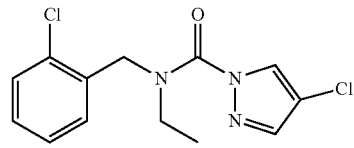

The title compound was prepared from [(2-chlorophenyl)methyl](ethyl)amine (200 mg, 1.18 mmol) and 4-chloro-1H-pyrazole (128 mg, 1.25 mmol) according to the representative procedure of Example 127 to provide 4-chloro-N-(2-chlorobenzyl)-N-ethyl-1H-pyrazole-1-carboxamide (203.9 mg, 66% yield) as yellow oil. $^1$H NMR (400 MHz, Chloroform-d) δ 8.16 (s, 1H), 7.52 (br, 1H), 7.35-7.39 (m, 2H), 7.21-7.29 (m, 2H), 4.96 (br, 2H), 3.60 (br, 2H), 1.27 (t, J=7.2 Hz, 3H). LCMS (ESI, m/z): 298 [M+H]$^+$.

Example 131: 4-chloro-N-(4-chlorobenzyl)-N-ethyl-1H-pyrazole-1-carboxamide

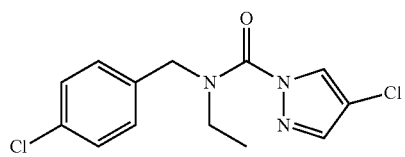 [SMILES: CCN(Cc1ccc(Cl)cc1)C(=O)n1cc(Cl)cn1]

The title compound was prepared from [(4-chlorophenyl)methyl](ethyl)amine (200 mg, 1.18 mmol) and 4-chloro-1H-pyrazole (128 mg, 1.25 mmol) according to the representative procedure of Example 127 to provide 4-chloro-N-(4-chlorobenzyl)-N-ethyl-1H-pyrazole-1-carboxamide (224.9 mg, 73% yield) as yellow oil. $^1$H NMR (400 MHz, Chloroform-d) δ 8.15 (s, 1H), 7.53 (s, 1H), 7.27-7.33 (m, 4H), 4.80 (br, 2H), 3.56 (br, 2H), 1.24 (t, J=7.0 Hz, 3H). LCMS (ESI, m/z): 298 [M+H]$^+$.

Example 132: 4-Chloro-N-(2-methylbenzyl)-N-ethyl-1H-pyrazole-1-carboxamide

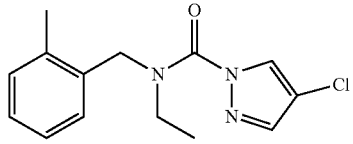 [SMILES: CCN(Cc1ccccc1C)C(=O)n1cc(Cl)cn1]

The title compound was prepared from ethyl[(2-methylphenyl)methyl]amine (200 mg, 1.34 mmol) and 4-chloro-1H-pyrazole (163 mg, 1.59 mmol) according to the representative procedure of Example 127 to provide 4-chloro-N-ethyl-N-(2-methylbenzyl)-1H-pyrazole-1-carboxamide (190.9 mg, 52% yield) as yellow oil. $^1$H NMR (300 MHz, Chloroform-d) δ 8.15 (s, 1H), 7.52 (s, 1H), 7.17-7.26 (m, 4H), 4.85 (br, 2H), 3.60 (br, 2H), 2.29 (s, 3H), 1.22 (t, J=7.0 Hz, 3H). LCMS (ESI, m/z): 278 [M+H]$^+$.

Example 133: 4-Chloro-N-ethyl-N-(4-methylbenzyl)-1H-pyrazole-1-carboxamide

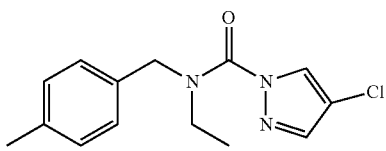 [SMILES: CCN(Cc1ccc(C)cc1)C(=O)n1cc(Cl)cn1]

The title compound was prepared from ethyl[(4-methylphenyl)methyl]amine (200 mg, 1.34 mmol) and 4-chloro-1H-pyrazole (163 mg, 1.59 mmol) according to the representative procedure of Example 127 to provide 4-chloro-N-ethyl-N-(4-methylbenzyl)-1H-pyrazole-1-carboxamide (193.9 mg, 53% yield) as yellow oil. $^1$H NMR (400 MHz, Chloroform-d) δ 8.14 (s, 1H), 7.53 (s, 1H), 7.21-7.23 (m, 2H), 7.14-7.16 (m, 2H), 4.80 (br, 2H), 3.55 (br, 2H), 2.34 (s, 3H), 1.22 (t, J=7.2 Hz, 3H). LCMS (ESI, m/z): 278 [M+H]$^+$.

Example 134: 4-Chloro-N-(3-chlorobenzyl)-N-ethyl-1H-pyrazole-1-carboxamide

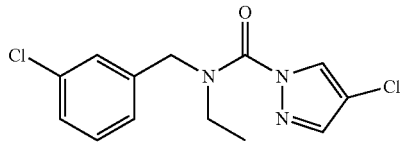 [SMILES: CCN(Cc1cccc(Cl)c1)C(=O)n1cc(Cl)cn1]

The title compound was prepared from [(3-chlorophenyl)methyl](ethyl)amine (100 mg, 0.590 mmol) and 4-chloro-1H-pyrazole (69.0 mg, 0.670 mmol) according to the representative procedure of Example 127 to provide 4-chloro-N-(3-chlorobenzyl)-N-ethyl-1H-pyrazole-1-carboxamide (110.6 mg, 66% yield) as yellow oil. $^1$H NMR (300 MHz, Chloroform-d) δ 8.16 (s, 1H), 7.53 (s, 1H), 7.33 (br, 2H), 7.21-7.31 (m, 2H), 4.82 (br, 2H), 3.57-3.58 (m, 2H), 1.25 (t, J=7.0 Hz, 3H). LCMS (ESI, m/z): 298 [M+H]$^+$.

Example 135: 4-Chloro-N-ethyl-N-(3-methylbenzyl)-1H-pyrazole-1-carboxamide

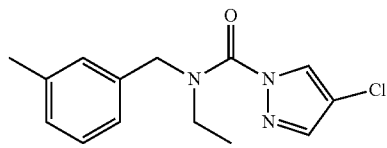 [SMILES: CCN(Cc1cccc(C)c1)C(=O)n1cc(Cl)cn1]

The title compound was prepared from ethyl[(3-methylphenyl)methyl]amine (100 mg, 0.67 mmol) and 4-chloro-1H-pyrazole (82.0 mg, 0.800 mmol) according to the representative procedure of Example 127 to provide 4-chloro-N-ethyl-N-(3-methylbenzyl)-1H-pyrazole-1-carboxamide (94.0 mg, 51% yield) as yellow oil. $^1$H NMR (300 MHz, Chloroform-d) δ 8.15 (s, 1H), 7.53 (s, 1H), 7.21-7.23 (m, 1H), 7.09-7.12 (m, 3H), 4.81 (br, 2H), 3.57 (br, 2H), 2.35 (s, 3H), 1.23 (t, J=7.0 Hz, 3H). LCMS (ESI, m/z): 319 [M+CH$_3$CN]$^+$.

Example 136: (4-Phenyl-1H-pyrazol-1-yl)(piperidin-1-yl)methanone

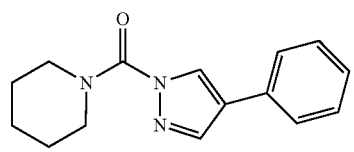 [SMILES: O=C(N1CCCCC1)n1cc(-c2ccccc2)cn1]

Step 1: Preparation of piperidine-1-carbonyl chloride

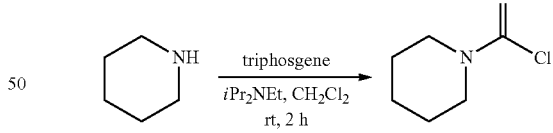

A 50-mL round-bottom flask was charged with triphosgene (350 mg, 1.18 mmol, 0.50 equiv), dichloromethane (15 mL). Piperidine (200 mg, 2.35 mmol, 1.00 equiv) and N,N-diisopropylethylamine (606 mg, 4.69 mmol, 2.00 equiv) were added at 0° C. The resulting solution was stirred for 2 h at room temperature and quenched with water (20 mL). The mixture was extracted with dichloromethane (3×30 mL) and the organic layers were combined, washed with brine (3×50 mL), dried over anhydrous sodium sulfate, filtered and concentrated under reduced pressure to provide piperidine-1-carbonyl chloride (340 mg, 98% yield) as yellow oil. LCMS (ESI, m/z): 148 [M+H]$^+$.

Step 2: Preparation of (4-phenyl-1H-pyrazol-1-yl)(piperidin-1-yl)methanone

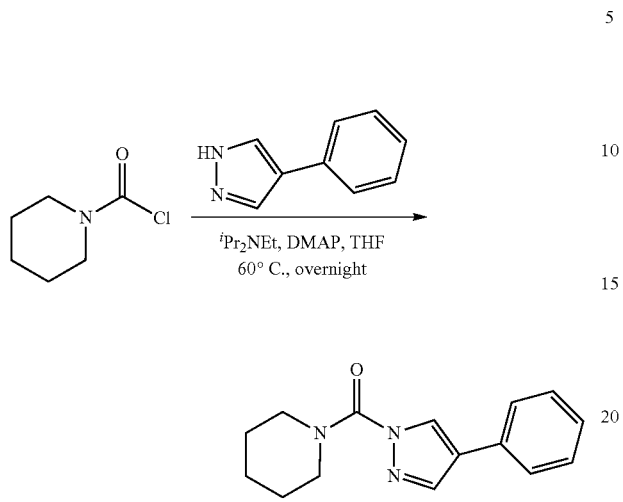

A 40-mL round-bottom flask was charged with piperidine-1-carbonyl chloride (350 mg, 2.37 mmol, 1.00 equiv), 4-phenyl-1H-pyrazole (412 mg, 2.86 mmol, 1.20 equiv), N,N-diisopropylethylamine (921 mg, 7.13 mmol, 3.00 equiv), 4-dimethylaminopyridine (29.0 mg, 0.240 mmol, 0.10 equiv), tetrahydrofuran (5 mL). The resulting solution was stirred overnight at 60° C. and concentrated under reduced pressure. The crude product (990 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: X-bridge Prep C$_{18}$, 19*150 mm 5 μm; Mobile phase: Phase A: aqueous NH$_4$HCO$_3$ (0.05%); Phase B: CH$_3$CN; Detector, UV 220 & 254 nm. Purification yielded (4-phenyl-1H-pyrazol-1-yl)(piperidin-1-yl)methanone (166.1 mg, 27% yield) as an off-white solid. $^1$H NMR (300 MHz, Chloroform-d) δ 8.32 (s, 1H), 7.91 (s, 1H), 7.51-7.54 (m, 2H), 7.36-7.41 (m, 2H), 7.25-7.30 (m, 1H), 3.78 (br, 4H), 1.71 (s, 6H). LCMS (ESI, m/z): 256 [M+H]$^+$.

Example 137: (4-Chloro-1H-pyrazol-1-yl)(4-((3-methylbiphenyl-4-yl)methyl)piperazin-1-yl)methanone

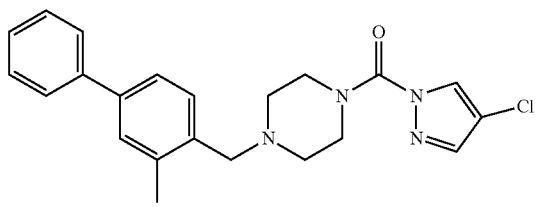 [SMILES: Cc1cc(-c2ccccc2)ccc1CN1CCN(C(=O)n2cc(Cl)cn2)CC1]

Step 1: Preparation of 3-methylbiphenyl-4-carbaldehyde

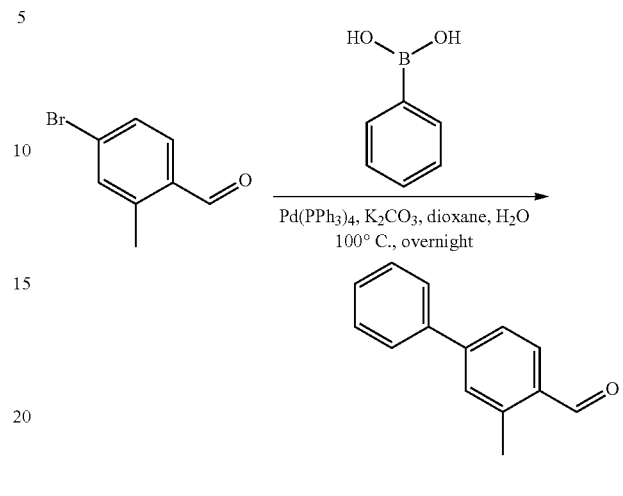

A 1000-mL round-bottom flask was charged with 4-bromo-2-methylbenzaldehyde (10.0 g, 50.2 mmol, 1.00 equiv), phenylboronic acid (12.2 g, 100 mmol, 2.00 equiv), tetrakis(triphenylphosphine)palladium (5.77 g, 4.99 mmol, 0.10 equiv), potassium carbonate (20.7 g, 150 mmol, 3.00 equiv), dioxane (320 mL), H$_2$O (40 mL) under nitrogen. The resulting solution was stirred overnight at 100° C. and quenched with H$_2$O (100 mL). The mixture was extracted with dichloromethane (3×200 mL) and the organic layers were combined, washed with brine (3×100 mL), dried over anhydrous sodium sulfate, filtered and concentrated under reduced pressure. The residue was chromatographed on a silica gel column with ethyl acetate/petroleum ether (1/9) to provide 3-methylbiphenyl-4-carbaldehyde (8.01 g, 81% yield) as a light yellow solid. LCMS (ESI, m/z): 197 [M+H]$^+$.

Step 2: Preparation of tert-butyl 4-((3-methylbiphenyl-4-yl)methyl)piperazine-1-carboxylate

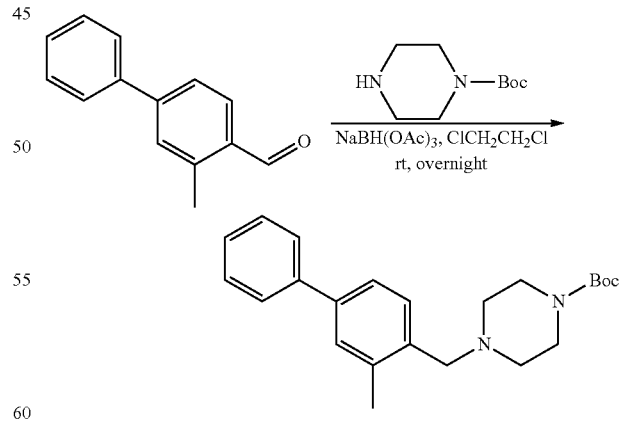

A 1000-mL round-bottom flask was charged with 3-methylbiphenyl-4-carbaldehyde (8.01 g, 40.8 mmol, 1.00 equiv), tert-butyl piperazine-1-carboxylate (8.35 g, 44.9 mmol, 1.10 equiv), 1,2-dichloroethane (200 mL). The resulting solution was stirred for 2 h at room temperature. Sodium triacetoxyborohydride (25.9 g, 122 mmol, 3.00 equiv) was added. The resulting solution was stirred overnight at room temperature and quenched with H₂O (100 mL). The mixture was extracted with dichloromethane (3×200 mL) and the organic layers were combined, washed with brine (3×100 mL), dried over anhydrous sodium sulfate, filtered and concentrated under reduced pressure. The residue was chromatographed on a silica gel column with ethyl acetate/petroleum ether (1/4) to provide tert-butyl 4-((3-methylbiphenyl-4-yl)methyl)piperazine-1-carboxylate (9.20 g, 62% yield) as a white solid. LCMS (ESI, m/z): 367 [M+H]⁺.

Step 3: Preparation of 1-((3-methylbiphenyl-4-yl)methyl)piperazine

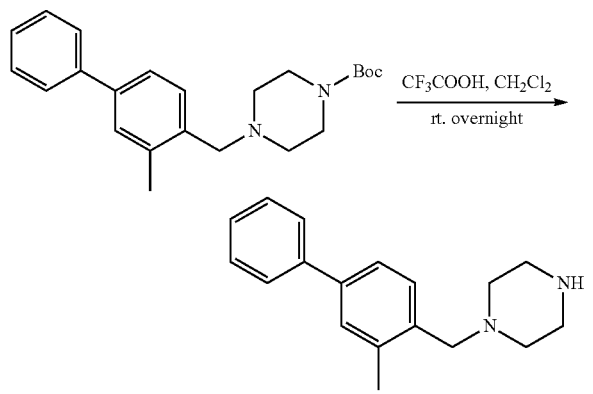

A 500-mL round-bottom flask was charged with tert-butyl 4-((3-methylbiphenyl-4-yl)methyl)piperazine-1-carboxylate (9.20 g, 25.1 mmol, 1.00 equiv), trifluoroacetic acid (15 mL), dichloromethane (100 mL). The resulting solution was stirred overnight at room temperature and quenched with H₂O (50 mL). The pH value of the solution was adjusted to 9 with sodium hydroxide solution (1 M). The mixture was extracted with dichloromethane (3×100 mL) and the organic layers were combined, washed with brine (3×100 mL), dried over anhydrous sodium sulfate, filtered and concentrated under reduced pressure to provide 1-((3-methylbiphenyl-4-yl)methyl)piperazine (4.60 g, 69% yield) as a white solid. LCMS (ESI, m/z): 267 [M+H]⁺.

Step 4: Preparation of 4-((3-methylbiphenyl-4-yl)methyl)piperazine-1-carbonyl chloride

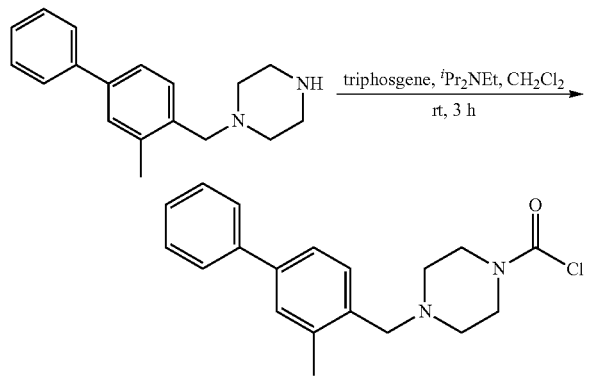

A 250-mL round-bottom flask was charged with triphosgene (1.19 g, 4.01 mmol, 0.40 equiv), dichloromethane (50 mL). 1-((3-Methylbiphenyl-4-yl)methyl)piperazine (2.67 g, 10.0 mmol, 1.00 equiv) was added at 0° C. N,N-Diisopropylethylamine (3.87 g, 30.0 mmol, 3.00 equiv) was added at 0° C. The resulting solution was stirred for 3 h at room temperature and quenched with H₂O (30 mL). The mixture was extracted with dichloromethane (3×100 mL) and the organic layers were combined, washed with brine (3×50 mL), dried over anhydrous sodium sulfate, filtered and concentrated under reduced pressure to provide 4-((3-methylbiphenyl-4-yl)methyl)piperazine-1-carbonyl chloride (3.29 g, 99% yield) as a yellow oil. LCMS (ESI, m/z): 329 [M+H]⁺.

Step 5: Preparation of (4-chloro-1H-pyrazol-1-yl)(4-((3-methylbiphenyl-4-yl)methyl)piperazin-1-yl)methanone

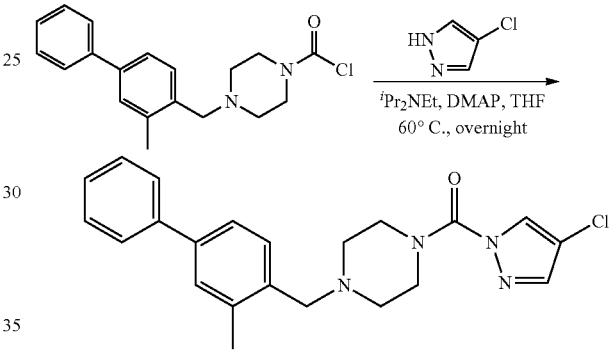

A 100-mL round-bottom flask was charged with 4-((3-methylbiphenyl-4-yl)methyl)piperazine-1-carbonyl chloride (329 mg, 1.00 mmol, 1.00 equiv), 4-chloro-1H-pyrazole (156 mg, 1.50 mmol, 1.50 equiv), N,N-diisopropylethylamine (387 mg, 3.00 mmol, 3.00 equiv), 4-dimethylaminopyridine (12.3 g, 0.10 mmol, 0.10 equiv), tetrahydrofuran (5 mL). The resulting solution was stirred overnight at 60° C. and quenched with H₂O (30 mL). The mixture was extracted with dichloromethane (3×30 mL) and the organic layers were combined, washed with brine (3×30 mL), dried over anhydrous sodium sulfate, filtered and concentrated under reduced pressure. The crude product (172 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C₁₈, 19*150 mm 5 μm; Mobile phase: Phase A: aqueous NH₄HCO₃ (0.05%); Phase B: CH₃CN; Detector, UV 220 & 254 nm. Purification yielded (4-chloro-1H-pyrazol-1-yl)(4-((3-methylbiphenyl-4-yl)methyl)piperazin-1-yl)methanone (99.0 mg, 25% yield) as a white solid. ¹H NMR (400 MHz, Chloroform-d) δ 8.07 (s, 1H), 7.54-7.59 (m, 3H), 7.30-7.45 (m, 6H), 3.84 (br, 4H), 3.54 (br, 2H), 2.57 (br, 4H), 2.44 (s, 3H). LCMS (ESI, m/z): 395 [M+H]⁺

Example 138: 1-(4-((3-methylbiphenyl-4-yl)methyl)piperazine-1-carbonyl)-1H-pyrazole-4-carbonitrile

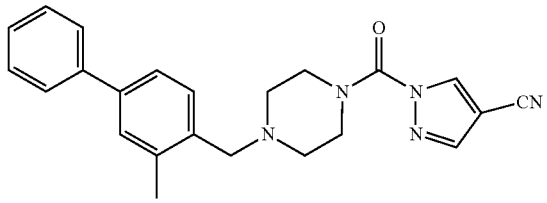 [SMILES: Cc1cc(-c2ccccc2)ccc1CN1CCN(C(=O)n2cc(C#N)cn2)CC1]

The title compound was synthesized directly from 4-((3-methylbiphenyl-4-yl)methyl)piperazine-1-carbonyl chloride (329 mg, 1.00 mmol) and 1H-pyrazole-4-carbonitrile (156 mg, 1.50 mmol) according to the representative procedure of Example 137, Steps 1-5 to provide 1-(4-((3-methylbiphenyl-4-yl)methyl)piperazine-1-carbonyl)-1H-pyrazole-4-carbonitrile (56.2 mg, 15% yield) as a white solid. $^1$H NMR (300 MHz, Chloroform-d) δ 8.53 (s, 1H), 7.87 (s, 1H), 7.57-7.61 (m, 2H), 7.32-7.45 (m, 6H), 3.84 (br, 4H), 3.55 (br, 2H), 2.59 (br, 4H), 2.44 (s, 3H). LCMS (ESI, m/z): 386 [M+H]$^+$.

Example 139: (4-chloro-1H-pyrazol-1-yl)(4-((3-chlorobiphenyl-4-yl)methyl)piperazin-1-yl)methanone

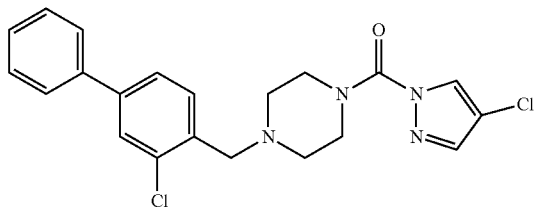 [SMILES: O=C(N1CCN(Cc2ccc(-c3ccccc3)cc2Cl)CC1)n1cc(Cl)cn1]

The title compound was synthesized from 4-bromo-2-chlorobenzaldehyde, phenylboronic acid, tert-butyl piperazine-1-carboxylate, and 4-chloro-1H-pyrazole according to the representative procedure of Example 137, Steps 1-5 to provide (4-chloro-1H-pyrazol-1-yl)(4-((3-chlorobiphenyl-4-yl)methyl)piperazin-1-yl)methanone (35.4 mg, 15% yield) as a yellow oil. $^1$H NMR (300 MHz, Chloroform-d) δ 8.08 (s, 1H), 7.52-7.60 (m, 4H), 7.40-7.52 (m, 4H), 7.32-7.38 (m, 1H), 3.88 (br, 4H), 3.71 (s, 2H), 2.63-2.66 (m, 4H). LCMS (ESI, m/z): 415 [M+H]$^+$.

Example 140: 1-(4-((3-chlorobiphenyl-4-yl)methyl)piperazine-1-carbonyl)-1H-pyrazole-4-carbonitrile

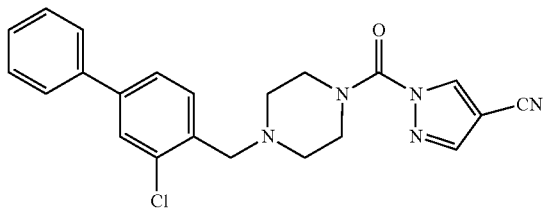 [SMILES: N#Cc1cnn(C(=O)N2CCN(Cc3ccc(-c4ccccc4)cc3Cl)CC2)c1]

The title compound was synthesized from 4-bromo-2-chlorobenzaldehyde, phenylboronic acid, tert-butyl piperazine-1-carboxylate, and 1H-pyrazole-4-carbonitrile according to the representative procedure of Example 137, Steps 1-5 to provide -([4-[(2-chloro-4-phenylphenyl)methyl]piperazin-1-yl]carbonyl)-1H-pyrazole-4-carbonitrile (62.6 mg, 35% yield) as a white solid. $^1$H NMR (300 MHz, Chloroform-d) δ 8.53 (s, 1H), 7.88 (s, 1H), 7.56-7.62 (m, 3H), 7.38-7.48 (m, 5H), 3.88 (br, 4H), 3.72 (br, 2H), 2.67 (br, 4H). LCMS (ESI, m/z): 406 [M+H]$^+$.

Example 141: (4-Chloro-1H-pyrazol-1-yl)(4-((3-methoxybiphenyl-4-yl)methyl)piperazin-1-yl)methanone

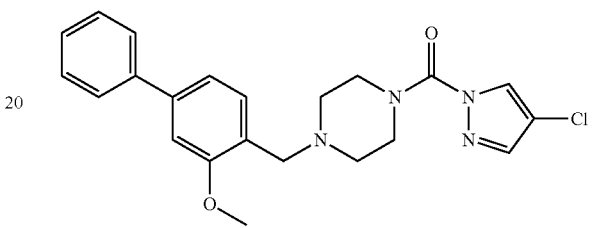

The title compound was synthesized from 4-bromo-2-methoxybenzaldehyde, phenylboronic acid, tert-butyl piperazine-1-carboxylate, and 4-chloro-1H-pyrazole according to the representative procedure of Example 137, Steps 1-5 to provide (4-chloro-1H-pyrazol-1-yl)(4-((3-methoxybiphenyl-4-yl)methyl)piperazin-1-yl)methanone (65.2 mg, 27% yield) as light yellow oil. $^1$H NMR (300 MHz, Chloroform-d) δ 8.06 (br, 1H), 7.57-7.60 (m, 2H), 7.53 (s, 1H), 7.31-7.46 (m, 4H), 7.14-7.18 (m, 1H), 7.08 (br, 1H), 3.88 (br, 7H), 3.65 (br, 2H), 2.60-2.64 (m, 4H). LCMS (ESI, m/z): 411 [M+H]$^+$.

Example 142: (4-((3-Methylbiphenyl-4-yl)methyl)piperazin-1-yl)(4-(trifluoromethyl)-1H-pyrazol-1-yl)methanone

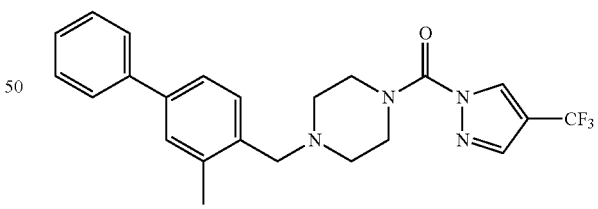

The title compound was synthesized from 4-bromo-2-methylbenzaldehyde, phenylboronic acid, tert-butyl piperazine-1-carboxylate, and 4-(trifluoromethyl)-1H-pyrazole according to the representative procedure of Example 137, Steps 1-5 to provide (4-((3-methylbiphenyl-4-yl)methyl)piperazin-1-yl)(4-(trifluoromethyl)-1H-pyrazol-1-yl)methanone (65.1 mg, 50% yield) as a white semi-solid. $^1$H NMR (300 MHz, Chloroform-d) δ 8.40 (s, 1H), 7.80 (s, 1H), 7.57-7.60 (m, 2H), 7.31-7.45 (m, 6H), 3.86 (br, 4H), 3.56 (br, 2H), 2.60 (br, 4H), 2.45 (s, 3H). LCMS (ESI, m/z): 429 [M+H]$^+$.

Example 143: (4-((3-Chlorobiphenyl-4-yl)methyl)piperazin-1-yl)(4-(trifluoromethyl)-1H-pyrazol-1-yl)methanone

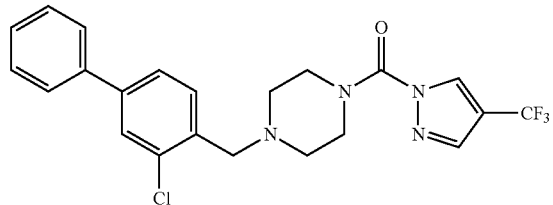 [SMILES: O=C(N1CCN(Cc2ccc(-c3ccccc3)cc2Cl)CC1)n1cc(C(F)(F)F)cn1]

The title compound was synthesized from 4-bromo-2-chlorobenzaldehyde, phenylboronic acid, tert-butyl piperazine-1-carboxylate, and 4-(trifluoromethyl)-1H-pyrazole according to the representative procedure of Example 137, Steps 1-5 to provide (4-((3-chlorobiphenyl-4-yl)methyl)piperazin-1-yl)(4-(trifluoromethyl)-1H-pyrazol-1-yl)methanone (65.4 mg, 33% yield) as a white solid. $^1$H NMR (400 MHz, Chloroform-d) δ 8.43 (s, 1H), 7.82 (s, 1H), 7.58-7.63 (m, 3H), 7.42-7.58 (m, 4H), 7.28-7.42 (m, 1H), 3.91 (br, 4H), 3.74 (s, 2H), 2.69 (br, 4H). LCMS (ESI, m/z): 449 [M+H]$^+$.

Example 144: (4-((3-Methoxybiphenyl-4-yl)methyl)piperazin-1-yl)(4-(trifluoromethyl)-1H-pyrazol-1-yl)methanone

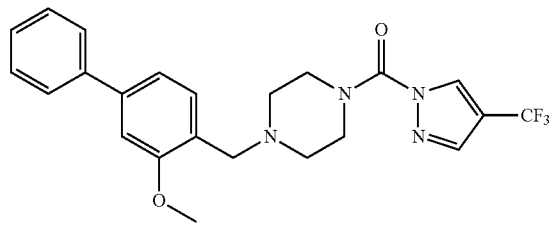 [SMILES: COc1cc(-c2ccccc2)ccc1CN1CCN(C(=O)n2cc(C(F)(F)F)cn2)CC1]

The title compound was synthesized from 4-bromo-2-methoxybenzaldehyde, phenylboronic acid, tert-butyl piperazine-1-carboxylate, and 4-(trifluoromethyl)-1H-pyrazole according to the representative procedure of Example 137, Steps 1-5 to provide (4-((3-methoxybiphenyl-4-yl)methyl)piperazin-1-yl)(4-(trifluoromethyl)-1H-pyrazol-1-yl)methanone (59.2 mg, 14% yield) as a white solid. $^1$H NMR (400 MHz, Chloroform-d) δ 8.42 (s, 1H), 7.82 (s, 1H), 7.60-7.62 (m, 2H), 7.35-7.48 (m, 4H), 7.18-7.20 (m, 1H), 7.10-7.11 (br, 1H), 3.91 (br, 7H), 3.69-3.73 (m, 2H), 2.67 (br, 4H). LCMS (ESI, m/z): 445 [M+H]$^+$.

Example 145: 1-(4-((3-Methoxybiphenyl-4-yl)methyl)piperazine-1-carbonyl)-1H-pyrazole-4-carbonitrile

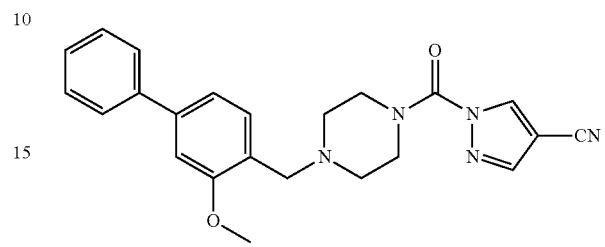

The title compound was synthesized from 4-bromo-2-methoxybenzaldehyde, phenylboronic acid, tert-butyl piperazine-1-carboxylate, and 1H-pyrazole-4-carbonitrile according to the representative procedure of Example 137, Steps 1-5 to provide 1-(4-((3-methoxybiphenyl-4-yl)methyl)piperazine-1-carbonyl)-1H-pyrazole-4-carbonitrile (21.7 mg, 5% yield) as a white solid. $^1$H NMR (400 MHz, Chloroform-d) δ 8.54 (s, 1H), 7.89 (s, 1H), 7.60-7.62 (m, 2H), 7.44-7.48 (m, 2H), 7.36-7.41 (m, 2H), 7.28 (s, 1H), 7.10 (br, 1H), 3.91 (br, 7H), 3.73 (br, 2H), 2.66 (br, 4H). LCMS (ESI, m/z): 402 [M+H]$^+$.

Example 146: 1-(4-((3-(Benzyloxy)biphenyl-4-yl)methyl)piperazine-1-carbonyl)-1H-pyrazole-4-carbonitrile

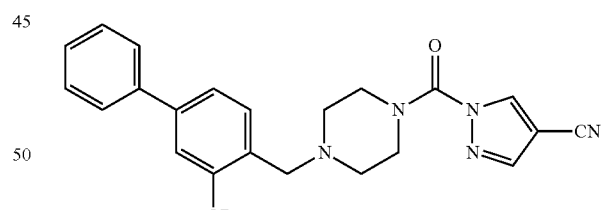

The title compound was synthesized from 2-(benzyloxy)-4-bromobenzaldehyde, phenylboronic acid, tert-butyl piperazine-1-carboxylate, and 1H-pyrazole-4-carbonitrile according to the representative procedure of Example 137, Steps 1-5 to provide 1-(4-((3-(benzyloxy)biphenyl-4-yl)methyl)piperazine-1-carbonyl)-1H-pyrazole-4-carbonitrile (133.9 mg, 51% yield) as a white solid. $^1$H NMR (300 MHz, Chloroform-d) δ 8.57 (s, 1H), 7.86 (s, 1H), 7.54-7.60 (m, 2H), 7.40-7.46 (m, 6H), 7.34-7.37 (m, 3H), 7.15-7.20 (m, 2H), 5.16 (s, 2H), 3.86 (br, 4H), 3.60 (br, 2H), 2.73 (br, 4H). LCMS (ESI, m/z): 478 [M+H]$^+$.

Example 147: (4-((3-(Benzyloxy)biphenyl-4-yl)methyl)piperazin-1-yl)(4-(trifluoromethyl)-1H-pyrazol-1-yl)methanone

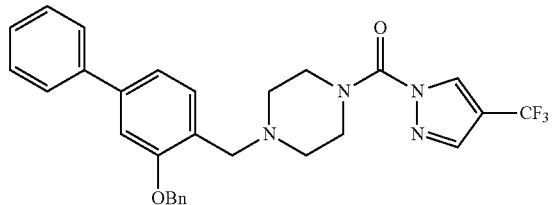 [SMILES: O=C(N1CCN(Cc2ccc(-c3ccccc3)cc2OCc2ccccc2)CC1)n1cc(C(F)(F)F)cn1]

The title compound was synthesized from 2-(benzyloxy)-4-bromobenzaldehyde, phenylboronic acid, tert-butyl piperazine-1-carboxylate, and 4-(trifluoromethyl)-1H-pyrazole according to the representative procedure of Example 137, Steps 1-5 to provide (4-((3-(benzyloxy)biphenyl-4-yl)methyl)piperazin-1-yl)(4-(trifluoromethyl)-1H-pyrazol-1-yl)methanone (69.1 mg, 24% yield) as a white solid. $^1$H NMR (300 MHz, Chloroform-d) δ 8.39 (s, 1H), 7.79 (s, 1H), 7.54-7.57 (m, 2H), 7.40-7.47 (m, 6H), 7.32-7.37 (m, 3H), 7.17-7.20 (m, 2H), 5.16 (s, 2H), 3.87 (br, 4H), 3.72 (br, 2H), 2.65 (br, 4H). LCMS (ESI, m/z): 521 [M+H]$^+$.

Example 148: (4-((3-(Benzyloxy)biphenyl-4-yl)methyl)piperazin-1-yl)(4-chloro-1H-pyrazol-1-yl)methanone

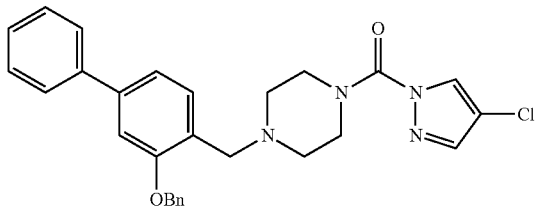 [SMILES: O=C(N1CCN(Cc2ccc(-c3ccccc3)cc2OCc2ccccc2)CC1)n1cc(Cl)cn1]

The title compound was synthesized from 2-(benzyloxy)-4-bromobenzaldehyde, phenylboronic acid, tert-butyl piperazine-1-carboxylate, and 4-chloro-1H-pyrazole according to the representative procedure of Example 137, Steps 1-5 to provide (4-((3-(benzyloxy)biphenyl-4-yl)methyl)piperazin-1-yl)(4-chloro-1H-pyrazol-1-yl)methanone (74.5 mg, 28% yield) as a white solid. $^1$H NMR (300 MHz, Chloroform-d) δ 8.06 (s, 1H), 7.53-7.57 (m, 3H), 7.37-7.45 (m, 6H), 7.32-7.35 (m, 3H), 7.16-7.20 (m, 2H), 5.16 (s, 2H), 3.86 (br, 4H), 3.71 (br, 2H), 2.27 (br, 4H). LCMS (ESI, m/z): 487 [M+H]$^+$.

Example 149: 1-(4-(4-(Trifluoromethyl)-1H-pyrazole-1-carbonyl)piperazin-1-yl)ethanone

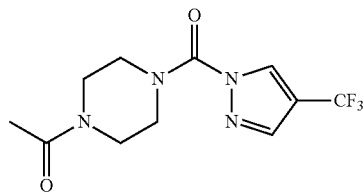

Step 1: Preparation of 4-acetylpiperazine-1-carbonyl chloride

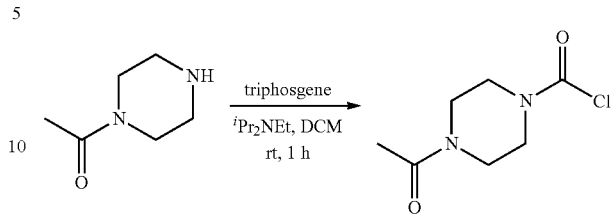

A 50-mL round-bottom flask was charged with triphosgene (174 mg, 0.590 mmol, 0.50 equiv), dichloromethane (5 mL) and 1-(piperazin-1-yl)ethan-1-one (150 mg, 1.17 mmol, 1.00 equiv). N,N-Diisopropylethylamine (454 mg, 3.51 mmol, 3.00 equiv) was added dropwise at 0° C. The resulting solution was stirred for 1 h at room temperature and quenched by water (40 mL). The resulting solution was extracted with dichloromethane (3×80 mL) and the organic layers were combined, washed with water (3×20 mL), dried over anhydrous sodium sulfate, filtered and concentrated under reduced pressure to provide crude 4-acetylpiperazine-1-carbonyl chloride (220 mg) as brown oil.

Step 2: Preparation of 1-(4-[[4-(trifluoromethyl)-1H-pyrazol-1-yl]carbonyl]piperazin-1-yl)ethan-1-one

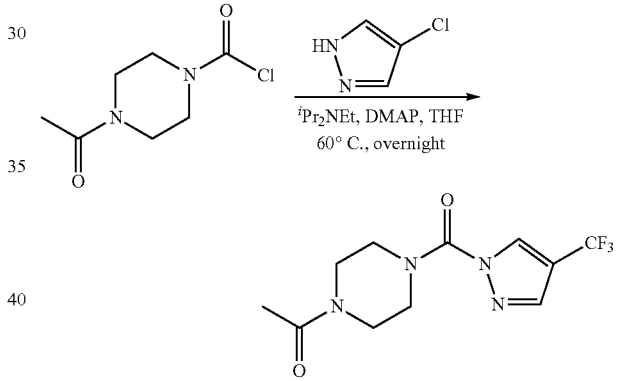

A 50-mL round-bottom flask was charged with 4-acetylpiperazine-1-carbonyl chloride (220 mg, 1.15 mmol, 1.00 equiv), tetrahydrofuran (10 mL), 4-(trifluoromethyl)-1H-pyrazole (159 mg, 1.17 mmol, 1.00 equiv), N,N-diisopropylethylamine (448 mg, 3.47 mmol, 3.00 equiv) and 4-dimethylaminopyridine (28.0 mg, 0.230 mmol, 0.20 equiv). The resulting solution was stirred overnight at 60° C. and quenched by water (40 mL). The resulting solution was extracted with dichloromethane (3×80 mL) and the organic layers were combined, washed with water (3×20 mL), dried over anhydrous sodium sulfate, filtered and concentrated under reduced pressure. The crude product was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5

µm; Mobile phase: Phase A: aqueous NH₄HCO₃ (0.05%); Phase B: CH₃CN; Detector, UV220 & 254 nm. Purification yielded 1-(4-[[4-(trifluoromethyl)-1H-pyrazol-1-yl]carbonyl]piperazin-1-yl)ethan-1-one (59.1 mg, 18% yield) as a white solid. ¹H NMR (300 MHz, Chloroform-d) δ 8.44 (s, 1H), 7.83 (s, 1H), 3.82-3.90 (m, 4H), 3.72-3.78 (m, 2H), 3.59-3.65 (m, 2H), 2.15 (s, 3H). LCMS (ESI, m/z): 291 [M+H]⁺.

Example 150: (4-(Methylsulfonyl)piperazin-1-yl)(4-(trifluoromethyl)-1H-pyrazol-1-yl)methanone

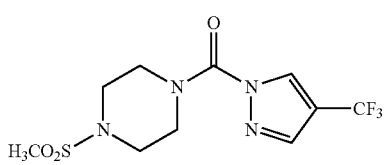

The title compound was synthesized from 1-(methylsulfonyl)piperazine, triphosgene, and 4-(trifluoromethyl)-1H-pyrazole according to the representative procedure of Example 149, Steps 1-2 to provide (4-(methylsulfonyl)piperazin-1-yl)(4-(trifluoromethyl)-1H-pyrazol-1-yl)methanone as a white solid. ¹H NMR (400 MHz, DMSO-d₆) δ 8.90 (s, 1H), 8.27 (s, 1H), 3.75-3.82 (m, 4H), 3.24-3.26 (m, 4H), 2.93 (s, 3H). LCMS (ESI, m/z): 327 [M+H]⁺.

Example 151: (4-Methylpiperazin-1-yl)(4-(trifluoromethyl)-1H-pyrazol-1-yl)methanone

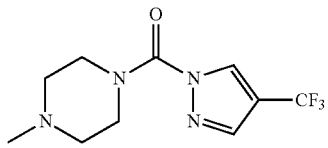 [SMILES: CN1CCN(C(=O)n2cc(C(F)(F)F)cn2)CC1]

The title compound was synthesized from 1-methylpiperazine, triphosgene, and 4-(trifluoromethyl)-1H-pyrazole according to the representative procedure of Example 149, Steps 1-2 to provide (4-methylpiperazin-1-yl)(4-(trifluoromethyl)-1H-pyrazol-1-yl)methanone as a yellow oil. ¹H NMR (300 MHz, DMSO-d₆) δ 8.86 (s, 1H), 8.22 (s, 1H), 3.62-3.65 (m, 4H), 2.37-2.40 (m, 4H), 2.20 (s, 3H). LCMS (ESI, m/z): 263 [M+H]⁺.

Example 152: (4-Benzylpiperazin-1-yl)(4-(trifluoromethyl)-1H-pyrazol-1-yl)methanone

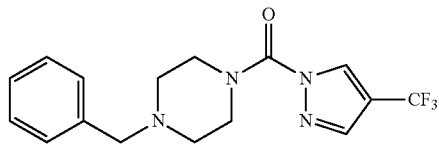 [SMILES: O=C(N1CCN(Cc2ccccc2)CC1)n1cc(C(F)(F)F)cn1]

The title compound was synthesized from 1-benzylpiperazine, triphosgene, and 4-(trifluoromethyl)-1H-pyrazole according to the representative procedure of Example 149, Steps 1-2 to provide (4-benzylpiperazin-1-yl)(4-(trifluorom-ethyl)-1H-pyrazol-1-yl)methanone as a white solid. ¹H NMR (400 MHz, DMSO-d₆) δ 8.86 (s, 1H), 8.22 (s, 1H), 7.24-7.36 (m, 5H), 3.62-3.68 (m, 4H), 3.32 (s, 2H), 2.45-2.51 (m, 4H). LCMS (ESI, m/z): 339 [M+H]⁺.

Example 153: (4-Benzoylpiperazin-1-yl)(4-(trifluoromethyl)-1H-pyrazol-1-yl)methanone

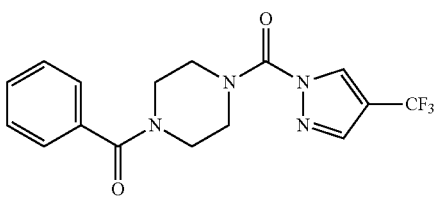 [SMILES: O=C(c1ccccc1)N1CCN(C(=O)n2cc(C(F)(F)F)cn2)CC1]

The title compound was synthesized from phenyl(piperazin-1-yl)methanone, triphosgene, and 4-(trifluoromethyl)-1H-pyrazole to the representative procedure of Example 149, Steps 1-2 to provide (4-benzoylpiperazin-1-yl)(4-(trifluoromethyl)-1H-pyrazol-1-yl)methanone as a white solid. ¹H NMR (400 MHz, DMSO-d₆) δ 8.90 (s, 1H), 8.25 (s, 1H), 7.41-7.50 (m, 5H), 3.40-3.90 (m, 8H). LCMS (ESI, m/z): 353 [M+H]⁺.

Example 154: 1-(4-(4-(trifluoromethyl)-1H-pyrazole-1-carbonyl)-1,4-diazepan-1-yl)ethanone

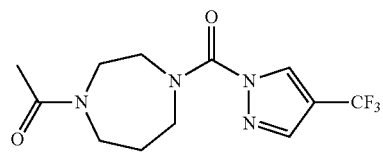 [SMILES: CC(=O)N1CCCN(C(=O)n2cc(C(F)(F)F)cn2)CC1]

Step 1: Preparation of 4-nitrophenyl 4-(trifluoromethyl)-1H-pyrazole-1-carboxylate

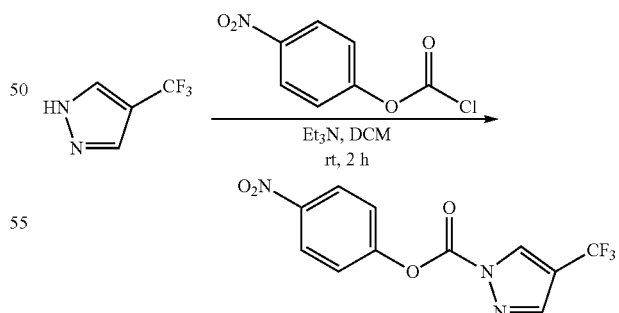

A 100-mL round-bottom flask was charged with 4-(trifluoromethyl)-1H-pyrazole (200 mg, 1.47 mmol, 1.00 equiv), dichloromethane (10 mL) and triethylamine (442 mg, 4.37 mmol, 3.00 equiv). 4-Nitrophenyl chloroformate (354 mg, 1.76 mmol, 1.20 equiv) in dichloromethane (5 mL)) was added dropwise at 0° C. The resulting solution was stirred for 2 h at room temperature and concentrated under reduced pressure to provide crude 4-nitrophenyl (trifluoromethyl)-1H-pyrazole-1-carboxylate (430 mg) as a yellow solid.

Step 2: Preparation of tert-butyl 4-(4-(trifluoromethyl)-1H-pyrazole-1-carbonyl)-1,4-diazepane-1-carboxylate

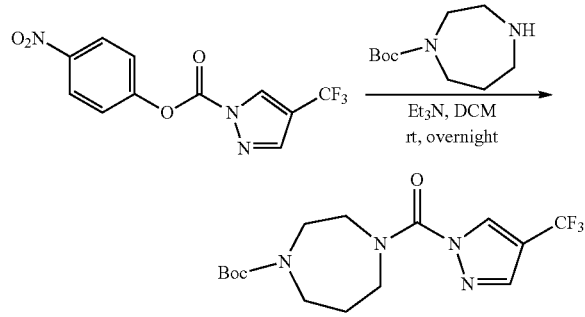

A 100-mL round-bottom flask was charged with 4-nitrophenyl 4-(trifluoromethyl)-1H-pyrazole-1-carboxylate (1.09 g, 3.62 mmol, 1.20 equiv), dichloromethane (20 mL), tert-butyl 1,4-diazepane-1-carboxylate (604 mg, 3.00 mmol, 1.00 equiv) and triethylamine (915 mg, 9.00 mmol, 3.00 equiv). The resulting solution was stirred overnight at room temperature and quenched by water (40 mL). The resulting solution was extracted with dichloromethane (3×80 mL) and the organic layers were combined, washed with water (3×20 mL), dried over anhydrous sodium sulfate, filtered and concentrated under reduced pressure. The residue was chromatographed on a silica gel column with ethyl acetate/petroleum ether (1/5) to provide tert-butyl 4-[[4-(trifluoromethyl)-1H-pyrazol-1-yl]carbonyl]-1,4-diazepane-1-carboxylate (890 mg, 81% yield) as a yellow solid. LCMS (ESI, m/z): 307 [M-Bu+H]$^+$.

Step 3: Preparation of (1,4-diazepan-1-yl)(4-(trifluoromethyl)-1H-pyrazol-1-yl)methanone

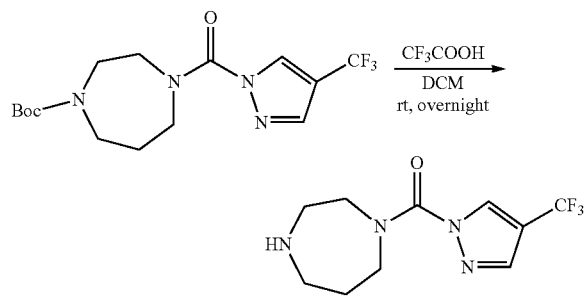

A 100-mL round-bottom flask was charged with tert-butyl 4-[[4-(trifluoromethyl)-1H-pyrazol-1-yl]carbonyl]-1,4-diazepane-1-carboxylate (890 mg, 2.46 mmol, 1.00 equiv), dichloromethane (12 mL) and trifluoroacetic acid (4 mL). The resulting solution was stirred overnight at room temperature and concentrated under reduced pressure to provide crude 1-[[4-(trifluoromethyl)-1H-pyrazol-1-yl]carbonyl]-1,4-diazepane (1.12 g) as yellow oil. LCMS (ESI, m/z): 263 [M+H]$^+$.

Step 4: Preparation of 1-(4-(4-(Trifluoromethyl)-1H-pyrazole-1-carbonyl)-1,4-diazepan-1-yl)ethanone

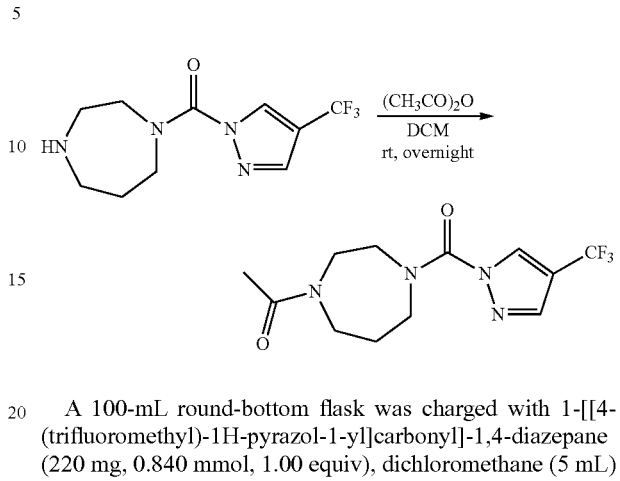

A 100-mL round-bottom flask was charged with 1-[[4-(trifluoromethyl)-1H-pyrazol-1-yl]carbonyl]-1,4-diazepane (220 mg, 0.840 mmol, 1.00 equiv), dichloromethane (5 mL) and acetyl acetate (86.0 mg, 0.840 mmol, 1.00 equiv). The resulting solution was stirred overnight at room temperature and quenched by water (40 mL). The resulting solution was extracted with dichloromethane (3×80 mL) and the organic layers were combined, washed with water (3×20 mL), dried over anhydrous sodium sulfate, filtered and concentrated under reduced pressure. The crude product was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification yielded 1-(4-[[4-(trifluoromethyl)-1H-pyrazol-1-yl]carbonyl]-1,4-diazepan-1-yl)ethan-1-one (106.9 mg, 42% yield) as a light yellow solid. $^1$H NMR (300 MHz, DMSO-d$_6$) δ 8.89 (d, J=10.2 Hz, 1H), 8.23 (d, J=3.9 Hz, 1H), 3.69-3.80 (m, 1H), 3.63-3.67 (m, 5H), 3.48-3.56 (m, 2H), 2.01 (s, 3H), 1.84-1.92 (m, 1H), 1.76 (br, 1H). LCMS (ESI, m/z): 305 [M+H]$^+$.

Example 155: (4-(Methylsulfonyl)-1,4-diazepan-1-yl)(4-(trifluoromethyl)-1H-pyrazol-1-yl)methanone

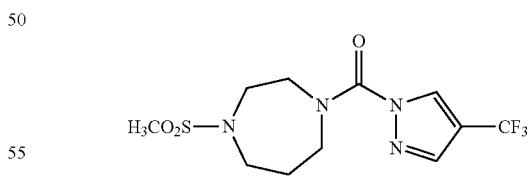

The title compound was directly synthesized from (1,4-diazepan-1-yl)(4-(trifluoromethyl)-1H-pyrazol-1-yl)methanone (Example 154, Steps 1-3) and trifluoromethanesulfonic anhydride according to the representative procedure of Example 154, Steps 1-4 to provide (4-(methylsulfonyl)-1,4-diazepan-1-yl)(4-(trifluoromethyl)-1H-pyrazol-1-yl) methanone as a white solid. $^1$H NMR (300 MHz, Chloroform-d) δ 8.46 (s, 1H), 7.80 (s, 1H), 3.90-4.00 (m, 4H), 3.44-3.64 (m, 4H), 2.87 (s, 3H), 2.09-2.12 (m, 2H). LCMS (ESI, m/z): 341 [M+H]$^+$.

Example 156: (4-Methyl-1,4-diazepan-1-yl)(4-(trifluoromethyl)-1H-pyrazol-1-yl)methanone

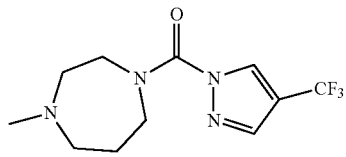 [SMILES: CN1CCCN(C(=O)n2cc(C(F)(F)F)cn2)CC1]

The title compound was synthesized from (1,4-diazepan-1-yl)(4-(trifluoromethyl)-1H-pyrazol-1-yl)methanone (Example 154, Steps 1-3), formaldehyde, and sodium triacetoxyborohydride according to the representative procedure of Example 154, Steps 1-4 to provide (4-Methyl-1,4-diazepan-1-yl)(4-(trifluoromethyl)-1H-pyrazol-1-yl)methanone as a light yellow oil. $^1$H NMR (300 MHz, Chloroform-d) δ 8.43 (s, 1H), 7.79 (s, 1H), 3.79-3.92 (m, 4H), 2.66-2.81 (m, 4H), 2.42 (s, 3H), 2.06 (br, 2H). LCMS (ESI, m/z): 277 [M+H]$^+$.

Example 157: (4-Benzyl-1,4-diazepan-1-yl)(4-(trifluoromethyl)-1H-pyrazol-1-yl)methanone

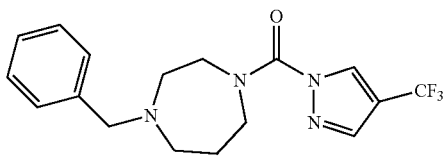 [SMILES: O=C(N1CCCN(Cc2ccccc2)CC1)n1cc(C(F)(F)F)cn1]

The title compound was synthesized from (1,4-diazepan-1-yl)(4-(trifluoromethyl)-1H-pyrazol-1-yl)methanone (Example 154, Steps 1-3), benzaldehyde, and sodium triacetoxyborohydride according to the representative procedure of Example 154, Steps 1-4 to provide (4-benzyl-1,4-diazepan-1-yl)(4-(trifluoromethyl)-1H-pyrazol-1-yl)methanone as a colorless oil. $^1$H NMR (400 MHz, Chloroform-d) δ 8.69 (s, 1H), 7.80 (s, 1H), 7.30-7.34 (m, 5H), 3.79-3.93 (m, 6H), 2.72-2.84 (m, 4H), 2.02 (br, 2H). LCMS (ESI, m/z): 353 [M+H]$^+$.

Example 158: (4-Benzoyl-1,4-diazepan-1-yl)(4-(trifluoromethyl)-1H-pyrazol-1-yl)methanone

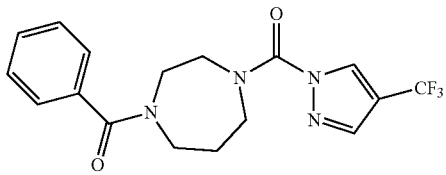 [SMILES: O=C(c1ccccc1)N1CCCN(C(=O)n2cc(C(F)(F)F)cn2)CC1]

The title compound was synthesized from (1,4-diazepan-1-yl)(4-(trifluoromethyl)-1H-pyrazol-1-yl)methanone (Example 154, Steps 1-3) and benzoyl chloride according to the representative procedure of Example 154, Steps 1-4 to provide (4-benzoyl-1,4-diazepan-1-yl)(4-(trifluoromethyl)-1H-pyrazol-1-yl)methanone (122.6 mg, 99.8% purity) as a white solid. $^1$H NMR (300 MHz, Chloroform-d) δ 8.46 (s, 1H), 7.64-7.82 (m, 1H), 7.27-7.41 (m, 5H), 3.52-4.01 (m, 8H), 2.18 (s, 1H), 1.89 (br, 1H). LCMS (ESI, m/z): 367 [M+H]$^+$.

Example 159: N-Methyl-N-(2-(N-methylacetamido)ethyl)-4-(trifluoromethyl)-1H-pyrazole-1-carboxamide

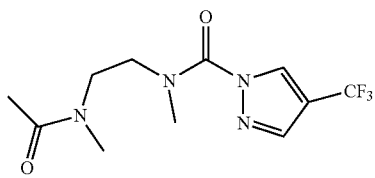 [SMILES: CC(=O)N(C)CCN(C)C(=O)n1cc(C(F)(F)F)cn1]

Step 1: Preparation of tert-butyl methyl(2-(N-methylacetamido)ethyl)carbamate

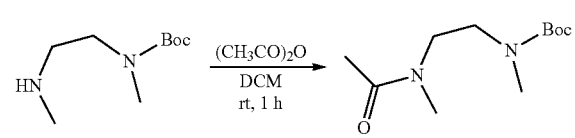

A 50-mL round-bottom flask was charged with tert-butyl N-methyl-N-[2-(methylamino)ethyl]carbamate (600 mg, 3.19 mmol, 1.00 equiv), dichloromethane (10 mL) and acetyl acetate (326 mg, 3.19 mmol, 1.00 equiv). The resulting solution was stirred for 1 h at room temperature. and quenched by water (40 mL). The resulting solution was extracted with dichloromethane (3×80 mL) and the organic layers were combined, washed with water (3×20 mL), dried over anhydrous sodium sulfate, filtered and concentrated under reduced pressure to provide crude tert-butyl N-methyl-N-[2-(N-methylacetamido)ethyl]carbamate (770 mg) as colorless oil. LCMS (ESI, m/z): 231 [M+H]$^+$.

Step 2: Preparation of N-Methyl-N-(2-(methylamino)ethyl)acetamide

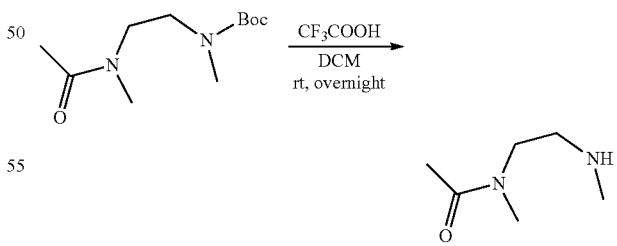

A 100-mL round-bottom flask was charged with tert-butyl N-methyl-N-[2-(N-methylacetamido)ethyl]carbamate (1.00 g, 3.59 mmol, 1.00 equiv), dichloromethane (10 mL) and trifluoroacetic acid (2 mL). The resulting solution was stirred overnight at room temperature and concentrated under reduced pressure to provide crude N-methyl-N-(2-(methylamino)ethyl)acetamide (900 mg) as light yellow oil. LCMS (ESI, m/z): 131 [M+H]$^+$.

Step 3: Preparation of 4-nitrophenyl 4-(trifluoromethyl)-1H-pyrazole-1-carboxylate

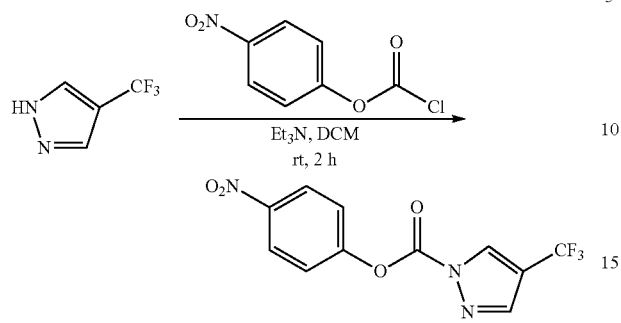

A 100-mL round-bottom flask was charged with 4-(trifluoromethyl)-1H-pyrazole (200 mg, 1.47 mmol, 1.00 equiv), dichloromethane (10 mL) and triethylamine (442 mg, 4.37 mmol, 3.00 equiv). 4-Nitrophenyl chloroformate (354 mg, 1.76 mmol, 1.20 equiv) in dichloromethane (5 mL) was added dropwise at 0° C. The resulting solution was stirred for 2 h at room temperature and concentrated under reduced pressure to provide crude 4-nitrophenyl 4-(trifluoromethyl)-1H-pyrazole-1-carboxylate (430 mg) as a yellow solid.

Step 4: Preparation of N-Methyl-N-(2-(N-methylacetamido)ethyl)-4-(trifluoromethyl)-1H-pyrazole-1-carboxamide

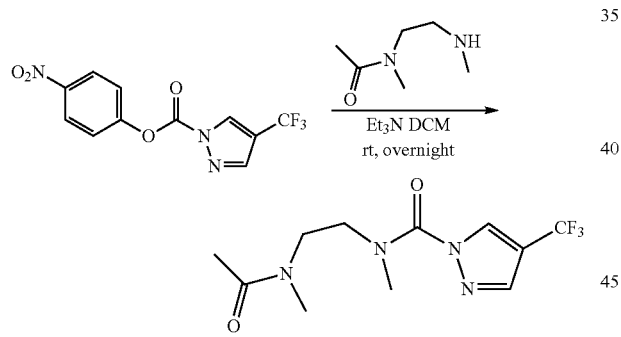

A 50-mL round-bottom flask was charged with N-methyl-N-[2-(methylamino)ethyl]acetamide (100 mg, 0.770 mmol, 1.00 equiv), dichloromethane (5 mL), 4-nitrophenyl 4-(trifluoromethyl)-1H-pyrazole-1-carboxylate (230 mg, 0.760 mmol, 1.00 equiv) and triethylamine (233 mg, 2.30 mmol, 3.00 equiv). The resulting solution was stirred overnight at room temperature and quenched by water (40 mL). The resulting solution was extracted with dichloromethane (3×80 mL) and the organic layers were combined, washed with water (3×20 mL), dried over anhydrous sodium sulfate, filtered and concentrated under reduced pressure. The crude product was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification provided N-methyl-N-(2-(N-methylacetamido)ethyl)-4-(trifluoromethyl)-1H-pyrazole-1-carboxamide (54.4 mg, 24% yield) as colorless oil. $^1$H NMR (300 MHz, Chloroform-d) δ 8.41-8.45 (m, 1H), 7.81 (d, J=3.9 Hz, 1H), 3.70-3.80 (m, 4H), 3.20-3.35 (m, 3H), 2.98-3.06 (m, 3H), 2.07-2.16 (m, 3H). LCMS (ESI, m/z): 293 [M+H]$^+$.

Example 160: N-methyl-N-(2-(N-methylbenzamido)ethyl)-4-(trifluoromethyl)-1H-pyrazole-1-carboxamide

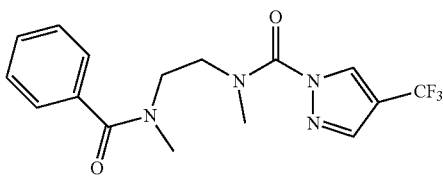 [SMILES: CN(CCN(C)C(=O)n1cc(C(F)(F)F)cn1)C(=O)c1ccccc1]

The title compound was synthesized from 4-nitrophenyl 4-(trifluoromethyl)-1H-pyrazole-1-carboxylate (Example 154, Step 1), tert-butyl methyl(2-(methylamino)ethyl)carbamate, and trifluoroacetic acid according to the representative procedure of Example 154, Steps 1-4 to provide N-methyl-N-(2-(N-methylbenzamido)ethyl)-4-(trifluoromethyl)-1H-pyrazole-1-carboxamide as white solid. $^1$H NMR (300 MHz, Chloroform-d) δ 8.27-8.56 (m, 1H), 7.61-7.81 (m, 1H), 7.38 (s, 5H), 3.58-4.11 (m, 4H), 3.28-3.40 (m, 2H), 2.82-3.20 (m, 4H). LCMS (ESI, m/z): 355 [M+H]$^+$.

Example 161: 1-(4-(4-Methyl-1H-pyrazole-1-carbonyl)piperazin-1-yl)ethanone

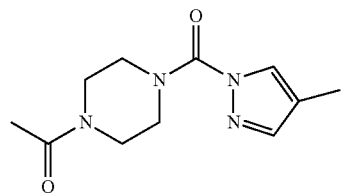 [SMILES: CC(=O)N1CCN(C(=O)n2cc(C)cn2)CC1]

The title compound was synthesized from 4-acetylpiperazine-1-carbonyl chloride (Example 149, Step 1) and 4-methyl-1H-pyrazole according to the representative procedure of Example 149, Steps 1-2 to provide 1-(4-(4-methyl-1H-pyrazole-1-carbonyl)piperazin-1-yl)ethanone as white solid. $^1$H NMR (300 MHz, DMSO-d$_6$) δ 7.97 (s, 1H), 7.61 (s, 1H), 3.68-3.74 (m, 4H), 3.51-3.58 (m, 4H), 2.03-2.05 (m, 6H). LCMS (ESI, m/z): 237 [M+H]$^+$.

Example 162: (4-Methyl-1H-pyrazol-1-yl)(4-(methylsulfonyl)piperazin-1-yl)methanone

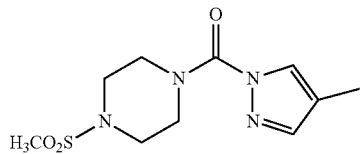

The title compound was synthesized from 1-(methylsulfonyl)piperazine, triphosgene and 4-methyl-1H-pyrazole according to the representative procedure of Example 149, Steps 1-2 to provide (4-methyl-1H-pyrazol-1-yl)(4-(methylsulfonyl)piperazin-1-yl)methanone as a white solid. $^1$H NMR (300 MHz, DMSO-d$_6$) δ 7.98 (s, 1H), 7.62 (s, 1H), 3.80-3.85 (m, 4H), 3.20-3.24 (m, 4H), 2.91 (s, 3H), 2.05 (s, 3H). LCMS (ESI, m/z): 273 [M+H]$^+$.

Example 163: (4-Methyl-1H-pyrazol-1-yl)(4-methylpiperazin-1-yl)methanone

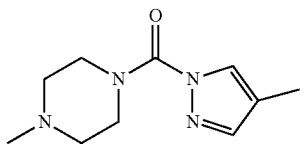

The title compound was synthesized from 1-methylpiperazine, triphosgene and 4-methyl-1H-pyrazole according to the representative procedure of Example 149, Steps 1-2 to provide (4-methyl-1H-pyrazol-1-yl)(4-methylpiperazin-1-yl)methanone as a light yellow oil. $^1$H NMR (400 MHz, DMSO-d$_6$) δ 7.94 (s, 1H), 7.58 (s, 1H), 3.65-3.70 (m, 4H), 2.36-2.39 (m, 4H), 2.20 (s, 3H), 2.04 (s, 3H). LCMS (ESI, m/z): 209 [M+H]$^+$.

Example 164: (4-Benzoylpiperazin-1-yl)(4-methyl-1H-pyrazol-1-yl)methanone

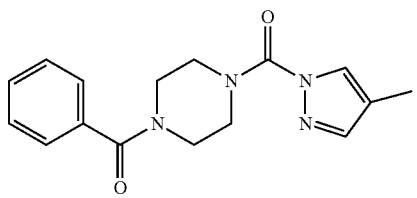 [SMILES: Cc1cnn(C(=O)N2CCN(C(=O)c3ccccc3)CC2)c1]

The title compound was synthesized from phenyl(piperazin-1-yl)methanone, triphosgene and 4-methyl-1H-pyrazole according to the representative procedure of Example 149, Steps 1-2 to provide (4-benzoylpiperazin-1-yl)(4-methyl-1H-pyrazol-1-yl)methanone as a white solid. $^1$H NMR (400 MHz, DMSO-d$_6$) δ 7.98 (s, 1H), 7.61 (s, 1H), 7.42-7.48 (m, 5H), 3.46-3.90 (m, 8H), 2.05 (s, 3H). LCMS (ESI, m/z): 299 [M+H]$^+$.

Example 165: 1-(4-(4-Methyl-1H-pyrazole-1-carbonyl)-1,4-diazepan-1-yl)ethanone

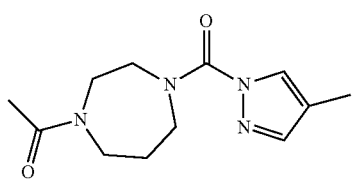 [SMILES: CC(=O)N1CCCN(C(=O)n2cc(C)cn2)CC1]

The title compound was synthesized from 4-methyl-1H-pyrazole, 4-nitrophenyl chloroformate, tert-butyl 1,4-diazepane-1-carboxylate, and acetic anhydride according to the representative procedure of Example 154, Steps 1-4 to provide 1-(4-(4-methyl-1H-pyrazole-1-carbonyl)-1,4-diazepan-1-yl)ethanone as a light yellow oil. $^1$H NMR (400 MHz, DMSO-d$_6$) δ 7.97 (d, J=12.0 Hz, 1H), 7.60 (d, J=6.0 Hz, 1H), 3.58-3.65 (m, 6H), 3.46-3.53 (m, 2H), 2.04 (s, 3H), 1.96-2.01 (m, 3H), 1.86 (m, 1H), 1.70-1.77 (m, 1H). LCMS (ESI, m/z): 251 [M+H]$^+$.

Example 166: (4-Methyl-1H-pyrazol-1-yl)(4-(methylsulfonyl)-1,4-diazepan-1-yl)methanone

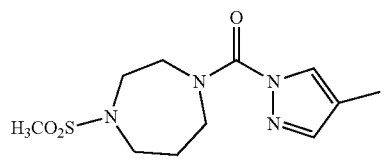

The title compound was synthesized from 4-methyl-1H-pyrazole, 4-nitrophenyl chloroformate, tert-butyl 1,4-diazepane-1-carboxylate, and trifluoromethansulfonic anhydride according to the representative procedure of Example 154, Steps 1-4 to provide (4-methyl-1H-pyrazol-1-yl)(4-(methylsulfonyl)-1,4-diazepan-1-yl)methanone as a white solid. $^1$H NMR (400 MHz, DMSO-d$_6$) δ 7.99 (s, 1H), 7.60 (s, 1H), 3.65-3.95 (m, 4H), 3.45 (t, J=5.4 Hz, 2H), 3.35 (t, J=6.0 Hz, 2H), 2.90 (s, 3H), 2.05 (s, 3H), 1.84-1.90 (m, 2H). LCMS (ESI, m/z): 287 [M+H]$^+$.

Example 167: (4-Methyl-1,4-diazepan-1-yl)(4-methyl-1H-pyrazol-1-yl)methanone

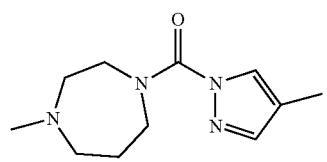

The title compound was synthesized from 4-methyl-1H-pyrazole, 4-nitrophenyl chloroformate, tert-butyl 1,4-diazepane-1-carboxylate, sodium triacetoxyborohydride, and formaldehyde according to the representative procedure of Example 154, Steps 1-4 to provide (4-methyl-1,4-diazepan-1-yl)(4-methyl-1H-pyrazol-1-yl)methanone as a light yellow oil. $^1$H NMR (300 MHz, Chloroform-d) δ 7.87 (s, 1H), 7.43 (s, 1H), 3.70-4.00 (m, 4H), 2.78 (t, J=4.8 Hz, 2H), 2.64 (t, J=4.8 Hz, 2H), 2.40 (s, 3H), 2.09 (s, 3H), 2.00-2.06 (m, 2H). LCMS (ESI, m/z): 223 [M+H]$^+$.

Example 168: (4-Benzyl-1,4-diazepan-1-yl)(4-methyl-1H-pyrazol-1-yl)methanone

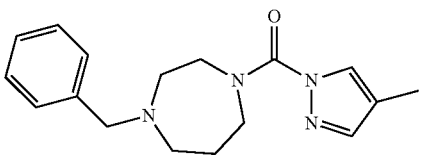 [SMILES: Cc1cnn(C(=O)N2CCCN(Cc3ccccc3)CC2)c1]

The title compound was synthesized from 4-methyl-1H-pyrazole, 4-nitrophenyl chloroformate, tert-butyl 1,4-diazepane-1-carboxylate, and sodium triacetoxyborohydride, and benzaldehyde according to the representative procedure of Example 154, Steps 1-4 to provide (4-benzyl-1,4-diazepan-1-yl)(4-methyl-1H-pyrazol-1-yl)methanone as a colorless oil. $^1$H NMR (300 MHz, DMSO-d$_6$) δ 7.96 (s, 1H), 7.55 (s, 1H), 7.20-7.31 (m, 5H), 3.61-3.83 (m, 6H), 2.70 (t, J=4.8 Hz, 2H), 2.55-2.60 (m, 2H), 2.04 (s, 3H), 1.80-1.88 (m, 2H). LCMS (ESI, m/z): 299 [M+H]$^+$.

Example 169: (4-Benzoyl-1,4-diazepan-1-yl)(4-methyl-1H-pyrazol-1-yl)methanone

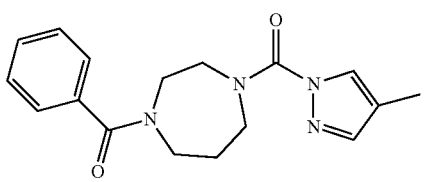 [SMILES: Cc1cnn(C(=O)N2CCCN(C(=O)c3ccccc3)CC2)c1]

The title compound was synthesized 4-methyl-1H-pyrazole, 4-nitrophenyl chloroformate, tert-butyl 1,4-diazepane-1-carboxylate, and benzoyl chloride according to the representative procedure of Example 154, Steps 1-4 to provide (4-benzoyl-1,4-diazepan-1-yl)(4-methyl-1H-pyrazol-1-yl)methanone as white solid. $^1$H NMR (400 MHz, DMSO-d$_6$) δ 7.99 (d, J=8.0 Hz, 1H), 7.61 (s, 1H), 7.13-7.53 (m, 5H), 3.67-3.88 (m, 6H), 3.37-3.46 (m, 2H), 2.04 (d, J=5.2 Hz, 3H), 1.88-1.92 (m, 1H), 1.70-1.78 (m, 1H). LCMS (ESI, m/z): 313 [M+H]$^+$.

Example 170: N,4-Dimethyl-N-(2-(N-methylacetamido)ethyl)-1H-pyrazole-1-carboxamide

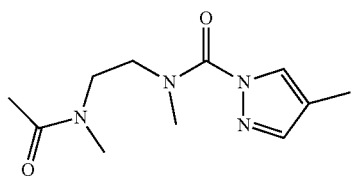 [SMILES: CC(=O)N(C)CCN(C)C(=O)n1cc(C)cn1]

The title compound was synthesized from N-methyl-N-(2-(methylamino)ethyl)acetamide (Example 159, Step 2), 4-methyl-1H-pyrazole, and 4-nitrophenyl chloroformate according to the representative procedure of Example 159, Steps 1-4 to provide N,4-dimethyl-N-(2-(N-methylacetamido)ethyl)-1H-pyrazole-1-carboxamide as a light yellow oil. $^1$H NMR (300 MHz, Chloroform-d) δ 7.88 (d, J=10.8 Hz, 1H), 7.44 (s, 1H), 3.68-3.80 (m, 4H), 3.20-3.30 (m, 3H), 2.97-3.05 (m, 3H), 2.16 (s, 1H), 2.06-2.10 (m, 5H). LCMS (ESI, m/z): 239 [M+H]$^+$.

Example 171: N-(2-(Benzyl(methyl)amino)ethyl)-N,4-dimethyl-1H-pyrazole-1-carboxamide

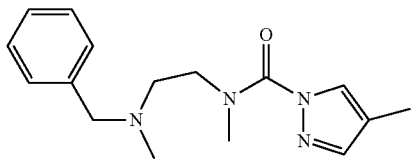 [SMILES: Cc1cnn(C(=O)N(C)CCN(C)Cc2ccccc2)c1]

The title compound was synthesized from N$^1$-benzyl-N$^1$,N$^2$-dimethylethane-1,2-diamine, 4-methyl-1H-pyrazole, and 4-nitrophenyl chloroformate according to the representative procedure of Example 159, Steps 1-4 to provide N-(2-(benzyl(methyl)amino)ethyl)-N,4-dimethyl-1H-pyrazole-1-carboxamide as a light yellow oil. $^1$H NMR (300 MHz, Chloroform-d) δ 7.83 (s, 1H), 7.42 (s, 1H), 7.24-7.31 (m, 5H), 3.75-3.84 (m, 2H), 3.52-3.56 (m, 2H), 3.15 (s, 3H), 2.65-2.70 (m, 2H), 2.18 (s, 3H), 2.08 (s, 3H). LCMS (ESI, m/z): 287 [M+H]$^+$.

Example 172: N,4-Dimethyl-N-(2-(N-methylbenzamido)ethyl)-1H-pyrazole-1-carboxamide

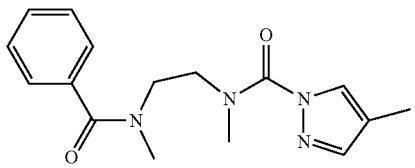 [SMILES: Cc1cnn(C(=O)N(C)CCN(C)C(=O)c2ccccc2)c1]

The title compound was synthesized in a manner according to the representative procedure of Example 154, Steps 1-4 to provide N,4-Dimethyl-N-(2-(N-methylbenzamido)ethyl)-1H-pyrazole-1-carboxamide as a light yellow oil. $^1$H NMR (300 MHz, DMSO-d$_6$) δ 7.85-7.96 (m, 1H), 7.54-7.59 (m, 1H), 7.38-7.42 (m, 3H), 7.29-7.32 (m, 2H), 3.74-3.84 (m, 3H), 3.45-3.52 (m, 1H), 3.15-3.23 (m, 2H), 2.80-3.00 (m, 4H), 2.04 (s, 3H). LCMS (ESI, m/z): 301 [M+H]$^+$.

Example 173: 1-(4-Acetylpiperazine-1-carbonyl)-1H-pyrazole-4-carbonitrile

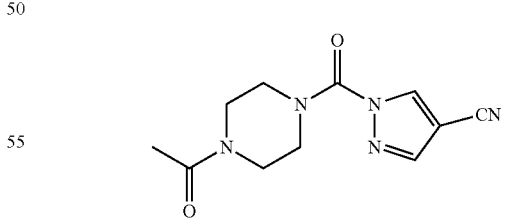

The title compound was synthesized from 4-acetylpiperazine-1-carbonyl chloride (Example 149, Step 1) and 1H-pyrazole-4-carbonitrile according to the representative procedure of Example 149, Steps 1-2 to provide 1-(4-acetylpiperazine-1-carbonyl)-1H-pyrazole-4-carbonitrile as a white solid. $^1$H NMR (400 MHz, DMSO-d$_6$) δ 9.08 (s, 1H), 8.34 (s, 1H), 3.56-3.67 (m, 8H), 2.01 (s, 3H). LCMS (ESI, m/z): 248 [M+H]$^+$.

Example 174: 1-(4-(Methylsulfonyl)piperazine-1-carbonyl)-1H-pyrazole-4-carbonitrile

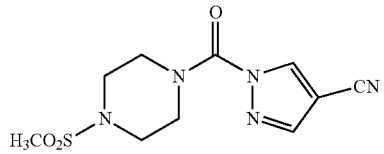

The title compound was synthesized from 1-(methylsulfonyl)piperazine, triphosgene, and 1H-pyrazole-4-carbonitrile according to the representative procedure of Example 149, Steps 1-2 to provide 1-(4-(methylsulfonyl)piperazine-1-carbonyl)-1H-pyrazole-4-carbonitrile as a white solid. $^1$H NMR (400 MHz, DMSO-$d_6$) δ 9.10 (s, 1H), 8.37 (s, 1H), 3.74-3.76 (m, 4H), 3.23-3.26 (m, 4H), 2.92 (s, 3H). LCMS (ESI, m/z): 306 [M+Na]$^+$.

Example 175: 1-(4-Methylpiperazine-1-carbonyl)-1H-pyrazole-4-carbonitrile

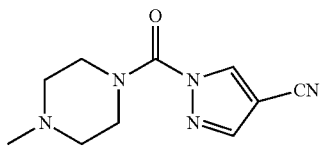 [SMILES: CN1CCN(C(=O)n2cc(C#N)cn2)CC1]

The title compound was synthesized from 1-methylpiperazine, triphosgene, and 1H-pyrazole-4-carbonitrile according to the representative procedure of Example 149, Steps 1-2 to provide 1-(4-methylpiperazine-1-carbonyl)-1H-pyrazole-4-carbonitrile as a white solid. $^1$H NMR (300 MHz, DMSO-$d_6$) δ 9.06 (s, 1H), 8.33 (s, 1H), 3.60-3.63 (m, 4H), 2.37-2.40 (m, 4H), 2.01 (s, 3H). LCMS (ESI, m/z): 220 [M+H]$^+$.

Example 176: 1-(4-Benzoylpiperazine-1-carbonyl)-1H-pyrazole-4-carbonitrile

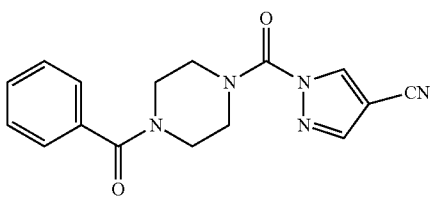 [SMILES: N#Cc1cnn(C(=O)N2CCN(C(=O)c3ccccc3)CC2)c1]

The title compound was synthesized from phenyl(piperazin-1-yl)methanone, triphosgene, and 1H-pyrazole-4-carbonitrile according to the representative procedure of Example 149, Steps 1-2 to provide 1-(4-benzoylpiperazine-1-carbonyl)-1H-pyrazole-4-carbonitrile as an off-white solid. $^1$H NMR (300 MHz, Chloroform-d) δ 9.09 (s, 1H), 8.35 (s, 1H), 7.43-7.48 (m, 5H), 3.40-3.85 (m, 8H). LCMS (ESI, m/z): 310 [M+H]$^+$.

Example 177: 1-(4-Acetyl-1,4-diazepane-1-carbonyl)-1H-pyrazole-4-carbonitrile

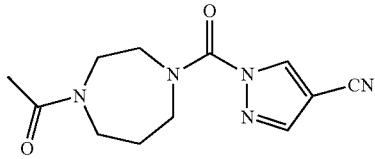 [SMILES: CC(=O)N1CCCN(C(=O)n2cc(C#N)cn2)CC1]

The title compound was synthesized from 1H-pyrazole-4-carbonitrile, 4-nitrophenyl chloroformate, tert-butyl 1,4-diazepane-1-carboxylate and acetic anhydride according to the representative procedure of Example 154, Steps 1-4 to provide 1-(4-acetyl-1,4-diazepane-1-carbonyl)-1H-pyrazole-4-carbonitrile as a light yellow solid. $^1$H NMR (300 MHz, DMSO-$d_6$) δ 9.08 (d, J=9.6 Hz, 1H), 8.33 (d, J=3.0 Hz, 1H), 3.76-3.80 (m, 1H), 3.62-3.68 (m, 5H), 3.47-3.55 (m, 2H), 1.95-2.01 (m, 3H), 1.84-1.89 (m, 1H), 1.70-1.80 (m, 1H). LCMS (ESI, m/z): 262 [M+H]$^+$.

Example 178: 1-(4-(methylsulfonyl)-1,4-diazepane-1-carbonyl)-1H-pyrazole-4-carbonitrile

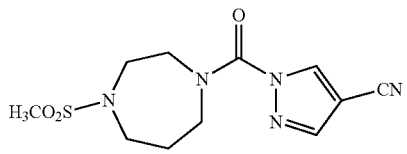

The title compound was synthesized from 1H-pyrazole-4-carbonitrile, 4-nitrophenyl chloroformate, tert-butyl 1,4-diazepane-1-carboxylate and trifluoromethanesulfonic anhydride according to the representative procedure of Example 154, Steps 1-4 to provide 1-(4-(methylsulfonyl)-1,4-diazepane-1-carbonyl)-1H-pyrazole-4-carbonitrile as a white solid. $^1$H NMR (300 MHz, Chloroform-d) δ 8.59 (s, 1H), 7.89 (s, 1H), 3.89-3.98 (m, 4H), 3.50-3.68 (m, 2H), 3.46 (t, J=6.0 Hz, 2H), 2.88 (s, 3H), 2.05-2.15 (m, 2H). LCMS (ESI, m/z): 320 [M+Na]$^+$.

Example 179: 1-(4-Benzyl-1,4-diazepane-1-carbonyl)-1H-pyrazole-4-carbonitrile

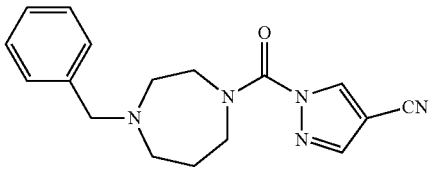 [SMILES: N#Cc1cnn(C(=O)N2CCCN(Cc3ccccc3)CC2)c1]

The title compound was synthesized from 1H-pyrazole-4-carbonitrile, 4-nitrophenyl chloroformate, tert-butyl 1,4-diazepane-1-carboxylate, sodium triacetoxyborohydride and benzaldehyde according to the representative procedure of Example 154, Steps 1-4 to provide 1-(4-benzyl-1,4-diazepane-1-carbonyl)-1H-pyrazole-4-carbonitrile as an off-white solid. $^1$H NMR (300 MHz, Chloroform-d) δ 8.55 (s, 1H), 7.85 (s, 1H), 7.26-7.31 (m, 5H), 3.57-3.97 (m, 6H), 2.69-2.81 (m, 4H), 1.95-2.05 (m, 2H). LCMS (ESI, m/z): 310 [M+H]⁺.

Example 180: 1-(4-Benzoyl-1,4-diazepane-1-carbonyl)-1H-pyrazole-4-carbonitrile

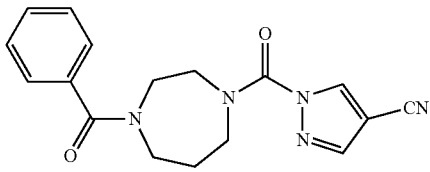 [SMILES: N#Cc1cnn(C(=O)N2CCCN(C(=O)c3ccccc3)CC2)c1]

The title compound was synthesized from 1H-pyrazole-4-carbonitrile, 4-nitrophenyl chloroformate, tert-butyl 1,4-diazepane-1-carboxylate and benzoyl chloride according to the representative procedure of Example 154, Steps 1-4 to provide 1-(4-benzoyl-1,4-diazepane-1-carbonyl)-1H-pyrazole-4-carbonitrile as a white solid. $^1$H NMR (300 MHz, Chloroform-d) δ 8.58 (s, 1H), 7.71-7.90 (m, 1H), 7.26-7.42 (m, 5H), 3.52-4.07 (m, 8H), 2.11-2.25 (m, 1H), 1.80-1.95 (m, 1H). LCMS (ESI, m/z): 324 [M+H]⁺.

Example 181: 4-Cyano-N-methyl-N-(2-(N-methylacetamido)ethyl)-1H-pyrazole-1-carboxamide

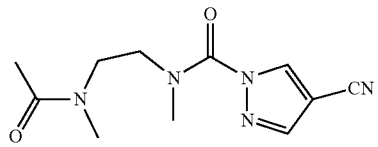 [SMILES: CC(=O)N(C)CCN(C)C(=O)n1cc(C#N)cn1]

The title compound was synthesized from N-methyl-N-(2-(methylamino)ethyl)acetamide (Example 159, Steps 1-2), and 1H-pyrazole-4-carbonitrile, 4-nitrophenyl chloroformate according to the representative procedure of Example 159, Steps 1-4 to provide 4-cyano-N-methyl-N-(2-(N-methylacetamido)ethyl)-1H-pyrazole-1-carboxamide as a white solid. $^1$H NMR (300 MHz, Chloroform-d) δ 8.51-8.51 (m, 1H), 7.89 (d, J=4.2 Hz, 1H), 3.60-3.85 (m, 4H), 3.20-3.40 (m, 3H), 2.90-3.10 (m, 3H), 2.07-2.15 (m, 3H). LCMS (ESI, m/z): 250 [M+H]⁺.

Example 182: 4-Cyano-N-methyl-N-(2-(N-methylbenzamido)ethyl)-1H-pyrazole-1-carboxamide

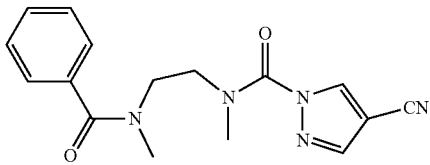 [SMILES: CN(CCN(C)C(=O)n1cc(C#N)cn1)C(=O)c1ccccc1]

The title compound was synthesized in a manner according to the representative procedure of Example 154, Steps 1-4 to provide 4-cyano-N-methyl-N-(2-(N-methylbenzamido)ethyl)-1H-pyrazole-1-carboxamide as a semi-white solid. $^1$H NMR (300 MHz, Chloroform-d) δ 8.45-8.65 (m, 1H), 7.75-7.90 (m, 1H), 7.32-7.45 (m, 5H), 3.66-4.00 (m, 4H), 3.30-3.55 (m, 2H), 2.80-3.20 (m, 4H). LCMS (ESI, m/z): 312 [M+H]⁺.

Example 183: 1-(4-(4-Chloro-1H-pyrazole-1-carbonyl)piperazin-1-yl)ethanone

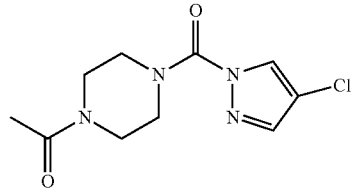 [SMILES: CC(=O)N1CCN(C(=O)n2cc(Cl)cn2)CC1]

The title compound was synthesized from 4-acetylpiperazine-1-carbonyl chloride (Example 149, Step 1) and 4-chloro-1H-pyrazole according to the representative procedure of Example 149, Steps 1-2 to provide 1-(4-(4-chloro-1H-pyrazole-1-carbonyl)piperazin-1-yl)ethanone as a white solid. $^1$H NMR (300 MHz, DMSO-d$_6$) δ 8.46 (s, 1H), 7.93 (s, 1H), 3.59-3.71 (m, 4H), 3.50-3.58 (m, 4H), 2.03 (s, 3H). LCMS (ESI, m/z): 257 [M+H]⁺.

Example 184: (4-Chloro-1H-pyrazol-1-yl)(4-(methylsulfonyl)piperazin-1-yl)methanone

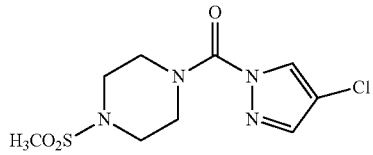

The title compound was synthesized from 1-(methylsulfonyl)piperazine, triphosgene, and 4-chloro-1H-pyrazole according to the representative procedure of Example 149, Steps 1-2 to provide (4-chloro-1H-pyrazol-1-yl)(4-(methylsulfonyl)piperazin-1-yl)methanone as a white solid. $^1$H NMR (400 MHz, DMSO-d$_6$) δ 8.47 (s, 1H), 7.94 (s, 1H), 3.75-3.82 (m, 4H), 3.22-3.25 (m, 4H), 2.92 (s, 3H). LCMS (ESI, m/z): 293 [M+H]⁺.

Example 185: (4-Chloro-1H-pyrazol-1-yl)(4-methylpiperazin-1-yl)methanone

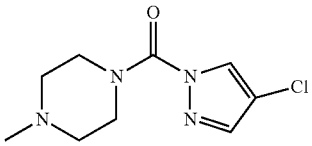

The title compound was synthesized from 1-methylpiperazine, triphosgene, and 4-chloro-1H-pyrazole according to the representative procedure of Example 149, Steps 1-2 to provide (4-chloro-1H-pyrazol-1-yl)(4-methylpiperazin-1-yl)methanone as a light yellow oil. $^1$H NMR (300 MHz, DMSO-d$_6$) δ 8.43 (s, 1H), 7.90 (s, 1H), 3.63-3.66 (m, 4H), 2.36-2.39 (m, 4H), 2.20 (s, 3H). LCMS (ESI, m/z): 229 [M+H]⁺.

Example 186: (4-Benzylpiperazin-1-yl)(4-chloro-1H-pyrazol-1-yl)methanone

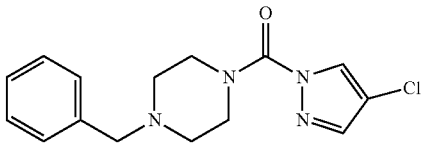 [SMILES: O=C(N1CCN(Cc2ccccc2)CC1)n1cc(Cl)cn1]

The title compound was synthesized from 1-benzylpiperazine, triphosgene, and 4-chloro-1H-pyrazole in a manner according to the representative procedure of Example 149, Steps 1-2 to provide (4-benzylpiperazin-1-yl)(4-chloro-1H-pyrazol-1-yl)methanone as a white solid. $^1$H NMR (300 MHz, DMSO-d$_6$) δ 8.43 (s, 1H), 7.89 (s, 1H), 7.23-7.36 (m, 5H), 3.60-3.75 (m, 4H), 3.52 (s, 2H), 2.43-2.46 (m, 4H). LCMS (ESI, m/z): 305 [M+H]$^+$.

Example 187: (4-Benzoylpiperazin-1-yl)(4-chloro-1H-pyrazol-1-yl)methanone

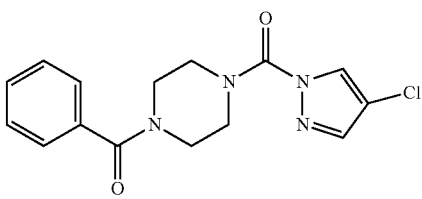 [SMILES: O=C(c1ccccc1)N1CCN(C(=O)n2cc(Cl)cn2)CC1]

The title compound was synthesized from phenyl(piperazin-1-yl)methanone, triphosgene, and 4-chloro-1H-pyrazole according to the representative procedure of Example 149, Steps 1-2 to provide (4-benzoylpiperazin-1-yl)(4-chloro-1H-pyrazol-1-yl)methanone as an off-white solid. $^1$H NMR (300 MHz, Chloroform-d) δ 8.46 (s, 1H), 7.92 (s, 1H), 7.42-7.48 (m, 5H), 3.40-3.85 (m, 8H). LCMS (ESI, m/z): 319 [M+H]$^+$.

Example 188: 1-(4-(4-Chloro-1H-pyrazole-1-carbonyl)-1,4-diazepan-1-yl)ethanone

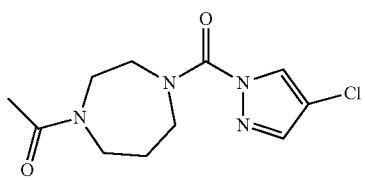 [SMILES: CC(=O)N1CCCN(C(=O)n2cc(Cl)cn2)CC1]

The title compound was synthesized from 4-chloro-1H-pyrazole, 4-nitrophenyl chloroformate, tert-butyl 1,4-diazepane-1-carboxylate, and acetic anhydride according to the representative procedure of Example 154, Steps 1-4 to provide 1-(4-(4-chloro-1H-pyrazole-1-carbonyl)-1,4-diazepan-1-yl)ethanone as a light yellow oil. $^1$H NMR (300 MHz, DMSO-d$_6$) δ 8.46 (d, J=9.9 Hz, 1H), 7.90 (d, J=4.5 Hz, 1H), 3.60-3.85 (m, 6H), 3.46-3.54 (m, 2H), 1.97-2.01 (m, 3H), 1.84-1.91 (m, 1H), 1.70-1.80 (m, 1H). LCMS (ESI, m/z): 271 [M+H]$^+$.

Example 189: (4-Chloro-1H-pyrazol-1-yl)(4-(methylsulfonyl)-1,4-diazepan-1-yl)methanone

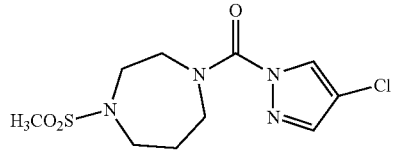

The title compound was synthesized 4-chloro-1H-pyrazole, 4-nitrophenyl chloroformate, tert-butyl 1,4-diazepane-1-carboxylate, and trifluoromethanesulfonic anhydride according to the representative procedure of Example 154, Steps 1-4 to provide (4-chloro-1H-pyrazol-1-yl)(4-(methylsulfonyl)-1,4-diazepan-1-yl)methanone as a white solid. $^1$H NMR (300 MHz, Chloroform-d) δ 8.13 (s, 1H), 7.55 (s, 1H), 3.80-4.10 (m, 4H), 3.50-3.65 (m, 2H), 3.45 (t, J=6.1 Hz, 2H), 2.86 (s, 3H), 2.08-2.14 (m, 2H). LCMS (ESI, m/z): 307 [M+H]$^+$.

Example 190: (4-Chloro-1H-pyrazol-1-yl)(4-methyl-1,4-diazepan-1-yl)methanone

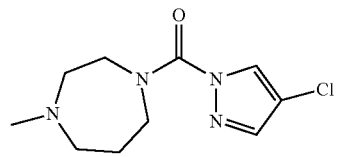 [SMILES: CN1CCCN(C(=O)n2cc(Cl)cn2)CC1]

The title compound was synthesized from 4-chloro-1H-pyrazole, 4-nitrophenyl chloroformate, tert-butyl 1,4-diazepane-1-carboxylate, sodium triacetoxyborohydride, and formaldehyde according to the representative procedure of Example 154, Steps 1-4 to provide (4-chloro-1H-pyrazol-1-yl)(4-methyl-1,4-diazepan-1-yl)methanone as a colorless oil. $^1$H NMR (400 MHz, Chloroform-d) δ 8.11 (s, 1H), 7.54 (s, 1H), 3.70-4.00 (m, 4H), 2.76-2.79 (m, 2H), 2.60-2.68 (m, 2H), 2.40 (s, 3H), 1.98-2.08 (m, 2H). LCMS (ESI, m/z): 243 [M+H]$^+$.

Example 191: (4-Benzyl-1,4-diazepan-1-yl)(4-chloro-1H-pyrazol-1-yl)methanone

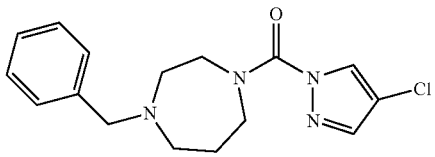 [SMILES: O=C(N1CCCN(Cc2ccccc2)CC1)n1cc(Cl)cn1]

The title compound was synthesized from 4-chloro-1H-pyrazole, 4-nitrophenyl chloroformate, tert-butyl 1,4-diazepane-1-carboxylate, and sodium triacetoxyborohydride, and benzaldehyde according to the representative procedure of Example 154, Steps 1-4 to provide (4-benzyl-1,4-diazepan-1-yl)(4-chloro-1H-pyrazol-1-yl)methanone as light yellow oil. $^1$H NMR (300 MHz, Chloroform-d) δ 8.10 (s, 1H), 7.52 (s, 1H), 7.26-7.33 (m, 5H), 3.67-4.04 (m, 6H), 2.69-2.82 (m, 4H), 1.95-2.10 (m, 2H). LCMS (ESI, m/z): 319 [M+H]⁺.

Example 192: (4-Benzoyl-1,4-diazepan-1-yl)(4-chloro-1H-pyrazol-1-yl)methanone

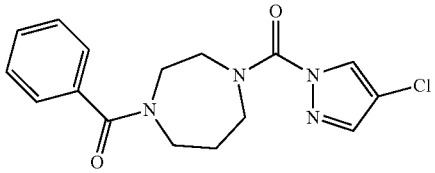 [SMILES: O=C(c1ccccc1)N1CCCN(C(=O)n2cc(Cl)cn2)CC1]

The title compound was synthesized from 4-chloro-1H-pyrazole, 4-nitrophenyl chloroformate, tert-butyl 1,4-diazepane-1-carboxylate, and benzoyl chloride according to the representative procedure of Example 154, Steps 1-4 to provide (4-benzoyl-1,4-diazepan-1-yl)(4-chloro-1H-pyrazol-1-yl)methanone as a white solid. ¹H NMR (300 MHz, Chloroform-d) δ 8.13 (s, 1H), 7.30-7.60 (m, 6H), 3.49-4.20 (m, 8H), 2.10-2.25 (m, 1H), 1.80-1.95 (m, 1H). LCMS (ESI, m/z): 333 [M+H]⁺.

Example 193: 4-Chloro-N-methyl-N-(2-(N-methylacetamido)ethyl)-1H-pyrazole-1-carboxamide

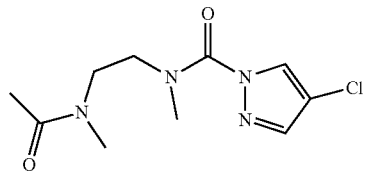 [SMILES: CC(=O)N(C)CCN(C)C(=O)n1cc(Cl)cn1]

The title compound was synthesized from N-methyl-N-(2-(methylamino)ethyl)acetamide (Example 159, Step 2), 4-chloro-1H-pyrazole, and 4-nitrophenyl chloroformate according to the representative procedure of Example 159, Steps 1-4 to provide 4-chloro-N-methyl-N-(2-(N-methylacetamido)ethyl)-1H-pyrazole-1-carboxamide as a light yellow oil. ¹H NMR (300 MHz, Chloroform-d) δ 8.09-8.13 (m, 1H), 7.55 (s, 1H), 3.65-3.80 (m, 4H), 3.15-3.35 (m, 3H), 2.97-3.05 (m, 3H), 2.07-2.16 (m, 3H). LCMS (ESI, m/z): 259 [M+H]⁺.

Example 194: 4-Chloro-N-methyl-N-(2-(N-methylbenzamido)ethyl)-1H-pyrazole-1-carboxamide

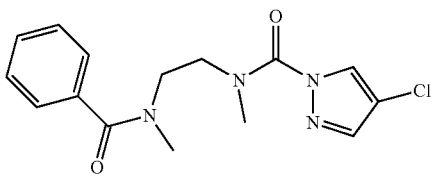 [SMILES: CN(CCN(C)C(=O)n1cc(Cl)cn1)C(=O)c1ccccc1]

The title compound was synthesized from synthesized from tert-butyl methyl(2-(methylamino)ethyl)carbamate, 4-chloro-1H-pyrazole, and 4-nitrophenyl chloroformate according to the representative procedure of Example 154, Steps 1-4 to provide 4-chloro-N-methyl-N-(2-(N-methylbenzamido)ethyl)-1H-pyrazole-1-carboxamide as a white solid. ¹H NMR (400 MHz, Chloroform-d) δ 8.04-8.11 (m, 1H), 7.49-7.56 (m, 1H), 7.40-7.42 (m, 5H), 3.65-4.00 (m, 4H), 3.25-3.50 (m, 2H), 2.85-3.20 (m, 4H). LCMS (ESI, m/z): 321 [M+H]⁺.

Example 195: N-Methyl-N-(2-(N-methylmethylsulfonamido)ethyl)-4-(trifluoromethyl)-1H-pyrazole-1-carboxamide

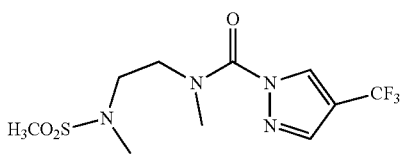

Step 1: Preparation of tert-butyl methyl(2-(N-methylmethylsulfonamido)ethyl)carbamate

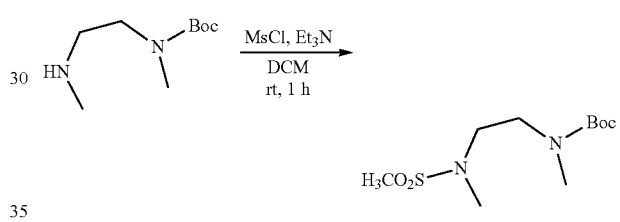

A 50-mL round-bottom flask was charged with tert-butyl N-methyl-N-[2-(methylamino)ethyl]carbamate (600 mg, 3.19 mmol, 1.00 equiv), dichloromethane (10 mL) and triethylamine (967 mg, 9.56 mmol, 3.00 equiv). Methanesulfonyl chloride (436 mg, 3.82 mmol, 1.20 equiv) was added dropwise at 0° C. The resulting solution was stirred for 1 h at room temperature and quenched by water (40 mL). The resulting solution was extracted with dichloromethane (3×80 mL) and the organic layers were combined, washed with water (3×20 mL), dried over anhydrous sodium sulfate, filtered and concentrated under reduced pressure to provide crude tert-butyl N-methyl-N-[2-(N-methylmethanesulfonamido)ethyl]carbamate (880 mg) as light yellow oil. LCMS (ESI, m/z): 208 [M-Bu+H]⁺.

Step 2: Preparation of N-methyl-N-(2-(methylamino)ethyl)methanesulfonamide

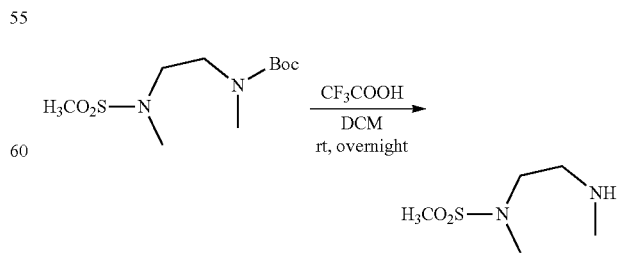

A 50-mL round-bottom flask was charged with tert-butyl N-methyl-N-[2-(N-methylmethanesulfonamido)ethyl]carbamate (880 mg, 3.30 mmol, 1.00 equiv), dichloromethane (5 mL) and trifluoroacetic acid (2 mL). The resulting solution was stirred overnight at room temperature and concentrated under reduced pressure to provide crude N-methyl-N-[2-(methylamino)ethyl]methanesulfonamide (540 mg) as white solid. LCMS (ESI, m/z): 167 [M+H]⁺.

Step 3: Preparation of N-methyl-N-(2-(N-methylmethylsulfonamido)ethyl)-4-(trifluoromethyl)-1H-pyrazole-1-carboxamide

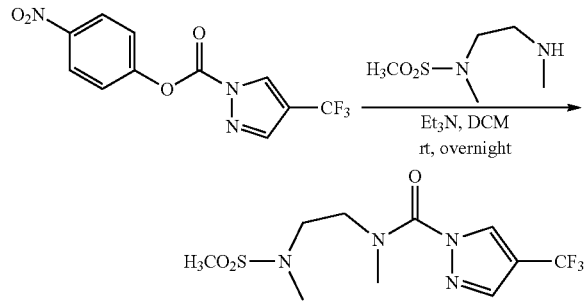

A 50-mL round-bottom flask was charged with N-methyl-N-[2-(methylamino)ethyl]methanesulfonamide (195 mg, 1.17 mmol, 1.00 equiv), dichloromethane (8 mL), 4-nitrophenyl 4-(trifluoromethyl)-1H-pyrazole-1-carboxylate (Example 154, Step 1, 353 mg, 1.17 mmol, 1.00 equiv) and triethylamine (356 mg, 3.52 mmol, 3.00 equiv). The resulting solution was stirred overnight at room temperature and quenched by water (40 mL). The resulting solution was extracted with dichloromethane (3×80 mL) and the organic layers were combined, washed with water (3×20 mL), dried over anhydrous sodium sulfate, filtered and concentrated under reduced pressure. The crude product was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C₁₈, 19*150 mm 5 μm; Mobile phase: Phase A: aqueous NH₄HCO₃ (0.05%); Phase B: CH₃CN; Detector, UV220 & 254 nm. Purification provided N-methyl-N-[2-(N-methylmethanesulfonamido)ethyl]-4-(trifluoromethyl)-1H-pyrazole-1-carboxamide (240.2 mg, 62% yield) as a white solid. ¹H NMR (300 MHz, Chloroform-d) δ 8.44 (s, 1H), 7.81 (s, 1H), 3.72-3.90 (m, 2H), 3.24-3.52 (m, 5H), 2.84-2.93 (m, 6H). LCMS (ESI, m/z): 329 [M+H]⁺.

Example 196: N,4-Dimethyl-N-(2-(N-methylmethylsulfonamido)ethyl)-1H-pyrazole-1-carboxamide

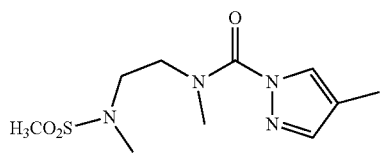

The title compound was synthesized from N-methyl-N-(2-(methylamino)ethyl)methanesulfonamide (Example 195, Steps 1-2) and 4-nitrophenyl 4-methyl-1H-pyrazole-1-carboxylate according to the representative procedure of Example 195, Steps 1-5 to provide N,4-dimethyl-N-[2-(N-methylmethanesulfonamido)ethyl]-1H-pyrazole-1-carboxamide (106.5 mg, 61% yield) as a white solid. ¹H NMR (300 MHz, Chloroform-d) δ 7.89 (s, 1H), 7.44 (s, 1H), 3.75-3.90 (m, 2H), 3.50 (t, J=6.6 Hz, 2H), 3.27 (s, 3H), 2.91 (s, 3H), 2.83 (s, 3H), 2.10 (s, 3H). LCMS (ESI, m/z): 275 [M+H]⁺.

Example 197: 4-Cyano-N-methyl-N-(2-(N-methylmethylsulfonamido)ethyl)-1H-pyrazole-1-carboxamide

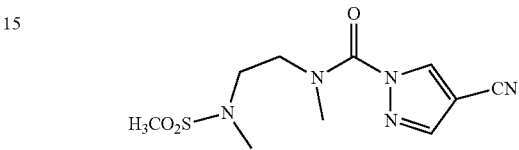

The title compound was synthesized from N-methyl-N-(2-(methylamino)ethyl)methanesulfonamide (Example 195, Steps 1-2) and 4-nitrophenyl 4-cyano-1H-pyrazole-1-carboxylate according to the representative procedure of Example 195, Steps 1-5 to provide 4-cyano-N-methyl-N-(2-(N-methylmethylsulfonamido)ethyl)-1H-pyrazole-1-carboxamide as a semi-white solid (67.7 mg, 38% yield). ¹H NMR (300 MHz, Chloroform-d) δ 8.56 (s, 1H), 7.89 (s, 1H), 3.74-3.89 (m, 2H), 3.48 (t, J=6.3 Hz, 2H), 3.24-3.35 (m, 3H), 2.84-2.96 (m, 6H). LCMS (ESI, m/z): 308 [M+Na]⁺.

Example 198: 4-Chloro-N-methyl-N-(2-(N-methylmethylsulfonamido)ethyl)-1H-pyrazole-1-carboxamide

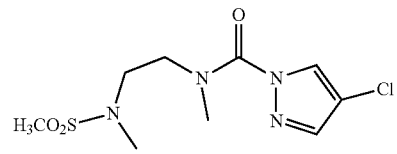

The title compound was synthesized from N-methyl-N-(2-(methylamino)ethyl)methanesulfonamide (Example 195, Steps 1-2) and 4-nitrophenyl 4-chloro-1H-pyrazole-1-carboxylate according to the representative procedure of Example 195, Steps 1-5 to provide 4-Chloro-N-methyl-N-(2-(N-methylmethylsulfonamido)ethyl)-1H-pyrazole-1-carboxamide (268.0 mg, 60% yield) as a white oil. ¹H NMR (300 MHz, Chloroform-d) δ 8.11 (s, 1H), 7.55 (s, 1H), 3.75-3.90 (m, 2H), 3.49 (t, J=6.6 Hz, 2H), 3.20-3.35 (m, 3H), 2.91 (s, 3H), 2.83 (s, 3H). LCMS (ESI, m/z): 295 [M+H]⁺.

Example 199: Pyrrolidin-1-yl(4-(trifluoromethyl)-1H-pyrazol-1-yl)methanone

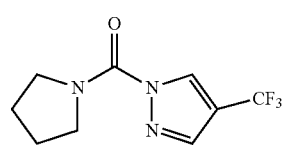 [SMILES: O=C(N1CCCC1)n1cc(C(F)(F)F)cn1]

Step 1: Preparation of pyrrolidine-1-carbonyl chloride

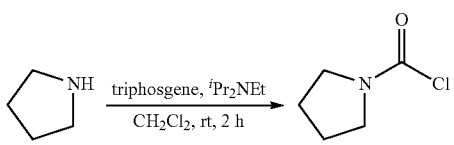 [SMILES: C1CCNC1 ; O=C(Cl)N1CCCC1]

A 40-mL vial was charged with triphosgene (0.766 g, 2.58 mmol, 0.40 equiv), pyrrolidine (0.458 g, 6.44 mmol, 1.00 equiv) and dichloromethane (10 mL). N,N-Diisopropylethylamine (1.66 g, 12.9 mmol, 2.00 equiv) in dichloromethane (5 mL) was added dropwise at 0° C. Then the resulting solution was stirred for 2 hours at room temperature and quenched by water (10 mL). The mixture was extracted with dichloromethane (3×10 mL) and the organic layers were combined, washed with water (3×10 mL), dried over anhydrous sodium sulfate, filtered and concentrated under reduced pressure to provide crude pyrrolidine-1-carbonyl chloride (0.860 g) as a brown oil.

Step 2: Preparation of pyrrolidin-1-yl(4-(trifluoromethyl)-1H-pyrazol-1-yl)methanone

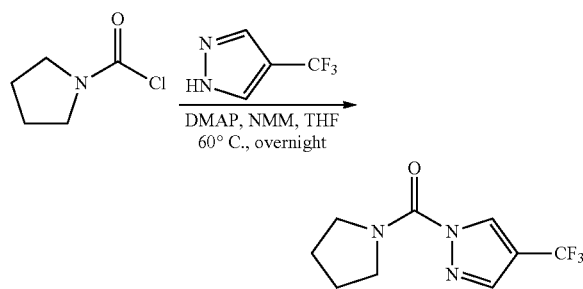

A 40-mL vial was charged with pyrrolidine-1-carbonyl chloride (197 mg, 1.47 mmol, 1.00 equiv), tetrahydrofuran (10 mL), 4-(trifluoromethyl)-1H-pyrazole (200 mg, 1.47 mmol, 1.00 equiv), 4-dimethylaminopyridine (35.9 mg, 0.291 mmol, 0.20 equiv) and N-methylmorpholine (297 mg, 2.94 mmol, 2.00 equiv). The resulting solution was stirred overnight at 60° C. and concentrated under reduced pressure. The resulting solution was diluted with water (10 mL), extracted with dichloromethane (3×10 mL) and the organic layers were combined, washed with water (3×10 mL), dried over anhydrous sodium sulfate, filtered and concentrated under reduced pressure. The crude product was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 μm; Mobile phase: Phase A: aqueous NH$_4$HCO$_3$ (0.05%); Phase B: CH$_3$CN; Detector, UV 220 & 254 nm. Purification yielded pyrrolidin-1-yl(4-(trifluoromethyl)-1H-pyrazol-1-yl)methanone (65.1 mg, 19% yield) as a yellow solid. $^1$H NMR (300 MHz, Chloroform-d) δ 8.54 (s, 1H), 7.80 (s, 1H), 3.95-3.97 (m, 2H), 3.70-3.81 (m, 2H), 1.90-2.04 (m, 4H). LCMS (ESI, m/z): 234 [M+H]$^+$.

Example 200: Piperidin-1-yl(4-(trifluoromethyl)-1H-pyrazol-1-yl)methanone

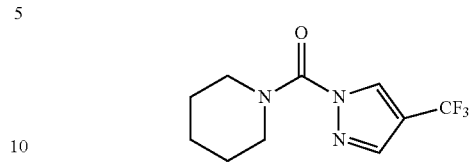

The title compound was synthesized from piperidine (219 mg, 2.58 mmol), triphosgene (306 mg, 1.03 mmol), and 4-(trifluoromethyl)-1H-pyrazole (138 mg, 1.01 mmol) according to the representative procedure of Example 199, Steps 1-2 to provide piperidin-1-yl(4-(trifluoromethyl)-1H-pyrazol-1-yl)methanone (105 mg, 42% yield) as a yellow solid. $^1$H NMR (300 MHz, Chloroform-d) δ 8.37 (s, 1H), 7.80 (s, 1H), 3.60-3.85 (m, 4H), 1.63-1.71 (m, 6H). LCMS (ESI, m/z): 248 [M+H]$^+$.

Example 201: Morpholino(4-(trifluoromethyl)-1H-pyrazol-1-yl)methanone

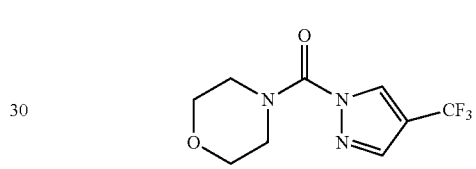

The title compound was synthesized from morpholine (128 mg, 1.47 mmol), triphosgene (175 mg, 0.591 mmol), and 4-(trifluoromethyl)-1H-pyrazole (200 mg, 1.47 mmol) according to the representative procedure of Example 199, Steps 1-2 to provide morpholino(4-(trifluoromethyl)-1H-pyrazol-1-yl)methanone (111 mg, 30% yield) as a light yellow oil. $^1$H NMR (300 MHz, Chloroform-d) δ 8.43 (s, 1H), 8.13 (s, 1H), 3.56-4.07 (m, 8H). LCMS (ESI, m/z): 250 [M+H]$^+$.

Example 202: (4-Phenylpiperazin-1-yl)(4-(trifluoromethyl)-1H-pyrazol-1-yl)methanone

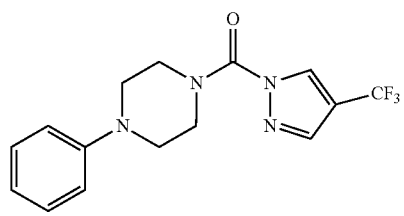 [SMILES: O=C(N1CCN(c2ccccc2)CC1)n1cc(C(F)(F)F)cn1]

The title compound was synthesized from 1-phenylpiperazine (238 mg, 1.47 mmol), triphosgene (175 mg, 0.590 mmol), and 4-(trifluoromethyl)-1H-pyrazole (200 mg, 1.47 mmol) according to the representative procedure of Example 199, Steps 1-2 to provide (4-phenylpiperazin-1-yl)(4-(trifluoromethyl)-1H-pyrazol-1-yl)methanone (75.5 mg, 16% yield) as a white solid. $^1$H NMR (300 MHz, Chloroform-d) δ 8.45 (s, 1H), 7.89 (s, 1H), 7.26-7.48 (m, 2H), 6.91-6.96 (m, 3H), 4.18-4.93 (m, 4H), 3.30 (m, 4H). LCMS (ESI, m/z): 325 [M+H]$^+$.

Example 203: 1-(Pyrrolidine-1-carbonyl)-1H-pyrazole-4-carbonitrile

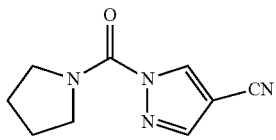 [SMILES: N#Cc1cnn(C(=O)N2CCCC2)c1]

The title compound was synthesized from pyrrolidine (0.458 mg, 6.44 mmol), triphosgene (0.766 g, 2.58 mmol), and 1H-pyrazole-4-carbonitrile (200 mg, 2.15 mmol) according to the representative procedure of Example 199, Steps 1-2 to provide 1-(Pyrrolidine-1-carbonyl)-1H-pyrazole-4-carbonitrile (115.1 mg, 28% yield) as a white solid. $^1$H NMR (300 MHz, Chloroform-d) δ 8.66 (s, 1H), 7.87 (s, 1H), 3.95 (t, J=6.0 Hz, 2H), 3.69 (t, J=6.0 Hz, 2H), 1.94-1.99 (m, 4H). LCMS (ESI, m/z): 213 [M+Na]$^+$.

Example 204: 1-(4-(4-Chlorobenzyl)piperazine-1-carbonyl)-1H-pyrazole-4-carboxamide

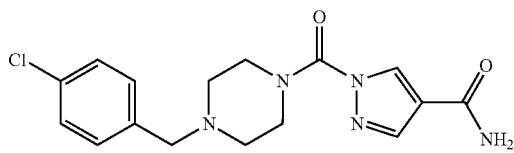 [SMILES: NC(=O)c1cnn(C(=O)N2CCN(Cc3ccc(Cl)cc3)CC2)c1]

Step 1: Preparation of 4-(4-chlorobenzyl)piperazine-1-carbonyl chloride

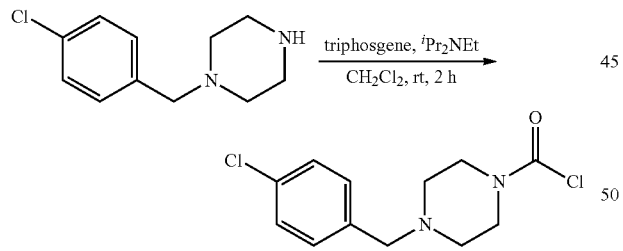

A 100-mL round-bottom flask was charged with 1-[(4-chlorophenyl)methyl]piperazine (105 mg, 0.498 mmol, 1.00 equiv), triphosgene (74.7 mg, 0.251 mmol, 0.50 equiv) and dichloromethane (10 mL). N,N-Diisopropylethylamine (129 mg, 1.00 mmol, 2.01 equiv) was added dropwise at 0° C. The resulting solution was stirred for 2 hours at room temperature and quenched by water (10 ml). The mixture was extracted with dichloromethane (3×30 mL) and the organic layers were combined, washed with water (3×10 mL), dried over anhydrous sodium sulfate, filtered and concentrated under reduced pressure to provide crude of 4-(4-chlorobenzyl)piperazine-1-carbonyl chloride (112 mg) as brown oil.

Step 2: Preparation of 1-(4-(4-chlorobenzyl)piperazine-1-carbonyl)-1H-pyrazole-4-carboxamide

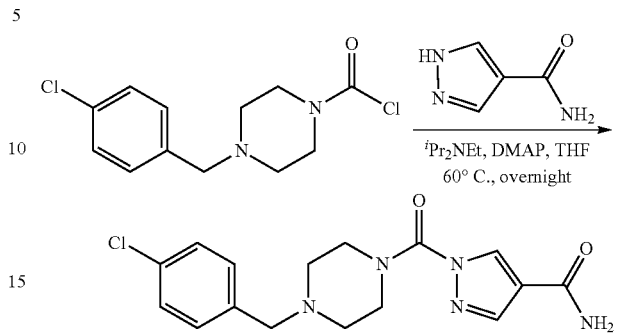

A 100-mL round-bottom flask was charged with 44-(4-chlorobenzyl)piperazine-1-carbonyl chloride (110 mg, 0.403 mmol, 1.00 equiv), 1H-pyrazole-4-carboxamide (45.1 mg, 0.406 mmol, 1.00 equiv), tetrahydrofuran (10 mL), N,N-diisopropylethylamine (103 mg, 0.800 mmol, 2.00 equiv) and 4-dimethylaminopyridine (10.1 mg, 0.0827 mmol, 0.21 equiv). The resulting solution was stirred overnight at 60° C. and quenched by water (10 mL). The mixture was extracted with dichloromethane (3×30 mL) and the organic layers were combined, washed with water (3×10 mL), dried over anhydrous sodium sulfate, filtered and concentrated under reduced pressure. The crude product was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19×150 mm, 5 um; Mobile phase: Phase A: aqueous NH$_4$HCO$_3$ (0.05%); Phase B: CH$_3$CN; Detector, UV220 & 254 nm. Purification yielded of 1-(4-(4-chlorobenzyl)piperazine-1-carbonyl)-1H-pyrazole-4-carboxamide (79.6 mg, 57% yield) as a white solid. $^1$H NMR (300 MHz, DMSO-d$_6$) δ 8.65 (s, 1H), 8.05 (s, 1H), 7.78 (s, 1H), 7.28-7.52 (m, 4H), 7.24 (s, 1H), 3.60-3.81 (m, 4H), 3.45-3.56 (m, 2H), 2.35-2.51 (m, 4H). LCMS (ESI, m/z): 348 [M+H]$^+$.

Example 205: 1-(Morpholine-4-carbonyl)-1H-pyrazole-4-carbonitrile

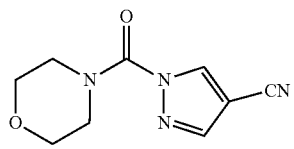 [SMILES: N#Cc1cnn(C(=O)N2CCOCC2)c1]

The title compound was synthesized from morpholine (300 mg, 3.44 mmol), triphosgene (410 mg, 1.38 mmol), and 1H-pyrazole-4-carbonitrile (385 mg, 4.14 mmol) according to the representative procedure of Example 199, Steps 1-2 to provide 1-(morpholine-4-carbonyl)-1H-pyrazole-4-carbonitrile (145 mg, 20% yield) as a white solid. $^1$H NMR (400 MHz, DMSO-d$_6$) δ 9.08 (s, 1H), 8.34 (s, 1H), 3.66 (m, 8H). LCMS (ESI, m/z): 229 [M+Na]$^+$.

Example 206: 1-(4-Phenylpiperazine-1-carbonyl)-1H-pyrazole-4-carbonitrile

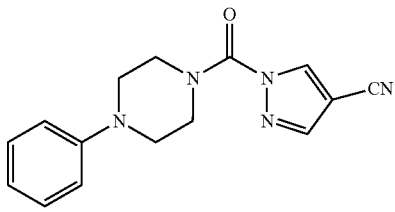 [SMILES: N#Cc1cnn(C(=O)N2CCN(c3ccccc3)CC2)c1]

The title compound was synthesized from 1-phenylpiperazine (349 mg, 2.15 mmol), triphosgene (255 mg, 0.860 mmol), and 1H-pyrazole-4-carbonitrile (200 mg, 2.15 mmol) according to the representative procedure of Example 199, Steps 1-2 to provide 1-(4-phenylpiperazine-1-carbonyl)-1H-pyrazole-4-carbonitrile (98.7 mg, 16% yield) as a light yellow solid. $^1$H NMR (300 MHz, Chloroform-d) δ 8.57 (s, 1H), 7.90 (s, 1H), 7.28-7.36 (m, 2H), 6.96-7.14 (m, 3H), 4.15 (br, 4H), 3.30-3.37 (m, 4H). LCMS (ESI, m/z): 282 [M+H]$^+$.

Example 207: (4-(2-Methylquinolin-4-yl)piperazin-1-yl)(4-phenyl-1H-pyrazol-1-yl)methanone

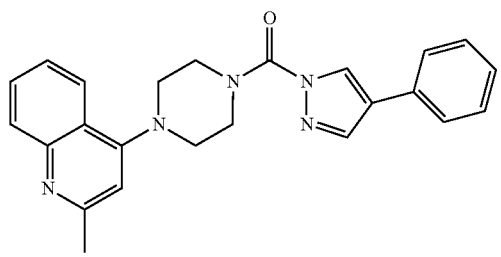 [SMILES: Cc1cc(N2CCN(C(=O)n3cc(-c4ccccc4)cn3)CC2)c2ccccc2n1]

Step 1: Preparation of 4-(2-methylquinolin-4-yl)piperazine-1-carbonyl chloride

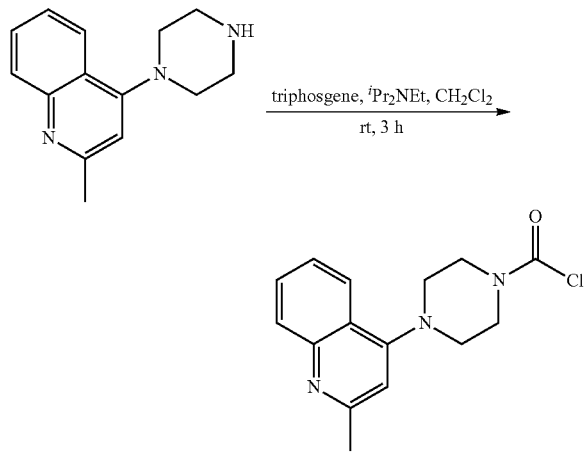

A 40-mL round-bottom flask was charged with triphosgene (588 mg, 1.98 mmol, 0.50 equiv) in dichloromethane (10 mL), 2-methyl-4-(piperazin-1-yl)quinoline (900 mg, 3.96 mmol, 1.00 equiv) under nitrogen. N,N-Diisopropylethylamine (1.02 g, 7.91 mmol, 2.00 equiv) was added dropwise at 0° C. The resulting solution was stirred for 3 h at room temperature and quenched with water (10 mL). The mixture was extracted with dichloromethane (3×20 mL) and the organic layers were combined, washed with brine (15 mL), dried over anhydrous sodium sulfate, filtered and concentrated under reduced pressure to provide 4-(2-methylquinolin-4-yl)piperazine-1-carbonyl chloride (1.14 g, 99% yield) as a tan solid. LCMS (ESI, m/z): 290 [M+H]$^+$.

Step 2: Preparation of (4-(2-methylquinolin-4-yl)piperazin-1-yl)(4-phenyl-1H-pyrazol-1-yl)methanone

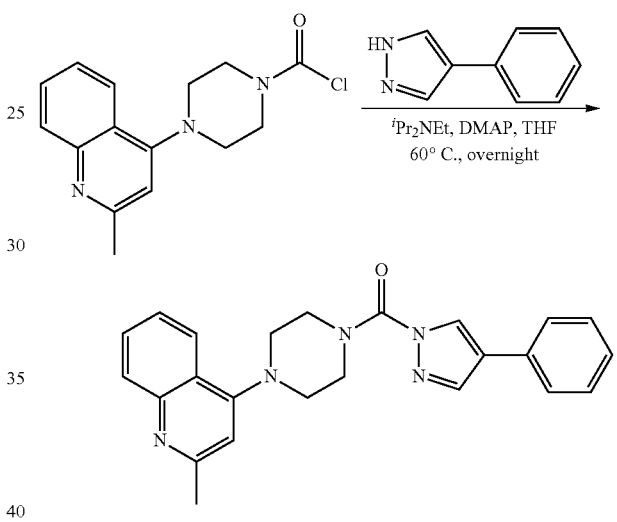

A 40-mL round-bottom flask was charged with 4-dimethylaminopyridine (14.8 mg, 0.121 mmol, 0.20 equiv), 4-(2-methylquinolin-4-yl)piperazine-1-carbonyl chloride (190 mg, 0.655 mmol, 1.00 equiv), 4-phenyl-1H-pyrazole (143 mg, 0.993 mmol, 1.50 equiv), tetrahydrofuran (5 mL) under nitrogen. N,N-Diisopropylethylamine (255 mg, 1.97 mmol, 3.00 equiv) was added. The resulting solution was stirred overnight at 60° C. and quenched with water (10 mL). The mixture was extracted with dichloromethane (3×20 mL) and the organic layers were combined, washed with brine (15 mL), dried over anhydrous sodium sulfate, filtered and concentrated under reduced pressure. The crude product (200 mg) was purified by preparative HPLC using the following gradient conditions: 30% CH$_3$CN/70% Phase A increasing to 70% CH$_3$CN over 10 min, then to 100% CH$_3$CN over 0.1 min, holding at 100% CH$_3$CN for 1.9 min, then reducing to 30% CH$_3$CN over 0.1 min, and holding at 30% for 1.9 min, on a Waters 2767-5 Chromatograph. Column: Xbridge Prep C18, 19*150 mm 5 μm; Mobile phase: Phase A: aqueous NH$_4$HCO$_3$ (0.05%); Phase B: CH$_3$CN; Detector, UV 220 & 254 nm. Purification provided (4-(2-methylquinolin-4-yl)piperazin-1-yl)(4-phenyl-1H-pyrazol-1-yl)methanone (46.2 mg, 18% yield) as an off-white solid. $^1$H NMR (300 MHz, Chloroform-d) δ 8.41 (s, 1H), 8.12 (br, 1H), 7.95-8.01 (m, 2H), 7.66-7.71 (m, 1H), 7.50-7.61 (m, 3H), 7.31-7.47 (m, 2H), 7.28-7.36 (m, 1H), 6.79 (s, 1H), 4.22 (br, 4H), 3.41 (br, 4H), 2.74 (s, 3H). LCMS (ESI, m/z): 398 [M+H]+.

Example 208: (4-Chloro-1H-pyrazol-1-yl)(4-(2-methylquinolin-4-yl)piperazin-1-yl)methanone

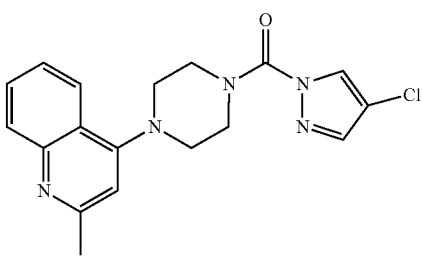 [SMILES: Cc1cc(N2CCN(C(=O)n3cc(Cl)cn3)CC2)c2ccccc2n1]

The title compound was synthesized from 4-(2-methylquinolin-4-yl)piperazine-1-carbonyl chloride (191 mg, 0.655 mmol, Example 207, Step 1), and 4-chloro-1H-pyrazole (101 mg, 0.990 mmol) according to the representative procedure of Example 207, Steps 1-2 to provide (4-chloro-1H-pyrazol-1-yl)(4-(2-methylquinolin-4-yl)piperazin-1-yl)methanone (57.5 mg, 25% yield) as an orange solid. 1H NMR (300 MHz, Chloroform-d) δ 8.14 (s, 1H), 8.07 (d, J=8.1 Hz, 1H), 7.98 (d, J=5.7 Hz, 1H), 7.65-7.70 (m, 1H), 7.59 (s, 1H), 7.45-7.51 (m, 1H), 6.78 (s, 1H), 4.16 (br, 4H), 3.35 (t, J=4.8 Hz, 4H), 2.72 (s, 3H). LCMS (ESI, m/z): 356 [M+H]+.

Example 209: 1-(4-(2-Methylquinolin-4-yl)piperazine-1-carbonyl)-1H-pyrazole-4-carbonitrile

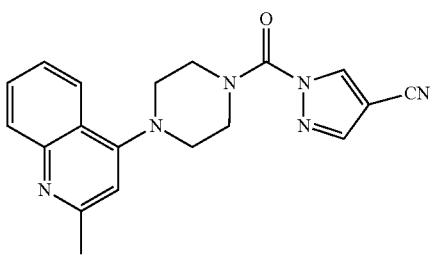 [SMILES: Cc1cc(N2CCN(C(=O)n3cc(C#N)cn3)CC2)c2ccccc2n1]

The title compound was synthesized from 4-(2-methylquinolin-4-yl)piperazine-1-carbonyl chloride (191 mg, 0.655 mmol, Example 207, Step 1), and 1H-pyrazole-4-carbonitrile (92.1 mg, 0.990 mmol) according to the representative procedure of Example 207, Steps 1-2 to provide 1-(4-(2-methylquinolin-4-yl)piperazine-1-carbonyl)-1H-pyrazole-4-carbonitrile (103.3 mg, 45% yield) as a yellow solid. 1H NMR (300 MHz, Chloroform-d) δ 8.61 (s, 1H), 7.97-8.04 (m, 2H), 7.93 (s, 1H), 7.66-7.70 (m, 1H), 7.47-7.51 (m, 1H), 6.80 (s, 1H), 4.17 (br, 4H), 3.35 (t, J=3.6 Hz, 4H), 2.72 (s, 3H). LCMS (ESI, m/z): 347 [M+H]+.

Example 210: (4-(2-Methylquinolin-4-yl)piperazin-1-yl)(4-(trifluoromethyl)-1H-pyrazol-1-yl)methanone

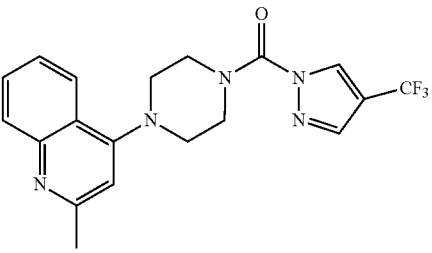 [SMILES: Cc1cc(N2CCN(C(=O)n3cc(C(F)(F)F)cn3)CC2)c2ccccc2n1]

The title compound was synthesized from 4-(2-methylquinolin-4-yl)piperazine-1-carbonyl chloride (191 mg, 0.655 mmol, Example 207, Step 1), and 4-trifluoromethyl-1H-pyrazole (135 mg, 0.993 mmol) according to the representative procedure of Example 207, Steps 1-2 to provide (4-(2-methylquinolin-4-yl)piperazin-1-yl)(4-(trifluoromethyl)-1H-pyrazol-1-yl)methanone (179.6 mg, 70% yield) as a yellow solid. 1H NMR (300 MHz, Chloroform-d) δ 8.47 (s, 1H), 7.97-8.05 (m, 2H), 7.85 (s, 1H), 7.64-7.70 (m, 1H), 7.45-7.51 (m, 1H), 6.79 (s, 1H), 4.17 (br, 4H), 3.35 (t, J=4.8 Hz, 4H), 2.71 (s, 3H). LCMS (ESI, m/z): 390 [M+H]+.

Example 211: (4-Chloro-1H-pyrazol-1-yl)(4-(3,4-dichlorobenzyl)piperazin-1-yl)methanone

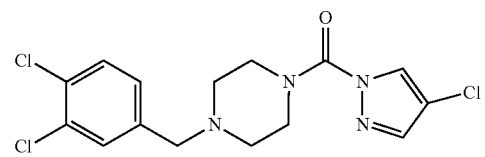 [SMILES: O=C(N1CCN(Cc2ccc(Cl)c(Cl)c2)CC1)n1cc(Cl)cn1]

Step 1: Preparation of tert-butyl 4-(chlorocarbonyl)piperazine-1-carboxylate

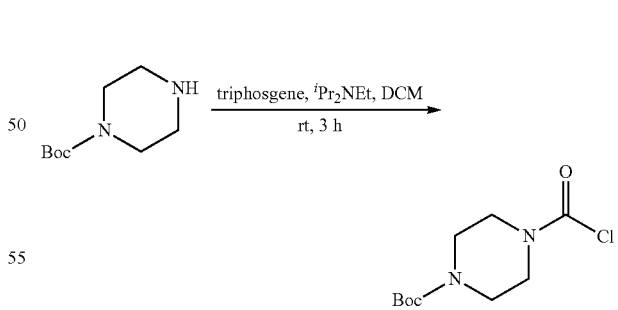

A 100-mL round-bottom flask was charged with triphosgene (3.19 g, 10.7 mmol, 0.50 equiv), dichloromethane (30 mL). Tert-butyl piperazine-1-carboxylate (4.00 g, 21.5 mmol, 1.00 equiv) in dichloromethane (30 mL) was added dropwise at 0° C. N,N-Diisopropylethylamine (5.55 g, 42.9 mmol, 2.00 equiv) was added dropwise at 0° C. The resulting solution was stirred for 3 h at room temperature and quenched with water (30 mL). The mixture was extracted with dichloromethane (3×40 mL) and the organic layers were combined, washed with brine (3×10 mL), dried over anhydrous sodium sulfate, filtered and concentrated under reduced pressure to yield tert-butyl 4-(carbonochloridoyl)piperazine-1-carboxylate (5.33 g, 100% yield) as a yellow solid. LCMS (ESI, m/z): 249 [M+H]+.

Step 2: Preparation of tert-butyl 4-(4-chloro-1H-pyrazole-1-carbonyl)piperazine-1-carboxylate

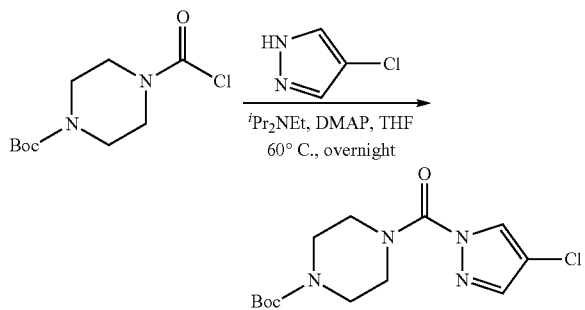

A 100-mL round-bottom flask was charged with tert-butyl 4-(carbonochloridoyl)piperazine-1-carboxylate (5.33 g, 21.4 mmol, 1.00 equiv), 4-chloro-1H-pyrazole (2.63 g, 25.7 mmol, 1.20 equiv), 4-dimethylaminopyridine (0.482 g, 3.95 mmol, 0.20 equiv), tetrahydrofuran (50 mL) under nitrogen. N,N-Diisopropylethylamine (8.32 g, 64.4 mmol, 3.00 equiv) was added. The resulting solution was stirred overnight at 60° C. and quenched with water (30 mL). The mixture was extracted with dichloromethane (3×30 mL) and the organic layers were combined, washed with brine (30 mL), dried over anhydrous sodium sulfate, filtered and concentrated under reduced pressure. The residue was chromatographed on a silica gel column with petroleum ether/ethyl acetate (5/1) to yield tert-butyl 4-[(4-chloro-1H-pyrazol-1-yl)carbonyl]piperazine-1-carboxylate (5.87 g, 87% yield) as a yellow solid. LCMS (ESI, m/z): 315 [M+H]+.

Step 3: Preparation of (4-chloro-1H-pyrazol-1-yl)(piperazin-1-yl)methanone

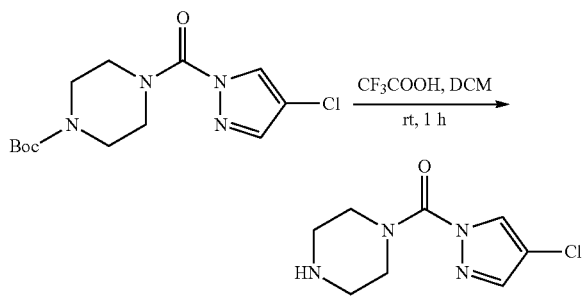

A 100-mL round-bottom flask was charged with tert-butyl 4-[(4-chloro-1H-pyrazol-1-yl)carbonyl]piperazine-1-carboxylate (3.45 g, 11.0 mmol, 1.00 equiv), trifluoroacetic acid (5 mL), dichloromethane (20 mL). The resulting solution was stirred for 1 h at room temperature and concentrated under reduced pressure. The pH value of the solution was adjusted to 9 with NaOH solution (1M). The mixture was extracted with dichloromethane (3×40 mL) and the organic layers were combined, washed with brine (30 mL), dried over anhydrous sodium sulfate, filtered and concentrated under reduced pressure to yield (4-chloro-1H-pyrazol-1-yl)(piperazin-1-yl)methanone (2.35 g, 100% yield) as yellow oil. LCMS (ESI, m/z): 215 [M+H]+.

Step 4: Preparation of (4-chloro-1H-pyrazol-1-yl)(4-(3,4-dichlorobenzyl)piperazin-1-yl)methanone

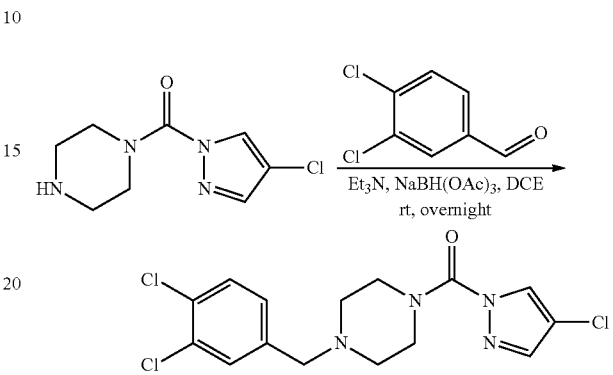

A 40-mL round-bottom flask was charged with 1-[(4-chloro-1H-pyrazol-1-yl)carbonyl]piperazine (163 mg, 0.762 mmol, 1.00 equiv), 3,4-dichlorobenzaldehyde (200 mg, 1.14 mmol, 1.50 equiv), 1,2-dichloroethane (10 mL), triethylamine (230 mg, 2.28 mmol, 3.00 equiv). The resulting solution was stirred for 1 h at room temperature. Sodium triacetoxyborohydride (483 mg, 2.28 mmol, 3.00 equiv) was added. The resulting solution was stirred overnight at room temperature and quenched with water (10 mL). The mixture was extracted with dichloromethane (3×20 mL) and the organic layers were combined, washed with brine (15 mL), dried over anhydrous sodium sulfate, filtered and concentrated under reduced pressure. The crude product (200 mg) was purified by preparative HPLC using the following gradient conditions: 30% CH$_3$CN/70% Phase A increasing to 70% CH$_3$CN over 10 min, then to 100% CH$_3$CN over 0.1 min, holding at 100% CH$_3$CN for 1.9 min, then reducing to 30% CH$_3$CN over 0.1 min, and holding at 30% for 1.9 min, on a Waters 2767-5 Chromatograph. Column: Xbridge Prep C18, 19*150 mm 5 μm; Mobile phase: Phase A: aqueous NH$_4$HCO$_3$ (0.05%); Phase B: CH$_3$CN; Detector, UV 220 & 254 nm. Purification provided (4-chloro-1H-pyrazol-1-yl)(4-(3,4-dichlorobenzyl)piperazin-1-yl)methanone (135.9 mg, 48% yield) as a white solid. $^1$H NMR (300 MHz, Chloroform-d) δ 8.07 (s, 1H), 7.54 (s, 1H), 7.38-7.45 (m, 2H), 7.15-7.18 (m, 1H), 3.85 (br, 4H), 3.49 (s, 2H), 2.53 (t, J=5.1 Hz, 4H). LCMS (ESI, m/z): 373 [M+H]+.

Example 212: (4-Chloro-1H-pyrazol-1-yl)(4-(4-(pyrrolidin-1-yl)benzyl)piperazin-1-yl)methanone

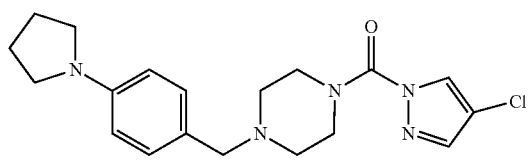 [SMILES: O=C(N1CCN(Cc2ccc(N3CCCC3)cc2)CC1)n1cc(Cl)cn1]

The title compound was synthesized from (4-chloro-1H-pyrazol-1-yl)(piperazin-1-yl)methanone (164 mg, 0.762 mmol, Example 211, Steps 1-3), and 4-(pyrrolidin-1-yl)benzaldehyde (200 mg, 1.14 mmol) according to the representative procedure of Example 211, Steps 1-4 to provide (4-chloro-1H-pyrazol-1-yl)(4-(4-(pyrrolidin-1-yl)benzyl)piperazin-1-yl)methanone (112.0 mg, 39% yield) as a white solid. $^1$H NMR (300 MHz, Chloroform-d) δ 8.05 (s, 1H), 7.53 (s, 1H), 7.14 (d, J=8.4 Hz, 2H), 6.50-6.54 (m, 2H), 3.82 (br, 4H), 3.50 (s, 2H), 3.27 (t, J=6.6 Hz, 4H), 2.52 (t, J=5.1 Hz, 4H), 1.94-2.05 (m, 4H). LCMS (ESI, m/z): 396 [M+Na]$^+$.

Example 213: (4-Chloro-1H-pyrazol-1-yl)(4-(4-(trifluoromethyl)benzyl)piperazin-1-yl)methanone

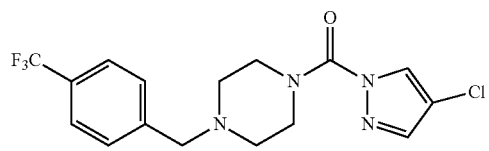 [SMILES: O=C(N1CCN(Cc2ccc(C(F)(F)F)cc2)CC1)n1cc(Cl)cn1]

The title compound was synthesized from (4-chloro-1H-pyrazol-1-yl)(piperazin-1-yl)methanone (163 mg, 0.762 mmol, Example 211, Steps 1-3), and 4-(trifluoromethyl)benzaldehyde (200 mg, 1.15 mmol) according to the representative procedure of Example 211, Steps 1-4 to provide (4-chloro-1H-pyrazol-1-yl)(4-(4-(trifluoromethyl)benzyl)piperazin-1-yl)methanone as a white solid. $^1$H NMR (300 MHz, Chloroform-d) δ 8.07 (s, 1H), 7.59 (d, J=8.1 Hz, 2H), 7.54 (s, 1H), 7.46 (d, J=8.1 Hz, 2H), 3.87 (br, 4H), 3.59 (s, 2H), 2.55 (t, J=5.1 Hz, 4H). LCMS (ESI, m/z): 373 [M+H]$^+$.

Example 214: (4-Chloro-1H-pyrazol-1-yl)(4-(4-(morpholinomethyl)benzyl)piperazin-1-yl)methanone

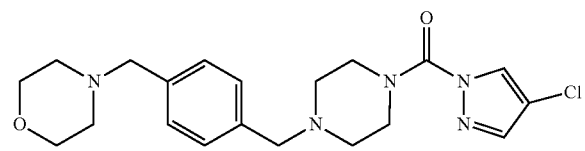 [SMILES: O=C(N1CCN(Cc2ccc(CN3CCOCC3)cc2)CC1)n1cc(Cl)cn1]

Step 1: Preparation of 4-(morpholinomethyl)benzonitrile

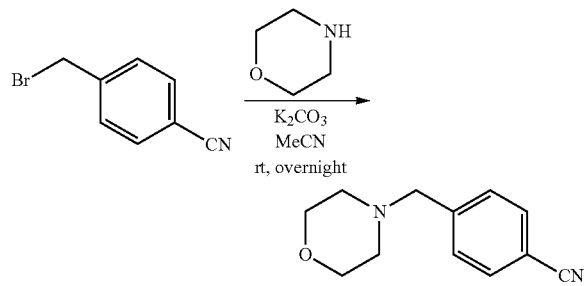

A 250-mL round-bottom flask was charged with 4-(bromomethyl)benzonitrile (10.0 g, 51.0 mmol, 1.00 equiv) in acetonitrile (30 mL) under nitrogen. Morpholine (6.70 g, 76.9 mmol, 1.50 equiv), potassium carbonate (14.2 g, 103 mmol, 2.00 equiv) was added. The resulting solution was stirred overnight at room temperature and quenched with water (20 mL). The resulting solution was extracted with ethyl acetate (3×20 mL) and the organic layers were combined, washed with brine (2×20 mL), dried over sodium sulfate, filtered and concentrated under reduced pressure. The residue was chromatographed on a silica gel column with ethyl acetate/petroleum ether (1/2) to provide 4-(morpholin-4-ylmethyl)benzonitrile (8.84 g, 86% yield) as an off-white solid. LCMS (ESI, m/z): 203 [M+H]$^+$ Step 2: Preparation of 4-(morpholinomethyl)benzaldehyde

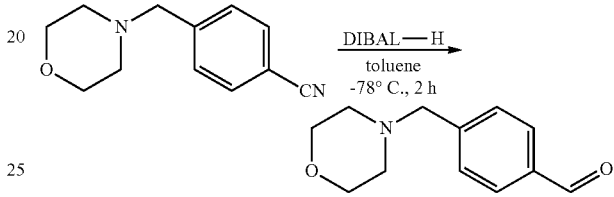

A 500-mL round-bottom flask was charged with 4-(morpholin-4-ylmethyl)benzonitrile (8.54 g, 42.2 mmol, 1.00 equiv) in toluene (50 mL). Diisobutylaluminum hydride (1M in hexane, 84.5 mL, 84.5 mmol, 2.00 equiv) was added dropwise at −78° C. The resulting solution was stirred for 2 h at −78° C. and quenched with saturated NH$_4$Cl solution (50 mL). The resulting solution was extracted with ethyl acetate (3×50 mL) and the organic layers were combined, washed with brine (2×50 mL), dried over anhydrous sodium sulfate, filtered and concentrated under reduced pressure. The residue was chromatographed on a silica gel column with ethyl acetate/petroleum ether (1/4) to yield 4-(morpholin-4-ylmethyl)benzaldehyde (8.50 g, 98% yield) as a yellow solid. LCMS (ESI, m/z): 206 [M+H]$^+$.

Step 3: Preparation of (4-chloro-1H-pyrazol-1-yl)(4-(4-(morpholinomethyl)benzyl) piperazin-1-yl)methanone

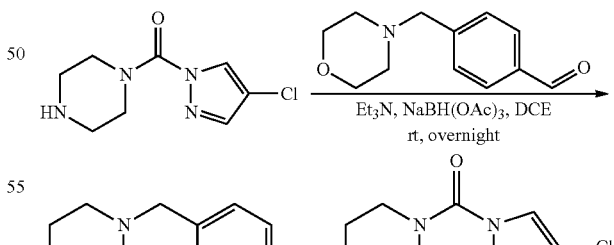

A 40-mL round-bottom flask was charged with 1-[(4-chloro-1H-pyrazol-1-yl)carbonyl]piperazine (200 mg, 0.935 mmol, 1.00 equiv, Example 211, Steps 1-3), 4-(morpholin-4-ylmethyl)benzaldehyde (192 mg, 0.935 mmol, 1.00 equiv), 1,2-dichloroethane (10 mL), triethylamine (230 mg, 2.28 mmol, 3.00 equiv). The resulting solution was stirred for 1 h at room temperature. Sodium triacetoxyborohydride (483 mg, 2.28 mmol, 3.00 equiv) was added. The resulting solution was stirred overnight at room temperature and quenched with water (10 mL). The mixture was extracted with dichloromethane (3×20 mL) and the organic layers were combined, washed with brine (15 mL), dried over anhydrous sodium sulfate, filtered and concentrated under reduced pressure. The crude product (200 mg) was purified by preparative HPLC using the following gradient conditions: 30% CH$_3$CN/70% Phase A increasing to 70% CH$_3$CN over 10 min, then to 100% CH$_3$CN over 0.1 min, holding at 100% CH$_3$CN for 1.9 min, then reducing to 30% CH$_3$CN over 0.1 min, and holding at 30% for 1.9 min, on a Waters 2767-5 Chromatograph. Column: Xbridge Prep C18, 19*150 mm 5 µm; Mobile phase: Phase A: aqueous NH$_4$HCO$_3$ (0.05%); Phase B: CH$_3$CN; Detector, UV 220 & 254 nm. Purification yielded (4-chloro-1H-pyrazol-1-yl)(4-(4-(morpholinomethyl)benzyl)piperazin-1-yl)methanone (156.6 mg, 42% yield) as a white solid. $^1$H NMR (300 MHz, Chloroform-d) δ 8.06 (s, 1H), 7.53 (s, 1H), 7.25-7.31 (m, 4H), 3.84 (br, 4H), 3.01 (t, J=4.8 Hz, 4H), 3.53 (s, 2H), 3.49 (s, 2H), 2.53 (t, J=5.1 Hz, 4H), 2.44 (t, J=4.5 Hz, 4H). LCMS (ESI, m/z): 404 [M+H]$^+$.

Example 215: (4-Chloro-1H-pyrazol-1-yl)(4-(cyclopropylmethyl)piperazin-1-yl)methanone

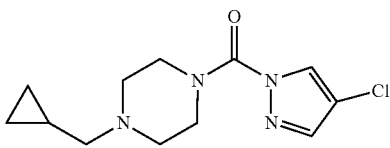 [SMILES: O=C(N1CCN(CC2CC2)CC1)n1cc(Cl)cn1]

The title compound was synthesized from (4-chloro-1H-pyrazol-1-yl)(piperazin-1-yl)methanone (163 mg, 0.762 mmol, Example 211, Steps 1-3), and cyclopropanecarbaldehyde (53.3 mg, 0.762 mmol) according to the representative procedure of Example 211, Steps 1-4 to provide (4-chloro-1H-pyrazol-1-yl)(4-(cyclopropylmethyl)piperazin-1-yl)methanone (108.0 mg, 98% yield) as a white solid. $^1$H NMR (300 MHz, Chloroform-d) δ 8.07 (s, 1H), 7.55 (s, 1H), 3.88 (br, 4H), 2.63 (t, J=5.1 Hz, 4H), 2.30 (d, J=6.6 Hz, 2H), 0.83-0.94 (m, 1H), 0.51-0.57 (m, 2H), 0.09-0.14 (m, 2H). LCMS (ESI, m/z): 269 [M+H]$^+$.

Example 216: (4-Chloro-1H-pyrazol-1-yl)(4-(3-phenoxybenzyl)piperazin-1-yl)methanone

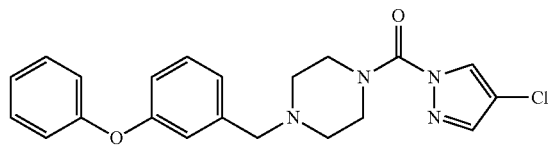 [SMILES: O=C(N1CCN(Cc2cccc(Oc3ccccc3)c2)CC1)n1cc(Cl)cn1]

The title compound was synthesized from (4-chloro-1H-pyrazol-1-yl)(piperazin-1-yl)methanone (185 mg, 0.935 mmol, Example 211, Steps 1-3), and 3-phenoxybenzaldehyde (200 mg, 1.01 mmol) according to the representative procedure of Example 211, Steps 1-4 to provide (4-Chloro-1H-pyrazol-1-yl)(4-(3-phenoxybenzyl)piperazin-1-yl)methanone (231.5 mg, 68% yield) as a yellow oil. $^1$H NMR (300 MHz, Chloroform-d) δ 8.06 (s, 1H), 7.53 (s, 1H), 7.25-7.37 (m, 3H), 6.87-7.13 (m, 6H), 3.83 (br, 4H), 3.49 (s, 2H), 2.53 (t, J=5.1 Hz, 4H). LCMS (ESI, m/z): 397 [M+H]$^+$.

Example 217: (4-Chloro-1H-pyrazol-1-yl)(4-(4-morpholinobenzyl)piperazin-1-yl)methanone

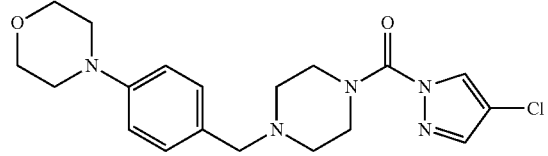 [SMILES: O=C(N1CCN(Cc2ccc(N3CCOCC3)cc2)CC1)n1cc(Cl)cn1]

The title compound was synthesized from (4-chloro-1H-pyrazol-1-yl)(piperazin-1-yl)methanone (200 mg, 0.935 mmol, Example 211, Steps 1-3) and 4-(morpholin-4-yl)benzaldehyde (179 mg, 0.935 mmol) according to the representative procedure of Example 211, Steps 1-4 to provide (4-chloro-1H-pyrazol-1-yl)(4-(4-morpholinobenzyl)piperazin-1-yl)methanone (95.7 mg, 26% yield) as a white solid. $^1$H NMR (300 MHz, Chloroform-d) δ 8.06 (s, 1H), 7.53 (s, 1H), 7.21 (d, J=5.7 Hz, 2H), 6.87 (d, J=5.7 Hz, 2H), 3.86 (t, J=4.5 Hz, 8H), 3.47 (s, 2H), 3.15 (t, J=5.1 Hz, 4H), 2.51 (t, J=5.1 Hz, 4H). LCMS (ESI, m/z): 412 [M+Na]$^+$.

Example 218: (4-Chloro-1H-pyrazol-1-yl)(4-(2-methyl-4-morpholinobenzyl)piperazin-1-yl)methanone

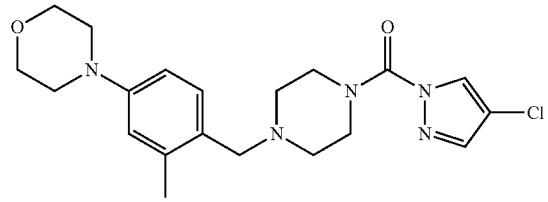 [SMILES: Cc1cc(N2CCOCC2)ccc1CN1CCN(C(=O)n2cc(Cl)cn2)CC1]

The title compound was synthesized from (4-chloro-1H-pyrazol-1-yl)(piperazin-1-yl)methanone (200 mg, 0.935 mmol, Example 211, Steps 1-3) and 2-methyl-4-(morpholin-4-yl)benzaldehyde (192 mg, 0.935 mmol) according to the representative procedure of Example 211, Steps 1-4 to provide (4-Chloro-1H-pyrazol-1-yl)(4-(2-methyl-4-morpholinobenzyl)piperazin-1-yl)methanone (171.5 mg, 46% yield) as an off-white solid. $^1$H NMR (300 MHz, Chloroform-d) δ 8.06 (s, 1H), 7.53 (s, 1H), 7.12 (d, J=5.1 Hz, 1H), 6.67-6.74 (m, 2H), 3.80-3.87 (m, 8H), 3.44 (s, 2H), 3.14 (t, J=4.8 Hz, 4H), 2.51 (s, 4H), 2.35 (s, 3H). LCMS (ESI, m/z): 426 [M+Na]$^+$.

Example 219: N-Methyl-4-phenyl-N-(3-(pyridin-4-yl)benzyl)-1H-pyrazole-1-carboxamide

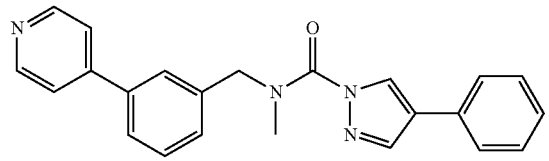 [SMILES: CN(Cc1cccc(-c2ccncc2)c1)C(=O)n1cc(-c2ccccc2)cn1]

Step 1: Preparation of methyl(3-(pyridin-4-yl)benzyl)carbamic chloride

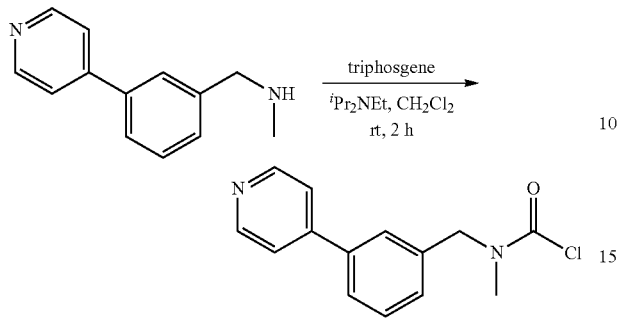

A 50-mL round-bottom flask was charged with triphosgene (150 mg, 0.510 mmol, 0.50 equiv), dichloromethane (20 mL). Methyl([[3-(pyridin-4-yl)phenyl]methyl])amine (200 mg, 1.01 mmol, 1.00 equiv) and N,N-diisopropylethylamine (261 mg, 2.02 mmol, 2.00 equiv) were added at 0° C. The resulting solution was stirred for 2 h at room temperature and quenched with water (20 mL). The mixture was extracted with dichloromethane (3×30 mL) and the organic layers were combined, washed with brine (3×50 mL), dried over anhydrous sodium sulfate, filtered and concentrated under reduced pressure to provide methyl(3-(pyridin-4-yl)benzyl)carbamic chloride (262 mg, 100% yield) as a yellow oil. LCMS (ESI, m/z): 261 [M+H]$^+$.

Step 2: Preparation of N-methyl-4-phenyl-N-(3-(pyridin-4-yl)benzyl)-1H-pyrazole-1-carboxamide

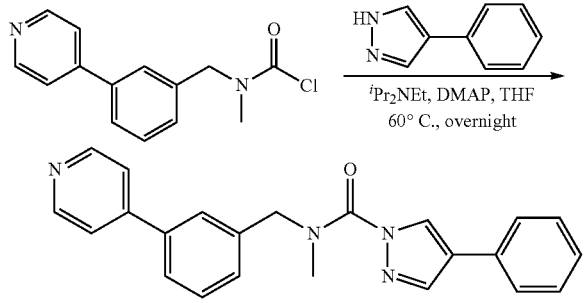

A 40-mL round-bottom flask was charged with methyl(3-(pyridin-4-yl)benzyl)carbamic chloride (260 mg, 1.00 mmol, 1.00 equiv), 4-phenyl-1H-pyrazole (173 mg, 1.20 mmol, 1.20 equiv), N,N-diisopropylethylamine (387 mg, 2.99 mmol, 3.00 equiv), 4-dimethylaminopyridine (12.2 mg, 0.100 mmol, 0.10 equiv), tetrahydrofuran (5 mL). The resulting solution was stirred overnight at 60° C. and concentrated under reduced pressure. The crude product (780 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: X-bridge Prep C$_{18}$, 19*150 mm 5 µm; Mobile phase: Phase A: aqueous NH$_4$HCO$_3$ (0.05%); Phase B: CH$_3$CN; Detector, UV 220 & 254 nm. Purification provided N-Methyl-4-phenyl-N-(3-(pyridin-4-yl)benzyl)-1H-pyrazole-1-carboxamide (25.3 mg, 7% yield) as a white solid. $^1$H NMR (300 MHz, Chloroform-d) δ 8.66 (d, J=5.7 Hz, 2H), 8.45 (s, 1H), 7.93 (s, 1H), 7.40-7.63 (m, 10H), 7.26-7.38 (m, 1H), 4.97 (br, 2H), 3.24 (br, 3H). LCMS (ESI, m/z): 369 [M+H]$^+$

Example 220: 4-Chloro-N-methyl-N-(3-(pyridin-4-yl)benzyl)-1H-pyrazole-1-carboxamide

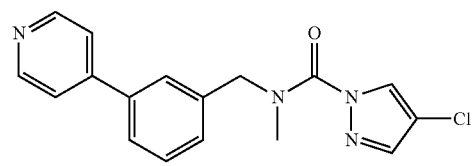 [SMILES: CN(Cc1cccc(-c2ccncc2)c1)C(=O)n1cc(Cl)cn1]

The title compound was synthesized from methyl(3-(pyridin-4-yl)benzyl)carbamic chloride (260 mg, 1.00 mmol, Example 219, Step 1), 4-chloro-1H-pyrazole (121 mg, 1.18 mmol) according to the representative procedure of Example 219, Steps 1-2 to provide 4-chloro-N-methyl-N-(3-(pyridin-4-yl)benzyl)-1H-pyrazole-1-carboxamide (99.4 mg, 31% yield) as a yellow oil. $^1$H NMR (300 MHz, Chloroform-d) δ 8.66 (d, J=5.7 Hz, 2H), 8.17 (s, 1H), 7.56-7.60 (m, 3H), 7.40-7.50 (m, 4H), 4.90 (br, 2H), 3.19 (br, 3H). LCMS (ESI, m/z): 327 [M+H]$^+$.

Example 221: 4-Cyano-N-methyl-N-(3-(pyridin-4-yl)benzyl)-1H-pyrazole-1-carboxamide

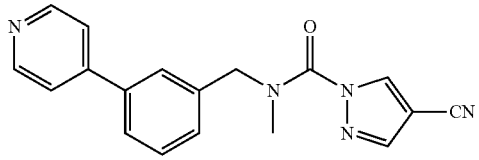 [SMILES: CN(Cc1cccc(-c2ccncc2)c1)C(=O)n1cc(C#N)cn1]

The title compound was synthesized from methyl(3-(pyridin-4-yl)benzyl)carbamic chloride (260 mg, 1.00 mmol, Example 219, Step 1) and 1H-pyrazole-4-carbonitrile (110 mg, 1.18 mmol) according to the representative procedure of Example 219, Steps 1-2 to provide 4-cyano-N-methyl-N-(3-(pyridin-4-yl)benzyl)-1H-pyrazole-1-carboxamide (38.3 mg, 12% yield) as a white solid. $^1$H NMR (300 MHz, Chloroform-d) δ 8.63-8.68 (m, 3H), 7.89 (s, 1H), 7.60-7.68 (m, 2H), 7.42-7.54 (m, 4H), 4.68-5.14 (m, 2H), 3.23 (br, 3H). LCMS (ESI, m/z): 318 [M+H]$^+$.

Example 222: N-methyl-N-(3-(pyridin-4-yl)benzyl)-4-(trifluoromethyl)-1H-pyrazole-1-carboxamide

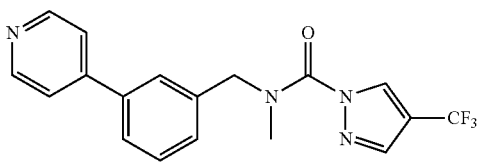 [SMILES: CN(Cc1cccc(-c2ccncc2)c1)C(=O)n1cc(C(F)(F)F)cn1]

The title compound was synthesized from methyl(3-(pyridin-4-yl)benzyl)carbamic chloride (260 mg, 1.00 mmol, Example 219, Step 1) and 4-(trifluoromethyl)-1H-pyrazole (163 mg, 1.20 mmol) according to the representative procedure of Example 219, Steps 1-2 to provide N-methyl-N-(3-(pyridin-4-yl)benzyl)-4-(trifluoromethyl)-1H-pyrazole-1-carboxamide (177.7 mg, 49% yield) as a yellow oil. $^1$H NMR (300 MHz, Chloroform-d) δ 8.67 (d, J=5.7 Hz, 2H), 8.51 (s, 1H), 7.82 (s, 1H), 7.59-7.62 (m, 2H), 7.41-7.53 (m, 4H), 4.90 (br, 2H), 3.22 (br, 3H). LCMS (ESI, m/z): 361 [M+H]$^+$ Example 223: 1-(4-(4-Chlorobenzyl)piperazine-1-carbonyl)-N-methyl-1H-pyrazole-4-carboxamide

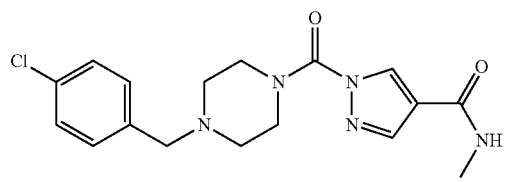 [SMILES: CNC(=O)c1cnn(C(=O)N2CCN(Cc3ccc(Cl)cc3)CC2)c1]

The title compound was synthesized from 1-(4-chlorobenzyl)piperazine and N-methyl-1H-pyrazole-4-carboxamide according to the representative procedure of Example 204, Steps 1-2 to provide 1-(4-(4-chlorobenzyl)piperazine-1-carbonyl)-N-methyl-1H-pyrazole-4-carboxamide as a white solid. $^1$H NMR (300 MHz, Chloroform-d) δ 8.45 (s, 1H), 7.92 (s, 1H), 7.26-7.35 (m, 3H), 7.21-7.25 (m, 1H), 5.95 (s, 1H), 3.72-3.99 (m, 4H), 3.42-3.60 (m, 2H), 2.95 (s, 3H), 2.45-2.62 (m, 4H). LCMS (ESI, m/z): 362 [M+H]$^+$.

Example 224: (4-Chloro-1H-pyrazol-1-yl)(4-(2-chlorobenzyl)piperazin-1-yl)methanone

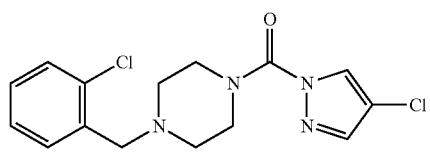 [SMILES: O=C(N1CCN(Cc2ccccc2Cl)CC1)n1cc(Cl)cn1]

Step 1: Preparation of tert-butyl 4-(2-chlorobenzyl)piperazine-1-carboxylate

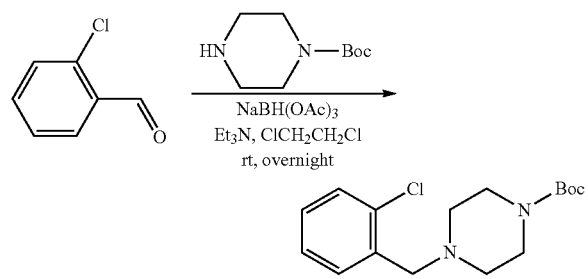

A 100-mL round-bottom flask was charged with 2-chlorobenzaldehyde (2.00 g, 14.2 mmol, 1.00 equiv) in dichloroethane (20 mL), tert-butyl piperazine-1-carboxylate (4.00 g, 21.5 mmol, 1.50 equiv), triethylamine (4.30 g, 42.6 mmol, 3.00 equiv). The resulting solution was stirred for 30 min at room temperature. Sodium triacetoxyborohydride (9.10 g, 42.9 mmol, 3.00 equiv) was added. The resulting solution was stirred overnight at room temperature and quenched with water (20 mL). The resulting solution was extracted with dichloromethane (3×20 mL) and the organic layers were combined, washed with brine (2×20 mL), dried over anhydrous sodium sulfate, filtered and concentrated under reduced pressure. The residue was chromatographed on a silica gel column with dichloromethane/methanol (20/1) to yield tert-butyl 4-[(2-chlorophenyl)methyl]piperazine-1-carboxylate (4.00 g, 90% yield) as a colorless oil. LCMS (ESI, m/z): 311 [M+H]$^+$.

Step 2: Preparation of 1-(2-chlorobenzyl)piperazine

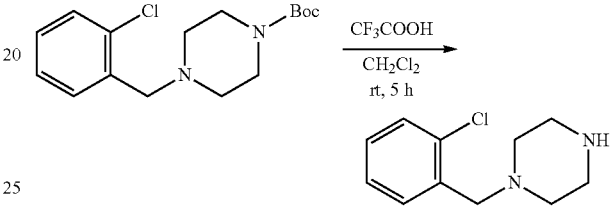

A 100 mL round-bottom flask was charged with tert-butyl 4-[(2-chlorophenyl)methyl]piperazine-1-carboxylate (1.00 g, 3.22 mmol, 1.00 equiv) in dichloromethane (20 mL), trifluoroacetic acid (5 mL). The resulting solution was stirred for 5 h at room temperature and concentrated under reduced pressure to yield 1-[(2-chlorophenyl)methyl]piperazine (660 mg, 97% yield) as yellow oil. LCMS (ESI, m/z): 211 [M+H]$^+$.

Step 3: Preparation of (4-chloro-1H-pyrazol-1-yl)(4-(2-chlorobenzyl)piperazin-1-yl)methanone

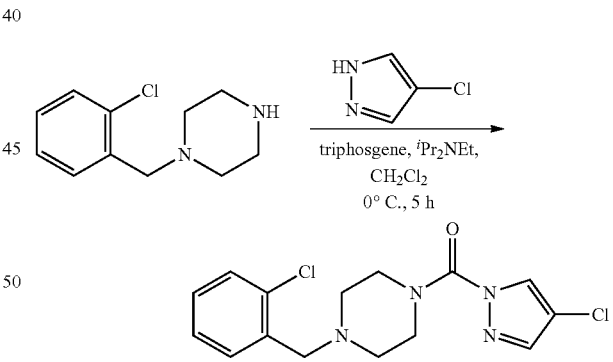

A 40-mL round-bottom flask was charged with triphosgene (117 mg, 0.390 mmol, 0.50 equiv) in dichloromethane (5 mL), 4-chloro-1H-pyrazole (120 mg, 1.17 mmol, 1.50 equiv) under nitrogen. N-Ethyl-N-isopropylpropan-2-amine (304 mg, 2.36 mmol, 3.00 equiv) was added dropwise at 0° C. The resulting solution was stirred for 2 h at 0° C. A solution of 1-[(2-chlorophenyl)methyl]piperazine (165 mg, 0.780 mmol, 1.00 equiv) in dichloromethane (5 mL) was added dropwise at 0° C. The resulting solution was stirred for 3 h at 0° C. and quenched with water (10 mL). The mixture was extracted with dichloromethane (3×10 mL) and the organic layers were combined, washed with brine (2×10 mL), dried over anhydrous sodium sulfate, filtered and Example 225: (4-Chloro-1H-pyrazol-1-yl)(4-(3-chlorobenzyl)piperazin-1-yl)methanone

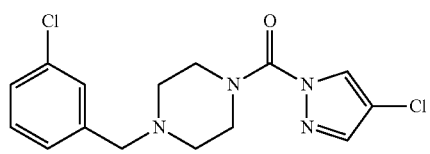 [SMILES: O=C(N1CCN(Cc2cccc(Cl)c2)CC1)n1cc(Cl)cn1]

The title compound was synthesized from 3-chlorobenzaldehyde according to the representative procedure of Example 224, Steps 1-3 to provide (4-chloro-1H-pyrazol-1-yl)(4-(3-chlorobenzyl)piperazin-1-yl)methanone (111.7 mg, 42% yield) as a light yellow semi-solid. $^1$H NMR (300 MHz, Chloroform-d) δ 8.07 (s, 1H), 7.54 (s, 1H), 7.34 (s, 1H), 7.20-7.26 (m, 3H), 3.85 (br, 4H), 3.52 (s, 2H), 2.52-2.55 (m, 4H). LCMS (ESI, m/z): 339 [M+H]$^+$.

Example 226: (4-Chloro-1H-pyrazol-1-yl)(4-(4-chlorobenzyl)piperazin-1-yl)methanone

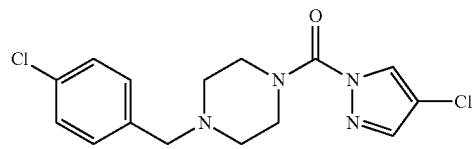 [SMILES: O=C(N1CCN(Cc2ccc(Cl)cc2)CC1)n1cc(Cl)cn1]

The title compound was synthesized from 4-chlorobenzaldehyde according to the representative procedure of Example 224, Steps 1-3 to provide (4-chloro-1H-pyrazol-1-yl)(4-(4-chlorobenzyl)piperazin-1-yl)methanone (101.0 mg, 29% yield) as a light yellow solid. $^1$H NMR (300 MHz, Chloroform-d) δ 8.06 (s, 1H), 7.54 (s, 1H), 7.24-7.32 (m, 4H), 3.84 (br, 4H), 3.51 (s, 2H), 2.51-2.54 (m, 4H). LCMS (ESI, m/z): 339 [M+H]$^+$.

Example 227: (4-(2-Chlorophenyl)piperazin-1-yl)(4-(trifluoromethyl)-1H-pyrazol-1-yl)methanone

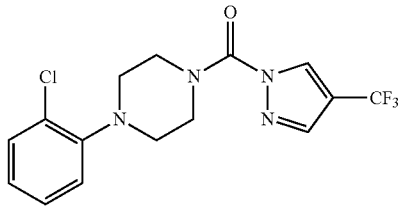

Step 1: Preparation of 4-(2-chlorophenyl)piperazine-1-carbonyl chloride

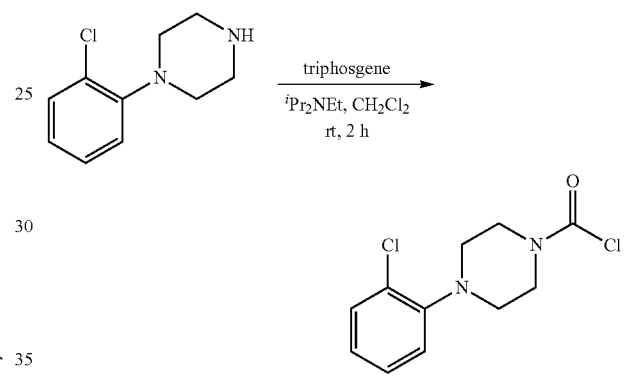

A 100-mL round-bottom flask was charged with triphosgene (0.363 g, 1.22 mmol, 0.40 equiv), dichloromethane (20 mL). 1-(2-Chlorophenyl)piperazine (0.600 g, 3.05 mmol, 1.00 equiv) was added at 0° C. N,N-Diisopropylethylamine (1.18 g, 9.13 mmol, 3.00 equiv) was added at 0° C. The resulting solution was stirred for 2 h at room temperature and quenched with H$_2$O (20 mL). The mixture was extracted with dichloromethane (3×30 mL) and the organic layers were combined, washed with brine (3×50 mL), dried over anhydrous sodium sulfate, filtered and concentrated under reduced pressure to provide 4-(2-chlorophenyl)piperazine-1-carbonyl chloride (0.780 g, 99% yield) as a yellow oil. LCMS (ESI, m/z): 259 [M+H]$^+$.

Step 2: Preparation of (4-(2-chlorophenyl)piperazin-1-yl)(4-(trifluoromethyl)-1H-pyrazol-1-yl)methanone

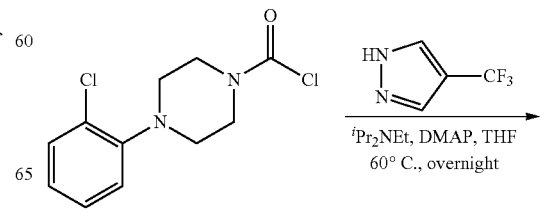

-continued

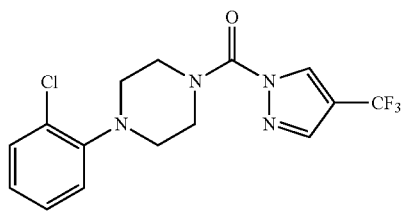 [SMILES: O=C(N1CCN(c2ccccc2Cl)CC1)n1cc(C(F)(F)F)cn1]

A 40-mL round-bottom flask was charged with 4-(2-chlorophenyl)piperazine-1-carbonyl chloride (260 mg, 1.00 mmol, 1.00 equiv), 4-(trifluoromethyl)-1H-pyrazole (165 mg, 1.21 mmol, 1.20 equiv), N,N-diisopropylethylamine (391 mg, 3.03 mmol, 3.00 equiv), 4-dimethylaminopyridine (12.3 mg, 0.100 mmol, 0.10 equiv), tetrahydrofuran (5 mL). The resulting solution was stirred overnight at 60° C. and concentrated under reduced pressure. The crude product (750 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: X-bridge Prep C$_{18}$, 19*150 mm 5 µm; Mobile phase: Phase A: aqueous NH$_4$HCO$_3$ (0.05%); Phase B: CH$_3$CN; Detector, UV 220 & 254 nm. Purification provided (4-(2-chlorophenyl)piperazin-1-yl)(4-(trifluoromethyl)-1H-pyrazol-1-yl)methanone (121.6 mg, 34% yield) as a white solid. $^1$H NMR (300 MHz, Chloroform-d) δ 8.44 (s, 1H), 7.83 (s, 1H), 7.38-7.41 (m, 1H), 7.22-7.28 (m, 1H), 7.00-7.07 (m, 2H), 4.05 (br, 4H), 3.17 (t, J=4.9 Hz, 4H). LCMS (ESI, m/z): 359 [M+H]$^+$.

Example 228: (4-(3-Chlorophenyl)piperazin-1-yl)(4-(trifluoromethyl)-1H-pyrazol-1-yl)methanone

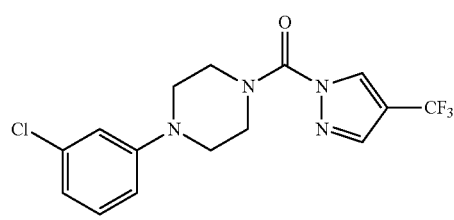 [SMILES: O=C(N1CCN(c2cccc(Cl)c2)CC1)n1cc(C(F)(F)F)cn1]

The title compound was synthesized from 1-(3-chlorophenyl)piperazine according to the representative procedure of Example 227, Steps 1-2 to provide (4-(3-chlorophenyl)piperazin-1-yl)(4-(trifluoromethyl)-1H-pyrazol-1-yl)methanone (123.0 mg, 34% yield) as a white solid. $^1$H NMR (300 MHz, Chloroform-d) δ 8.45 (s, 1H), 7.83 (s, 1H), 7.17-7.26 (m, 1H), 6.79-6.91 (m, 3H), 4.03 (br, 4H), 3.31 (t, J=5.1 Hz, 4H). LCMS (ESI, m/z): 359 [M+H]$^+$.

Example 229: (4-(4-Chlorophenyl)piperazin-1-yl)(4-(trifluoromethyl)-1H-pyrazol-1-yl)methanone

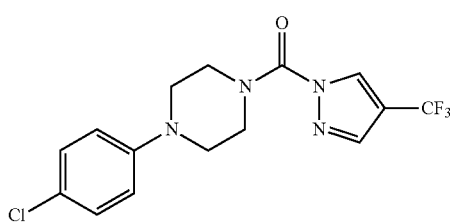 [SMILES: O=C(N1CCN(c2ccc(Cl)cc2)CC1)n1cc(C(F)(F)F)cn1]

The title compound was synthesized from 1-(4-chlorophenyl)piperazine according to the representative procedure of Example 227, Steps 1-2 to provide (4-(4-chlorophenyl)piperazin-1-yl)(4-(trifluoromethyl)-1H-pyrazol-1-yl)methanone (116.8 mg, 32% yield) as a white solid. $^1$H NMR (300 MHz, Chloroform-d) δ 8.44 (s, 1H), 7.83 (s, 1H), 7.23-7.28 (m, 2H), 6.90 (d, J=9.0 Hz, 2H), 4.05 (br, 4H), 3.28 (t, J=5.1 Hz, 4H). LCMS (ESI, m/z): 359 [M+H]$^+$.

Example 230: (4-o-Tolylpiperazin-1-yl)(4-(trifluoromethyl)-1H-pyrazol-1-yl)methanone

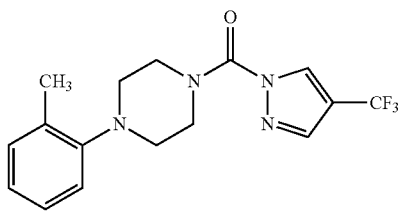 [SMILES: Cc1ccccc1N1CCN(C(=O)n2cc(C(F)(F)F)cn2)CC1]

The title compound was synthesized from 1-o-tolylpiperazine (0.800 g, 4.54 mmol), triphosgene (0.677 g, 2.28 mmol), and 4-(trifluoromethyl)-1H-pyrazole (171 mg, 1.26 mmol) according to the representative procedure of Example 227, Steps 1-2 to provide (4-o-tolylpiperazin-1-yl)(4-(trifluoromethyl)-1H-pyrazol-1-yl)methanone (198.6 mg, 56% yield) as a white solid. $^1$H NMR (300 MHz, Chloroform-d) δ 8.44 (s, 1H), 7.83 (s, 1H), 7.16-7.26 (m, 2H), 7.01-7.06 (m, 2H), 4.01 (br, 4H), 3.02 (t, J=4.9 Hz, 4H), 2.34 (s, 3H). LCMS (ESI, m/z): 339 [M+H]$^+$.

Example 231: (4-m-Tolylpiperazin-1-yl)(4-(trifluoromethyl)-1H-pyrazol-1-yl)methanone

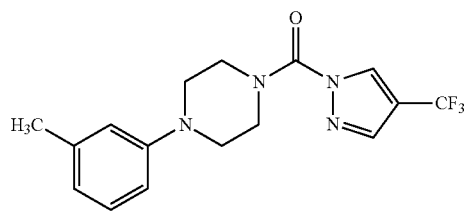 [SMILES: Cc1cccc(N2CCN(C(=O)n3cc(C(F)(F)F)cn3)CC2)c1]

The title compound was synthesized from 1-m-tolylpiperazine (0.800 g, 4.54 mmol), triphosgene (0.677 g, 2.28 mmol), and 4-(trifluoromethyl)-1H-pyrazole (171 mg, 1.26 mmol) according to the representative procedure of Example 227, Steps 1-2 to provide (4-m-tolylpiperazin-1-yl)(4-(trifluoromethyl)-1H-pyrazol-1-yl)methanone (171.5 mg, 48% yield) as a white solid. $^1$H NMR (300 MHz, Chloroform-d) δ 8.44 (s, 1H), 7.83 (s, 1H), 7.16-7.21 (m, 1H), 6.74-6.77 (m, 3H), 4.02 (br, 4H), 3.28 (t, J=5.1 Hz, 4H), 2.33 (s, 3H). LCMS (ESI, m/z): 339 [M+H]$^+$.

Example 232: (4-p-Tolylpiperazin-1-yl)(4-(trifluoromethyl)-1H-pyrazol-1-yl)methanone

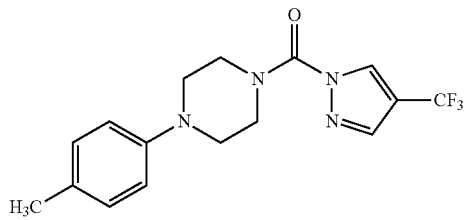

The title compound was synthesized from 1-p-tolylpiperazine (0.800 g, 4.54 mmol), triphosgene (0.677 g, 2.28 mmol), and 4-(trifluoromethyl)-1H-pyrazole (171 mg, 1.26 mmol) according to the representative procedure of Example 227, Steps 1-2 to provide (4-p-tolylpiperazin-1-yl)(4-(trifluoromethyl)-1H-pyrazol-1-yl)methanone (170.1 mg, 48% yield) as an off-white solid. $^1$H NMR (300 MHz, Chloroform-d) δ 8.44 (s, 1H), 7.83 (s, 1H), 7.11 (d, J=4.2 Hz, 2H), 6.87 (d, J=8.1 Hz, 2H), 4.03 (br, 4H), 3.24 (t, J=5.1 Hz, 4H), 2.29 (s, 3H). LCMS (ESI, m/z): 339 [M+H]$^+$.

Example 233: (4-(2-Methoxyphenyl)piperazin-1-yl)(4-(trifluoromethyl)-1H-pyrazol-1-yl)methanone

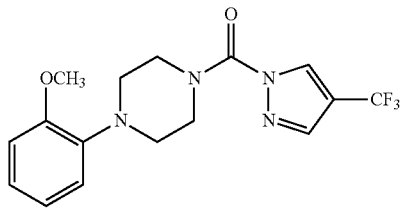 [SMILES: COc1ccccc1N1CCN(C(=O)n2cc(C(F)(F)F)cn2)CC1]

The title compound was synthesized from 1-(2-methoxyphenyl)piperazine (0.800 g, 4.16 mmol), triphosgene (0.619 g, 2.08 mmol), and 4-(trifluoromethyl)-1H-pyrazole (160 mg, 1.18 mmol) according to the representative procedure of Example 227, Steps 1-2 to provide (4-(2-methoxyphenyl)piperazin-1-yl)(4-(trifluoromethyl)-1H-pyrazol-1-yl)methanone (46.3 mg, 13% yield) as a white solid. $^1$H NMR (300 MHz, Chloroform-d) δ 8.44 (s, 1H), 7.82 (s, 1H), 6.89-7.07 (m, 4H), 3.90-4.13 (m, 7H), 3.20 (br, 4H). LCMS (ESI, m/z): 355 [M+H]$^+$.

Example 234: (4-(3-Methoxyphenyl)piperazin-1-yl)(4-(trifluoromethyl)-1H-pyrazol-1-yl)methanone

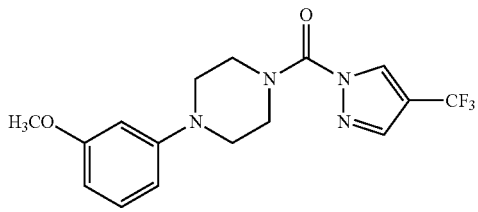 [SMILES: COc1cccc(N2CCN(C(=O)n3cc(C(F)(F)F)cn3)CC2)c1]

The title compound was synthesized from 1-(3-methoxyphenyl)piperazine (0.800 g, 4.16 mmol), triphosgene (0.619 g, 2.08 mmol), and 4-(trifluoromethyl)-1H-pyrazole (160 mg, 1.18 mmol) according to the representative procedure of Example 227, Steps 1-2 to provide (4-(3-methoxyphenyl)piperazin-1-yl)(4-(trifluoromethyl)-1H-pyrazol-1-yl)methanone (227.2 mg, 65% yield) as an off-white solid. $^1$H NMR (300 MHz, Chloroform-d) δ 8.44 (s, 1H), 7.83 (s, 1H), 7.18-7.23 (m, 1H), 6.47-6.57 (m, 3H), 4.03 (br, 4H), 3.80 (s, 3H), 3.30 (t, J=5.1 Hz, 4H). LCMS (ESI, m/z): 355 [M+H]$^+$.

Example 235: (4-(4-Methoxyphenyl)piperazin-1-yl)(4-(trifluoromethyl)-1H-pyrazol-1-yl)methanone

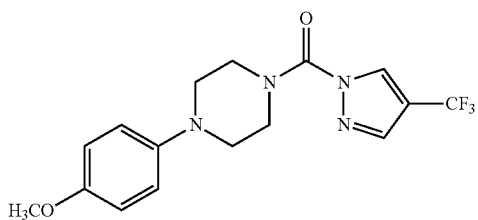 [SMILES: COc1ccc(N2CCN(C(=O)n3cc(C(F)(F)F)cn3)CC2)cc1]

The title compound was synthesized from 1-(4-methoxyphenyl)piperazine (200 mg, 1.04 mmol), triphosgene (154 mg, 0.520 mmol), and 4-(trifluoromethyl)-1H-pyrazole (160 mg, 1.18 mmol) according to the representative procedure of Example 227, Steps 1-2 to provide (4-(4-methoxyphenyl)piperazin-1-yl)(4-(trifluoromethyl)-1H-pyrazol-1-yl)methanone (152.9 mg, 40% yield) as a white solid. $^1$H NMR (300 MHz, Chloroform-d) δ 8.44 (s, 1H), 7.83 (s, 1H), 6.85-6.93 (m, 4H), 4.03 (br, 4H), 3.78 (s, 3H), 3.18 (br, 4H). LCMS (ESI, m/z): 355 [M+H]$^+$.

Example 236: (4-(2-Morpholinophenyl)piperazin-1-yl)(4-(trifluoromethyl)-1H-pyrazol-1-yl)methanone

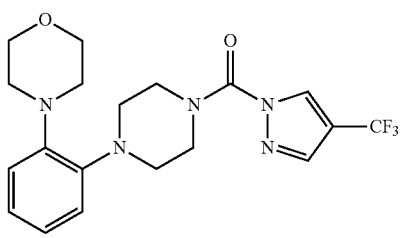 [SMILES: O=C(N1CCN(c2ccccc2N2CCOCC2)CC1)n1cc(C(F)(F)F)cn1]

Step 1: Preparation of tert-butyl 4-(2-morpholinophenyl)piperazine-1-carboxylate

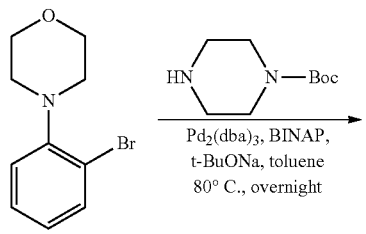

A 100-mL round-bottom flask was charged with 4-(2-bromophenyl)morpholine (5.00 g, 20.7 mmol, 1.00 equiv), tert-butyl piperazine-1-carboxylate (5.76 g, 30.9 mmol, 1.50 equiv), 2,2'-bis(diphenylphosphino)-1,1'-binaphthyl (1.93 g, 3.10 mmol, 0.15 equiv), sodium tert-butoxide (2.97 g, 30.9 mmol, 1.50 equiv), tetrakis(triphenylphosphine)Palladium (0.945 g, 1.03 mmol, 0.05 equiv), toluene (50 mL) under nitrogen. The resulting solution was stirred overnight at 80° C. and quenched with H₂O (80 mL). The mixture was extracted with dichloromethane (3×150 mL) and the organic layers were combined, washed with brine (3×100 mL), dried over anhydrous sodium sulfate, filtered and concentrated under reduced pressure. The residue was chromatographed on a silica gel column with ethyl acetate/petroleum ether (1/1) to provide tert-butyl 4-(2-morpholinophenyl)piperazine-1-carboxylate (4.51 g, 63% yield) as a yellow oil. LCMS (ESI, m/z): 348 [M+H]$^+$

Step 2: Preparation of 4-(2-(piperazin-1-yl)phenyl)morpholine

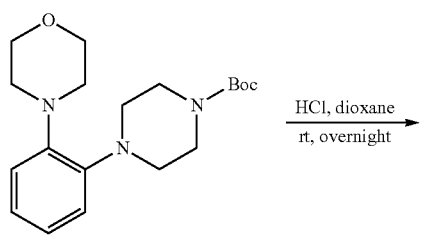

A 250-mL round-bottom flask was charged with tert-butyl 4-(2-morpholinophenyl)piperazine-1-carboxylate 4.51 g, 12.9 mmol, 1.00 equiv), hydrochloric acid (9 mL), dioxane (60 mL). The resulting solution was stirred overnight at room temperature and concentrated under reduced pressure to provide 4-(2-(piperazin-1-yl)phenyl)morpholine (3.10 g, 97% yield) as a brown solid. LCMS (ESI, m/z): 248 [M+H]$^+$

Step 3: Preparation of 4-(2-morpholinophenyl)piperazine-1-carbonyl chloride

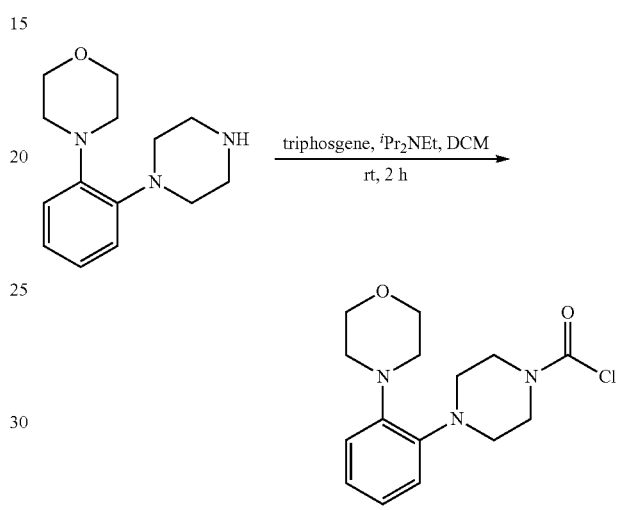

A 50-mL round-bottom flask was charged with triphosgene (0.591 g, 1.99 mmol, 0.40 equiv), dichloromethane (5 mL). 4-(2-(Piperazin-1-yl)phenyl)morpholine (1.23 g, 4.98 mmol, 1.00 equiv) was added at 0° C. N,N-Diisopropylethylamine (1.93 g, 14.9 mmol, 3.00 equiv) was added dropwise at 0° C. The resulting solution was stirred for 2 h at room temperature and quenched with H₂O (50 mL). The mixture was extracted with dichloromethane (3×50 mL) and the organic layers were combined, washed with brine (3×50 mL), dried over anhydrous sodium sulfate, filtered, and concentrated under reduced pressure to provide 4-(2-morpholinophenyl)piperazine-1-carbonyl chloride (1.50 g, 97% yield) as a yellow oil. LCMS (ESI, m/z): 310 [M+H]$^+$.

Step 4: Preparation of (4-(2-morpholinophenyl)piperazin-1-yl)(4-(trifluoromethyl)-1H-pyrazol-1-yl)methanone

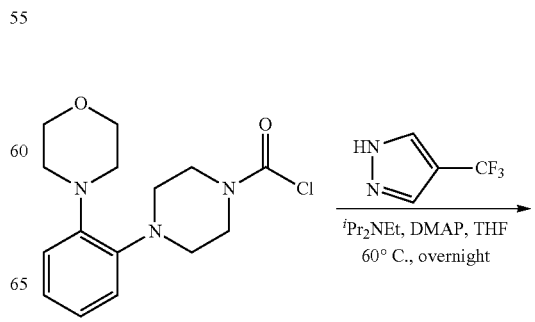

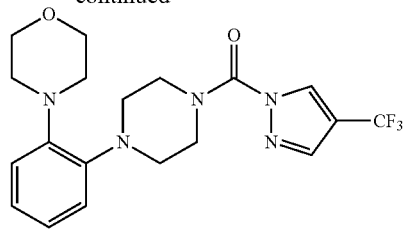

A 40-mL round-bottom flask was charged with 4-(2-morpholinophenyl)piperazine-1-carbonyl chloride (309 mg, 1.00 mmol, 1.00 equiv), 4-(trifluoromethyl)-1H-pyrazole (163 mg, 1.20 mmol, 1.20 equiv), N,N-diisopropylethylamine (387 mg, 3.00 mmol, 3.00 equiv), 4-dimethylaminopyridine (12.3 mg, 0.100 mmol, 0.10 equiv), tetrahydrofuran (5 mL). The resulting solution was stirred overnight at 60° C. and quenched with H$_2$O (30 mL). The mixture was extracted with dichloromethane (3×30 mL) and the organic layers were combined, washed with brine (3×30 mL), dried over anhydrous sodium sulfate, filtered and concentrated under reduced pressure. The crude product (109 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: X-bridge Prep C$_{18}$, 19*150 mm 5 μm; Mobile phase: Phase A: aqueous NH$_4$HCO$_3$ (0.05%); Phase B: CH$_3$CN; Detector, UV 220 & 254 nm. Purification yielded (4-(2-morpholinophenyl)piperazin-1-yl)(4-(trifluoromethyl)-1H-pyrazol-1-yl)methanone (25.6 mg, 6% yield) as a white solid. $^1$H NMR (400 MHz, Chloroform-d) δ 8.46 (s, 1H), 7.86 (s, 1H), 6.90-7.19 (m, 4H), 4.22 (br, 4H), 3.89 (br, 4H), 3.40 (t, J=6.0 Hz, 4H), 3.17 (t, J=4.8 Hz, 4H). LCMS (ESI, m/z): 410 [M+H]$^+$ Example 237: (4-(3-Morpholinophenyl)piperazin-1-yl)(4-(trifluoromethyl)-1H-pyrazol-1-yl)methanone

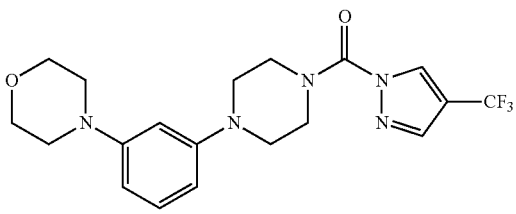 [SMILES: O=C(N1CCN(c2cccc(N3CCOCC3)c2)CC1)n1cc(C(F)(F)F)cn1]

The title compound was synthesized from 4-(3-bromophenyl)morpholine according to the representative procedure of Example 236, Steps 1-4 to provide (4-(3-morpholinophenyl)piperazin-1-yl)(4-(trifluoromethyl)-1H-pyrazol-1-yl)methanone (79.9 mg, 28% yield) as a white solid. $^1$H NMR (400 MHz, Chloroform-d) δ 8.44 (s, 1H), 7.83 (s, 1H), 7.19-7.23 (m, 1H), 6.52 (br, 3H), 4.03 (br, 4H), 3.86 (br, 4H), 3.30 (br, 4H), 3.17 (br, 4H). LCMS (ESI, m/z): 410 [M+H]$^+$.

Example 238: (4-(4-Morpholinophenyl)piperazin-1-yl)(4-(trifluoromethyl)-1H-pyrazol-1-yl)methanone

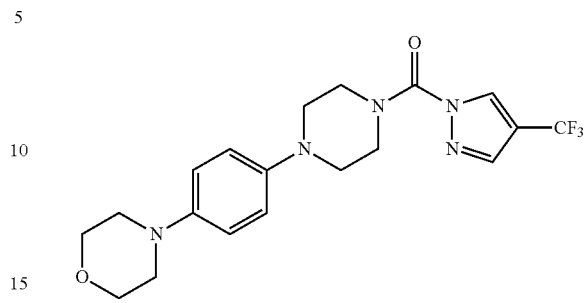

The title compound was synthesized from 4-(4-bromophenyl)morpholine according to the representative procedure of Example 236, Steps 1-4 to provide (4-(4-morpholinophenyl)piperazin-1-yl)(4-(trifluoromethyl)-1H-pyrazol-1-yl)methanone (36.2 mg, 9% yield) as a white solid. $^1$H NMR (400 MHz, Chloroform-d) δ 8.46 (s, 1H), 7.85 (s, 1H), 6.90-6.96 (m, 4H), 4.04 (br, 4H), 3.88 (t, J=4.8 Hz, 4H), 3.26-3.28 (m, 4H), 3.11 (t, J=4.8 Hz, 4H). LCMS (ESI, m/z): 410 [M+H]$^+$.

Example 239: (4-(2-(Pyrrolidin-1-yl)phenyl)piperazin-1-yl)(4-(trifluoromethyl)-1H-pyrazol-1-yl)methanone

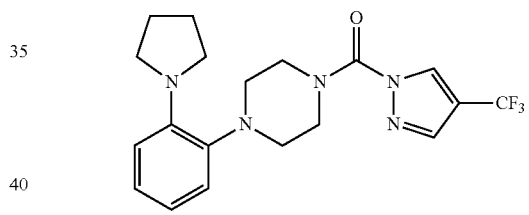

Step 1: Preparation of tert-butyl 4-(2-nitrophenyl)piperazine-1-carboxylate

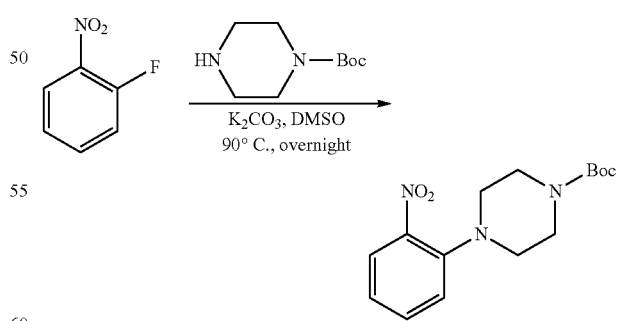

A 100-mL round-bottom flask was charged with 1-fluoro-2-nitrobenzene (1.00 g, 7.09 mmol, 1.00 equiv), tert-butyl piperazine-1-carboxylate (1.98 g, 10.6 mmol, 1.50 equiv), potassium carbonate (2.94 g, 21.3 mmol, 3.00 equiv), dimethyl sulfoxide (20 mL). The resulting solution was stirred overnight at 90° C. and quenched with H$_2$O (20 mL). The mixture was extracted with dichloromethane (3×30 mL) and the organic layers were combined, washed with brine (3×100 mL), dried over anhydrous sodium sulfate, filtered and concentrated under reduced pressure. The residue was chromatographed on a silica gel column with ethyl acetate/petroleum ether (2/3) to provide tert-butyl 4-(2-nitrophenyl)piperazine-1-carboxylate (2.01 g, 92% yield) as a yellow oil. LCMS (ESI, m/z): 308 [M+H]+.

Step 2: Preparation of tert-butyl 4-(2-aminophenyl)piperazine-1-carboxylate

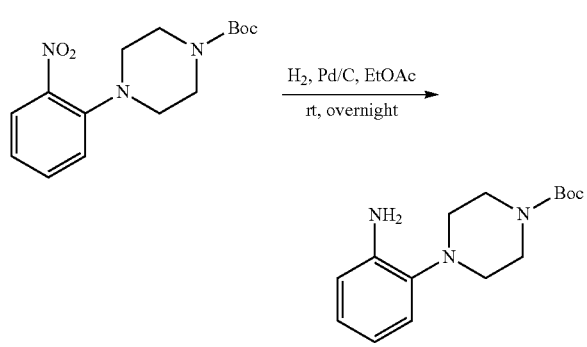

A 250-mL round-bottom flask was charged with tert-butyl 4-(2-nitrophenyl)piperazine-1-carboxylate (2.01 g, 6.54 mmol, 1.00 equiv), ethyl acetate (20 mL), palladium carbon (1.00 g). $H_2$ (g) was introduced in. The resulting solution was stirred overnight at room temperature. The solids were filtered out and the filtrate was concentrated under reduced pressure to provide tert-butyl 4-(2-aminophenyl)piperazine-1-carboxylate (1.76 g, 97% yield) as a pink solid. LCMS (ESI, m/z): 278 [M+H]+.

Step 3: Preparation of tert-butyl 4-(2-(pyrrolidin-1-yl)phenyl)piperazine-1-carboxylate

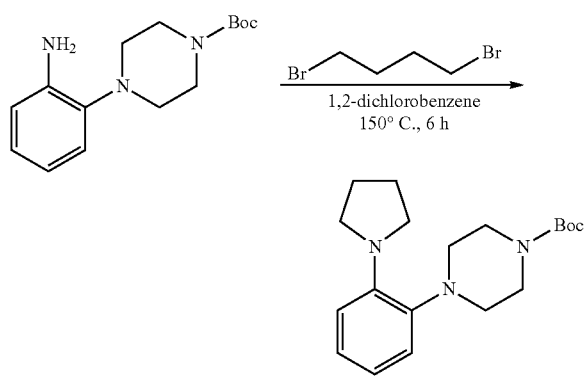

A 100-mL round-bottom flask was charged with tert-butyl 4-(2-aminophenyl)piperazine-1-carboxylate (1.30 g, 4.69 mmol, 1.00 equiv), 1,4-dibromobutane (1.51 g, 6.99 mmol, 1.50 equiv), 1,2-dichlorobenzene (20 mL). The resulting solution was stirred for 6 h at 150° C. and quenched with $H_2O$ (20 mL). The mixture was extracted with dichloromethane (3×30 mL) and the organic layers were combined, washed with brine (3×100 mL), dried over anhydrous sodium sulfate, filtered and concentrated under reduced pressure. The residue was chromatographed on a silica gel column with ethyl acetate/petroleum ether (1/1) to provide tert-butyl 4-[2-(pyrrolidin-1-yl)phenyl]piperazine-1-carboxylate (0.258 g, 17% yield) as a yellow oil. LCMS (ESI, m/z): 332 [M+H]+.

Step 4: Preparation of 1-(2-(pyrrolidin-1-yl)phenyl)piperazine

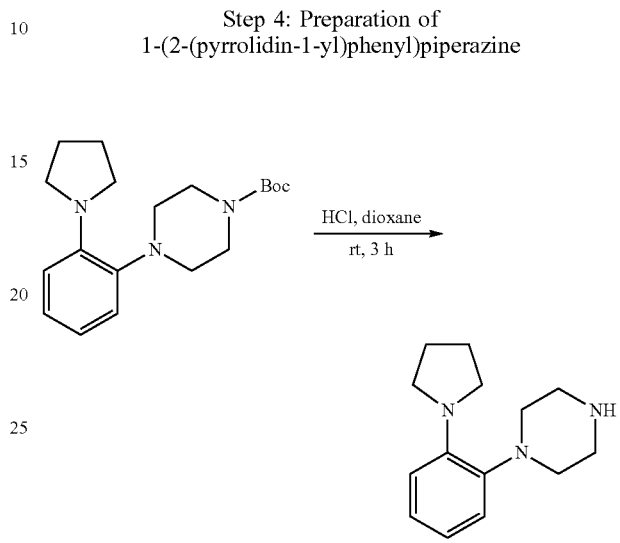

A 100-mL round-bottom flask was charged with tert-butyl 4-[2-(pyrrolidin-1-yl)phenyl]piperazine-1-carboxylate (250 mg, 0.750 mmol, 1.00 equiv), dioxane (35 mL), hydrochloric acid (5 mL). The resulting solution was stirred for 3 h at room temperature and concentrated under reduced pressure to provide 1-[2-(pyrrolidin-1-yl)phenyl]piperazine (174 mg, 100% yield) as a brown solid. LCMS (ESI, m/z): 232 [M+H]+.

Step 5: Preparation of 4-(2-(pyrrolidin-1-yl)phenyl)piperazine-1-carbonyl chloride

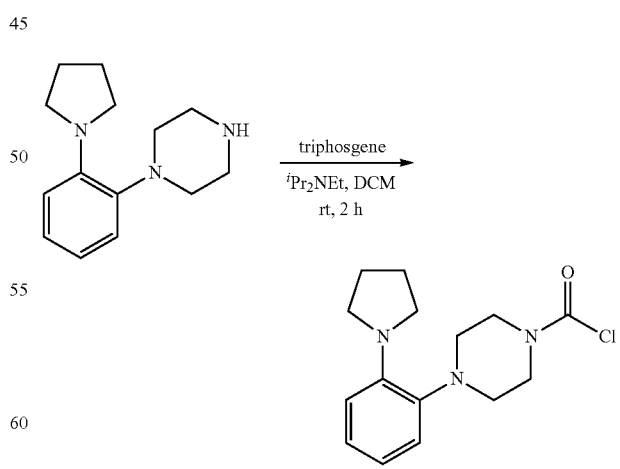

A 40-mL round-bottom flask was charged with triphosgene (109 mg, 0.370 mmol, 0.50 equiv), dichloromethane (10 mL). 1-[2-(Pyrrolidin-1-yl)phenyl]piperazine (170 mg, 0.730 mmol, 1.00 equiv) was added at 0° C. N,N-Diisopropylethylamine (285 mg, 2.21 mmol, 3.00 equiv) was added at 0° C. The resulting solution was stirred for 2 h at room temperature and quenched with H₂O (20 mL). The mixture was extracted with dichloromethane (3×30 mL) and the organic layers were combined, washed with brine (3×50 mL), dried over anhydrous sodium sulfate, filtered and concentrated under reduced pressure to provide 4-[2-(pyrrolidin-1-yl)phenyl]piperazine-1-carbonyl chloride (210 mg, 97% yield) as a yellow oil. LCMS (ESI, m/z): 294 [M+H]⁺.

Step 6: Preparation of (4-(2-(Pyrrolidin-1-yl)phenyl)piperazin-1-yl)(4-(trifluoromethyl)-1H-pyrazol-1-yl)methanone

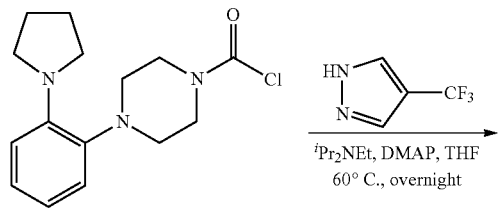

A 40-mL round-bottom flask was charged with 4-[2-(pyrrolidin-1-yl)phenyl]piperazine-1-carbonyl chloride (210 mg, 0.710 mmol, 1.00 equiv), 4-(trifluoromethyl)-1H-pyrazole (117 mg, 0.860 mmol, 1.20 equiv), N,N-diisopropylethylamine (277 mg, 2.14 mmol, 3.00 equiv), 4-dimethylaminopyridine (8.75 mg, 0.0700 mmol, 0.10 equiv), tetrahydrofuran (5 mL). The resulting solution was stirred overnight at 60° C. and concentrated under reduced pressure. The crude product (550 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: X-bridge Prep C₁₈, 19*150 mm 5 μm; Mobile phase: Phase A: aqueous NH₄HCO₃ (0.05%); Phase B: CH₃CN; Detector, UV 220 & 25 4 nm. Purification provided (4-(2-(pyrrolidin-1-yl)phenyl)piperazin-1-yl)(4-(trifluoromethyl)-1H-pyrazol-1-yl)methanone (113.4 mg, 40% yield) as a yellow syrup. ¹H NMR (300 MHz, Chloroform-d) δ 8.43 (s, 1H), 7.82 (s, 1H), 6.82-7.26 (m, 4H), 4.00 (br, 4H), 3.30 (t, J=6.4 Hz, 4H), 3.12 (t, J=5.0 Hz, 4H), 1.85-1.95 (m, 4H). LCMS (ESI, m/z): 394 [M+H]⁺.

Example 240: (4-(3-(Pyrrolidin-1-yl)phenyl)piperazin-1-yl)(4-(trifluoromethyl)-1H-pyrazol-1-yl)methanone

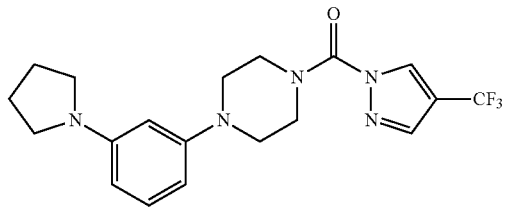 [SMILES: O=C(N1CCN(c2cccc(N3CCCC3)c2)CC1)n1cc(C(F)(F)F)cn1]

The title compound was synthesized from 1-(3-(pyrrolidin-1-yl)phenyl)piperazine according to the representative procedure of Example 239, Steps 1-6 to provide (4-(3-(pyrrolidin-1-yl)phenyl)piperazin-1-yl)(4-(trifluoromethyl)-1H-pyrazol-1-yl)methanone (12.4 mg, 7% yield) as a yellow solid. ¹H NMR (300 MHz, DMSO-d₆) δ 8.90 (s, 1H), 8.26 (s, 1H), 7.00 (t, J=8.2 Hz, 1H), 6.22-6.25 (m, 1H), 6.07 (d, J=7.2 Hz, 2H), 3.80 (t, J=4.4 Hz, 4H), 3.20 (t, J=6.3 Hz, 8H), 1.93 (t, J=6.6 Hz, 4H). LCMS (ESI, m/z): 394 [M+H]⁺.

Example 241: (4-(4-(Pyrrolidin-1-yl)phenyl)piperazin-1-yl)(4-(trifluoromethyl)-1H-pyrazol-1-yl)methanone

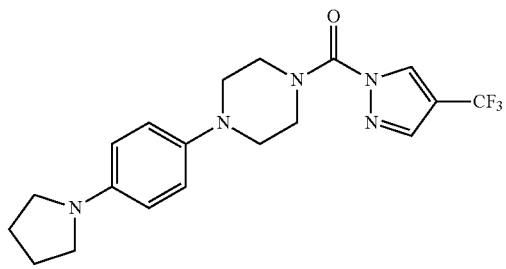 [SMILES: O=C(N1CCN(c2ccc(N3CCCC3)cc2)CC1)n1cc(C(F)(F)F)cn1]

The title compound was synthesized from 1-(4-(pyrrolidin-1-yl)phenyl)piperazine according to the representative procedure of Example 239, Steps 1-6 to provide (4-(4-(pyrrolidin-1-yl)phenyl)piperazin-1-yl)(4-(trifluoromethyl)-1H-pyrazol-1-yl)methanone (21.8 mg, 9% yield) as a white solid. ¹H NMR (300 MHz, DMSO-d₆) δ 8.90 (s, 1H), 8.25 (s, 1H), 6.87 (d, J=8.9 Hz, 2H), 6.48 (d, J=8.9 Hz, 2H), 3.79 (t, J=4.6 Hz, 4H), 3.15 (t, J=3.3 Hz, 4H), 3.03 (t, J=4.6 Hz, 4H), 1.90-1.93 (m, 4H). LCMS (ESI, m/z): 394 [M+H]⁺

Example 242: 4-Cyano-N-ethyl-N-(3-morpholinobenzyl)-1H-pyrazole-1-carboxamide

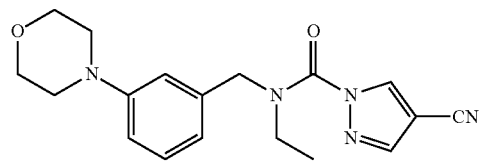 [SMILES: CCN(Cc1cccc(N2CCOCC2)c1)C(=O)n1cc(C#N)cn1]

Step 1: Preparation of 3-morpholinobenzaldehyde

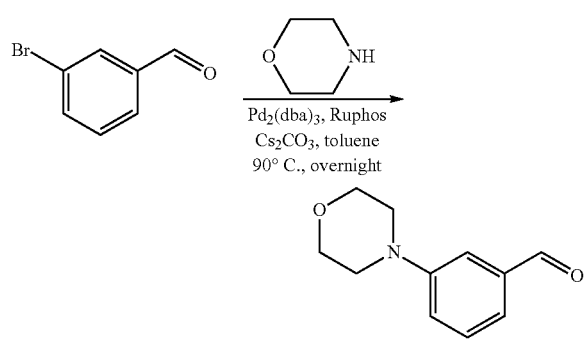

A 500-mL round-bottom flask was charged with 3-bromobenzaldehyde (6.44 g, 35.0 mmol, 1.00 equiv), morpholine (9.13 g, 105 mmol, 3.00 equiv), tris(dibenzylideneacetone)dipalladium (1.81 g, 1.75 mmol, 0.05 equiv), dicyclohexyl(2',6'-diisopropoxybiphenyl-2-yl)phosphine (3.26 g, 7.00 mmol, 0.20 equiv), cesium carbonate (34.2 g, 105 mmol, 3.00 equiv), toluene (100 mL) under nitrogen. The resulting solution was stirred overnight at 90° C. and quenched with water (50 mL). The resulting solution was extracted with dichloromethane (3×200 mL) and the organic layers were combined, washed with brine (3×100 mL), dried over anhydrous sodium sulfate, filtered and concentrated under reduced pressure. The residue was chromatographed on a silica gel column with ethyl acetate/petroleum ether (3/17) to provide 3-morpholinobenzaldehyde (2.10 g, 32% yield) as yellow oil. LCMS (ESI, m/z): 192 [M+H]$^+$.

Step 2: Preparation of N-(3-morpholinobenzyl)ethanamine

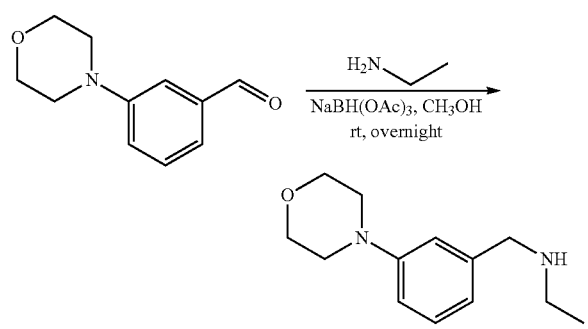

A 250-mL round-bottom flask was charged with 3-morpholinobenzaldehyde (4.58 g, 23.9 mmol, 1.00 equiv), ethanamine (5.39 g, 120 mmol, 5.00 equiv), methanol (100 mL). The resulting solution was stirred for 2 h at room temperature. Sodium triacetoxyborohydride (15.2 g, 72.0 mmol, 3.00 equiv) was added. The resulting solution was stirred overnight at room temperature and quenched with water (50 mL). The resulting solution was extracted with dichloromethane (3×100 mL) and the organic layers were combined, washed with brine (3×100 mL), dried over anhydrous sodium sulfate, filtered, and concentrated under reduced pressure. The residue was chromatographed on a silica gel column with ethyl acetate/petroleum ether (5/1) to provide N-(3-morpholinobenzyl)ethanamine (4.00 g, 75% yield) as a yellow solid. LCMS (ESI, m/z): 221 [M+H]$^+$

Step 3: Preparation of ethyl(3-morpholinobenzyl)carbamic chloride

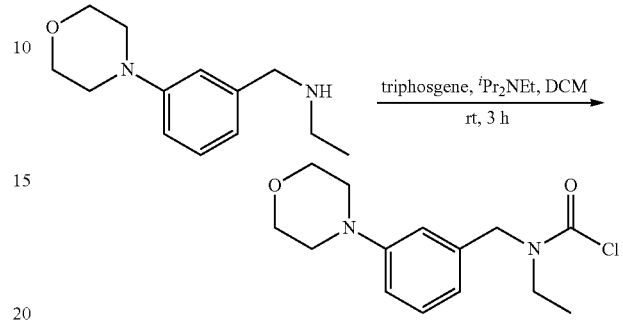

A 100-mL round-bottom flask was charged with triphosgene (0.832 g, 2.80 mmol, 0.40 equiv), dichloromethane (30 mL). The mixture was cooled to 0° C. N-(3-morpholinobenzyl)ethanamine (1.54 g, 7.00 mmol, 1.00 equiv) was added at 0° C. N,N-Diisopropylethylamine (2.71 g, 21.0 mmol, 3.00 equiv) was added dropwise at 0° C. The resulting solution was stirred for 3 h at room temperature and quenched with water (10 mL). The resulting solution was extracted with dichloromethane (3×50 mL) and the organic layers were combined, washed with brine (3×50 mL), dried over anhydrous sodium sulfate, filtered and concentrated under reduced pressure to provide ethyl(3-morpholinobenzyl)carbamic chloride (1.80 g, 91% yield) as yellow oil. LCMS (ESI, m/z): 283 [M+H]$^+$.

Step 4: Preparation of 4-Cyano-N-ethyl-N-(3-morpholinobenzyl)-1H-pyrazole-1-carboxamide

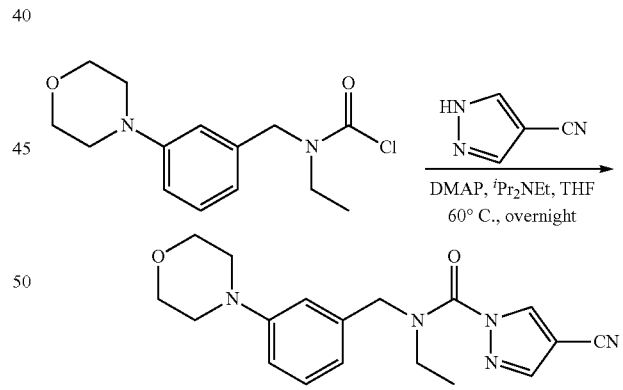

A 40-mL round-bottom flask was charged with ethyl(3-morpholinobenzyl)carbamic chloride (408 mg, 1.44 mmol, 1.00 equiv), 1H-pyrazole-4-carbonitrile (134 mg, 1.44 mmol, 1.00 equiv), N,N-diisopropylethylamine (557 mg, 4.32 mmol, 3.00 equiv), 4-dimethylaminopyridine (17.7 mg, 0.144 mmol, 0.10 equiv), tetrahydrofuran (5 mL). The resulting solution was stirred overnight at 60° C. and quenched with H$_2$O (10 mL). The mixture was extracted with dichloromethane (3×30 mL) and the organic layers were combined, washed with brine (3×30 mL), dried over anhydrous sodium sulfate, filtered and concentrated under reduced pressure. The crude product (198 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm 5 μm; Mobile phase: Phase A: aqueous NH₄HCO₃ (0.05%); Phase B: CH₃CN; Detector, UV 220 & 254 nm. Purification provided 4-cyano-N-ethyl-N-(3-morpholinobenzyl)-1H-pyrazole-1-carboxamide (119.8 mg, 24% yield) as a white solid. $^1$H NMR (400 MHz, Chloroform-d) δ 8.59 (s, 1H), 7.86 (s, 1H), 7.23-7.27 (m, 1H), 6.80-6.88 (m, 3H), 4.78 (br, 2H), 3.86 (t, J=4.8 Hz, 4H), 3.57 (br, 2H), 3.15 (t, J=4.8 Hz, 4H), 1.26 (t, J=7.2 Hz, 3H). LCMS (ESI, m/z): 340 [M+H]⁺

Example 243: N-(3-chlorobenzyl)-4-cyano-N-ethyl-1H-pyrazole-1-carboxamide

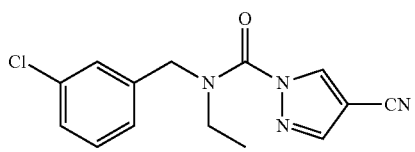 [SMILES: CCN(Cc1cccc(Cl)c1)C(=O)n1cc(C#N)cn1]

The title compound was synthesized from N-(3-chlorobenzylethanamine), triphosgene, and 1H-pyrazole-4-carbonitrile according to the representative procedure of Example 242, Steps 3-4 to provide N-(3-chlorobenzyl)-4-cyano-N-ethyl-1H-pyrazole-1-carboxamide as a purple solid. $^1$H NMR (300 MHz, Chloroform-d) δ 8.62 (s, 1H), 7.87 (s, 1H), 7.27-7.33 (m, 3H), 7.22 (br, 1H), 4.80 (br, 2H), 3.58 (br, 2H), 1.25-1.28 (m, 3H). LCMS (ESI, m/z): 311 [M+Na]⁺.

Example 244: N-(3-Chlorobenzyl)-N-ethyl-4-(trifluoromethyl)-1H-pyrazole-1-carboxamide

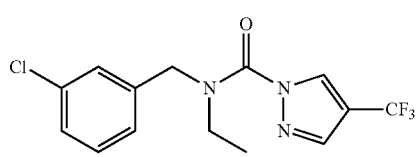 [SMILES: CCN(Cc1cccc(Cl)c1)C(=O)n1cc(C(F)(F)F)cn1]

The title compound was synthesized from N-(3-chlorobenzylethanamine), triphosgene, and 4-trifluoromethyl-1H-pyrazole according to the representative procedure of Example 242, Steps 3-4 to provide N-(3-chlorobenzyl)-N-ethyl-4-(trifluoromethyl)-1H-pyrazole-1-carboxamide as a purple oil. $^1$H NMR (300 MHz, Chloroform-d) δ 8.50 (s, 1H), 7.80 (s, 1H), 7.37 (s, 1H), 7.28-7.32 (m, 2H), 7.14-7.26 (m, 1H), 4.81 (br, 2H), 3.59 (br, 2H), 1.25-1.29 (m, 3H). LCMS (ESI, m/z): 354 [M+Na]⁺.

Example 245: N-(3-chlorobenzyl)-N-ethyl-4-methyl-1H-pyrazole-1-carboxamide

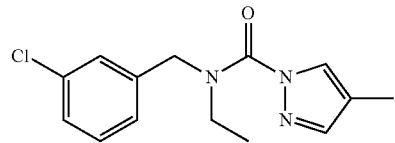 [SMILES: CCN(Cc1cccc(Cl)c1)C(=O)n1cc(C)cn1]

The title compound was synthesized from N-(3-chlorobenzylethanamine), triphosgene, and 4-methyl-1H-pyrazole according to the representative procedure of Example 242, Steps 3-4 to provide N-(3-chlorobenzyl)-N-ethyl-4-methyl-1H-pyrazole-1-carboxamide as a purple oil. $^1$H NMR (300 MHz, Chloroform-d) δ 7.94 (s, 1H), 7.43 (s, 1H), 7.34 (s, 1H), 7.26-7.31 (m, 1H), 7.17-7.25 (m, 2H), 4.85 (br, 2H), 3.58 (br, 2H), 2.10 (s, 3H), 1.21-1.26 (m, 3H). LCMS (ESI, m/z): 278 [M+H]⁺.

Example 246: 4-Cyano-N-ethyl-N-(3-methylbenzyl)-1H-pyrazole-1-carboxamide

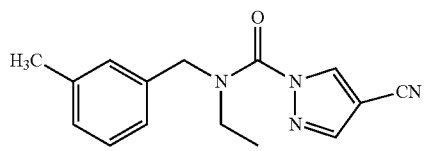 [SMILES: CCN(Cc1cccc(C)c1)C(=O)n1cc(C#N)cn1]

The title compound was synthesized from N-(3-methylbenzyl)ethanamine, triphosgene, and 1H-pyrazole-4-carbonitrile according to the representative procedure of Example 242, Steps 3-4 to provide 4-cyano-N-ethyl-N-(3-methylbenzyl)-1H-pyrazole-1-carboxamide as an off-white solid. $^1$H NMR (300 MHz, Chloroform-d) δ 8.60 (s, 1H), 7.86 (s, 1H), 7.11-7.24 (m, 4H), 4.80 (br, 2H), 3.58 (br, 2H), 2.35 (s, 3H), 1.26 (t, J=7.0 Hz, 3H). LCMS (ESI, m/z): 291 [M+Na]⁺.

Example 247: N-Ethyl-N-(3-methylbenzyl)-4-(trifluoromethyl)-1H-pyrazole-1-carboxamide

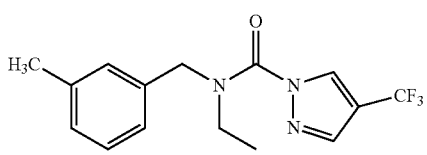 [SMILES: CCN(Cc1cccc(C)c1)C(=O)n1cc(C(F)(F)F)cn1]

The title compound was synthesized from N-(3-methylbenzyl)ethanamine, triphosgene, and 4-(trifluoromethyl)-1H-pyrazole according to the representative procedure of Example 242, Steps 3-4 to provide N-ethyl-N-(3-methylbenzyl)-4-(trifluoromethyl)-1H-pyrazole-1-carboxamide as a light yellow oil. $^1$H NMR (300 MHz, Chloroform-d) δ 8.48 (s, 1H), 7.79 (s, 1H), 7.22-7.26 (m, 1H), 7.10-7.13 (m, 3H), 4.82 (br, 2H), 3.59 (br, 2H), 2.35 (s, 3H), 1.25 (t, J=6.9 Hz, 3H). LCMS (ESI, m/z): 334 [M+Na]⁺.

Example 248: N-ethyl-4-methyl-N-(3-methylbenzyl)-1H-pyrazole-1-carboxamide

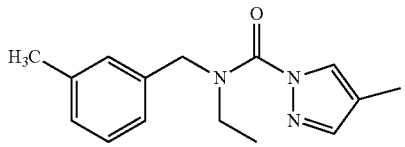

The title compound was synthesized from N-(3-methylbenzyl)ethanamine, triphosgene, and 4-methyl-1H-pyrazole according to the representative procedure of Example 242, Steps 3-4 to provide N-ethyl-4-methyl-N-(3-methylbenzyl)-1H-pyrazole-1-carboxamide as a yellow oil. $^1$H NMR (300 MHz, Chloroform-d) δ 7.94 (s, 1H), 7.43 (s, 1H), 7.08-7.25 (m, 4H), 4.85 (br, 2H), 3.57-3.59 (m, 2H), 2.34 (s, 3H), 2.10 (s, 3H), 1.22 (t, J=7.0 Hz, 3H). LCMS (ESI, m/z): 280 [M+Na]$^+$.

Example 249: 4-Cyano-N-ethyl-N-(3-methoxybenzyl)-1H-pyrazole-1-carboxamide

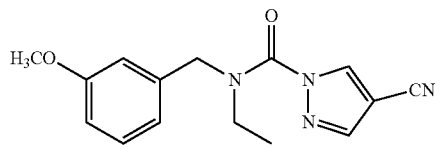 [SMILES: CCN(Cc1cccc(OC)c1)C(=O)n1cc(C#N)cn1]

The title compound was synthesized from N-(3-methoxybenzyl)ethanamine, triphosgene, and 1H-pyrazole-4-carbonitrile according to the representative procedure of Example 242, Steps 3-4 to provide 4-cyano-N-ethyl-N-(3-methoxybenzyl)-1H-pyrazole-1-carboxamide as a yellow oil. $^1$H NMR (300 MHz, Chloroform-d) δ 8.59 (s, 1H), 7.86 (s, 1H), 7.24-7.30 (m, 1H), 6.83-6.90 (m, 3H), 4.80 (br, 2H), 3.80 (s, 3H), 3.57 (br, 2H), 1.26 (t, J=7.0 Hz, 3H). LCMS (ESI, m/z): 306 [M+Na]$^+$.

Example 250: N-Ethyl-N-(3-methoxybenzyl)-4-(trifluoromethyl)-1H-pyrazole-1-carboxamide

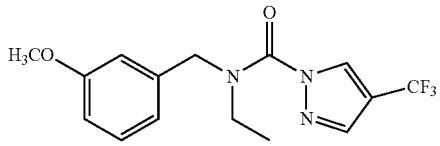 [SMILES: CCN(Cc1cccc(OC)c1)C(=O)n1cc(C(F)(F)F)cn1]

The title compound was synthesized from N-(3-methoxybenzyl)ethanamine, triphosgene, and 4-(trifluoromethyl)-1H-pyrazole according to the representative procedure of Example 242, Steps 3-4 to provide N-ethyl-N-(3-methoxybenzyl)-4-(trifluoromethyl)-1H-pyrazole-1-carboxamide as a light yellow solid. $^1$H NMR (300 MHz, Chloroform-d) δ 8.48 (s, 1H), 7.79 (s, 1H), 7.24-7.30 (m, 1H), 6.83-6.92 (m, 3H), 4.83 (br, 2H), 3.80 (s, 3H), 3.59 (br, 2H), 1.26 (t, J=7.0 Hz, 3H). LCMS (ESI, m/z): 350 [M+Na]$^+$.

Example 251: N-Ethyl-N-(3-methoxybenzyl)-4-methyl-1H-pyrazole-1-carboxamide

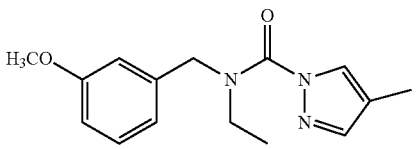 [SMILES: CCN(Cc1cccc(OC)c1)C(=O)n1cc(C)cn1]

The title compound was synthesized from N-(3-methoxybenzyl)ethanamine, triphosgene, and 4-methyl-1H-pyrazole according to the representative procedure of Example 242, Steps 3-4 to provide N-ethyl-N-(3-methoxybenzyl)-4-methyl-1H-pyrazole-1-carboxamide as a yellow oil. $^1$H NMR (300 MHz, Chloroform-d) δ 7.93 (s, 1H), 7.43 (s, 1H), 7.22-7.27 (m, 1H), 6.89-6.92 (m, 2H), 6.80-6.83 (m, 1H), 4.86 (br, 2H), 3.79 (s, 3H), 3.55-3.60 (m, 2H), 2.09 (s, 3H), 1.22 (t, J=7.0 Hz, 3H). LCMS (ESI, m/z): 274 [M+H]$^+$.

Example 252 N-(4-Chlorobenzyl)-4-cyano-N-ethyl-1H-pyrazole-1-carboxamide

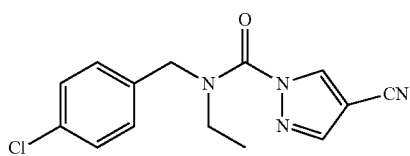 [SMILES: CCN(Cc1ccc(Cl)cc1)C(=O)n1cc(C#N)cn1]

The title compound was synthesized from N-(4-chlorobenzyl)ethanamine, triphosgene, and 1H-pyrazole-4-carbonitrile according to the representative procedure of Example 242, Steps 3-4 to provide N-(4-chlorobenzyl)-4-cyano-N-ethyl-1H-pyrazole-1-carboxamide as a white solid. $^1$H NMR (300 MHz, Chloroform-d) δ 8.60 (s, 1H), 7.86 (s, 1H), 7.26-7.35 (m, 4H), 4.78 (br, 2H), 3.57 (br, 2H), 1.23-1.28 (m, 3H). LCMS (ESI, m/z): 311 [M+Na]$^+$.

Example 253: N-(4-Chlorobenzyl)-N-ethyl-4-(trifluoromethyl)-1H-pyrazole-1-carboxamide

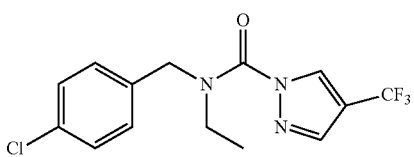 [SMILES: CCN(Cc1ccc(Cl)cc1)C(=O)n1cc(C(F)(F)F)cn1]

The title compound was synthesized from N-(4-chlorobenzyl)ethanamine, triphosgene, and 4-(trifluoromethyl)-1H-pyrazole according to the representative procedure of Example 242, Steps 3-4 to provide N-(4-chlorobenzyl)-N-ethyl-4-(trifluoromethyl)-1H-pyrazole-1-carboxamide as a white solid. $^1$H NMR (300 MHz, Chloroform-d) δ 8.48 (s, 1H), 7.79 (s, 1H), 7.26-7.35 (m, 4H), 4.80 (br, 2H), 3.58 (br, 2H), 1.23-1.28 (m, 3H). LCMS (ESI, m/z): 354 [M+Na]$^+$.

Example 254: N-(4-Chlorobenzyl)-N-ethyl-4-methyl-1H-pyrazole-1-carboxamide

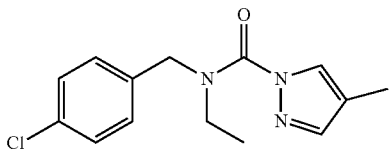 [SMILES: CCN(Cc1ccc(Cl)cc1)C(=O)n1cc(C)cn1]

The title compound was synthesized from N-(4-chlorobenzyl)ethanamine, triphosgene, and 4-methyl-1H-pyrazole according to the representative procedure of Example 242, Steps 3-4 to provide N-(4-chlorobenzyl)-N-ethyl-4-methyl-1H-pyrazole-1-carboxamide as a white solid. $^1$H NMR (300 MHz, Chloroform-d) δ 7.93 (s, 1H), 7.42 (s, 1H), 7.26-7.33 (m, 4H), 4.83 (s, 2H), 3.56-3.58 (m, 2H), 2.09 (s, 3H), 1.19-1.24 (m, 3H). LCMS (ESI, m/z): 278 [M+H]$^+$.

Example 255: 4-Cyano-N-ethyl-N-(4-methylbenzyl)-1H-pyrazole-1-carboxamide

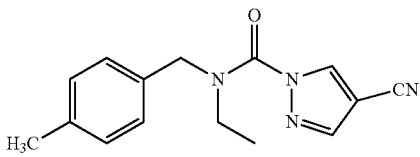 [SMILES: CCN(Cc1ccc(C)cc1)C(=O)n1cc(C(F)(F)F)cn1]

The title compound was synthesized from N-(4-methylbenzyl)ethanamine, triphosgene, and 1H-pyrazole-4-carbonitrile according to the representative procedure of Example 242, Steps 3-4 to provide 4-cyano-N-ethyl-N-(4-methylbenzyl)-1H-pyrazole-1-carboxamide as a white solid. $^1$H NMR (300 MHz, Chloroform-d) δ 8.58 (s, 1H), 7.85 (s, 1H), 7.14-7.22 (m, 4H), 4.78 (br, 2H), 3.56 (br, 2H), 2.34 (s, 3H), 1.24 (t, J=7.0 Hz, 3H). LCMS (ESI, m/z): 291 [M+Na]$^+$

Example 256: N-Ethyl-N-(4-methylbenzyl)-4-(trifluoromethyl)-1H-pyrazole-1-carboxamide

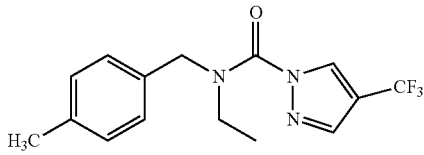

The title compound was synthesized from N-(4-methylbenzyl)ethanamine, triphosgene, and 4-(trifluoromethyl)-1H-pyrazole according to the representative procedure of Example 242, Steps 3-4 to provide N-ethyl-N-(4-methylbenzyl)-4-(trifluoromethyl)-1H-pyrazole-1-carboxamide as white solid. $^1$H NMR (300 MHz, Chloroform-d) δ 8.47 (s, 1H), 7.78 (s, 1H), 7.14-7.25 (m, 4H), 4.80 (br, 2H), 3.57 (br, 2H), 2.34 (s, 3H), 1.24 (t, J=7.0 Hz, 3H). LCMS (ESI, m/z): 334 [M+Na]$^+$.

Example 257: N-Ethyl-4-methyl-N-(4-methylbenzyl)-1H-pyrazole-1-carboxamide

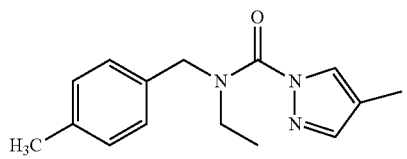

The title compound was synthesized from N-(4-methylbenzyl)ethanamine, triphosgene, and 4-methyl-1H-pyrazole according to the representative procedure of Example 242, Steps 3-4 to provide N-ethyl-4-methyl-N-(4-methylbenzyl)-1H-pyrazole-1-carboxamide as a white solid. $^1$H NMR (300 MHz, Chloroform-d) δ 7.92 (s, 1H), 7.42 (s, 1H), 7.20-7.25 (m, 2H), 7.12-7.15 (m, 2H), 4.83 (br, 2H), 3.53-3.58 (m, 2H), 2.33 (s, 3H), 2.09 (s, 3H), 1.20 (t, J=7.0 Hz, 3H). LCMS (ESI, m/z): 280 [M+Na]$^+$

Example 258: 4-Cyano-N-ethyl-N-(4-methoxybenzyl)-1H-pyrazole-1-carboxamide

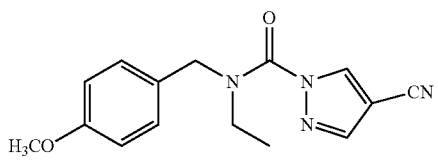 [SMILES: CCN(Cc1ccc(OC)cc1)C(=O)n1cc(C#N)cn1]

The title compound was synthesized from N-(4-methoxybenzyl)ethanamine, triphosgene, and 1H-pyrazole-4-carbonitrile according to the representative procedure of Example 242, Steps 3-4 to provide 4-cyano-N-ethyl-N-(4-methoxybenzyl)-1H-pyrazole-1-carboxamide as a white solid. $^1$H NMR (300 MHz, Chloroform-d) δ 8.51 (s, 1H), 7.86 (s, 1H), 7.25-7.28 (m, 2H), 6.85-6.90 (m, 2H), 4.74 (br, 2H), 3.80 (s, 3H), 3.54 (br, 2H), 1.24 (t, J=7.0 Hz, 3H). LCMS (ESI, m/z): 307 [M+Na]$^+$

Example 259: N-Ethyl-N-(4-methoxybenzyl)-4-(trifluoromethyl)-1H-pyrazole-1-carboxamide

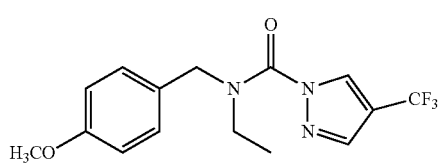 [SMILES: CCN(Cc1ccc(OC)cc1)C(=O)n1cc(C(F)(F)F)cn1]

The title compound was synthesized from N-(4-methoxybenzyl)ethanamine, triphosgene, and 4-(trifluoromethyl)-1H-pyrazole according to the representative procedure of Example 242, Steps 3-4 to provide N-ethyl-N-(4-methoxybenzyl)-4-(trifluoromethyl)-1H-pyrazole-1-carboxamide as a colorless oil. $^1$H NMR (300 MHz, Chloroform-d) δ 8.47 (s, 1H), 7.79 (s, 1H), 7.26-7.29 (m, 2H), 6.86-6.89 (m, 2H), 4.77 (br, 2H), 3.80 (s, 3H), 3.56 (br, 2H), 1.24 (t, J=7.2 Hz, 3H). LCMS (ESI, m/z): 350 [M+Na]$^+$

Example 260: N-Ethyl-N-(4-methoxybenzyl)-4-methyl-1H-pyrazole-1-carboxamide

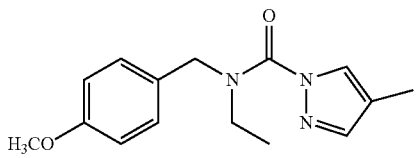 [SMILES: CCN(Cc1ccc(OC)cc1)C(=O)n1cc(C)cn1]

The title compound was synthesized from N-(4-methoxybenzyl)ethanamine, triphosgene, and 4-methyl-1H-pyrazole according to the representative procedure of Example 242, Steps 3-4 to provide N-ethyl-N-(4-methoxybenzyl)-4-methyl-1H-pyrazole-1-carboxamide as a white solid. $^1$H NMR (300 MHz, Chloroform-d) δ 7.92 (s, 1H), 7.43 (s, 1H), 7.26-7.29 (m, 2H), 6.85-6.88 (m, 2H), 4.79 (br, 2H), 3.80 (s, 3H), 3.54-3.57 (m, 2H), 1.20 (t, J=7.0 Hz, 3H). LCMS (ESI, m/z): 274 [M+H]$^+$

Example 261: N-Ethyl-N-(3-morpholinobenzyl)-4-(trifluoromethyl)-1H-pyrazole-1-carboxamide

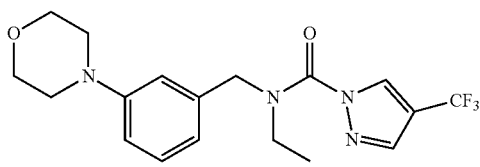 [SMILES: CCN(Cc1cccc(N2CCOCC2)c1)C(=O)n1cc(C(F)(F)F)cn1]

The title compound was synthesized from ethyl(3-morpholinobenzyl)carbamic chloride (Example 242, Steps 1-3) and 4-(trifluoromethyl)-1H-pyrazole according to the representative procedure of Example 242, Steps 1-4 to provide N-ethyl-N-(3-morpholinobenzyl)-4-(trifluoromethyl)-1H-pyrazole-1-carboxamide as a yellow solid. $^1$H NMR (400 MHz, Chloroform-d) δ 8.47 (s, 1H), 7.79 (s, 1H), 7.23-7.27 (m, 1H), 6.90 (br, 1H), 6.81-6.86 (m, 2H), 4.80 (br, 2H), 3.86 (t, J=4.8 Hz, 4H), 3.58 (br, 2H), 3.15 (t, J=4.8 Hz, 4H), 1.26 (t, J=7.0 Hz, 3H). LCMS (ESI, m/z): 383 [M+H]$^+$

Example 262: N-Ethyl-4-methyl-N-(3-morpholinobenzyl)-1H-pyrazole-1-carboxamide

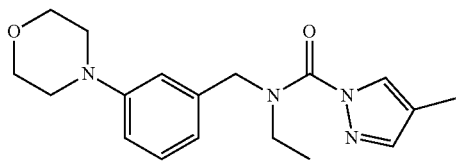 [SMILES: CCN(Cc1cccc(N2CCOCC2)c1)C(=O)n1cc(C)cn1]

The title compound was synthesized from ethyl(3-morpholinobenzyl)carbamic chloride (Example 242, Steps 1-3) and 4-methyl-1H-pyrazole according to the representative procedure of Example 242, Steps 1-4 to provide N-ethyl-4-methyl-N-(3-morpholinobenzyl)-1H-pyrazole-1-carboxamide as a yellow oil. $^1$H NMR (400 MHz, Chloroform-d) δ 7.92 (s, 1H), 7.43 (s, 1H), 7.21-7.26 (m, 1H), 6.92 (s, 1H), 6.81-6.84 (m, 2H), 4.84 (br, 2H), 3.85 (t, J=4.8 Hz, 4H), 3.58 (br, 2H), 3.15 (t, J=4.8 Hz, 4H), 1.22 (t, J=7.0 Hz, 3H). LCMS (ESI, m/z): 329 [M+H]$^+$

Example 263: 4-Cyano-N-ethyl-N-(4-morpholinobenzyl)-1H-pyrazole-1-carboxamide

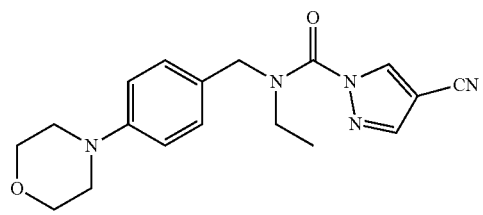 [SMILES: CCN(Cc1ccc(N2CCOCC2)cc1)C(=O)n1cc(C#N)cn1]

The title compound was synthesized from ethyl(4-morpholinobenzyl)carbamic chloride and 1H-pyrazole-4-carbonitrile according to the representative procedure of Example 242, Steps 1-4 to provide 4-cyano-N-ethyl-N-(4-morpholinobenzyl)-1H-pyrazole-1-carboxamide as a white solid. $^1$H NMR (300 MHz, Chloroform-d) δ 8.58 (s, 1H), 7.86 (s, 1H), 7.23-7.26 (m, 2H), 6.89-6.92 (m, 2H), 4.73 (br, 2H), 3.87 (t, J=4.8 Hz, 4H), 3.54 (br, 2H), 3.16 (t, J=4.8 Hz, 4H), 1.24 (t, J=7.0 Hz, 3H). LCMS (ESI, m/z): 340 [M+H]$^+$

Example 264: N-Ethyl-N-(4-morpholinobenzyl)-4-(trifluoromethyl)-1H-pyrazole-1-carboxamide

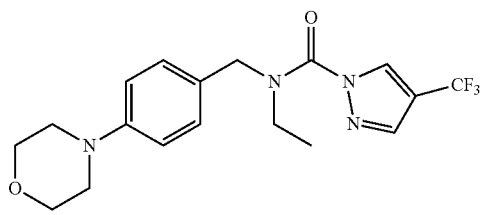 [SMILES: CCN(Cc1ccc(N2CCOCC2)cc1)C(=O)n1cc(C(F)(F)F)cn1]

The title compound was synthesized from ethyl(4-morpholinobenzyl)carbamic chloride and 4-(trifluoromethyl)-1H-pyrazole according to the representative procedure of Example 242, Steps 1-4 to provide N-ethyl-N-(4-morpholinobenzyl)-4-(trifluoromethyl)-1H-pyrazole-1-carboxamide as a white solid. $^1$H NMR (300 MHz, Chloroform-d) δ 8.46 (s, 1H), 7.79 (s, 1H), 7.24-7.27 (m, 2H), 6.88-6.91 (m, 2H), 4.75 (br, 2H), 3.86 (t, J=4.8 Hz, 4H), 3.56 (br, 2H), 3.16 (t, J=4.8 Hz, 4H), 1.24 (t, J=7.0 Hz, 3H). LCMS (ESI, m/z): 383 [M+H]$^+$

Example 265: N-Ethyl-4-methyl-N-(4-morpholinobenzyl)-1H-pyrazole-1-carboxamide

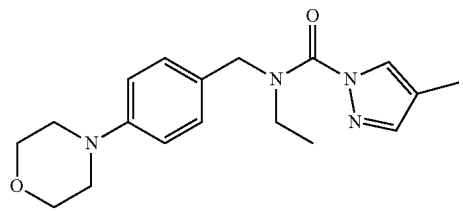 [SMILES: CCN(Cc1ccc(N2CCOCC2)cc1)C(=O)n1cc(C)cn1]

The title compound was synthesized from ethyl(4-morpholinobenzyl)carbamic chloride and 4-methyl-1H-pyrazole according to the representative procedure of Example 242, Steps 1-4 to provide N-ethyl-4-methyl-N-(4-morpholinobenzyl)-1H-pyrazole-1-carboxamide as a light yellow solid. $^1$H NMR (300 MHz, Chloroform-d) δ 7.92 (s, 1H), 7.43 (s, 1H), 7.24-7.27 (m, 2H), 6.85-6.91 (m, 2H), 4.75 (br, 2H), 3.85 (t, J=4.8 Hz, 4H), 3.54-3.57 (m, 2H), 3.14 (t, J=4.8 Hz, 4H), 2.09 (s, 3H), 1.24 (t, J=7.0 Hz, 3H). LCMS (ESI, m/z): 329 [M+H]$^+$ Example 266: 4-Chloro-N-ethyl-N-(3-morpholinobenzyl)-1H-pyrazole-1-carboxamide

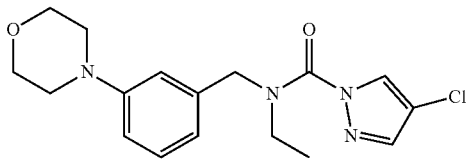 [SMILES: CCN(Cc1cccc(N2CCOCC2)c1)C(=O)n1cc(Cl)cn1]

The title compound was synthesized from ethyl(3-morpholinobenzyl)carbamic chloride (Example 242, Steps 1-3) and 4-chloro-1H-pyrazole according to the representative procedure of Example 242, Steps 1-4 to provide 4-chloro-N-ethyl-N-(3-morpholinobenzyl)-1H-pyrazole-1-carboxamide as a yellow oil. $^1$H NMR (400 MHz, Chloroform-d) δ 8.14 (s, 1H), 7.53 (s, 1H), 7.24-7.28 (m, 1H), 6.86-7.00 (m, 3H), 4.80 (br, 2H), 3.88 (br, 4H), 3.57 (br, 2H), 3.17 (br, 4H), 1.24 (t, J=7.2 Hz, 3H). LCMS (ESI, m/z): 349 [M+H]$^+$ Example 267: 4-Chloro-N-ethyl-N-(4-morpholinobenzyl)-1H-pyrazole-1-carboxamide

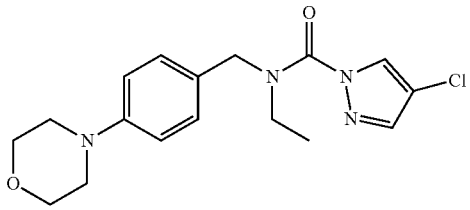 [SMILES: CCN(Cc1ccc(N2CCOCC2)cc1)C(=O)n1cc(Cl)cn1]

The title compound was synthesized from ethyl(4-morpholinobenzyl)carbamic chloride and 4-chloro-1H-pyrazole according to the representative procedure of Example 242, Steps 1-4 to provide 4-chloro-N-ethyl-N-(4-morpholinobenzyl)-1H-pyrazole-1-carboxamide as a white solid. $^1$H NMR (300 MHz, Chloroform-d) δ 8.14 (s, 1H), 7.54 (s, 1H), 7.25-7.28 (m, 2H), 6.89-6.92 (m, 2H), 4.76 (br, 2H), 3.88 (t, J=4.8 Hz, 4H), 3.54-3.56 (m, 2H), 3.17 (t, J=4.8 Hz, 4H), 1.23 (t, J=7.2 Hz, 3H). LCMS (ESI, m/z): 349 [M+H]$^+$ Example 268: (4-(3-Chlorobenzyl)piperazin-1-yl)(4-(trifluoromethyl)-1H-pyrazol-1-yl)methanone

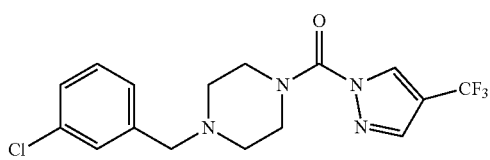 [SMILES: O=C(N1CCN(Cc2cccc(Cl)c2)CC1)n1cc(C(F)(F)F)cn1]

Step 1: Preparation of tert-butyl 4-((4-(trifluoromethyl)-1H-pyrazol-1-yl)carbonyl)piperazine-1-carboxylate

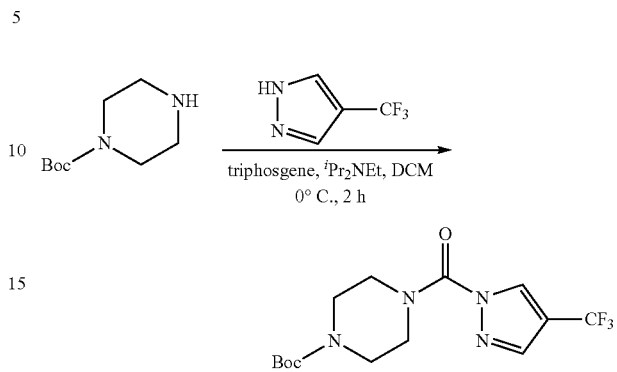

A 100-mL round-bottom flask was charged with triphosgene (1.40 g, 4.72 mmol, 0.40 equiv), dichloromethane (30 mL). 4-(Trifluoromethyl)-1H-pyrazole (1.60 g, 11.8 mmol, 1.00 equiv) was added at 0° C. N,N-Diisopropylethylamine (4.57 g, 35.4 mmol, 3.00 equiv) was added at 0° C. The resulting solution was stirred for 2 h at room temperature. Tert-butyl piperazine-1-carboxylate (2.68 g, 14.4 mmol, 1.20 equiv) was added. The resulting solution was stirred overnight at room temperature and quenched with water (50 mL). The mixture was extracted with dichloromethane (3×70 mL) and the organic layers were combined, washed with brine (100 mL), dried over anhydrous sodium sulfate, filtered and concentrated under reduced pressure. The residue was chromatographed on a silica gel column with ethyl acetate/petroleum ether (8/92) to provide tert-butyl 4-[[4-(trifluoromethyl)-1H-pyrazol-1-yl]carbonyl]piperazine-1-carboxylate (2.37 g, 58% yield) as a yellow solid. LCMS (ESI, m/z): 349 [M+H]$^+$ Step 2: Preparation of 1-((4-(trifluoromethyl)-1H-pyrazol-1-yl)carbonyl)piperazine

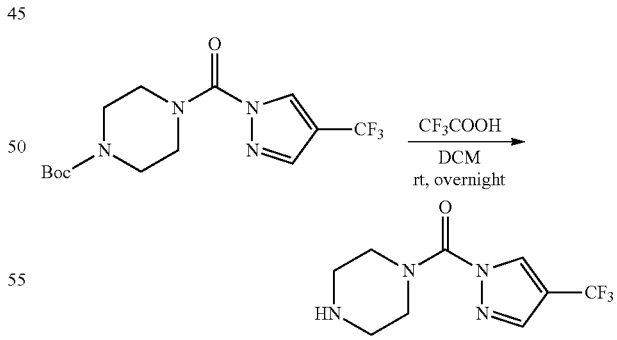

A 100-mL round-bottom flask was charged with tert-butyl 4-[[4-(trifluoromethyl)-1H-pyrazol-1-yl]carbonyl]piperazine-1-carboxylate (2.37 g, 6.80 mmol, 1.00 equiv), dichloromethane (20 mL), trifluoroacetic acid (10 mL). The resulting solution was stirred overnight at room temperature and concentrated under reduced pressure to provide 1-[[4-(trifluoromethyl)-1H-pyrazol-1-yl]carbonyl]piperazine (1.60 g, 95% yield) as a yellow oil. LCMS (ESI, m/z): 249 [M+H]$^+$

Step 3: Preparation of (4-(3-Chlorobenzyl)piperazin-1-yl)(4-(trifluoromethyl)-1H-pyrazol-1-yl) methanone

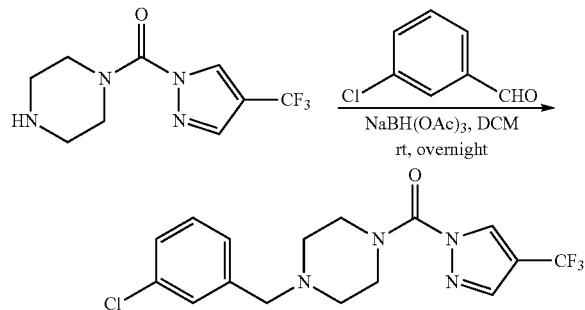

A 40-mL round-bottom flask was charged with 3-chlorobenzaldehyde (77.8 mg, 0.556 mmol, 1.00 equiv), dichloromethane (10 mL), 1-[[4-(trifluoromethyl)-1H-pyrazol-1-yl]carbonyl]piperazine (165 mg, 0.667 mmol, 1.20 equiv). The mixture was stirred for 1 h at room temperature. Sodium triacetoxyborohydride (354 mg, 1.67 mmol, 3.00 equiv) was added. The resulting solution was stirred overnight at room temperature and quenched with H$_2$O (10 mL). The mixture was extracted with dichloromethane (3×30 mL) and the organic layers were combined, washed with brine (30 mL), dried over anhydrous sodium sulfate, filtered and concentrated under reduced pressure. The crude product (180 mg) was purified by preparative HPLC using the following gradient conditions: 35% CH$_3$CN/65% Phase A increasing to 65% CH$_3$CN over 10 min, then to 100% CH$_3$CN over 0.1 min, holding at 100% CH$_3$CN for 1.9 min, then reducing to 35% CH$_3$CN over 0.1 min, and holding at 35% for 1.9 min, on a Waters 2767-5 Chromatograph. Column: Xbridge Prep C18, (19*150) mm 5 um; Mobile phase: Phase A: aqueous NH$_4$HCO$_3$ (0.05%); Phase B: CH$_3$CN; Detector, UV 220 & 254 nm. Purification provided (4-(3-Chlorobenzyl)piperazin-1-yl)(4-(trifluoromethyl)-1H-pyrazol-1-yl)methanone as a white solid (68.3 mg, 33% yield). $^1$H NMR (300 MHz, Chloroform-d) δ 8.40 (s, 1H), 7.79 (s, 1H), 7.35 (s, 1H), 7.25-7.29 (m, 2H), 7.19-7.23 (m, 1H), 3.87 (br, 4H), 3.53 (s, 2H), 2.55 (t, J=5.0 Hz, 4H). LCMS (ESI, m/z): 373 [M+H]$^+$

Example 269: (4-(3-Fluorobenzyl)piperazin-1-yl)(4-(trifluoromethyl)-1H-pyrazol-1-yl)methanone

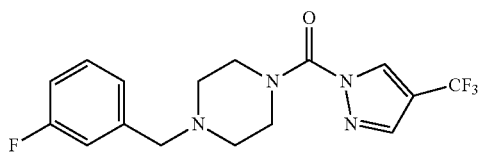 [SMILES: O=C(N1CCN(Cc2cccc(F)c2)CC1)n1cc(C(F)(F)F)cn1]

The title compound was synthesized from 1-((4-(trifluoromethyl)-1H-pyrazol-1-yl)carbonyl)piperazine (Example 268, Steps 1-2) and 3-fluorobenzaldehyde according to the representative procedure of Example 268, Steps 1-3 to provide (4-(3-fluorobenzyl)piperazin-1-yl)(4-(trifluoromethyl)-1H-pyrazol-1-yl)methanone as a white solid. $^1$H NMR (300 MHz, Chloroform-d) δ 8.40 (s, 1H), 7.79 (s, 1H), 7.25-7.32 (m, 1H), 7.06-7.10 (m, 2H), 6.93-7.00 (m, 1H), 3.87 (br, 4H), 3.55 (s, 2H), 2.56 (t, J=5.0 Hz, 4H). LCMS (ESI, m/z): 357 [M+H]$^+$

Example 270: (4-(3-Methylbenzyl)piperazin-1-yl)(4-(trifluoromethyl)-1H-pyrazol-1-yl)methanone

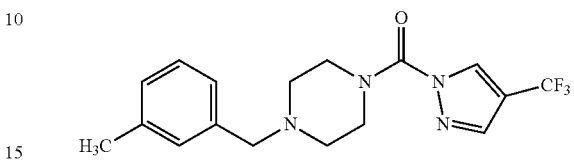

The title compound was synthesized from 1-((4-(trifluoromethyl)-1H-pyrazol-1-yl)carbonyl)piperazine (Example 268, Steps 1-2) and 3-methylbenzaldehyde according to the representative procedure of Example 268, Steps 1-3 to provide (4-(3-methylbenzyl)piperazin-1-yl)(4-(trifluoromethyl)-1H-pyrazol-1-yl)methanone as white solid. $^1$H NMR (300 MHz, Chloroform-d) δ 8.39 (s, 1H), 7.79 (s, 1H), 7.20-7.24 (m, 1H), 7.08-7.13 (m, 3H), 3.86 (br, 4H), 3.52 (s, 2H), 2.55 (t, J=5.1 Hz, 4H), 2.35 (s, 3H). LCMS (ESI, m/z): 353 [M+H]$^+$.

Example 271: (4-(3-Methoxybenzyl)piperazin-1-yl)(4-(trifluoromethyl)-1H-pyrazol-1-yl)methanone

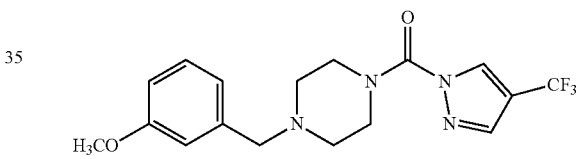

The title compound was synthesized from 1-((4-(trifluoromethyl)-1H-pyrazol-1-yl)carbonyl)piperazine (Example 268, Steps 1-2) and 3-methoxybenzaldehyde according to the representative procedure of Example 268, Steps 1-3 to provide (4-(3-methoxybenzyl)piperazin-1-yl)(4-(trifluoromethyl)-1H-pyrazol-1-yl)methanone as a white solid. $^1$H NMR (300 MHz, Chloroform-d) δ 8.40 (s, 1H), 7.79 (s, 1H), 7.22-7.24 (m, 1H), 6.89-6.92 (m, 2H), 6.80-6.83 (m, 1H), 3.86 (br, 4H), 3.82 (s, 3H), 3.53 (s, 2H), 2.56 (t, J=5.0 Hz, 4H). LCMS (ESI, m/z): 367 [M+H]$^+$.

Example 272: (4-(Trifluoromethyl)-1H-pyrazol-1-yl)(4-(3-(trifluoromethyl)benzyl) piperazin-1-yl) methanone

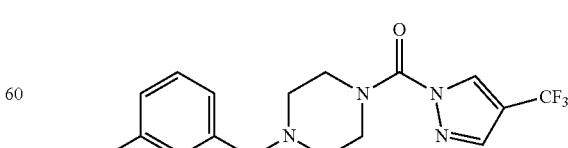

The title compound was synthesized from 1-((4-(trifluoromethyl)-1H-pyrazol-1-yl)carbonyl)piperazine (Example 268, Steps 1-2) and 3-trifluoromethylbenzaldehyde according to the representative procedure of Example 268, Steps 1-3 to provide (4-(trifluoromethyl)-1H-pyrazol-1-yl)(4-(3-(trifluoromethyl)benzyl)piperazin-1-yl)methanone as a white solid. ¹H NMR (300 MHz, Chloroform-d) δ 8.40 (s, 1H), 7.79 (s, 1H), 7.61 (s, 1H), 7.52-7.55 (m, 2H), 7.42-7.48 (m, 1H), 3.88 (br, 4H), 3.60 (s, 2H), 2.56 (t, J=5.0 Hz, 4H). LCMS (ESI, m/z): 407 [M+H]⁺.

Example 273: (4-(3-(Pyrrolidin-1-yl)benzyl)piperazin-1-yl)(4-(trifluoromethyl)-1H-pyrazol-1-yl)methanone

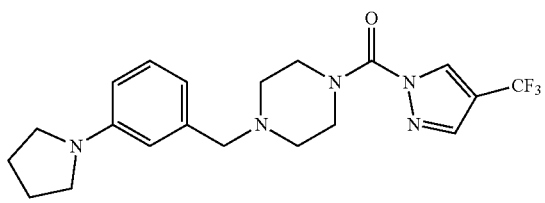 [SMILES: O=C(N1CCN(Cc2cccc(N3CCCC3)c2)CC1)n1cc(C(F)(F)F)cn1]

The title compound was synthesized from 1-((4-(trifluoromethyl)-1H-pyrazol-1-yl)carbonyl)piperazine (Example 268, Steps 1-2) and 3-(pyrrolidin-1-yl)benzaldehyde according to the representative procedure of Example 268, Steps 1-3 to provide (4-(3-(pyrrolidin-1-yl)benzyl)piperazin-1-yl)(4-(trifluoromethyl)-1H-pyrazol-1-yl)methanone as a white solid. ¹H NMR (300 MHz, Chloroform-d) δ 8.39 (s, 1H), 7.79 (s, 1H), 7.18 (t, J=7.8 Hz, 1H), 6.62 (d, J=7.2 Hz, 1H), 6.48-6.53 (m, 2H), 3.86 (br, 4H), 3.52 (br, 2H), 3.29 (t, J=6.4 Hz, 4H), 2.57 (br, 4H), 1.96-2.05 (m, 4H). LCMS (ESI, m/z): 408 [M+H]⁺.

Example 274: (4-(3-Morpholinobenzyl)piperazin-1-yl)(4-(trifluoromethyl)-1H-pyrazol-1-yl)methanone

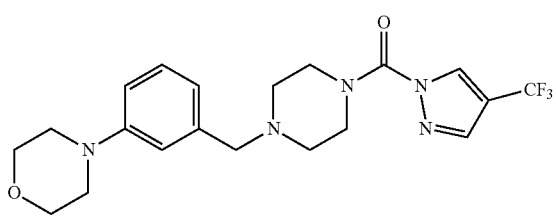 [SMILES: O=C(N1CCN(Cc2cccc(N3CCOCC3)c2)CC1)n1cc(C(F)(F)F)cn1]

The title compound was synthesized from 1-((4-(trifluoromethyl)-1H-pyrazol-1-yl)carbonyl)piperazine (Example 268, Steps 1-2) and 3-morpholinobenzaldehyde according to the representative procedure of Example 268, Steps 1-3 to provide (4-(3-Morpholinobenzyl)piperazin-1-yl)(4-(trifluoromethyl)-1H-pyrazol-1-yl)methanone as a light yellow oil. ¹H NMR (300 MHz, Chloroform-d) δ 8.40 (s, 1H), 7.79 (s, 1H), 7.21-7.24 (m, 1H), 6.83-6.90 (m, 3H), 4.09-4.14 (m, 8H), 3.87 (br, 2H), 3.18 (br, 4H), 2.56 (br, 4H). LCMS (ESI, m/z): 424 [M+H]⁺.

Example 275: (4-(2-Chlorobenzyl)piperazin-1-yl)(4-(trifluoromethyl)-1H-pyrazol-1-yl)methanone

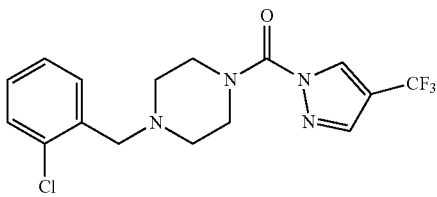 [SMILES: O=C(N1CCN(Cc2ccccc2F)CC1)n1cc(C(F)(F)F)cn1]

The title compound was synthesized from 1-((4-(trifluoromethyl)-1H-pyrazol-1-yl)carbonyl)piperazine (Example 268, Steps 1-2) and 2-chlorobenzaldehyde according to the representative procedure of Example 268, Steps 1-3 to provide (4-(2-chlorobenzyl)piperazin-1-yl)(4-(trifluoromethyl)-1H-pyrazol-1-yl)methanone as an off-white semi-solid. ¹H NMR (300 MHz, Chloroform-d) δ 8.40 (s, 1H), 7.80 (s, 1H), 7.44-7.46 (m, 1H), 7.36-7.38 (m, 1H), 7.18-7.28 (m, 2H), 3.87 (br, 4H), 3.72 (s, 2H), 2.63 (t, J=4.8 Hz, 4H). LCMS (ESI, m/z): 373 [M+H]⁺.

Example 276: (4-(2-Fluorobenzyl)piperazin-1-yl)(4-(trifluoromethyl)-1H-pyrazol-1-yl)methanone

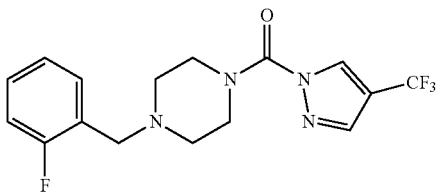

The title compound was synthesized from 1-((4-(trifluoromethyl)-1H-pyrazol-1-yl)carbonyl)piperazine (Example 268, Steps 1-2) and 2-fluorobenzaldehyde according to the representative procedure of Example 268, Steps 1-3 to provide (4-(2-fluorobenzyl)piperazin-1-yl)(4-(trifluoromethyl)-1H-pyrazol-1-yl)methanone as a white solid. ¹H NMR (300 MHz, Chloroform-d) δ 8.39 (s, 1H), 7.79 (s, 1H), 7.34-7.39 (m, 1H), 7.23-7.31 (m, 1H), 7.02-7.15 (m, 2H), 3.87 (br, 4H), 3.65 (s, 2H), 2.60 (t, J=4.8 Hz, 4H). LCMS (ESI, m/z): 357 [M+H]⁺.

Example 277: (4-(2-Methylbenzyl)piperazin-1-yl)(4-(trifluoromethyl)-1H-pyrazol-1-yl)methanone

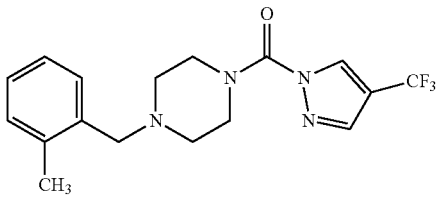

The title compound was synthesized from 1-((4-(trifluoromethyl)-1H-pyrazol-1-yl)carbonyl)piperazine (Example 268, Steps 1-2) and 2-methylbenzaldehyde according to the representative procedure of Example 268, Steps 1-3 to provide (4-(2-methylbenzyl)piperazin-1-yl)(4-(trifluoromethyl)-1H-pyrazol-1-yl)methanone as a light yellow semi-solid. ¹H NMR (300 MHz, Chloroform-d) δ 8.40 (s, 1H), 7.79 (s, 1H), 7.12-7.23 (m, 4H), 3.83 (br, 4H), 3.51 (s, 2H), 2.55 (t, J=4.8 Hz, 4H), 2.38 (s, 3H). LCMS (ESI, m/z): 353 [M+H]⁺.

Example 278: (4-(2-Methoxybenzyl)piperazin-1-yl)(4-(trifluoromethyl)-1H-pyrazol-1-yl)methanone

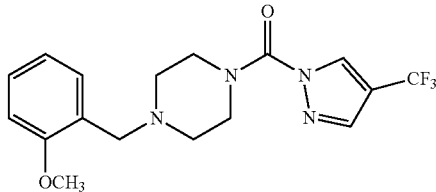 [SMILES: COc1ccccc1CN1CCN(C(=O)n2cc(C(F)(F)F)cn2)CC1]

The title compound was synthesized from 1-((4-(trifluoromethyl)-1H-pyrazol-1-yl)carbonyl)piperazine (Example 268, Steps 1-2) and 2-methoxybenzaldehyde according to the representative procedure of Example 268, Steps 1-3 to provide (4-(2-methoxybenzyl)piperazin-1-yl)(4-(trifluoromethyl)-1H-pyrazol-1-yl)methanone as a light yellow semi-solid. ¹H NMR (300 MHz, Chloroform-d) δ 8.39 (s, 1H), 7.79 (s, 1H), 7.32-7.35 (m, 1H), 7.23-7.26 (m, 1H), 6.87-6.97 (m, 2H), 3.86 (br, 3H), 3.82 (s, 4H), 3.63 (s, 2H), 2.60 (t, J=4.8 Hz, 4H). LCMS (ESI, m/z): 369 [M+H]⁺.

Example 279: (4-(Trifluoromethyl)-1H-pyrazol-1-yl)(4-(2-(trifluoromethyl)benzyl) piperazin-1-yl)methanone

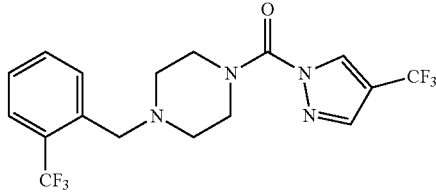 [SMILES: O=C(N1CCN(Cc2ccccc2C(F)(F)F)CC1)n1cc(C(F)(F)F)cn1]

The title compound was synthesized from 1-((4-(trifluoromethyl)-1H-pyrazol-1-yl)carbonyl)piperazine (Example 268, Steps 1-2) and 2-trifluoromethylbenzaldehyde according to the representative procedure of Example 268, Steps 1-3 to provide (4-(trifluoromethyl)-1H-pyrazol-1-yl)(4-(2-(trifluoromethyl)benzyl)piperazin-1-yl)methanone as a light yellow semi-solid. ¹H NMR (300 MHz, Chloroform-d) δ 8.40 (s, 1H), 7.79 (s, 1H), 7.76 (s, 1H), 7.61-7.66 (m, 1H), 7.54 (t, J=7.8 Hz, 1H), 7.36 (t, J=7.8 Hz, 1H), 3.88 (br, 4H), 3.72 (s, 2H), 2.59 (t, J=4.8 Hz, 4H). LCMS (ESI, m/z): 407 [M+H]⁺.

Example 280: (4-(2-(Pyrrolidin-1-yl)benzyl)piperazin-1-yl)(4-(trifluoromethyl)-1H-pyrazol-1-yl)methanone

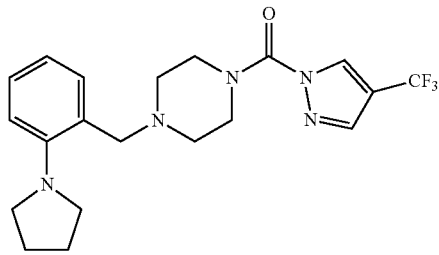 [SMILES: O=C(N1CCN(Cc2ccccc2N2CCCC2)CC1)n1cc(C(F)(F)F)cn1]

The title compound was synthesized from 1-((4-(trifluoromethyl)-1H-pyrazol-1-yl)carbonyl)piperazine (Example 268, Steps 1-2) and 2-(pyrrolidin-1-yl)benzaldehyde according to the representative procedure of Example 268, Steps 1-3 to provide (4-(2-(pyrrolidin-1-yl)benzyl)piperazin-1-yl)(4-(trifluoromethyl)-1H-pyrazol-1-yl)methanone as a white solid. ¹H NMR (300 MHz, Chloroform-d) δ 8.40 (s, 1H), 7.79 (s, 1H), 7.34-7.48 (m, 1H), 7.19-7.24 (m, 1H), 6.91-6.96 (m, 2H), 3.85 (br, 4H), 3.59 (br, 2H), 3.19 (t, J=6.3 Hz, 4H), 2.57 (br, 4H), 1.92 (br, 4H). LCMS (ESI, m/z): 408 [M+H]⁺.

Example 281: (4-(2-Morpholinobenzyl)piperazin-1-yl)(4-(trifluoromethyl)-1H-pyrazol-1-yl)methanone

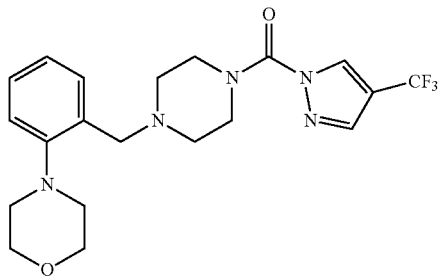 [SMILES: O=C(N1CCN(Cc2ccccc2N2CCOCC2)CC1)n1cc(C(F)(F)F)cn1]

The title compound was synthesized from 1-((4-(trifluoromethyl)-1H-pyrazol-1-yl)carbonyl)piperazine (Example 268, Steps 1-2) and 2-morpholinobenzaldehyde according to the representative procedure of Example 268, Steps 1-3 to provide (4-(2-morpholinobenzyl)piperazin-1-yl)(4-(trifluoromethyl)-1H-pyrazol-1-yl)methanone as a light yellow solid. ¹H NMR (300 MHz, Chloroform-d) δ 8.40 (s, 1H), 7.83 (s, 1H), 7.43 (d, J=7.5 Hz, 1H), 7.28-7.31 (m, 1H), 7.08-7.14 (m, 2H), 3.84 (t, J=4.8 Hz, 8H), 3.64 (s, 2H), 2.97 (t, J=4.5 Hz, 4H), 2.60 (t, J=5.1 Hz, 4H). LCMS (ESI, m/z): 424 [M+H]⁺.

Example 282: 1-(4-(2-Chloro-4-(piperidine-1-carbonyl)benzyl)piperazine-1-carbonyl)-1H-pyrazole-4-carbonitrile

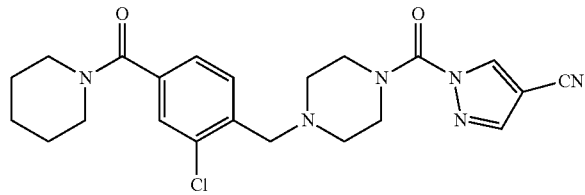 [SMILES: N#Cc1cnn(C(=O)N2CCN(Cc3ccc(C(=O)N4CCCCC4)cc3Cl)CC2)c1]

Step 1: Preparation of tert-butyl 4-(2-chloro-4-(methoxycarbonyl)benzyl)piperazine-1-carboxylate

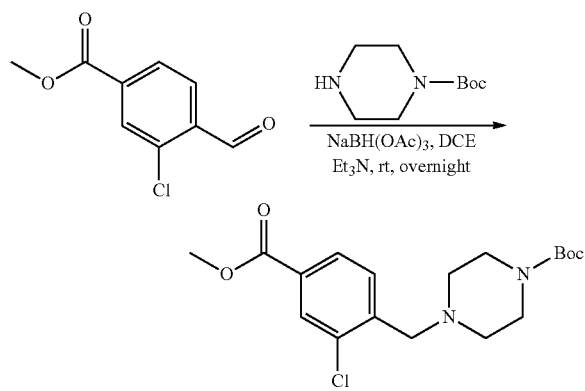

A 250-mL round-bottom flask was charged with methyl 3-chloro-4-formylbenzoate (3.00 g, 15.1 mmol, 1.00 equiv), tert-butyl piperazine-1-carboxylate (3.36 g, 18.0 mmol, 1.20 equiv), triethylamine (1.52 g, 15.0 mmol, 1.00 equiv), 1,2-dichloroethane (30 mL). The mixture was stirred at room temperature for 30 min. Sodium triacetoxyborohydride (9.59 g, 45.2 mmol, 3.00 equiv) was added. The resulting solution was stirred overnight at room temperature and quenched with water (30 mL). The resulting solution was extracted with dichloromethane (3×50 mL) and the organic layers were combined, washed with water (3×20 mL), dried over anhydrous sodium sulfate, filtered and concentrated under reduced pressure. The residue was chromatographed on a silica gel column with ethyl acetate/petroleum ether (1/9) to provide tert-butyl 4-(2-chloro-4-(methoxycarbonyl)benzyl)piperazine-1-carboxylate (4.90 g, 88% yield) as a yellow oil. LCMS (ESI, m/z): 369 [M+H]$^+$.

Step 2: Preparation of 4-((4-(tert-butoxycarbonyl)piperazin-1-yl)methyl)-3-chlorobenzoic acid

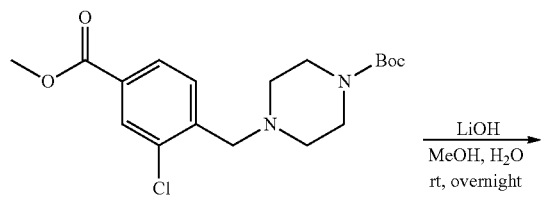

A 250-mL round-bottom flask was charged with tert-butyl 4-(2-chloro-4-(methoxycarbonyl)benzyl)piperazine-1-carboxylate (4.90 g, 13.3 mmol, 1.00 equiv), lithium hydroxide (1.59 g, 66.4 mmol, 5.00 equiv), methanol (33 mL), water (17 mL). The resulting solution was stirred overnight at room temperature. The pH value of the solution was adjusted to 5 with hydrochloric acid (1 M). The solids were collected by filtration to provide 4-((4-(tert-butoxycarbonyl)piperazin-1-yl)methyl)-3-chlorobenzoic acid (2.20 g, 47% yield) as a yellow solid. LCMS (ESI, m/z): 355 [M+H]$^+$.

Step 3: Preparation of tert-butyl 4-(2-chloro-4-(piperidine-1-carbonyl)benzyl)piperazine-1-carboxylate

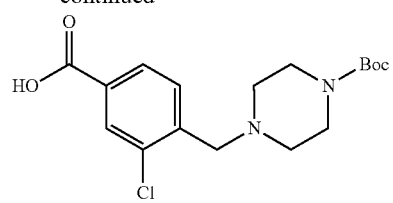

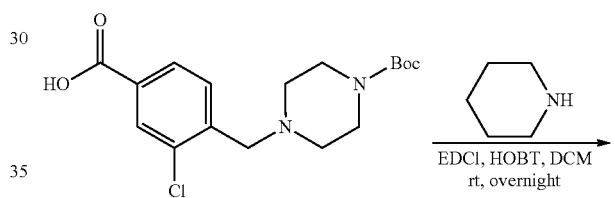

A 100-mL round-bottom flask was charged with 4-((4-(tert-butoxycarbonyl)piperazin-1-yl)methyl)-3-chlorobenzoic acid (1.10 g, 3.10 mmol, 1.00 equiv), N-(3-dimethylaminopropyl)-N'-ethylcarbodiimide hydrochloride (773 mg, 4.03 mmol, 1.30 equiv), 1-hydroxybenzotrizole (544 mg, 4.03 mmol, 1.30 equiv), dichloromethane (10 mL). The mixture was stirred at room temperature for 30 min. Piperidine (527 mg, 6.19 mmol, 2.00 equiv) was added. The resulting solution was stirred overnight at room temperature and quenched with water (20 mL). The resulting solution was extracted with dichloromethane (3×30 mL) and the organic layers were combined, washed with water (3×10 mL), dried over anhydrous sodium sulfate, filtered and concentrated under reduced pressure. The residue was chromatographed on a silica gel column with ethyl acetate/petroleum ether (1/1) to provide tert-butyl 4-(2-chloro-4-(piperidine-1-carbonyl)benzyl)piperazine-1-carboxylate (887 mg, 68% yield) as a yellow oil. LCMS (ESI, m/z): 422 [M+H]$^+$.

Step 4: Preparation of (3-chloro-4-(piperazin-1-ylmethyl)phenyl)(piperidin-1-yl)methanone

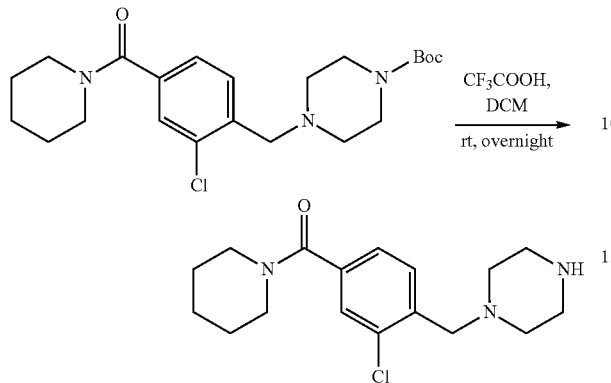

A 100-mL round-bottom flask was charged with tert-butyl 4-(2-chloro-4-(piperidine-1-carbonyl)benzyl)piperazine-1-carboxylate (887 mg, 2.10 mmol, 1.00 equiv), dichloromethane (10 mL). The mixture was cooled to 0° C. Trifluoroacetic acid (2.5 mL) was added dropwise. The resulting solution was stirred for 3 h at room temperature and concentrated under reduced pressure to provide 670 mg (99% yield) of (3-chloro-4-(piperazin-1-ylmethyl)phenyl)(piperidin-1-yl)methanone (670 mg, 99% yield) as a yellow oil. LCMS (ESI, m/z): 322 [M+H]$^+$.

Step 5: Preparation of 4-(2-chloro-4-(piperidine-1-carbonyl)benzyl)piperazine-1-carbonyl chloride

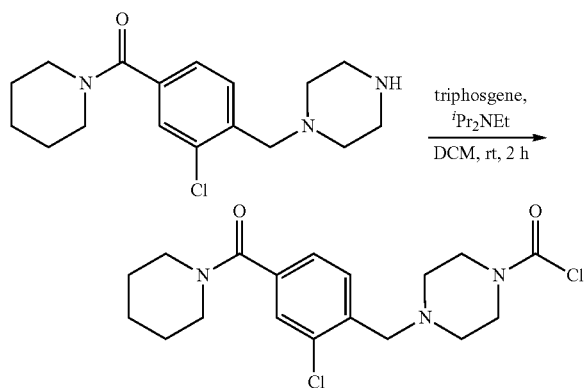

A 100-mL round-bottom flask was charged with triphosgene (309 mg, 1.04 mmol, 0.50 equiv), dichloromethane (10 mL). The mixture was cooled to 0° C. (3-chloro-4-(piperazin-1-ylmethyl)phenyl)(piperidin-1-yl)methanone (670 mg, 2.08 mmol, 1.00 equiv) was added. N,N-Diisopropylethylamine (1.07 g, 8.29 mmol, 4.00 equiv) was added dropwise. The resulting solution was stirred for 2 h at room temperature and quenched with water (20 mL). The resulting solution was extracted with dichloromethane (3×30 mL) and the organic layers were combined, washed with water (3×10 mL), dried over anhydrous sodium sulfate, filtered and concentrated under reduced pressure to provide 4-(2-chloro-4-(piperidine-1-carbonyl)benzyl)piperazine-1-carbonyl chloride (780 mg, 97% yield) as a yellow solid. LCMS (ESI, m/z): 384 [M+H]$^+$.

Step 6: Preparation of 1-(4-(2-Chloro-4-(piperidine-1-carbonyl)benzyl)piperazine-1-carbonyl)-1H-pyrazole-4-carbonitrile

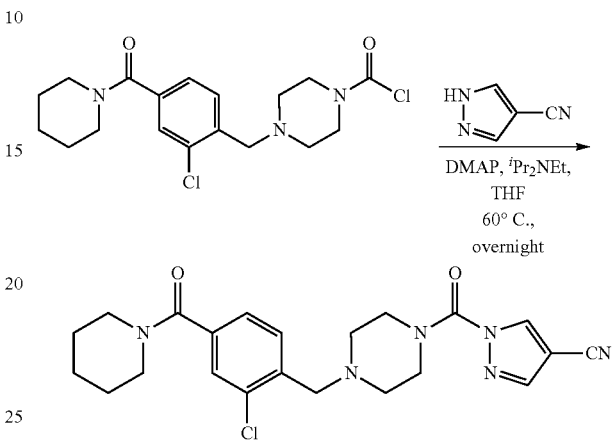

A 25-mL round-bottom flask was charged with 4-(2-chloro-4-(piperidine-1-carbonyl)benzyl)piperazine-1-carbonyl chloride (195 mg, 0.508 mmol, 1.00 equiv), 1H-pyrazole-4-carbonitrile (94.4 mg, 1.01 mmol, 2.00 equiv), 4-dimethylaminopyridine (12.4 mg, 0.10 mmol, 0.20 equiv), N,N-diisopropylethylamine (196 mg, 1.52 mmol, 3.00 equiv), tetrahydrofuran (5 mL). The resulting solution was stirred overnight at 60° C. and concentrated under reduced pressure. The crude product (200 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm 5 µm; Mobile phase: Phase A: aqueous NH$_4$HCO$_3$ (0.05%); Phase B: CH$_3$CN; Detector, UV220 & 254 nm. Purification resulted in 52.8 mg (24% yield) of 1-(4-(2-Chloro-4-(piperidine-1-carbonyl)benzyl)piperazine-1-carbonyl)-1H-pyrazole-4-carbonitrile as a white solid. $^1$H NMR (300 MHz, Chloroform-d) δ 8.53 (s, 1H), 7.88 (s, 1H), 7.50 (d, J=7.8 Hz, 1H), 7.41 (d, J=1.8 Hz, 1H), 7.26-7.29 (m, 1H), 3.68-3.86 (m, 8H), 3.36 (br, 2H), 2.62-2.65 (m, 4H), 1.60-1.69 (m, 6H). LCMS (ESI, m/z): 441 [M+H]$^+$.

Example 283: 1-(4-(4-(Azetidine-1-carbonyl)-2-chlorobenzyl)piperazine-1-carbonyl)-1H-pyrazole-4-carbonitrile

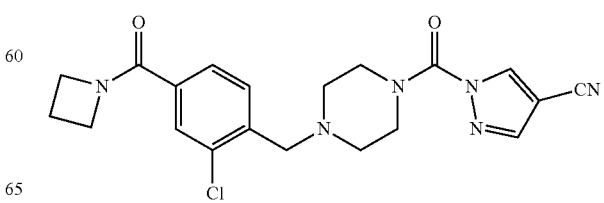

313

The title compound was synthesized from 4-((4-(tert-butoxycarbonyl)piperazin-1-yl)methyl)-3-chlorobenzoic acid (Example 282, Steps 1-2), azetidine, triphosgene, and 1H-pyrazole-4-carbonitrile according to the representative procedure of Example 282, Steps 1-6 to provide 1-(4-(4-(azetidine-1-carbonyl)-2-chlorobenzyl)piperazine-1-carbonyl)-1H-pyrazole-4-carbonitrile (52.9 mg, 19% yield) as a white solid. $^1$H NMR (300 MHz, Chloroform-d) δ 8.53 (s, 1H), 7.87 (s, 1H), 7.65 (s, 1H), 7.49-7.54 (m, 2H), 4.21-4.35 (m, 4H), 3.86 (br, 4H), 3.69 (br, 2H), 2.62-2.65 (m, 4H), 2.31-2.42 (m, 2H). LCMS (ESI, m/z): 413 [M+H]$^+$.

Example 284: 1-(4-(2-Fluoro-4-(piperidine-1-carbonyl)benzyl)piperazine-1-carbonyl)-1H-pyrazole-4-carbonitrile

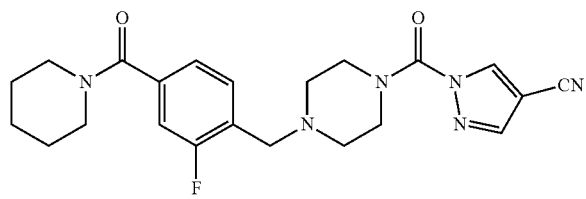 [SMILES: N#Cc1cnn(C(=O)N2CCN(Cc3ccc(C(=O)N4CCCCC4)cc3F)CC2)c1]

The title compound was synthesized from methyl 3-fluoro-4-formylbenzoate according to the representative procedure of Example 282, Steps 1-6 to provide 1-(4-(2-fluoro-4-(piperidine-1-carbonyl)benzyl)piperazine-1-carbonyl)-1H-pyrazole-4-carbonitrile (71.9 mg, 21% yield) as a white solid. $^1$H NMR (300 MHz, Chloroform-d) δ 8.53 (s, 1H), 7.87 (s, 1H), 7.41 (t, J=7.5 Hz, 1H), 7.08-7.18 (m, 2H), 3.65-3.85 (m, 8H), 3.35 (br, 2H), 2.60 (br, 4H), 1.55-1.69 (m, 6H). LCMS (ESI, m/z): 425 [M+H]$^+$.

Example 285: 1-(4-(4-(Azetidine-1-carbonyl)-2-fluorobenzyl)piperazine-1-carbonyl)-1H-pyrazole-4-carbonitrile

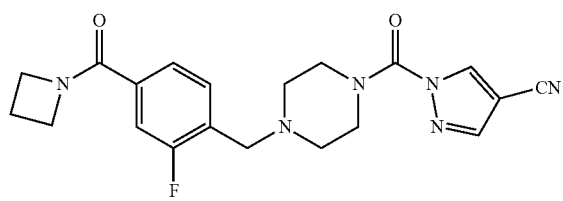 [SMILES: N#Cc1cnn(C(=O)N2CCN(Cc3ccc(C(=O)N4CCC4)cc3F)CC2)c1]

The title compound was synthesized from 4-(4-(azetidine-1-carbonyl)-2-fluorobenzyl)piperazine-1-carbonyl chloride and 1H-pyrazole-4-carbonitrile according to the representative procedure of Example 282, Steps 1-6 to provide 1-(4-(4-(azetidine-1-carbonyl)-2-fluorobenzyl)piperazine-1-carbonyl)-1H-pyrazole-4-carbonitrile as a white solid. $^1$H NMR (300 MHz, Chloroform-d) δ 8.52 (s, 1H), 7.87 (s, 1H), 7.38-7.46 (m, 2H), 7.32-7.36 (m, 1H), 4.21-4.35 (m, 4H), 3.85 (br, 4H), 3.65 (br, 2H), 2.58-2.61 (br, 4H), 2.32-2.42 (m, 2H). LCMS (ESI, m/z): 397 [M+H]$^+$.

Example 286: 1-(4-(3-Phenoxybenzyl)piperazine-1-carbonyl)-1H-pyrazole-4-carboxamide

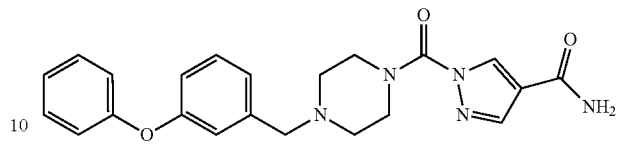

Step 1: Preparation of tert-butyl 4-(3-phenoxybenzyl)piperazine-1-carboxylate

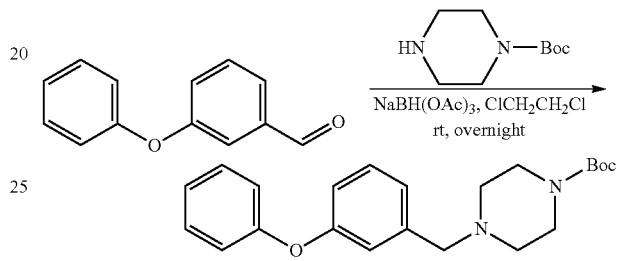

A 100-mL round-bottom flask was charged with 3-phenoxybenzaldehyde (198 mg, 1.00 mmol, 1.00 equiv), tert-butyl piperazine-1-carboxylate (223 mg, 1.20 mmol, 1.20 equiv), 1,2-dichloroethane (10 mL) and sodium triacetoxyborohydride (424 mg, 2.00 mmol, 2.00 equiv). The resulting solution was stirred overnight at room temperature and quenched by water (10 mL). The mixture was extracted with dichloromethane (3×30 mL) and the organic layers were combined, washed with water (3×10 mL), dried over anhydrous sodium sulfate, filtered and concentrated under reduced pressure. The residue was chromatographed on a silica gel column with ethyl acetate/petroleum ether (1/3) to provide tert-butyl 4-(3-phenoxybenzyl)piperazine-1-carboxylate (300 mg, 81% yield) as yellow oil. LCMS (ESI, m/z): 369 [M+H]$^+$.

Step 2: Preparation of 1-(3-phenoxybenzyl)piperazine

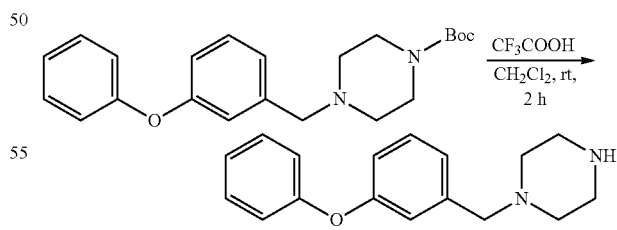

A 100-mL round-bottom flask was charged with tert-butyl 4-(3-phenoxybenzyl)piperazine-1-carboxylate (300 mg, 0.813 mmol, 1.00 equiv), dichloromethane (10 mL) and trifluoroacetic acid (1 mL). The resulting solution was stirred for 2 hours at room temperature and concentrated under reduced pressure to provide of 1-(3-phenoxybenzyl)piperazine (260 mg) as a yellow oil. LCMS (ESI, m/z): 269 [M+H]$^+$.

Step 3: Preparation of 4-(3-phenoxybenzyl)piperazine-1-carbonyl chloride

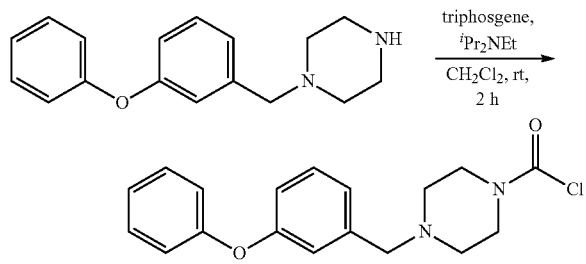

A 100-mL round-bottom flask was charged with 1 1-(3-phenoxybenzyl)piperazine (100 mg, 0.373 mmol, 1.00 equiv), triphosgene (55.5 mg, 0.187 mmol, 0.50 equiv) and dichloromethane (10 mL). N,N-Diisopropylethylamine (96.2 mg, 0.746 mmol, 2.00 equiv) was added dropwise at 0° C. The resulting solution was stirred for 2 hours at room temperature and quenched by water (10 ml). The mixture was extracted with dichloromethane (3×30 mL) and the organic layers were combined, washed with water (3×10 mL), dried over anhydrous sodium sulfate, filtered and concentrated under reduced pressure to provide crude 4-(3-phenoxybenzyl)piperazine-1-carbonyl chloride (135 mg) as a brown oil. LCMS (ESI, m/z): 331 [M+H]$^+$.

Step 4: Preparation of 1-(4-(3-phenoxybenzyl)piperazine-1-carbonyl)-1H-pyrazole-4-carboxamide

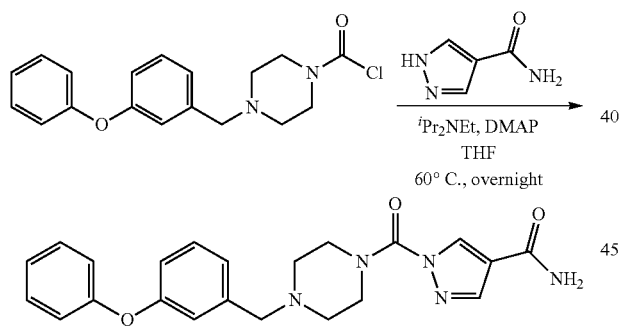

A 100-mL round-bottom flask was charged with 4-(3-phenoxybenzyl)piperazine-1-carbonyl chloride (135 mg, 0.410 mmol, 1.00 equiv), 1H-pyrazole-4-carboxamide (46.2 mg, 0.410 mmol, 1.01 equiv), tetrahydrofuran (10 mL), N,N-diisopropylethylamine (106 mg, 0.820 mmol, 2.00 equiv) and 4-dimethylaminopyridine (10.1 mg, 0.0827 mmol, 0.20 equiv). The resulting solution was stirred overnight at 60° C. and quenched by water (10 mL). The mixture was extracted with dichloromethane (3×30 mL) and the organic layers were combined, washed with water (3×10 mL), dried over anhydrous sodium sulfate, filtered and concentrated under reduced pressure. The crude product was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: X bridge Prep C$_{18}$, 19×150 mm, 5 µm; Mobile phase: Phase A: aqueous NH$_4$HCO$_3$ (0.05%); Phase B: CH$_3$CN; Detector, UV220 & 254 nm. Purification provided 1-(4-(3-phenoxybenzyl)piperazine-1-carbonyl)-1H-pyrazole-4-carboxamide (85.4 mg, 52% yield) as a white solid. $^1$H NMR (400 MHz, Chloroform-d) δ 8.54 (s, 1H), 7.95 (s, 1H), 7.27-7.41 (m, 3H), 6.99-7.17 (m, 5H), 6.93 (d, J=8.4 Hz, 1H), 5.75 (br, 2H), 3.69-4.15 (m, 4H), 3.32-3.65 (m, 2H), 2.42-2.71 (m, 4H). LCMS (ESI, m/z): 406 [M+H]$^+$.

Example 287: N-Methyl-1-(4-(3-phenoxybenzyl)piperazine-1-carbonyl)-1H-pyrazole-4-carboxamide

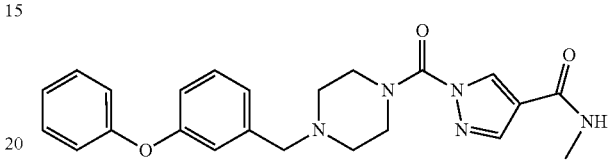

The title compound was synthesized from 4-(3-phenoxybenzyl)piperazine-1-carbonyl chloride (Example 286, Steps 1-3) and N-methyl-1H-pyrazole-4-carboxamide according to the representative procedure of Example 286, Steps 1-4 to provide N-Methyl-1-(4-(3-phenoxybenzyl)piperazine-1-carbonyl)-1H-pyrazole-4-carboxamide (96.3 mg, 56% yield) as a white solid. $^1$H NMR (400 MHz, Chloroform-d) δ 8.48 (s, 1H), 7.95 (s, 1H), 7.28-7.42 (m, 3H), 6.98-7.18 (m, 5H), 6.91 (d, J=8.4 Hz, 1H), 5.95 (s, 1H), 3.69-4.08 (m, 4H), 3.42-3.65 (m, 2H), 2.98 (s, 3H), 2.38-2.71 (m, 4H). LCMS (ESI, m/z): 420 [M+H]$^+$.

Example 288: 1-(4-(4-Chlorobenzyl)piperazine-1-carbonyl)-1H-pyrazole-4-carboxylic acid

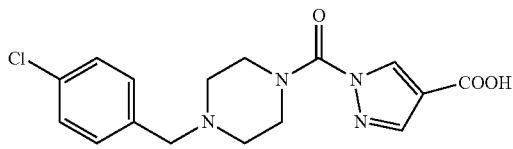 [SMILES: O=C(O)c1cnn(C(=O)N2CCN(Cc3ccc(Cl)cc3)CC2)c1]

Step 1: Preparation of di-tert-butyl 1H-pyrazole-1,4-dicarboxylate

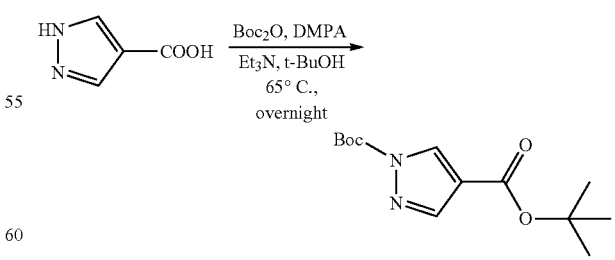

A 100-mL round-bottom flask was charged with 1H-pyrazole-4-carboxylic acid (5.00 g, 44.6 mmol, 1.00 equiv), tert-butanol (50 mL), di-tert-butyl dicarbonate (39.0 g, 179 mmol, 4.01 equiv) and 4-dimethylaminopyridine (1.10 g, 9.01 mmol, 0.20 equiv). The resulting solution was stirred overnight at 65° C. and quenched by water (5 mL). The mixture was extracted with ethyl acetate (3×30 mL) and the organic layers were combined, washed with water (3×10 mL), dried over anhydrous sodium sulfate, filtered and concentrated under reduced pressure to provide crude 1,4-di-tert-butyl 1H-pyrazole-1,4-dicarboxylate (11.2 g) as yellow oil. LCMS (ESI, m/z): 169 [M+H-Boc]+.

Step 2: Preparation of tert-butyl 1H-pyrazole-4-carboxylate

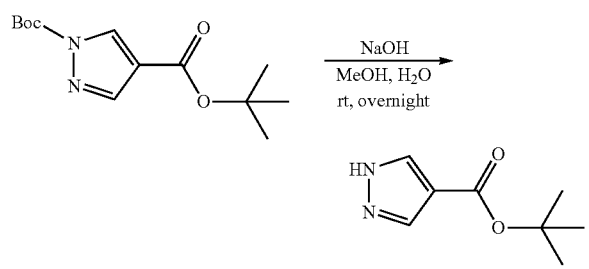

A 250-mL round-bottom flask was charged with 1,3-di-tert-butyl 1H-pyrazole-1,3-dicarboxylate (5.00 g, 18.6 mmol, 1.00 equiv), methanol (30 mL), sodium hydroxide (2.50 g, 62.5 mmol, 3.35 equiv) and water (10 mL). The resulting solution was stirred overnight at room temperature and quenched by water (5 mL). The mixture was extracted with ethyl acetate (3×30 mL) and the organic layers were combined, washed with water (3×10 mL), dried over anhydrous sodium sulfate, filtered and concentrated under reduced pressure to provide crude tert-butyl 1H-pyrazole-3-carboxylate (2.32 g) as a yellow solid. LCMS (ESI, m/z): 169 [M+H]+.

Step 3: Preparation of 4-(4-chlorobenzyl)piperazine-1-carbonyl chloride

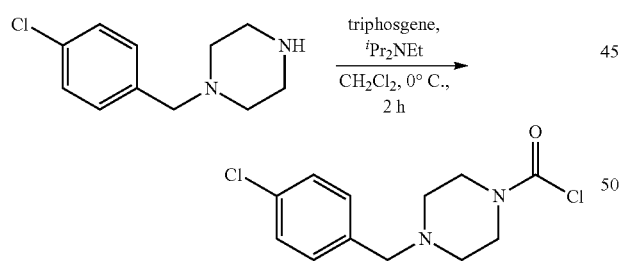

A 100-mL round-bottom flask was charged with 1-[(4-chlorophenyl)methyl]piperazine (1.47 g, 6.98 mmol, 1.00 equiv), triphosgene (1.04 g, 3.50 mmol, 0.50 equiv) and dichloromethane (20 mL). N,N-Diisopropylethylamine (1.80 g, 13.9 mmol, 2.00 equiv) was added dropwise at 0° C. The resulting solution was stirred for 2 hours at room temperature and quenched by water (10 ml). The mixture was extracted with dichloromethane (3×30 mL) and the organic layers were combined, washed with water (3×10 mL), dried over anhydrous sodium sulfate, filtered and concentrated under reduced pressure to provide crude 4-(4-chlorobenzyl)piperazine-1-carbonyl chloride (1.50 g) as yellow oil.

Step 4: Preparation of tert-butyl 1-(4-(4-chlorobenzyl)piperazine-1-carbonyl)-1H-pyrazole-4-carboxylate

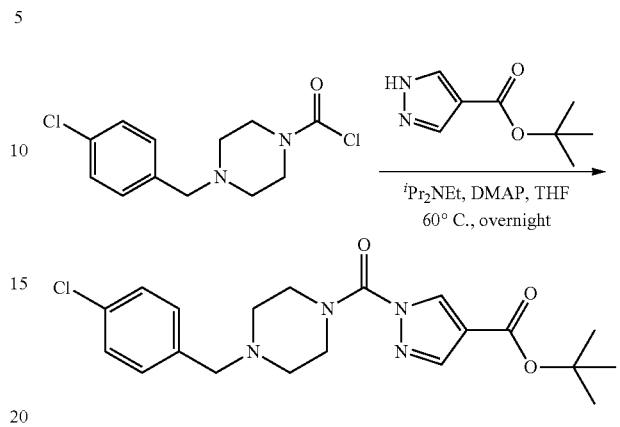

A 40-mL round-bottom flask was charged with 4-[(4-chlorophenyl)methyl]piperazine-1-carbonyl chloride (250 mg, 0.920 mmol, 1.00 equiv), tetrahydrofuran (10 mL), tert-butyl 1H-pyrazole-4-carboxylate (155 mg, 0.920 mmol, 1.00 equiv), N,N-diisopropylethylamine (237 mg, 1.83 mmol, 2.00 equiv) and 4-dimethylaminopyridine (22.0 mg, 0.180 mmol, 0.20 equiv). The resulting solution was stirred overnight at 60° C. and quenched by water (5 mL). The mixture was extracted with ethyl acetate (3×30 mL) and the organic layers were combined, washed with water (3×10 mL), dried over anhydrous sodium sulfate, filtered and concentrated under reduced pressure to provide crude tert-butyl 1-(4-(4-chlorobenzyl)piperazine-1-carbonyl)-1H-pyrazole-4-carboxylate (350 mg) as a yellow oil. LCMS (ESI, m/z): 405 [M+H]+.

Step 5: Preparation of 1-(4-(4-chlorobenzyl)piperazine-1-carbonyl)-1H-pyrazole-4-carboxylic acid

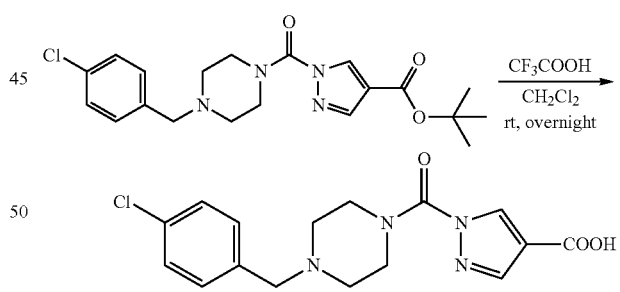

A 40-mL round-bottom flask was charged with tert-butyl 1-(4-(4-chlorobenzyl)piperazine-1-carbonyl)-1H-pyrazole-4-carboxylate (350 mg, 0.860 mmol, 1.00 equiv), dichloromethane (10 mL) and trifluoroacetic acid (10 mL). The resulting solution was stirred overnight at room temperature and concentrated under reduced pressure. The crude product was purified by preparative HPLC using the following gradient conditions: 20% CH3CN/80% Phase A increasing to 80% CH3CN over 10 min, then to 100% CH3CN over 0.1 min, holding at 100% CH3CN for 1.9 min, then reducing to 20% CH3CN over 0.1 min, and holding at 20% for 1.9 min, on a Waters 2767-5 Chromatograph. Column: X bridge Prep C18, 19*150 mm 5 μm; Mobile phase: Phase A: aqueous NH₄HCO₃ (0.05%); Phase B: CH₃CN; Detector, UV220 & 254 nm. Purification provided 1-(4-(4-chlorobenzyl)piperazine-1-carbonyl)-1H-pyrazole-4-carboxylic acid (66.6 mg, 22% yield) as a yellow solid. $^1$H NMR (400 MHz, CD₃OD) δ 8.38 (s, 1H), 7.93 (s, 1H), 7.33-7.39 (m, 4H), 3.81-3.90 (br, 4H), 3.57 (s, 2H), 2.55-2.58 (m, 4H). LCMS (ESI, m/z): 349 [M+H]⁺.

Example 289: (4-((3-Chlorobiphenyl-4-yl)methyl)piperazin-1-yl)(4-(pyrrolidine-1-carbonyl)-1H-pyrazol-1-yl)methanone

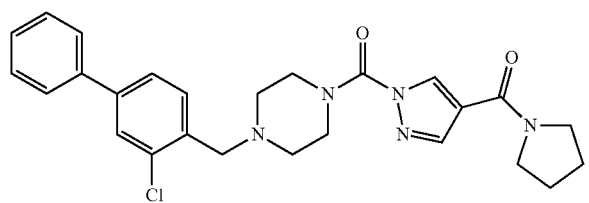 [SMILES: O=C(c1cnn(C(=O)N2CCN(Cc3ccc(-c4ccccc4)cc3Cl)CC2)c1)N1CCCC1]

Step 1: Preparation of 1H-pyrazole-4-carbonyl chloride

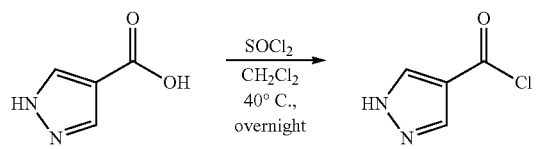 [SMILES: O=C(O)c1cn[nH]c1 ; "SOCl2" ; O=C(Cl)c1cn[nH]c1]

A 250-mL round-bottom flask was charged with 1H-pyrazole-4-carboxylic acid (3.00 g, 26.8 mmol, 1.00 equiv) in dichloromethane (50 mL), sulfuroyl dichloride (9.40 g, 79.0 mmol, 3.00 equiv). The resulting solution was stirred overnight at 40° C. and concentrated under reduced pressure to provide 1H-pyrazole-4-carbonyl chloride (3.48 g, 100% yield) as yellow oil.

Step 2: Preparation of (1H-pyrazol-4-yl)(pyrrolidin-1-yl)methanone

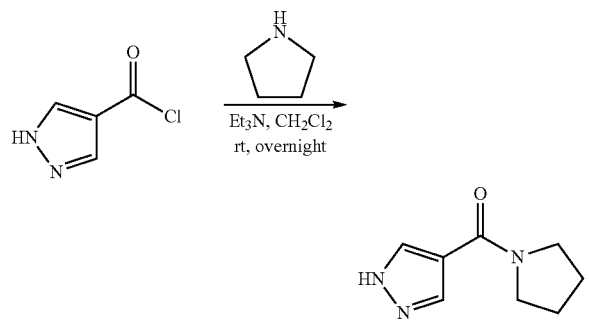

A 250-mL round-bottom flask was charged with 1H-pyrazole-4-carbonyl chloride (3.48 g, 26.7 mmol, 1.00 equiv) in dichloromethane (50 mL), pyrrolidine (2.85 g, 40.1 mmol, 1.50 equiv), triethylamine (5.41 g, 53.6 mmol, 2.00 equiv). The resulting solution was stirred overnight at room temperature and quenched with water (50 mL). The resulting solution was extracted with dichloromethane (3×50 mL) and the organic layers were combined, washed with brine (2×50 mL), dried over anhydrous sodium sulfate, filtered and concentrated under reduced pressure. The residue was chromatographed on a silica gel column with dichloromethane/methanol (15/1) to provide (1H-pyrazol-4-yl)(pyrrolidin-1-yl)methanone (1.50 g, 34% yield) as a white solid. LCMS (ESI, m/z): 166 [M+H]⁺.

Step 3: Preparation of (4-((3-chlorobiphenyl-4-yl)methyl)piperazin-1-yl)(4-(pyrrolidine-1-carbonyl)-1H-pyrazol-1-yl)methanone

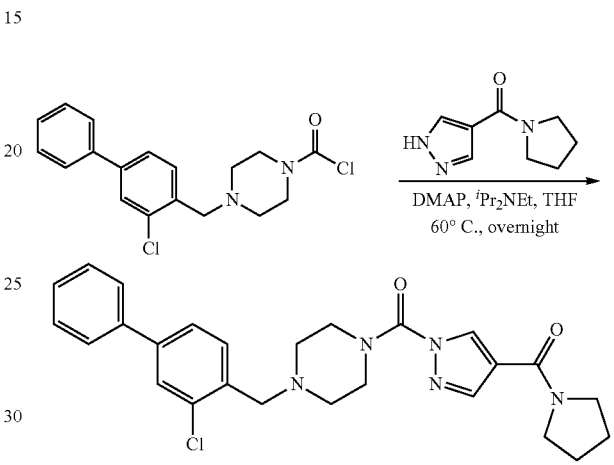

A 50-mL round-bottom flask was charged with 4-[(2-chloro-4-phenylphenyl)methyl]piperazine-1-carbonyl chloride (Example 137, Steps 1-4, 200 mg, 0.570 mmol, 1.00 equiv) in tetrahydrofuran (10 mL), 4-[(pyrrolidin-1-yl)carbonyl]-1H-pyrazole (142 mg, 0.860 mmol, 1.50 equiv), 4-dimethylaminopyridine (7.01 mg, 0.0574 mmol, 0.10 equiv), N-ethyl-N-isopropylpropan-2-amine (222 mg, 1.71 mmol, 3.00 equiv). The resulting solution was stirred overnight at 60° C. and quenched with water (10 mL). The mixture was extracted with dichloromethane (3×10 mL) and the organic layers were combined, washed with brine (2×10 mL), dried over anhydrous sodium sulfate, filtered and concentrated under reduced pressure. The crude product (400 mg) was purified by preparative HPLC using the following gradient conditions: 30% CH₃CN/70% Phase A increasing to 70% CH₃CN over 10 min, then to 100% CH₃CN over 0.1 min, holding at 100% CH₃CN for 1.9 min, then reducing to 30% CH₃CN over 0.1 min, and holding at 30% for 1.9 min, on a Waters 2767-5 Chromatograph. Column: Xbridge Prep C18, 19*150 mm 5 μm; Mobile phase: Phase A: aqueous NH₄HCO₃ (0.05%); Phase B: CH₃CN; Detector, UV220 & 254 nm. Purification provided (4-((3-chlorobiphenyl-4-yl)methyl)piperazin-1-yl)(4-(pyrrolidine-1-carbonyl)-1H-pyrazol-1-yl)methanone (99.0 mg, 36% yield) as a white solid. $^1$H NMR (400 MHz, Chloroform-d) δ 8.42 (s, 1H), 8.02 (s, 1H), 7.31-7.70 (m, 8H), 3.74-4.11 (m, 5H), 3.64-3.70 (m, 5H), 2.69 (br, 4H), 1.92-2.06 (m, 4H). LCMS (ESI, m/z): 478 [M+H]⁺.

Example 290: (4-((3-Methoxybiphenyl-4-yl)methyl)piperazin-1-yl)(4-(pyrrolidine-1-carbonyl)-1H-pyrazol-1-yl)methanone

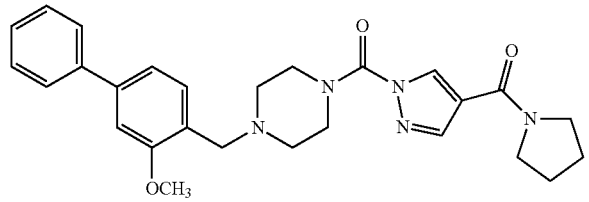 [SMILES: COc1cc(-c2ccccc2)ccc1CN1CCN(C(=O)n2cc(C(=O)N3CCCC3)cn2)CC1]

The title compound was synthesized from 4-((3-methoxybiphenyl-4-yl)methyl)piperazine-1-carbonyl chloride (Example 137, Steps 1-4) and (1H-pyrazol-4-yl)(pyrrolidin-1-yl)methanone (Example 289, Steps 1-2) according to the representative procedure of Example 289, Steps 1-3 to provide (4-((3-methoxybiphenyl-4-yl)methyl)piperazin-1-yl)(4-(pyrrolidine-1-carbonyl)-1H-pyrazol-1-yl)methanone (83.7 mg, 18% yield) as colorless oil. $^1$H NMR (300 MHz, Chloroform-d) δ 8.38 (s, 1H), 8.00 (s, 1H), 7.57-7.60 (m, 2H), 7.32-7.46 (m, 4H), 7.15-7.18 (m, 1H), 7.08 (d, J=1.5 Hz, 1H), 3.89 (br, 7H), 3.61-3.66 (m, 6H), 2.64 (br, 4H), 1.88-2.05 (m, 4H). LCMS (ESI, m/z): 474 [M+H]$^+$ Example 291: (4-((3-(Benzyloxy)biphenyl-4-yl)methyl)piperazin-1-yl)(4-(pyrrolidine-1-carbonyl)-1H-pyrazol-1-yl)methanone

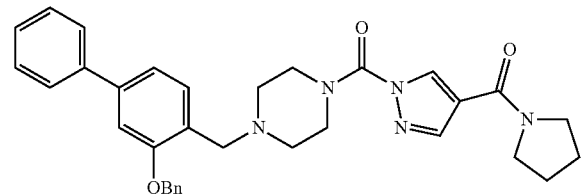 [SMILES: O=C(c1cnn(C(=O)N2CCN(Cc3ccc(-c4ccccc4)cc3OCc3ccccc3)CC2)c1)N1CCCC1]

The title compound was synthesized from 4-((3-(benzyloxy)biphenyl-4-yl)methyl)piperazine-1-carbonyl chloride (Example 137, Steps 1-4) and (1H-pyrazol-4-yl)(pyrrolidin-1-yl)methanone (Example 289, Steps 1-2) according to the representative procedure of Example 289, Steps 1-3 to provide (4-((3-(benzyloxy)biphenyl-4-yl)methyl)piperazin-1-yl)(4-(pyrrolidine-1-carbonyl)-1H-pyrazol-1-yl)methanone (160.6 mg, 53% yield) as a white solid. $^1$H NMR (300 MHz, Chloroform-d) δ 8.38 (s, 1H), 8.00 (s, 1H), 7.54-7.57 (m, 2H), 7.45-7.48 (m, 4H), 7.40-7.43 (m, 2H), 7.33-7.37 (m, 3H), 7.17-7.20 (m, 2H), 5.16 (s, 2H), 3.88 (br, 4H), 3.68-3.72 (m, 2H), 3.61-3.66 (m, 4H), 2.64 (br, 4H), 1.88-2.02 (m, 4H). LCMS (ESI, m/z): 550 [M+H]$^+$.

Example 292: 1-(Azepane-1-carbonyl)-1H-pyrazole-4-carbonitrile

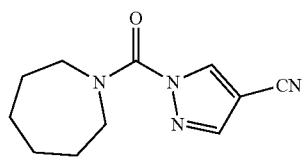 [SMILES: N#Cc1cnn(C(=O)N2CCCCCC2)c1]

The title compound was synthesized from azepane (128 mg, 1.29 mmol), triphosgene (153 mg, 0.520 mmol), and 1H-pyrazole-4-carbonitrile (100 mg, 1.29 mmol) according to the representative procedure of Example 199, Steps 1-2 to provide 1-(Azepane-1-carbonyl)-1H-pyrazole-4-carbonitrile (70.2 mg, 25% yield) as a white solid. $^1$H NMR (300 MHz, Chloroform-d) δ 8.54 (s, 1H), 7.86 (s, 1H), 3.67-3.79 (m, 4H), 1.89 (m, 4H), 1.58-1.84 (m, 4H). LCMS (ESI, m/z): 219 [M+H]$^+$.

The following examples were prepared according to the procedures described above.

Example 293: N-(4-(Benzyloxy)benzyl)-4-methyl-1H-pyrazole-1-carboxamide

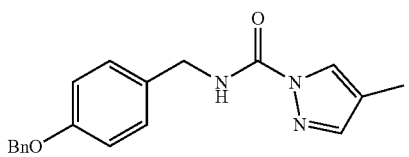 [SMILES: Cc1cnn(C(=O)NCc2ccc(OCc3ccccc3)cc2)c1]

LCMS (ESI, m/z): 183 [M–C$_6$H$_8$N$_3$O]+.

Example 294: (4-Methyl-1H-pyrazol-1-yl)(4-(3-phenoxybenzyl)piperazin-1-yl)methanone

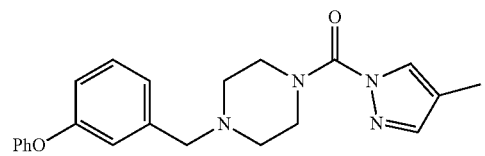 [SMILES: Cc1cnn(C(=O)N2CCN(Cc3cccc(Oc4ccccc4)c3)CC2)c1]

LCMS (ESI, m/z): 377 [M+H]$^+$.

Example 295: 1-(4-(3-Phenoxybenzyl)piperazine-1-carbonyl)-1H-pyrazole-4-carbonitrile

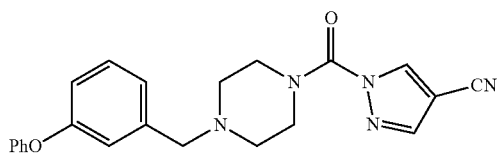 [SMILES: N#Cc1cnn(C(=O)N2CCN(Cc3cccc(Oc4ccccc4)c3)CC2)c1]

LCMS (ESI, m/z): 388 [M+H]$^+$.

Example 296: (4-(3-(Benzyloxy)benzyl)piperazin-1-yl)(1H-pyrazol-1-yl)methanone

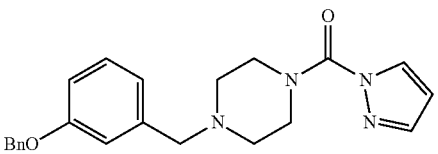 [SMILES: O=C(N1CCN(Cc2cccc(OCc3ccccc3)c2)CC1)n1cccn1]

LCMS (ESI, m/z): 377 [M+H]$^+$.

Example 297: (4-(3-(Benzyloxy)benzyl)piperazin-1-yl)(4-methyl-1H-pyrazol-1-yl)methanone

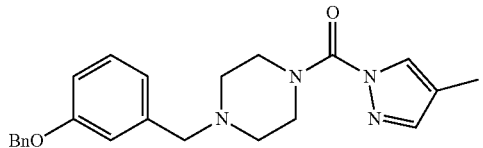

LCMS (ESI, m/z): 391 [M+H]$^+$.

Example 298: (4-Methyl-1H-pyrazol-1-yl)(4-(3-phenoxybenzyl)-1,4-diazepan-1-yl)methanone

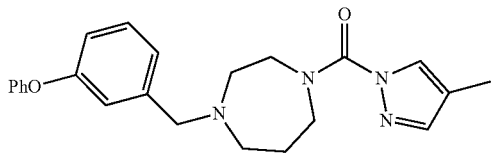 [SMILES: Cc1cnn(C(=O)N2CCCN(Cc3cccc(Oc4ccccc4)c3)CC2)c1]

LCMS (ESI, m/z): 391 [M+H]$^+$.

Example 299: 1-(4-(3-Phenoxybenzyl)-1,4-diazepane-1-carbonyl)-1H-pyrazole-4-carbonitrile

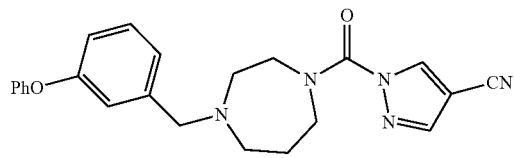 [SMILES: N#Cc1cnn(C(=O)N2CCCN(Cc3cccc(Oc4ccccc4)c3)CC2)c1]

LCMS (ESI, m/z): 402 [M+H]$^+$.

Example 300: 1-(4-(3-(Benzyloxy)benzyl)-1,4-diazepane-1-carbonyl)-1H-pyrazole-4-carbonitrile

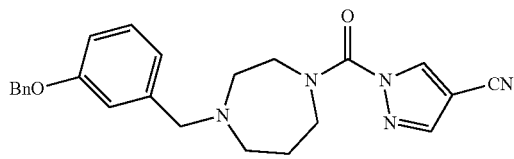 [SMILES: N#Cc1cnn(C(=O)N2CCCN(Cc3cccc(OCc4ccccc4)c3)CC2)c1]

LCMS (ESI, m/z): 416 [M+H]$^+$.

Example 301: 1-(4-(4-Phenoxybenzyl)-1,4-diazepane-1-carbonyl)-1H-pyrazole-4-carbonitrile

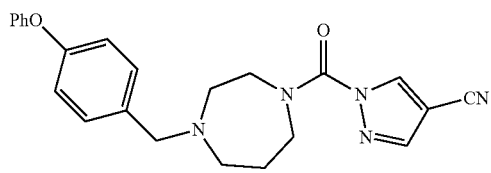 [SMILES: N#Cc1cnn(C(=O)N2CCCN(Cc3ccc(Oc4ccccc4)cc3)CC2)c1]

LCMS (ESI, m/z): 402 [M+H]$^+$.

Example 302: (4-(4-(Benzyloxy)benzyl)-1,4-diazepan-1-yl)(4-methyl-1H-pyrazol-1-yl)methanone

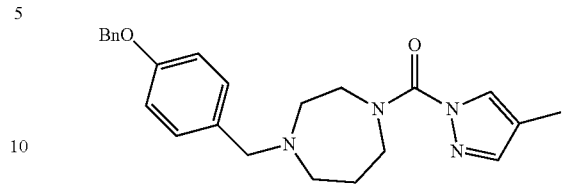

LCMS (ESI, m/z): 405 [M+H]$^+$.

Example 303: 1-(4-(4-(Benzyloxy)benzyl)-1,4-diazepane-1-carbonyl)-1H-pyrazole-4-carbonitrile

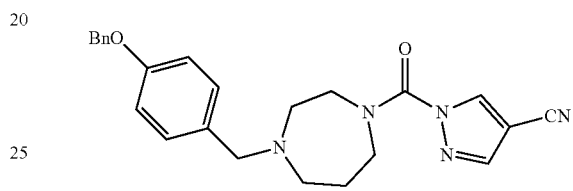

LCMS (ESI, m/z): 416 [M+H]$^+$.

II. Biological Evaluation

Compounds are tested to assess their MAGL and other serine hydrolase activity using the following in vitro and in vivo assays.

In Vitro Competitive Activity-Based Protein Profiling.

Proteomes (mouse brain membrane fraction or cell lysates) (50 μL, 1.0 mg/mL total protein concentration) were preincubated with varying concentrations of inhibitors at 37° C. After 30 min, FP-Rh or HT-01 (1.04, 50 μM in DMSO) was added and the mixture was incubated for another 30 min at 37° C. Reactions were quenched with SDS loading buffer (15 μL—4×) and run on SDS-PAGE. Following gel imaging, serine hydrolase activity was determined by measuring fluorescent intensity of gel bands corresponding to MAGL, ABHD6, FAAH, and PLA2G7 using ImageJ 1.43u software.

Preparation of Mouse Brain Proteomes from Inhibitor Treated Mice.

Inhibitors were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44)

Compounds demonstrated activity in the assays described herein as indicated in the following tables (Tables 2 and 3).

TABLE 2

| Compd | Mouse (IC$_{50}$ value, nM) | | | |
|---|---|---|---|---|
| | MAGL | FAAH | ABHD6 | PLA2G7 |
| 9 | *** | ** | *** | |
| 10 | *** | | | |
| 21 | *** | *** | *** | |
| 46 | *** | * | * | |

TABLE 2-continued

| Compd | Mouse (IC$_{50}$ value, nM) | | | |
|---|---|---|---|---|
| | MAGL | FAAH | ABHD6 | PLA2G7 |
| 47 | *** | ** | *** | |
| 48 | ** | * | ** | |
| 49 | ** | * | ** | |
| 50 | *** | ** | *** | |
| 51 | | | ** | |
| 57 | ** | *** | ** | |
| 58 | | | ** | |
| 59 | | | ** | |
| 60 | | | ** | |
| 63 | | | ** | |
| 66 | ** | * | ** | |
| 67 | ** | * | ** | |
| 68 | ** | * | ** | |
| 76 | ** | *** | ** | |
| 85 | ** | *** | ** | |
| 91 | | * | | |
| 93 | ** | *** | ** | |
| 94 | *** | ** | * | |
| 100 | *** | * | ** | |
| 102 | *** | * | *** | |
| 107 | | | ** | |
| 110 | *** | * | *** | |
| 111 | ** | * | ** | |
| 112 | | | ** | |
| 113 | *** | * | ** | |
| 114 | | | ** | |
| 115 | | | ** | |
| 116 | | | * | |
| 117 | *** | * | * | |
| 118 | *** | * | ** | |
| 121 | *** | * | * | |
| 125 | *** | * | ** | |
| 126 | *** | ** | ** | |
| 128 | * | ** | * | |
| 129 | * | ** | * | |
| 131 | * | *** | * | |
| 133 | * | *** | * | |
| 134 | * | ** | * | |
| 135 | * | ** | * | |
| 137 | *** | *** | ** | * |
| 138 | *** | *** | *** | *** |
| 139 | *** | *** | ** | * |
| 141 | *** | ** | ** | |
| 142 | *** | *** | ** | |
| 143 | *** | *** | ** | |
| 157 | * | ** | * | * |
| 158 | * | * | * | * |
| 179 | * | *** | * | * |
| 180 | ** | ** | * | * |
| 186 | *** | ** | *** | * |
| 200 | * | ** | ** | ** |
| 204 | *** | ** | *** | * |
| 210 | *** | * | ** | *** |
| 211 | *** | *** | *** | |
| 212 | *** | ** | ** | |
| 213 | *** | *** | *** | ** |
| 216 | *** | *** | *** | * |
| 218 | *** | ** | ** | ** |
| 219 | *** | *** | ** | *** |
| 220 | *** | *** | ** | * |
| 223 | ** | ** | *** | |
| 224 | *** | ** | ** | ** |
| 225 | *** | *** | ** | * |
| 226 | *** | *** | *** | * |
| 227 | *** | *** | *** | *** |
| 233 | *** | *** | *** | *** |
| 234 | *** | *** | *** | *** |
| 235 | *** | *** | *** | *** |
| 241 | *** | *** | *** | *** |
| 243 | ** | *** | * | * |
| 244 | * | *** | * | * |
| 246 | ** | ** | ** | * |
| 247 | ** | ** | ** | * |
| 249 | ** | *** | * | |
| 250 | * | *** | * | |
| 252 | ** | *** | * | |

TABLE 2-continued

| Compd | Mouse (IC$_{50}$ value, nM) | | | |
|---|---|---|---|---|
| | MAGL | FAAH | ABHD6 | PLA2G7 |
| 253 | * | *** | * | * |
| 255 | ** | *** | * | * |
| 256 | * | *** | * | * |
| 258 | ** | *** | * | * |
| 259 | * | *** | * | * |
| 261 | ** | *** | * | * |
| 263 | ** | *** | * | * |
| 264 | ** | *** | * | * |
| 266 | * | ** | * | * |
| 268 | *** | *** | *** | ** |
| 269 | *** | *** | *** | *** |
| 271 | *** | *** | *** | *** |
| 272 | *** | *** | *** | ** |
| 273 | *** | *** | *** | *** |
| 274 | *** | ** | *** | *** |
| 275 | *** | *** | *** | *** |
| 276 | *** | *** | *** | *** |
| 279 | *** | *** | *** | ** |
| 280 | *** | ** | ** | *** |
| 286 | *** | *** | *** | ** |
| 287 | *** | *** | *** | *** |
| 292 | * | ** | * | * |

\*\*\* is less than or equal to 100 nM;
\*\* is between 1000 and 100 nM;
\* is greater than or equal to 1000 nM

TABLE 3

| Compd | % Inhibition at 1 µM* | | | | % Inhibition at 10 µM* | | | |
|---|---|---|---|---|---|---|---|---|
| | A | B | C | D | A | B | C | D |
| 1 | # | # | # | # | ## | ### | ### | ## |
| 2 | # | # | ## | # | ## | ### | ### | ### |
| 3 | ### | ### | ### | ### | ### | ### | ### | ### |
| 4 | # | ### | ## | # | ## | ### | ### | ### |
| 5 | # | # | ## | ### | ## | ### | ### | ### |
| 6 | ### | ### | ### | ### | ### | ### | ### | ### |
| 7 | ### | # | # | # | ### | ### | ### | # |
| 8 | ## | # | ### | # | ### | ## | ### | ### |
| 9 | ### | ### | ### | ### | ### | ### | ### | ### |
| 10 | ### | ### | ### | # | ### | ### | ### | # |
| 11 | # | ### | ### | # | ### | ## | ### | ### |
| 12 | ### | ### | ### | ### | ### | ### | ### | ### |
| 13 | ### | ### | ### | ### | ### | ### | ### | ### |
| 14 | ### | ### | ### | ### | ### | ### | ### | ### |
| 15 | ### | ### | ### | ### | ### | ### | ### | ### |
| 16 | ### | # | ### | # | ### | ### | ### | ### |
| 17 | ### | ## | ### | ## | ### | ### | ### | # |
| 18 | ### | ### | ### | ### | ### | ### | ### | ### |
| 19 | ## | ### | # | # | ### | ### | ### | # |
| 20 | ## | # | ## | # | ### | ### | ### | ## |
| 21 | ### | ### | ### | # | ### | ### | ### | ### |
| 22 | ### | # | # | # | ### | ### | ### | # |
| 23 | ### | # | ## | # | ### | ## | ### | ### |
| 24 | ### | ### | ### | ### | ### | ### | ### | ### |
| 25 | # | # | # | # | # | # | ## | # |
| 26 | # | ## | ## | # | ## | ### | ### | # |
| 27 | ### | ### | ### | ### | ### | ### | ### | ### |
| 28 | # | # | # | # | ## | ## | ## | # |
| 29 | # | # | # | # | ## | ## | ### | # |
| 31 | | | | | # | # | # | # |
| 32 | | | | | # | # | # | # |
| 33 | # | # | # | # | # | ### | # | # |
| 34 | | | | | # | # | # | # |
| 35 | | | | | # | # | # | # |
| 36 | # | ## | # | # | ## | ### | ## | # |
| 37 | | | | | # | # | # | # |
| 38 | | | | | # | # | # | # |
| 39 | # | # | # | # | ## | ### | # | # |
| 40 | # | # | # | # | ### | # | # | # |
| 41 | # | # | # | # | ### | # | # | # |
| 42 | # | # | # | # | ### | # | # | # |

TABLE 3-continued

| Compd | % Inhibition at 1 μM* | | | | % Inhibition at 10 μM* | | | |
|---|---|---|---|---|---|---|---|---|
| | A | B | C | D | A | B | C | D |
| 43 | # | # | # | # | ## | ### | # | # |
| 44 | | | | | # | # | # | |
| 45 | # | # | # | # | ## | ### | # | # |
| 51 | # | # | ### | # | ### | ### | ### | ### |
| 52 | | ## | # | | | # | # | # |
| 53 | | # | # | ## | # | ### | | ### |
| 54 | | # | # | ## | # | ## | | ### |
| 55 | | ## | # | # | ## | ### | ### | ### |
| 56 | | # | # | # | # | ### | ### | ### |
| 57 | ### | ### | ### | # | ### | ### | ### | ### |
| 58 | # | ### | ### | ### | ### | ### | ### | ### |
| 59 | | ### | ### | ## | ### | ### | ### | |
| 60 | | ### | ### | ### | ### | ### | ### | ### |
| 61 | | ### | ### | # | ### | ### | ### | ### |
| 62 | | ### | ### | # | ### | ### | ### | ### |
| 63 | | ### | ### | # | ### | ### | ### | ### |
| 64 | | ### | ### | # | # | ### | ### | |
| 65 | # | ### | ### | ### | ### | ### | ### | ### |
| 66 | ### | # | ### | | ### | ## | ### | |
| 67 | ### | # | ### | ### | ### | ## | ### | ### |
| 68 | ### | # | ### | | ### | ### | ### | |
| 69 | ## | ### | ### | ### | ### | ### | ### | |
| 70 | # | # | ## | ### | # | ## | ### | ### |
| 71 | # | # | ## | ### | # | ## | ### | ### |
| 72 | # | # | # | ### | # | ### | ### | ### |
| 73 | # | # | # | ### | # | ## | ### | ### |
| 74 | # | # | ### | ### | # | ### | ### | ### |
| 75 | # | # | # | ### | # | # | ### | ### |
| 76 | ### | ### | ### | ### | ### | ### | ### | ### |
| 77 | | | # | # | | # | ### | ### |
| 78 | # | ### | ### | # | ### | ### | ### | ### |
| 79 | | ## | # | # | # | ## | ### | ### |
| 80 | | ## | # | # | # | ### | ### | ### |
| 81 | | # | # | # | # | ### | ### | ### |
| 82 | | # | # | # | # | ## | ### | ### |
| 83 | # | # | # | # | # | # | ### | ### |
| 84 | # | # | # | # | # | # | ## | ### |
| 85 | ### | ### | ### | ### | ### | ### | ### | ### |
| 86 | # | ### | ## | # | ### | ### | ### | ### |
| 87 | # | # | # | # | # | ### | ### | ### |
| 88 | | | | | # | ## | ### | ### |
| 89 | | | | | # | ### | ## | ### |
| 90 | | # | # | # | # | ## | ### | ### |
| 91 | | # | # | # | # | ### | ### | ### |
| 92 | | # | # | # | # | # | ### | ### |
| 93 | ### | ### | ### | # | ### | ### | ### | ### |
| 95 | ### | # | ### | | | | | |
| 96 | | | | | ### | ### | ### | |
| 97 | | | | | # | ### | # | |
| 98 | | | | | ## | ### | # | |
| 99 | ### | ### | ### | | | | | |
| 101 | ### | ### | ### | | | | | |
| 102 | ### | # | ### | | | | | |
| 103 | | | | | # | ### | # | ### |
| 104 | | | | | # | ### | ### | |
| 105 | | | | | # | ### | ### | |
| 106 | | ## | # | | # | # | ### | ## |
| 107 | # | # | ### | # | ### | # | ### | ## |
| 108 | | | | | # | # | ### | |
| 109 | | | | | ## | ### | ### | |
| 110 | ### | # | ### | ### | ### | ### | ### | ### |
| 111 | | | | | ### | ## | ### | |
| 112 | # | # | ### | # | ### | # | ### | ### |
| 113 | ### | ## | ### | | ### | ### | ### | |
| 114 | # | # | ### | | # | ## | ### | |
| 115 | # | # | ### | ## | ## | ## | ## | ### |
| 116 | ## | # | ### | | ### | # | ### | ### |
| 117 | ### | # | # | | ### | # | ### | |
| 118 | ### | # | ### | | ### | ### | ### | |
| 119 | ## | # | # | | ### | # | ### | |
| 120 | ## | # | ## | | # | ## | ### | |
| 121 | ### | # | # | | # | ### | ### | |
| 122 | | # | ## | | # | # | ### | ### |
| 123 | | ## | # | | # | ### | ### | ## |
| 124 | | ### | ## | | # | ### | ### | ### |
| 125 | ### | # | ### | | | | | |
| 126 | ### | ### | ### | | | | | |
| 127 | # | # | # | # | ### | ### | ### | # |
| 128 | | | | | ### | ### | ### | # |
| 129 | # | # | # | # | ### | ### | ## | # |
| 130 | # | # | # | # | | | | |
| 131 | # | ### | # | # | | | | |
| 132 | # | # | # | # | | | | |
| 133 | # | ### | # | # | ### | ### | ### | # |
| 134 | ## | # | # | # | ### | ### | ### | # |
| 135 | ## | ### | # | # | ### | ### | ### | # |
| 136 | # | ### | ### | ### | # | ### | ### | ### |
| 137 | ### | ### | ### | # | ### | ### | ### | ## |
| 138 | ### | ### | ### | ### | ### | ### | ### | ### |
| 139 | ### | ### | ### | # | ### | ### | ### | ### |
| 140 | ### | ### | ### | ### | ### | ### | ### | ### |
| 141 | ### | ### | ### | # | ### | ### | ### | ### |
| 142 | ### | ### | ### | ### | ### | ### | ### | ### |
| 143 | ### | ### | ### | ## | ### | ### | ### | ### |
| 144 | ### | ### | ### | ### | ### | ### | ### | ### |
| 145 | ### | ### | ### | ### | ### | ### | ### | ### |
| 146 | ### | ### | ### | ### | ### | ### | # | ### |
| 147 | ### | ### | ### | # | ### | ### | ### | ### |
| 148 | ### | ### | ### | # | ### | ### | ### | # |
| 149 | # | # | # | ### | ## | # | ## | ### |
| 150 | # | # | ### | ## | ## | ## | ### | ### |
| 151 | # | ### | ### | ## | ### | ### | ### | ### |
| 152 | ### | ### | ### | ### | ### | ### | ### | ### |
| 153 | ### | # | # | ### | ### | ## | ### | ### |
| 154 | # | # | # | ## | # | ## | ### | ### |
| 155 | # | ## | # | ### | ## | ### | ### | ### |
| 156 | # | # | # | # | # | ## | # | ### |
| 157 | ### | ### | ### | # | ### | ### | ### | ### |
| 158 | ### | ### | ### | ### | ### | ### | ### | ### |
| 159 | # | # | # | # | # | ## | ### | ### |
| 160 | # | ### | # | ### | ### | ### | ### | ### |
| 161 | # | # | # | # | # | # | # | ### |
| 162 | # | # | # | # | # | # | ## | ### |
| 163 | # | # | # | # | # | # | # | ### |
| 164 | # | # | # | # | ## | # | # | ### |
| 165 | | | | | # | ## | # | # |
| 166 | | | | | # | # | # | # |
| 167 | | | | | # | ### | # | # |
| 168 | | | | | # | # | # | # |
| 169 | | | | | ## | # | ## | # |
| 170 | | | | | # | # | # | # |
| 171 | | | | | # | # | # | # |
| 172 | | | | | # | # | # | # |
| 173 | # | # | # | ### | ## | # | ## | ### |
| 174 | # | # | ### | ### | ## | ## | ### | ### |
| 175 | ### | # | ### | # | ### | # | ### | ### |
| 176 | ### | # | # | ### | ### | ## | ### | ### |
| 177 | # | # | # | # | # | ### | ### | ### |
| 178 | # | ### | ### | ### | ### | ### | ### | ## |
| 179 | ### | ### | ### | ### | ### | ### | ### | ### |
| 180 | ### | ### | ### | ### | ### | ### | ### | ### |
| 181 | # | # | # | # | # | ### | ### | ### |
| 182 | # | ### | # | # | # | ### | ### | ### |
| 183 | # | # | # | ### | # | # | # | ### |
| 184 | # | # | ### | ### | # | ### | ### | ### |
| 185 | # | # | ### | # | ## | ### | ### | ### |
| 186 | ### | ### | ### | # | ### | ### | ### | ### |
| 187 | ## | # | # | ### | ### | ### | ## | ### |
| 188 | | | | | # | ### | ## | |
| 189 | # | ### | ### | # | ## | ### | ### | # |
| 190 | | | | | # | # | # | |
| 191 | # | ### | ## | # | ### | ### | ### | # |
| 192 | ## | # | ## | # | ### | ### | ### | # |
| 193 | | | | | # | # | # | # |
| 194 | # | ## | # | # | ### | ### | # | # |
| 195 | # | # | # | # | # | ### | ### | ## |
| 196 | | | | | # | # | # | # |
| 197 | # | ## | # | # | # | ### | ### | ### |
| 198 | | | | | # | # | # | # |
| 199 | # | ### | # | # | ### | ### | ### | ### |
| 200 | ### | ### | ### | ### | ### | ### | ### | ### |
| 201 | # | ### | ### | ### | ## | ### | ### | ### |

TABLE 3-continued

| | % Inhibition at 1 μM* | | | | % Inhibition at 10 μM* | | | |
|---|---|---|---|---|---|---|---|---|
| Compd | A | B | C | D | A | B | C | D |
| 202 | ### | ### | ### | ### | ### | ### | ### | ### |
| 203 | # | ### | # | # | ### | ### | ### | ### |
| 204 | ### | ### | ### | # | | | | |
| 205 | # | ### | ## | ### | ## | ### | ### | ### |
| 206 | ### | ### | ### | ### | ### | ### | ### | ### |
| 207 | ## | ### | ### | ## | ### | ### | ### | ### |
| 208 | ### | ### | ### | ### | ### | ### | ### | ### |
| 209 | ### | ### | ### | ### | ### | ### | ### | ### |
| 210 | ### | ### | ### | ## | ### | ### | ### | ### |
| 211 | ### | ### | ### | # | ### | ### | ### | ### |
| 212 | ### | ### | ### | # | ### | ### | ### | ### |
| 213 | ### | ### | ### | # | ### | ### | ### | ### |
| 214 | ### | ### | ### | ### | | | | |
| 215 | ## | ### | ### | # | ### | ### | ### | ### |
| 216 | ### | ### | ### | # | | | | |
| 217 | ### | ### | ### | ### | | | | |
| 218 | ### | ### | ### | ### | | | | |
| 219 | ### | ### | ### | ### | ### | ### | ### | ### |
| 220 | ### | ### | ### | ## | ### | ### | ### | ### |
| 221 | ### | ### | ### | ## | ### | ### | ### | # |
| 222 | ### | ### | ### | ### | ### | ### | ### | # |
| 223 | ### | ### | ### | ### | | | | |
| 224 | ### | ### | ### | # | | | | |
| 225 | ### | ### | ### | # | | | | |
| 226 | ### | ### | ### | # | | | | |
| 227 | ### | ### | ### | ### | ### | ### | ### | ### |
| 228 | ### | ### | ### | ### | ### | ### | ### | ### |
| 229 | ### | ### | ### | ### | ### | ### | ### | ### |
| 230 | ### | ### | ### | ### | ### | ### | ### | ### |
| 231 | ### | ### | ### | ### | ### | ### | ### | ### |
| 232 | ### | ### | ### | ### | ### | ### | ### | ### |
| 233 | ### | ### | ### | ### | ### | ### | ### | ### |
| 234 | ### | ### | ### | ### | ### | ### | ### | ### |
| 235 | ### | ### | ### | ### | ### | ### | ### | ### |
| 236 | ### | ## | ### | ### | ### | ### | ### | ### |
| 237 | ### | ### | ### | ### | ### | ### | ### | ### |
| 238 | ### | ### | ### | ### | ### | ### | ### | ### |
| 239 | ### | ### | ### | ### | ### | ### | ### | ### |
| 240 | ### | ### | ### | ### | ### | ### | ### | ### |
| 241 | ### | ### | ### | ### | ### | ### | ### | ### |
| 242 | ### | ### | ## | # | | | | |
| 243 | ### | ### | ### | # | | | | |
| 244 | ## | ### | ## | # | | | | |
| 245 | # | # | # | # | | | | |
| 246 | ### | ### | ### | # | | | | |
| 247 | # | ### | ## | # | ### | ### | ### | # |
| 248 | # | ### | # | # | | | | |
| 249 | ### | ### | # | # | ### | ### | ### | ## |
| 250 | ### | ### | ## | # | ### | ### | ### | ### |
| 251 | # | # | # | # | | | | |
| 252 | ### | ### | # | # | ### | ### | ### | ## |
| 253 | ## | ### | # | # | | | | |
| 254 | # | # | # | # | | | | |
| 255 | ### | ### | # | # | | | | |
| 256 | ## | ### | # | # | | | | |
| 257 | # | # | # | # | | | | |
| 258 | ### | ### | # | # | | | | |
| 259 | ### | ### | # | # | | | | |
| 260 | # | # | # | # | | | | |
| 261 | ## | ### | ## | # | | | | |
| 262 | # | # | # | # | | | | |
| 263 | ### | ### | ## | # | | | | |
| 264 | ### | ### | # | # | | | | |
| 265 | # | # | # | # | | | | |
| 266 | # | ### | # | # | ### | ### | ### | # |
| 267 | ## | ## | # | # | | | | |
| 268 | ### | ### | ### | ### | | | | |
| 269 | ### | ### | ### | ### | | | | |
| 270 | ### | ### | ### | ### | | | | |
| 271 | ### | ### | ### | ### | | | | |
| 272 | ### | ### | ### | ### | | | | |
| 273 | ### | ### | ### | ### | | | | |
| 274 | ### | ### | ### | ### | | | | |
| 275 | ### | ### | ### | ### | | | | |
| 276 | ### | ### | ### | ### | | | | |
| 277 | ### | ### | ### | ### | | | | |
| 278 | ### | ### | ### | ### | | | | |
| 279 | ### | ### | ### | ### | | | | |
| 280 | ### | ### | ### | ### | | | | |
| 281 | ### | ### | ### | ### | | | | |
| 282 | ### | ### | ### | ### | ### | ### | ### | ### |
| 283 | ### | ### | ### | ### | ### | ### | ### | ### |
| 284 | ### | ### | ### | ### | ### | ### | ### | ### |
| 285 | ### | ### | ### | ### | ### | ### | ### | ### |
| 286 | ### | ### | ### | ## | | | | |
| 287 | ### | ### | ### | ### | | | | |
| 288 | # | ## | # | # | # | ### | # | # |
| 289 | ### | ### | ### | ### | ### | ### | ### | ### |
| 290 | ### | ### | ### | # | ### | ### | ### | ### |
| 291 | ### | ### | ### | # | ### | ### | ### | ## |
| 292 | ## | ### | ## | # | ### | ### | ### | ### |
| 293 | # | # | # | # | | | | |
| 294 | ### | ### | ### | # | | | | |
| 295 | ### | ### | ### | # | | | | |
| 296 | ### | ### | ### | # | | | | |
| 297 | ### | ### | ### | # | | | | |
| 298 | # | ### | # | # | | | | |
| 299 | ### | ### | ### | # | | | | |
| 300 | ### | ### | ### | # | | | | |
| 301 | ### | ### | ### | # | | | | |
| 302 | ## | # | # | # | | | | |
| 303 | ### | ### | # | # | | | | |

*A = MAGL, B = FAAH, C = ABHD6, D = PLA2G7
### is ≥75%;
## is between 25 and 75%;
is ≤25%

We claim:

1. A compound of Formula (I):

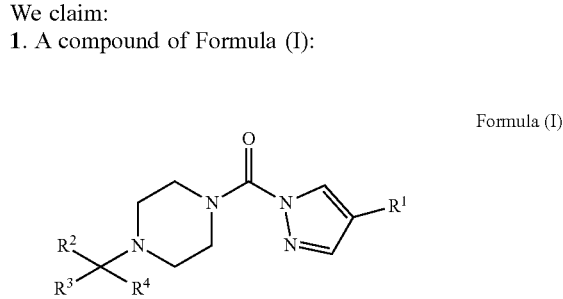

Formula (I)

wherein:

$R^1$ is optionally substituted phenyl;

$R^2$ is phenyl optionally substituted with one or more groups independently selected from alkyl, —O—alkyl, alkenyl, alkynyl, halo, fluoroalkyl, cyano, nitro, aryl, —O-aryl, aralkyl, —O-aralkyl, carbocyclyl, heterocyclyl, heterocyclylalkyl, and heteroaryl;

$R^3$ is H; and $R^4$ is phenyl optionally substituted with one or more groups independently selected from alkyl, halo, and fluoroalkyl;

or a solvate, hydrate, tautomer, N-oxide, or pharmaceutically acceptable salt thereof.

2. The compound of claim 1, or a solvate, hydrate, tautomer, N-oxide, or pharmaceutically acceptable salt thereof, wherein $R^4$ is phenyl substituted with one or more groups independently selected from alkyl, halo, and fluoroalkyl.

3. The compound of claim 2, or a solvate, hydrate, tautomer, N-oxide, or pharmaceutically acceptable salt thereof, wherein $R^4$ is phenyl substituted with one group selected from alkyl, halo, and fluoroalkyl.

4. The compound of claim 1, or a solvate, hydrate, tautomer, N-oxide, or pharmaceutically acceptable salt thereof, wherein $R^4$ is phenyl substituted with one halo.

5. The compound of claim 2, or a solvate, hydrate, tautomer, N-oxide, or pharmaceutically acceptable salt thereof, wherein $R^2$ is phenyl optionally substituted with one or two groups independently selected from alkyl, —O-alkyl, halo, fluoroalkyl, aryl, —O-aryl, aralkyl, —O— aralkyl, heterocyclyl, and heterocyclylalkyl.

6. The compound of claim 5, or a solvate, hydrate, tautomer, N-oxide, or pharmaceutically acceptable salt thereof, wherein $R^2$ is phenyl substituted with one or two groups independently selected from alkyl, halo, and fluoroalkyl.

7. The compound of claim 6, or a solvate, hydrate, tautomer, N-oxide, or pharmaceutically acceptable salt thereof, wherein $R^2$ is phenyl substituted with one halo.

8. The compound of claim 6, or a solvate, hydrate, tautomer, N-oxide, or pharmaceutically acceptable salt thereof, wherein $R^1$ is phenyl optionally substituted with one or more groups independently selected from alkyl, halo, and fluoroalkyl.

9. The compound of claim 6, or a solvate, hydrate, tautomer, N-oxide, or pharmaceutically acceptable salt thereof, wherein $R^1$ is phenyl substituted with one or more groups independently selected from alkyl, halo, and fluoroalkyl.

10. The compound of claim 6, or a solvate, hydrate, tautomer, N-oxide, or pharmaceutically acceptable salt thereof, wherein $R^1$ is phenyl substituted with one or two groups independently selected from alkyl, halo, and fluoroalkyl.

11. The compound of claim 6, or a solvate, hydrate, tautomer, N-oxide, or pharmaceutically acceptable salt thereof, wherein $R^1$ is phenyl substituted with one group selected from alkyl, halo, and fluoroalkyl.

12. The compound of claim 6, or a solvate, hydrate, tautomer, N-oxide, or pharmaceutically acceptable salt thereof, wherein $R^1$ is unsubstituted phenyl.

13. The compound of claim 1 selected from:

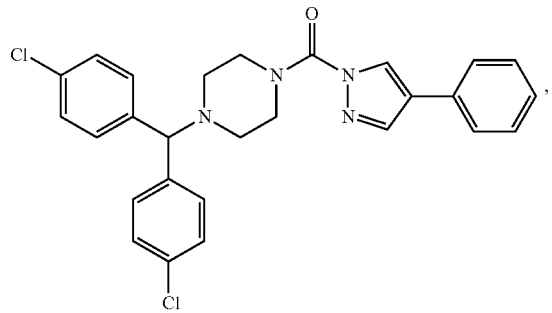

,

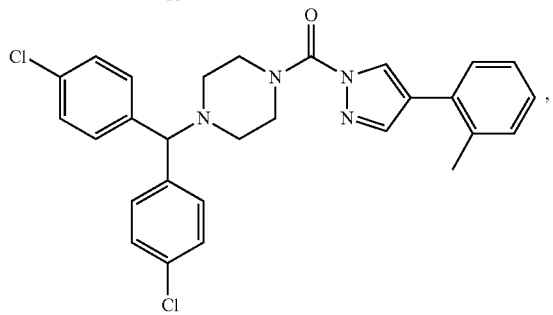

,

-continued

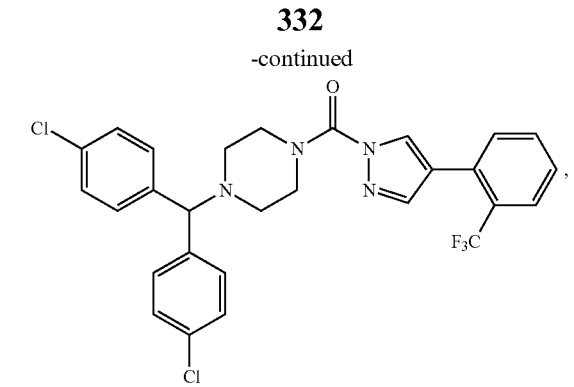

and

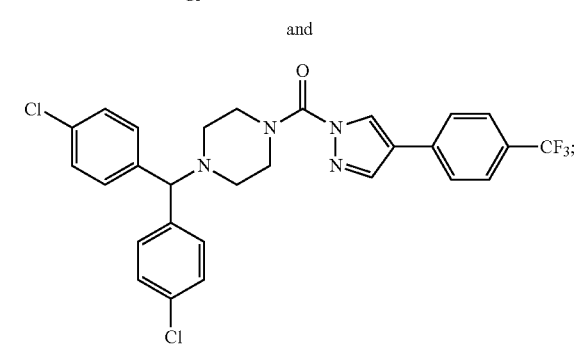

;

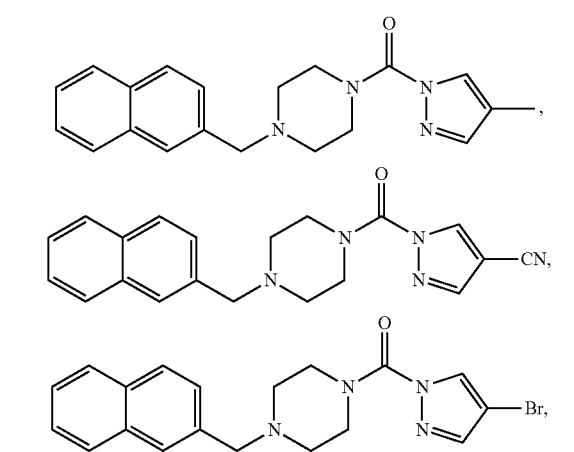

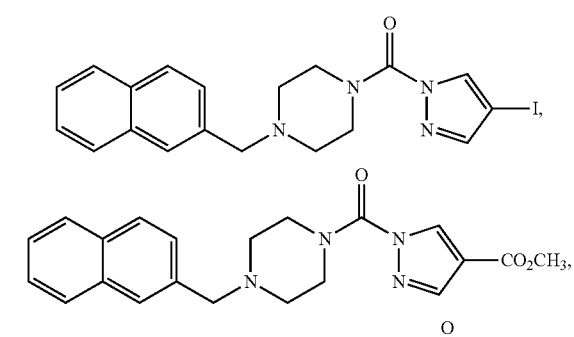

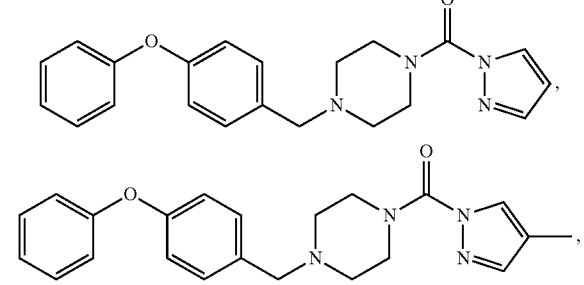

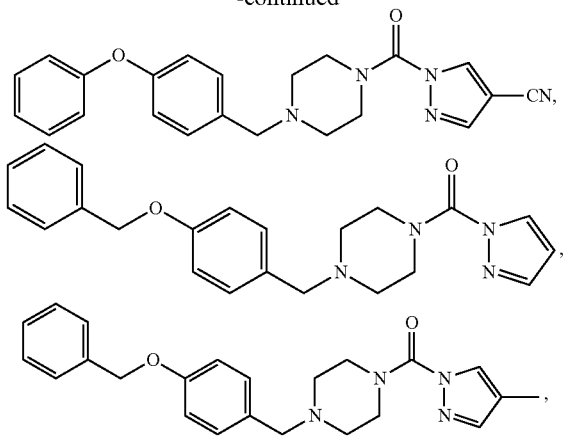

or a solvate, hydrate, tautomer, N-oxide, or pharmaceutically acceptable salt thereof.

14. A pharmaceutical composition comprising a compound of claim 1, or a solvate, hydrate, tautomer, N-oxide, or a pharmaceutically acceptable salt thereof, and at least one pharmaceutically acceptable excipient.

15. A method of therapeutically treating a disorder selected from the group consisting of a solid tumor cancer, obesity, Down's syndrome, Alzheimer's disease, and inflammation, in a patient in need thereof, comprising administering a therapeutically effective amount of a compound of claim 1, or a solvate, hydrate, tautomer, N-oxide, or a pharmaceutically acceptable salt thereof, to the patient.

16. A method of therapeutically treating pain in a patient in need thereof, comprising administering a therapeutically effective amount of a compound of claim 1, or a solvate, hydrate, tautomer, N-oxide, or a pharmaceutically acceptable salt thereof, to the patient.

* * * * *

UNITED STATES PATENT AND TRADEMARK OFFICE
CERTIFICATE OF CORRECTION

PATENT NO. : 10,093,630 B2
APPLICATION NO. : 15/312998
DATED : October 9, 2018
INVENTOR(S) : Boger et al.

Page 1 of 1

It is certified that error appears in the above-identified patent and that said Letters Patent is hereby corrected as shown below:

In the Specification

Column 1, at Line 13, please insert the following paragraph:
-- STATEMENT OF GOVERNMENT LICENSE RIGHTS
This invention was made with government support under grant number DA015648 awarded by The National Institutes of Health. The government has certain rights in the invention. --

Signed and Sealed this
Eleventh Day of August, 2020

Andrei Iancu
*Director of the United States Patent and Trademark Office*